United States Patent
Mahboobi et al.

(10) Patent No.: US 10,106,540 B2
(45) Date of Patent: Oct. 23, 2018

(54) HDAC6 INHIBITORS AND THEIR USES

(71) Applicants: Universität Regensburg, Regensburg (DE); Friedrich-Schiller-Universität Jena, Jena (DE); Universitätsklinikum Jena, Jena (DE)

(72) Inventors: Siavosh Mahboobi, Regensburg (DE); Andreas Sellmer, Lappersdorf (DE); Herwig Pongratz, Regensburg (DE); Michel Leonhardt, Dachau (DE); Oliver Krämer, Nackenheim (DE); Frank-Dietmar Böhmer, Dornburg-Camburg (DE); Gerhard Kelter, Ehrekirchen (DE)

(73) Assignees: UNIVERSITÄT REGENSBURG, Regensburg (DE); FRIEDRICH-SCHILLER-UNIVERSITÄT JENA, Jena (DE); UNIVERSITÄTSKLINIKUM JENA, Jena (DE)

( * ) Notice: Subject to any disclaimer, the term of this patent is extended or adjusted under 35 U.S.C. 154(b) by 0 days.

(21) Appl. No.: 15/329,175

(22) PCT Filed: Aug. 4, 2015

(86) PCT No.: PCT/EP2015/067920
§ 371 (c)(1),
(2) Date: Jan. 25, 2017

(87) PCT Pub. No.: WO2016/020369
PCT Pub. Date: Feb. 11, 2016

(65) Prior Publication Data
US 2017/0210743 A1    Jul. 27, 2017

(30) Foreign Application Priority Data

Aug. 4, 2014    (EP) .................................. 14179728

(51) Int. Cl.
| C07D 471/18 | (2006.01) |
| C07D 471/22 | (2006.01) |
| A61K 31/529 | (2006.01) |
| C07D 455/03 | (2006.01) |
| C07C 259/10 | (2006.01) |
| C07C 259/06 | (2006.01) |
| C07D 471/14 | (2006.01) |

(52) U.S. Cl.
CPC .......... *C07D 471/18* (2013.01); *C07C 259/06* (2013.01); *C07C 259/10* (2013.01); *C07D 455/03* (2013.01); *C07D 471/14* (2013.01); *C07D 471/22* (2013.01)

(58) Field of Classification Search
CPC .. C07D 471/18; C07D 471/22; A61K 31/529; A61K 31/551
USPC ................... 544/247; 540/494; 514/257, 219
See application file for complete search history.

(56) References Cited

FOREIGN PATENT DOCUMENTS

WO    WO 2013/062344 A1    5/2013
WO    WO 2013/078544 A1    6/2013

*Primary Examiner* — Charanjit Aulakh
(74) *Attorney, Agent, or Firm* — Saliwanchik, Lloyd & Eisenschenk

(57) ABSTRACT

The present invention relates to small molecule compounds and their use as HDAC inhibitors and in the treatment of various diseases, such as cancer. The present invention further relates to methods of synthesizing the compounds and methods of treatment. H-L(HA), H is a head group selected from (head group 1), (head group 2), (head group 3), (head group 4), (head group 5) and (head group 6).

14 Claims, 23 Drawing Sheets

Figure 1C
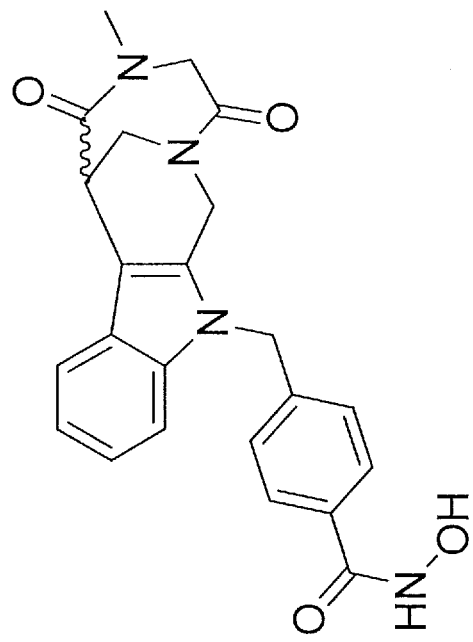
MARB2; 41
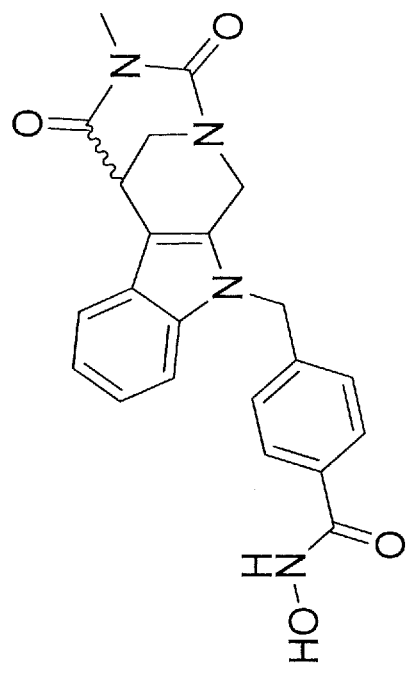
MARB1; 39a

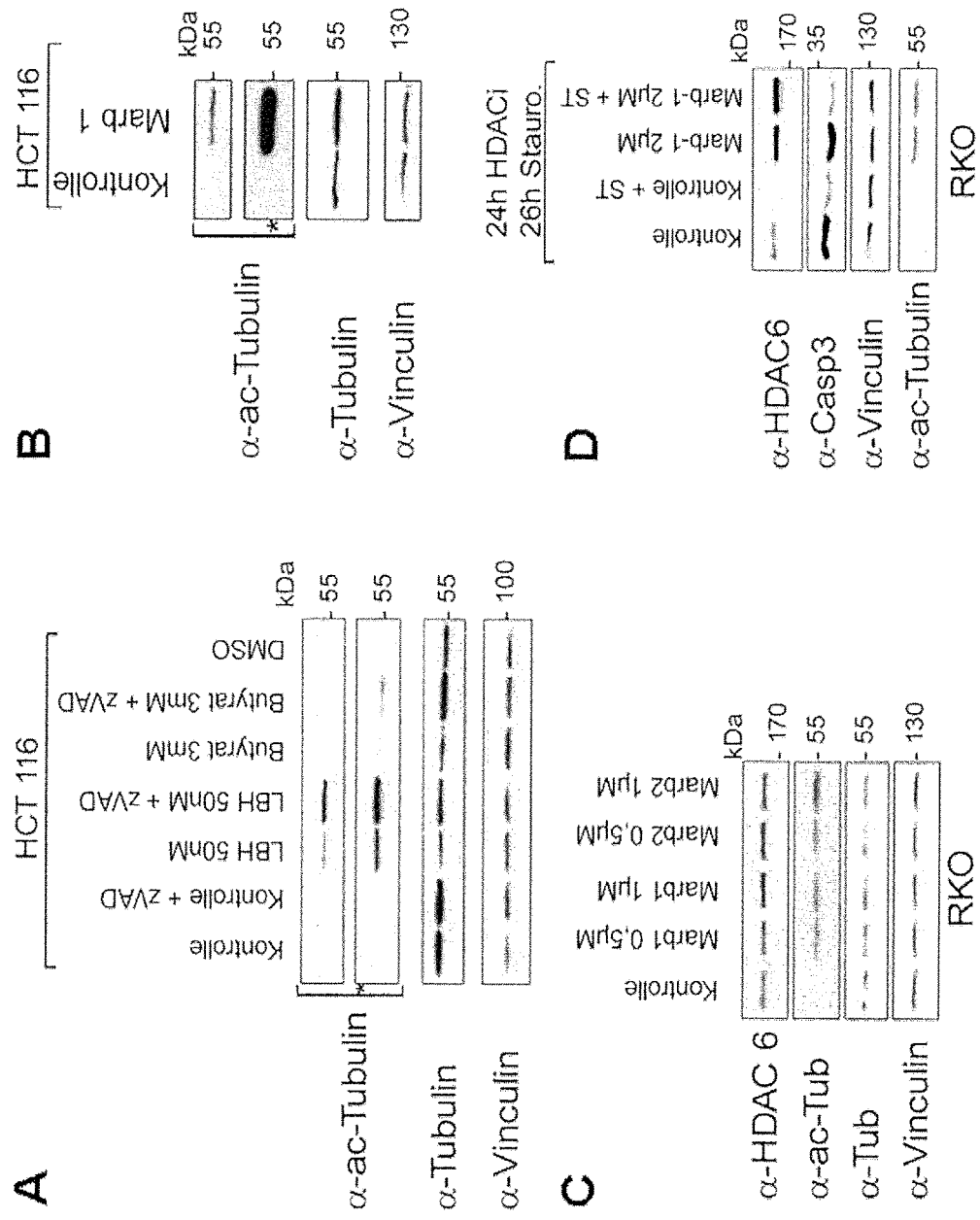

HDAC6 INHIBITORS AND THEIR USES

CROSS REFERENCE TO A RELATED APPLICATION

This application is a National Stage Application of International Application Number PCT/EP2015/067920, filed Aug. 4, 2015; which claims priority to European Patent Application No. 14179728.2, filed Aug. 4, 2014; which are incorporated herein by reference in their entirety.

The present invention relates to small molecule compounds and their use as HDAC inhibitors and in the treatment of various diseases, such as cancer. The present invention further relates to methods of synthesizing the compounds and methods of treatment.

BACKGROUND OF THE INVENTION

Epigenetic alterations are involved in the pathogenesis of many diseases. Histone deacetylases (HDACs) are epigenetic regulators that are frequently overexpressed in tumor cells and cause dysregulation of cell growth and differentiation. Histone deacetylase inhibitors (HDACi) are therefore considered as promising agents for tumor therapy and characterized extensively clinically and on a molecular level. HDACi inhibit the deacetylation of histones and many other proteins (Buchwald et al., 2009; Spange et al., 2009). As a result, HDACi modulate chromatin structure and gene expression. This further includes reexpression of tumor suppressor genes which effect differentiation, inhibition of cell growth and apoptosis. At the moment, HDACi of different drug classes are in development or in preclinical and clinical trials for cancer therapy (Quintas-Cardama et al., 2011; Pietschmann et al., 2012; Schneider et al., 2010).

HDACs can be grouped in four classes (I-IV) (Spange et al., 2009; Brandl et al., 2009), whereby class I, II and IV are defined by a zinc depending mechanism. Class II HDACs can be subdivided in IIa (HDAC4, -5, -7, -9) and IIb (HDAC6, -10). Class III HDACs need $NAD^+$ as a cofactor. Whilst HDACs of class I and IV are expressed ubiquitously, they are primarily localized in the nucleus. In contrast, class II HDACs can move from the nucleus to the cytoplasm and show higher tissue specifity (Spange et al., 2009; Brandl et al., 2009).

So-called pan-HDACi have a wide range of cytotoxic profile due to the inhibition of several HDAC isoforms. In contrast, isoenzyme-selective HDAC inhibitors appear to be more suitable considering the therapy and to have fewer side effects. They usually do not generate the undesired side effects which are associated with the broad inhibition of HDACs ("off-target" effects) (Pandey et al., 2007).

Several HDACi are currently in clinical trials and the HDACi SAHA and depsipeptide have been FDA approved for the treatment of cutaneous T-cell lymphomas (Müller & Krämer 2010). Nevertheless, HDACi show its full activity against cancer only in combination with other cytostatic compounds (see e.g. Spange et al., 2009).

Along with the generally increasing importance of enzymes as therapy targets, HDAC6 is closely associated with the development of cancer. Whilst the expression of HDAC6 is induced by oncogenic RAS transformation and it is necessary for an efficient tumor formation. For example, HDAC6 is highly overexpressed in acute myeloid leukemia cells (AML) compared to normal cells (Lee et al., 2008).

Beneficial therapeutic effects on tumor cells have been described not only for pan-HDACi, but also for HDAC6 selective inhibitors. For example, ST80 (see FIG. 1A, compound 2) is an HDAC6 selective inhibitor with an $IC_{50}$ value of circa 1 µM for HDAC6 and 31 times more selective against HDAC6 than against HDAC1 (Scott et al., 2008), which has the same antiproliferative effect in low micro molar range in myeloid cell lines and primary AML blasts as pan-HDACi. Thus, HDAC6 is a potential target structure of antileukemic therapy regimens.

Further, the influence of HDAC6 on the HSP-90 activity can also be important for the treatment efficiency (Chou et al., 2012). Amongst other things, HSP90 serves the folding and stabilization of oncogenic kinases, including the leukemia fusion protein BCR-ABL, mutated FLT3 (FLT3-ITD), c-KIT, AKT and c-RAF. HSP90 is also important for the stability of the pan-leukemic marker protein WT1 and for the leukemic fusion protein AML1-ETO (see e.g. Choudhary et al., 2009). New and highly selective HDAC6 activity modulating compounds are necessary, in order to capture the detailed molecular mechanisms.

Tubastatin A (see FIG. 1A, compound 3) and its derivatives are currently the most selective HDAC6 inhibitors. The development of this compound is based on rational structure-based design. A further increase in selectivity is possible by derivatization of the residue R. Correspondingly, the introduction of α, β-unsaturated or aromatic substituents results in a higher specificity and activity (Kalin et al., 2012).

There is a need in the art for improved HDAC inhibitors.

SUMMARY OF THE INVENTION

According to the present invention this object is solved by a compound having the general formula I

H-L(HA)

wherein
H is a head group selected from

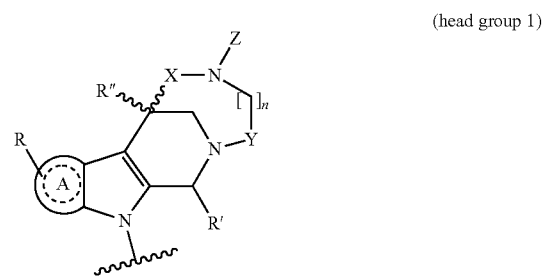

(head group 1)

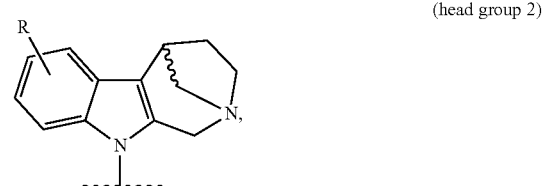

(head group 2)

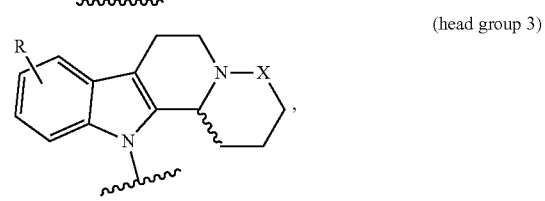

(head group 3)

-continued (head group 4)

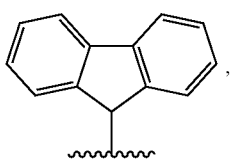

(head group 5)

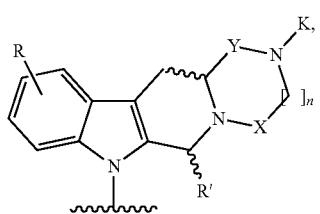

(head group 6)

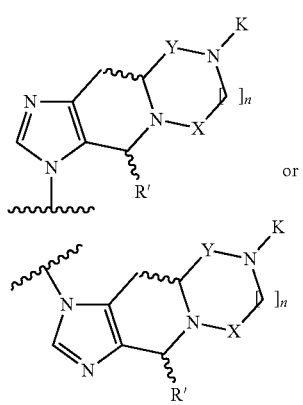

or wherein
A in head group 1 comprises 5 and 6 cyclic aryl and heteroaryl-systems,
n is 0 to 6, preferably 0 to 3, more preferably 0 or 1;
p is 0 to 6;
X is selected from the group comprising $CH_2$, $C=O$ and $C=S$;
Y is selected from the group comprising $CH_2$, $C=O$ and $C=S$;
Z is selected from the group comprising H, alkyl (preferably $CH_3$) and

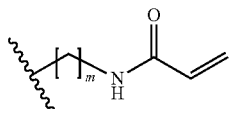

with m being 0 to 6;
R is selected from the group comprising H, alkoxy (preferably $OCH_3$), hydroxy, alkyl (preferably $C_1$-$C_{10}$ alkyl), alkoxyaryl, aryl, halogenyl, nitro, amino, amidyl, cyano, sulfanyl, sulfinyl, sulfonyl, formyl, acetyl,

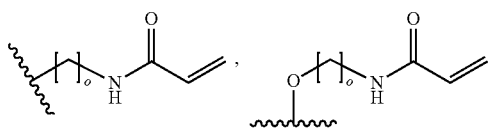

with o being 0 to 6,
R' and R" are each independently selected from the group comprising H, alkyl (preferably C1-C10 alkyl), aryl and substituted aryl;

K is selected from the group comprising alkyl residues (preferably propyl) and

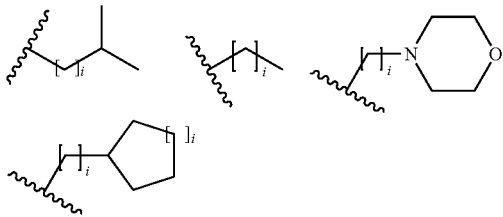

with i being 0 to 6;
L is a linker comprising a hydroxamic acid (HA) and having the formula

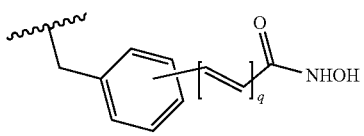

with q being 0 or 1;
or a pharmaceutically acceptable salt thereof.

According to the present invention this object is solved by a pharmaceutical composition comprising
(a) at least one compound according to the invention,
(b) optionally, a further agent or drug,
(c) optionally, pharmaceutically acceptable excipient(s) and/or carrier.

According to the present invention this object is solved by the use of a compound according to the invention as histone deacetylase (HDAC) inhibitor, preferably HDAC6 inhibitor.

According to the present invention this object is solved by a compound according to the invention or pharmaceutical composition of the present invention for use in medicine.

According to the present invention this object is solved by a compound according to the invention or pharmaceutical composition of the present invention for use in the treatment of cancer (such as leukemia, breast cancer, colon cancer, uterus cancer, prostate cancer) neurological disorders, neurodegenerative diseases, stroke, inflammatory diseases, traumatic brain injury, rheumatoid arthritis, graft rejection after organ transplantation and autoimmune diseases.

According to the present invention this object is solved by a method of synthesizing a compound according to the invention, comprising the steps of
(1) reduction of a methyl 2-(1H-indol-3-yl)-3-nitropropanoate derivative,
(2) ring closure employing a pictet-spengler reaction,
(3) transformation to the respective urea or thiourea derivative by use of 2,5-dioxopyrrolidin-1-yl carbamate derivatives, isocyanates or isothiocyanates, and
(4) ring closure mediated by a base, such as $Cs_2CO_3$.

According to the present invention this object is solved by a method of treatment of a disease, comprising the step of administering to a subject a therapeutically effective amount of a compound according to the invention or a pharmaceutical composition according to the invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "0.03 to 60 mg per kg" should be interpreted to include not only the explicitly recited values of 0.03 to 60, but also include individual values and sub-ranges within the indicated range. Thus, included in this numerical range are individual values such as 0.03, 0.035, 0.04, 0.045, . . . 59, 60 and sub-ranges such as from 14 to 20, from 14 to 30, from 15 to 25, from 19 to 25, from 20 to 25, from 20 to 30 and from 15 to 30, etc. This same principle applies to ranges reciting only one numerical value, such as "at least 0.03 mg per kg". Furthermore, such an interpretation should apply regardless of the breadth of the range or the characteristics being described.

HDAC Inhibitory Compounds

As discussed above, the present invention provides a compound having the general formula I

H-L(HA)

wherein
H is a head group selected from

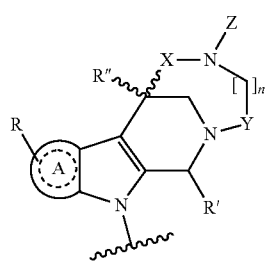
(head group 1)

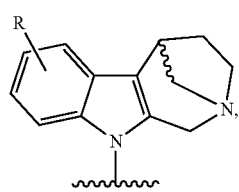
(head group 2)

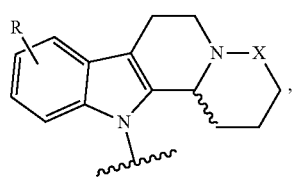
(head group 3)

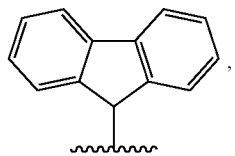
(head group 4)

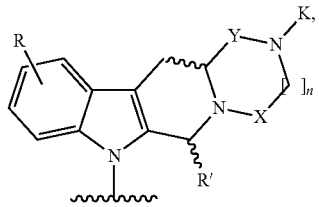
(head group 5)

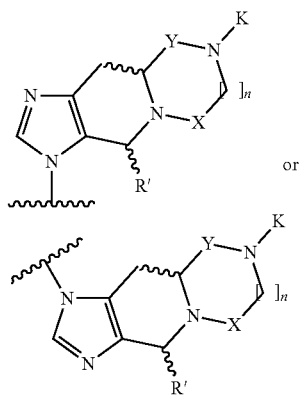
(head group 6)

or

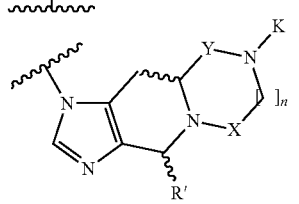

wherein
A in head group 1 comprises 5 and 6 cyclic aryl and heteroaryl-systems,
n is 0 to 6, preferably 0 to 3, more preferably 0 or 1;
p is 0 to 6;
X is selected from the group comprising $CH_2$, $C=O$ and $C=S$;
Y is selected from the group comprising $CH_2$, $C=O$ and $C=S$;
Z is selected from the group comprising H, alkyl (preferably $CH_3$) and

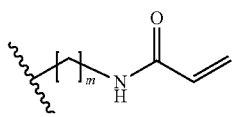

with m being 0 to 6,
R is selected from the group comprising H, alkoxy (preferably $OCH_3$), hydroxy, alkyl (preferably $C_1$-$C_{10}$ alkyl), alkoxyaryl, aryl, halogenyl, nitro, amino, amidyl, cyano, sulfanyl, sulfinyl, sulfonyl, formyl, acetyl,

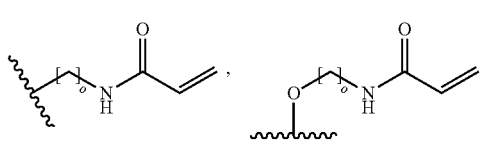

with o being 0 to 6,

R' and R" are each independently selected from the group comprising H, alkyl (preferably C1-C10 alkyl), aryl and substituted aryl;

K is selected from the group comprising alkyl residues (preferably propyl) and

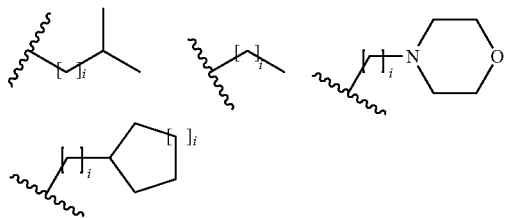

with i being 0 to 6;

L is a linker comprising a hydroxamic acid (HA) and having the formula

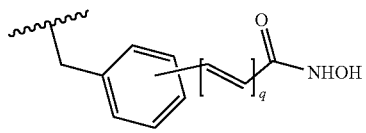

with q being 0 or 1, or a pharmaceutically acceptable salt thereof.

In one embodiment, the compounds of the present invention are pharmaceutical acceptable prodrugs bearing carbamate protected hydroxamic acid(s).

The compound of the present invention is preferably a pharmaceutical acceptable prodrug, wherein the hydroxamic acid(s) HA is/are protected by carbamate, preferably

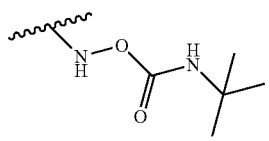

The compounds of the present invention are novel HDAC inhibitors, in particular HDAC6 inhibitors. Their basic structure is characterized by their bulky head group, which contributes to the specificity for HDAC6.

A compound of the present invention is not tubastatin A (see FIG. 1A, compound 3) or the following compound

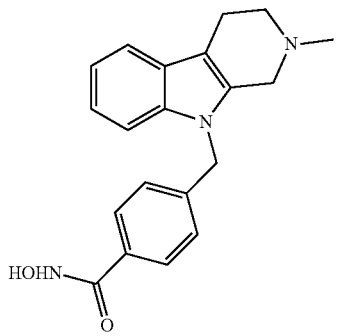

In one embodiment, the compound of the present invention has the head group 1 as H.

In a preferred embodiment the compound of the present invention has the head group 1 as H, which is

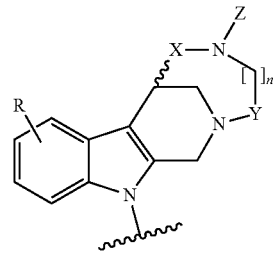

Thereby, the compound of the invention is preferably selected from the general formula II

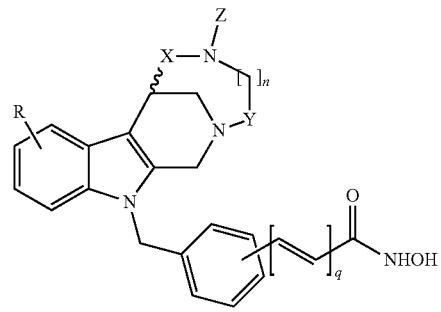

wherein X, Y, Z, R, n and q are as defined in claim 1, wherein preferably

X and Y are each independently selected from $CH_2$, $C=O$ and $C=S$;

Z is selected from the group comprising alkyl (preferably $CH_3$) and

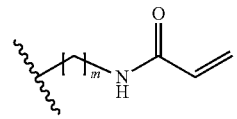

with m being 2 to 6, preferably 2 or 3;

R is selected from the group comprising H, alkoxy (preferably $OCH_3$),

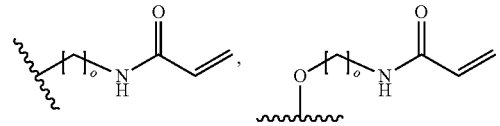

with o being 1 to 6, preferably 1 or 2.

Preferably the compound is selected from the general formula IIa

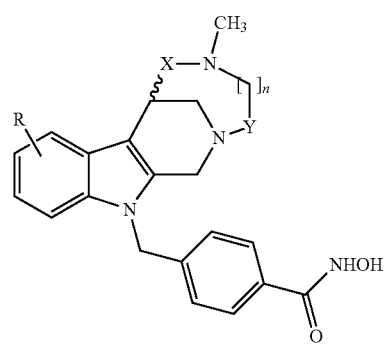

wherein
n is 0 or 1
X and Y are each independently selected from C=O and C=S;
R is selected from the group comprising H, alkoxy (preferably OCH₃),

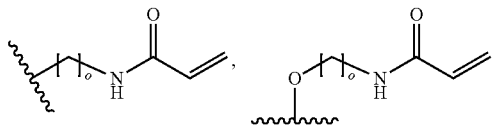

with o being 1 or 2,
wherein R is preferably H.
More preferably, the compound is selected from (MARB1; 39a)

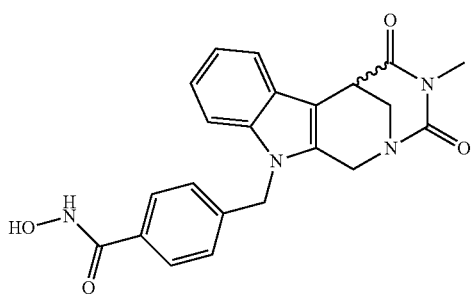

N-Hydroxy-4-((4-methyl-3,5-dioxo-3,4,5,6-tetrahydro-2,6-methano[1,3]diazocino[5,6-b]indol-11(1H)-yl)methyl)benzamide (156a)

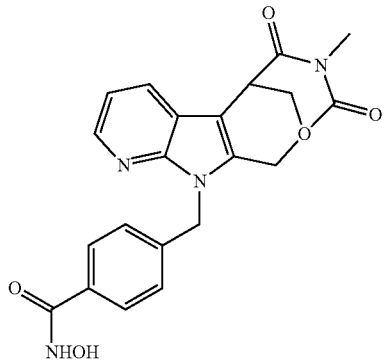

N-Hydroxy-4-((7-methyl-6,8-dioxo-5,7,8,10-tetrahydro-5,9-methanopyrido[3',2':4,5]pyrrolo[2,3-e][1,3]diazocin-11(6H)-yl)methyl)benzamide (39b)

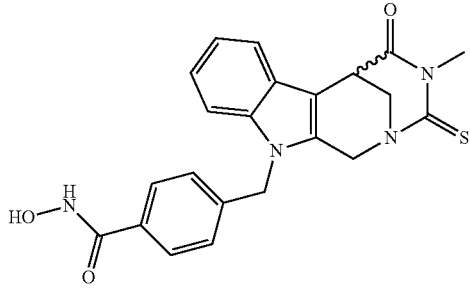

N-Hydroxy-4-((4-methyl-5-oxo-3-thioxo-3,4,5,6-tetrahydro-2,6-methano[1,3]diazocino[5,6-b]indol-11(1H)-yl)methyl)benzamide (39c)

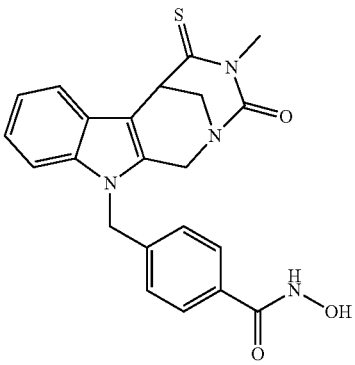

N-Hydroxy-4-((4-methyl-3-oxo-5-thioxo-3,4,5,6-tetrahydro-2,6-methano[1,3]diazocino[5,6-b]indol-11(1H)-yl)methyl)benzamide (39e)

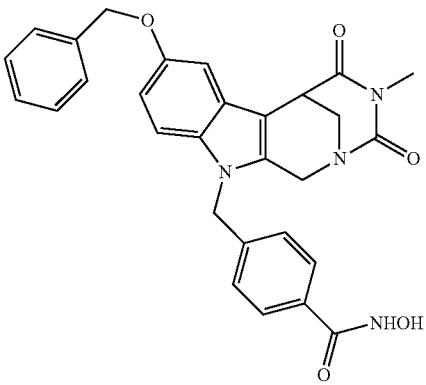

4-((8-(Benzyloxy)-4-methyl-3,5-dioxo-3,4,5,6-tetrahydro-2,6-methano[1,3]diazocino[5,6-b]indol-11(1H)-yl)methyl)-N-hydroxybenzamide (39f)

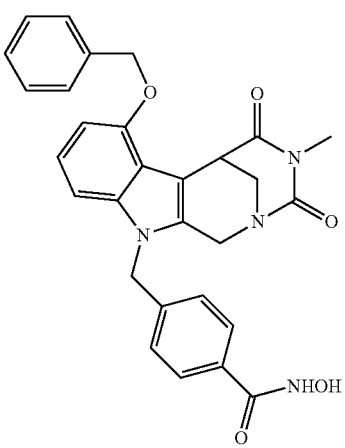

4-((7-(Benzyloxy)-4-methyl-3,5-dioxo-3,4,5,6-tetrahydro-2,6-methano[1,3]diazocino[5,6-b]indol-11(1H)-yl)methyl)-N-hydroxybenzamide

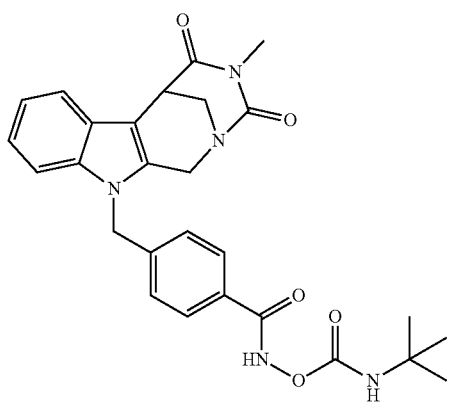

(39h)

N-((tert-butylcarbamoyl)oxy)-4-((4-methyl-3,5-dioxo-3,4,5,6-tetrahydro-2,6-methano[1,3]diazocino[5,6-b]indol-11(1H)-yl)methyl)benzamide

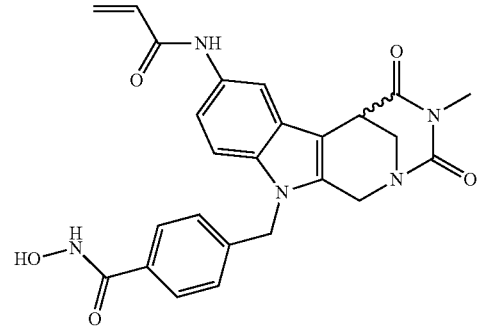

(40c)

4-((8-Acrylamido-4-methyl-3,5-dioxo-3,4,5,6-tetrahydro-2,6-methano[1,3]diazocino[5,6-b]indol-11(1H)-yl)methyl)-N-hydroxybenzamide

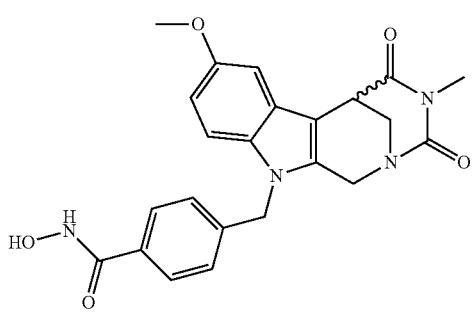

(40a)

N-Hydroxy-4-((8-methoxy-4-methyl-3,5-dioxo-3,4,5,6-tetrahydro-2,6-methano[1,3]diazocino[5,6-b]indol-11(1H)-yl)methyl)benzamide

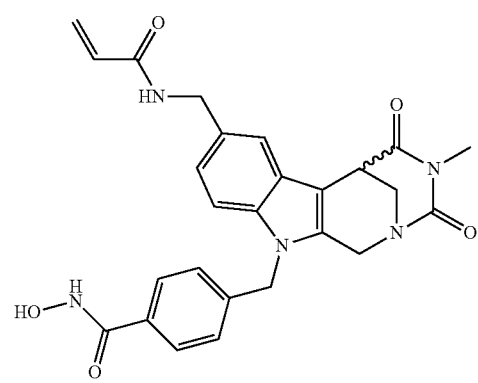

(40d)

4-((8-(Acrylamidomethyl)-4-methyl-3,5-dioxo-3,4,5,6-tetrahydro-2,6-methano[1,3]diazocino[5,6-b]indol-11(1H)-yl)methyl)-N-hydroxybenzamide (40b)

N-hydroxy-4-((9-methoxy-4-methyl-3,5-dioxo-3,4,5,6-tetrahydro-2,6-methano[1,3]diazocino[5,6-b]indol-11(1H)-yl)methyl)benzamide

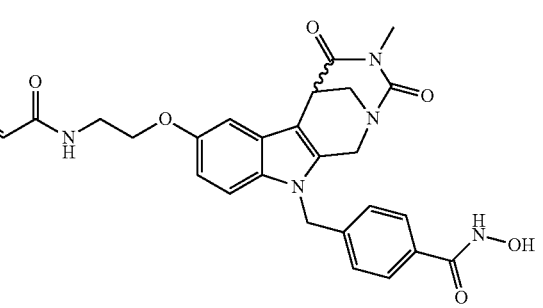

(40e)

4-((8-(2-Acrylamidoethoxy)-4-methyl-3,5-dioxo-3,4,5,6-tetrahydro-2,6-methano[1,3]diazocino[5,6-b]indol-11(1H)-yl)methyl)-N-hydroxybenzamide

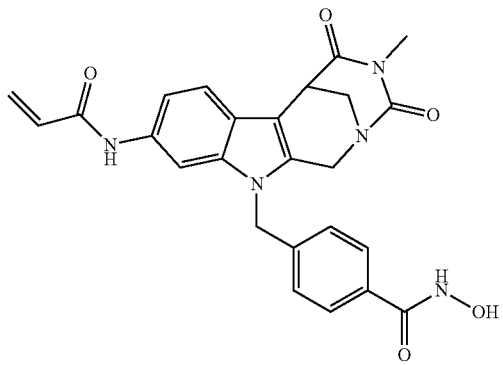

(40f)

4-((9-Acrylamido-4-methyl-3,5-dioxo-
3,4,5,6-tetrahydro-2,6-
methano[1,3]diazocino[5,6-b]indol-11(1H)-
yl)methyl)-N-hydroxybenzamide

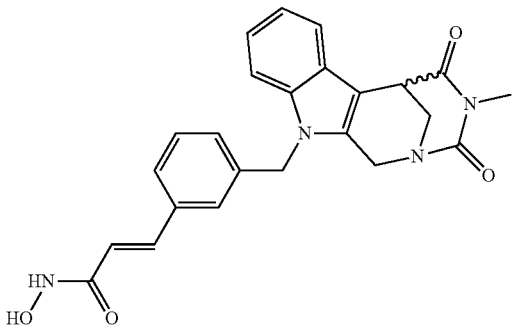

(51)

(E)-N-Hydroxy-3-(3-((4-methyl-3,5-dioxo-
3,4,5,6-tetrahydro-2,6-
methano[1,3]diazocino[5,6-b]indol-11(1H)-
yl)methyl)phenyl)acrylamide

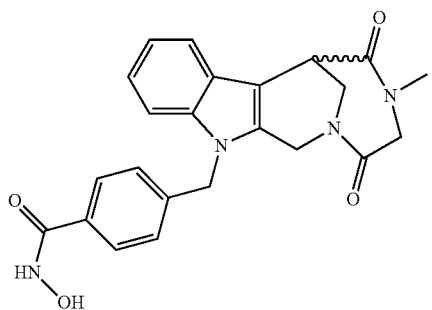

(MARB2, 41)

N-Hydroxy-4-((5-methyl-3,6-dioxo-4,5,6,7-
tetrahydro-1H-2,7-
methano[1,4]diazonino[6,7-b]indol-12(3H)-
yl)methyl)benzamide

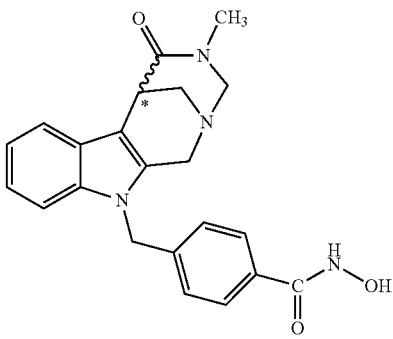

(56a)

N-Hydroxy-4-((4-methyl-5-oxo-3,4,5,6-
tetrahydro-2,6-methano[1,3]diazocino-[5,6-
b]indol-11(1H)-yl)methyl)benzamide

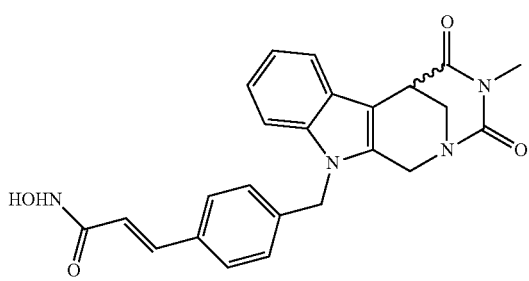

(50)

(E)-N-Hydroxy-3-(4-((4-methyl-3,5-dioxo-
3,4,5,6-tetrahydro-2,6-
methano[1,3]diazocino[5,6-b]indol-11(1H)-
yl)methyl)phenyl)acrylamide

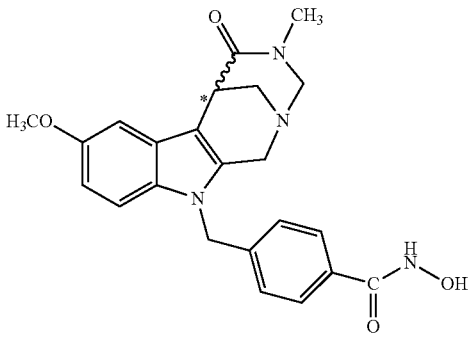

(56b)

N-Hydroxy-4-((8-methoxy-4-methyl-5-oxo-
3,4,5,6-tetrahydro-2,6-
methano[1,3]diazocino[5,6-b]indol-11(1H)-
yl)methyl)benazmide -continued (62)

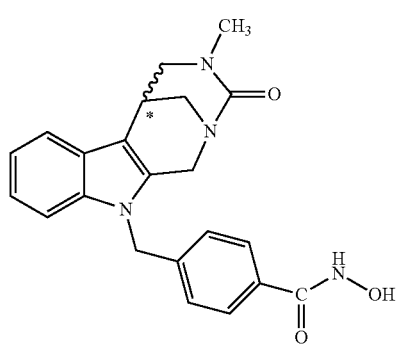

N-Hydroxy-4-((4-methyl-3-oxo-3,4,5,6-tetrahydro-2,6-methano[1,3]diazocino-[5,6-b]indol-11(1H)-yl)methyl)benzamide (101a)

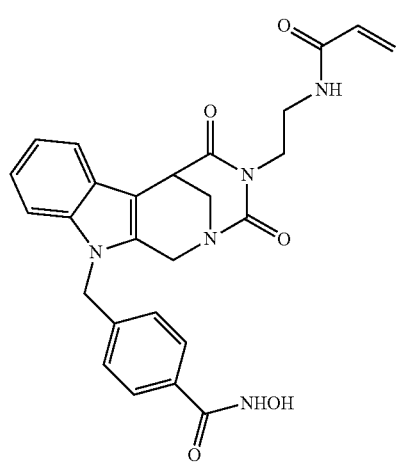

4-((4-(2-Acrylamidoethyl)-3,5-dioxo-3,4,5,6-tetrahydro-2,6-methano[1,3]diazocino[5,6-b]indol-11(1H)-yl)methyl)-N-hydroxybenzamide (101b)

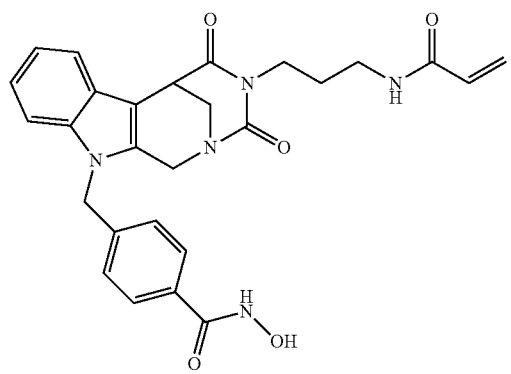

4-((4-(3-acrylamidopropyl)-3,5-dioxo-3,4,5,6-tetrahydro-2,6-methano[1,3]diazocino[5,6-b]indol-11(1H)-yl)methyl)benzoic acid -continued (101c)

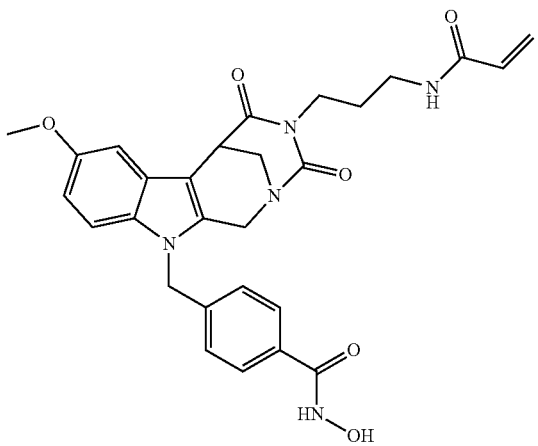

4-((4-(3-Acrylamidopropyl)-8-methoxy-3,5-dioxo-3,4,5,6-tetrahydro-2,6-methano[1,3]diazocino[5,6-b]indol-11(1H)-yl)methyl)-N-hydroxybenzamide (141d)

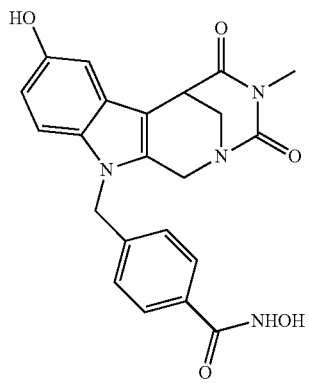

N-Hydroxy-4-((8-hydroxy-4-methyl-3,5-dioxo-3,4,5,6-tetrahydro-2,6-methano[1,3]diazocino[5,6-b]indol-11(1H)-yl)methyl)benzamide In a preferred embodiment the compound is selected from 39a

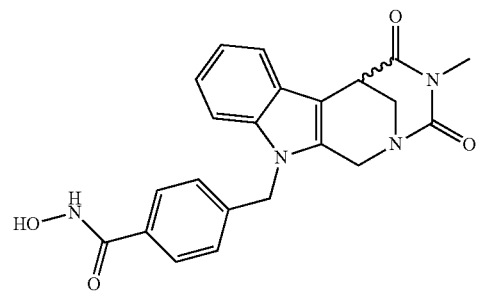

and

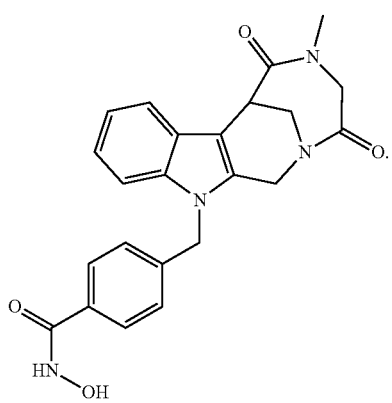

In one embodiment, the compound of the present invention has the head group 2 as H.

A preferred example is
4-((4,5-Dihydro-1H-2,5-methanoazepino[3,4-b]indol-10(3H)-yl)methyl)-N-hydroxybenzamide 2,2,2-trifluoroacetate (70)

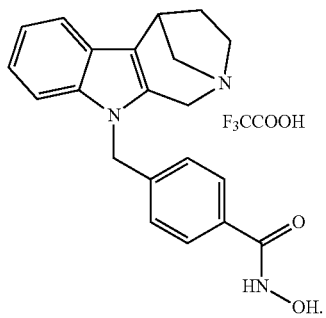

In one embodiment, the compound of the present invention has the head group 3 as H.

Preferred examples are
N-Hydroxy-4-((4-oxo-1,3,4,6,7,12b-hexahydroindolo[2,3-a]quinolizin-12(2H)-yl)methyl)benzamide (84)

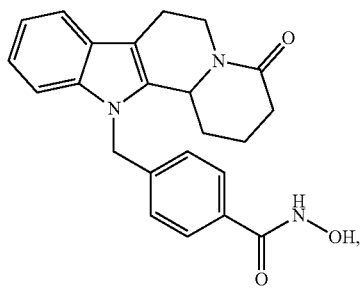 [SMILES: O=C(NO)c1ccc(Cn2c3c(c4ccccc42)CCN2C(=O)CCCC32)cc1]

(E)-N-Hydroxy-3-(4-((4-oxo-1,3,4,6,7,12b-hexahydroindolo[2,3-a]quinolizin-12(2H)-yl)methyl)phenyl)acrylamide (85)

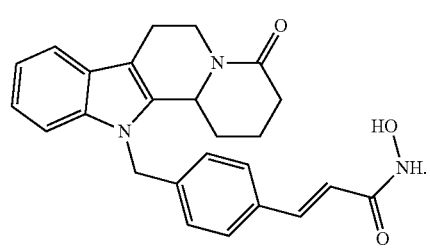 [SMILES: O=C(/C=C/c1ccc(Cn2c3c(c4ccccc42)CCN2C(=O)CCCC32)cc1)NO]

In one embodiment, the compound of the present invention has the head group 4 as H.

Preferred examples are
4-((9H-Fluoren-9-yl)methyl)-N-hydroxybenzamide (88)

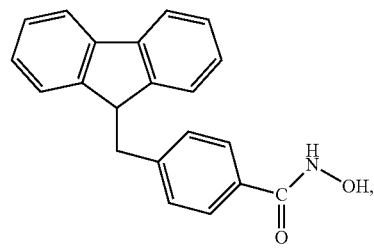 [SMILES: O=C(NO)c1ccc(CC2c3ccccc3-c3ccccc32)cc1]

(E)-3-(4-((9H-Fluoren-9-yl)methyl)phenyl)-N-hydroxyacrylamide (93)

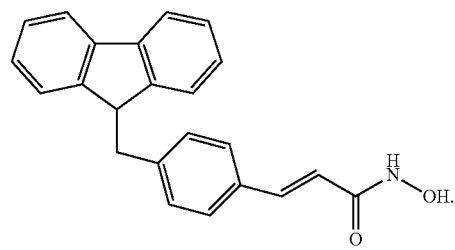 [SMILES: O=C(/C=C/c1ccc(CC2c3ccccc3-c3ccccc32)cc1)NO]

In one embodiment, the compound of the present invention has the head group 5 as H.

In a preferred embodiment the compound of the present invention has the head group 5 as H, which is

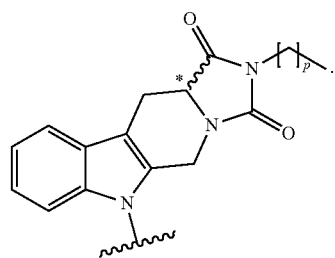

Preferred examples are
N-hydroxy-4-((2-methyl-1,3-dioxo-2,3,11,11a-tetrahydro-1H-imidazo[1',5':1,6]pyrido[3,4-b]indol-6(5H)-yl)methyl)benzamide (116)

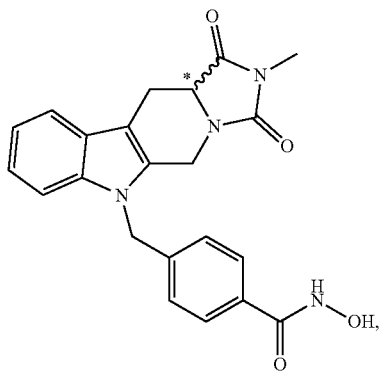 [SMILES: CN1C(=O)C2Cc3c(n(Cc4ccc(C(=O)NO)cc4)c4ccccc34)CN2C1=O]

4-((2-Butyl-1,3-dioxo-2,3,11,11a-tetrahydro-1H-imidazo
[1',5':1,6]pyrido[3,4-b]indol-6(5H)-yl)methyl)-N-hy-
droxybenzamide (117a)

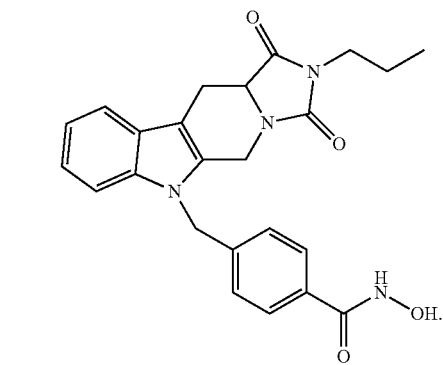

N-hydroxy-4-((((6S,12aS)-6-methyl-1,4-dioxo-2-propyl-1,3,
4,6,12,12a-hexahydropyrazino[1',2':1,6]pyrido[3,4-b]in-
dol-7(2H)-yl)methyl)benzamide (136i)

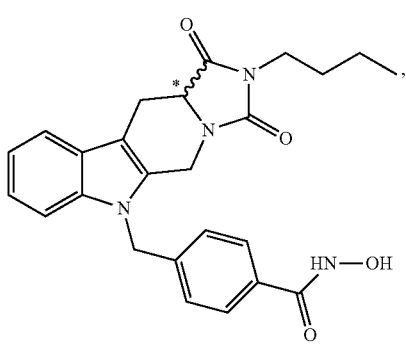 [SMILES: CCCCN1C(=O)C2Cc3c(n(Cc4ccc(C(=O)NO)cc4)c4ccccc34)CN2C1=O]

4-((2-Ethyl-1,3-dioxo-1,2,3,5,11,11a-hexahydro-6H-imi-
dazo[1',5':1,6]pyrido[3,4-b]indol-6-yl)methyl)-N-hy-
droxybenzamid (117b)

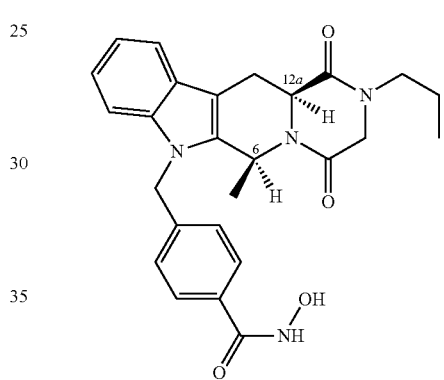

N-hydroxy-4-((2-(2-morpholinoethyl)-1,4-dioxo-1,3,4,6,12,
12a-hexahydropyrazino[1',2':1,6]pyrido[3,4-b]indol-7
(2H)-yl)methyl)benzamide (136g)

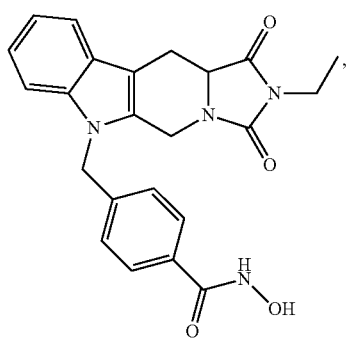 [SMILES: CCN1C(=O)C2Cc3c(n(Cc4ccc(C(=O)NO)cc4)c4ccccc34)CN2C1=O]

4-((1,3-Dioxo-2-propyl-1,2,3,5,11,11a-hexahydro-6H-imi-
dazo[1',5':1,6]pyrido[3,4-b]indole-6-yl)methyl)-N-hy-
droxybenzamide (117c)

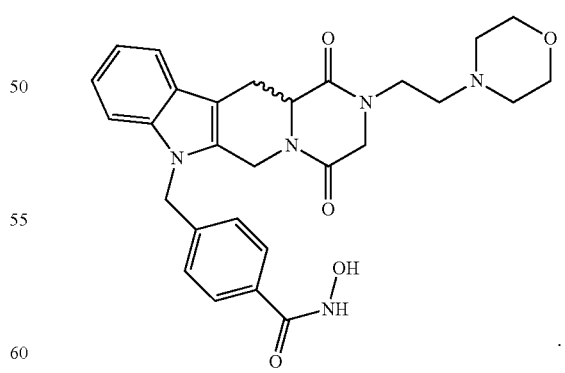

N-hydroxy-4-((10-hydroxy-1,4-dioxo-2-propyl-1,3,4,6,12,
12a-hexahydropyrazino[1',2':1,6]pyrido[3,4-b]indol-7
(2H)-yl)methyl)benzamide (136l)

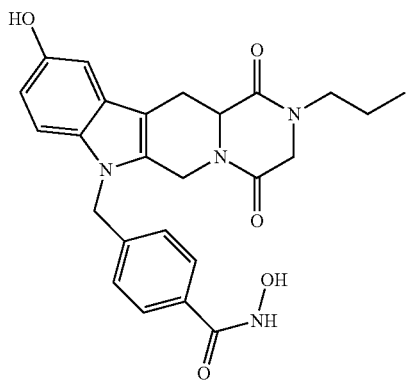

N-hydroxy-4-((10-methoxy-1,4-dioxo-2-propyl-1,3,4,6,12,12a-hexahydropyrazino[1',2':1,6]pyrido[3,4-b]indol-7(2H)-yl)methyl)benzamide (136k)

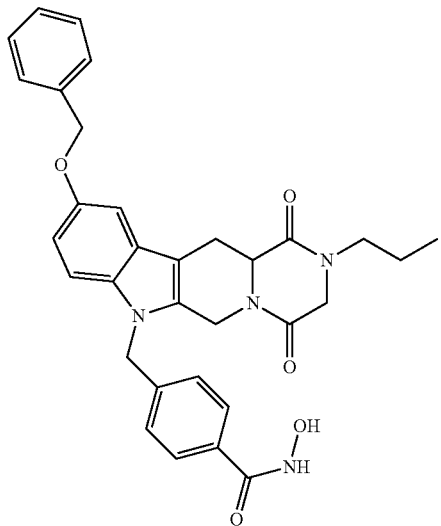

N-hydroxy-4-((10-methoxy-1,4-dioxo-2-propyl-1,3,4,6,12,12a-hexahydropyrazino[1',2':1,6]pyrido[3,4-b]indol-7(2R)-yl)methyl)benzamide (136k)

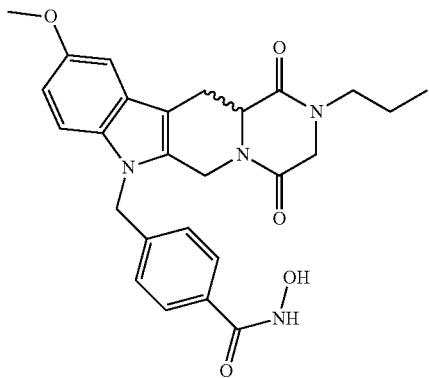

N-hydroxy-4-((10-methoxy-1,4-dioxo-2-propyl-1,3,4,6,12,12a-hexahydropyrazino[1',2':1,6]pyrido[3,4-b]indol-7(2R)-yl)methyl)benzamide (136c)

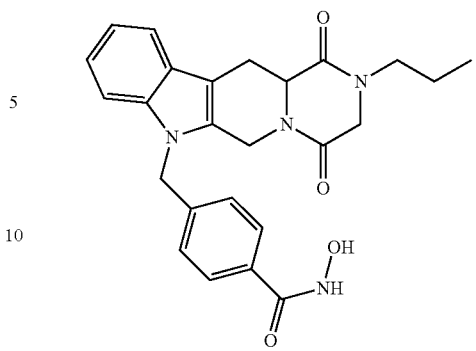

In one embodiment, the compound of the present invention has the head group 6 as H.

Pharmaceutical Compositions and Medical Uses

As discussed above, the present invention provides a pharmaceutical composition comprising
(a) at least one compound according to the present invention,
(b) optionally, a further agent or drug,
   such as cytostatic compound(s), e.g. tyrosine kinase inhibitor(s) or proteasome inhibitors (e.g. Bortezomib (PS-341)),
(c) optionally, pharmaceutically acceptable excipient(s) and/or carrier.

As discussed above, the present invention provides the use of a compound according to the invention as histone deacetylase (HDAC) inhibitor, preferably HDAC6 inhibitor.

As discussed above, the present invention provides the compound according to the present invention or the pharmaceutical composition according to the present invention for use in medicine.

As discussed above, the present invention provides a compound according to the present invention or the pharmaceutical composition according to the present invention for use in the treatment of a disease.

Preferably, the disease is selected from
cancer
   such as leukemia, breast cancer, colon cancer, uterus cancer, prostate cancer, ovarian cancer,
neurological disorders,
neurodegenerative diseases,
   such as Huntington's disease, spinal muscular atrophy or Alzheimer's
stroke,
inflammatory diseases,
traumatic brain injury,
rheumatoid arthritis,
graft rejection after organ transplantation
and
autoimmune diseases.

In one embodiment, the compound or pharmaceutical composition is used in combination with further agent(s) or drug(s),
such as cytostatic compound(s), e.g. tyrosine kinase inhibitor(s), or proteasome inhibitors (e.g. Bortezomib (PS-341)).

In one embodiment, the use comprises sensitization of cancer cells, preferably during radiation therapy.

Acetylated chromatin is more open and has been implicated in the increased radiation sensitivities observed in some cell types. (Oleinick et al., 1994). Thus, HDAC inhibitors may be useful as radiation sensitizing agents.

The administration of the compounds according to this invention and pharmaceutical compositions according to the invention may be performed in any of the generally accepted modes of administration available in the art. Illustrative examples of suitable modes of administration include intravenous, oral, nasal, inhalativ, parenteral, topical, transdermal and rectal delivery. Oral and intravenous delivery are preferred.

Methods for Treatment

As discussed above, the present invention provides a method of treatment of a disease.

Said treatment method comprises the step of
administering to a subject a therapeutically effective amount of a compound according to the invention or a pharmaceutical composition of the invention.

A "therapeutically effective amount" of a compound according to the invention preferably refers to the amount necessary to achieve the therapeutic outcome.

The dosage of the compounds according to the invention is carried out in the order of magnitude customary for histone deacetylases inhibitors. For example, the customary dose in the case of systemic therapy (p.o.) may be between 0.03 and 60 mg/kg body weight per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

Preferably, the disease is selected from
cancer
such as leukemia, breast cancer, colon cancer, uterus cancer, prostate cancer, ovarian cancer,
neurological disorders,
neurodegenerative diseases,
such as Huntington's disease, spinal muscular atrophy or Alzheimer's,
stroke,
inflammatory diseases,
traumatic brain injury,
rheumatoid arthritis,
graft rejection after organ transplantation
and
autoimmune diseases.

In one embodiment, the treatment method of the invention comprises
administering to a subject a therapeutically effective amount of a compound according to the invention or a pharmaceutical composition of the invention
in combination with further agent(s) or drug(s),
such as cytostatic compound(s), e.g. tyrosine kinase inhibitor(s),
as discussed above.

In one embodiment, the treatment method of the invention comprises
sensitization of cancer cells, preferably during radiation therapy,
as discussed above.

As discussed above, the administration of the compounds according to this invention and pharmaceutical compositions according to the invention may be performed in any of the generally accepted modes of administration available in the art. Illustrative examples of suitable modes of administration include intravenous, oral, nasal, inhalativ, parenteral, topical, transdermal and rectal delivery. Oral and intravenous delivery are preferred.

Synthesis of the Compounds of the Invention

As discussed above, the present invention provides a method of generating/synthesizing a compound according to the invention.

Said method comprises the steps of
(1) reduction of a methyl 2-(1H-indol-3-yl)-3-nitropropanoate derivative,
(2) ring closure employing a pictet-spengler reaction,
(3) transformation to the respective urea or thiourea derivative by use of 2,5-dioxopyrrolidin-1-yl carbamate derivatives, isocyanates or isothiocyanates, and
(4) ring closure mediated by a base, such as $Cs_2CO_3$.

Said method steps are shown below in Scheme A:

Scheme A

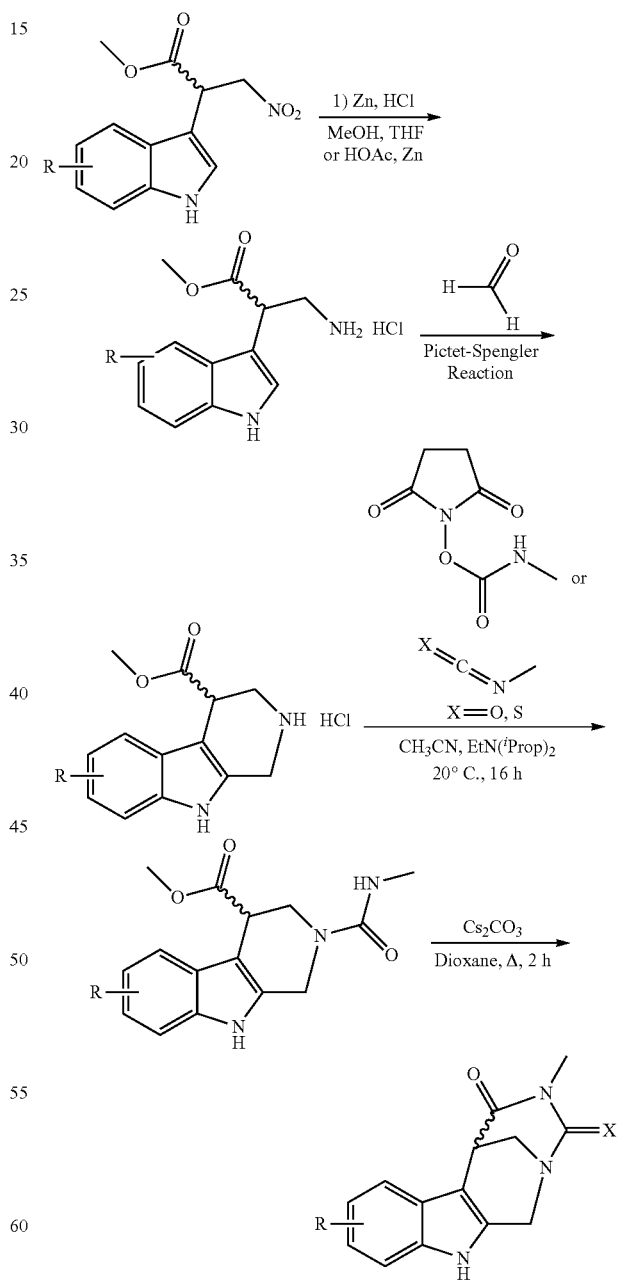

Regarding the compounds of the invention with head group 1:

Tetrahydrro-β-carboline-systems, fused with bridged ring systems, were synthesized for the first time. See Scheme 1 below.

Scheme 1: Synthesis of the tetrahydro-β-carboline basic structure illustrated with 18a-19i as examples.
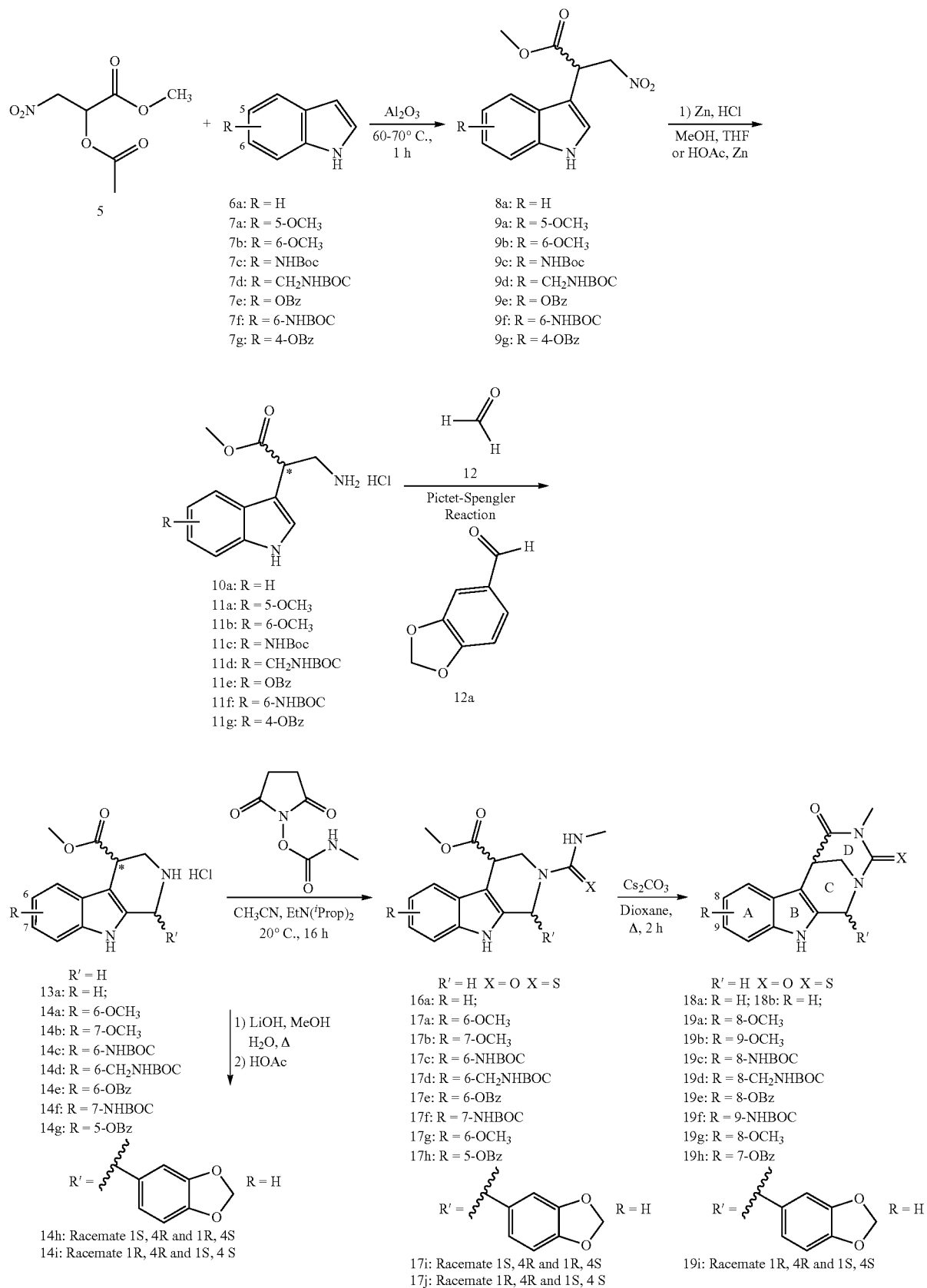

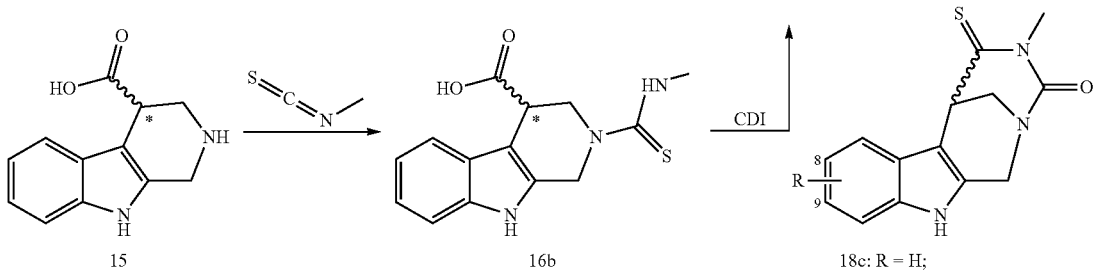

15    16b    18c: R = H;

Al₂O₃ catalyzed addition of methyl 2-acetoxy-3-nitropropanoate (5) to the indoles (6a-7e) according to Ballini et al. (2008) initially leads to racemic methyl 2-(1H-indol-3-yl)-3-nitropropanoates (8a-9e). Reduction with Zn/HCl or HOAc/Zn, alternatively, and alkaline work-up gives methyl 3-amino-2-(1H-indol-3-yl) propanoates 11a-11e, which were purified by conversion into their hydrochlorides. Pictet-Spengler reaction of the hydrochlorides with formaldehyde (according to Shi et al., 2008) leads to the formation of methyl-2,3,4,9-tetrahydro-1H-pyrido[3,4-b]indole-4-carboxylate hydrochlorides (13a-14e) (Bartoli et al., 2005). The structure of the six-membered D-ring can be obtained by reaction of 13a-14e with 2,5-dioxopyrrolidin-1-yl methylcarbamate and subsequent cyclization of the methyl-2-(methylcarbamoyl)-2,3,4,9-tetrahydro-1H-pyrido[3,4-b]indole-4-carboxylates (16a-17e) to yield 18a-19e.

Alternatively the sulfur analoga 18b can be obtained by alkaline cleavage of the ester 13a, reaction of the resulting 2,3,4,9-tetrahydro-1H-pyrido[3,4-b]indole-4-carboxylic acid 15 with methyl isothiocyanate (Walton et al., 2009) and ring closure by use of CDI (Kumar et al., 2012). Another sulfur analoga, 18, was prepared by reaction of 18a with Lawesson's reagent. The basic structure was confirmed, in addition to the characterization by 1H NMR spectroscopic data, on the basis of model compound 19a by X-ray structure analysis (data not shown).

A further set of different head groups can be achieved by modifications of the tetrahydro-β-carboline basic structure, e.g. by introduction of acrylic systems as michael akzeptors, which might interact additionally. Several examples therefore are shown in the following schemes 2a and 2b.

Scheme 2a: Modifications of the tetrahydro-β-carboline basic structure by introduction of acrylic systems to an amino part introduced into the basic structure.

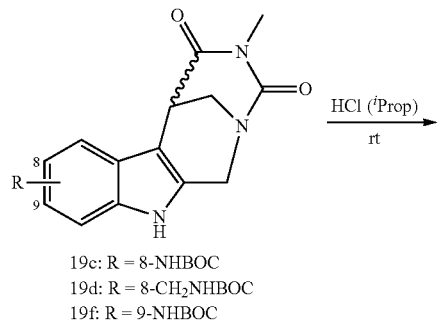

19c: R = 8-NHBOC
19d: R = 8-CH₂NHBOC
19f: R = 9-NHBOC

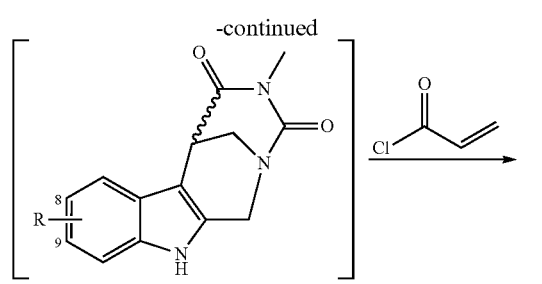

20c: R = 8-NH₂ x HCl
20d: R = 8-CH₂NH₂ x HCl
20e: R = 9-NH₂ x HCl

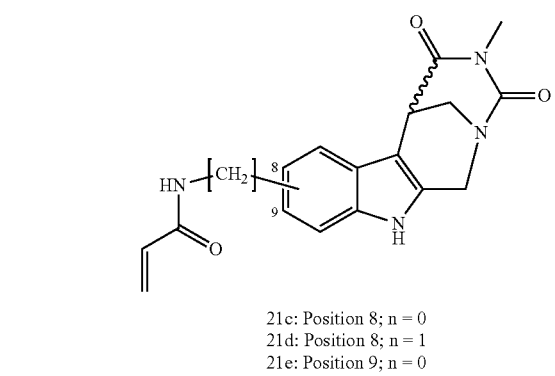

21c: Position 8; n = 0
21d: Position 8; n = 1
21e: Position 9; n = 0

Scheme 2b: Modifications of the tetrahydro-β-carboline by introduction of acrylic systems

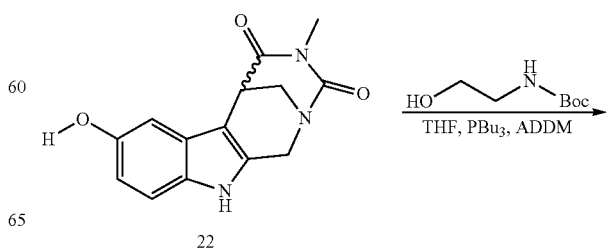

22

29

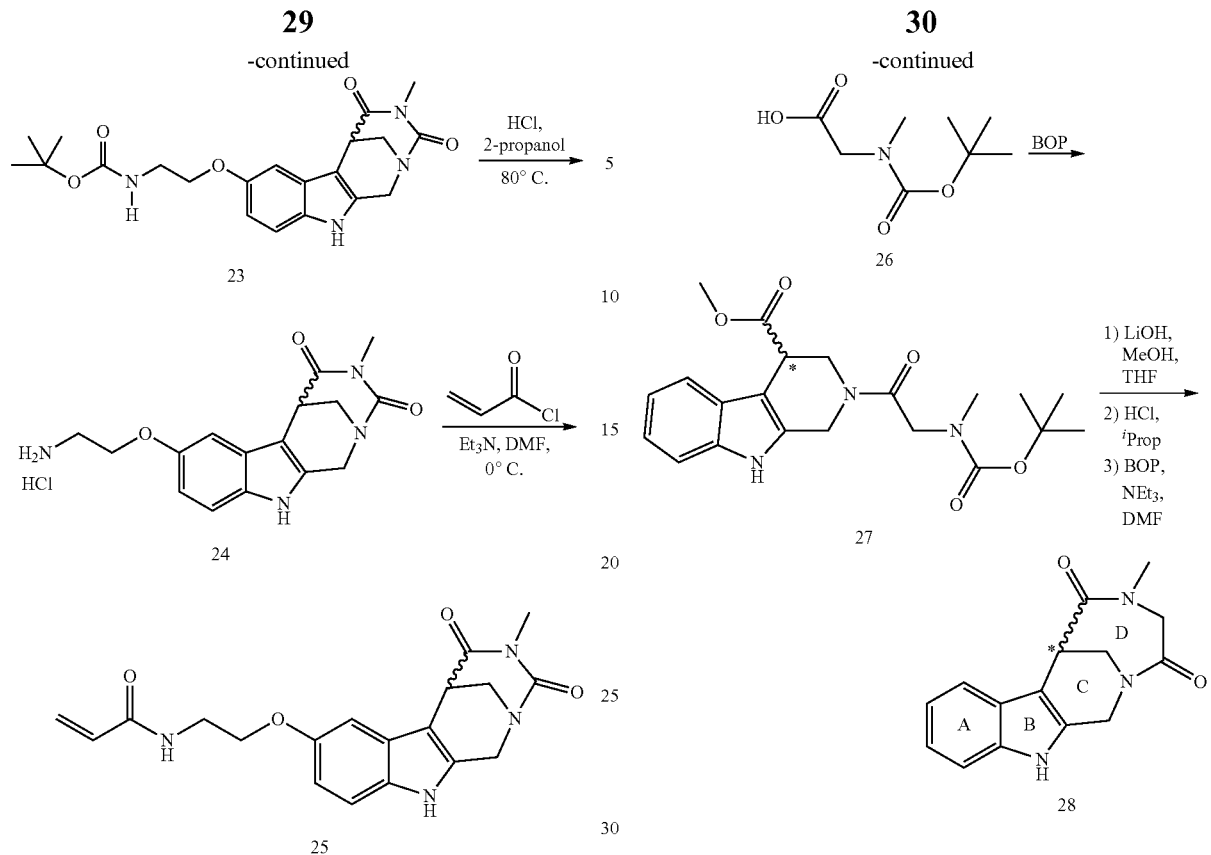

Compound 28 with seven-membered D-ring system is accessible according to Scheme 2c.

Scheme 2c: Synthesis of compound 28.

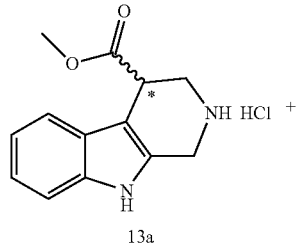

30

The introduction of the $Zn^{2+}$-chelating head group was performed in these systems by alkylation of the indole nitrogen using tert-butyl 4-(bromomethyl)benzoate (29) (Motoshima et al., 2011), followed by acidic cleavage of the t-butyl protecting group, amidation with $NH_2OTHP$ and acidic cleavage of the acetals (see Scheme 3 below).

Based on the shown reaction pathways the synthesis of diverse modified compounds in any amount is possible, using appropriate carbamates or isocyanates as coupling components, respectively appropriately substituted indole derivatives. Further modifications of the hydroxamate bearing head group (i.e. head group 1) can also be achieved by use of different substituted alkylating agents (Scheme 4). An example is the synthesis of compounds 50 and 51 by reaction with (E)-tert-butyl 3-(4-(bromomethyl) phenyl) acrylate (42) (Tao et al., 2010; Tercel et al., 2012) or (E)-tert-butyl 3-(3-(bromomethyl) phenyl) acrylate (43), as shown.

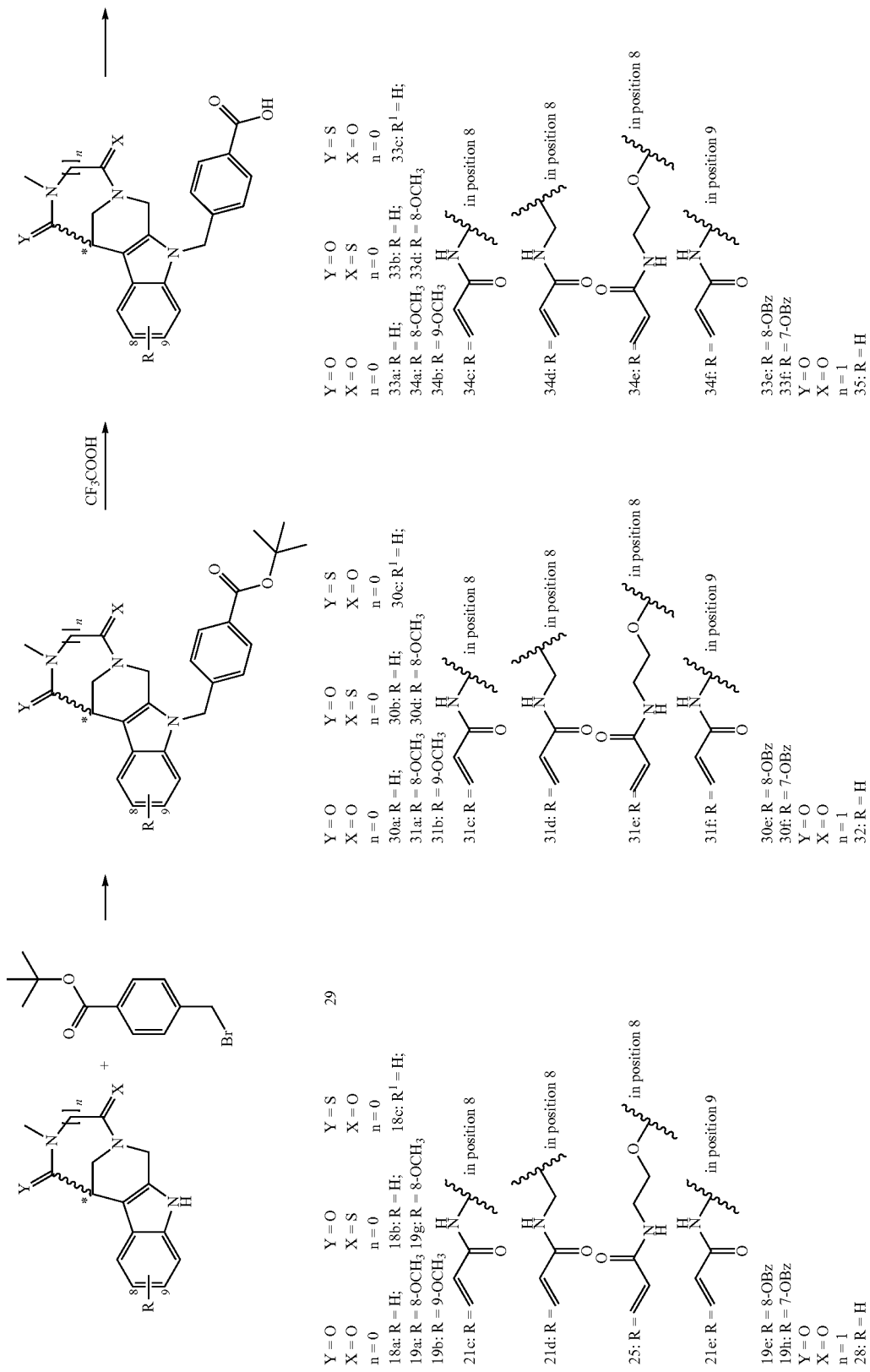

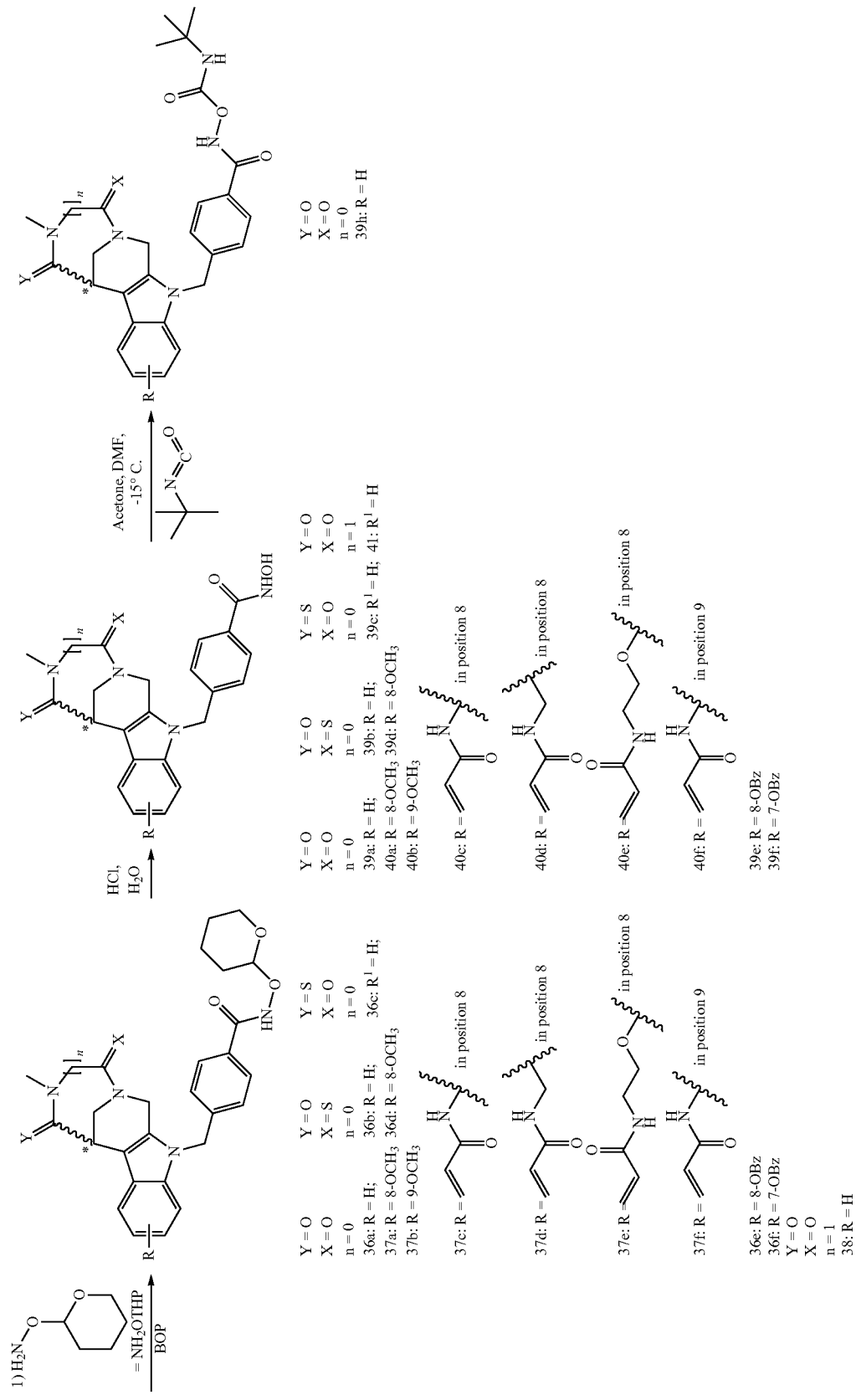

Scheme 4: Synthesis and structures of the HDAC6-inhibitors 50 and 51.
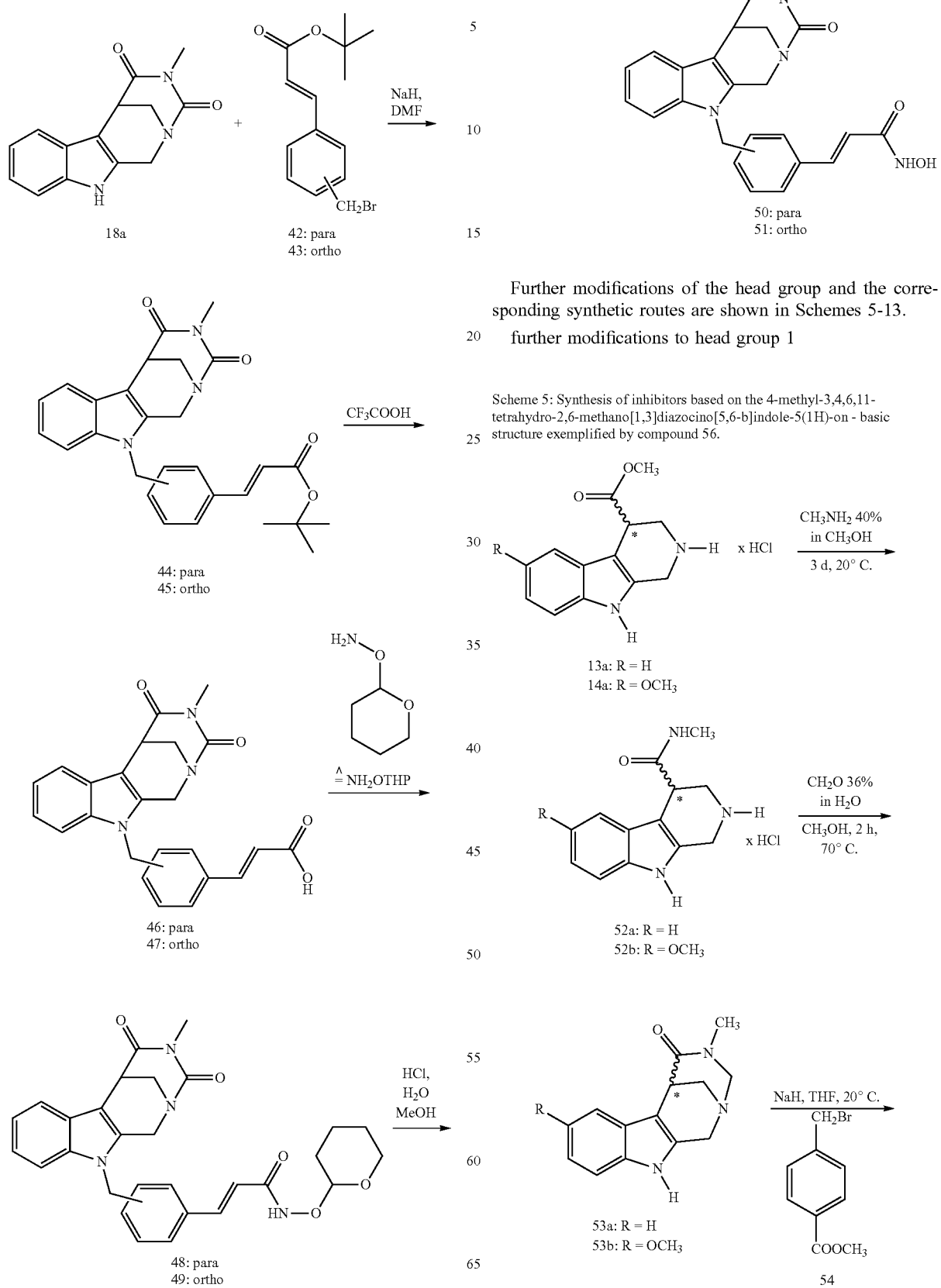
Further modifications of the head group and the corresponding synthetic routes are shown in Schemes 5-13.
further modifications to head group 1
Scheme 5: Synthesis of inhibitors based on the 4-methyl-3,4,6,11-tetrahydro-2,6-methano[1,3]diazocino[5,6-b]indole-5(1H)-on - basic structure exemplified by compound 56.

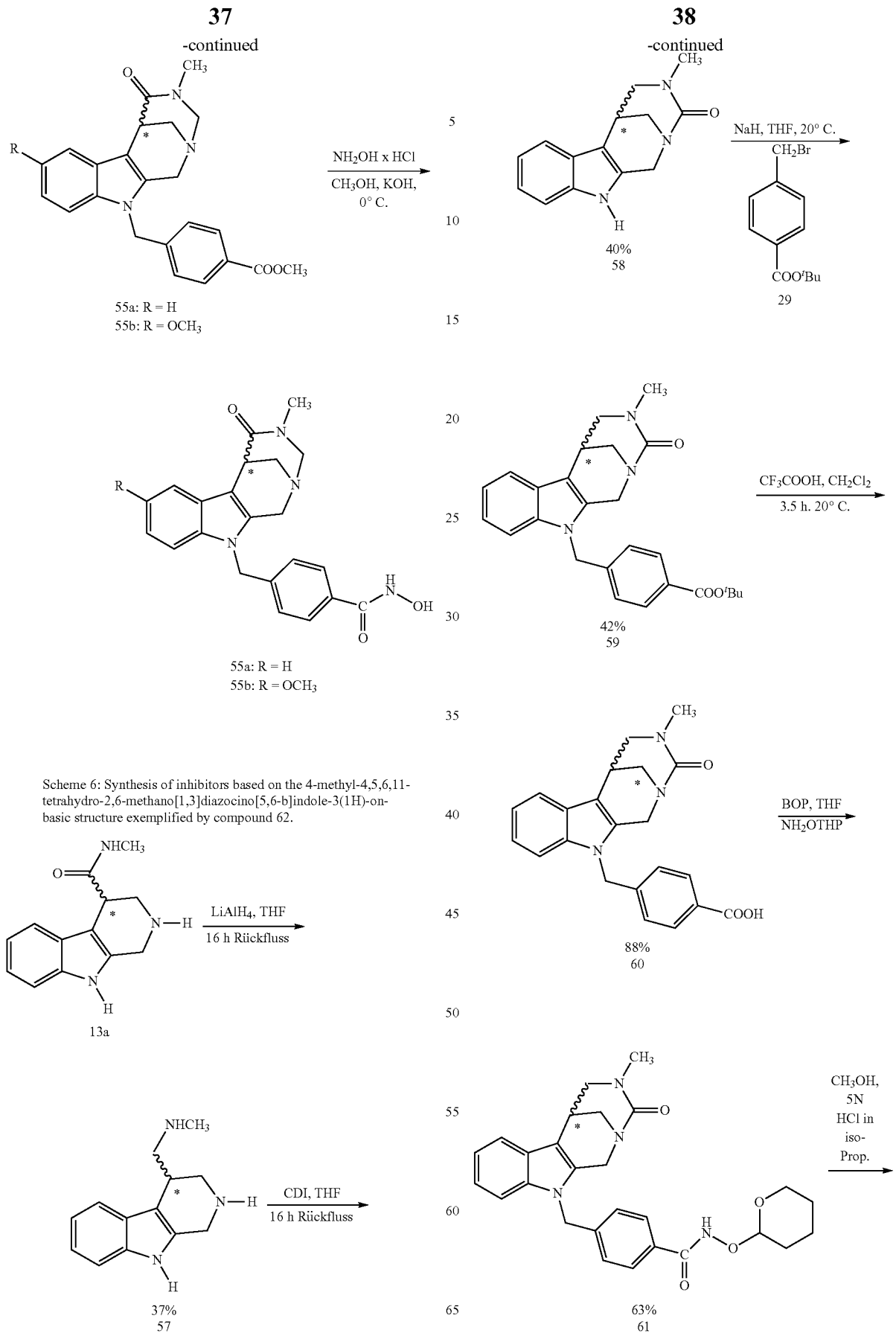

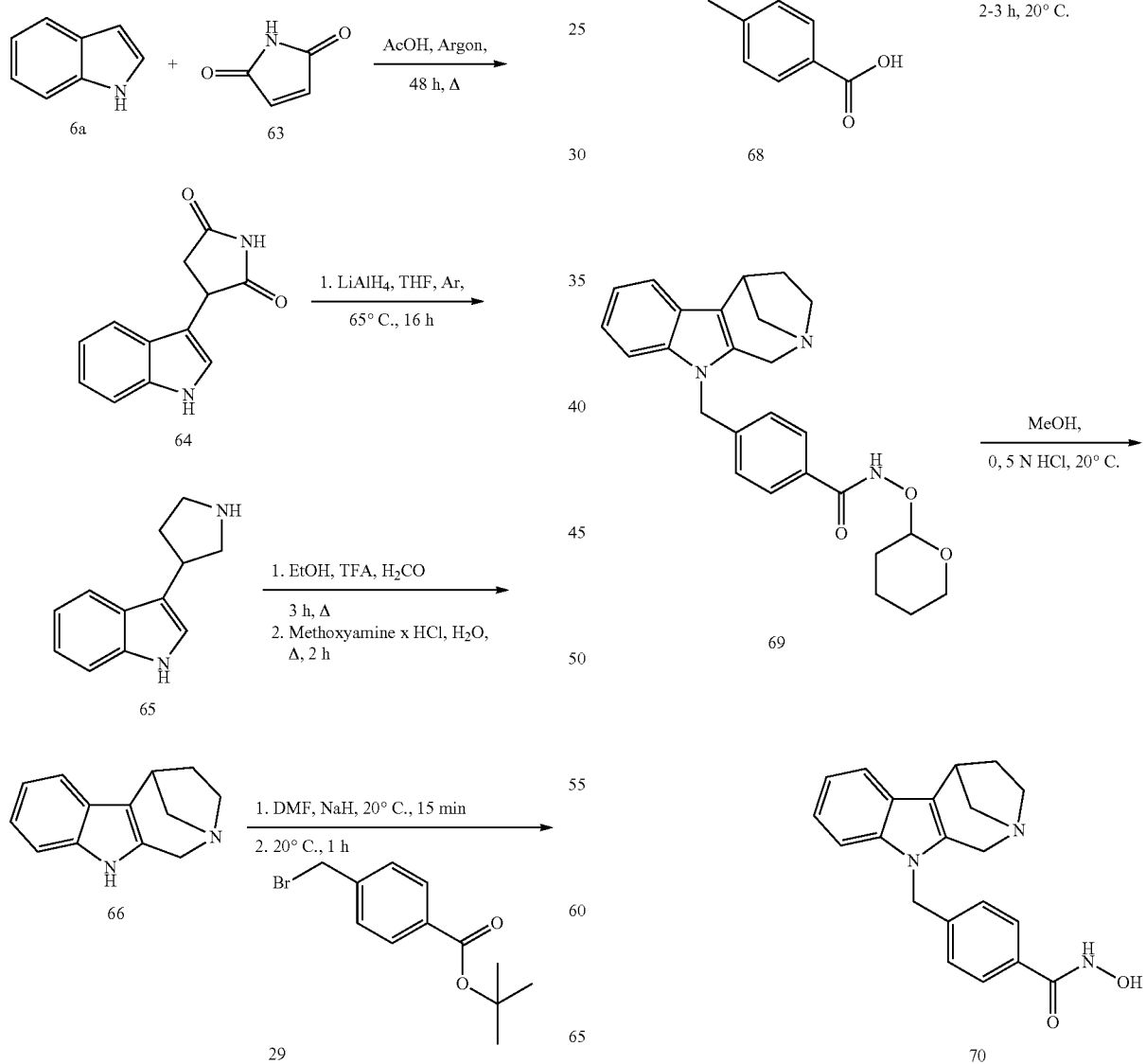

Compounds with head group 3:
Scheme 8: Synthesis of inhibitors based on the 1,2,3,6,7,12b-hexahydroindolo[2,3-a]quinolizine-4(12H)-on-basic strucure exemplified by compounds 84 and 85.
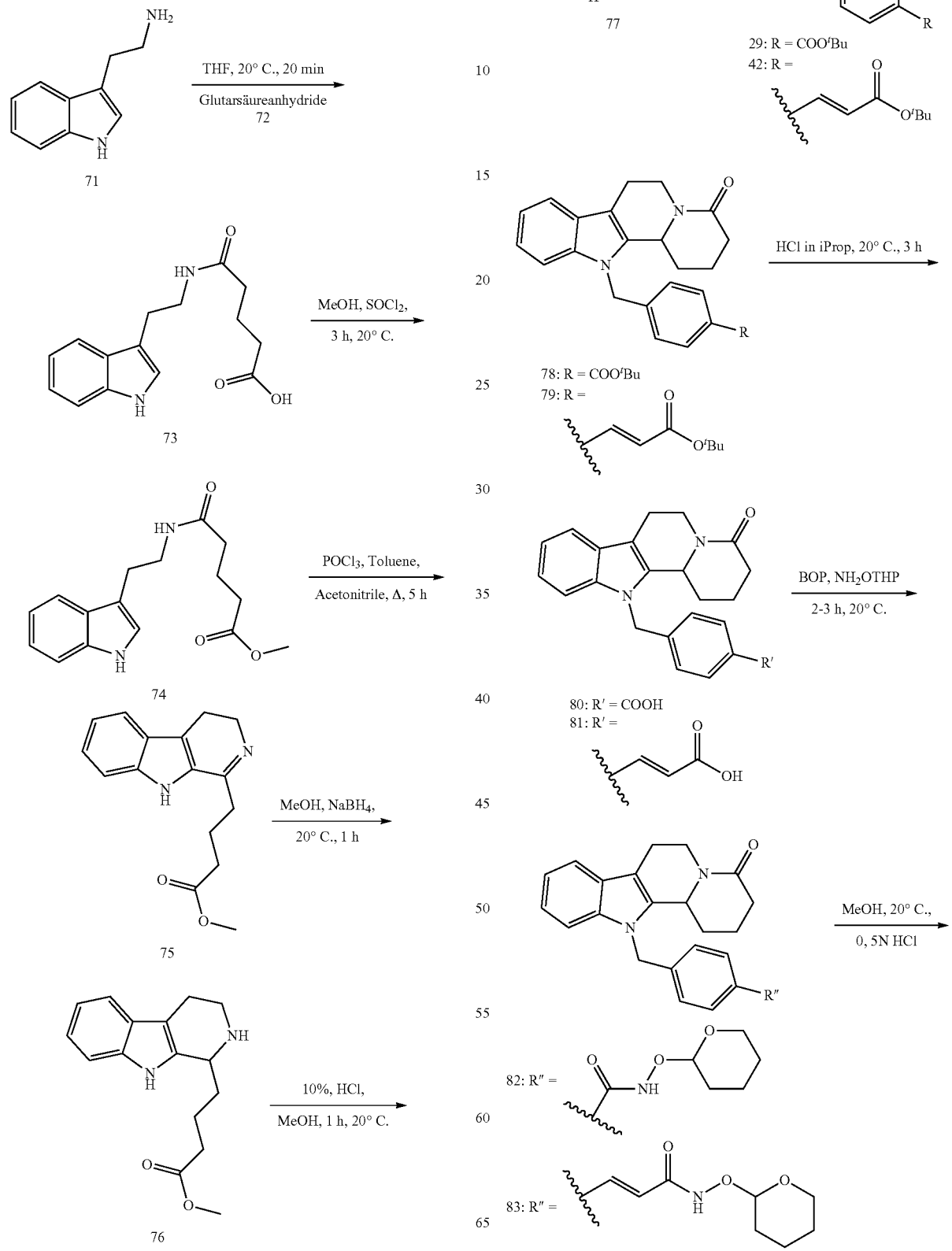

-continued
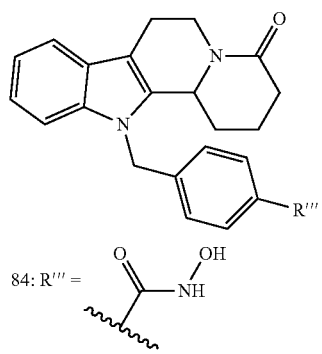
84: R''' = [hydroxamic acid group]
85: R''' = [cinnamic hydroxamic acid group]
Compounds with head group 4:
Scheme 9: Synthesis of 4-((9H-fluoren-9-yl)methyl)-N-hydroxybenzamide (88)
Scheme 10: (E)-3-(4-((9H-fluoren-9-yl)methyl)phenyl)-N-hydroxyacrylamide (93).
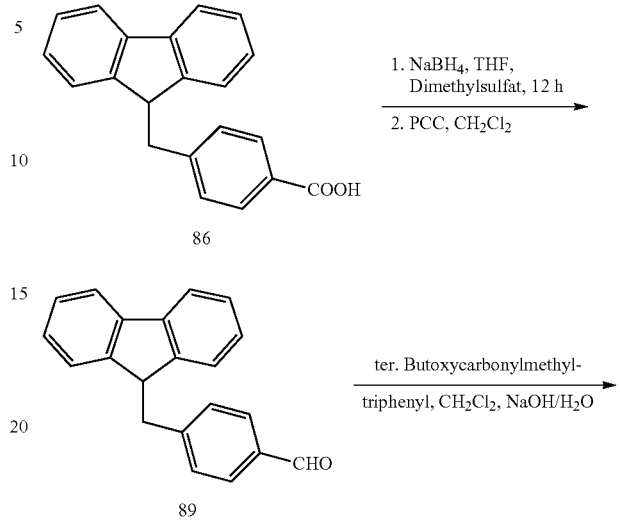
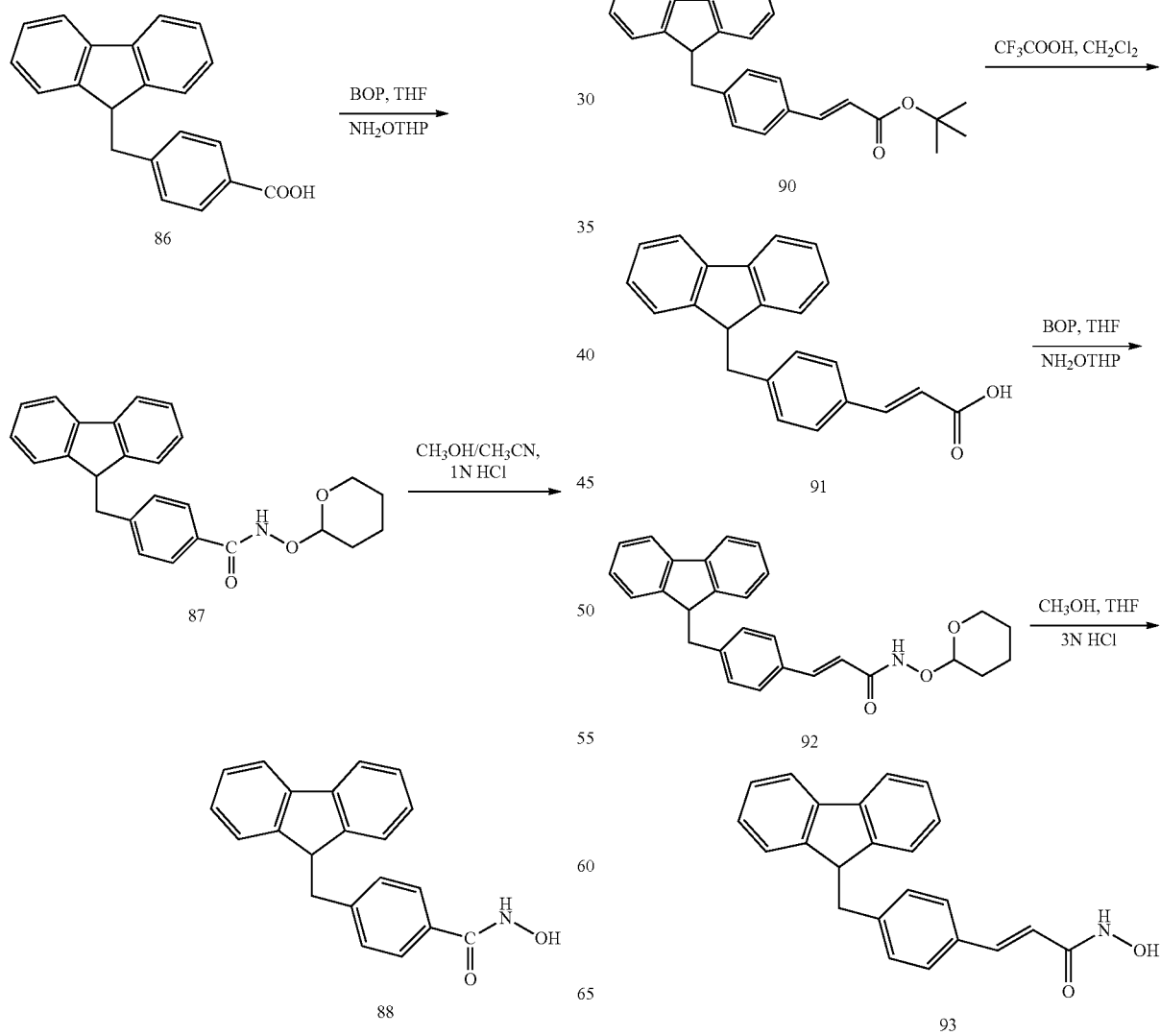

further modifications to head group 1:
Scheme 11: Synthesis of inhibitors by modification of the 4-methyl-6,11-dihydro-2,6-methano[1,3]diazocino[5,6-b]indole-3,5(1H,4H)-dion head group exemplified by compounds 101a to 101c.
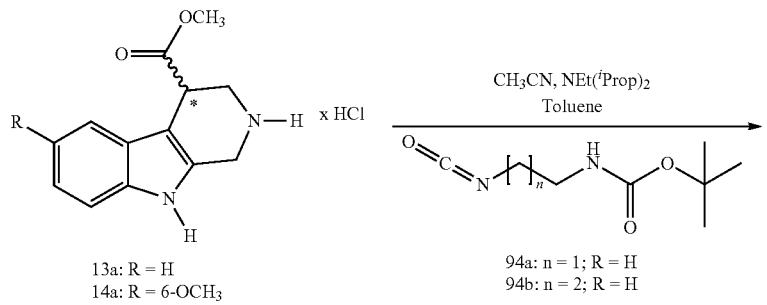
13a: R = H
14a: R = 6-OCH₃
94a: n = 1; R = H
94b: n = 2; R = H
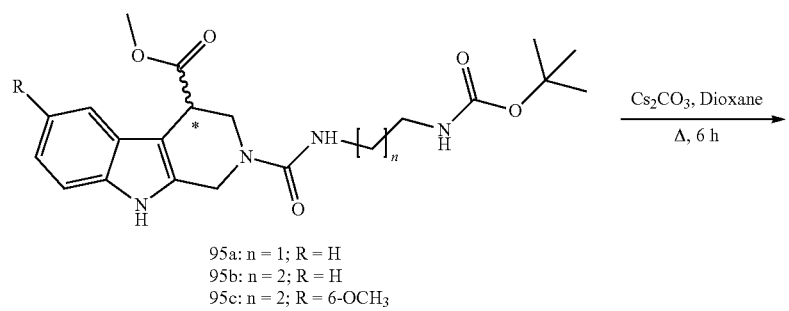
95a: n = 1; R = H
95b: n = 2; R = H
95c: n = 2; R = 6-OCH₃
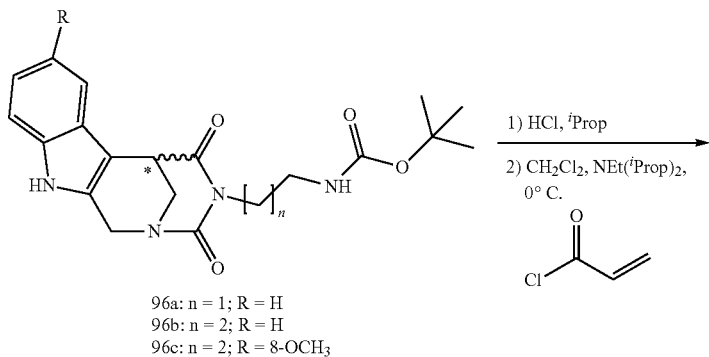
96a: n = 1; R = H
96b: n = 2; R = H
96c: n = 2; R = 8-OCH₃
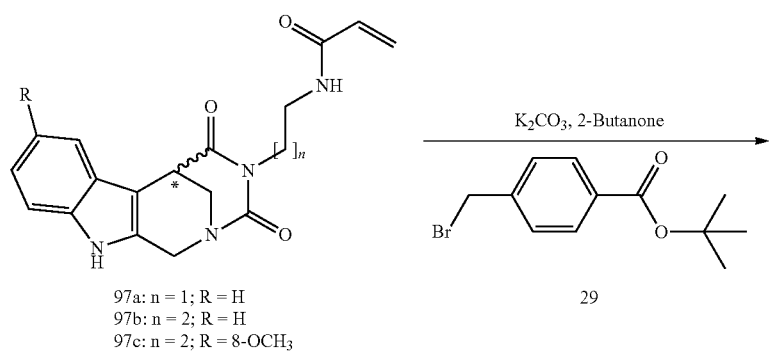
97a: n = 1; R = H
97b: n = 2; R = H
97c: n = 2; R = 8-OCH₃
29

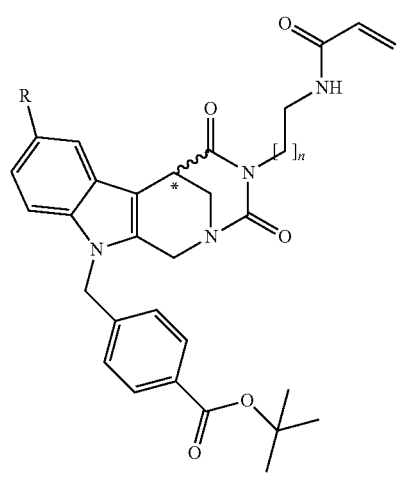
98a: n = 1; R = H
98b: n = 2; R = H
98c: n = 2; R = 8-OCH₃
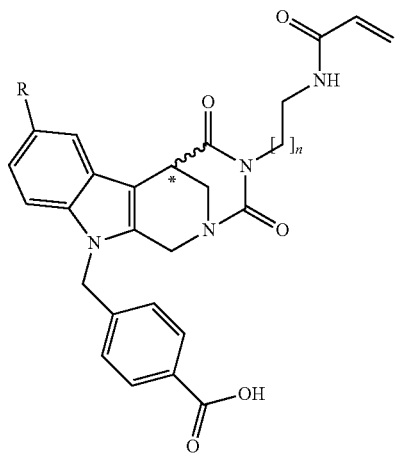
99a: n = 1; R = H
99b: n = 2; R = H
99c: n = 2; R = 8-OCH₃
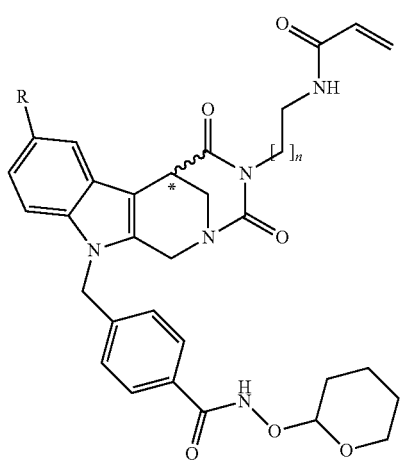
100a: n = 1; R = H
100b: n = 2; R = H
100c: n = 2; R = 8-OCH₃
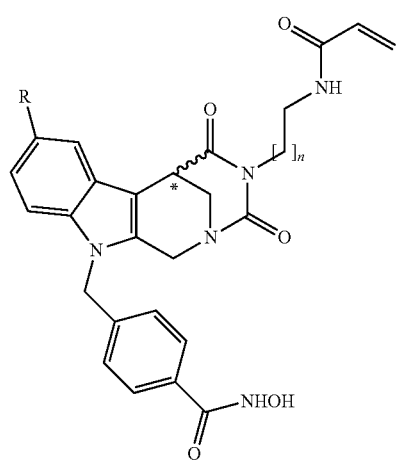
101a: n = 1; R = H
101b: n = 2; R = H
101c: n = 2; R = 8-OCH₃
Compounds with head group 5:
Schema 12: Synthesis of tetrahydro-β-carboline structures exemplified by compounds 108 and 109a to 109c.
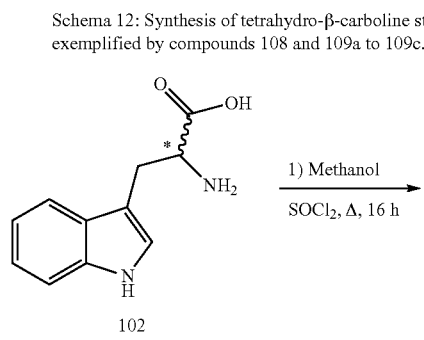
102
-continued
12
or
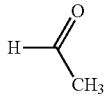
12b
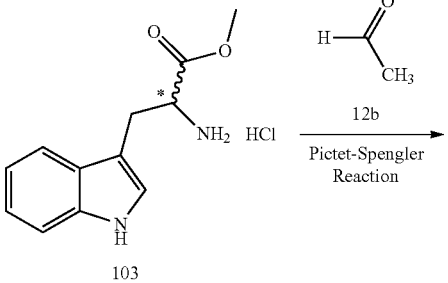
103
Pictet-Spengler Reaction

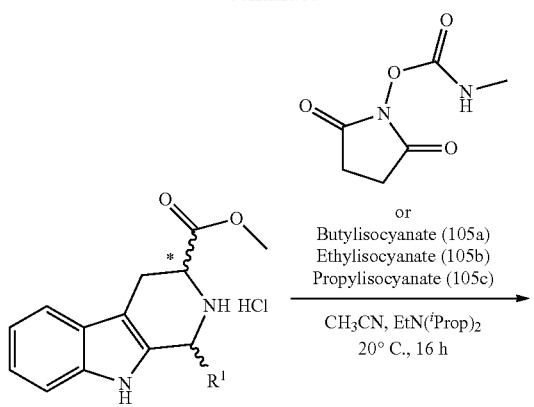
104a: R¹ = H;
104b: R¹ = CH₃; (1S; 3R)
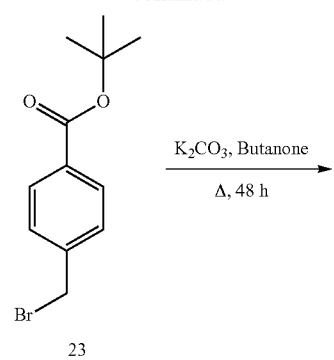
106: R¹ = H, R² = CH₃;
107a: R¹ = H, R² = n-Bu
107b: R¹ = H, R² = Et
107c: R¹ = H, R² = n-Pr
108: R¹ = H, R² = CH₃;
109a: R¹ = H, R² = n-Bu
109b: R¹ = H, R² = Et
109c: R¹ = H, R² = n-Pr
Scheme 13: Synthesis of inhibitors by modification of the 5,6,11,11a tetrahydro-1H-imidazo[1',5':1,6]pyrido[3,4-b]indole-1,3(2H)-dion structure.
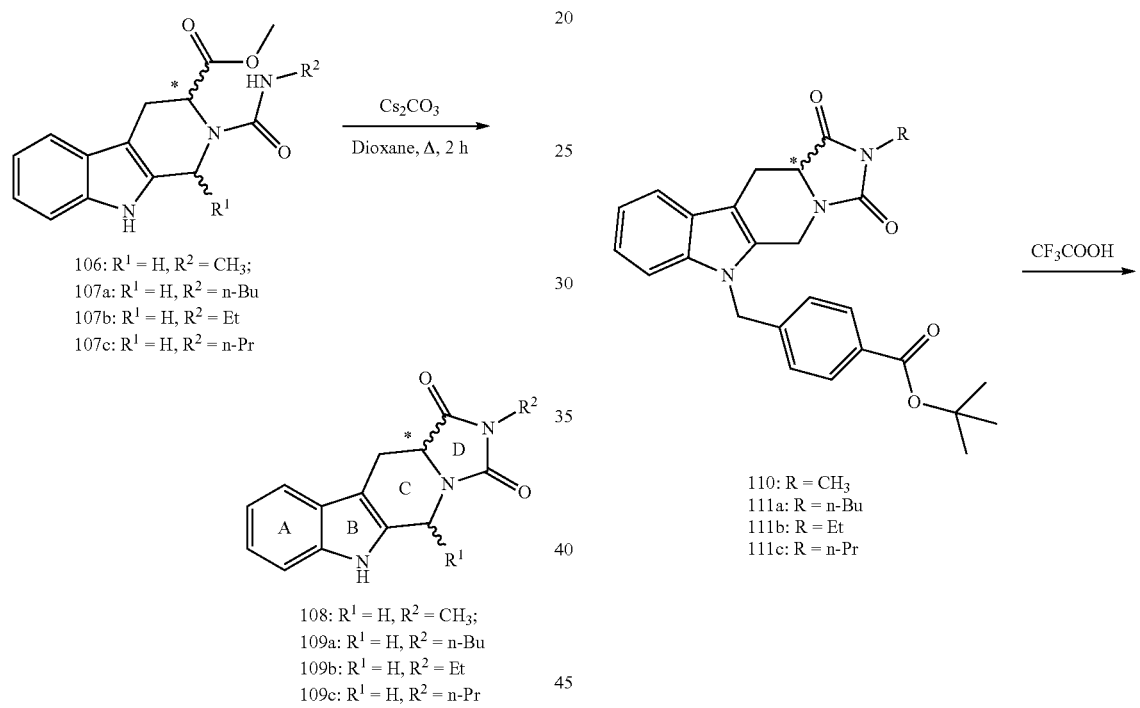
108: R = CH₃
109a: R = n-Bu
109b: R = Et
109c: R = n-Pr
110: R = CH₃
111a: R = n-Bu
111b: R = Et
111c: R = n-Pr
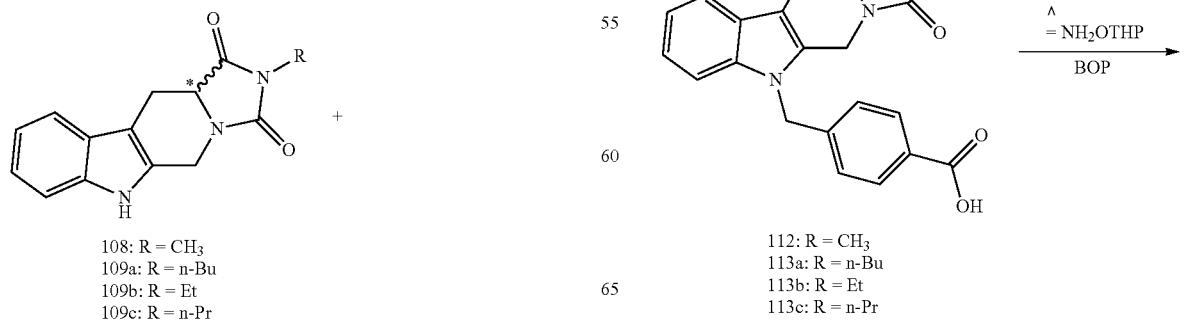
112: R = CH₃
113a: R = n-Bu
113b: R = Et
113c: R = n-Pr

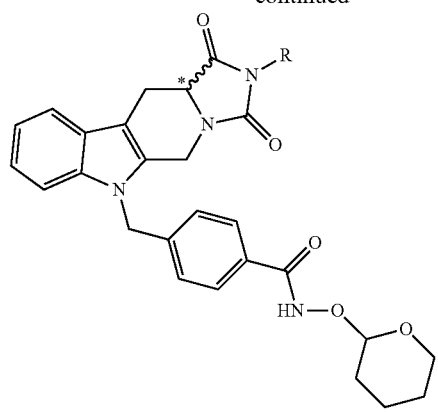
114: R = CH₃
115a: R = n-Bu
115b: R = Et
115c: R = n-Pr
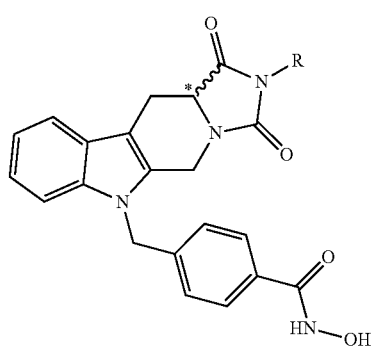
116: R = CH₃
117a: R = n-Bu
117b: R = Et
117c: R = n-Pr
Scheme 14: Synthesis tetrahydro-β-carbonline structures exemplified by compounds 130a and 130b.
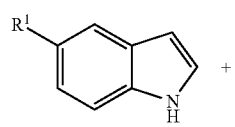
122a: R¹ = OBn
122b: R¹ = OMe
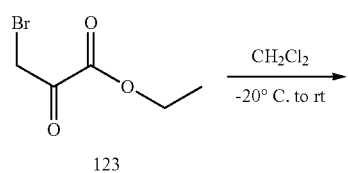
123
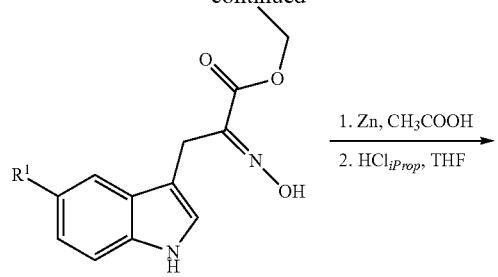
124a: R¹ = OBn
124b: R¹ = OMe
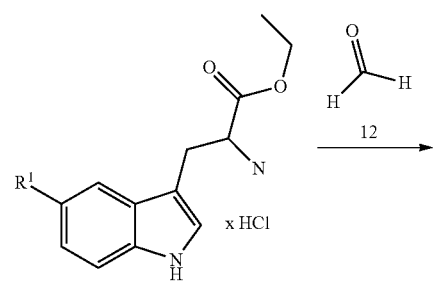
125a: R¹ = OBn
125b: R¹ = OMe
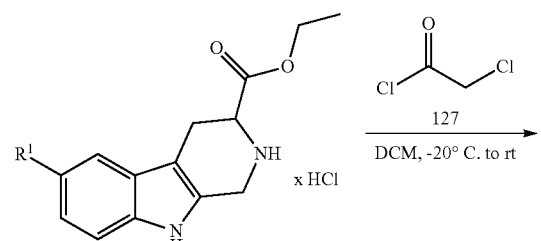
126a: R¹ = OBn
126b: R¹ = OMe
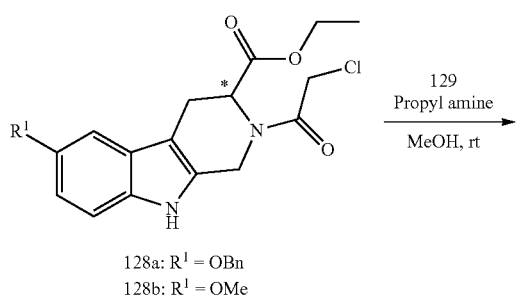
128a: R¹ = OBn
128b: R¹ = OMe
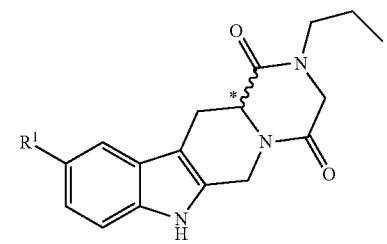
130a: R¹ = OBn
130b: R¹ = OMe Scheme 15: Synthesis of tetrahydro-β-carboline structures exemplified by compounds 132a to 132i.
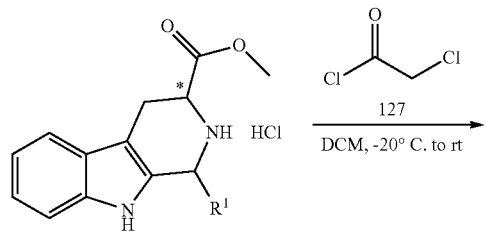
104a: R¹ = H
104b: R¹ = CH₃ (1S; 3S)
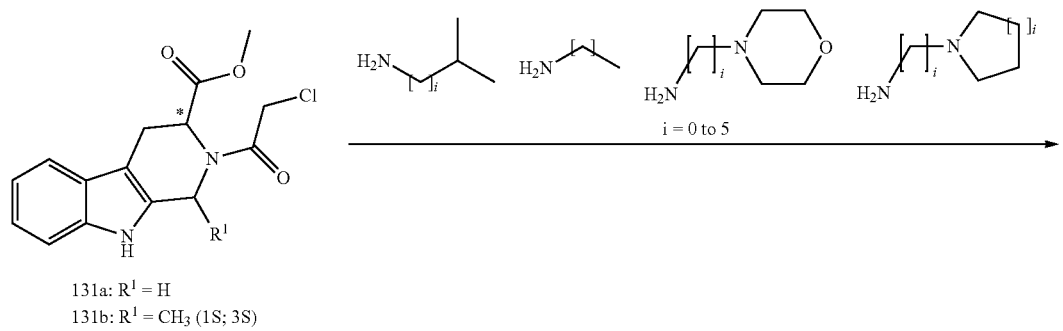
131a: R¹ = H
131b: R¹ = CH₃ (1S; 3S)
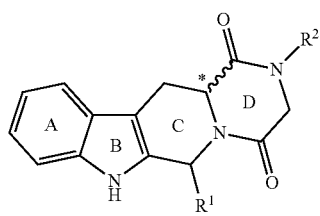
132a: R¹ = H, R² = CH₃
132b: R¹ = H, R² = Et
132c: R¹ = H, R² = n-Pr
132e: R¹ = H, R² = i-Bu
132f: R¹ = H, R² = i-Pentyl
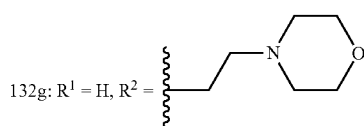
132g: R¹ = H, R² =
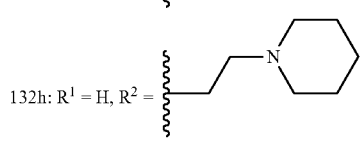
132h: R¹ = H, R² =
132i: (6S, 12aS): R¹ = CH₃, R² = n-Pr Scheme 16a: Synthesis of inhibitors by modification of the 2,3,6,7,12,12a-hexahydropyrazino [1′,2′:1,6]pyrido[3,4-b]indole-1,4-dione structure

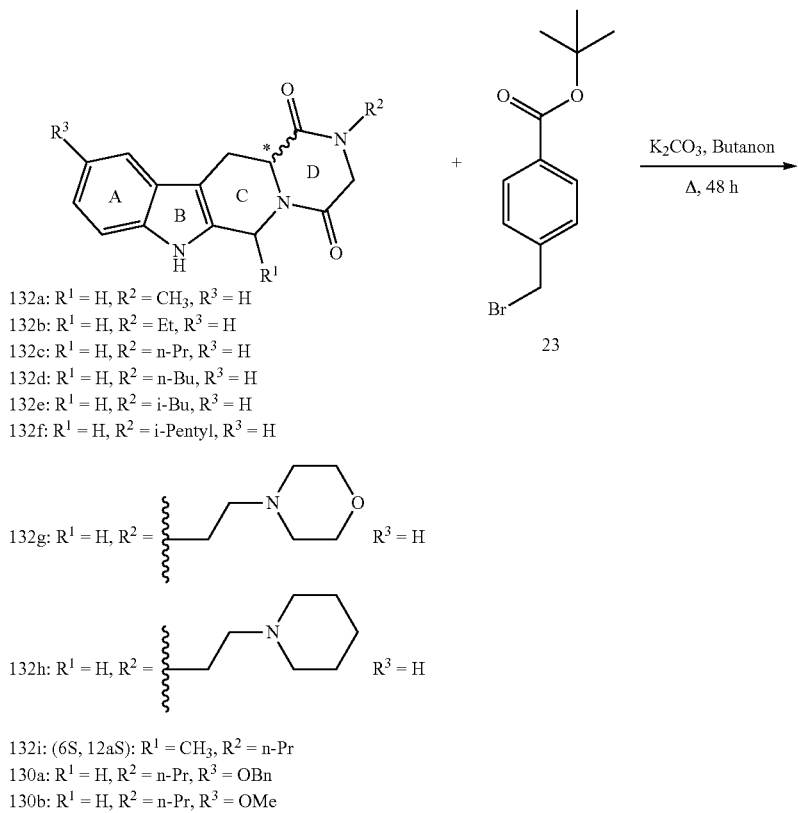

132a: $R^1$ = H, $R^2$ = $CH_3$, $R^3$ = H
132b: $R^1$ = H, $R^2$ = Et, $R^3$ = H
132c: $R^1$ = H, $R^2$ = n-Pr, $R^3$ = H
132d: $R^1$ = H, $R^2$ = n-Bu, $R^3$ = H
132e: $R^1$ = H, $R^2$ = i-Bu, $R^3$ = H
132f: $R^1$ = H, $R^2$ = i-Pentyl, $R^3$ = H 132g: $R^1$ = H, $R^2$ = [CH₂CH₂-morpholine], $R^3$ = H 132h: $R^1$ = H, $R^2$ = [CH₂CH₂-piperidine], $R^3$ = H 132i: (6S, 12aS): $R^1$ = $CH_3$, $R^2$ = n-Pr
130a: $R^1$ = H, $R^2$ = n-Pr, $R^3$ = OBn
130b: $R^1$ = H, $R^2$ = n-Pr, $R^3$ = OMe

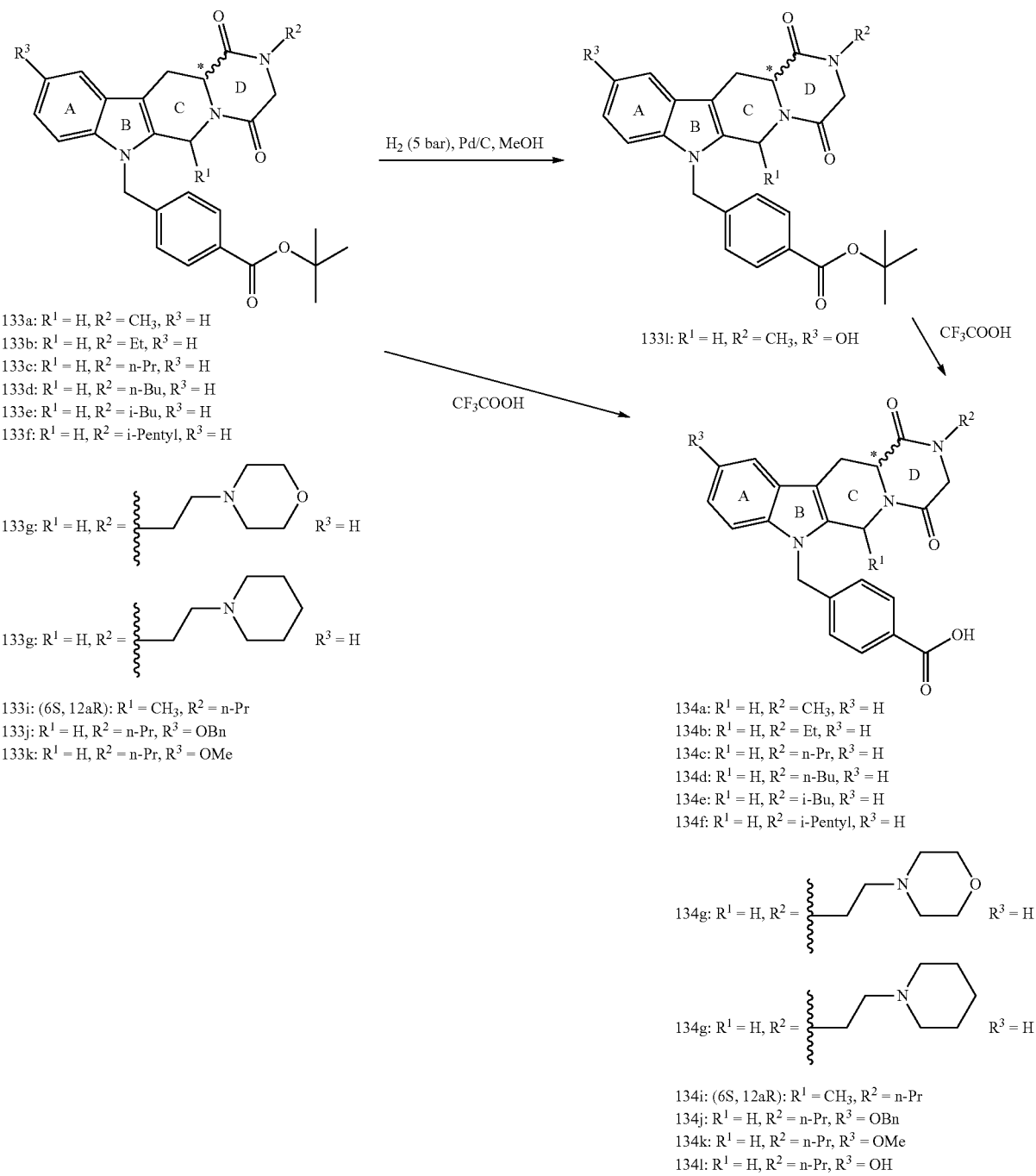

Scheme 16b: Synthesis of inhibitors by modification of the 2,3,6,7,12,12a-hexahydropyrazino[1′,2′:1,6]pyrido[3,4-b]indole-1,4-dione structure

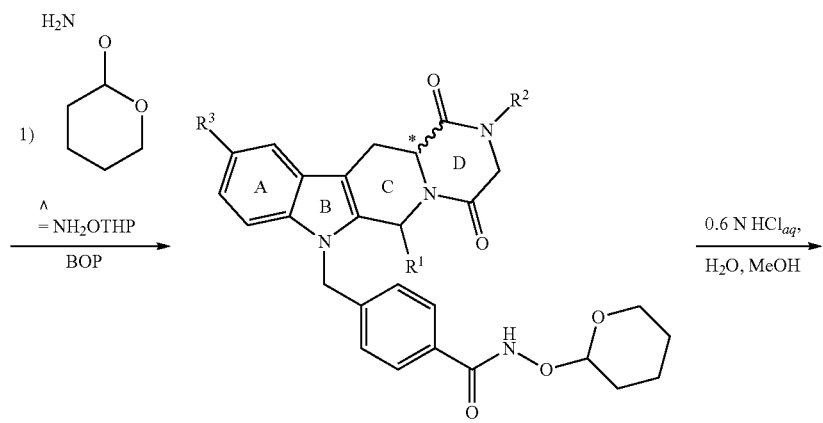

135a: $R^1 = H$, $R^2 = CH_3$, $R^3 = H$
135b: $R^1 = H$, $R^2 = Et$, $R^3 = H$
135c: $R^1 = H$, $R^2 = n\text{-}Pr$, $R^3 = H$
135d: $R^1 = H$, $R^2 = n\text{-}Bu$, $R^3 = H$
135e: $R^1 = H$, $R^2 = i\text{-}Bu$, $R^3 = H$
135f: $R^1 = H$, $R^2 = i\text{-}Pentyl$, $R^3 = H$

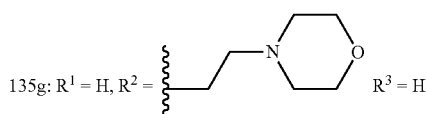

135g: $R^1 = H$, $R^2 =$     $R^3 = H$

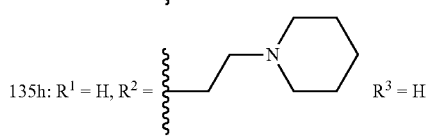

135h: $R^1 = H$, $R^2 =$     $R^3 = H$

135i: (6S, 12aR): $R^1 = CH_3$, $R^2 = n\text{-}Pr$
135j: $R^1 = H$, $R^2 = n\text{-}Pr$, $R^3 = OBn$
135k: $R^1 = H$, $R^2 = n\text{-}Pr$, $R^3 = OMe$
135l: $R^1 = H$, $R^2 = n\text{-}Pr$, $R^3 = OH$

61           62

-continued

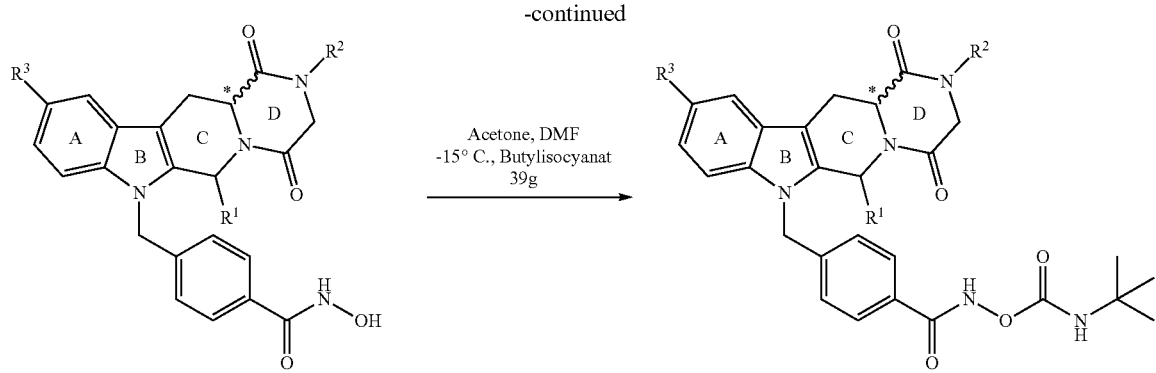

136a: $R^1$ = H, $R^2$ = $CH_3$, $R^3$ = H
136b: $R^1$ = H, $R^2$ = Et, $R^3$ = H
136c: $R^1$ = H, $R^2$ = n-Pr, $R^3$ = H
136d: $R^1$ = H, $R^2$ = n-Bu, $R^3$ = H
136e: $R^1$ = H, $R^2$ = i-Bu, $R^3$ = H
136f: $R^1$ = H, $R^2$ = i-Pentyl, $R^3$ = H 136m: $R^1$ = H, $R^2$ = n-Pr, $R^3$ = H

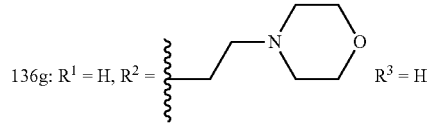

136g: $R^1$ = H, $R^2$ = [morpholinoethyl], $R^3$ = H

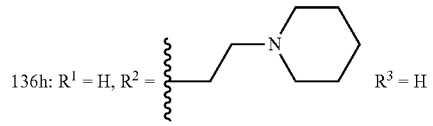

136h: $R^1$ = H, $R^2$ = [piperidinoethyl], $R^3$ = H

136i: (6S, 12aR): $R^1$ = $CH_3$, $R^2$ = n-Pr
136j: $R^1$ = H, $R^2$ = n-Pr, $R^3$ = OBn
136k: $R^1$ = H, $R^2$ = n-Pr, $R^3$ = OMe
136l: $R^1$ = H, $R^2$ = n-Pr, $R^3$ = OH

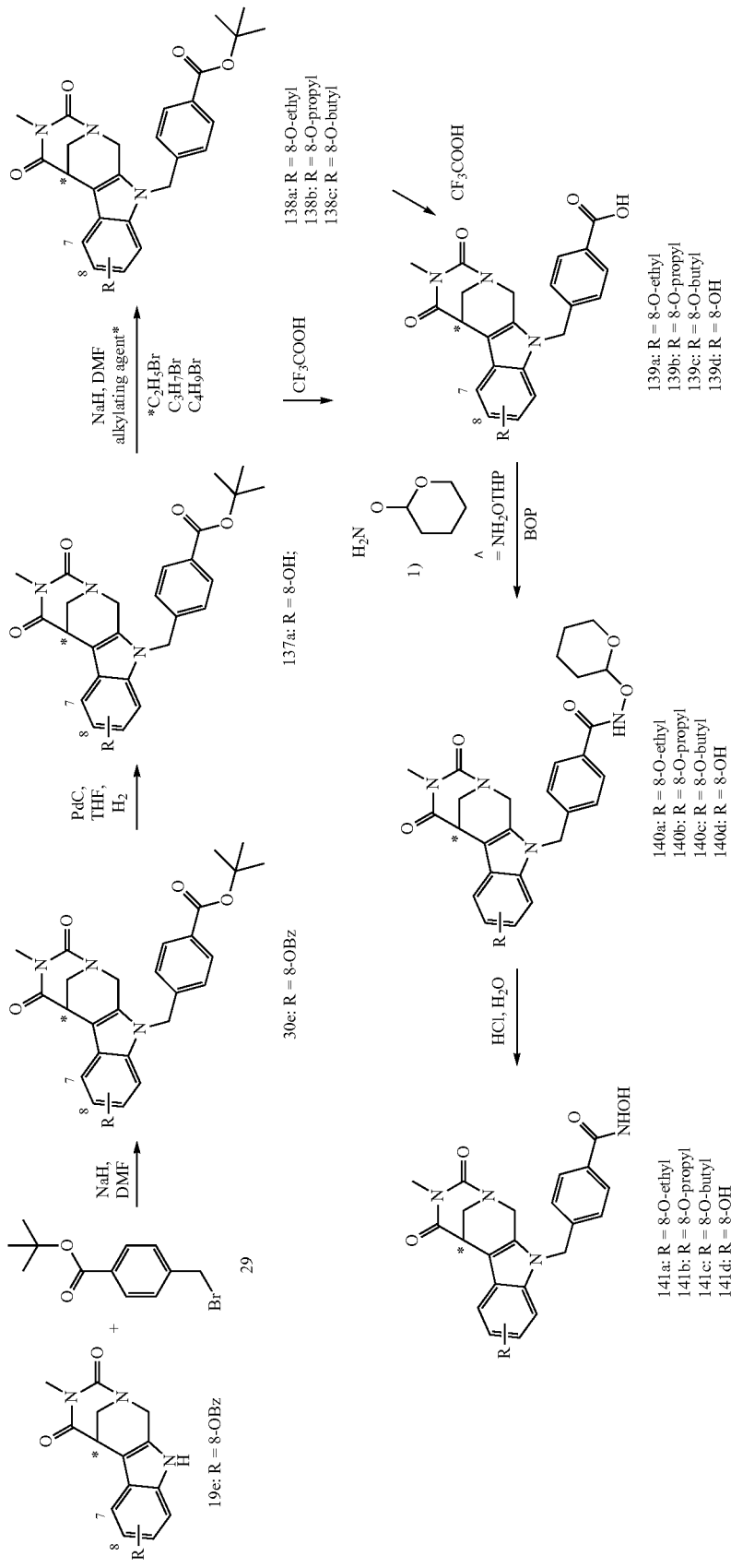

65

Scheme 18. Synthesis of derivatives with 3,4,8a,9-tetrahydro-6H-diimidazo[1,5-a:4',5'-d]pyridine-6,8(7H)-dione structure.

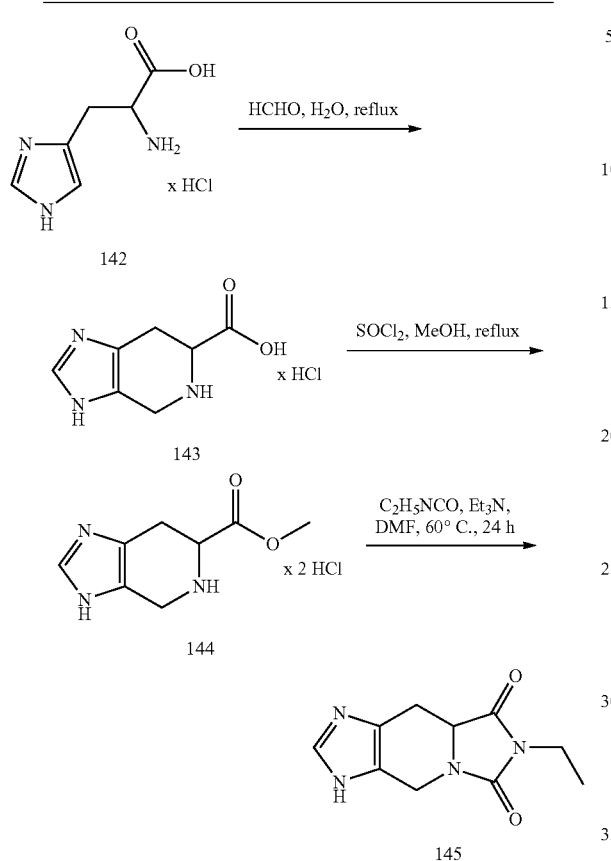

Scheme 19. Example for modification of the A ring system of head group 1, exploying heteroaryl derivatives.

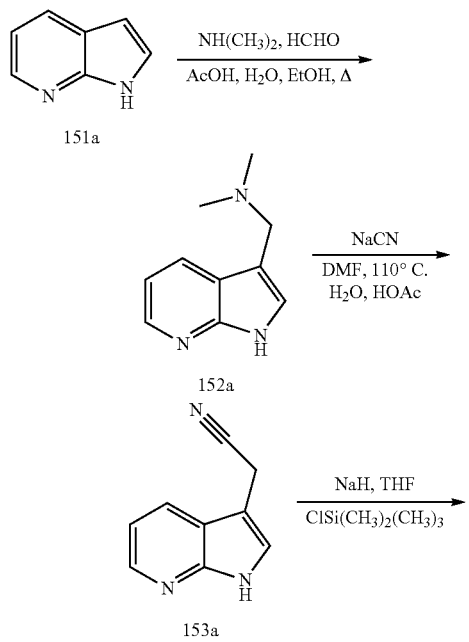

66

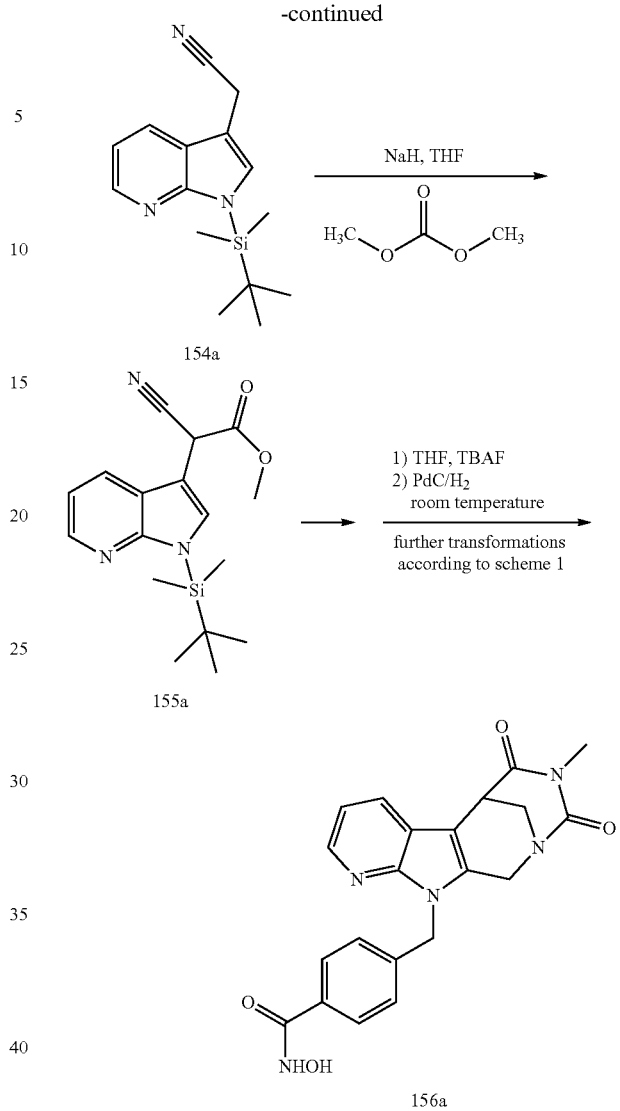

FURTHER DESCRIPTION OF PREFERRED EMBODIMENTS

The present invention discloses novel HDAC inhibitors. Furthermore, the present invention discloses pharmaceutical compositions comprising HDAC inhibitor(s) and exemplary treatment regimens for various diseases. These especially include cancer, neurological disorders, neurodegenerative diseases, stroke, inflammatory diseases, traumatic brain injury, rheumatoid arthritis, graft rejection after organ transplantation and autoimmune diseases. The present invention further discloses comprises the use of HDAC inhibitors in adjuvant therapy with various standard cytostatic compounds and the sensitization of cancer cells in the context of a radiation therapy.

Histone deacetylases (HDACs) are epigenetic regulators that cleave the acetyl groups from lysine residues in proteins. HDACs are often overexpressed in tumors and thus involved in carcinogenesis. Histone deacetylase inhibitors (HDACi) inhibit the protein-deacetylation and modulate gene expression. Thereby, the growth of abnormal cells is inhibited. HDACi have shown promising effects, for example, in leukemia therapy which is up to now often impossible. Transcriptional dysregulation also seems to be involved in the molecular pathogenesis of certain neurodegenerative diseases, such as Huntington's disease, spinal muscular atrophy or Alzheimer's. While pan-HDACi have broad cytotoxic profiles due to the inhibition of several HDAC isoforms, isoform-specific HDACi have fewer side effects.

HDAC6 has two catalytic domains and a specific substrate spectrum. Substrates of HDAC6 are, for example, Tubulin-α and the chaperone HSP90. Deacetylated HSP90 stabilizes the leukemia fusion proteins BCR-ABL, PML-RAR and AML1-ETO, mutant FLT3, the pan-leukemic marker protein WT1 and oncogenic p53. As these and other substrates of HDAC6 are critically involved in tumorigenesis, HDAC6 inhibitors are suitable for the treatment of cancer.

The HDAC6 inhibitors of the present invention effect potent cytostatic and cytotoxic effects in different cell models. We also show for the first time that the expression of the protein survivin, an important factor for tumorigenesis and chemoresistance, is HDAC6 dependent. Furthermore, our selective HDAC6 inhibitors in combination with imatinib generate cytotoxic effects on BCR-ABL positive cells. At a molecular level, this is linked to a reduction of BCR-ABL, WT1 and the accumulation of acetylated tubulin.

Moreover, a synergism in killing of ovarian cancer cells by application of the proteasome inhibitor Bortezomib (PS-341) has been shown (Bazzaro et al., 2008).

The following examples and drawings illustrate the present invention without, however, limiting the same thereto.

Flow cytometric analysis of the induction of (A) apoptotic DNA fragmentation and (B) Cell cycle analysis of BV 173 cells. The cells were kept as control cells (Ctl), treated with 1 μM or 2 μM MARB1 MARB2 and 0.2 or 0.5 μM imatinib for 48 h. The data was received by two independent experiments. The individual compounds show only slight effects in the used concentrations; whereas their combination can effectively kill leukemic cells. (C) Western blot analysis on data from the BCR-ABL, acetylated tubulin and α-sliced PARP1; the total amount of tubulin-α serves as a loading control. BV-173 cells were treated for 24 h with 1 μM, or 2 μM MARB1 or MARB2. A significant degradation of BCR-ABL occurs in cells incubated with imatinib and MARB1 in comparison to control cells and cells only treated with imatinib.

Figure 4:
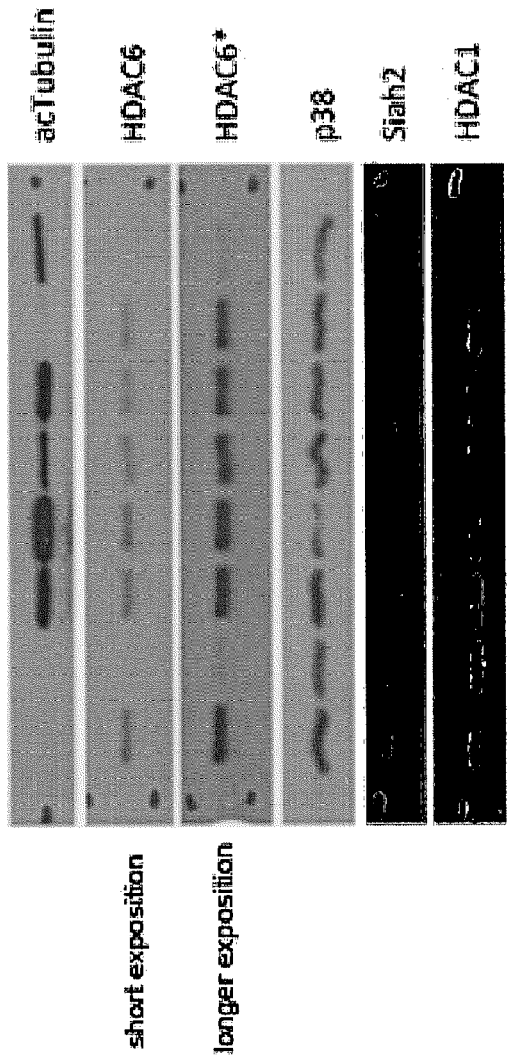

FIG. 4. Human leukemic cells with the JAK2 V617F mutation (polycythemia vera) were treated for 24 h as shown in the figure (top lines). Western blot analyzes shows the amount of the acetylated form of tubulin, the total amount of HDAC6 (*longer film exposure) and p38, and SIAH2 HDAC1 as a control of the loading process.

FIG. 5. Various cancer cells were treated for 24 h as shown and tested by Western blot analysis.
(A) shows the acetylated form of tubulin and vinculin as a loading control (kDa relative molecular mass in kilo Daltons) in patients treated with LBH589 or butyrate HCT-116 colon cancer cells (* prolonged film exposure).
(B) 1 μM MARB1 triggers the hyperacetylation of tubulin without causing its degradation (* prolonged film exposure).
(C) Already 0.5 μM MARB1 and MARB2 are sufficient to induce hyperacetylation of tubulin in colorectal cancer cell line RKO.
(D) Inhibition of HDAC6 protects it from degradation by the addition of a pro-apoptotic agent (staurosporine, ST).
The total amount of vinculin serves as a loading control; Proof of tubulin acetylation serves as proof of the treatment accuracy. The loss of the caspase-3 corresponds to the induction of apoptosis (programmed cell death).

Figure 6A:
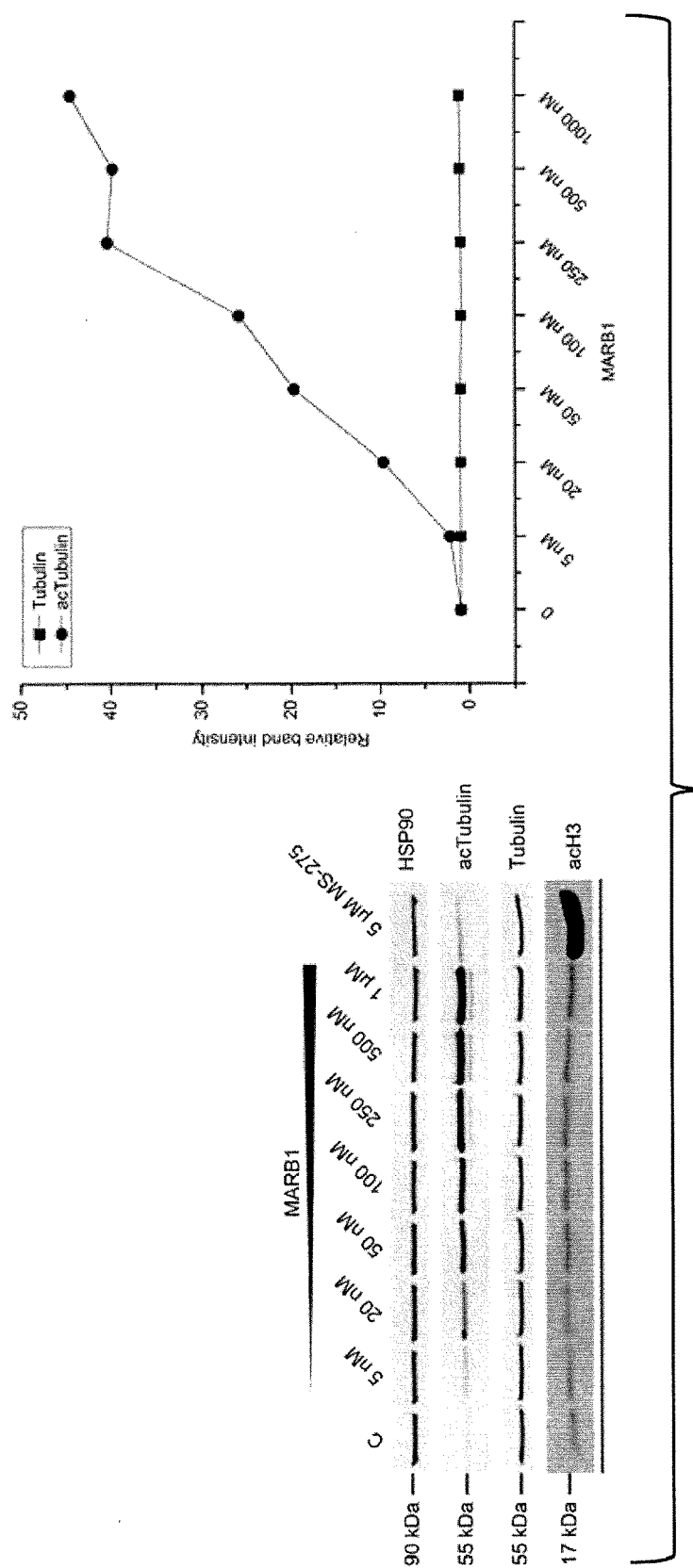
Figure 6B:
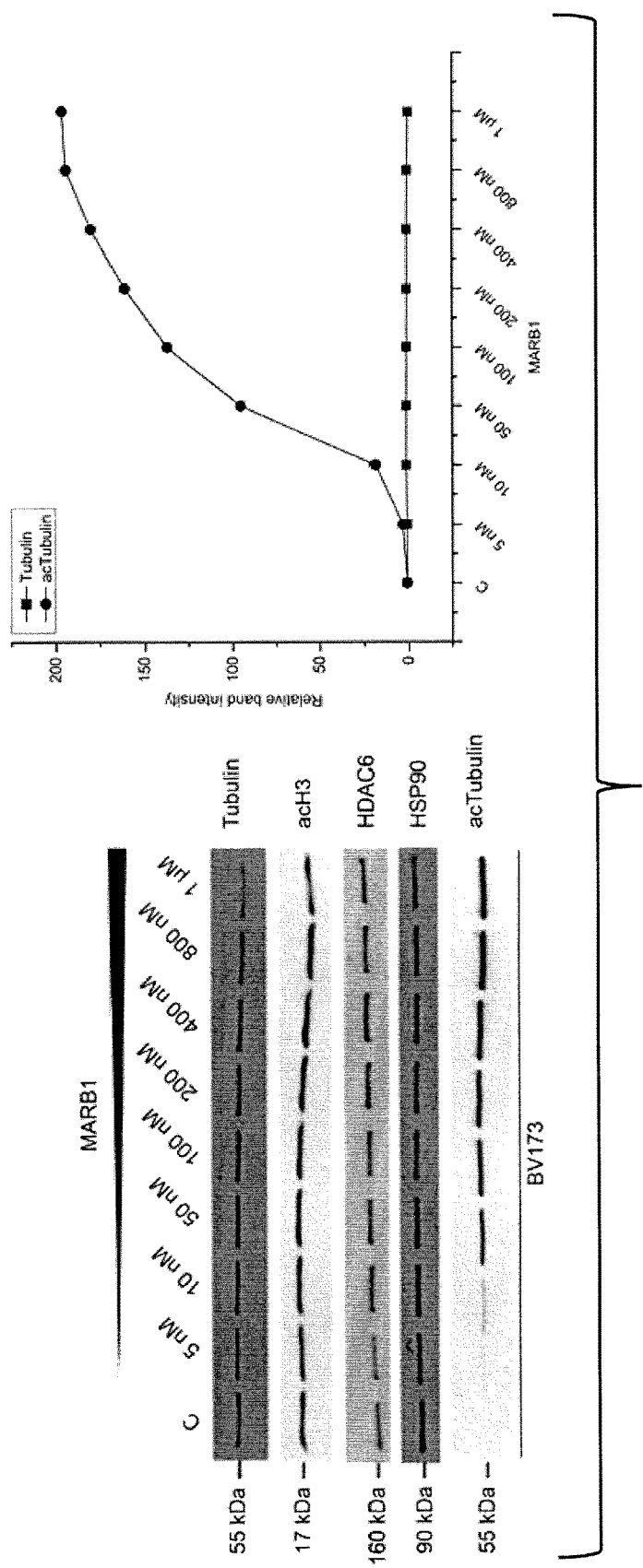
Figure 6C:
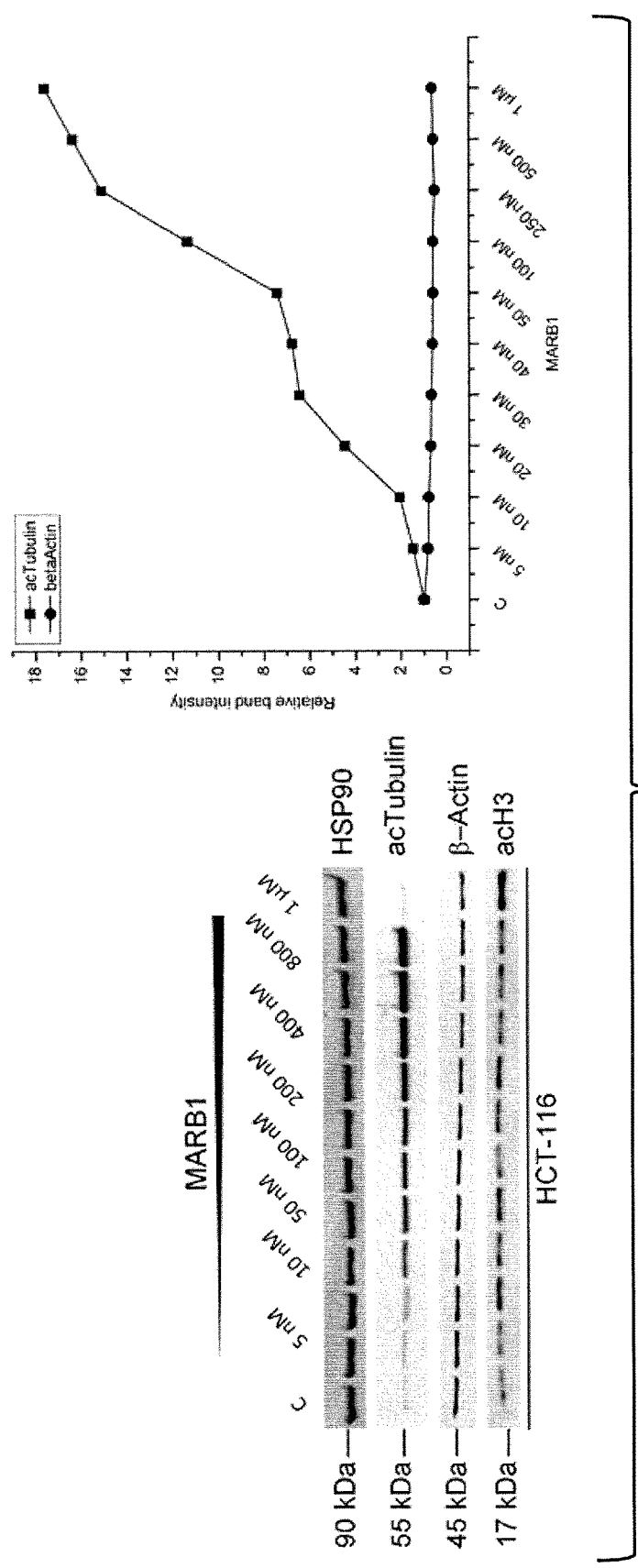

FIG. 6. Dose dependency of MARB1
Cells were seeded on a 6 well plate and incubated as shown. The blots were quantified with Image Studio Lite Version 5.0. (A) 1 Mio cells per sample were seeded and after 2 h adaption time the cells were stimulated as shown, followed by incubation and harvesting of the cells. Tubulin and HSP90 were used as loading control. The diagram shows a representative quantification of Tubulin and acTub. n=3 (B) The cells were handled according to (A). HSP90 and Tubulin were used as loading control. n=1 (C) 200,000 cells were seeded in a 6 well plate and incubated over night for adhesion. The stimulation started as shown in the figure. B-Actin was used as loading control. n=1

Figure 2:
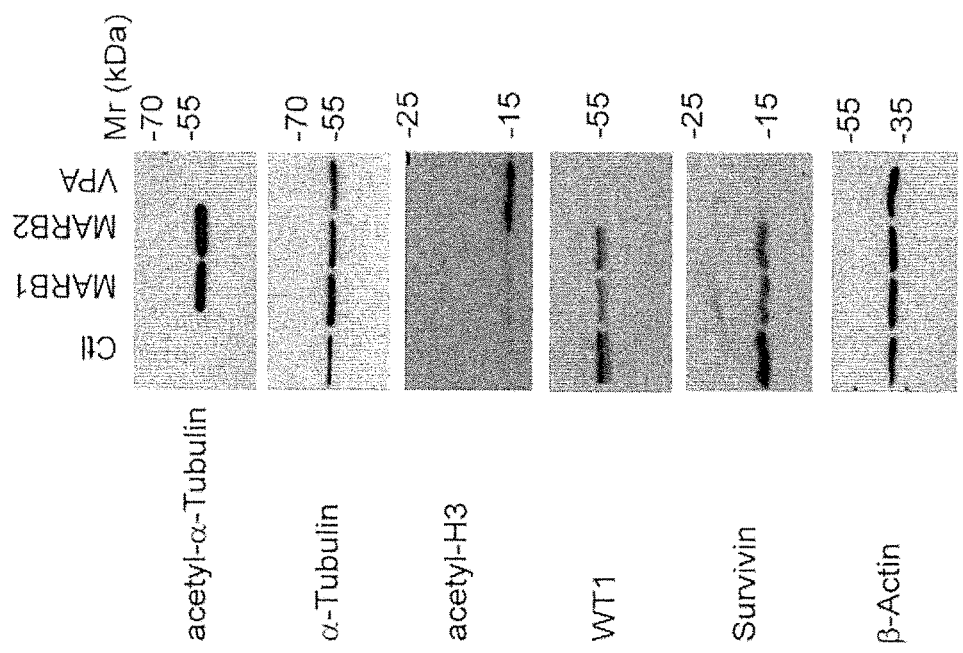
FIG. 2. The novel HDAC6 inhibitors of the invention induce acetylation of tubulin and the degradation of WT1 and survivin.
BV-173 cells (BCR-ABL positive leukemic cells) were used as control cells left (Ctl) or with 1 μM MARB1, 2 μM MARB2 or 2 mM VPA treated for 24 h. These concentrations were chosen to achieve equipotent effects on cells which was in preliminary tests (data not shown). Shown are acetylated tubulin-α, α-tubulin, acetylated histone H3, WT1, survivin and β-actin. The total amount of α-tubulin and β-actin were used as loading control. Mr, relative molecular weight in kilodaltons. The degradation of WT1 in patients treated with VPA cells bases on a loss of WT1 mRNA and the increased degradation of WT1 protein by induction of the E2 ubiquitin conjugase UbcH8.
Figure 7A:
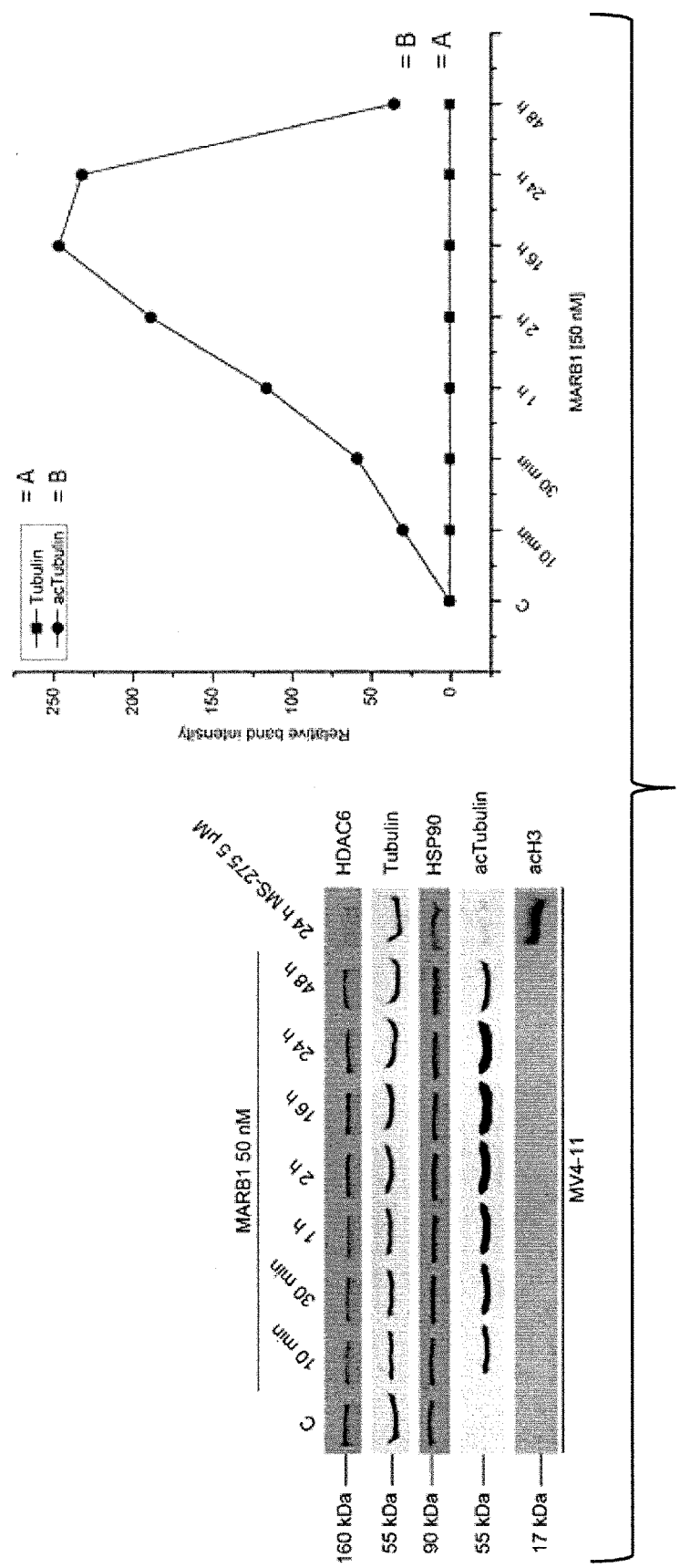
Figure 7B:
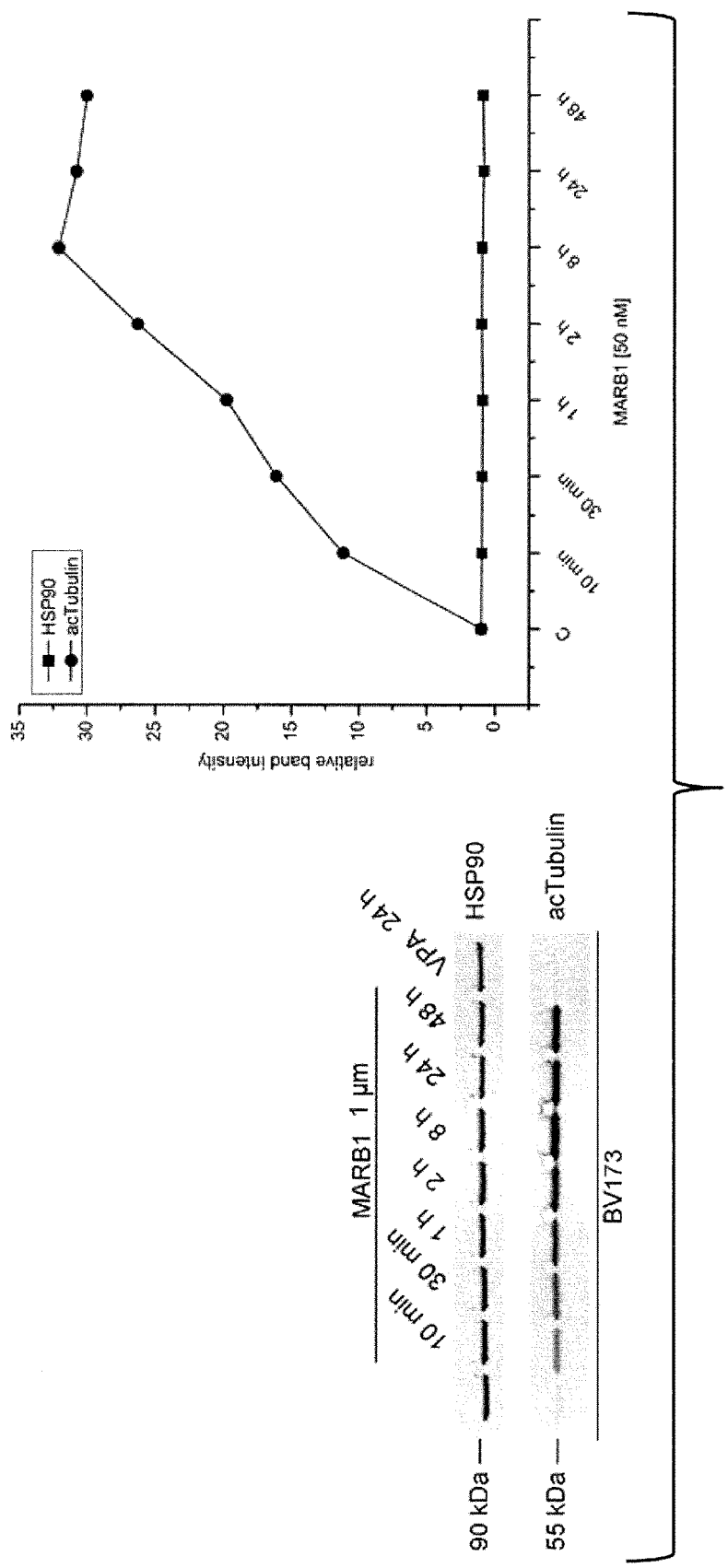
Figure 7C:
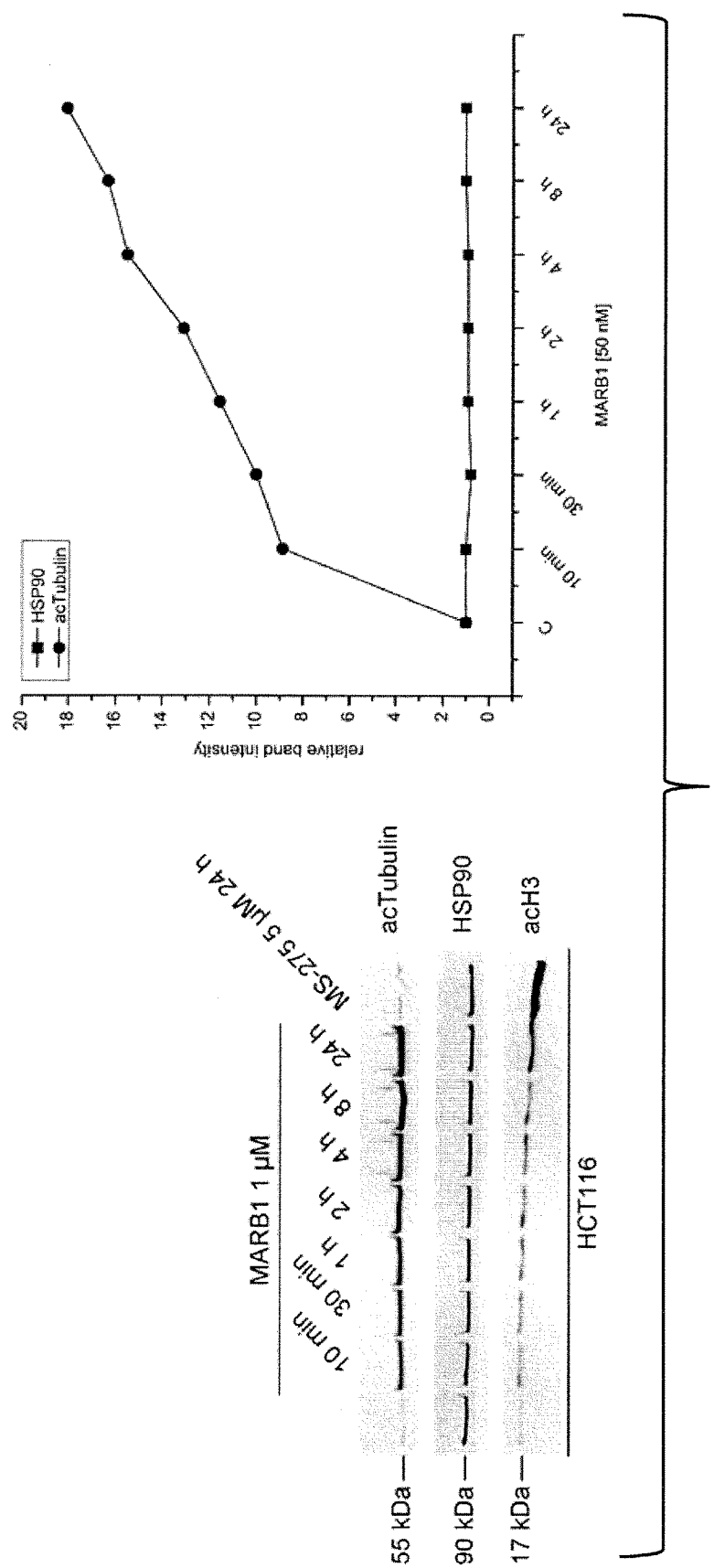

FIG. 7. Time dependency of MARB1
For the examination of the time dependency of MARB1 MV4-11, BV173 and HCT116 cells were tested by western blot. All cells were seeded on a 6 well plate. The blots were quantified with Image Studio Lite Version 5.0. (A) 1 Mio cells per sample were seeded and after 2 h adaption time the cells were stimulated as shown. Following the incubation, the cells were harvested as described earlier. Tubulin and HSP90 were used as loading control. The diagram shows a representative quantification of Tubulin and acTubulin. n=2 (B) Cells were handled as described in (A). HSP90 was used as loading control. The diagram shows a representative quantification of HSP90 and acTub. n=1 (C) 200,000 cells were seeded on 6 well plate and incubated over night for adhesion. After this time cells were stimulated as shown in FIG. 2 C. Cells were harvested with Trypsin/EDTA and then prepared for SDS-PAGE and western blotting. HSP90 was used as loading control. The diagram shows a representative quantification of HSP90 and acTub. n=1

Figure 3:
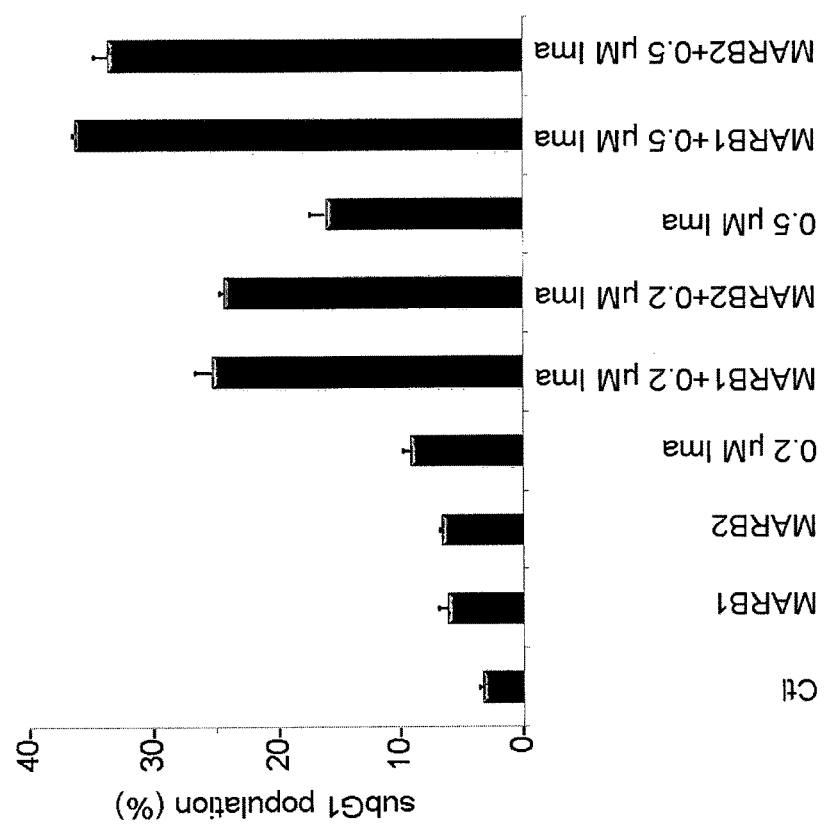
FIG. 3. The novel HDAC6 inhibitors of the invention destabilize BCR-ABL and induce enhanced apoptosis in combination with imatinib.
Figure 3:
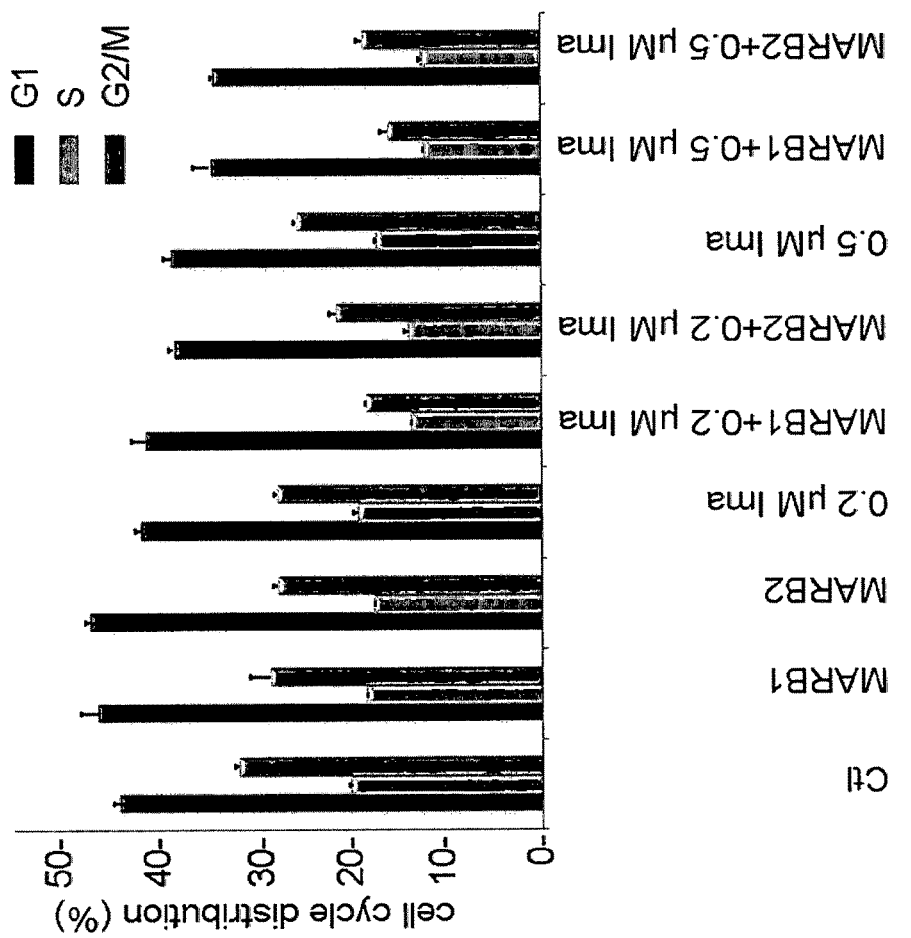
Figure 3:
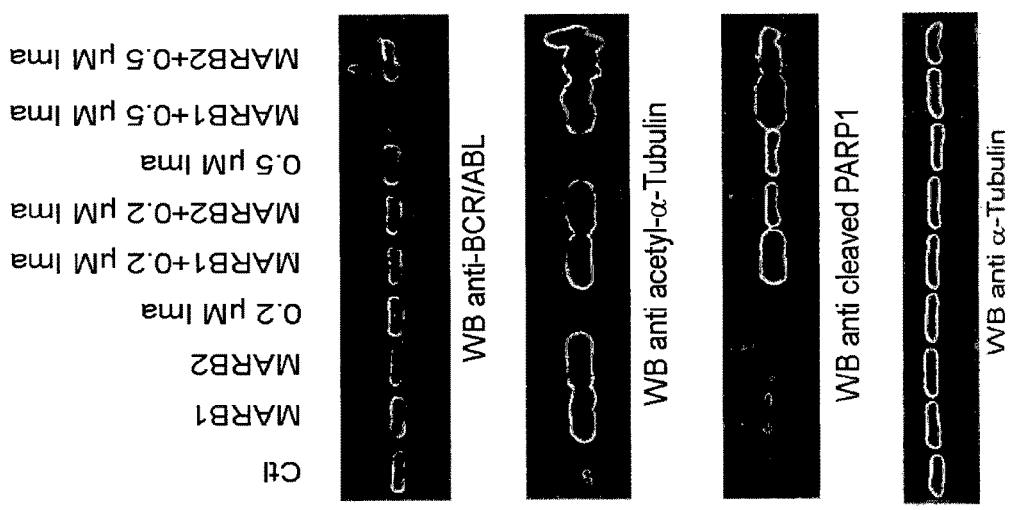
Figure 8:
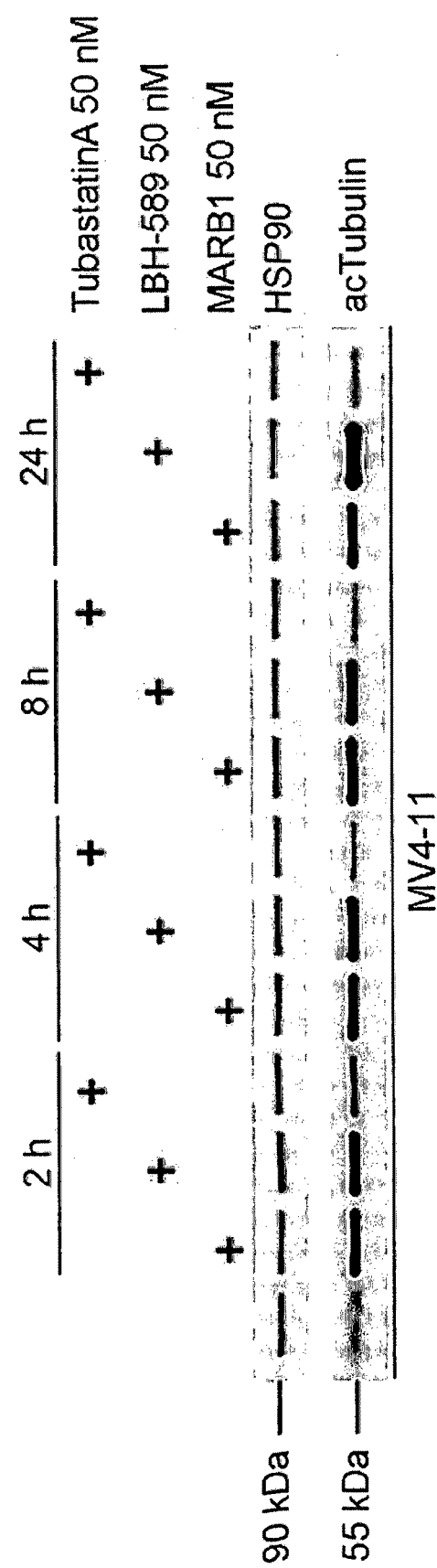

FIG. 8 Effectiveness of MARB1 compared with a pan-HDACi and the established HDAC6 inhibitor Tubastatin A LBH589 an effective pan-HDACi and Tubastatin A a selective inhibitor were used in comparison to MARB1. All 3 substances were incubated with 50 nM and in a short time course. FIG. 3 exhibits these results. 1 Mio cells were seeded in 6 well plate. Thereafter the cells were incubated 2 h for adapting and afterward the stimulation as shown in the figure started. HSP90 was used as loading control. n=3

Figure 9:
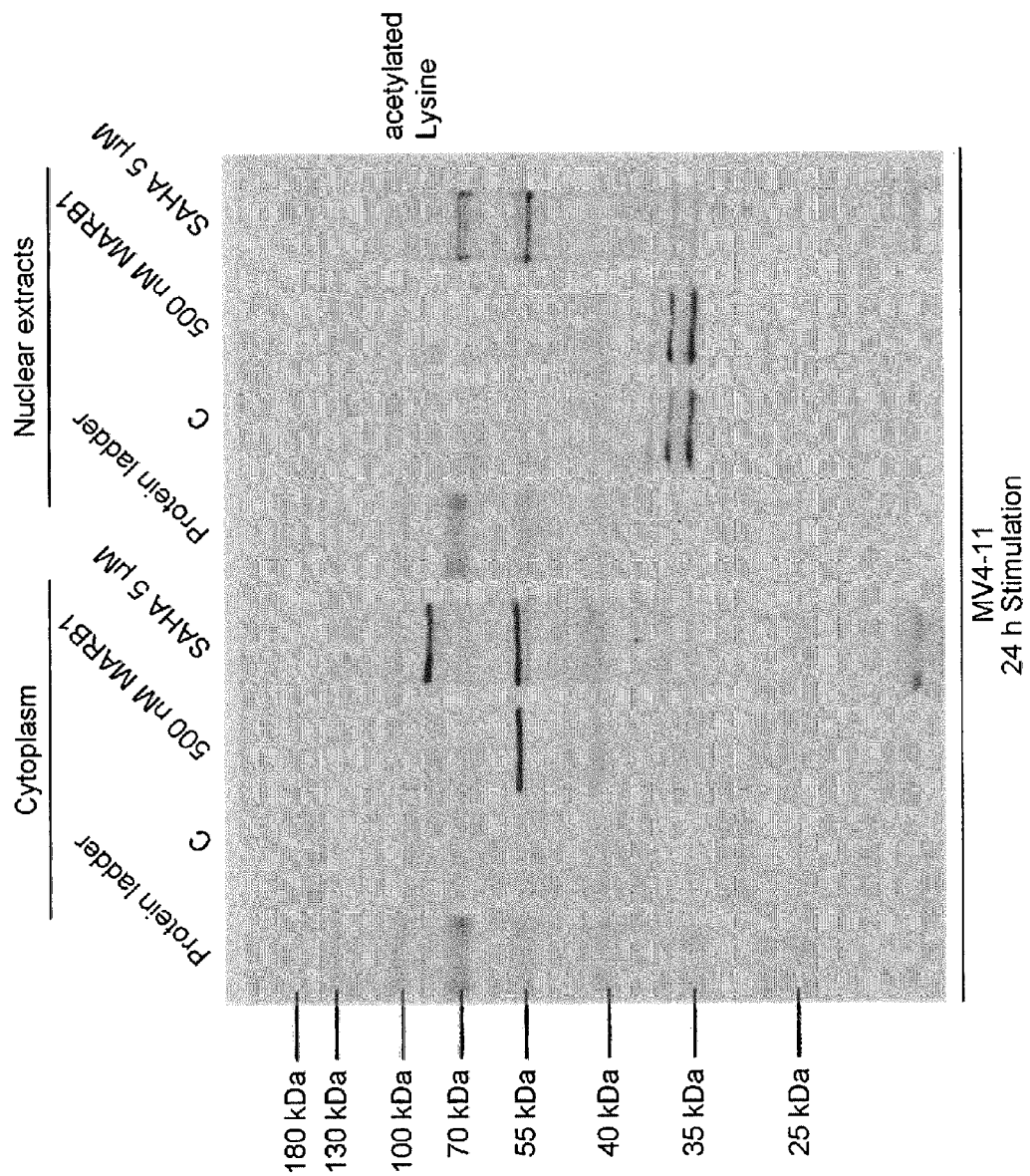
Figure 9B:
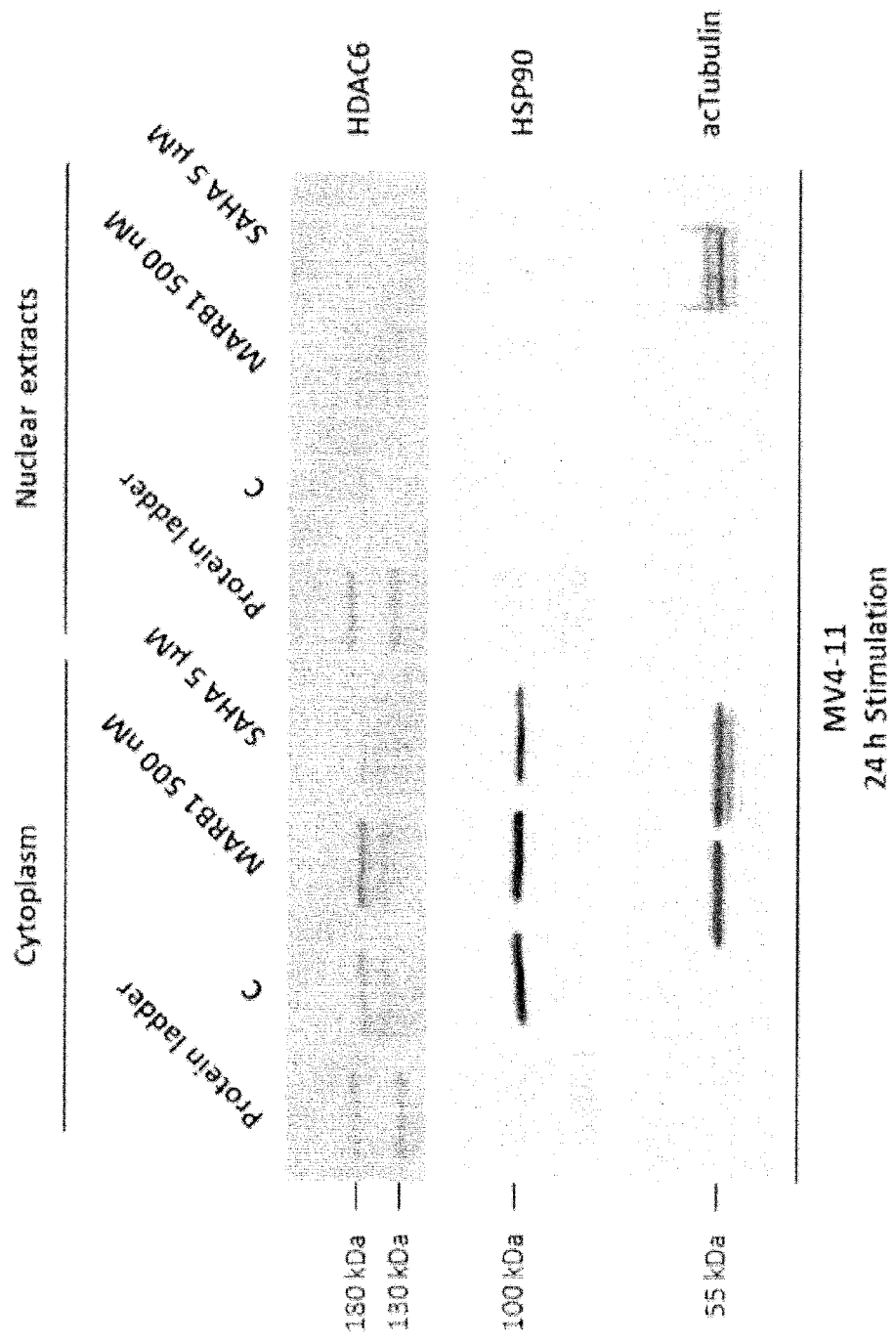

FIG. 9. Hyperacetylation of proteins in nuclear extracts and in the cytoplasm after MARB1 stimulation Nuclear extracts were generated and compared to the cytoplasm by western blotting. 6 Mio cells were seeded on a 10 cm dish and incubated 2 h in the medium for adaption. The cells were stimulated as shown in the figure. SAHA and Vorinostat are pan-HDACi. HSP90 was used as a loading control for the cytoplasm. n=2

Figure 10A:
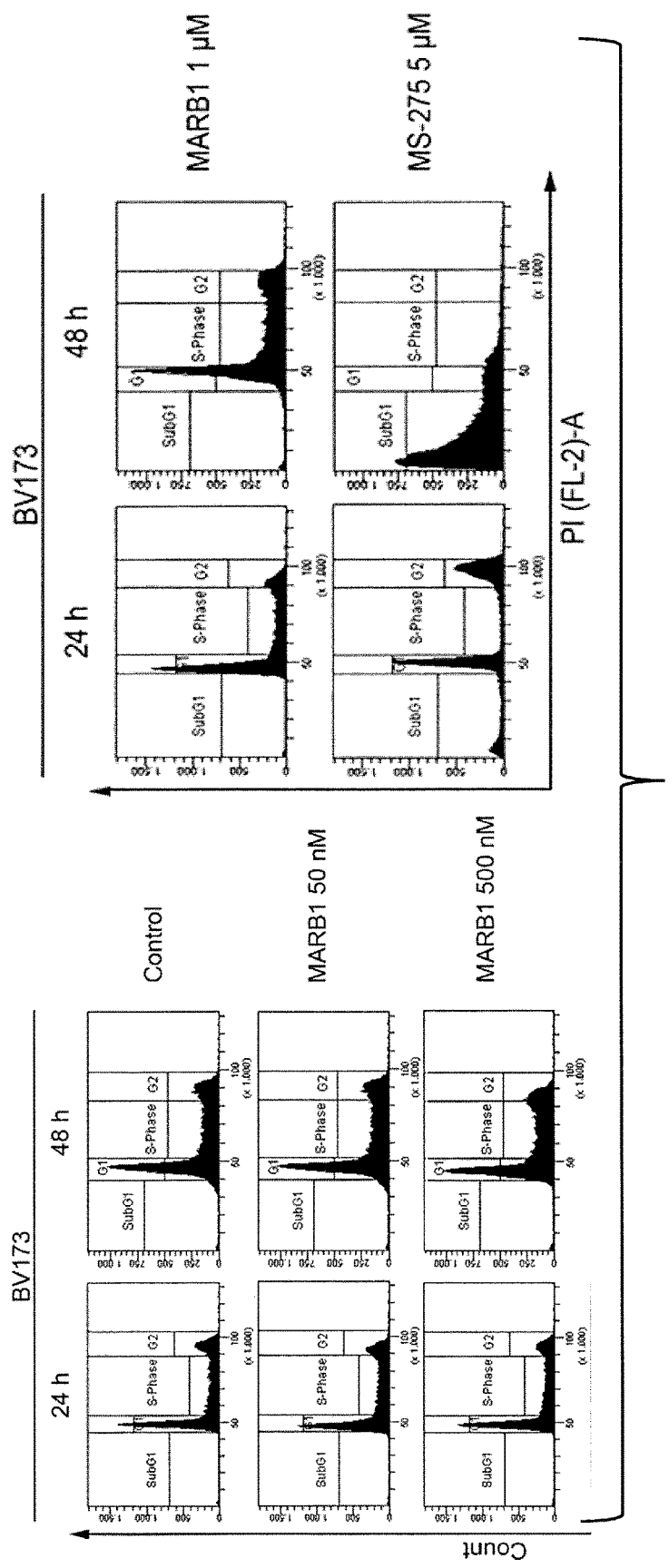
Figure 10:
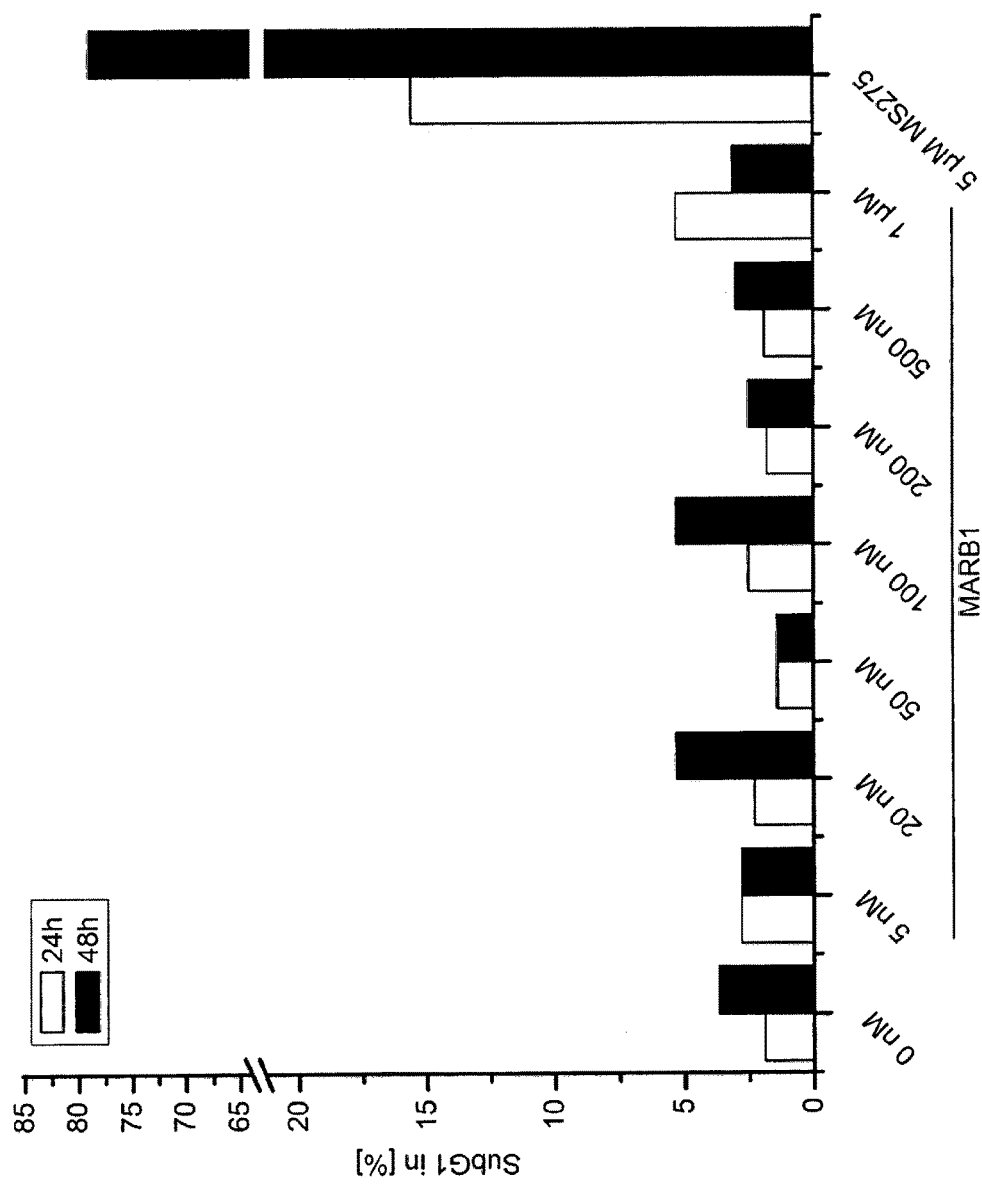

FIG. 10. Influence on the cell cycle after MARB1 stimulation 150,000 cells were seeded in 12 well plate and incubated for 2 h for adaption. Cells were harvested on ice and prepared for FACS analysis (following method b). The FACS blots were generated using FACS diva software. n=1

Figure 11:
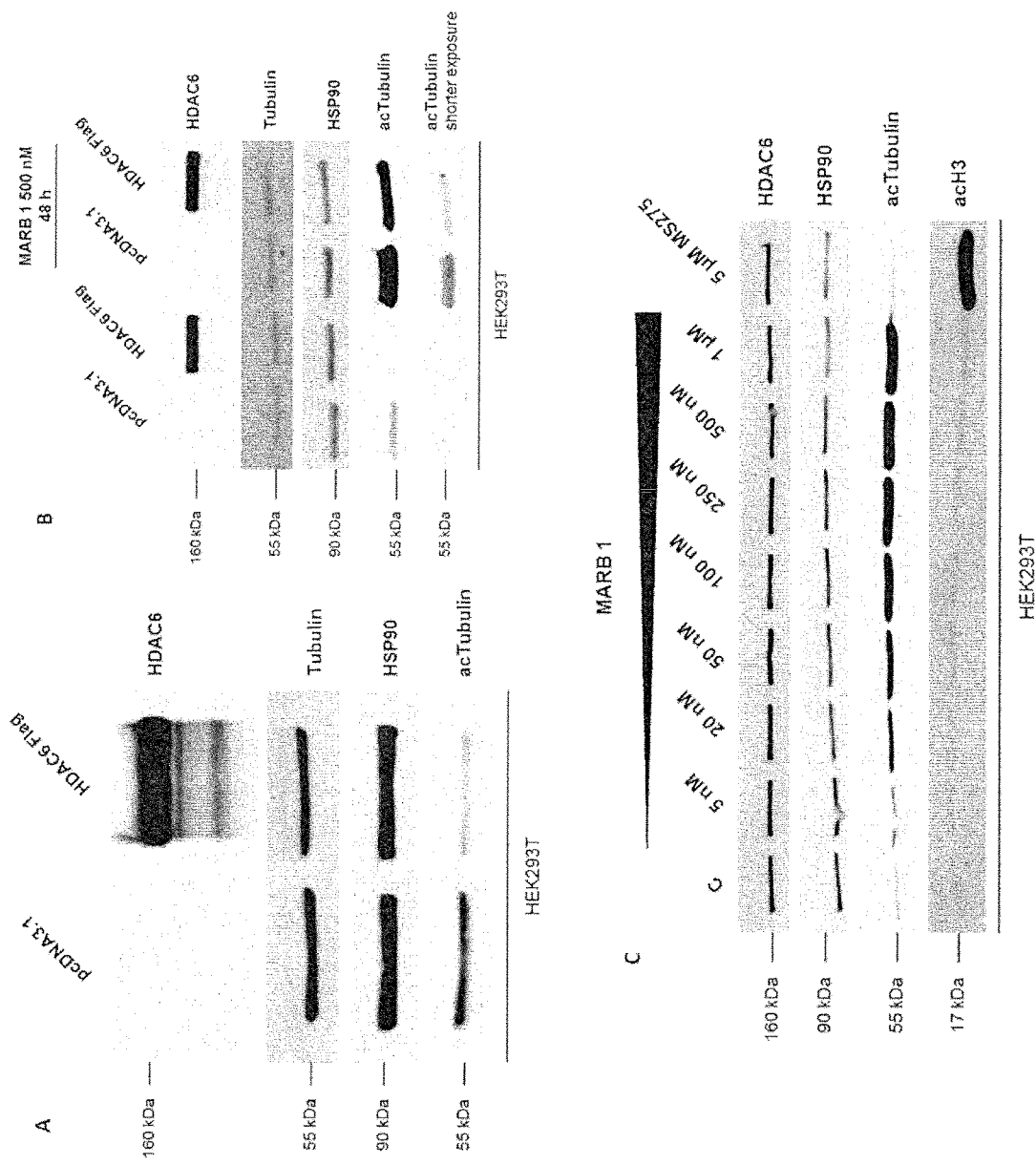

FIG. 11. Overexpression of HDAC6 in HEK293T cells

The cells were either transfected with the empty vector pcDNA3.1 which resulted in a higher level of acTub or with HDAC6 flag causing overexpression of HDAC6. However, it is mention worth that MARB1 increases the amount of acetylated tubulin in cells with HDAC6 overexpression. 400,000 cells were seeded on a 6 well plate and incubated for 24 h for adapting and the transfection was allowed for 48 h. (A) The figure shows how the transfection works. HSP90 and Tubulin were used as loading control. The cells were collected on ice using Trypsin/EDTA. The overexpression was identified by using the HDAC6 antibody described in Antibodies and Plasmids. n=3 (B) The cells were transfected as described previously and collected under sterile conditions using Trypsin/EDTA. Cells were centrifuged and resuspended in new DMEM with FBS and pen/strep. The cells were splitted 1:2 and seeded per sample into two wells. After 24 h adhesion time cells were stimulated with MARB1 for 48 h. Thereafter cells were collected on ice using Trypsin/EDTA and prepared for SDS-PAGE. Tubulin and HSP90 were used as loading control. n=1 (C) This figure shows the sensitivity of HEK293T cells against MARB1. The samples were generated as described previously. HSP90 was used as loading control. n=1

Figure 12:
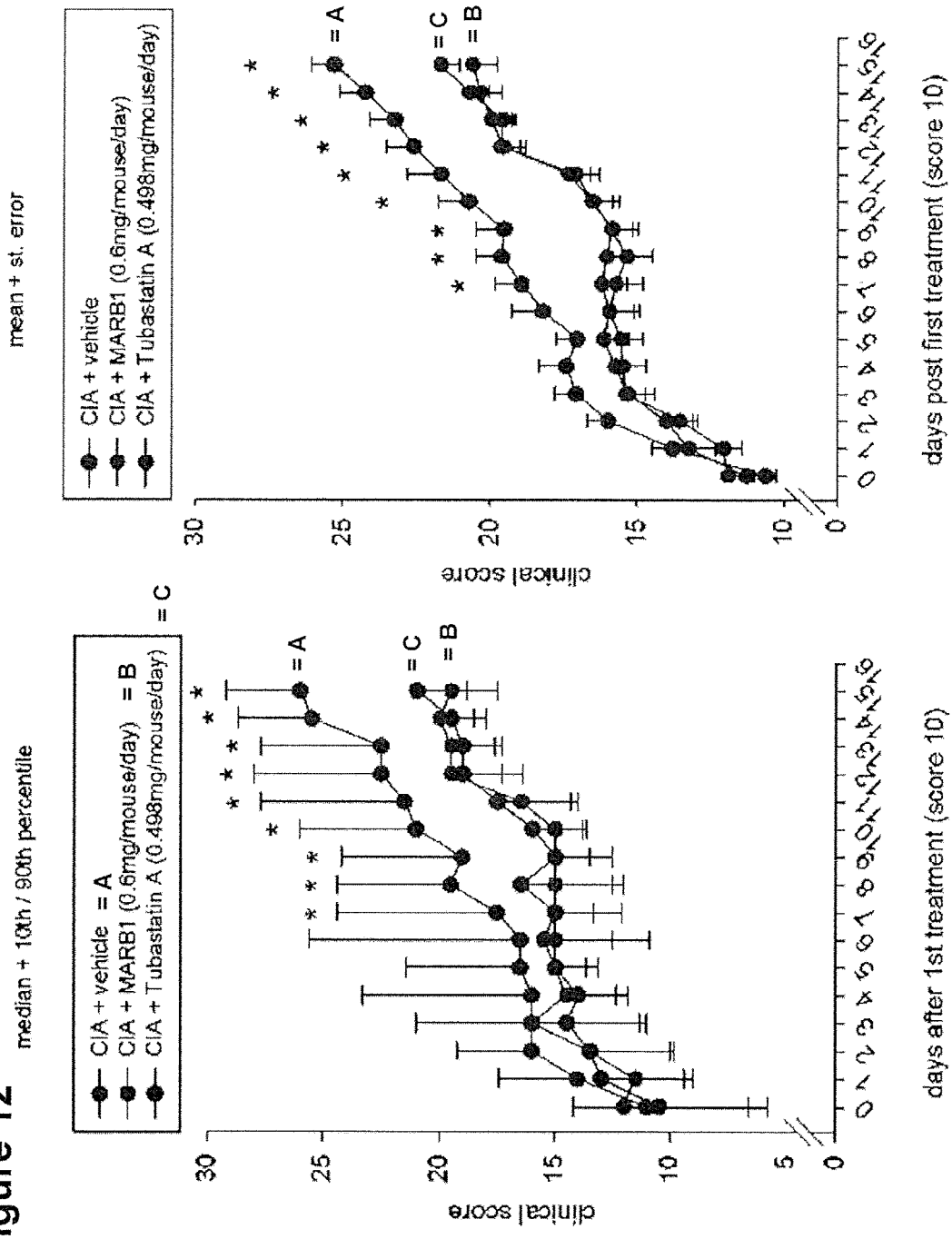

FIG. 12. Effect of MARB1 and Tubastatin on the clinical score of collagen induced arthritic mice.

Figure 13:
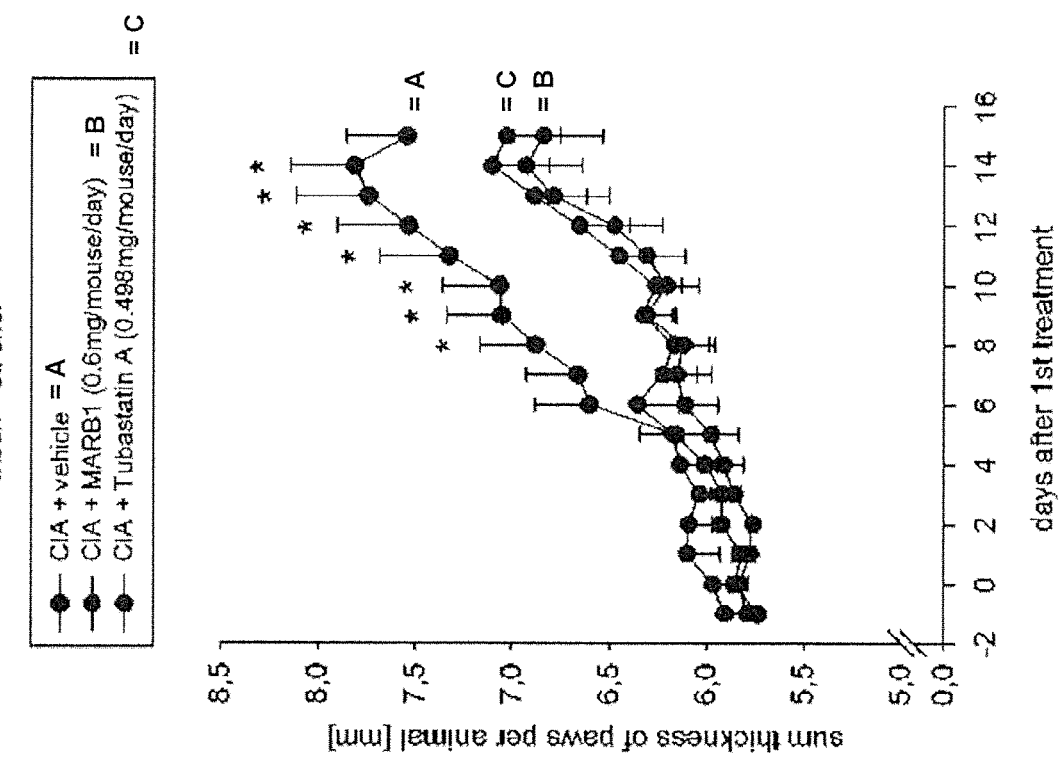

FIG. 13. The Effect of MARB1 and Tubastatin A on paw thickness [mm]

EXAMPLES

1. Materials and Methods

Tumor Cell Lines

The following tumor cell lines were used:

Human breast cancer cell lines MAXF 401 and MAXF MCF-7 (Oncotest GmbH, Freiburg, Germany)

Human prostate cancer cell lines PRXF DU-145, PRXF LNCaP, PRXF PC-3M (Oncotest GmbH, Freiburg, Germany)

Human uterus cancer cell line UXF 1138 (Oncotest GmbH, Freiburg, Germany)

Human leukemia cell lines BV 173 and K562 with BCR-ABL mutation (Leibniz Institute DSMZ—German Collection of Microorganisms and Cell Cultures, DSMZ Accession Nos: ACC-20 and ACC-10).

Human embryonic kidney cell line HEK293T/Dulbecco's Modified Medium (DMEM) (Sigma) with 10% FBS and 1% Pen/Strep were used for culturing.

Human leukemia cell line HEL with JAK2 V617F mutation (DSMZ Accession No: ACC-11).

Human leukemia cell line MV4-11 with FLT3-ITD mutation (American Type Culture Collection, ATCC Accession No: CRL-9591).

Human colon cancer cell lines RKO (ATCC Accession No: CRL-2577) and HCT-116 (DSMZ Accession No: ACC-581).

Cells are cultured in DMEM (colon cancer cells) or RPMI (leukemic cells) plus 10% fetal calf serum and penicillin/streptomycin.

Substances

The following commercially available substances and compounds were used:

Imatinib (Selleckehem), Pan-HDACi TSA (Selleckchem), TMP 269 (Reaction Biology.com), LBH589 (Selleckchem), Butyrate (Sigma Aldrich), and Staurosporin (SP) (Sigma Aldrich).

HPLC Methods

Analytical HPLC using a system from Merck (Darmstadt, Germany) with a L-5000 controller, a 655A-12 pump, 655A-40 autosampler and L-4250 UV-Vis detector at a Eurospher-100 C-18 column (250×4 mm, 5 microns, Knauer, Berlin), was carried out at a flow rate of 0.8 mL min$^{-1}$. A system of Merck with a L-5000 controller, a L6200A pump, a AS2000A autosampler, an L-4000 UV-Vis detector and an Eurospher-100 C-18 column (250×4 mm, 5 micron, Knauer, Berlin) was used. Mobile phase: 0.10% trifluoroacetic acid/acetonitrile (aqu.) (gradient from 80:20 to 20:80); constant degassed with helium. The degree of purity is calculated by integrating the peak area at 220 nm.

Preparative HPLC was performed using a HPLC system from Knauer (Berlin) with two K-1800 pumps, a K-2001 UV-Vis detector (at 220 nm), and a RP column (VP Nucleodur 100-5 C-18 ec, 250×21 mm, 5 micron, Macherey Nagel, Duren) at a flow rate of 15.0 mL min$^{-1}$. The mobile phase consists of ≤0.10% trifluoroacetic acid and acetonitrile (gradient from 80:20 to 20:80). 30 mg of the substance were dissolved in DMF (1.00 mL) and mobile phase 2.00 mL (0.10% trifluoroacetic acid and acetonitrile [80:20]). Per run 1.00 mL was injected. The acetonitrile was evaporated from the eluate prior to freeze-drying at 45° C.

Fluorescence HDAC Assay

Testing was performed by Reaction Biology Corp., Malvern, Pa., USA, using human HDAC1 (CAT#: HDAC1), human HDAC2 (CAT#: HDAC2), human HDAC6 (CAT#: HDAC6), human HDAC8 (CAT#:HDAC8) or human HDAC11 (CAT#:HDAC11) and fluorogenic peptide from p53 residues 379-382 (RHKKAc) as substrate. In case of HDAC4 (Histone Deacetylase 4, Class IIa) (CAT#:HDAC4) human HDAC4 and (Boc-Lys(trifluoroacetyl)-AMC) as fluorogenic HDAC Class2a substrate was used. For details, see http://www.reactionbiology.com/webapps/site/HDACAssay.aspx?page=HDACs&id=3.

FACS Analysis

The assay is carried out as described in Pietschmann et al., 2012 and Brandl et al. 2012. Briefly, $10^5$ cells were fixed in 1 ml 70% EtOH with 0.05% Tween-20 overnight at 4° C. The following day, cells were washed with 3 ml 38 mM sodium citrate, pH 7.4, and incubated for 20 min at 37° C.

in 0.5 ml 38 mM sodium citrate, pH 7.4, supplemented with 50 µg/ml propidium iodide and 10 µg/ml RNase-A. DNA contents of the cells were measured by fluorescence-activated cell sorter (FACS). This method allows detection of the apoptotic subG1-fraction, which has a DNA content below 2n due to apoptotic cleavage of DNA. Equally, the cell cycle profile can be assessed with this method.

FACS Analysis Method b

After harvesting the cells on ice and washing them with 1 ml cold PBS, the Pellet were fixed for 1 h in 80% Ethanol by −20° C. After centrifugation the supernatant was discarded and the pellet was resuspended in 333 µl PBS with 10 µg RNase. The cells were incubated 1 h at room temperature with RNase before adding propidium iodide to a final concentration of 16.4 µg/ml and measured by flow cytometry (BD FACS Canto II).

Western Blot Analysis a

The assay is carried out as described in Buchwald et al. 2010 and Buchwald et al. 2013. Briefly, cells were collected and lysed in NET-N buffer (150 mM NaCl, 1 mM EDTA, 50 mM Tris-HCl (pH 7.8), 0.5% Nonidet P-40 (NP-40), 1 mM phenylmethylsulfonyl fluoride, 0.5 mg/ml leupeptin and 0.5 mg/ml pepstatin) followed by mild sonification on ice. Protein lysate (50-100 mg) was boiled in Laemmli buffer and separated on SDS-polyacrylamide gel electrophoresis for western blotting with specific antibodies. All lysates were assessed by Bradford assay for protein concentrations.

SDS-PAGE and Western Blot Analysis Method b

Western Blot analysis method b was used for the blots illustrated in FIGS. 6 to 9 and 11: Equal amounts of proteins were separated with a sodium dodecyl sulfate-polyacrylamide gel electrophoresis (SDS-PAGE) using an electrophoresis buffer by Laemmli with 1% SDS. The proteins were transferred to a nitrocellulose membrane by western blotting using a wet blot chamber. The blots were incubated with the primary antibody, after blocking the membrane for 1 h in 5% non-fat dry milk in tris-buffered saline (TBS) containing 0.05% Tween-20. Fluorescence coupled secondary antibodies (LI-COR) were used and the signal was measured on the Odyssey to detect the proteins.

Antibodies and Plasmids

For the transfection of HEK293T with HDAC6 by the plasmid 13823: HDAC6-Flag was purchased from addgene. The empty vector pcDNA3.1 was received from Invitrogen. The following antibodies were used for western blot analysis: HSP90 AC88 (Enzo), HDAC6 (Cell Signaling), Tubulin (Abcam), β-Actin (Sigma), acetylated Histone 3 (acH3) (Millipore), acetylated Tubulin (acTubulin) (Sigma) and acetylated Lysine (acLys) (Cell Signaling).

Cell Lysis, Immunoprecipitation and Nuclear Extracts

The cells were harvested on ice and lysed in NET-N lysis buffer containing 100 mM NaCl, 10 mM Tris-HCl pH 8.0, 10% Glycerol, 1 mM EDTA, 0.5% NP-40 and phosphatase (phosphatase inhibitor cocktail 2 from sigma) and a protease inhibitor (protease inhibitor cocktail tablets mini cOmplete from Roche). The cells were homogenized by a sonifier, after centrifugation a 6-fold SDS-loading buffer by Laemmli was added and the samples were stored at −80° C. (Buchwald et al., 2010).

For immunoprecipitation cells were seeded on a 10 cm dish, collected on ice and lysed in a lysis buffer containing 50 mM HEPES, 0.15 M NaCl, 1 mM EDTA, 0.5% NP-40, 40 mM 3-Glycerophosphat and 1 mM DTT, phosphatase und protease inhibitors as described previously. The cells were incubated for 10 min-20 min and homogenized by sonication. The protein level was measured by Bradford assay. After normalization of the protein level 1-2 µg antibody were added to the samples and incubated rotating over night at 4° C. On the next day 100 µl of Protein G Sepharose Beats (Sigma) were added to the lysates, after washing 3 times. The samples were incubated for 4 h rotating at 4° C. After the incubation the beats were washed 3 times with lysis buffer and/or PBS and a 6 fold loading buffer was added. The beats with loading buffer were heated for 5 min at 95° C. and the buffer was transferred with an insulin syringe into a new 1.5 reaction vessel, in order to get the samples for the SDS-PAGE (Buchwald et al., 2010).

The cells for nuclear extracts were harvested on ice after stimulation and washed with cold PBS. The pellet was resuspended in lysis buffer A (10 mM HEPES pH 7.9, 1.5 mM $MgCl_2$, 10 mM KCl, 1 mM DTT and protease and phosphatase inhibitor) and incubated for 15 min on ice followed by addition of NP-40 to a final concentration of 1%. Samples were centrifuged to get the cytoplasmic fraction. The pellet was washed with an isotonic buffer (10 mM Tris-HCl pH 7.4, 150 mM NaCl). Thereafter, the pellet containing nuclei was lysed in lysis buffer B (20 mM HEPES-KOH pH 7.9, 420 mM NaCl, 1.5 mM $MgCl_2$, 0.5 mM EDTA, 25% Glycerol) to get the nuclear fraction. The used buffer also contained protease and phosphatase inhibitor. The pellet was incubated for 20 min at 4° C. and after incubation time, the samples were centrifuged and the supernatant—nuclear fraction—was stored at −80° C. The protein level was assessed by Bradford assay (Goder et al. 2015).

Transfection of HEK293T Cells

Cells were seeded on a 6 well plate. After 24 h adaption time the cells were transfected. Therefore 4 µl Turbofectamin (Thermoscientific) and 2 µg plasmid were mixed in 200 µl Opti-MEM® (modified Eagle's Minimum Essential Medium) (Gibco) and incubated for 20 min at room temperature. After the incubation the mix was added to the cells and incubated for 48 h. Afterwards the cells were either collected on ice and prepared for SDS-PAGE or seeded again and stimulated for 48 h with 500 nM MARB1.

Example 1 Synthesis

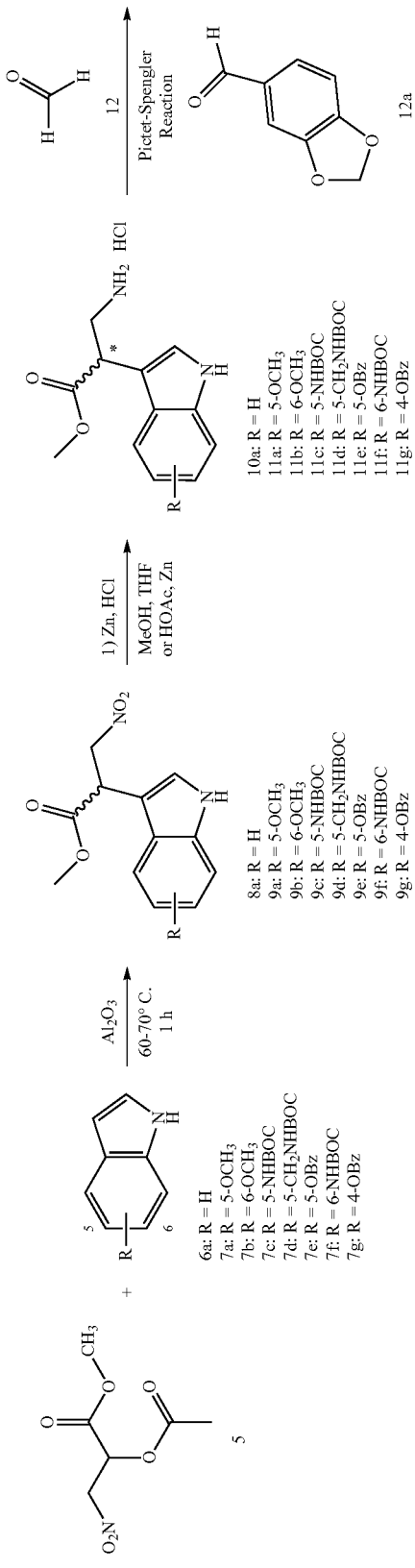
Scheme 1: Synthesis of the tetrahydro-β-carboline basic structure illustrated with 18a-19e as examples.

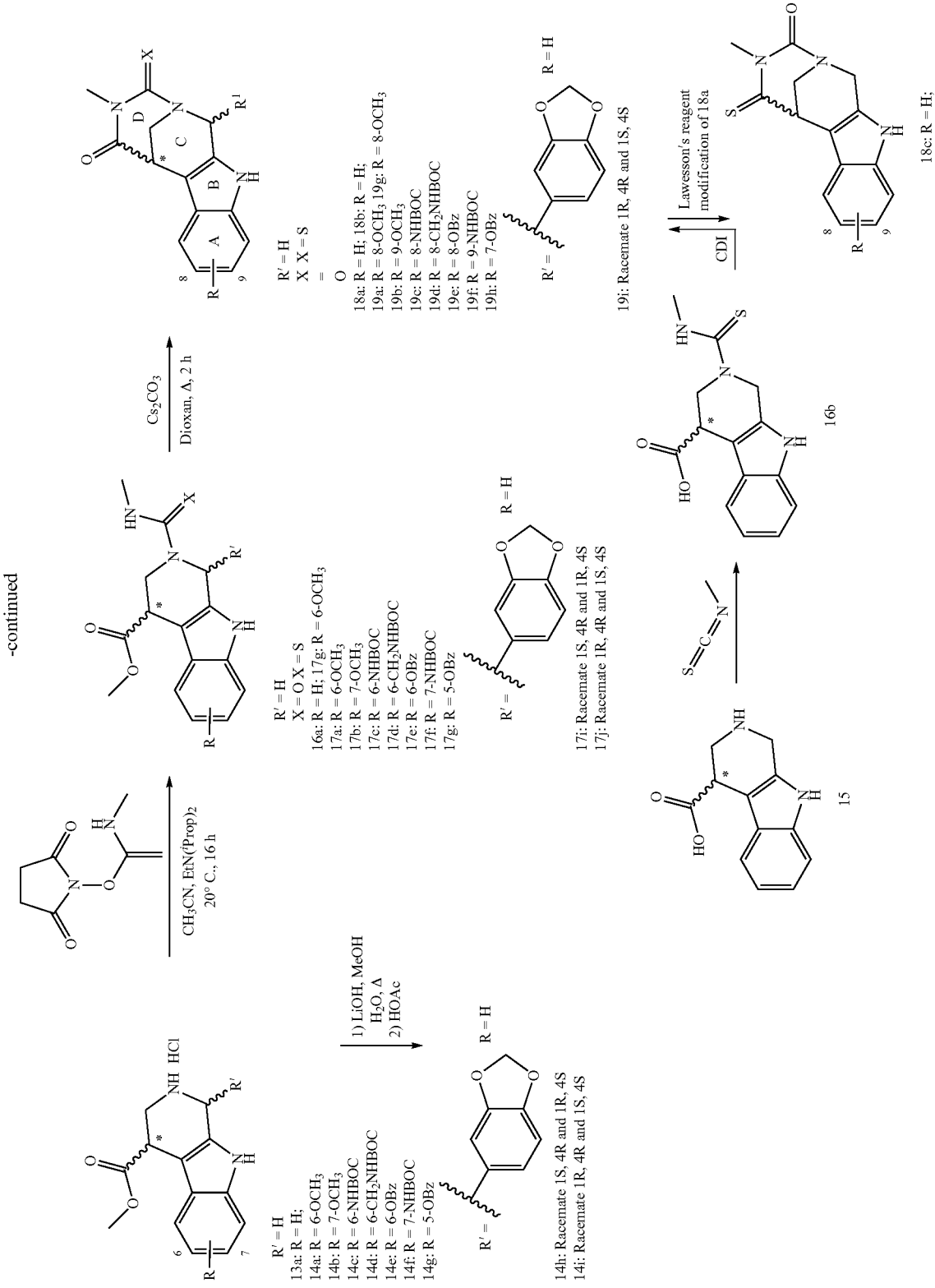

Methyl 2-(1H-indol-3-yl)-3-nitropropanoate (8a) according to Ballini et al., 2008

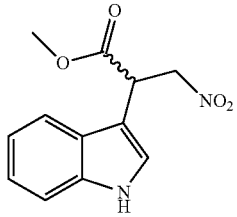 [SMILES: COC(=O)C(C[N+](=O)[O-])c1c[nH]c2ccccc12]

$^1$H NMR (300 MHz, DMSO-d$_6$): δ 11.22 (s, 1H), 7.63 (d, J=7.8 Hz, 1H), 7.39 (dd, J=5.3, 2.7 Hz, 2H), 7.22-7.08 (m, 1H), 7.08-6.98 (m, 1H), 5.30 (dd, J=14.9, 10.4 Hz, 1H), 4.95 (dd, J=14.9, 5.1 Hz, 1H), 4.74 (dt, J=12.0, 6.0 Hz, 1H), 3.62 (s, 3H).

Methyl 2-(5-methoxy-1H-indol-3-yl)-3-nitropropanoate (9a) according to Ballini et al., 2008

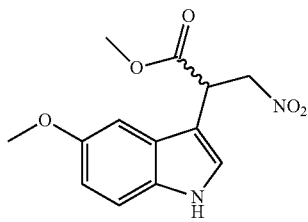 [SMILES: COC(=O)C(C[N+](=O)[O-])c1c[nH]c2ccc(OC)cc12]

$^1$H NMR (300 MHz, CDCl$_3$): δ 8.24 (s, 1H), 7.27 (d, J=8.8 Hz, 1H), 7.08 (dd, J=5.1, 2.5 Hz, 2H), 6.90 (dd, J=8.8, 2.4 Hz, 1H), 5.20 (dd, J=14.2, 9.7 Hz, 1H), 4.72 (dd, J=9.7, 5.0 Hz, 1H), 4.63 (dd, J=14.2, 5.0 Hz, 1H), 3.87 (s, 3H), 3.74 (s, 3H).

Methyl 2-(6-methoxy-1H-indol-3-yl)-3-nitropropanoate (9b) according to Ballini et al., 2008

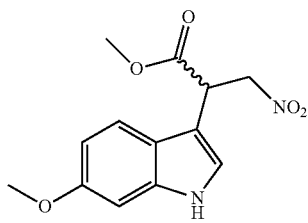 [SMILES: COC(=O)C(C[N+](=O)[O-])c1c[nH]c2cc(OC)ccc12]

$^1$H NMR (400 MHz, DMSO): δ 10.99 (s, 1H), 7.49 (d, J=8.7 Hz, 1H), 7.23 (d, J=2.4 Hz, 1H), 6.88 (d, J=2.2 Hz, 1H), 6.71 (dd, J=8.7, 2.3 Hz, 1H), 5.26 (dd, J=14.9, 10.4 Hz, 1H), 4.92 (dd, J=14.9, 5.1 Hz, 1H), 4.69 (dd, J=10.4, 5.0 Hz, 1H), 3.76 (s, 3H).

Methyl 2-(5-((tert-butoxycarbonyl)amino)-1H-indol-3-yl)-3-nitropropanoate (9c) according to Ballini et al., 2008

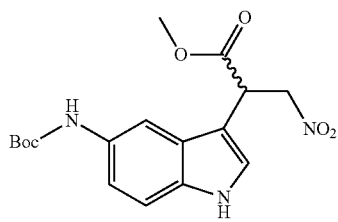 [SMILES: COC(=O)C(C[N+](=O)[O-])c1c[nH]c2ccc(NC(=O)OC(C)(C)C)cc12]

mp 78-80° C. IR (KBr): 1728 cm$^{-1}$. $^1$H NMR (300 MHz, DMSO): δ 11.09 (d, J=1.9 Hz, 1H), 9.11 (s, 1H), 7.76 (s, 1H), 7.34 (d, J=2.5 Hz, 1H), 7.25 (d, J=8.7 Hz, 1H), 7.13 (d, J=8.6 Hz, 1H), 5.26 (dd, J=14.9, 10.4 Hz, 1H), 4.93 (dd, J=14.9, 5.1 Hz, 1H), 4.64 (dd, J=10.4, 5.1 Hz, 1H), 3.62 (s, 3H), 1.49 (s, 9H). ESI-MS m/z (%): 727 [2MH$^+$] (100), 381 [MNH$_4^+$] (75), 364 [MH$^+$] (30).

Methyl 2-(5-(((tert-butoxycarbonyl)amino)methyl)-1H-indol-3-yl)-3-nitropropanoate (9d)

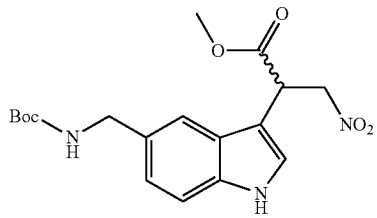 [SMILES: COC(=O)C(C[N+](=O)[O-])c1c[nH]c2ccc(CNC(=O)OC(C)(C)C)cc12]

mp 120-123° C. $^1$H NMR (300 MHz, DMSO): δ 11.18 (s, 1H), 7.49 (s, 1H), 7.34 (dt, J=16.4, 5.1 Hz, 3H), 7.04 (d, J=8.3 Hz, 1H), 5.30 (dd, J=14.9, 10.4 Hz, 1H), 4.93 (dd, J=14.9, 5.0 Hz, 1H), 4.72 (dd, J=10.4, 5.0 Hz, 1H), 4.20 (d, J=6.0 Hz, 2H), 3.67-3.57 (m, 3H), 1.41 (s, 9H). ESI-MS m/z (%): 755 [2MH$^+$] (93), 395 [MNH$_4^+$] (100), 378 [MH$^+$] (50).

Methyl 2-(5-(benzyloxy)-1H-indol-3-yl)-3-nitropropanoate (9e) was prepared according to Sui et al., 2007

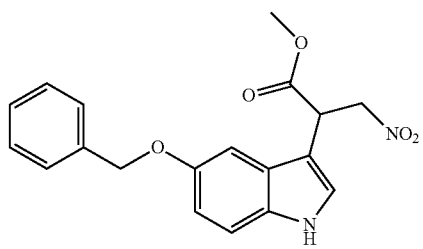 [SMILES: COC(=O)C(C[N+](=O)[O-])c1c[nH]c2ccc(OCc3ccccc3)cc12]

Methyl 2-(6-((tert-butoxycarbonyl)amino)-1H-indol-3-yl)-3-nitropropanoate (9f)

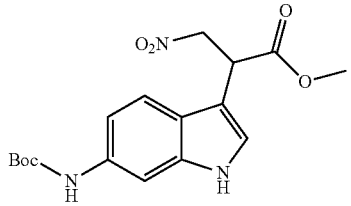 [SMILES: COC(=O)C(C[N+](=O)[O-])c1c[nH]c2cc(NC(=O)OC(C)(C)C)ccc12]

Methyl 2-(6-((tert-butoxycarbonyl)amino)-1H-indol-3-yl)-3-nitropropanoate (9f) was prepared according to Sui et al., 2007. Colorless crystals (7.00 g, 19.23 mmol, 29%), mp: 167.7-172.0° C.; IR (KBr): 3343, 1725, 1702 cm$^{-1}$; $^1$H NMR (300 MHz, DMSO): δ 11.04 (s, J=1.7 Hz, 1H), 9.25 (s, 1H), 7.70 (s, 1H), 7.47 (d, J=8.6 Hz, 1H), 7.26 (d, J=2.3 Hz, 1H), 7.05 (dd, J=8.7, 1.6 Hz, 1H), 5.28 (dd, J=14.9, 10.5 Hz, 1H), 4.93 (dd, J=15.0, 5.0 Hz, 1H), 4.69 (dd, J=10.4, 4.9 Hz, 1H), 3.62 (s, 3H), 1.49 (s, 9H). ESI-MS m/z (%): 308 [MH$^+$–C$_4$H$_8$] (100), 364 [MH$^+$] (4).

Methyl 2-(4-(benzyloxy)-1H-indol-3-yl)-3-nitropropanoate (9g) was prepared according to Sui et al. (2007)

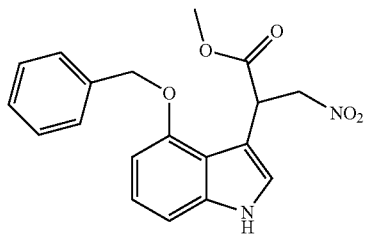 [SMILES: COC(=O)C(C[N+](=O)[O-])c1c[nH]c2cccc(OCc3ccccc3)c12]

1.1 General procedure 1 (GP1) using the example of methyl 3-amino-2-(1H-indol-3-yl)propanoate hydrochloride (10a)

To a solution of methyl 2-(1H-indol-3-yl)-3-nitropropanoate (8a) (6.20 g; 25.0 mmol) in THF (155 mL) and MeOH (155 mL) was added zinc dust (31.0 g) and CuSO$_4$ (0.62 g). The solution was stirred and HCl (3N, 310 mL) was added dropwise in a rate, that the solution heated to reflux. The solution was stirred for 2 h, filtrated and then adjusted to pH 14 with NH$_3$ conc. The product was extracted with CH$_2$Cl$_2$ (3×100 mL). The combined organic layers were dried (Na$_2$SO$_4$) and evaporated. The residue was dissolved in THF (60 mL) and HCl (6N in dioxane) was added with stirring. The colorless product was filtered off, washed with THF and Et$_2$O and dried.

Methyl 3-amino-2-(1H-indol-3-yl)propanoate hydrochloride (10a) (Bartoli et al., 2005)

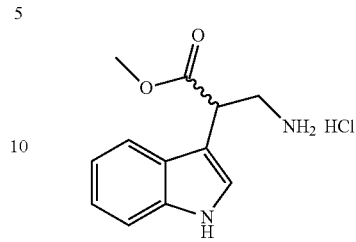

5.30 g (83%) colorless crystals. mp 199.5-199.7° C. IR (KBr): 3312, 3022, 2977, 1732 cm$^{-1}$. $^1$H NMR (300 MHz, DMSO-d$_6$): δ 11.28 (s, 1H), 8.20 (s, 3H), 7.57 (d, J=7.8 Hz, 1H), 7.40 (d, J=8.0 Hz, 1H), 7.34 (d, J=2.5 Hz, 1H), 7.17-6.98 (m, 2H), 4.35 (dd, J=7.9, 6.8 Hz, 1H), 3.61 (d, J=7.6 Hz, 3H), 3.49 (s, 1H), 3.17 (s, 1H). ESI-MS m/z (%): 219 [MH$^+$] (100). Anal. calcd for C$_{12}$H$_{15}$ClN$_2$O$_2$: C, 56.58; H, 5.94; N, 11.00; found: C, 56.74; H, 6.27; N, 10.86.

Methyl 3-amino-2-(5-methoxy-1H-indol-3-yl)propanoate hydrochloride (11a)

According to 10 (GP1) from Methyl 2-(5-methoxy-1H-indol-3-yl)-3-nitropropanoate (9a) (7.18 g; 25.00 mmol). 5.96 g (84%) colorless crystals. mp 197.5-197.7° C. $^1$H NMR (300 MHz, DMSO-d$_6$): δ 11.12 (d, J=1.9 Hz, 1H), 8.20 (s, 3H), 7.28 (t, J=5.1 Hz, 1H), 7.26 (d, J=2.6 Hz, 1H), 7.10 (d, J=2.4 Hz, 1H), 6.77 (dd, J=8.8, 2.4 Hz, 1H), 4.33 (dd, J=8.1, 6.4 Hz, 1H), 3.76 (s, 3H), 3.64 (s, 3H), 3.46 (dd, J=12.7, 8.3 Hz, 1H), 3.13 (dd, J=12.7, 6.3 Hz, 1H). ESI-MS m/z (%): 285 [MH$^+$] (100). Anal. calcd for C$_{13}$H$_{17}$ClN$_2$O$_3$: C, 54.84; H, 6.02; N, 9.84; found: C, 54.74; H, 6.07; N, 10.06.

Methyl 3-amino-2-(6-methoxy-1H-indol-3-yl)propanoate hydrochloride (11b)

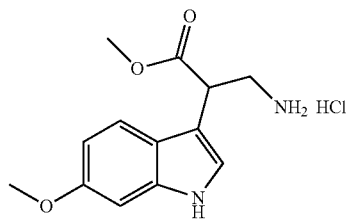 [SMILES: COC(=O)C(CN)c1c[nH]c2cc(OC)ccc12 ; Cl]

According to 10 (GP1) from Methyl 2-(6-methoxy-1H-indol-3-yl)-3-nitropropanoate (9b) (5.00 g; 20.00 mmol).

3.80 g; 13.30 mmol (67%) colorless crystals. IR (KBr): 1724, 3414 cm$^{-1}$. $^1$H NMR (400 MHz, DMSO): δ 11.06 (d, J=1.5 Hz, 1H), 8.19 (s, 3H), 7.44 (d, J=8.7 Hz, 1H), 7.18 (d, J=2.4 Hz, 1H), 6.89 (d, J=2.2 Hz, 1H), 6.70 (dd, J=8.7, 2.3 Hz, 1H), 4.30 (dd, J=8.1, 6.5 Hz, 1H), 3.76 (s, 3H), 3.62 (s, 3H), 3.54-3.39 (m, 1H), 3.14 (s, 1H). ESI-MS m/z (%): 249 [MH$^+$] (100).

Methyl 3-amino-2-(5-((tert-butoxycarbonyl)amino)-1H-indol-3-yl)propanoate hydrochloride (11c)

Methyl 2-(5-((tert-butoxycarbonyl)amino)-1H-indol-3-yl)-3-nitropropanoate (9c) (8.40 g; 23.10 mmol) was dissolved in acetic acid (84 mL) and a catalytic amount of CuSO$_4$ (0.5 g) and zinc dust (16.8 g) was added in small portions whilst stirring within 3 h at room temperature. After completion of the addition the mixture was stirred for an additional hour, diluted with H$_2$O (100 mL), excess of zinc removed by filtration, ice (100 g) added to the solution and the mixture carefully alkalized (pH=14) with concentrated aqueous ammonia. The mixture was extracted with CH$_2$Cl$_2$ (3×100 mL), dried (Na$_2$SO$_4$), the solvent removed under reduced pressure and the remaining crude product dissolved in THF (50 mL). Whilst stirring 1.2 equivalents of hydrochloride acid (5N-6N in 2-propanol), followed by addition of ether (150 mL), was added. The precipitating colorless crystals were collected by filtration, washed with a small amount of THF and ether and dried. Yield 5.00 g; 13.54 mmol (59%) colorless crystals. $^1$H NMR (300 MHz, DMSO): δ 11.18 (d, J=2.1 Hz, 1H), 9.11 (s, 1H), 8.24 (s, 3H), 7.73 (s, 1H), 7.30 (d, J=2.5 Hz, 1H), 7.26 (d, J=8.7 Hz, 1H), 7.10 (d, J=8.8 Hz, 1H), 4.26 (t, J=7.4 Hz, 1H), 3.61 (d, J=9.0 Hz, 3H), 3.48 (dd, J=12.7, 8.4 Hz, 1H), 3.12 (dd, J=12.7, 6.6 Hz, 1H), 1.48 (s, 9H). ESI-MS m/z (%): 333 [MH$^+$] (100).

Methyl 3-amino-2-(5-(((tert-butoxycarbonyl)amino)methyl)-1H-indol-3-yl)propanoate hydrochloride (11d)

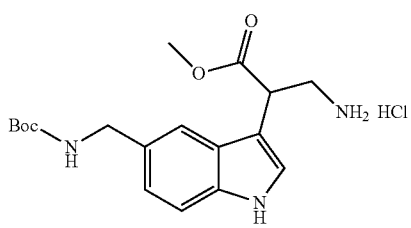 [SMILES: COC(=O)C(CN)c1c[nH]c2ccc(CNC(=O)OC(C)(C)C)cc12 ; Cl]

Methyl 3-amino-2-(5-(((tert-butoxycarbonyl)amino)methyl)-1H-indol-3-yl)propanoate hydrochloride (11d) was prepared from methyl 2-(5-(((tert-butoxycarbonyl)amino)methyl)-1H-indol-3-yl)-3-nitropropanoate (9d) (12.70 g; 36.91 mmol) as described above. Yield 8.20 g; 21.40 mmol (58%) colorless crystals after chromatography over silica gel with EE/MeOH/NH$_3$ (1:1:1%) and precipitation as hydrochloride. mp: 186-189° C. $^1$H NMR (300 MHz, DMSO): δ 11.23 (s, 1H), 8.17 (s, 3H), 7.48-7.23 (m, 4H), 7.13-6.79 (m, 1H), 4.29 (t, J=7.4 Hz, 1H), 4.18 (d, J=6.1 Hz, 2H), 3.61 (d, J=7.4 Hz, 3H), 3.49 (dd, J=12.5, 8.3 Hz, 1H), 3.14 (dd, J=12.7, 6.6 Hz, 1H), 1.40 (s, 9H). ESI-MS m/z (%): 348 [MH$^+$] (100).

Methyl 3-amino-2-(5-(benzyloxy)-1H-indol-3-yl)propanoate hydrochloride (11e)

(Perez-Alvarez et al., 1997) was prepared from methyl 2-(5-(benzyloxy)-1H-indol-3-yl)-3-nitropropanoate (9e) (18.58 g; 52.4 mmol) as described above. Yield 14.98 g; 79% colorless crystals.

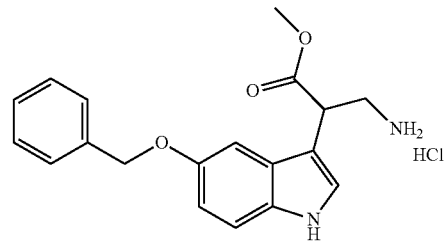 [SMILES: COC(=O)C(CN)c1c[nH]c2ccc(OCc3ccccc3)cc12 ; Cl]

Methyl 3-amino-2-(6-((tert-butoxycarbonyl)amino)-1H-indol-3-yl)propanoate hydrochloride (11f)

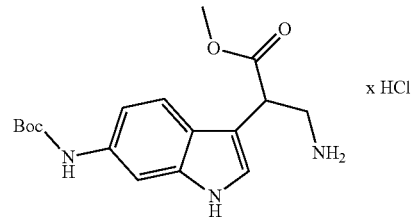 [SMILES: COC(=O)C(CN)c1c[nH]c2cc(NC(=O)OC(C)(C)C)ccc12]

From Methyl 2-(6-((tert-butoxycarbonyl)amino)-1H-indol-3-yl)-3-nitropropanoate (9f) prepared as described above. Colorless crystals (4.70 g, 12.74 mmol, 67%), mp: 183.0-184.5° C.; IR (KBr): 1724, 1630 cm$^{-1}$; $^1$NMR (300 MHz, DMSO): δ 11.08 (d, J=2.0 Hz, 1H), 9.23 (s, 1H), 8.16 (s, 3H), 7.68 (s, 1H), 7.40 (d, J=8.6 Hz, 1H), 7.20 (d, J=2.4 Hz, 1H), 7.03 (dd, J=8.6, 1.7 Hz, 1H), 4.27 (dd, J=8.0, 6.6 Hz, 1H), 3.62 (s, 3H), 3.46 (dd, J=12.5, 8.4 Hz, 1H), 3.13 (dd, J=12.6, 6.3 Hz, 1H), 1.48 (s, 9H). ESI-MS m/z (%): 334 [MH$^+$] (100).

Methyl 3-amino-2-(4-(benzyloxy)-1H-indol-3-yl)propanoate hydrochloride (11g)

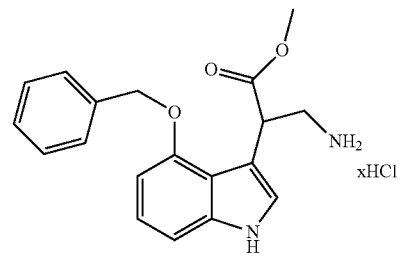 [SMILES: COC(=O)C(CN)c1c[nH]c2cccc(OCc3ccccc3)c12]

According to GP1 from methyl 2-(4-(benzyloxy)-1H-indol-3-yl)-3-nitropropanoate (9g). The precipitated colorless crystals were filtered off, washed with ether and dried. Yield 5.88 g (18.13 mmol; 71%). $^1$H NMR (300 MHz, DMSO): δ 11.12 (d, J=2.1 Hz, 1H), 8.17 (s, 3H), 7.48 (d, J=7.1 Hz, 2H), 7.38 (d, J=7.6 Hz, 2H), 7.31 (d, J=3.7 Hz, 1H), 7.29-7.25 (m, 1H), 7.20 (d, J=2.3 Hz, 1H), 6.85 (dd, J=8.8, 2.3 Hz, 1H), 5.10 (s, 2H), 3.61 (s, J=4.2 Hz, 3H), 3.41 (dd, J=19.0, 7.2 Hz, 2H), 3.14 (dd, J=11.7, 5.5 Hz, 1H).

1.2 General procedure 2a (GP2a) using the example of methyl 2,3,4,9-tetrahydro-1H-pyrido[3,4-b]indole-4-carboxylate hydrochloride (13a)

Methyl 3-amino-2-(1H-indol-3-yl)propanoate hydrochloride (10a) (Bartoli et al., 2005) (2.54 g; 10.00 mmol) and formaldehyde (12) (12.00 mmol; 1.06 mL 35% in H$_2$O) were dissolved in MeOH and heated to 60° C. for 1 h. The solution was cooled to room temperature and stirred overnight. After addition of Et$_2$O (20.0 mL) the colorless product was filtered off, washed with Et$_2$O and dried.

General procedure 2b (GP2b using the example of racemic mixture of (1S,4S)-methyl 1-(benzo[d][1,3]dioxol-5-yl)-2,3,4,9-tetrahydro-1H-pyrido[3,4-b]indole-4-carboxylate hydrochloride and (1R,4R)-methyl 1-(benzo[d][1,3]dioxol-5-yl)-2,3,4,9-tetrahydro-1H-pyrido[3,4-b]indole-4-carboxylate hydrochloride (17j) and racemic mixture of (1S,4R)-methyl 1-(benzo[d][1,3]dioxol-5-yl)-2,3,4,9-tetrahydro-1H-pyrido[3,4-b]indole-4-carboxylate hydrochloride and (1R,4S)-methyl 1-(benzo[d][1,3]dioxol-5-yl)-2,3,4,9-tetrahydro-1H-pyrido[3,4-b]indole-4-carboxylate (17i)

Methyl 3-amino-2-(1H-indol-3-yl)propanoate hydrochloride (10a) (Bartoli et al., 2005) (2.54 g; 10.00 mmol) and piperonal (12a) (12.00 mmol; 1.80 g) were dissolved in isopropanol (150 ml and heated to reflux for 48 h. The solution was cooled to room temperature and the precipitated solid (17j) filtered off. The remaining liquid was concentrated to a volume of 50 ml in total and cooled to room temperature, to obtain a second crystalline fraction (17i). To obtain an analytical pure sample, both fractions were crystallized separately from isopropanol.

Methyl 2,3,4,9-tetrahydro-1H-pyrido[3,4-b]indole-4-carboxylate hydrochloride (13a) (Saiga et al., 1987)

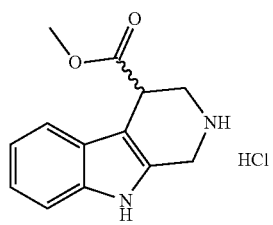 [SMILES: COC(=O)C1CNCc2[nH]c3ccccc3c21 ; Cl]

2.29 g (86%) colorless crystals. mp 245.3-245.4° C. IR (KBr): 3166, 1729 cm$^{-1}$. $^1$H NMR (300 MHz, DMSO-d$_6$): δ 11.28 (s, 1H), 9.38 (s, 2H), 7.52 (d, J=7.7 Hz, 1H), 7.39 (d, J=8.0 Hz, 1H), 7.12 (dd, J=11.0, 4.1 Hz, 1H), 7.05 (dd, J=10.9, 4.0 Hz, 1H), 4.43-4.27 (m, 2H), 4.24 (t, J=4.8 Hz, 1H), 3.71 (dd, 1H, J=12.9, 4.6 Hz, 1H), 3.70 (s, 3H), 3.53 (dd, J=12.9, 5.3 Hz, 1H). ESI-MS m/z (%): 272 [MH$^+$+CH$_3$CN] (100), 231 [MH$^+$] (65). Anal. calcd for C$_{13}$H$_{15}$ClN$_2$O$_2$: C, 54.54; H, 5.67; N, 10.50; found: C, 58.06; H, 5.69; N, 10.37.

2,3,4,9-Tetrahydro-1H-pyrido[3,4-b]indole-4-carboxylic acid (15)

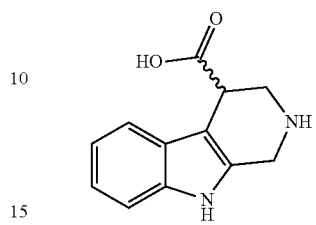

Methyl 2,3,4,9-tetrahydro-1H-pyrido[3,4-b]indole-4-carboxylate hydrochloride (13a) (5.32 g; 20.0 mmol) was dissolved in a mixture of MeOH (40 mL), THF (40.0 mL) and water (20 mL). LiOH (1.01 g, 42.0 mmol) was added and the mixture stirred over night at room temperature. The solution was heated till reflux for 2 h and the organic solvents removed under reduced pressure. Water was added (30 mL) and the solution acidified till pH=6 with diluted acetic acid. The precipitating colorless crystals were collected by filtration, washed with a small amount of water and dried. Yield 3.98 g (18.4 mmol, 92%). $^1$H NMR (300 MHz, DMSO-d$_6$): δ 10.93 (s, 1H), 7.51 (d, J=7.6 Hz, 1H), 7.29 (d, J=7.9 Hz, 1H), 7.04-6.91 (m, 2H), 4.70 (s, 2H), 4.06 (d, J=16.7 Hz, 1H), 4.00 (d, J=16.7 Hz, 1H), 3.61 (d, J=12.8 Hz, 1H), 3.43-3.26 (m, 1H), 3.00 (dd, J=12.5, 3.8 Hz, 1H).

Methyl 6-methoxy-2,3,4,9-tetrahydro-1H-pyrido[3,4-b]indole-4-carboxylate hydrochloride (14a) (Van et al. 1981)

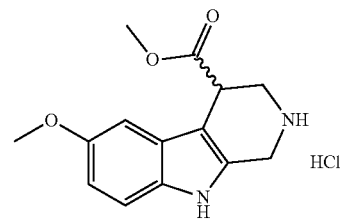 [SMILES: COC(=O)C1CNCc2[nH]c3ccc(OC)cc3c21 ; Cl]

According to GP2 from methyl 3-amino-2-(5-methoxy-1H-indol-3-yl)propanoate hydrochloride (11a). 2.58 g (87%) colorless crystals. $^1$H NMR (300 MHz, DMSO-d$_6$): δ 11.21 (s, 1H), 10.26 (s, 1H), 9.21 (s, 1H), 7.29 (d, J=8.8 Hz, 1H), 7.00 (d, J=2.3 Hz, 1H), 6.77 (dd, J=8.8, 2.4 Hz, 1H), 4.39-4.26 (m, 2H), 4.22 (t, J=4.8 Hz, 1H), 3.75 (s, J=7.3 Hz, 3H), 3.72 (s, 3H), 3.66 (d, J=4.6 Hz, 1H), 3.52 (dd, J=12.8, 5.2 Hz, 1H).

Methyl 7-methoxy-2,3,4,9-tetrahydro-1H-pyrido[3,4-b]indole-4-carboxylate hydrochloride (14b)

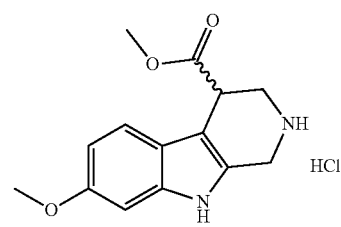 [SMILES: COC(=O)C1CNCc2[nH]c3cc(OC)ccc3c21 ; Cl]

According to GP2 from methyl 3-amino-2-(6-methoxy-1H-indol-3-yl)propanoate hydrochloride (11b). 3.53 g; 11.90 mmol (89%) colorless crystals. mp 233-235° C. $^{1}$H NMR (400 MHz, DMSO): δ 11.20 (s, 1H), 10.31 (s, 1H), 9.25 (s, 1H), 7.39 (d, J=8.7 Hz, 1H), 6.90 (d, J=2.2 Hz, 1H), 6.70 (dd, J=8.7, 2.3 Hz, 1H), 4.39-4.24 (m, 2H), 4.21 (t, J=5.0 Hz, 1H), 3.76 (s, 3H), 3.69 (d, J=5.5 Hz, 3H), 3.66 (dd, J=12.9, 4.9 Hz, 1H), 3.55-3.46 (m, 1H). ESI-MS m/z (%): 261 [MH$^{+}$] (100).

Methyl 6-((tert-butoxycarbonyl)amino)-2,3,4,9-tetrahydro-1H-pyrido[3,4-b]indole-4-carboxylate (14c) (Van et al., 1981)

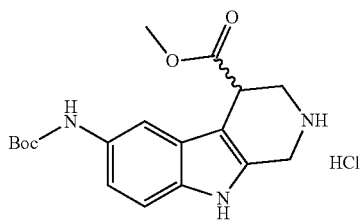 [SMILES: COC(=O)C1CNCc2[nH]c3ccc(NC(=O)OC(C)(C)C)cc3c21 ; Cl]

According to GP2 from Methyl 3-amino-2-(5-((tert-butoxycarbonyl)amino)-1H-indol-3-yl)propanoate hydrochloride (11c). 4.01 g; 10.50 mmol (83%) colorless crystals. $^{1}$H NMR (300 MHz, DMSO): δ 11.24 (s, 1H), 10.21 (s, 1H), 9.32 (s, J=44.4 Hz, 1H), 9.14 (s, 1H), 7.70 (s, 1H), 7.25 (d, J=8.7 Hz, 1H), 7.15 (dd, J=8.8, 1.4 Hz, 1H), 4.32 (s, 2H), 4.19 (t, J=5.1 Hz, 1H), 3.73 (s, 3H), 3.63 (dd, J=12.8, 5.3 Hz, 1H), 3.54 (dd, J=12.8, 5.3 Hz, 1H), 1.48 (s, 9H). ESI-MS m/z (%): 387 [MH$^{+}$+MeCN] (70), 346 [MH$^{+}$] (100).

Methyl 6-(((tert-butoxycarbonyl)amino)methyl)-2,3,4,9-tetrahydro-1H-pyrido[3,4-b]indole-4-carboxylate hydrochloride (14d)

According to GP2 from methyl 3-amino-2-(5-(((tert-butoxycarbonyl)amino)methyl)-1H-indol-3-yl)propanoate hydrochloride (5.60 g; 14.58 mmol) (11d). 4.81 g; 12.17 mmol (83%) colorless crystals. $^{1}$H NMR (300 MHz, DMSO): δ 11.30 (s, 1H), 9.66 (s, 2H), 7.41-7.28 (m, 3H), 7.03 (dd, J=8.4, 1.2 Hz, 1H), 4.45-4.25 (m, 2H), 4.20 (dd, J=14.5, 5.5 Hz, 3H), 3.72 (s, 3H), 3.70-3.47 (m, 2H), 1.37 (s, 9H). ESI-MS m/z (%): 401 [MH$^{+}$+MeCN] (66), 360 [MH$^{+}$] (100). Anal. calcd for C$_{19}$H$_{25}$N$_{3}$O$_{4}$×HCl: C, 57.64; H, 6.62; N, 10.61; found: C, 57.46; H, 6.48; N, 10.37.

Methyl 6-(benzyloxy)-2,3,4,9-tetrahydro-1H-pyrido[3,4-b]indole-4-carboxylate hydrochloride (14e)

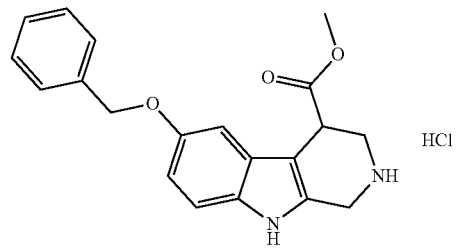 [SMILES: COC(=O)C1CNCc2[nH]c3ccc(OCc4ccccc4)cc3c21 ; Cl]

According to GP2 from methyl 3-amino-2-(5-(benzyloxy)-1H-indol-3-yl)propanoate hydrochloride (1e) (14.0 g; 38.8 mmol). Yield 11.2 g; 30.0 mmol (77%) colorless crystals. $^{1}$H NMR (300 MHz, DMSO): δ 11.23 (s, 1H), 9.72 (s, 2H), 7.54-7.24 (m, 6H), 7.08 (d, J=2.4 Hz, 1H), 6.86 (dd, J=8.8, 2.5 Hz, 1H), 5.09 (s, 2H), 4.35 (d, J=16.1 Hz, 1H), 4.29 (d, J=15.9 Hz, 1H), 4.19 (t, J=4.8 Hz, 1H), 3.68 (dd, J=12.1, 3.8 Hz, 1H), 3.65 (s, 3H), 3.51 (dd, J=12.9, 5.3 Hz, 1H).

Methyl 7-((tert-butoxycarbonyl)amino)-2,3,4,9-tetrahydro-1H-pyrido[3,4-b]indole-4-carboxylate hydrochloride (14f)

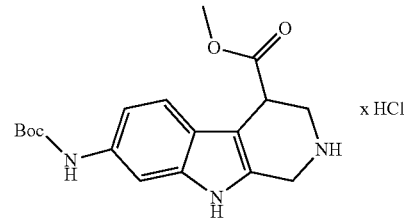 [SMILES: COC(=O)C1CNCc2[nH]c3cc(NC(=O)OC(C)(C)C)ccc3c21]

According to GP2 from Methyl 3-amino-2-(6-((tert-butoxycarbonyl)amino)-1H-indol-3-yl)propanoate hydrochloride (11f) yield: Colorless crystals (3.25 g, 8.53 mmol, 93%), mp: 196.2-197.8° C.; IR (KBr): 1729, 1631 cm$^{-1}$; $^{1}$H NMR (300 MHz, DMSO): δ 11.29 (s, 1H), 9.27 (s, 2H), 7.68 (s, 1H), 7.35 (d, J=8.6 Hz, 1H), 7.04 (d, J=8.6 Hz, 1H), 4.31 (s, 2H), 4.21 (t, J=4.5 Hz, 1H), 3.69 (s, 3H), 3.67-3.60 (m, 1H), 3.51 (dd, J=12.7, 5.1 Hz, 1H), 3.42-3.31 (m, 1H), 1.48 (s, 9H). ESI-MS m/z (%): 346 [MH$^{+}$] (100). Anal. (C$_{25}$H$_{26}$N$_{4}$O$_{4}$+½ MeOH): Calcd. C, 55.85; H, 6.59; N, 10.56; found. C, 55.91; H, 6.38; N, 10.66.

Methyl 5-(benzyloxy)-2,3,4,9-tetrahydro-1H-pyrido[3,4-b]indole-4-carboxylate hydrochloride (14g)

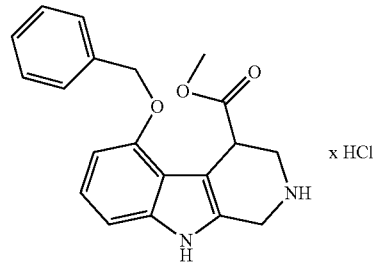 [SMILES: COC(=O)C1CNCc2[nH]c3cccc(OCc4ccccc4)c3c21]

According to GP2a from methyl 3-amino-2-(4-(benzyloxy)-1H-indol-3-yl)propanoate hydrochloride (11g). The precipitated colorless crystals were filtered off, washed with ether and dried. Yield 10.00 g (26.82 mmol; 58%). $^{1}$H NMR (300 MHz, DMSO): δ 11.12 (s, 1H), 7.47 (s, 1H), 7.40 (t, J=7.3 Hz, 3H), 7.31 (d, J=3.5 Hz, 1H), 7.27 (d, J=2.5 Hz, 1H), 7.20 (d, J=2.2 Hz, 1H), 6.85 (dd, J=8.8, 2.2 Hz, 1H), 5.10 (s, 2H), 4.31 (d, J=6.4 Hz, 1H), 3.61 (s, 3H), 3.43 (d, J=11.9 Hz, 2H), 3.38 (d, J=7.0 Hz, 1H), 3.13 (s, 1H).

Racemate of (1S,4S)-Methyl 1-(benzo[d][1,3]dioxol-5-yl)-2,3,4,9-tetrahydro-1H-pyrido[3,4-b]indole-4-carboxylate hydrochloride and (1R,4R)-methyl 1-(benzo[d][1,3]dioxol-5-yl)-2,3,4,9-tetrahydro-1H-pyrido[3,4-b]indole-4-carboxylate hydrochloride (14h)

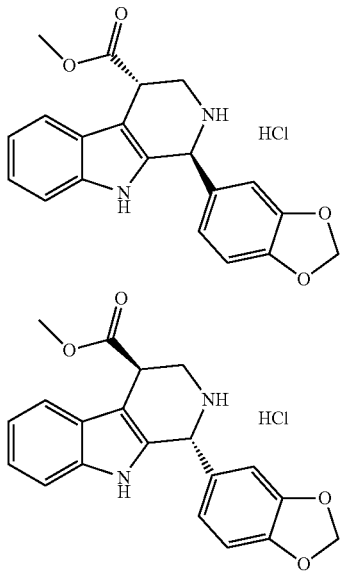

According to GP2b from (10a) (Bartoli et al. 2005) (2.54 g; 10.0 mmol). Yield 1.20 g; 3.10 mmol (31%) colorless crystals. mp 261.1-261.3° C. IR (KBr): 3222, 2880, 2780, 1735 cm$^{-1}$. $^1$H NMR (300 MHz, DMSO): δ 11.10 (s, 1H), 10.19 (s, 2H), 7.53 (d, J=7.7 Hz, 1H), 7.32 (d, J=7.9 Hz, 1H), 7.18-6.99 (m, 3H), 6.95 (d, J=1.5 Hz, 1H), 6.88 (dd, J=8.1, 1.7 Hz, 1H), 6.08 (s, 2H), 5.91 (s, 1H), 4.51 (t, J=6.0 Hz, 1H), 3.74 (s, 3H), 3.68-3.51 (m, 2H). ESI-MS m/z (%): 351[MH$^+$] (100), 392 [MH$^+$+CH$_3$CN]. Anal. Calcd for C$_{20}$H$_{19}$ClN$_2$O$_4$: C, 62.10; H, 4.95; N, 7.24; found: C, 61.60; H, 5.08; N, 7.12.

Racemate of (1S,4R)-Methyl 1-(benzo[d][1,3]dioxol-5-yl)-2,3,4,9-tetrahydro-1H-pyrido[3,4-b]indole-4-carboxylate hydrochloride and (1R,4S)-methyl 1-(benzo[d][1,3]dioxol-5-yl)-2,3,4,9-tetrahydro-1H-pyrido[3,4-b]indole-4-carboxylate (14i)

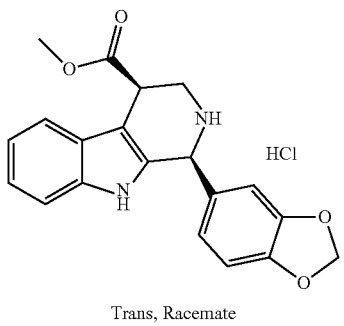

Trans, Racemate

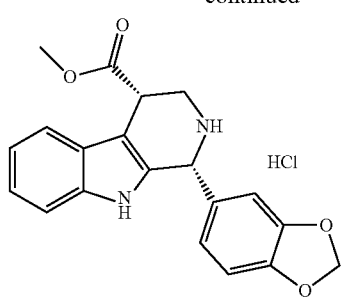

According to GP2b from (10a) (Bartoli et al. 2005) (2.54 g; 10.0 mmol). Yield 0.95 g; 2.46 mmol (25%) colorless crystals. mp 237.5-238.5° C. IR (KBr): 3178, 2910, 1736, 1717 cm$^{-1}$. $^1$H NMR (300 MHz, DMSO): δ 11.23 (s, 1H), 10.70 (s, 1H), 9.39 (s, 1H), 7.51 (d, J=7.8 Hz, 1H), 7.33 (d, J=8.0 Hz, 1H), 7.20-7.10 (m, 1H), 7.10-6.99 (m, 2H), 6.95 (d, J=1.6 Hz, 1H), 6.87 (dd, J=8.1, 1.7 Hz, 1H), 6.09 (s, 2H), 5.93 (s, 1H), 4.37 (t, J=6.0 Hz, 1H), 3.74 (s, 3H), 3.57 (ddd, J=26.7, 13.0, 6.2 Hz, 2H). The constitution of the racemates was determined by NOE spectroscopy. ESI-MS m/z (%): 351 [MH$^+$] (100), 392 [MH$^+$+CH$_3$CN]. Anal. Calcd for C$_{20}$H$_{19}$ClN$_2$O$_4$: C, 62.10; H, 4.95; N, 7.24; found: C, 61.88; H, 5.14; N, 7.03.

1.3 General procedure 3 (GP3) using the example of methyl 2-(methylcarbamoyl)-2,3,4,9-tetrahydro-1H-pyrido[3,4-b]indole-4-carboxylate (16a)

Methyl 2,3,4,9-tetrahydro-1H-pyrido[3,4-b]indole-4-carboxylate hydrochloride (13a) (0.67 g; 2.50 mmol) was suspended in acetonitrile (13.4 mL). With stirring diisopropylethylamine (2.5 mL) was added. After addition of N-succinimidyl-N-methyl-carbamate (0.52 g; 3.00 mmol) stirring was continued for 16 h at room temperature. The mixture was poured into water and the crude product was extracted with ethyl acetate (3×50 mL). The combined organic layers were dried (Na$_2$SO$_4$) and evaporated.

Methyl 2-(methylcarbamoyl)-2,3,4,9-tetrahydro-1H-pyrido[3,4-b]indole-4-carboxylate (16a)

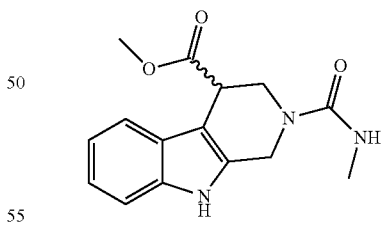

Recrystallization from ethyl acetate: 0.66 g (2.30 mmol; 92%) colorless crystals; mp 202.5-203.1° C. IR (KBr): 3380, 3275, 2945, 1716 cm$^{-1}$. $^1$H NMR (300 MHz, DMSO-d$_6$): δ 11.06 (s, 1H), 7.33 (d, J=8.0 Hz, 2H), 7.10-7.01 (m, 1H), 7.00-6.89 (m, 1H), 6.65 (q, J=4.0 Hz, 1H), 4.61 (d, J=16.4 Hz, 1H), 4.51 (d, J=16.2 Hz, 1H), 4.03-3.87 (m, 2H), 3.73 (dd, J=12.7, 3.9 Hz, 1H), 3.64 (s, 3H), 2.61 (d, J=4.3 Hz, 3H). ESI-MS m/z (%): 675 [2 MH$^+$](100), 288 [MH$^+$] (35). Anal. calcd for C$_{15}$H$_{17}$N$_3$O$_3$: C, 62.71; H, 5.96; N, 14.63; found: C, 62.39; H, 6.26; N, 14.62.

Methyl 6-methoxy-2-(methylcarbamoyl)-2,3,4,9-tetrahydro-1H-pyrido[3,4-b]indole-4-carboxylate (17a)

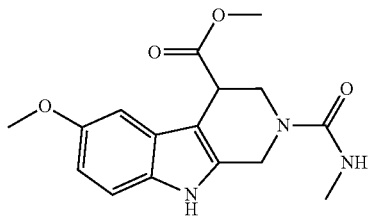 [SMILES: CNC(=O)N1Cc2[nH]c3ccc(OC)cc3c2C(C(=O)OC)C1]

According to GP3 from methyl methyl 6-methoxy-2,3,4,9-tetrahydro-1H-pyrido[3,4-b]indole-4-carboxylate hydrochloride (14a) (0.75 g; 2.53 mol) and N-succinimidyl-N-methyl-carbamate (0.52 g; 3.00 mol). Colorless crystals 0.61 g (1.92 mmol; 76%); mp 233.5-234.2° C. IR (KBr): 3345, 1730, 1634 cm$^{-1}$. $^1$H NMR (300 MHz, DMSO-d$_6$): δ 10.88 (s, 1H), 7.21 (d, J=8.7 Hz, 1H), 6.82 (d, J=2.4 Hz, 1H), 6.69 (dd, J=8.7, 2.5 Hz, 1H), 6.63 (q, J=3.9 Hz, 1H), 4.57 (d, J=16.4 Hz, 1H), 4.47 (d, J=16.6 Hz, 1H), 3.96 (dd, J=13.1, 5.7 Hz, 1H), 3.78-3.67 (m, 4H), 3.65 (s, 3H), 2.60 (d, J=4.2 Hz, 3H). ESI-MS m/z (%): 635 [2MH$^+$](100), 318 [MH$^+$] (62). Anal. calcd for C$_{16}$H$_{19}$N$_3$O$_4$): C, 60.56; H, 6.03; N, 13.24; found: C, 60.66; H, 6.08; N, 13.32.

Methyl 7-methoxy-2-(methylcarbamoyl)-2,3,4,9-tetrahydro-1H-pyrido[3,4-b]indole-4-carboxylate (17b)

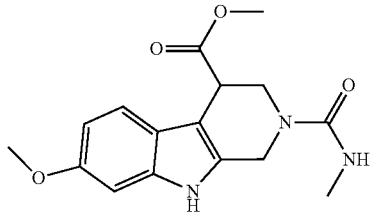 [SMILES: CNC(=O)N1Cc2[nH]c3cc(OC)ccc3c2C(C(=O)OC)C1]

According to GP3 from methyl methyl 7-methoxy-2,3,4,9-tetrahydro-1H-pyrido[3,4-b]indole-4-carboxylate hydrochloride (14b) (3.45 g; 11.63 mmol) and N-succinimidyl-N-methyl-carbamate (2.40 g; 13.95 mmol). Colorless crystals 2.90 g (9.13 mmol; 79%); mp 237.0-239.2° C. IR (KBr): 3241, 1728 cm$^{-1}$. $^1$H NMR (300 MHz, DMSO): δ 10.86 (s, 1H), 7.20 (d, J=8.6 Hz, 1H), 6.83 (d, J=2.2 Hz, 1H), 6.71-6.46 (m, 2H), 4.54 (d, J=16.0 Hz, 1H), 4.46 (d, J=16.0 Hz, 1H), 3.99-3.80 (m, 2H), 3.74 (s, 3H), 3.74-3.67 (m, 1H), 3.63 (s, 3H), 2.60 (d, J=4.3 Hz, 3H). ESI-MS m/z (%): 635 [2MH$^+$] (100), 318 [MH$^+$] (62).

Methyl 6-((tert-butoxycarbonyl)amino)-2-(methylcarbamoyl)-2,3,4,9-tetrahydro-1H-pyrido[3,4-b]indole-4-carboxylate (17c)

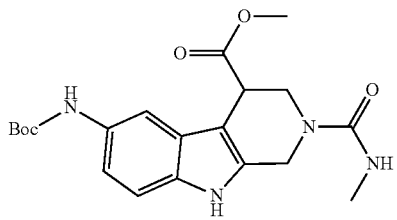 [SMILES: CNC(=O)N1Cc2[nH]c3ccc(NC(=O)OC(C)(C)C)cc3c2C(C(=O)OC)C1]

According to GP3 from methyl 6-((tert-butoxycarbonyl)amino)-2,3,4,9-tetrahydro-1H-pyrido[3,4-b]indole-4-carboxylate (14c) (4.90 g; 12.83 mmol) and N-succinimidyl-N-methyl-carbamate (13.50 mmol). Colorless crystals 2.60 g (6.46 mmol; 50%); $^1$H NMR (300 MHz, DMSO): δ 10.89 (s, 1H), 9.04 (s, 1H), 7.50 (s, 1H), 7.18 (d, J=8.7 Hz, 1H), 7.07 (d, J=8.6 Hz, 1H), 6.64 (d, J=4.4 Hz, 1H), 4.74-4.33 (m, 2H), 3.94-3.71 (m, 3H), 3.67 (s, 3H), 2.59 (d, J=4.2 Hz, 3H), 1.47 (s, 9H). ESI-MS m/z (%): 420 [MNH$_4^+$] (13), 403 [MH$^+$] (100).

Methyl 6-(((tert-butoxycarbonyl)amino)methyl)-2-(methylcarbamoyl)-2,3,4,9-tetrahydro-1H-pyrido[3,4-b]indole-4-carboxylate (17d)

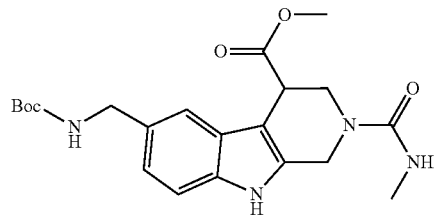 [SMILES: CNC(=O)N1Cc2[nH]c3ccc(CNC(=O)OC(C)(C)C)cc3c2C(C(=O)OC)C1]

According to GP3 from methyl 6-(((tert-butoxycarbonyl)amino)methyl)-2,3,4,9-tetrahydro-1H-pyrido[3,4-b]indole-4-carboxylate hydrochloride (14d) (4.71 g; 11.89 mmol) and N-succinimidyl-N-methyl-carbamate (13.08 mmol). Colorless crystals 4.13 g (9.91 mmol; 83%); mp: 201-203° C. $^1$H NMR (300 MHz, DMSO): δ 10.99 (s, 1H), 7.32 (t, J=6.2 Hz, 1l), 7.25 (d, J=8.3 Hz, 1H), 7.19 (s, 1H), 6.95 (dd, J=8.3, 1.3 Hz, 1H), 6.64 (d, J=4.4 Hz, 1H), 4.72-4.36 (m, 2H), 4.15 (d, J=6.1 Hz, 2H), 3.98-3.84 (m, 2H), 3.81-3.70 (m, 1H), 3.65 (s, 3H), 2.59 (d, J=4.3 Hz, 3H), 1.39 (s, J=12.0 Hz, 8H). ESI-MS m/z (%): 417 [MH$^+$] (100), 361 [MH$^+$−C$_4$H$_8$] (19). Anal. calcd for C$_{21}$H$_{28}$N$_4$O$_5$: C, 60.56; H, 6.78; N, 13.45; found: C, 60.33; H, 6.66; N, 13.33.

Methyl 6-(benzyloxy)-2-(methylcarbamoyl)-2,3,4,9-tetrahydro-1H-pyrido[3,4-b]indole-4-carboxylate (17e)

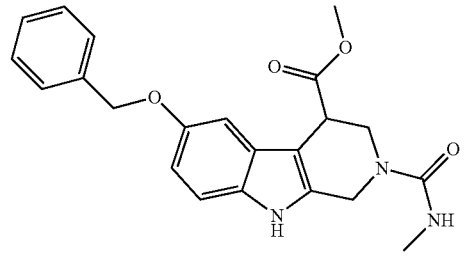 [SMILES: CNC(=O)N1Cc2[nH]c3ccc(OCc4ccccc4)cc3c2C(C(=O)OC)C1]

According to GP3 from methyl 6-(benzyloxy)-2,3,4,9-tetrahydro-1H-pyrido[3,4-b]indole-4-carboxylate hydrochloride (14e) (10.17 g; 27.35 mmol). Colorless crystals 10.69 g (27.17 mmol; 99%). $^1$H NMR (300 MHz, DMSO): δ 10.90 (s, 1H), 7.52-7.27 (m, 5H), 7.22 (d, J=8.7 Hz, 1H), 6.91 (d, J=2.4 Hz, 1H), 6.78 (dd, J=8.7, 2.4 Hz, 1H), 6.62 (d, J=4.4 Hz, 1H), 5.06 (s, 2H), 4.57 (d, J=16.5 Hz, 1H), 4.47 (d, J=16.7 Hz, 1H), 3.96 (dd, J=13.3, 5.6 Hz, 1H), 3.85 (t, J=4.8 Hz, 1H), 3.69 (dd, J=13.3, 4.5 Hz, 1H), 3.60 (s, 3H), 2.59 (d, J=4.2 Hz, 3H).

Methyl 7-((tert-butoxycarbonyl)amino)-2-(methylcarbamoyl)-2,3,4,9-tetrahydro-1H-pyrido[3,4-b]indole-4-carboxylate (17f)

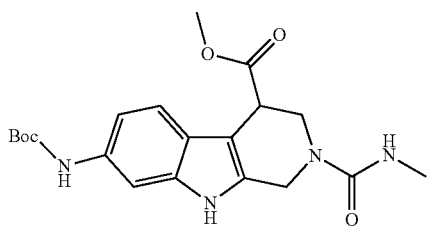 [SMILES: CNC(=O)N1Cc2[nH]c3cc(NC(=O)OC(C)(C)C)ccc3c2C(C(=O)OC)C1]

According to GP3 from methyl 7-((tert-butoxycarbonyl)amino)-2,3,4,9-tetrahydro-1H-pyrido[3,4-b]indole-4-carboxylate hydrochloride (14f). Yield: Colorless crystals (3.09 g, 7.68 mmol, 98%) mp: 202.8-203.2° C.; IR (KBr): 1732, 1704 cm$^{-1}$; $^1$H NMR (300 MHz, DMSO): δ 10.87 (s, 1H), 9.18 (s, 1H), 7.62 (s, 1H), 7.16 (d, J=4.5 Hz, 1H), 6.97 (dd, J=8.6, 1.6 Hz, 1H), 6.62 (d, J=4.3 Hz, 1H), 4.55 (d, J=16.3 Hz, 1H), 4.47 (d, J=16.5 Hz, 1H), 3.96-3.83 (m, 2H), 3.72 (dd, J=12.7, 3.9 Hz, 1H), 3.63 (s, 3H), 2.67 (d, J=4.6 Hz, 3H), 1.48 (s, 9H). ESI-MS m/z (%): 403 [MH$^+$] (100). Anal. (C$_{20}$H$_{26}$N$_4$O$_5$+⅕ ethyl acetate): Calcd. C, 59.47; H, 6.62; N, 13.34; found. C, 58.99; H, 6.49; N, 13.67.

Methyl 5-(benzyloxy)-2-(methylcarbamoyl)-2.3.4.9-tetrahydro-1H-pyrido[3.4-b]indole-4-carboxylate (17h)

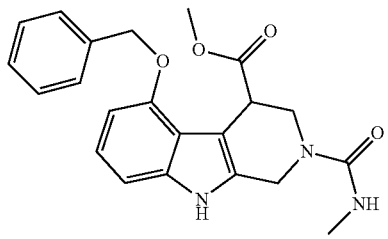 [SMILES: CNC(=O)N1Cc2[nH]c3cccc(OCc4ccccc4)c3c2C(C(=O)OC)C1]

According to GP3 from methyl 5-(benzyloxy)-2.3.4.9-tetrahydro-1H-pyrido[3,4-b]indole-4-carboxylate hydrochloride (14g). The precipitated crystals were filtered off, washed with ether and dried. Yield 8.44 g (21.45 mmol; 80%). $^1$H NMR (300 MHz, DMSO): δ 11.00 (s, 1H), 7.42-7.31 (m, 5H), 6.93 (s, 1H), 6.61 (d, J=4.3 Hz, 1H), 6.51 (t, J=4.3 Hz, 1H), 5.09 (s, 2H), 4.66 (d, J=16.2 Hz, 1H), 4.35 (d, J=16.2 Hz, 1H), 4.09 (dd, J=13.4, 4.1 Hz, 1H), 3.99 (t, J=4.2 Hz, 1H), 3.54 (dd, J=13.4, 4.8 Hz, 1H), 3.37 (s, 3H), 2.57 (d, J=4.2 Hz, 3H).

Racemate of (1S,4R)-methyl 1-(benzo[d][1,3]dioxol-5-yl)-2-(methylcarbamoyl)-2,3,4,9-tetrahydro-1H-pyrido[3,4-b]indole-4-carboxylate and (1R,4S)-methyl 1-(benzo[d][1,3]dioxol-5-yl)-2-(methylcarbamoyl)-2,3,4,9-tetrahydro-1H-pyrido[3,4-b]indole-4-carboxylate (17i)

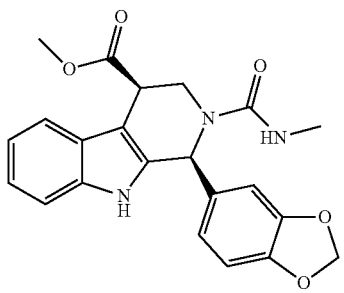

Trans, Racemate

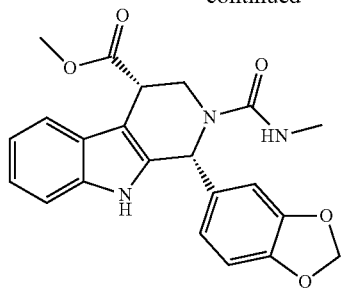

According to general procedure 3 (GP3) from (14i) (0.70 g; 1.81 mmol). Yield 0.73 g; 1.80 mmol (99%) colorless crystals. mp 243.3-243.8° C. IR (KBr): 3440, 3155, 2950, 1718 cm$^{-1}$. $^1$H NMR (300 MHz, DMSO): δ 11.21 (s, 1H), 7.32 (d, J=8.7 Hz, 2H), 7.14-7.04 (m, 1H), 6.99 (dd, J=11.2, 4.7 Hz, 1H), 6.89 (d, J=8.0 Hz, 1H), 6.85 (d, J=4.3 Hz, 1H), 6.79 (d, J=1.5 Hz, 1H), 6.68 (dd, J=8.1, 1.5 Hz, 1H), 6.46 (s, 1H), 6.01 (d, J=3.1 Hz, 2H), 4.09 (ddd, J=15.8, 12.3, 5.3 Hz, 2H), 3.74 (s, 3H), 3.19 (dd, J=13.7, 10.6 Hz, 1H), 2.62 (d, J=4.1 Hz, 3H). The constitution of the racemates was determined by NOE spectroscopy. ESI-MS m/z (%): 422 [MH$^+$] (100). Anal. Calcd for C$_{22}$H$_{21}$N$_3$O$_5$: C, 64.86; H, 5.20; N, 10.31; found: C, 64.62; H, 5.16; N, 10.37.

Racemate of (1R,4R)-methyl 1-(benzo[d][1,3]dioxol-5-yl)-2-(methylcarbamoyl)-2,3,4,9-tetrahydro-1H-pyrido[3,4-b]indole-4-carboxylate and (1S,4S)-methyl 1-(benzo[d][1,3]dioxol-5-yl)-2-(methylcarbamoyl)-2,3,4,9-tetrahydro-1H-pyrido[3,4-b]indole-4-carboxylate (17j)

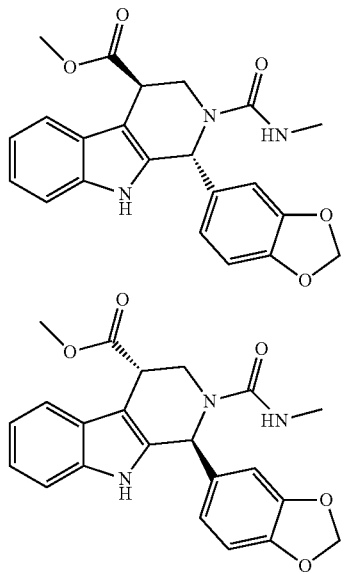

According to general procedure 3 (GP3) from (14h) (0.70 g; 1.81 mmol). Yield 0.67 g; 1.64 mmol (91%) colorless crystals. mp 214.1-214.4° C. IR (KBr): 3387, 3189, 2940, 1712 cm$^{-1}$. $^1$H NMR (300 MHz, DMSO): δ 11.04 (s, 1H), 7.47 (d, J=7.6 Hz, 1H), 7.30 (d, J=7.9 Hz, 1H), 7.14-6.93 (m, 1H), 6.84 (d, J=8.0 Hz, 1H), 6.76 (d, J=1.6 Hz, 1H), 6.59 (dd, J=8.1, 1.6 Hz, 1H), 6.52 (d, J=4.4 Hz, 1H), 6.47 (s, 1H), 5.98 (d, J=3.0 Hz, 1H), 4.35 (d, J=14.4 Hz, 1H), 3.94 (d, J=3.9 Hz, 1H), 3.58 (s, 1H), 3.25 (dd, J=14.5, 4.5 Hz, 1H), 2.62 (d, J=4.2 Hz, 1H). The constitution of the racemates was determined by NOE spectroscopy. ESI-MS m/z (%):

422 [MH⁺] (100). Anal. Calcd for $C_{22}H_{21}N_3O_5$: C, 64.86; H, 5.20; N, 10.31; found: C, 64.92; H, 5.30; N, 10.54.

2-(Methylcarbamothioyl)-2,3,4,9-tetrahydro-1H-pyrido[3,4-b]indole-4-carboxylic acid (16b)

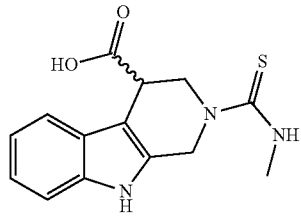 [SMILES: CNC(=S)N1Cc2[nH]c3ccccc3c2C(C(=O)O)C1]

2,3,4,9-Tetrahydro-1H-pyrido[3,4-b]indole-4-carboxylic acid (15) (1.15 g (5.00 mmol) was suspended in a mixture of aceton (17.5 mL) and DMSO (17.5 mL). Methylisothiocyanate (0.37 g; 5.00 mmol) was added and the mixture heated till reflux for 2 h. The resulting solution was poured onto water (200 mL), the solution acidified with water and extracted with ethyl acetate (3×50 mL). The combined organic layers were dried ($Na_2SO_4$), and the solvent removed under reduced pressure. Recrystallization from ethyl acetate afforded 0.95 g (3.28 mmol; 66%) beige crystals; mp 205.3-205.8° C. ¹H NMR (300 MHz, DMSO): δ 12.61 (s, 1H), 11.08 (s, 1H), 7.98 (d, J=4.2 Hz, 1H), 7.47 (d, J=7.7 Hz, 1H), 7.32 (d, J=7.9 Hz, 1H), 7.13-7.01 (m, 1H), 7.01-6.89 (m, 1H), 5.32-4.88 (m, 2H), 4.24 (dd, J=13.7, 6.5 Hz, 1H), 4.14 (dd, J=13.7, 4.6 Hz, 1H), 3.92 (t, J=5.3 Hz, 1H), 2.95 (d, J=4.0 Hz, 3H), 2.54 (s, 2H). ESI-MS m/z (%): 290 [MH⁺] (100).

1.4 General procedure 4 (GP4) using the example of 4-methyl-6,11-dihydro-2,6-methano[1,3]diazocino[5,6-b]indole-3,5(1H,4H)-dione (18a)

To a solution of methyl 2-(methylcarbamoyl)-2,3,4,9-tetrahydro-1H-pyrido[3,4-b]indole-4-carboxylate (16a) (0.48 g; 1.67 mmol) in dioxane (50 mL) under nitrogen atmosphere was added $Cs_2CO_3$ (1.2 equ., 0.65 g; 2.00 mol). After being stirred for 4 h under reflux, the mixture was filtered. The clear solution was charged with silica gel (5-10 mL) and the solvent was removed under reduced pressure. Silica gel chromatography "dry load" afforded the desired product.

4-Methyl-6,11-dihydro-2,6-methano[1,3]diazocino[5,6-b]indole-3,5(1H,4H)-dione (18a)

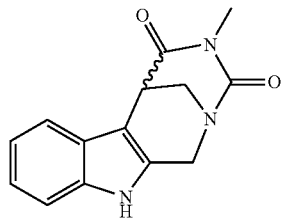 [SMILES: CN1C(=O)C2CN(Cc3[nH]c4ccccc4c32)C1=O]

0.31 g (1.21 mmol; 72%) colorless crystals after silica gel chromatography ($CH_2Cl_2$, ethyl acetate; 1:1); mp 248.7-249.0° C. IR (KBr): 3357, 1717, 1687 cm⁻¹. ¹H NMR (300 MHz, DMSO-d₆): δ 11.14 (s, 1H), 7.48 (d, J=7.4 Hz, 1H), 7.34 (d, J=7.4 Hz, 1H), 7.00-7.11 (m, 2H), 4.67 (s, 2H), 3.89 (dd, J=13.1, 1.2 Hz, 1H), 3.82 (s, 1H), 3.44 (dd, J=13.1, 2.3 Hz, 1H), 2.89 (s, 3H). ESI-MS m/z (%): 297 [MH⁺+CH₃CN] (100), 256 [MH⁺] (7). Anal. calcd for $C_{14}H_{13}N_3O_2$: C, 65.87; H, 5.13; N, 16.46; found: C, 65.69; H, 5.28; N, 16.32.

4-Methyl-3-thioxo-3,4,6,11-tetrahydro-2,6-methano[1,3]diazocino[5,6-b]indol-5(1H)-one (18b)

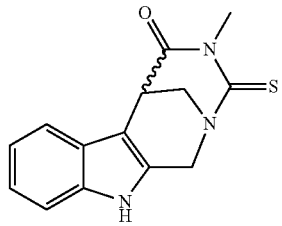 [SMILES: CN1C(=O)C2CN(Cc3[nH]c4ccccc4c32)C1=S]

Synthesis of 4-methyl-3-thioxo-3,4,6,11-tetrahydro-2,6-methano[1,3]diazocino[5,6-b]indol-5(1H)-one (18b) was performed as a modification of the method described by Kumar⁷² as follows: 2-(Methylcarbamothioyl)-2,3,4,9-tetrahydro-1H-pyrido[3,4-b]indole-4-carboxylic acid (16b) (1.80 g; 6.22 mmol) was dissolved in acetonitrile (50 mL) and CDI (1.10 g; 6.78 mmol) were added. The solution was stirred for 30 min. and poured onto water. The precipitating product was removed by filtration, washed with water and dried. Yield 1.48 g (5.46 mmol; 88%) colorless crystals; mp 233.0-236.7° C. ¹H NMR (300 MHz, DMSO): δ 11.22 (s, 1H), 7.46 (d, J=7.3 Hz, 1H), 7.34 (d, J=7.5 Hz, 1H), 7.14-6.89 (m, 2H), 5.40 (d, J=15.8 Hz, 1H), 5.10 (d, J=15.8 Hz, 1H), 4.06 (d, J=12.8 Hz, 1H), 3.92 (s, 1H), 3.75 (dd, J=12.7, 2.0 Hz, 1H), 3.21 (s, 3H). ESI-MS m/z (%): 312 [MH⁺+MeCN] (40), 271 [MH⁺] (100).

4-methyl-5-thioxo-4,5,6,11-tetrahydro-2,6-methan[1,3]diazocino[5,6-b]indol-3(1H)-one (18c)

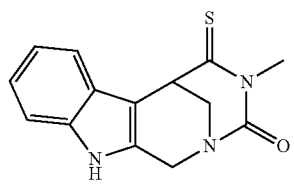 [SMILES: CN1C(=O)N2Cc3[nH]c4ccccc4c3C(C2)C1=S]

A solution of 18a (0.50 g, 1.96 mmol) and Lawesson's reagent (0.80 g, 1.96 mmol) in THF (25 mL) was refluxed for 48 h. The mixture was poured into water (80 mL) and extracted with ethyl acetate (2×30 mL). The organic phase was separated, dried over $Na_2SO_4$ and the solvent removed under reduced pressure. The residue was purified by column chromatography (eluent: dichloromethane/MeOH 20:1). Colorless crystals (0.50 g, 1.84 mmol, 47%); mp: 226.6-227.3° C. IR (KBr): 3389, 1698 cm⁻¹. ¹H NMR (300 MHz, DMSO): δ 11.16 (s, 1H), 7.62 (d, J=7.3 Hz, 1H), 7.39-7.29 (m, 1H), 7.12-6.94 (m, 2H), 4.89-4.58 (m, 2H), 4.38 (s, 1H), 3.96-3.82 (m, 1H), 3.52-3.41 (m, 1H), 3.29 (s, 3H). ESI-MS m/z (%): 272 [MH⁺] (100). Anal. calcd. for $C_{14}H_{13}N_3OS$: C, 61.97; H, 4.83; N, 15.49; S, 11.82; found: C, 61.98; H, 4.83; N, 15.50; S, 11.78.

8-Methoxy-4-methyl-6,11-dihydro-2,6-methano[1,3]diazocino[5,6-b]indole-3,5(1H,4H)-dione (19a)

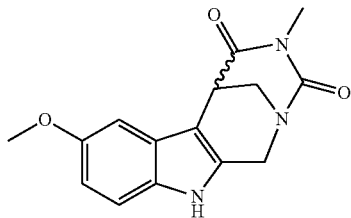 [SMILES: COc1ccc2[nH]c3c(c2c1)C1CN(C3)C(=O)N(C)C1=O]

According to GP4 from methyl 6-methoxy-2-(methylcarbamoyl)-2,3,4,9-tetrahydro-1H-pyrido[3,4-b]indole-4-carboxylate (17a). 0.52 g (1.82 mmol; 67%) colorless crystals after silica gel chromatography (CH$_2$Cl$_2$, ethyl acetate; 1:1); mp 253.0-253.6° C. IR (KBr): 3287, 1718, 1687 cm$^{-1}$. $^1$H NMR (300 MHz, DMSO-d$_6$): δ 11.02 (s, 1H), 7.24 (d, J=8.8 Hz, 1H), 6.94 (d, J=2.4 Hz, 1H), 6.73 (dd, J=8.8, 2.5 Hz, 1H), 4.65 (s, J=18.1 Hz, 2H), 3.93-3.83 (m, 1H), 3.78 (d, J=4.3 Hz, 1H), 3.76 (s, 3H), 3.42 (dd, J=13.1, 2.2 Hz, 1H), 2.89 (s, 3H). $^{13}$C NMR (75 MHz, DMSO-d$_6$) δ: 173.21 (s, 1C, quartär), 160.96 (s, 1C, quartär), 153.48 (s, 1C, quartär), 133.59 (s, 1C, quartär), 130.45 (s, 1C, quartär), 126.10 (s, 1C, quartär), 112.22 (s, 1C, CH), 111.12 (s, 1C, CH), 104.50 (s, 1C, quartär), 99.31 (s, 1C, CH), 55.21 (s, 1C, OCH$_3$), 49.58 (s, 1C, CH$_2$), 46.40 (s, 1C, CH$_2$), 35.96 (s, 1C, CH), 27.23 (s, 1C, CH$_3$). CI-MS (NH$_3$) m/z (%): 303 [M+NH$_4^+$] (100), 286 [MH$^+$] (24). Anal. calcd for C$_{15}$H$_{15}$N$_3$O$_3$: C, 63.15; H, 5.30; N, 14.83; found: C, 63.03; H, 5.40; N, 14.93.

9-Methoxy-4-methyl-6,11-dihydro-2,6-methano[1,3]diazocino[5,6-b]indole-3,5(1H,4H)-dione (19b)

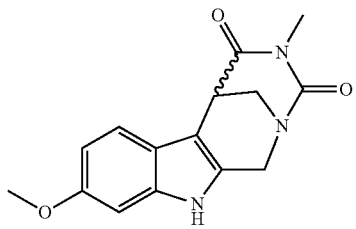 [SMILES: COc1ccc2c3c([nH]c2c1)CN1CC3C(=O)N(C)C1=O]

According to GP4 from methyl 7-methoxy-2-(methylcarbamoyl)-2,3,4,9-tetrahydro-1H-pyrido[3,4-b]indole-4-carboxylate (17b). 1.52 g (5.33 mmol; 63%) colorless crystals after silica gel chromatography (CH$_2$Cl$_2$, ethyl acetate; 1:1); mp 223.1-225.3° C. IR (KBr): 3306, 1724 cm$^{-1}$. $^1$H NMR (300 MHz, DMSO-d$_6$): δ 10.93 (s, 1H), 7.32 (d, J=8.6 Hz, 1H), 6.85 (d, J=2.2 Hz, 1H), 6.68 (dd, J=8.6, 2.3 Hz, 1H), 4.63 (d, J=12.6 Hz, 1H), 4.58 (d, J=16.8 Hz, 2H), 3.86 (d, J=13.1 Hz, 1H), 3.75 (d, J=3.6 Hz, 1H), 3.74 (s, 3H), 3.41 (dd, J=13.1, 2.2 Hz, 1H), 2.87 (s, 3H). ESI-MS m/z (%): 327 [MH$^+$+MeCN] (100), 571 [2MH$^+$] (61), 286 [MH$^+$] (14).

tert-Butyl (4-methyl-3,5-dioxo-1,3,4,5,6,11-hexahydro-2,6-methano[1,3]diazocino[5,6-b]indol-8-yl)carbamate (19c)

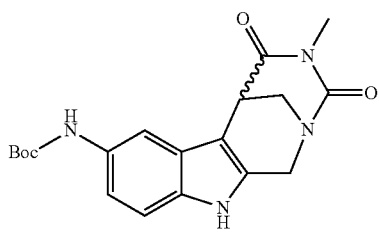 [SMILES: CN1C(=O)C2CN(Cc3[nH]c4ccc(NC(=O)OC(C)(C)C)cc4c32)C1=O]

According to GP4 from methyl 6-((tert-butoxycarbonyl)amino)-2-(methylcarbamoyl)-2,3,4,9-tetrahydro-1H-pyrido[3,4-b]indole-4-carboxylate (17c). 1.65 g (4.46 mmol; 72%) colorless crystals after silica gel chromatography (ethyl acetate) and crystallization from dichlormethan and heptane $^1$H NMR (300 MHz, DMSO): δ 10.98 (s, 1H), 9.10 (s, 1H), 7.71 (s, 1H), 7.19 (d, J=8.7 Hz, 1H), 7.12-6.94 (m, 1H), 4.63 (s, 2H), 3.87 (d, J=12.3 Hz, 1H), 3.69 (d, J=23.8 Hz, 1H), 3.42 (dd, J=13.1, 2.1 Hz, 1H), 2.88 (s, 3H), 1.48 (s, 9H). ESI-MS m/z (%): 412 [MH$^+$+MeCN] (30), 381 [MNH$_4^+$] (100), 286 [MH$^+$] (50).

tert-Butyl ((4-methyl-3,5-dioxo-1,3,4,5,6,11-hexahydro-2,6-methano[1,3]diazocino[5,6-b]indol-8-yl)methyl)carbamate (19d)

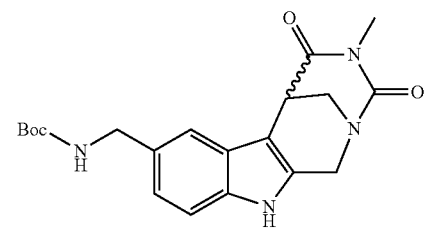 [SMILES: CN1C(=O)C2CN(Cc3[nH]c4ccc(CNC(=O)OC(C)(C)C)cc4c32)C1=O]

According to GP4 from methyl 6-(((tert-butoxycarbonyl)amino)methyl)-2-(methylcarbamoyl)-2,3,4,9-tetrahydro-1H-pyrido[3,4-b]indole-4-carboxylate (17d). 2.40 g (6.25 mmol; 65%) colorless crystals after silica gel chromatography (ethyl acetate/dichlormethane 1:1). mp: 214-217° C. $^1$H NMR (300 MHz, DMSO): δ 11.08 (s, 1H), 7.43-7.30 (m, 2H), 7.26 (d, J=8.3 Hz, 1H), 6.98 (dd, J=8.4, 1.5 Hz, 1H), 4.64 (s, 2H), 4.16 (d, J=6.2 Hz, 2H), 3.88 (d, J=12.1 Hz, 1H), 3.76 (s, 1H), 3.42 (dd, J=13.1, 2.1 Hz, 1H), 2.88 (s, 3H), 1.40 (s, 9H). ESI-MS m/z (%): 443 [MH$^+$+MeCN] (37), 402 [MNH$_4^+$] (60), 329 [MH$^+$—C$_4$H$_8$] (19), 266 (100).

8-(Benzyloxy)-4-methyl-6,11-dihydro-2,6-methano[1,3]diazocino[5,6-b]indole-3,5(1H,4H)-dione (19e)

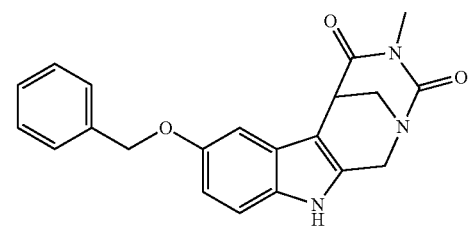 [SMILES: CN1C(=O)C2CN(Cc3[nH]c4ccc(OCc5ccccc5)cc4c32)C1=O]

According to GP4 from methyl 6-(benzyloxy)-2-(methylcarbamoyl)-2,3,4,9-tetrahydro-1H-pyrido[3,4-b]indole-4-carboxylate (17e) (10.0 g; 25.41 mmol). Yield 3.87 g (10.7 mmol; 42%). 1H NMR (300 MHz, DMSO): δ 11.00 (s, 1H), 7.48 (dd, J=8.1, 1.4 Hz, 2H), 7.43-7.28 (m, 3H), 7.24 (d, J=8.8 Hz, 1H), 7.05 (d, J=2.4 Hz, 1H), 6.81 (dd, J=8.8, 2.5 Hz, 1H), 5.09 (d, J=12.2 Hz, 1H), 5.05 (d, J=12.1 Hz, 1H), 4.63 (s, 2H), 3.88 (dd, J=13.1, 1.2 Hz, 1H), 3.77 (s, 1H), 3.43 (dd, J=13.1, 2.3 Hz, 1H), 2.88 (s, 3H).

tert-Butyl (4-methyl-3,5-dioxo-1,3,4,5,6,11-hexahydro-2,6-methano[1,3]diazocino[5,6-b]indol-9-yl)carbamate (19f)

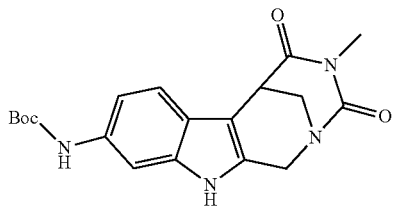 [SMILES: CN1C(=O)C2CN(Cc3[nH]c4cc(NC(=O)OC(C)(C)C)ccc4c32)C1=O]

According to GP4 from methyl 7-((tert-butoxycarbonyl)amino)-2-(methylcarbamoyl)-2,3,4,9-tetrahydro-1H-pyrido[3,4-b]indole-4-carboxylate (17f). Yield: Colorless crystals (1.90 g, 5.13 mmol, 67%) after silica gel chromatography with dichloromethane and methanol (10:1), mp: 240.1-240.3° C.; IR (KBr): 3316, 1721, 1670 cm$^{-1}$; $^1$H NMR (400 MHz, DMSO): δ 11.10 (s, 1H), 10.07 (s, 1H), 8.03 (d, J=1.3 Hz, 1H), 7.39 (d, J=8.5 Hz, 1H), 7.12 (dd, J=8.5, 1.6 Hz, 1H), 6.45 (dd, J=16.9, 10.1 Hz, 1H), 6.23 (dd, J=17.0, 2.0 Hz, 1H), 5.72 (dd, J=10.1, 2.0 Hz, 1H), 4.64 (s, 2H), 3.88 (d, J=13.0 Hz, 1H), 3.78 (s, 1H), 3.43 (dd, J=13.1, 2.1 Hz, 1H), 2.88 (s, 3H). ESI-MS m/z (%): 315 [MH$^+$–C$_4$H$_8$] (100) 371 [MH$^+$] (3). Anal. (C$_{19}$H$_{22}$N$_4$O$_4$): Calcd. C, 61.61; H, 5.99; N, 15.13; found. C, 61.52; H, 5.98; N, 14.97.

8-Methoxy-4-methyl-3-thioxo-3,4,6,1-tetrahydro-2,6-methan[1,3]diazocin[5,6-b]indol-5(1H)-one (19g)

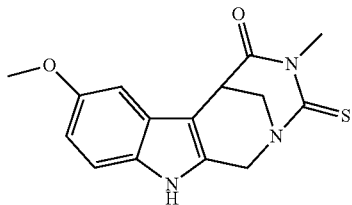 [SMILES: COc1ccc2[nH]c3c(c2c1)C1CN(C3)C(=S)N(C)C1=O]

Colorless crystals (4.76 g, 15.79 mmol, 95%) after crystallization from acetonitrile/water, mp: 232.0-232.1° C.; IR (KBr): 1692, 1628, cm$^{-1}$; $^1$H NMR (300 MHz, DMSO): δ 11.06 (s, 1H), 7.24 (d, J=8.8 Hz, 1H), 6.92 (d, J=2.4 Hz, 1H), 6.72 (dd, J=8.8, 2.5 Hz, 1H), 5.37 (d, J=15.8 Hz, 1H), 5.06 (d, J=15.8 Hz, 1H), 4.05 (d, J=12.7 Hz, 1H), 3.89 (s, 1H), 3.78-3.69 (m, 4H), 3.35 (s, 1H), 3.22 (s, 3H). ESI-MS m/z (%): 302 [MH$^+$] (100). Anal. (C$_{15}$H$_{15}$N$_3$O$_2$S): Calcd. C, 59.78; H, 5.02; N, 13.94; found. C, 59.66; H, 5.00; N, 14.04.

7-(Benzyloxy)-4-methyl-6.11-dihydro-2.6-methano[1.3]diazocino[5.6-b]indole-3.5(1H.4H)-dione (19h)

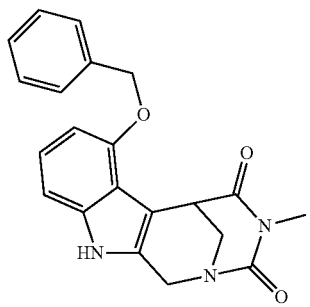 [SMILES: CN1C(=O)C2CN(Cc3[nH]c4cccc(OCc5ccccc5)c4c32)C1=O]

According to GP4 from methyl 5-(benzyloxy)-2-(methylcarbamoyl)-2.3.4.9-tetrahydro-1H-pyrido[3.4-b]indole-4-carboxylate (17h). Yield 3.50 g (9.68 mmol; 45%) colorless crystals after silica gel chromatography (CH$_2$Cl$_2$, Methanol; 10:1); mp: 259.05-261.9° C. $^1$H NMR (300 MHz, DMSO): δ 11.15 (s, 1H), 7.75 (dd, J=7.1 Hz, 2H), 7.43-7.27 (m, 3H), 6.96-6.91 (m, 2H), 6.57 (dd, J=6.7, 1.9 Hz, 1H), 5.22 (d, J=7.2 Hz, 2H), 4.63 (d, J=7.0 Hz, 2H), 4.08 (s, 1H), 3.86 (d, J=12.1 Hz, 1H), 3.43 (dd, J=13.2, 2.2 Hz, 1H), 2.92 (s, 3H).

Racemate of (1S,6S)-1-(benzo[d][1,3]dioxol-5-yl)-4-methyl-6,11-dihydro-2,6-methano[1,3]diazocino[5,6-b]indole-3,5(1H,4H)-dione and (1R,6R)-1-(benzo[d][1,3]dioxol-5-yl)-4-methyl-6,11-dihydro-2,6-methano[1,3]diazocino[5,6-b]indole-3,5(1H,4H)-dione (19i)

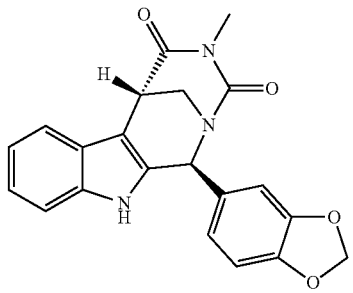

Trans, Racemate

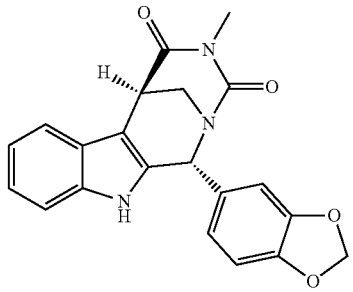

According to general procedure 4 (GP4) from (17i) (0.50 g; 1.22 mmol). Yield 0.25 g; 0.67 mmol (55%) colorless crystals. mp 297.4-298.9° C. IR (KBr): 3357, 1728, 1672 cm$^{-1}$. $^1$H NMR (300 MHz, DMSO): δ 11.37 (s, 1H), 7.54 (d, J=7.6 Hz, 1H), 7.36 (d, J=7.9 Hz, 1H), 7.20-7.01 (m, 2H), 6.92 (dd, J=15.6, 4.7 Hz, 2H), 6.69 (dd, J=8.0, 0.9 Hz, 1H), 6.06 (d, J=1.1 Hz, 2H), 5.98 (s, 1H), 3.86 (s, 1H), 3.60 (d, J=12.7 Hz, 1H), 3.21 (dt, J=15.6, 7.8 Hz, 1H), 2.92 (s, 3H). The constitution of the racemates was determined by NOE spectroscopy. ESI-MS m/z (%): 376 [MH$^+$] (100). Anal. Calcd for C$_{21}$H$_{17}$N$_3$O$_4$: C, 67.19; H, 4.56; N, 11.19; found: C, 66.74; H, 4.68; N, 11.33.

Remark: By use of a mixture of (17i) and (17j) exclusively (19i) can be obtained because of epimerization.

8-Hydroxy-4-methyl-6,11-dihydro-2,6-methano[1,3]diazocino[5,6-b]indole-3,5(1H,4H)-dione (22)

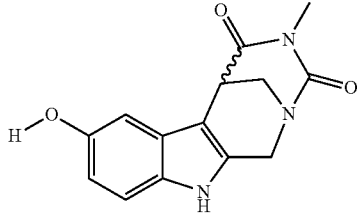 [SMILES: CN1C(=O)C2CN(Cc3[nH]c4ccc(O)cc4c32)C1=O]

8-(Benzyloxy)-4-methyl-6,11-dihydro-2,6-methano[1,3]diazocino[5,6-b]indole-3,5(1H,4H)-dione (19e) (3.30 g; 9.13 mmol) was dissolved in MeOH (330 mL), ammonium formate (3.30 g) and Pd on charcoal (0.66 g; 10%) were added and the mixture was heated to reflux for 30 min. After complete consumption of 19e (TLC-control; $SiO_2$; ethyl acetate), the catalyst was removed by filtration over a pad of celite, water was added and the organic solvent reduced under reduced pressure till the product precipitates as colorless crystals. Yield 2.14 g (7.88 mmol, 86%); mp 226-227° C. IR (KBr): 3384, 3301, 1720 cm$^{-1}$. $^1$H NMR (300 MHz, DMSO-d$_6$) δ 10.81 (s, 1H), 8.76 (s, 1H), 7.11 (d, J=8.6 Hz, 1H), 6.80 (d, J=2.2 Hz, 1H), 6.57 (dd, J=8.6, 2.4 Hz, 1H), 4.60 (s, 2H), 3.85 (dd, J=13.2, 1.6 Hz, 1H), 3.69 (d, J=1.9 Hz, 1H), 3.41 (dd, J=13.2, 2.4 Hz, 1H), 2.87 (s, 3H). ESI-MS m/z (%): 313 [MH$^+$+CH$_3$CN](100), 272 [MH]$^+$ (18). Anal. calcd for $C_{14}H_{13}N_3O_3 \times 0.5$ $CH_3OH$: C, 60.62; H, 5.26; N, 14.63; found: C, 60.32; H, 5.35; N, 14.43.

tert-butyl (2-((4-Methyl-3,5-dioxo-1,3,4,5,6,11-hexahydro-2,6-methano[1,3]diazocino[5,6-b]indol-8-yl)oxy)ethyl)carbamate (23)

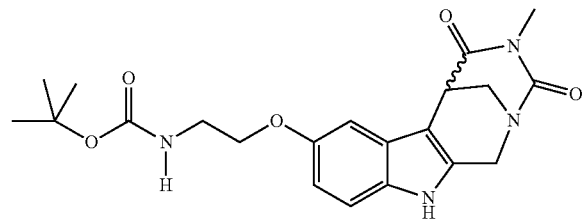 [SMILES: CN1C(=O)C2CN(Cc3[nH]c4ccc(OCCNC(=O)OC(C)(C)C)cc4c32)C1=O]

According to Lanning et al., 2013.

A solution of 22 (0.34 g, 1.25 mmol), tert-butyl-N-(hydroxyethyl)carbamate (0.41 g, 2.53 mmol), and PBu$_3$ (0.63 mL, 2.53 mmol) in anhydrous THF (18 mL) was stirred at RT for 2 min. ADDM (0.65 g, 2.53 mmol) was added in one portion. The reaction mixture was stirred at RT for 16 h under an inert atmosphere. The solvent was concentrated under reduced pressure, and the residue dissolved in ethyl acetate (40 mL) and water (20 mL). The organic phase was separated and dried over Na$_2$SO$_4$. The solvent was evaporated under reduced pressure, the residue absorbed onto silica gel and purified by column chromatography (eluent: $CH_2Cl_2$/MeOH 20:1).

0.28 g (0.68 mmol, 54%) colorless powder; mp 188-189° C. IR (KBr): 3378, 3339, 2980, 1728 cm$^{-1}$. $^1$H NMR (300 MHz, DMSO-d$_6$) δ 10.99 (s, 1H), 7.22 (d, J=8.8 Hz, 1H), 7.03 (t, J=5.7 Hz, 1H), 6.93 (d, J=2.4 Hz, 1H), 6.72 (dd, J=8.8, 2.4 Hz, 1H), 4.63 (s, 2H), 4.01-3.82 (m, 3H), 3.78 (d, J=1.7 Hz, 1H), 3.42 (dd, J=13.2, 2.4 Hz, 1H), 3.30 (q, J=5.8 Hz, 2H), 2.87 (s, 3H), 1.39 (s, 9H). ESI-MS m/z (%): 415 [MH]$^+$ (100). Anal. calcd for $C_{21}H_{26}N_4O_5$: C, 60.86; H, 6.32; N, 13.52; found: C, 60.47; H, 6.41; N, 13.28.

8-(2-Aminoethoxy)-4-methyl-6,11-dihydro-2,6-methano[1,3]diazocino[5,6-b]indole-3,5(1H,4H)-dione hydrochloride (24)

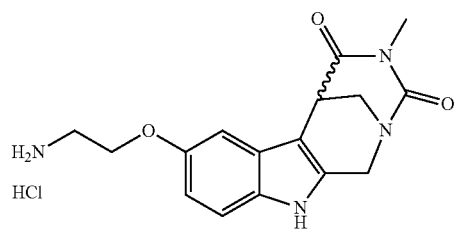 [SMILES: Cl ; CN1C(=O)C2CN(Cc3[nH]c4ccc(OCCN)cc4c32)C1=O]

A solution of 23 (0.10 g, 0.24 mmol) in HCl (6N in 2-propanol, 3.0 mL) was stirred at 80° C. for 15 min. The solvent was evaporated under reduced pressure and the residue was suspended in diethyl ether. The light beige crystals were filtered off und used in the next step without further purification. Yield 77.0 mg (0.22 mmol, 92%) light beige crystals; mp 260° C. (decomp.). IR (KBr): 3287, 2881, 1726 cm$^{-1}$. $^1$H NMR (300 MHz, DMSO-d$_6$) δ $^1$H NMR (300 MHz, DMSO-d$_6$) δ 11.13 (s, 1H), 8.19 (s, 3H), 7.27 (d, J=8.7 Hz, 1H), 7.00 (d, J=2.3 Hz, 1H), 6.80 (dd, J=8.8, 2.4 Hz, 1H), 4.64 (s, 2H), 4.15 (t, J=5.2 Hz, 2H), 3.88 (dd, J=13.2, 1.6 Hz, 1H), 3.79-3.75 (m, 1H), 3.43 (dd, J=13.1, 2.3 Hz, 1H), 3.27-3.15 (m, 2H), 2.87 (s, 3H). ESI-MS m/z (%): 315 [MH]$^+$ (100).

1.5 General procedure 5 (GP5) using the example of N-(4-methyl-3,5-dioxo-1,3,4,5,6,11-hexahydro-2,6-methano[1,3]diazocino[5,6-b]indol-8-yl)acrylamide (21c)

tert-Butyl (4-methyl-3,5-dioxo-1,3,4,5,6,11-hexahydro-2,6-methano[1,3]diazocino[5,6-b]indol-8-yl)carbamate (19c) 1.50 g (4.05 mmol) was dissolved in 2-propanol (30 mL) containing HCl (5-6N) and the mixture stirred at 60° C. for 1 h. The solvent was removed under reduced pressure and the remaining solid dissolved in DMF (15 mL), diisopropylethylamine (1.50 mL) and acryloylchloride (1.1 equivalents, 4.50 mmol, 0.36 mL) were added and the mixture stirred for 1 h. The mixture was poured into water, extracted with ethyl acetate (3×100 mL), the combined organic layers dried (Na$_2$SO$_4$) und the solvent removed under reduced pressure. Purification by cc (SiO$_2$; ethyl acetate, MeOH 10:1) and crystallization from etyl acetate.

N-(4-methyl-3,5-dioxo-1,3,4,5,6,11-hexahydro-2,6-methano[1,3]diazocino[5,6-b]indol-8-yl)acrylamide (21c)

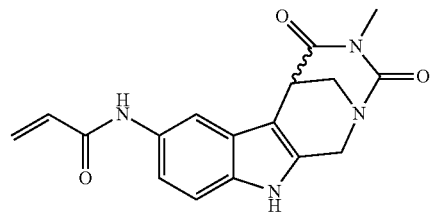 [SMILES: C=CC(=O)Nc1ccc2[nH]c3c(c2c1)C1CN(C3)C(=O)N(C)C1=O]

According to GP5 from tert-Butyl (4-methyl-3,5-dioxo-1,3,4,5,6,11-hexahydro-2,6-methano[1,3]diazocino[5,6-b]indol-8-yl)carbamate (19c). 0.48 g (1.48 mmol; 37% over 2 Steps) colorless crystals, crystallization from ethyl acetate, mp 293.1-295.9° C. $^1$H NMR (300 MHz, DMSO): δ 11.10 (s, 1H), 10.04 (s, 1H), 7.87 (d, J=1.6 Hz, 1H), 7.38 (dd, J=8.7, 1.9 Hz, 1H), 7.28 (d, J=8.7 Hz, 1H), 6.46 (dd, J=16.9, 10.0 Hz, 1H), 6.23 (dd, J=17.0, 2.2 Hz, 1H), 5.71 (dd, J=10.0, 2.2 Hz, 1H), 4.64 (s, 2H), 3.88 (d, J=12.9 Hz, 1H), 3.75 (s, 1H), 3.44 (dd, J=13.1, 2.1 Hz, 1H), 2.88 (s, 3H). ESI-MS m/z (%): 342 [MNH$_4^+$] (100); 324 [MH$^+$] (65).

N-((4-Methyl-3,5-dioxo-1,3,4,5,6,11-hexahydro-2,6-methano[1,3]diazocino[5,6-b]indol-8-yl)methyl)acrylamide (21d)

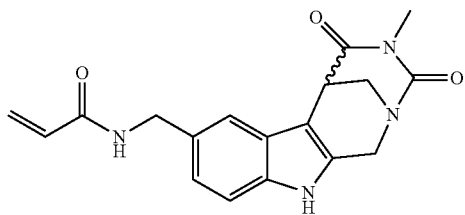 [SMILES: C=CC(=O)NCc1ccc2[nH]c3c(c2c1)C1CN(C3)C(=O)N(C)C1=O]

According to GP5 from tert-butyl ((4-methyl-3,5-dioxo-1,3,4,5,6,11-hexahydro-2,6-methano[1,3]diazocino[5,6-b]indol-8-yl)methyl)carbamate (19d). 0.58 g (1.71 mmol; 66% over 2 Steps) colorless crystals, crystallization from ethyl acetate/heptane, mp 249.3-253.0° C. $^1$H NMR (300 MHz, DMSO): δ 11.12 (s, 1H), 8.57 (t, J=5.8 Hz, 1H), 7.37 (s, 1H), 7.29 (d, J=8.3 Hz, 1H), 7.01 (dd, J=8.4, 1.5 Hz, 1H), 6.27 (dd, J=17.1, 10.0 Hz, 1H), 6.12 (dd, J=17.1, 2.4 Hz, 1H), 5.60 (dd, J=9.9, 2.4 Hz, 1H), 4.65 (s, 2H), 4.43 (dd, J=14.6, 6.0 Hz, 1H), 4.35 (dd, J=14.6, 5.9 Hz, 1H), 3.88 (d, J=13.0 Hz, 1H), 3.78 (s, 1H), 3.54-3.41 (m, 1H), 2.88 (d, J=3.9 Hz, 3H). ESI-MS m/z (%): 356 [MNH$_4^+$] (23); 339 [MH$^+$] (100). Anal. calcd for $C_{18}H_{18}N_4O_3 \times ⅕$ EE: C, 63.43; H, 5.55; N, 15.74; found: C, 63.20; H, 5.45; N, 16.01.

N-(4-Methyl-3,5-dioxo-1,3,4,5,6,11-hexahydro-2,6-methano[1,3]diazocino[5,6-b]indol-9-yl)acrylamide (21e)

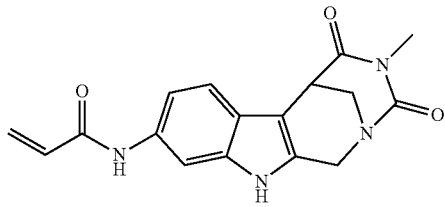 [SMILES: C=CC(=O)Nc1ccc2c3c([nH]c2c1)CN1CC3C(=O)N(C)C1=O]

According to GP5 from tert-butyl (4-methyl-3,5-dioxo-1,3,4,5,6,11-hexahydro-2,6-methano[1,3]diazocino[5,6-b]indol-9-yl)carbamate (19f). Yield: Colorless crystals (1.00 g, 3.08 mmol, 80%). Crystallization from ethyl acetate, mp: decomposition at 320° C.; IR (KBr): 1729, 1678, 1662 cm$^{-1}$; $^1$H NMR (400 MHz, DMSO): δ 11.10 (s, 1H), 10.07 (s, 1H), 8.03 (d, J=1.3 Hz, 1H), 7.39 (d, J=8.5 Hz, 1H), 7.12 (dd, J=8.5, 1.6 Hz, 1H), 6.45 (dd, J=16.9, 10.1 Hz, 1H), 6.23 (dd, J=17.0, 2.0 Hz, 1H), 5.72 (dd, J=10.1, 2.0 Hz, 1H), 4.64 (s, 2H), 3.88 (d, J=13.0 Hz, 1H), 3.78 (s, 1H), 3.43 (dd, J=13.1, 2.1 Hz, 1H), 2.88 (s, 3H). ESI-MS m/z (%): 325 [MH$^+$] (100). Anal. ($C_{17}H_{16}N_4O_3+⅓$ ethyl acetate): Calcd. C, 62.26; H, 5.32; N, 16.59; found. C, 62.39; H, 5.13; N, 16.60.

N-(2-((4-methyl-3,5-dioxo-1,3,4,5,6,11-hexahydro-2,6-methano[1,3]diazocino[5,6-b]indol-8-yl)oxy)ethyl)acrylamide (25)

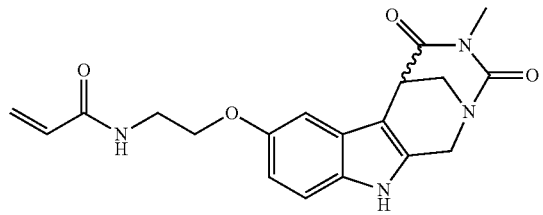 [SMILES: C=CC(=O)NCCOc1ccc2[nH]c3c(c2c1)C1CN(C3)C(=O)N(C)C1=O]

A solution of 24 (0.71 g, 2.02 mmol) and triethylamine (1.0 mL) was cooled to 0° C. Under stirring a solution of acryloyl chloride (0.17 mL, 2.02 mmoL) in DMF (1.0 mL) was added dropwise. The mixture was warmed to room temperature and stirred overnight. The mixture was poured into water (80 mL) and extracted with ethyl acetate (3×50 mL). The combined organic phases were dried over Na$_2$SO$_4$, the solvent removed under reduced pressure and the residue purified by column chromatography (eluent: ethyl acetate/MeOH 20:1).

0.24 g (0.65 mmol, 32%) colorless crystals; mp 193-197° C. IR (KBr): 3334, 3286, 2949, 1725 cm$^{-1}$. $^1$H NMR (300 MHz, DMSO-d$_6$) δ 10.99 (s, 1H), 8.40 (t, J=5.6 Hz, 1H), 7.23 (d, J=8.8 Hz, 1H), 6.95 (d, J=2.3 Hz, 1H), 6.74 (dd, J=8.8, 2.4 Hz, 1H), 6.29 (dd, J=17.1, 10.0 Hz, 1H), 6.11 (dd, J=17.1, 2.4 Hz, 1H), 5.60 (dd, J=10.0, 2.4 Hz, 1H), 4.63 (s, 2H), 4.04-3.95 (m, 2H), 3.88 (dd, J=13.2, 1.6 Hz, 1H), 3.80-3.73 (m, 1H), 3.52 (q, J=5.6 Hz, 2H), 3.43 (dd, J=13.3, 2.3 Hz, 1H), 2.87 (s, 3H). ESI-MS m/z (%): 369 [MH]$^+$ (100). Anal. calcd for $C_{19}H_{20}N_4O_4 \times 0.5\ C_4H_8O_2$: C, 61.15; H, 5.87; N, 13.58; found: C, 61.44; H, 5.80; N, 13.77.

Methyl 2-(2-((tert-butoxycarbonyl)(methyl)amino)acetyl)-2,3,4,9-tetrahydro-1H-pyrido[3,4-b]indole-4-carboxylate (27)

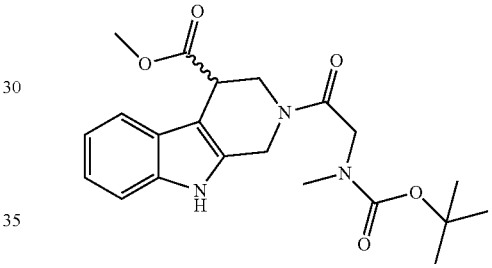

To a stirred suspension of methyl 2,3,4,9-tetrahydro-1H-pyrido[3,4-b]indole-4-carboxylate hydrochloride (13a) (1.33 g; 5.00 mmol) in acetonitrile (50.0 mL) were added triethylamine (5.00 mL), benzotriazol-1-yloxy-tris(dimethylamino)phosphonium-hexafluoro-phosphate (2.65 g; 6.00 mmol) and N-boc-sarcosine (1.13 g; 6.00 mmol). After being stirred for 16 h under room temperature, the mixture was poured into water. The product was collected by filtration.

1.76 g; 4.38 mmol; 88%) colorless crystals after silica gel chromatography (CH$_2$Cl$_2$, ethyl acetate; 1:1). IR (KBr): 3298, 3299, 2977, 1735, 1697 cm$^{-1}$. CI-MS (NH$_3$) m/z (%): 402 [MH$^+$] (100). Anal. calcd for $C_{21}H_{27}N_3O_5$): C, 62.83; H, 6.78; N, 10.47; found: C, 60.15; H, 6.84; N, 10.06.

5-Methyl-4,5-dihydro-1H-2,7-methano[1,4]diazonino[6,7-b]indole-3,6(7H,12H)-dione (28)

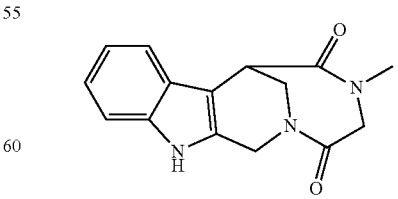

To a solution of methyl 2-(2-((tert-butoxycarbonyl)(methyl)amino)acetyl)-2,3,4,9-tetrahydro-1H-pyrido[3,4-b]indole-4-carboxylate (21) (1.50 g; 3.74 mmol) in THF (10.0 mL) and MeOH (10.0 mL) was added LiOH (0.108 g; 4.50 mmol) in water (10.0 mL). The mixture was stirred for 2 h at 60° C. The solvent was removed under reduced pressure und the residue dissolved in HCl (30.0 mL; 5-6 N in 2-propanol). After being stirred for 3 h at room temperature the solvent was removed under reduced pressure. To a solution of the residue in DMF (20.0 mL) and acetonitrile (40.0 mL) were added triethylamine (5.00 mL) and benzotriazol-1-yloxy-tris(dimethylamino)phosphonium-hexafluoro-phosphate (2.65 g; 6.00 mmol). After being stirred for 24 h under room temperature, the mixture was poured into HCl (1N in water). The crude product was extracted with ethyl acetate (3×50 mL). The combined organic layers were washed with brine, dried ($Na_2SO_4$) and evaporated.

0.41 g (1.52 mmol; 41%) colorless crystals after silica gel chromatography (ethyl acetate, MeOH 10:1) and recrystallization from ethyl acetate; mp 308.8-309.5° C. IR (KBr): 3232, 1670, 1608 $cm^{-1}$. $^1$H NMR (300 MHz, DMSO-$d_6$): δ 11.04 (s, 1H), 7.80 (d, J=7.6 Hz, 1H), 7.28 (d, J=7.9 Hz, 1H), 7.12-6.84 (m, 2H), 5.15 (d, J=15.7 Hz, 1H), 4.96 (d, J=13.8 Hz, 1H), 4.59 (d, J=15.1 Hz, 1H), 4.27 (dd, J=15.7, 1.7 Hz, 1H), 3.81 (s, 1H), 2.92 (s, 3H). ESI-MS m/z (%): 556 [$2MNH_4^+$] (100), 539 [$2MH^+$] (68), 270 [$MH^+$] (20). Anal. calcd for $C_{15}H_{15}N_3O_2$: C, 66.90; H, 5.61; N, 15.60; found: C, 66.79; H, 5.48; N, 15.32.

1.6 General Procedure 6 (GP6)

Modification a:

A solution of the β-carboline derivative (2.00 mmol) in DMF (10.0 mL) under nitrogen atmosphere was cooled to 0° C. After addition of NaH (2.20 mmol; 60% in paraffin) the mixture was stirred for 10 minutes. The alkylating agent (2.20 mmol) was added and stirring at room temperature continued until completion of the reaction was observed by TLC. The mixture was poured into water. The crude product was isolated by filtration or extraction of the aqueous phase with $CH_2Cl_2$ (4×50.0 mL). In both cases silica gel chromatography afforded the desired product.

Modification b:

A mixture of the β-carboline derivative (2.00 mmol) in 2-butanone (40.0 mL), the alkylating agent (2.20 mmol) and $K_2CO_3$ (20.0 mmol) was stirred at reflux overnight. The mixture was filtered off, the solvent removed under reduced pressure and the product purified by cc ($SiO_2$; $CH_2Cl_2$, ethyl acetate 2:1) and crystallization from $CH_2Cl_2$ by addition of light petrol.

tert-Butyl 4-((4-methyl-3,5-dioxo-3,4,5,6-tetrahydro-2,6-methano[1,3]diazocino[5,6-b]indol-11(1H)-yl)methyl)benzoate (30a)

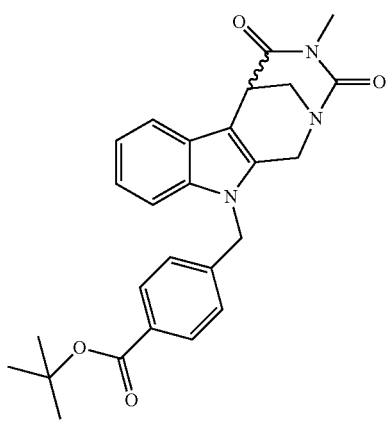 [SMILES: CN1C(=O)C2CN(Cc3c2c2ccccc2n3Cc2ccc(C(=O)OC(C)(C)C)cc2)C1=O]

According to GP6, modification a, from 4-methyl-6,11-dihydro-2,6-methano[1,3]diazocino[5,6-b]indole-3,5(1H,4H)-dione (18a) (0.51 g; 2.00 mmol) and tert-butyl 4-(brommethyl)benzoate (23) (Andrianjara et al., 2002). 0.65 g (1.46 mmol; 73%) colorless crystals after recrystallization from $CH_2Cl_2$/n-heptane; mp 191.5-191.9° C. IR (KBr): 1714, 1687 $cm^{-1}$. $^1$H NMR (300 MHz, DMSO-$d_6$): δ 7.82 (d, J=8.3 Hz, 2H), 7.53 (dd, J=6.2, 2.5 Hz, 1H), 7.41 (dd, J=6.5, 2.1 Hz, 1H), 7.15 (dd, J=8.5, 4.8 Hz, 2H), 7.12-6.95 (m, 2H), 5.45 (s, 2H), 4.83 (d, J=16.6 Hz, 1H), 4.54 (d, J=16.6 Hz, 1H), 3.90 (d, J=12.1 Hz, 2H), 3.45 (dd, J=13.6, 2.6 Hz, 1H), 2.89 (s, 3H), 1.51 (s, 9H). ESI-MS m/z (%): 463 [$MNH_4^+$] (70), 446 [$MH^+$] (100). Anal. calcd from $C_{26}H_{27}N_3O_4$: C, 70.09; H, 6.11; N, 9.43; found: C, 70.02; H, 6.02; N, 9.35.

tert-Butyl 4-((4-methyl-5-oxo-3-thioxo-3,4,5,6-tetrahydro-2,6-methano[1,3]diazocino[5,6-b]indol-11(1H)-yl)methyl)benzoate (30b)

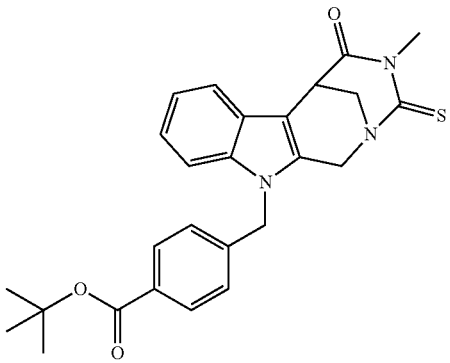 [SMILES: CN1C(=O)C2CN(Cc3c2c2ccccc2n3Cc2ccc(C(=O)OC(C)(C)C)cc2)C1=S]

According to GP6 from 4-Methyl-3-thioxo-3,4,6,11-tetrahydro-2,6-methano[1,3]diazocino[5,6-b]indol-5(1H)-one (18b) (1.48 g; 5.45 mmol) and tert-butyl 4-(brommethyl)benzoate (23) (Andrianjara et al., 2002). 2.40 g (5.20 mmol; 95%) colorless crystals after recrystallization from $CH_2Cl_2$/petrolether; mp 186.9-188.4° C. $^1$H NMR (300 MHz, DMSO): δ 7.80 (d, J=8.3 Hz, 2H), 7.57-7.46 (m, 1H), 7.42-7.34 (m, 1H), 7.20 (d, J=8.3 Hz, 2H), 7.14-7.01 (m, 2H), 5.53 (d, J=16.1 Hz, 1H), 5.42 (d, J=17.6 Hz, 2H), 5.03 (d, J=16.0 Hz, 1H), 4.08 (d, J=12.7 Hz, 1H), 3.98 (s, 1H), 3.77 (dd, J=12.8, 1.9 Hz, 1H), 3.23 (s, 3H), 1.50 (s, 9H). ESI-MS m/z (%): 462 [$MH^+$] (25), 406 [$MH^+-C_4H_8$] (100).

tert-Butyl 4-((4-methyl-3-oxo-5-thioxo-3,4,5,6-tetrahydro-2,6-methano[1,3]diazocino[5,6-b]indol-11(1H)-yl)methyl)benzoate (30c)

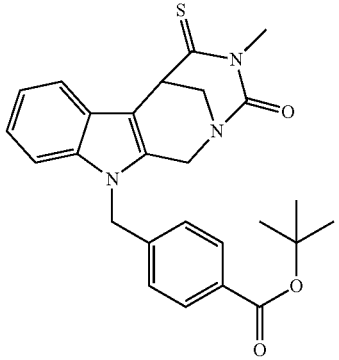 [SMILES: CN1C(=O)N2Cc3c(c4ccccc4n3Cc3ccc(C(=O)OC(C)(C)C)cc3)C(C2)C1=S]

According to GP6 from 4-methyl-5-thioxo-4,5,6,11-tetrahydro-2,6-methan[1,3]diazocino[5,6-b]indol-3(1H)-one (18c) (0.72 g; 2.76 mmol) and tert-butyl 4-(brommethyl)benzoate (23) (Andrianjara et al., 2002). Yellow crystals (0.52 g, 1.13 mmol, 40%) after crystallization from petrol ether and ethyl acetae (2:1). mp: 203.6-205.4 4° C. IR (KBr): 1701, 3433 cm$^{-1}$. $^1$H NMR (300 MHz, CDCl$_3$): δ 7.97-7.84 (m, 3H), 7.24-7.14 (m, 3H), 7.06 (d, J=8.3 Hz, 2H), 5.24 (dd, J=63.0, 17.0 Hz, 2H), 4.91 (d, J=16.3 Hz, 1H), 4.57-4.51 (m, 1H), 4.25 (dd, J=16.3, 1.0 Hz, 1H), 3.91 (d, J=12.7 Hz, 1H), 3.44 (s, 3H), 3.33 (dd, J=13.0, 2.3 Hz, 1H), 1.57 (s, 9H). ESI-MS m/z (%): 462 [MH$^+$] (100). Anal. calcd. for C$_{26}$H$_{27}$N$_3$O$_3$S×EE: C, 67.06; H, 6.04; N, 8.68; S, 6.63; found: C, 66.70; H, 5.96; N, 8.69; S, 6.64.

tert-Butyl 4-((8-methoxy-4-methyl-5-oxo-3-thioxo-3,4,5,6-tetrahydro-2,6-methano[1,3]diazocino[5,6-b]indol-11(1H)-yl)methyl)benzoate (30d)

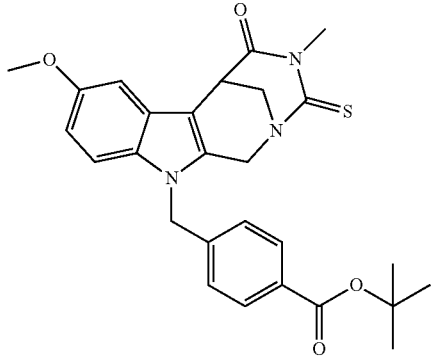 [SMILES: COc1ccc2c(c1)c1c(n2Cc2ccc(C(=O)OC(C)(C)C)cc2)CN2CC1C(=O)N(C)C2=S]

According to GP6 from 8-methoxy-4-methyl-3-thioxo-3,4,6,11-tetrahydro-2,6-methan[1,3]diazocin[5,6-b]indol-5(1H)-one (19g) and tert-butyl 4-(brommethyl)benzoate (23) (Andrianjara et al., 2002). Yellow crystals (1.70 g, 3.46 mmol, 59%). $^1$H NMR (300 MHz, DMSO): δ 7.79 (d, J=8.3 Hz, 2H), 7.28 (d, J=8.9 Hz, 1H), 7.18 (d, J=8.3 Hz, 2H), 6.97 (d, J=2.4 Hz, 1H), 6.74 (dd, J=8.9, 2.5 Hz, 1H), 5.50 (d, J=16.1 Hz, 1H), 5.40 (s, J=17.6 Hz, 2H), 5.00 (d, J=16.0 Hz, 1H), 4.07 (d, J=12.5 Hz, 1H), 3.97 (d, J=11.4 Hz, 1H), 3.81-3.69 (m, 4H), 3.23 (s, 3H), 1.50 (s, 9H).

tert-Butyl 4-((8-(benzyloxy)-4-methyl-3.5-dioxo-3.4.5.6-tetrahydro-2,6-methano[1.3]diazocino[5,6-b]indol-11(1H)-yl)methyl)benzoate (30e)

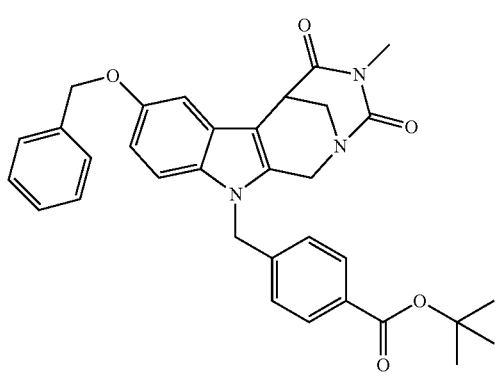 [SMILES: CN1C(=O)C2CN(Cc3c2c2cc(OCc4ccccc4)ccc2n3Cc2ccc(C(=O)OC(C)(C)C)cc2)C1=O]

According to GP6, modification a, from 8-(Benzyloxy)-4-methyl-6,11-dihydro-2,6-methano[1,3]diazocino[5,6-b]indole-3,5(1H.4l1)-dione (19e) and tert-Butyl4-(brommethyl)benzoate (29). Yield 12.4 g (22.48 mmol; 88%) colorless crystals after chromatography over silica gel with CH$_2$Cl$_2$/EtOAc (9:1); mp: 238.4-239.5° C. $^1$H NMR (300 MHz, DMSO): δ 7.81 (d, J=8.3 Hz, 1H), 7.50-7.28 (m, 6H), 7.14 (d, J=8.3 Hz, 2H), 7.10 (d, J=2.4 Hz, 1H), 6.83 (dd, J=8.9, 2.4 Hz, 1H), 5.40 (s, 2H), 5.08 (s, 2H), 4.80 (d, J=16.6 Hz, 1H), 4.51 (d, J=16.4 Hz, 1H), 3.89 (d, J=12.8 Hz, 1H), 3.43 (dd, J=13.1, 2.1 Hz, 1H), 2.90 (s, 3H), 1.51 (s, 9H). ESI-MS m/z (%): 496.19 [MH$^+$–C$_4$H$_8$] (100), 552.25 [MH$^+$] (38.95), 569.28 [MMH$_4^+$] (31.5), 1125.48 [2MNa$^+$] (15.21). Anal. calcd for C$_{33}$H$_{33}$N$_3$O$_5$: C, 71.85; H, 6.03; N, 7.62; found: C, 71.49; H, 5.99; N, 7.50.

tert-Butyl 4-((7-(benzyloxy)-4-methyl-3.5-dioxo-3.4.5.6-tetrahydro-2,6-methano[1.3]diazocino[5,6-b]indol-11(1H)-yl)methyl)benzoate (30f)

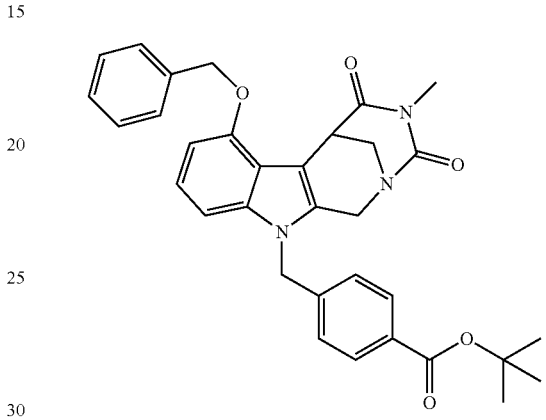

According to GP6, modification a, from 7-(benzyloxy)-4-methyl-6,11-dihydro-2,6-methano[1,3]diazocino[5,6-b]indole-3,5(1H.4H)-dione (19h) and tert-Butyl4-(brommethyl)benzoate (29). Yield 0.75 g (1.36 mmol; 49%) colorless crystals after chromatography over silica gel with CH$_2$Cl$_2$/C$_4$H$_8$O$_2$ (9:1); mp: 233.4-235.5° C. $^1$H NMR (300 MHz, DMSO): δ 7.81 (d, J=8.3 Hz, 2H), 7.75 (d, J=7.2 Hz, 2H), 7.35 (dt, J=27.6, 7.2 Hz, 3H), 7.13 (d, J=8.3 Hz, 2H), 6.98 (d, J=4.4 Hz, 2H), 6.67-6.60 (m, 1H), 5.41 (s, 2H), 5.24 (d, J=6.4 Hz, 2H), 4.82 (d, J=16.5 Hz, 1H), 4.48 (d, J=16.5 Hz, 1H), 4.14 (s, 1H), 3.86 (d, J=12.7 Hz, 1H), 3.41 (dd, J=9.5, 7.5 Hz, 1H), 2.93 (s, 3H), 1.51 (s, 9H).

tert-Butyl 4-((8-methoxy-4-methyl-3,5-dioxo-3,4,5,6-tetrahydro-2,6-methano[1,3]diazocino[5,6-b]indol-11(1H)-yl)methyl)benzoate (31a)

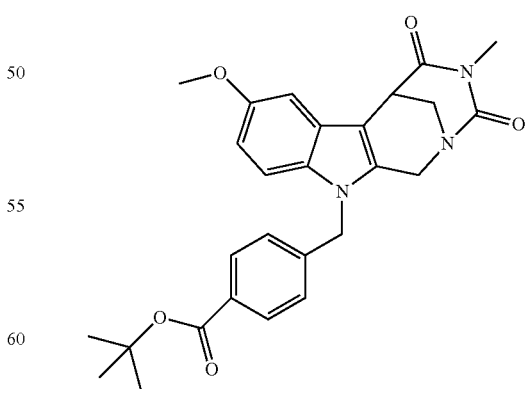

According to GP6, modification a, from 8-methoxy-4-methyl-6,11-dihydro-2,6-methano[1,3]diazocino[5,6-b]indole-3,5(1H,4H)-dione (19a) (0.50 g; 2.34 mmol) and tert-butyl 4-(brommethyl)benzoate (23) (Andrianjara et al., 2002). 0.50 g (1.05 mmol; 45%) colorless crystals after silica gel chromatography (CH$_2$Cl$_2$; ethyl acetate; 10:1), mp 241.0-243.5° C. IR (KBr): 2934, 1674 cm$^{-1}$. $^1$H NMR (300 MHz, CDCl$_3$): δ 7.98-7.86 (m, 4H), 7.14 (d, J=2.4 Hz, 2H), 7.09 (d, J=8.9 Hz, 2H), 7.03 (d, J=8.3 Hz, 4H), 6.83 (dd, J=8.9, 2.4 Hz, 2H), 5.29 (d, J=17.0 Hz, 2H), 5.10 (d, J=17.0 Hz, 2H), 4.85 (d, J=16.4 Hz, 2H), 4.25 (d, J=16.3 Hz, 2H), 3.94-3.83 (m, 10H), 3.32 (dd, J=13.6, 2.6 Hz, 2H), 3.07 (s, 6H), 1.57 (s, 17H). ESI-MS m/z (%): 476 [MH$^+$] (28), 420 [M–C$_4$H$_8$] (100). Anal. calcd for C$_{27}$H$_{29}$N$_3$O$_5$): C, 68.19; H, 6.15; N, 8.84; found: C, 67.90; H, 6.11; N, 8.79.

tert-Butyl 4-((9-methoxy-4-methyl-3,5-dioxo-3,4,5,6-tetrahydro-2,6-methano[1,3]diazocino[5,6-b]indol-11(1H)-yl)methyl)benzoate (31b)

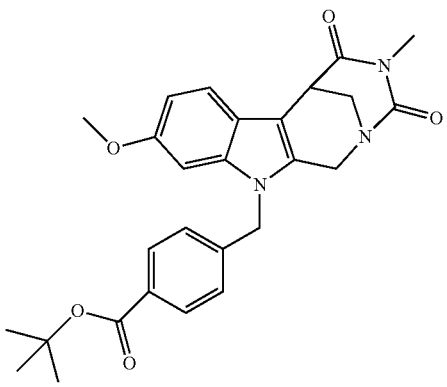 [SMILES: COc1ccc2c3c(n(Cc4ccc(C(=O)OC(C)(C)C)cc4)c2c1)CN1CC3C(=O)N(C)C1=O]

According to GP6, modification a, from 9-methoxy-4-methyl-6,11-dihydro-2,6-methano[1,3]diazocino[5,6-b]indole-3,5(1H,4H)-dione (19b) (1.40 g; 4.90 mmol) and tert-butyl 4-(brommethyl)benzoate (29) (Andrianjara et al., 2002). 1.50 g (3.16 mmol; 64%) colorless crystals after silica gel chromatography (CH$_2$Cl$_2$; ethyl acetate; 20:1) and crystallization from ethyl acetate, mp 210.3-213.7° C. IR (KBr): 3452, 1729, 1704, 1683 cm$^{-1}$. $^1$H NMR (300 MHz, DMSO): δ 7.82 (d, J=8.3 Hz, 2H), 7.39 (d, J=8.6 Hz, 1H), 7.17 (d, J=8.3 Hz, 2H), 7.01 (d, J=2.1 Hz, 1H), 6.74 (dd, J=8.6, 2.2 Hz, 1H), 5.44 (d, J=17.3 Hz, 1H), 5.38 (d, J=17.2 Hz, 1H), 4.76 (d, J=16.5 Hz, 1H), 4.46 (d, J=16.4 Hz, 1H), 3.86 (d, J=13.2 Hz, 1H), 3.82 (s, 1H), 3.71 (s, 3H), 3.40 (dd, J=13.0, 2.0 Hz, 1H), 2.88 (s, 3H), 1.51 (s, 10H). ESI-MS m/z (%): 476 [MH$^+$] (100).

tert-Butyl 4-((8-acrylamido-4-methyl-3,5-dioxo-3,4,5,6-tetrahydro-2,6-methano[1,3]diazocino[5,6-b]indol-11(1H)-yl)methyl)benzoate (31c)

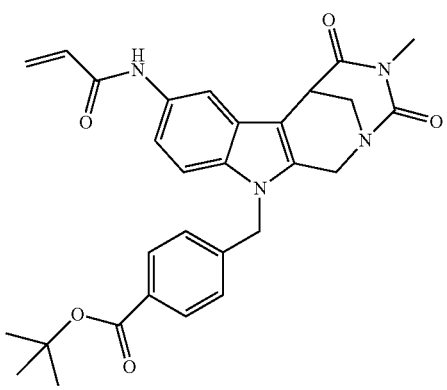 [SMILES: C=CC(=O)Nc1ccc2c(c1)c1c(n2Cc2ccc(C(=O)OC(C)(C)C)cc2)CN2CC1C(=O)N(C)C2=O]

According to GP6, modification b, from N-(4-methyl-3,5-dioxo-1,3,4,5,6,11-hexahydro-2,6-methano[1,3]diazocino[5,6-b]indol-8-yl)acrylamide (21c) (0.45 g; 1.39 mmol) and tert-butyl 4-(brommethyl)benzoate (29) (Andrianjara et al., 2002). 0.53 g (1.03 mmol; 74%) colorless crystals after silica gel chromatography (CH$_2$Cl$_2$; ethyl acetate; 1:2) and crystallization from ethyl acetate and petrolether, mp 201.5-203.1° C. $^1$H NMR (300 MHz, DMSO): δ 10.09 (s, 1H), 7.94 (s, 1H), 7.82 (d, J=8.2 Hz, 2H), 7.46-7.27 (m, 2H), 7.16 (d, J=8.3 Hz, 2H), 6.45 (dd, J=16.9, 10.0 Hz, 1H), 6.23 (dd, J=17.0, 2.2 Hz, 1H), 5.71 (dd, J=10.0, 2.2 Hz, 1H), 5.42 (s, 2H), 4.81 (d, J=16.6 Hz, 1H), 4.52 (d, J=16.5 Hz, 1H), 3.89 (d, J=12.8 Hz, 1H), 3.81 (s, 1H), 3.44 (d, J=11.2 Hz, 1H), 2.90 (s, 3H), 1.51 (s, 9H). ESI-MS m/z (%): 532 [MNH$_4^+$] (100), 515 [MH$^+$] (80).

tert-Butyl 4-((8-(acrylamidomethyl)-4-methyl-3,5-dioxo-3,4,5,6-tetrahydro-2,6-methano[1,3]diazocino[5,6-b]indol-1(1H)-yl)methyl)benzoate (31d)

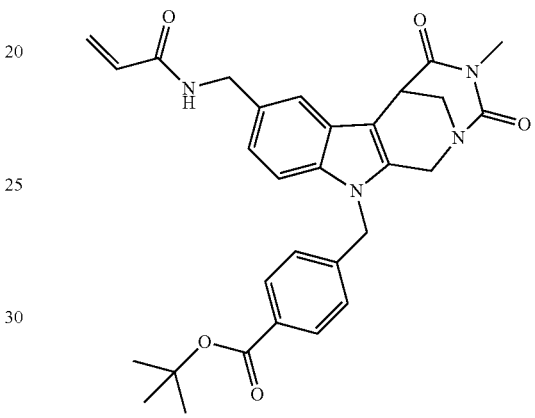

According to GP, modification b, from N-((4-Methyl-3,5-dioxo-1,3,4,5,6,1-hexahydro-2,6-methano[1,3]diazocino[5,6-b]indol-8-yl)methyl)acrylamide (21d) (0.75 g; 2.22 mmol) and tert-butyl 4-(brommethyl)benzoate (23) (Andrianjara et al., 2002). 0.89 g (1.69 mmol; 76%) colorless crystals, mp 205.4-208.6° C. $^1$H NMR (300 MHz, DMSO): δ 8.57 (t, J=5.8 Hz, 1H), 7.80 (d, J=8.2 Hz, 2H), 7.43 (s, 1H), 7.36 (d, J=8.5 Hz, 1H), 7.12 (d, J=8.3 Hz, 2H), 7.04 (dd, J=8.5, 1.3 Hz, 1H), 6.26 (dd, J=17.1, 9.9 Hz, 1H), 6.11 (dd, J=17.1, 2.4 Hz, 1H), 5.60 (dd, J=9.9, 2.4 Hz, 1H), 5.43 (s, 2H), 4.81 (d, J=16.6 Hz, 1H), 4.53 (d, J=16.5 Hz, 1H), 4.43 (dd, J=14.4, 5.7 Hz, 1H), 4.39-4.31 (m, 1H), 3.88 (t, J=8.4 Hz, 1H), 3.84 (s, 1H), 3.43 (dd, J=13.1, 1.9 Hz, 1H), 2.89 (s, 3H), 1.50 (s, 9H). ESI-MS m/z (%): 546 [MNH$_4^+$] (42), 529 [MH$^+$] (100), 473 [MH$^+$–C$_4$H$_8$] (30). Anal. calcd for C$_{30}$H$_{32}$N$_4$O$_5$: C, 68.17; H, 6.10; N, 10.60; found: C, 67.86; H, 6.06; N, 10.33.

tert-Butyl 4-((8-(2-acrylamidoethoxy)-4-methyl-3,5-dioxo-3,4,5,6-tetrahydro-2,6-methano[1,3]diazocino[5,6-b]indol-11(1H)-yl)methyl)benzoate (31e)

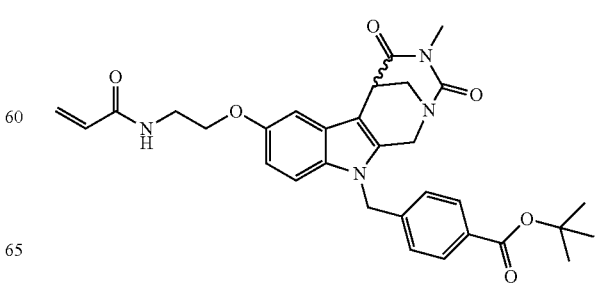

A solution of 25 (0.23 g, 0.62 mmol), tert-butyl 4-(brommethyl)benzoate (23) (Andrianjara et al., 2002) (0.19 g, 0.70 mmol), and K$_2$CO$_3$ (0.86 g, 6.20 mmol) in 2-butanone (10 mL) was stirred at 80° C. overnight. After cooling to room temperature the mixture was poured into water (15 mL) and extracted with ethyl acetate (3×20 mL). The combined organic phases were dried over Na$_2$SO$_4$ and the solvent evaporated under reduced pressure. The residue was purified by column chromatography (eluent: ethyl acetate). Yield 0.23 g (0.41 mmol, 66%) colorless foam; mp 95-98° C. IR (KBr): 3359, 2975, 1700 cm$^{-1}$. $^1$H NMR (300 MHz, DMSO-d$_6$) δ $^1$H NMR (300 MHz, DMSO-d$_6$) δ 8.39 (t, J=5.6 Hz, 1H), 7.85-7.75 (m, 2H), 7.30 (d, J=8.9 Hz, 1H), 7.19-7.08 (m, 2H), 7.01 (d, J=2.4 Hz, 1H), 6.77 (dd, J=8.8, 2.4 Hz, 1H), 6.28 (dd, J=17.1, 10.0 Hz, 1H), 6.10 (dd, J=17.1, 2.4 Hz, 1H), 5.59 (dd, J=10.0, 2.4 Hz, 1H), 5.40 (s, 2H), 4.65 (dd, J=86.0, 16.6 Hz, 2H), 4.03-3.97 (m, 2H), 3.94-3.80 (m, 2H), 3.52 (q, J=5.6 Hz, 2H), 3.43 (dd, J=13.1, 2.3 Hz, 1H), 2.89 (s, 3H), 1.51 (s, 9H). ESI-MS m/z (%): 559 [MH]$^+$ (100). Anal. calcd for C$_{31}$H$_{34}$N$_4$O$_6$×C$_4$H$_8$O$_2$: C, 64.99; H, 6.55; N, 8.65; found: C, 64.79; H, 6.26; N, 8.86.

tert-Butyl 4-((9-acrylamido-4-methyl-3,5-dioxo-3,4,5,6-tetrahydro-2,6-methano[1,3]diazocino[5,6-b]indol-11(1H)-yl)methyl)benzoate (31f)

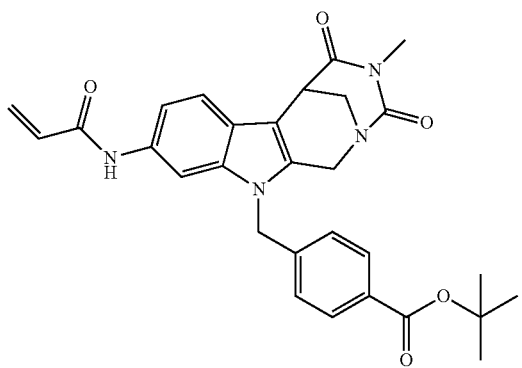 [SMILES: C=CC(=O)Nc1ccc2c3c(n(Cc4ccc(C(=O)OC(C)(C)C)cc4)c2c1)CN1CC3C(=O)N(C)C1=O]

According to GP6 modification b from N-(4-methyl-3,5-dioxo-1,3,4,5,6,11-hexahydro-2,6-methano[1,3]diazocino[5,6-b]indol-9-yl)acrylamide (21e). Yield: Colorless crystals (0.67 g, 1.30 mmol, 50%) silica gel chromatography ethyl acetate/dichloromethane (2:1), mp: 213.9-214.3° C.; IR (KBr): 1727, 1707, 1664 cm$^{-1}$; $^1$H NMR (400 MHz, DMSO): δ 10.10 (s, 1H), 7.94 (d, J=1.1 Hz, 1H), 7.83 (d, J=8.3 Hz, 2H), 7.46 (d, J=8.5 Hz, 1H), 7.22 (dd, J=8.5, 1.5 Hz, 1H), 7.15 (d, J=8.3 Hz, 2H), 6.42 (dd, J=16.9, 10.1 Hz, 1H), 6.21 (dd, J=17.0, 2.0 Hz, 1H), 5.70 (dd, J=10.1, 2.0 Hz, 1H), 5.40 (d, J=17.3 Hz, 1H), 5.35 (d, J=17.3 Hz, 1H), 4.82 (d, J=16.6 Hz, 1H), 4.55 (d, J=16.5 Hz, 1H), 3.89 (d, J=13.1 Hz, 1H), 3.86 (s, 1H), 3.45 (dd, J=13.0, 1.9 Hz, 1H), 2.90 (s, 3H), 1.51 (s, 9H). ESI-MS m/z (%): 459 [MH$^+$–C$_4$H$_8$] (100), 515 [MH$^+$] (24), 515 [MH$^+$] (5). Anal. (C$_{29}$H$_{30}$N$_4$O$_5$): Calcd. C, 67.69; H, 5.88; N, 10.89; found. C, 67.33; H, 6.01; N, 10.66.

tert-Butyl 4-((5-methyl-3,6-dioxo-4,5,6,7-tetrahydro-1H-2,7-methano[1,4]diazonino[6,7-b]indol-12(3H)-yl)methyl)benzoate (32)

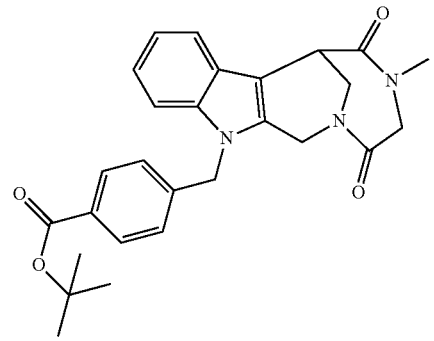 [SMILES: CN1CC(=O)N2Cc3c(c4ccccc4n3Cc3ccc(C(=O)OC(C)(C)C)cc3)C(C2)C1=O]

According to GP6, modification a, from 5-methyl-4,5-dihydro-1H-2,7-methano[1,4]diazonino[6,7-b]indole-3,6(7H,12H)-dione (28) (0.54 g; 2.00 mmol) und tert-butyl 4-(brommethyl)benzoate (29) (Andrianjara et al., 2002). 0.68 g (1.48 mmol; 74%) colorless crystals after recrystallization from CH$_2$Cl$_2$/n-Heptan; mp 239.4-240.2° C. IR (KBr): 2998, 2974, 1708, 1640 cm$^{-1}$. $^1$H NMR (300 MHz, DMSO-d$_6$): δ 7.87 (dd, J=6.9, 1.8 Hz, 1H), 7.82 (d, J=8.3 Hz, 2H), 7.35 (dd, J=7.1, 1.2 Hz, 1H), 7.22 (d, J=8.3 Hz, 2H), 7.04 (pd, J=7.1, 1.3 Hz, 2H), 5.45 (s, 2H), 5.29 (d, J=15.9 Hz, 1H), 4.97 (d, J=13.7 Hz, 1H), 4.61 (d, J=15.0 Hz, 1H), 4.18 (d, J=14.3 Hz, 1H), 3.87 (s, 1H), 3.60 (d, J=13.9 Hz, 1H), 3.54 (dd, J=15.2, 3.6 Hz, 1H), 3.32 (d, J=7.1 Hz, 1H), 2.93 (s, 3H), 1.51 (s, 9H). ESI-MS m/z (%): 477 [MNH$_4$$^+$] (75), 460 [MH$^+$] (100). Anal. calcd for C$_{27}$H$_{29}$N$_3$O$_4$: C, 70.57; H, 6.36; N, 9.14; found: C, 70.12; H, 6.23; N, 9.18.

(E)-tert-Butyl 3-(4-((4-Methyl-3,5-dioxo-3,4,5,6-tetrahydro-2,6-methano[1,3]diazocino[5,6-b]indol-11(1H)-yl)methyl)phenyl)acrylate (44)

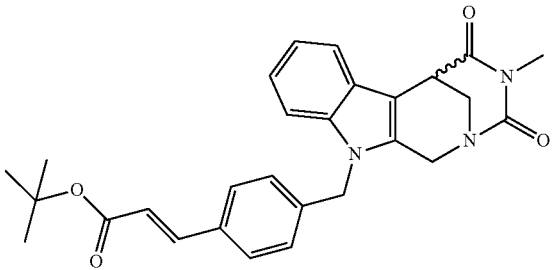 [SMILES: CN1C(=O)C2CN(Cc3c2c2ccccc2n3Cc2ccc(/C=C/C(=O)OC(C)(C)C)cc2)C1=O]

According to GP6, modification a, from 4-methyl-6,11-dihydro-2,6-methano[1,3]diazocino[5,6-b]indole-3,5(1H,4H)-dione (18a) (1.03 g; 4.00 mmol) and (E)-tert-butyl 3-(4-(brommethyl)phenyl) acrylate (42) (Tao et al., 2010; Tercel et al., 2012) 1.24 g (2.63 mmol; 66%) colorless crystals after recrystallization from n-Hexan; mp 117.0-124.0° C. IR (KBr): 2977, 1730, 1688 cm$^{-1}$. $^1$H NMR (300 MHz, DMSO-d$_6$): δ 7.62 (d, J=8.2 Hz, 2H), 7.57-7.45 (m, 2H), 7.43 (dd, J=6.8, 1.7 Hz, 1H), 7.28-6.94 (m, 4H), 6.47 (d, J=16.0 Hz, 1H), 5.38 (s, 2H), 4.86 (d, J=16.6 Hz, 1H), 4.57 (d, J=16.5 Hz, 1H), 3.90 (d, J=12.7 Hz, 2H), 3.45 (d, J=11.1 Hz, 1H), 2.89 (s, 3H), 1.46 (s, 9H). ESI-MS m/z (%):

489 [MNH$_4^+$] (17), 416 [MH$^+$–C$_4$H$_8$] (100). Anal. calcd for C$_{28}$H$_{29}$N$_3$O$_4$): C, 71.32; H, 6.20; N, 8.91; found: C, 71.08; H, 6.17; N, 8.79.

(E)-tert-Butyl 3-(3-((4-methyl-3,5-dioxo-3,4,5,6-tetrahydro-2,6-methano[1,3]diazocino[5,6-b]indol-11(1H)-yl)methyl)phenyl)acrylat (45)

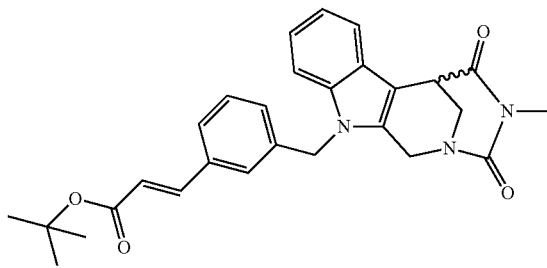 [SMILES: CN1C(=O)C2CN(Cc3c2c2ccccc2n3Cc2cccc(/C=C/C(=O)OC(C)(C)C)c2)C1=O]

According to GP6, modification a, from 4-methyl-6,11-dihydro-2,6-methano[1,3]diazocino[5,6-b]indole-3,5(1H,4H)-dione (18a) (1.03 g; 2.00 mmol) and (E)-tert-butyl 3-(3-(brommethyl)phenyl) acrylate (43). 1.56 g (3.31 mmol; 83%) colorless crystals after recrystallization from n-Hexan; mp 114.0-120.0° C. IR (KBr): 2976, 1730, 1685 cm$^{-1}$. $^1$H NMR (300 MHz, DMSO-d$_6$): δ 7.59-7.29 (m, 6H), 7.19-7.00 (m, 3H), 6.44 (d, J=16.0 Hz, 1H), 5.36 (s, 2H), 4.89 (d, J=16.6 Hz, 1H), 4.64 (d, J=16.5 Hz, 1H), 3.97-3.76 (m, 2H), 3.49 (dd, J=12.9, 1.9 Hz, 1H), 2.91 (s, 3H), 1.46 (s, 9H). ESI-MS m/z (%): 489 [MNH$_4^+$] (17), 472 [MH$^+$] (11), 416 [MH$^+$–C$_4$H$_8$] (100). Anal. calcd for C$_{28}$H$_{29}$N$_3$O$_4$: C, 71.32; H, 6.20; N, 8.91; found: C, 71.17; H, 6.17; N, 8.88.

1.7 General Procedure 7 (GP7): Deprotection of Tert-Butyl Carbamates

A solution of the tert-butyl carbamate (0.50 mmol) in trifluoroacetic acid (5.0 mL) was stirred for 15 minutes under room temperature. After completion of the reaction (TLC monitoring) the mixture was poured into water. The carboxylic acid was collected by filtration und dried. If the molecule contains an amino group, the excess of trifluoroacetic acid was removed under reduced pressure and the product was obtained as the salt of trifluoroacetic acid.

4-((4-Methyl-3,5-dioxo-3,4,5,6-tetrahydro-2,6-methano[1,3]diazocino[5,6-b]indol-11(1H)-yl)methyl)benzoic acid (33a)

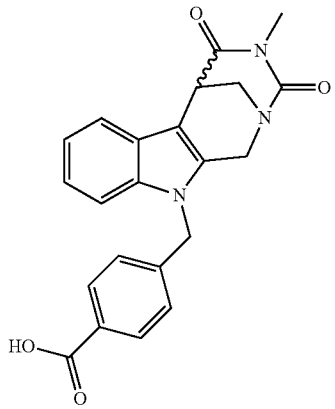

According to GP7 from tert-butyl 4-((4-methyl-3,5-dioxo-3,4,5,6-tetrahydro-2,6-methano[1,3]diazocino[5,6-b]indol-11(1H)-yl)methyl)benzoate (30a) (0.50 g; 1.12 mmol). 0.44 g (1.11 mmol; 99%) colorless crystals; mp 285.1-286.0° C. IR (KBr): 1726, 1684 cm$^{-1}$. $^1$H NMR (300 MHz, DMSO-d$_6$): δ 12.93 (s, 1H), 7.86 (d, J=8.3 Hz, 2H), 7.53 (dd, J=6.4, 2.3 Hz, 1H), 7.42 (dd, J=6.7, 1.9 Hz, 1H), 7.16 (d, J=8.3 Hz, 2H), 7.13-6.98 (m, 2H), 5.45 (s, 2H), 4.83 (d, J=16.6 Hz, 1H), 4.55 (d, J=16.5 Hz, 1H), 3.90 (d, J=11.9 Hz, 2H), 3.45 (dd, J=13.4, 2.5 Hz, 1H), 2.89 (s, 3H). ESI-MS m/z (%): 431 [MH$^+$+CH$_3$CN] (80), 390 [MH$^+$] (100). Anal. calcd for C$_{22}$H$_9$N$_3$O$_4$×¼H$_2$O: C, 67.08; H, 4.99; N, 10.67; found: C, 67.03; H, 4.97; N, 10.34.

4-((4-Methyl-5-oxo-3-thioxo-3,4,5,6-tetrahydro-2,6-methano[1,3]diazocino[5,6-b]indol-11(1H)-yl)methyl)benzoic acid (33b)

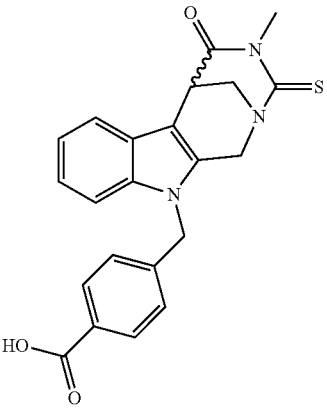 [SMILES: CN1C(=O)C2CN(Cc3c2c2ccccc2n3Cc2ccc(C(=O)O)cc2)C1=O]

According to GP7 from tert-butyl 4-((4-methyl-5-oxo-3-thioxo-3,4,5,6-tetrahydro-2,6-methano[1,3]diazocino[5,6-b]indol-11(1H)-yl)methyl)benzoate (30b) (2.40 g; 5.20 mmol). 1.35 g (3.33 mmol; 64%) colorless crystals; mp 285.5-286.5° C. $^1$H NMR (300 MHz, DMSO): δ 12.94 (s, 1H), 7.84 (d, J=8.2 Hz, 2H), 7.56-7.49 (m, 1H), 7.45-7.38 (m, 1H), 7.20 (d, J=8.3 Hz, 2H), 7.16-7.04 (m, 2H), 5.52 (d, J=16.1 Hz, 1H), 5.46 (s, 2H), 5.04 (d, J=16.0 Hz, 1H), 4.08 (d, J=12.6 Hz, 1H), 3.99 (s, 1H), 3.77 (dd, J=12.8, 1.8 Hz, 1H), 3.23 (s, 3H). ESI-MS m/z (%): 406 [MH$^+$] (100). Anal. calcd for C$_{22}$H$_9$N$_3$O$_4$×⅓H$_2$O: C, 64.22; H, 4.82; N, 10.21; S, 7.79. found: C, 64.33; H, 4.85; N, 9.88, S, 7.50.

4-((4-methyl-3-oxo-5-thioxo-3,4,5,6-tetrahydro-2,6-methano[1,3]diazocino[5,6-b]indol-11(1H)-yl)methyl)benzoic acid (33c)

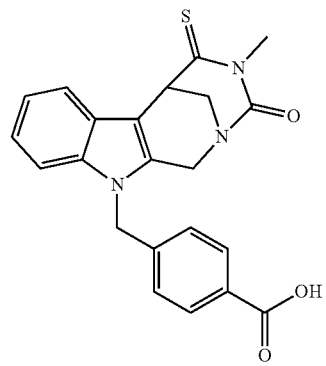 [SMILES: CN1C(=O)N2Cc3c(c4ccccc4n3Cc3ccc(C(=O)O)cc3)C(C2)C1=S]

According to GP7 from tert-butyl 4-((4-methyl-3-oxo-5-thioxo-3,4,5,6-tetrahydro-2,6-methano[1,3]diazocino[5,6-b]indol-11(1H)-yl)methyl)benzoate (18c) (0.54 g; 1.18 mmol). Yellow crystals (0.47 g, 1.11 mmol, 98%) after crystallization from water/aq. trifluoracetic acid; mp 271.1-271.9° C.; IR (KBr): 3432, 1718 cm$^{-1}$. $^1$H NMR (300 MHz, DMSO): δ 12.94 (s, 1H), 7.86 (d, J=8.2 Hz, 2H), 7.75-7.63 (m, 1H), 7.49-7.39 (m, 1H), 7.18 (d, J=8.2 Hz, 2H), 7.15-7.01 (m, 2H), 5.43 (d, J=13.1 Hz, 2H), 4.91 (d, J=16.5 Hz, 1H), 4.59 (d, J=16.5 Hz, 1H), 4.44 (s, 1H), 3.90 (d, J=12.8 Hz, 1H), 3.49 (dd, J=13.1, 2.2 Hz, 1H), 3.30 (s, 3H). ESI-MS m/z (%): 406 [MH$^+$] (100). Anal. calcd. for $C_{22}H_{13}N_3O_3S \times \frac{1}{5}$ tert-Butyl 2,2,2-trifluoracetat: C, 63.40; H, 4.77; N, 9.56; S, 7.29; found: C, 63.65; H, 4.90; N, 9.62; S, 7.20.

4-((8-Methoxy-4-methyl-5-oxo-3-thioxo-3,4,5,6-tetrahydro-2,6-methano[1,3]diazocino[5,6-b]indol-11(1H)-yl)methyl)benzoic acid (33d)

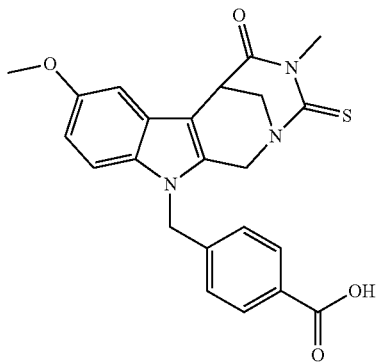 [SMILES: COc1ccc2c(c1)c1c(n2Cc2ccc(C(=O)O)cc2)CN2CC1C(=O)N(C)C2=S]

According to GP7 from tert-butyl 4-((8-methoxy-4-methyl-5-oxo-3-thioxo-3,4,5,6-tetrahydro-2,6-methano[1,3]diazocino[5,6-b]indol-11(1H)-yl)methyl)benzoate (30d). Yield: Colorless crystals (1.34 g, 3.08 mmol, 95%) after crystallization from trifluoroacetic acid/water, mp: decomposition at 332.0° C. ° C.; IR (KBr): 1706, 1610 cm$^{-1}$; $^1$H NMR (300 MHz, DMSO): δ 7.84 (d, J=8.3 Hz, 2H), 7.31 (d, J=8.9 Hz, 1H), 7.17 (d, J=8.3 Hz, 2H), 6.97 (d, J=2.4 Hz, 1H), 6.75 (dd, J=8.9, 2.5 Hz, 1H), 5.49 (d, J=16.1 Hz, 1H), 5.41 (s, 2H), 5.01 (d, J=16.0 Hz, 1H), 4.07 (d, J=12.5 Hz, 1H), 3.95 (s, 1H), 3.85-3.66 (m, 4H), 3.23 (s, 3H). ESI-MS m/z (%): 436 [MH$^+$] (100). Anal. ($C_{23}H_{21}N_3O_4S+\frac{1}{2}$ TFA): Calcd. C, 58.53; H, 4.40; N, 8.53; Found. C, 58.65; H, 4.58; N, 8.45.

4-((8-(Benzyloxy)-4-methyl-3.5-diozo-3.4.5.6-tetrahydro-2.6-methan[1.3]diazocino[5.6-b]indol-11(1H)-yl)methyl)benzoic acid (33e)

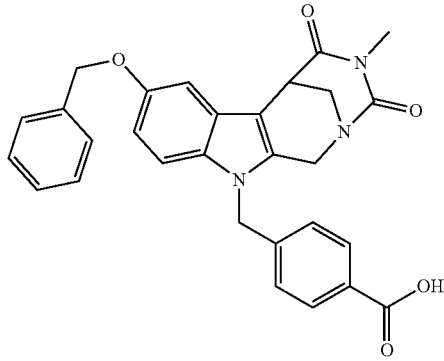 [SMILES: CN1C(=O)C2CN(Cc3c2c2cc(OCc4ccccc4)ccc2n3Cc2ccc(C(=O)O)cc2)C1=O]

According to GP 7 from tert-Butyl 4-((8-(benzyloxy)-4-methyl-3.5-dioxo-3.4.5.6-tetrahydro-2.6-methano[1.3]diazocino[5.6-b]indol-11(1H)-yl)methyl)benzoate (30e). Yield 0.59 g (1.19 mmol; 88%) colorless crystals; mp: 186.9-188.3° C. $^1$H NMR (300 MHz, DMSO): δ 12.95 (s, 1H), 7.85 (d, J=8.3 Hz, 21H), 7.75 (d, J=7.2 Hz, 2H), 7.40 (t, J=7.3 Hz, 2H), 7.31 (t, J=7.3 Hz, 1H), 7.13 (d, J=8.3 Hz, 2H), 7.01-6.96 (m, 2H), 6.64 (dd, J=5.5, 3.0 Hz, 1H), 5.42 (s, 2H), 5.24 (d, J=6.3 Hz, 2H), 4.82 (d, J=16.5 Hz, 1H), 4.49 (d, J=16.5 Hz, 1H), 4.14 (s, 1H), 3.86 (d, J=12.6 Hz, 1H), 3.43 (dd, 1H), 2.93 (s, 3H). ESI-MS m/z (%): 496.19 [MH](100). Anal. calcd for $C_{29}H_{25}N_3O_5 \times 0.33$ $H_2O$: C, 69.44; H, 5.16; N, 8.38; found: C, 69.70; H, 5.23; N, 8.40.

4-((7-(Benzyloxy)-4-methyl-3.5-dioxo-3.4.5.6-tetrahydro-2.6-methano[1.3]diazocino[5.6-b]indol-1(1H)-yl)methyl)benzoic acid (33f)

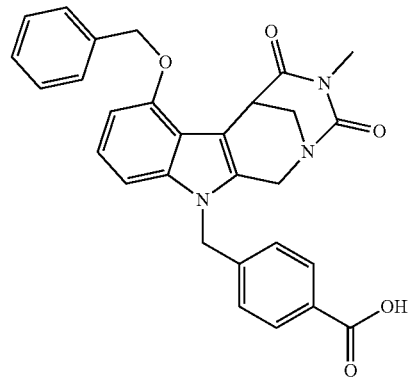 [SMILES: CN1C(=O)C2CN(Cc3c2c2c(OCc4ccccc4)cccc2n3Cc2ccc(C(=O)O)cc2)C1=O]

According to GP 7 from tert-Butyl 4-((7-(benzyloxy)-4-methyl-3.5-dioxo-3.4.5.6-tetrahydro-2.6-methano[1.3]diazocino[5.6-b]indol-11(1H)-yl)methyl)benzoate (30f). Yield 0.62 g (1.25 mmol; 92%) colorless crystals; mp: 180.9-182.3° C. $^1$H NMR (300 MHz, DMSO): δ 12.94 (s, 1H), 7.86 (d, J=8.2 Hz, 2H), 7.75 (d, J=7.2 Hz, 2H), 7.40 (t, J=7.3 Hz, 2H), 7.31 (t, J=7.3 Hz, 1H), 7.13 (d, J=8.3 Hz, 2H), 7.01-6.96 (m, 2H), 6.64 (dd, J=5.5, 3.1 Hz, 1H), 5.42 (s, 2H), 5.24 (d, J=6.3 Hz, 2H), 4.82 (d, J=16.5 Hz, 1H), 4.49 (d, J=16.5 Hz, 1H), 4.14 (s, 1H), 3.86 (d, J=12.7 Hz, 1H), 3.43 (dd, 1H), 2.93 (s, 3H).

4-((9-Methoxy-4-methyl-3,5-dioxo-3,4,5,6-tetrahydro-2,6-methano[1,3]diazocino[5,6-b]indol-11 (1H)-yl)methyl)benzoic acid (34b)

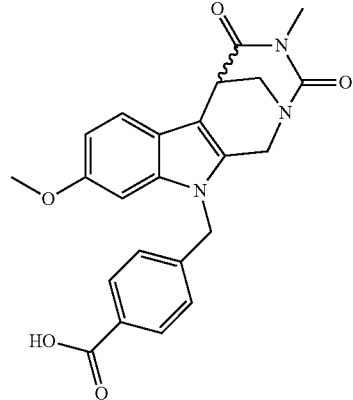 [SMILES: COc1ccc2c3c(n(Cc4ccc(C(=O)O)cc4)c2c1)CN1CC3C(=O)N(C)C1=O]

According to GP7 from tert-butyl 4-((9-methoxy-4-methyl-3,5-dioxo-3,4,5,6-tetrahydro-2,6-methano[1,3]diazocino[5,6-b]indol-11(1H)-yl)methyl)benzoate (31b) (1.10 g; 2.31 mmol). 0.96 g (2.29 mmol; 99%) colorless crystals; mp 270.3-274.2° C. IR (KBr): 2997, 1736, 1700 cm$^{-1}$. $^1$H NMR (300 MHz, DMSO): δ 12.95 (s, 1H), 7.87 (d, J=8.2 Hz, 2H), 7.39 (d, J=8.6 Hz, 1H), 7.17 (d, J=8.2 Hz, 2H), 7.02 (d, J=2.0 Hz, 1H), 6.75 (dd, J=8.6, 2.1 Hz, 1H), 5.45 (d, J=17.3 Hz, 1H), 5.39 (d, J=17.7 Hz, 1H), 4.76 (d, J=16.5 Hz, 1H), 4.46 (d, J=16.4 Hz, 1H), 3.86 (d, J=13.5 Hz, 1H), 3.79 (d, J=19.6 Hz, 1H), 3.71 (s, 3H), 3.41 (d, J=11.4 Hz, 1H), 2.89 (s, 3H). ESI-MS m/z (%): 461 [MH$^+$+CH$_3$CN] (90), 420 [MH$^+$] (100).

4-((8-Acrylamido-4-methyl-3,5-dioxo-3,4,5,6-tetrahydro-2,6-methano[1,3]diazocino[5,6-b]indol-11(1H)-yl)methyl)benzoic acid (34c)

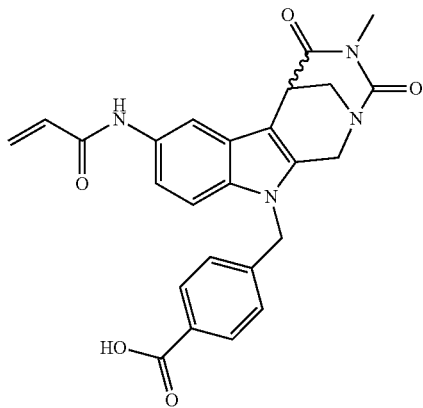 [SMILES: C=CC(=O)Nc1ccc2c(c1)c1c(n2Cc2ccc(C(=O)O)cc2)CN2CC1C(=O)N(C)C2=O]

According to GP7 from tert-butyl 4-((8-acrylamido-4-methyl-3,5-dioxo-3,4,5,6-tetrahydro-2,6-methano[1,3]diazocino[5,6-b]indol-11(1H)-yl)methyl)benzoate (31c) (0.46 g; 0.89 mmol). 0.39 g (0.85 mmol; 96%) colorless crystals; mp 282.9-284.1° C. $^1$H NMR (300 MHz, DMSO): δ 12.96 (s, 1H), 10.09 (s, 1H), 7.94 (s, 1H), 7.86 (d, J=8.2 Hz, 2H), 7.46-7.29 (m, 2H), 7.15 (d, J=8.3 Hz, 2H), 6.45 (dd, J=16.9, 10.0 Hz, 1H), 6.24 (dd, J=17.0, 2.1 Hz, 1H), 5.71 (dd, J=10.0, 2.1 Hz, 1H), 4.81 (d, J=16.6 Hz, 1H), 4.53 (d, J=16.5 Hz, 1H), 3.89 (d, J=12.8 Hz, 1H), 3.81 (s, 1H), 3.45 (d, J=11.2 Hz, 1H), 2.90 (s, 3H). ESI-MS m/z (%): 476 [MNH$_4^+$] (100), 459 [MH$^+$] (85). Anal. calcd for C$_{25}$H$_{22}$N$_4$O$_5$: C, 65.49; H, 4.84; N, 12.22; found: C, 65.03; H, 4.91; N, 11.98.

4-((8-(Acrylamidomethyl)-4-methyl-3,5-dioxo-3,4,5,6-tetrahydro-2,6-methano[1,3]diazocino[5,6-b]indol-11(1H)-yl)methyl)benzoic acid (34d)

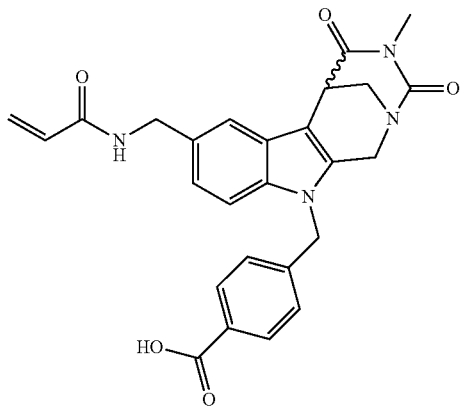 [SMILES: C=CC(=O)NCc1ccc2c(c1)c1c(n2Cc2ccc(C(=O)O)cc2)CN2CC1C(=O)N(C)C2=O]

According to GP6 from tert-butyl 4-((8-(acrylamidomethyl)-4-methyl-3,5-dioxo-3,4,5,6-tetrahydro-2,6-methano[1,3]diazocino[5,6-b]indol-11(1H)-yl)methyl)benzoate (31d) (0.89 g; 1.69 mmol). 0.80 g (1.69 mmol; 100%) colorless crystals after crystallization from acetone/ethyl acetae; mp 256.6-256.8° C. IR (KBr): 3300, 1730, 1684 cm$^{-1}$. $^1$H NMR (300 MHz, DMSO): δ 12.94 (s, 1H), 8.58 (t, J=5.8 Hz, 1H), 7.85 (d, J=8.3 Hz, 2H), 7.44 (s, 1H), 7.37 (d, J=8.5 Hz, 1H), 7.11 (d, J=8.3 Hz, 2H), 7.04 (dd, J=8.5, 1.4 Hz, 1H), 6.26 (dd, J=17.1, 9.9 Hz, 1H), 6.11 (dd, J=17.1, 2.4 Hz, 1H), 5.60 (dd, J=9.9, 2.5 Hz, 1H), 5.44 (s, 2H), 4.81 (d, J=16.6 Hz, 1H), 4.53 (d, J=16.5 Hz, 1H), 4.47-4.29 (m, 2H), 3.95-3.79 (m, 2H), 3.43 (dd, J=13.0, 1.9 Hz, 2H), 2.89 (s, 3H). ESI-MS m/z (%): 471 [MH$^-$] (100). Anal. calcd for C$_{26}$H$_{24}$N$_4$O$_5$×½H$_2$O: C, 64.86; H, 5.23; N, 11.64; found: C, 64.49; H, 5.22; N, 11.39.

4-((8-(2-Acrylamidoethoxy)-4-methyl-3,5-dioxo-3,4,5,6-tetrahydro-2,6-methano[1,3]diazocino[5,6-b]indol-11(1H)-yl)methyl)benzoic acid (34e)

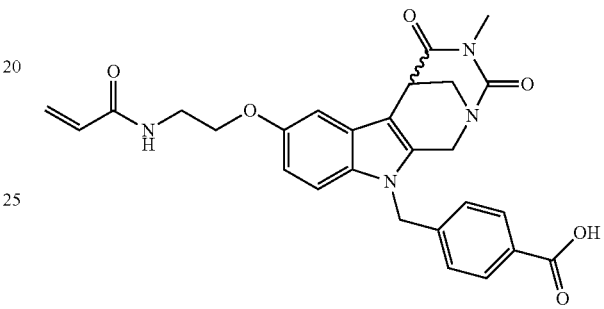

A solution of 31e (0.23 g, 0.41 mmol) in CH$_2$Cl$_2$ (6.0 mL) and trifluoroacetic acid (1.5 mL) was stirred for 40 minutes under room temperature. After completion of the reaction (TLC monitoring) the solvent was removed under reduced pressure and the residue dissolved in ethyl acetate (20 mL) and brine (10 mL). The organic phase was separated, dried over Na$_2$SO$_4$ and the solvent removed under reduced pressure. Yield 0.19 g (0.38 mmol, 92%) colorless foam. $^1$H NMR (300 MHz, DMSO-d$_6$) δ $^1$H NMR (300 MHz, DMSO-d$_6$) δ 12.95 (s, 1H), 8.39 (t, J=5.7 Hz, 1H), 7.92-7.80 (m, 2H), 7.31 (d, J=8.9 Hz, 1H), 7.13 (d, J=8.1 Hz, 2H), 7.01 (d, J=2.4 Hz, 1H), 6.77 (dd, J=9.0, 2.4 Hz, 1H), 6.28 (dd, J=17.1, 10.0 Hz, 1H), 6.10 (dd, J=17.1, 2.4 Hz, 1H), 5.59 (dd, J=10.0, 2.4 Hz, 1H), 5.41 (s, 2H), 4.66 (dd, J=84.2, 16.6 Hz, 2H), 4.08-3.95 (m, 2H), 3.94-3.81 (m, 2H), 3.55-3.48 (m, 2H), 3.48-3.43 (m, 1H), 2.89 (s, 3H).

4-((9-Acrylamido-4-methyl-3,5-dioxo-3,4,5,6-tetrahydro-2,6-methano[1,3]diazocino[5,6-b]indol-11(1H)-yl)methyl)benzoic acid (34f)

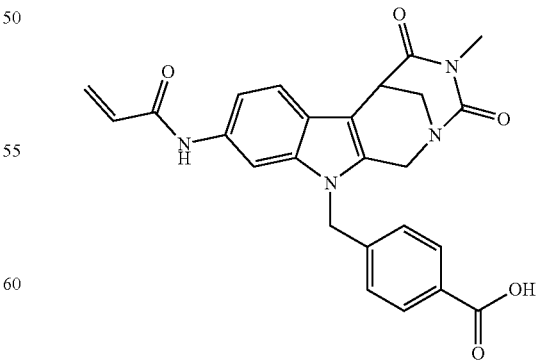

According to GP7 from tert-butyl 4-((9-acrylamido-4-methyl-3,5-dioxo-3,4,5,6-tetrahydro-2,6-methano[1,3]diazocino[5,6-b]indol-11(1H)-yl)methyl)benzoate (31f). Yield: Colorless crystals (0.52 g, 1.13 mmol, 96%) crystallization from trifluoroacetic acid/water, mp: Decomposition at 260° C.; IR (KBr): 3381, 1726, 1681 cm$^{-1}$; $^1$H NMR (300 MHz, DMSO): δ 12.96 (s, 1H), 10.12 (s, 1H), 7.93 (s, 1H), 7.87 (d, J=8.3 Hz, 2H), 7.46 (d, J=8.5 Hz, 1H), 7.23 (dd, J=8.5, 1.5 Hz, 1H), 7.14 (d, J=8.3 Hz, 2H), 6.41 (dd, J=16.9, 10.0 Hz, 1H), 6.20 (dd, J=16.9, 2.1 Hz, 1H), 5.70 (dd, J=10.0, 2.1 Hz, 1H), 5.42 (d, J=17.5 Hz, 1H), 5.35 (d, J=17.4 Hz, 1H), 4.82 (d, J=16.6 Hz, 1H), 4.55 (d, J=16.4 Hz, 1H), 3.89 (d, J=14.3 Hz, 2H), 3.46 (dd, J=12.8, 1.5 Hz, 1H), 2.90 (s, 3H). ESI-MS m/z (%): 459 [MH$^+$] (100). Anal. ($C_{25}H_{22}N_4O_5$+2½$H_2O$): Calcd. C, 59.64; H, 5.41; N, 11.13; found. C, 59.76; H, 5.27; N, 11.02.

4-((5-Methyl-3,6-dioxo-4,5,6,7-tetrahydro-1H-2,7-methano[1,4]diazonino[6,7-b]indol-12(3H)-yl)methyl)benzoic acid (35)

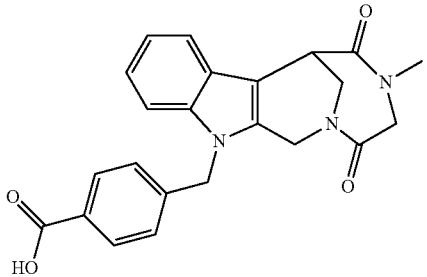 [SMILES: CN1CC(=O)N2Cc3c(c4ccccc4n3Cc3ccc(C(=O)O)cc3)C(C2)C1=O]

According to GP7 from tert-butyl 4-((5-methyl-3,6-dioxo-4,5,6,7-tetrahydro-H-2,7-methano[1,4]diazonino[6,7-b]indol-12(3H)-yl)methyl)benzoate (32) (0.50 g; 1.09 mmol). 0.49 g (1.08 mmol; 99%) colorless crystals; mp 295.3-296.6° C. IR (KBr): 1711, 1638 cm$^{-1}$. $^1$H NMR (300 MHz, DMSO-d$_6$): δ 12.91 (s, 1H), 8.04-7.71 (m, 3H), 7.41-7.32 (m, 1H), 7.22 (d, J=8.3 Hz, 2H), 7.11-6.99 (m, 2H), 5.46 (s, 2H), 5.30 (d, J=15.9 Hz, 1H), 4.97 (d, J=13.7 Hz, 1H), 4.61 (d, J=15.0 Hz, 1H), 4.19 (dd, J=15.9, 1.6 Hz, 1H), 3.87 (s, 1H), 3.60 (d, J=13.7 Hz, 1H), 3.54 (dd, J=15.1, 3.4 Hz, 1H), 2.93 (s, 3H). ESI-MS m/z (%): 477 [MNH$_4^+$] (55), 460 [MH$^+$] (100). Anal. calcd for $C_{23}H_{21}N_3O_4$×¼$H_2O$: C, 67.72; H, 5.31; N, 10.30; found: C, 67.68; H, 5.35; N, 10.20.

(E)-3-(4-((4-Methyl-3,5-dioxo-3,4,5,6-tetrahydro-2,6-methano[1,3]diazocino[5,6-b]indol-11(1H)-yl)methyl)phenyl)acrylic acid (46)

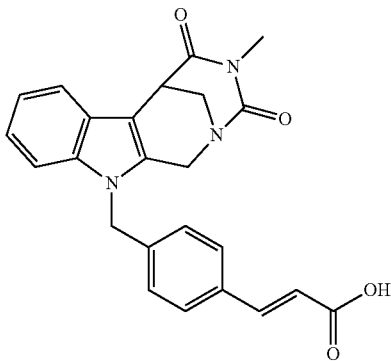 [SMILES: CN1C(=O)C2CN(Cc3c2c2ccccc2n3Cc2ccc(/C=C/C(=O)O)cc2)C1=O]

According to GP7 from (E)-tert-butyl 3-(4-((4-methyl-3,5-dioxo-3,4,5,6-tetrahydro-2,6-methano[1,3]diazocino[5,6-b]indol-11(1H)-yl)methyl)phenyl)acrylate (44) (1.14 g; 2.42 mmol). 1.00 g (2.41 mmol; 99%) colorless crystals; mp 266.0-271.0° C. IR (KBr): 1730, 1685 cm$^{-1}$. $^1$H NMR (300 MHz, DMSO-d$_6$): δ 12.38 (s, 1H), 7.61 (d, J=8.2 Hz, 2H), 7.57-7.49 (m, 2H), 7.42 (dd, J=6.8, 1.7 Hz, 1H), 7.16-7.02 (m, 4H), 6.48 (d, J=16.0 Hz, 1H), 5.46-5.26 (m, 2H), 4.87 (d, J=16.6 Hz, 1H), 4.57 (d, J=16.5 Hz, 1H), 4.00-3.75 (m, 2H), 3.45 (d, J=11.2 Hz, 2H), 2.89 (s, 3H). ESI-MS m/z (%): 416 [MH$^+$] (100). Anal. calcd for $C_{24}H_{21}N_3O_4$×⅓$H_2O$: C, 68.40; H, 5.18; N, 9.97; found: C, 68.48; H, 5.25; N, 9.72.

(E)-3-(3-((4-Methyl-3,5-dioxo-3,4,5,6-tetrahydro-2,6-methano[1,3]diazocino[5,6-b]indol-11(1H)-yl)methyl)phenyl)acrylic acid (47)

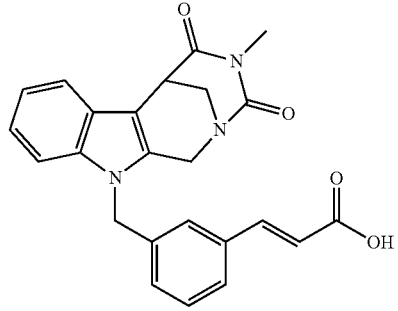 [SMILES: CN1C(=O)C2CN(Cc3c2c2ccccc2n3Cc2cccc(/C=C/C(=O)O)c2)C1=O]

According to GP7 from (E)-tert-butyl 3-(3-((4-methyl-3,5-dioxo-3,4,5,6-tetrahydro-2,6-methano[1,3]diazocino[5,6-b]indol-11(1H)-yl)methyl)phenyl)acrylate (45) (0.45 g; 1.00 mmol). 0.40 g (0.96 mmol; 97%) colorless crystals; mp 209.1-209.8° C. IR (KBr): 1726, 1684 cm$^{-1}$. $^1$H NMR (300 MHz, DMSO-d$_6$): $^1$H NMR (300 MHz, DMSO): δ 12.41 (s, 1H), 7.61-7.29 (m, 6H), 7.14-7.04 (m, 3H), 6.46 (d, J=16.0 Hz, 1H), 5.35 (d, J=12.7 Hz, 2H), 4.90 (d, J=16.6 Hz, 1H), 4.64 (d, J=16.5 Hz, 1H), 3.91 (d, J=13.5 Hz, 2H), 3.49 (dd, J=12.8, 1.8 Hz, 1H), 2.91 (s, 3H). ESI-MS m/z (%): 416 [MH$^+$] (100). Anal. calcd for $C_{24}H_{21}N_3O_4$×⅓$H_2O$: C, 68.40; H, 5.18; N, 9.97; found: C, 68.54; H, 5.18; N, 9.75.

1.8 General Procedure 8 (GP8)

The carboxylic acid (0.50 mmol) was dissolved in DMF (5.00 mL). After addition of benzotriazol-1-yloxy-tris (dimethylamino) phosphonium hexafluorophosphate (BOP) (0.50 mmol), triethylamine (1.50 mmol) and O-(tetrahydro-2H-pyran-2-yl)hydroxylamine (2.00 mmol) the mixture was stirred under room temperature until the reaction was completed (TLC monitoring). If the product crystallizes, it is filtered off and dried in vacuo. Alternatively, is extracted with dichloromethane (4×25.0 mL), the combined organic phases were washed with brine (25.0 mL) and dried over sodium sulfate. The solvent was removed and the residue dried in vacuo. Purification was achieved in both cases by chromatography on silica gel using the indicated eluent.

4-((4-Methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36a)

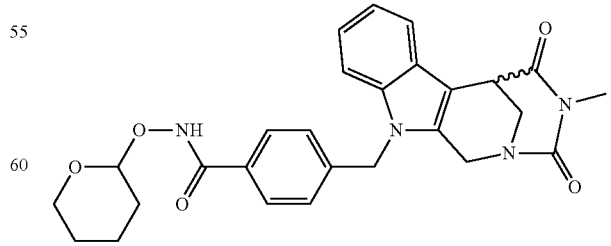

According to GP8 from 4-((4-methyl-3,5-dioxo-3,4,5,6-tetrahydro-2,6-methano[1,3]diazocino[5,6-b]indol-11(1H)-yl)methyl) benzoic acid (33a) (0.45 g; 1.16 mmol). 0.37 g (0.76 mmol; 65%) colorless crystals after crystallization from CH$_2$Cl$_2$ by addition of heptane; mp 197.7-198.5° C. IR (KBr): 2952, 1727, 1680 cm$^{-1}$. $^1$H NMR (300 MHz, DMSO-d$_6$): δ 11.59 (s, 1H), 7.68 (d, J=8.3 Hz, 2H), 7.52 (dd, J=6.3, 2.4 Hz, 1H), 7.41 (dd, J=6.6, 2.0 Hz, 1H), 7.15 (d, J=8.3 Hz, 2H), 7.12-6.99 (m, 2H), 5.42 (s, 1H), 4.96 (s, 1H), 4.86 (d, J=16.6 Hz, 1H), 4.56 (d, J=16.5 Hz, 1H), 4.07-3.96 (m, 1H), 3.90 (d, J=12.8 Hz, 2H), 3.47 (t, J=11.4 Hz, 2H), 2.90 (s, 3H), 1.70 (s, 3H), 1.53 (s, 3H). ESI-MS m/z (%): 506 [MNH$_4^+$] (38), 489 [MH$^+$] (100).

4-((4-Methyl-5-oxo-3-thioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36b)

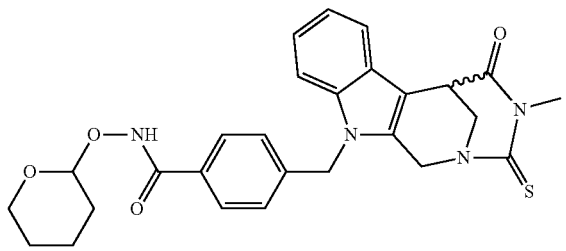 [SMILES: CN1C(=O)C2CN(Cc3c2c2ccccc2n3Cc2ccc(C(=O)NOC3CCCCO3)cc2)C1=S]

According to GP8 from 4-((4-methyl-5-oxo-3-thioxo-3,4,5,6-tetrahydro-2,6-methano[1,3]diazocino[5,6-b]indol-11(1H)-yl)methyl)benzoic acid (33b) (1.00 g; 2.47 mmol). 0.51 g (1.01 mmol; 40%) colorless crystals after chromatography over silica gel with dichloromethane/ethyl acetate (3:2); mp 127.0-132.1° C. IR (KBr): 1723, 1669 cm$^{-1}$. $^1$H NMR (300 MHz, DMSO): δ 11.60 (s, 1H), 7.67 (d, J=8.2 Hz, 2H), 7.51 (dd, J=5.8, 3.1 Hz, 1H), 7.39 (d, J=7.6 Hz, 1H), 7.20 (d, J=8.2 Hz, 2H), 7.14-7.02 (m, 2H), 5.56 (d, J=16.1 Hz, 1H), 5.50-5.34 (m, 2H), 5.05 (d, J=16.0 Hz, 1H), 4.95 (s, 1H), 4.08 (d, J=13.1 Hz, 1H), 3.98 (s, 1H), 3.78 (d, J=11.0 Hz, 1H), 3.49 (d, J=11.3 Hz, 1H), 3.23 (s, 3H), 1.69 (s, 3H), 1.53 (s, 3H). ESI-MS m/z (%): 505 [MH$^+$] (2), 421 [MH$^+$–C$_5$H$_8$O] (100).

4-((4-Methyl-3-oxo-5-thioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36c)

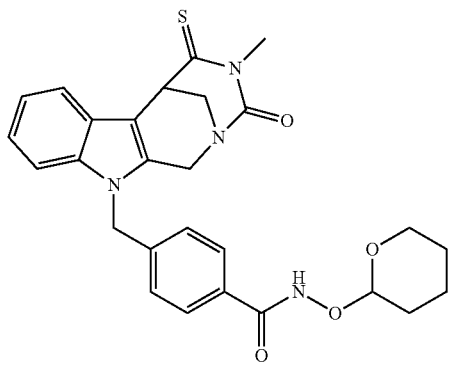 [SMILES: CN1C(=O)N2Cc3c(c4ccccc4n3Cc3ccc(C(=O)NOC4CCCCO4)cc3)C(C2)C1=S]

According to GP8 from 4-((4-methyl-3-oxo-5-thioxo-3,4,5,6-tetrahydro-2,6-methano[1,3]diazocino[5,6-b]indol-11(1H)-yl)methyl)benzoic acid (33c) (0.40 g; 0.99 mmol). Yellow crystals 0.39 g (0.77 mmol, 77%) after chromatography over silica gel with dichloromethane and ethyl acetate (3:2); $^1$H NMR (300 MHz, DMSO): δ 11.60 (s, 1H), 7.68 (t, J=5.3 Hz, 3H), 7.41 (dd, J=6.5, 2.1 Hz, 1H), 7.23-7.00 (m, 4H), 5.40 (d, J=13.2 Hz, 2H), 4.93 (dd, J=18.1, 3.7 Hz, 2H), 4.59 (dd, J=16.6, 5.1 Hz, 1H), 4.44 (s, 1H), 4.18-3.77 (m, 2H), 3.49 (d, J=11.0 Hz, 2H), 3.30 (s, 3H), 1.69 (s, 3H), 1.53 (s, 3H). ESI-MS m/z (%): 505 [MH$^+$] (100). Anal. calcd. for C$_{27}$H$_{28}$N$_4$O$_4$S×½ EE: C, 63.49; H, 5.88; N, 10.21; S, 5.84; found: C, 63.27; H, 5.82; N, 10.53; S, 5.88.

4-((8-Methoxy-4-methyl-5-oxo-3-thioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36d)

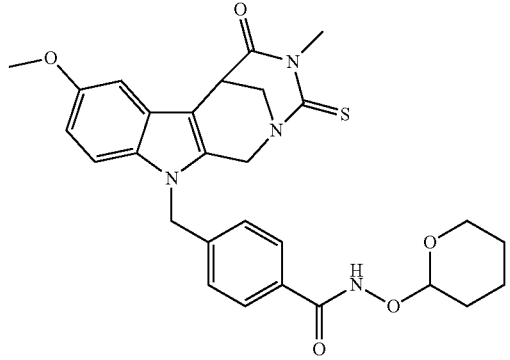 [SMILES: COc1ccc2c(c1)c1c(n2Cc2ccc(C(=O)NOC3CCCCO3)cc2)CN2CC1C(=O)N(C)C2=S]

According to GP8 from 4-((8-methoxy-4-methyl-5-oxo-3-thioxo-3,4,5,6-tetrahydro-2,6-methano[1,3]diazocino[5,6-b]indol-11(1H)-yl)methyl)benzoic acid (33d). Yield: Colorless crystals (0.60 g, 1.12 mmol, 43%) silica gel chromatography DCM/MeOH (20:1) and crystallization from ether, mp: 139.8-143.6° C.; IR (KBr): 1720, 1666 cm$^{-1}$; $^1$H NMR (400 MHz, DMSO): δ 11.57 (s, 1H), 7.67 (d, J=8.2 Hz, 2H), 7.28 (dd, J=8.9, 1.4 Hz, 1H), 7.18 (d, J=8.2 Hz, 2H), 6.97 (d, J=2.4 Hz, 1H), 6.74 (dd, J=8.9, 2.4 Hz, 1H), 5.54 (d, J=16.0 Hz, 1H), 5.45-5.26 (m, 2H), 5.02 (d, J=15.9 Hz, 1H), 4.96 (s, 1H), 4.08 (d, J=13.6 Hz, 1H), 4.03 (t, J=7.1 Hz, 1H), 3.95 (s, 1H), 3.81-3.72 (m, 4H), 3.50 (d, J=11.6 Hz, 1H), 3.25 (s, 3H), 1.70 (s, 3H), 1.53 (s, 3H). ESI-MS m/z (%): 451 [MH$^+$–C$_5$H$_8$O] (100); 557 [MNH$_4^+$] (5). Anal. (C$_{28}$H$_{30}$N$_4$O$_5$S+¾ ethyl acetate): Calcd. C, 61.98; H, 6.04; N, 9.33; found. C, 61.57; H, 5.87; N, 9.70.

4-((8-(Benzyloxy)-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36e)

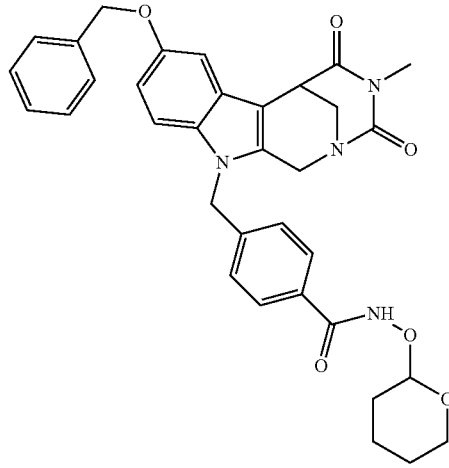 [SMILES: CN1C(=O)C2CN(Cc3c2c2cc(OCc4ccccc4)ccc2n3Cc2ccc(C(=O)NOC3CCCCO3)cc2)C1=O]

According to GP8 from 4-((8-(benzyloxy)-4-methyl-3,5-dioxo-3,4,5,6-tetrahydro-2,6-methano[1,3]diazocino[5,6-b]indol-11(1H)-yl)methyl)benzoic acid (33e). Yield 0.65 g (1.09 mmol; 54%) colorless crystals after chromatography over silica gel with CH$_2$C$_2$/Ethylacetate (1:2); mp: 162.1-

165.4° C. $^1$H NMR (300 MHz, DMSO): δ 11.60 (s, 1H), 7.67 (d, J=8.2 Hz, 2H), 7.48 (d, J=6.8 Hz, 2H), 7.43-7.27 (m, 5H), 7.13 (d, J=8.3 Hz, 2H), 7.10 (d, J=2.4 Hz, 1H), 6.83 (dd, J=8.9, 2.4 Hz, 1H), 5.37 (s, 2H), 5.14-5.01 (m, 2H), 4.83 (d, J=16.5 Hz, 1H), 4.53 (d, J=16.4 Hz, 1H), 3.93-3.79 (m, 2H), 3.47 (t, J=13.6 Hz, 2H), 2.89 (d, J=2.5 Hz, 3H), 1.85-1.13 (m, 9H). ESI-MS m/z (%): 511.20 [MH$^+$–3,4-dihydro-2H-pyran](100), 595.26 [MH$^+$] (9.14), 617 [MNa$^+$] (7.96). Anal. calcd for $C_{34}H_{34}N_4O_6$: C, 68.67; H, 5.76; N, 9.42, found: C, 68.4; H, 5.79; N, 9.39.

4-((7-(benzyloxy)-4-methyl-3,5-dioxo-3,4,5,6-tetrahydro-2,6-methano[1,3]diazocino[5,6-b]indol-11 (1H)-yl)methyl)-N-((tetrahydro-2H-pyran-2-yl)oxy) benzamide (36f)

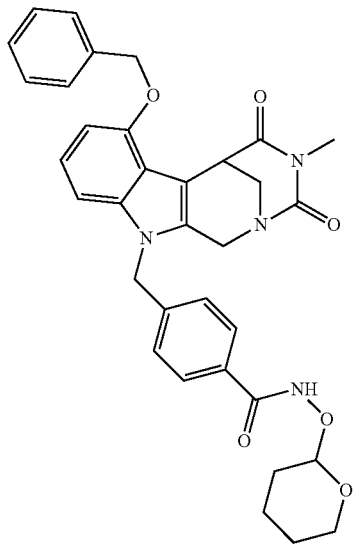 [SMILES: CN1C(=O)C2CN(Cc3c2c2c(OCc4ccccc4)cccc2n3Cc2ccc(C(=O)NOC3CCCCO3)cc2)C1=O]

According to GP8 from 4-((7-(benzyloxy)-4-methyl-3,5-dioxo-3,4,5,6-tetrahydro-2,6-methano[1,3]diazocino[5,6-b]indol-11(1H)-yl)methyl)benzoic acid (33f). Yield 0.33 g (0.55 mmol; 47%) colorless crystals after chromatography over silica gel with CH$_2$Cl$_2$/MeOH (10:1)+1% NH$_3$; mp: 158.1-161.4° C. $^1$H NMR (300 MHz, DMSO): δ 11.61 (s, 1H), 7.75 (d, J=7.2 Hz, 2H), 7.68 (d, J=8.2 Hz, 2H), 7.39 (d, J=7.6 Hz, 2H), 7.32 (d, J=7.3 Hz, 1H), 7.13 (d, J=8.2 Hz, 3H), 6.99 (s, 1H), 6.63 (dd, 1H), 5.38 (s, 2H), 5.23 (d, J=6.4 Hz, 2H), 4.96 (s, 1H), 4.50 (d, J=16.4 Hz, 1H), 4.14 (s, 1H), 3.86 (d, J=13.0 Hz, 1H), 3.46 (s, 1H), 2.93 (s, 3H), 1.81-1.02 (m, 9H).

4-((8-Methoxy-4-methyl-3,5-dioxo-3,4,5,6-tetrahydro-2,6-methano[1,3]diazocino[5,6-b]indol-11 (1H)-yl)methyl)-N-((tetrahydro-2H-pyran-2-yl)oxy) benzamide (37a)

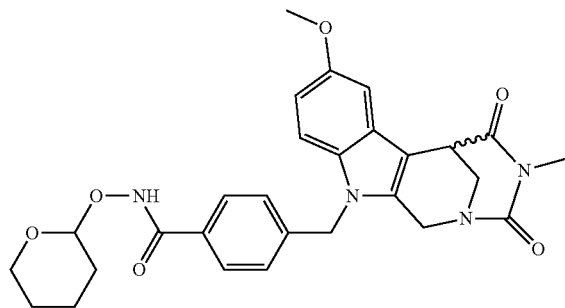 [SMILES: COc1ccc2c(c1)c1c(n2Cc2ccc(C(=O)NOC3CCCCO3)cc2)CN2CC1C(=O)N(C)C2=O]

tert-Butyl 4-((8-methoxy-4-methyl-3,5-dioxo-3,4,5,6-tetrahydro-2,6-methano[1,3]diazocino [5,6-b]indol-11(1H)-yl) methyl) benzoate (0.63 mmol) (31a) was dissolved in 5.00 mL of trifluoroacetic acid and stirred at room temperature for 15 minutes. After completion of the reaction (TLC monitoring), the solvent was removed and the mixture dissolved in 5.00 mL dimethylformamide. After addition of benzotriazol-1-yloxy-tris (dimethylamino)phosphonium hexafluorophosphate (BOP) (1 eq.), triethylamine (3 eq.) and O-(tetrahydro-2H-pyran-2-yl)hydroxylamine (4 eq.) the mixture was stirred at 20° C. until completion of the reaction (TLC monitoring). The mixture was poured into water. If the product crystallizes, it was filtered off and dried in vacuo. Alternatively, it was extracted with dichloromethane (4×25.0 mL), the combined organic phases were washed with brine (25.0 mL), and dried over sodium sulfate. The solvent was removed and the residue dried in vacuo. Purification is achieved in both cases by chromatography on silica gel using the indicated eluent. 0.16 g (0.31 mmol; 49% over 2 steps) after chromatography with methanol and dichloromethane (1:10) and crystallization from CH$_2$Cl$_2$ by addition of heptane; mp 157.5-160.4° C. IR (KBr): 2953, 1728 cm$^{-1}$. $^1$H NMR (300 MHz, CDCl$_3$): δ 7.68 (d, J=8.2 Hz, 2H), 7.14 (d, J=2.4 Hz, 1H), 7.08 (d, J=8.9 Hz, 1H), 7.04 (d, J=8.2 Hz, 2H), 6.83 (dd, J=8.9, 2.4 Hz, 1H), 5.26 (d, J=17.2 Hz, 1H), 5.10 (d, J=17.1 Hz, 1H), 5.05 (s, 1H), 4.82 (d, J=16.4 Hz, 1H), 4.26 (d, J=16.3 Hz, 1H), 3.86 (s, 3H), 3.68-3.58 (m, 1H), 3.32 (d, J=11.0 Hz, 1H), 3.06 (s, 3H), 1.89-1.82 (m, 2H), 1.73-1.52 (m, 7H). ESI-MS m/z (%): 519 [MH$^+$] (11), Anal. calcd for $C_{28}H_{30}N_4O_6$+⅛CH$_2$Cl$_2$+¼Heptane: C, 64.74; H, 6.23; N, 10.11; found: C, 0.64; 85 H, 6.67; N, 9.83.

4-((9-Methoxy-4-methyl-3,5-dioxo-3,4,5,6-tetrahydro-2,6-methano[1,3]diazocino[5,6-b]indol-11 (1H)-yl)methyl)-N-((tetrahydro-2H-pyran-2-yl)oxy) benzamide (37b)

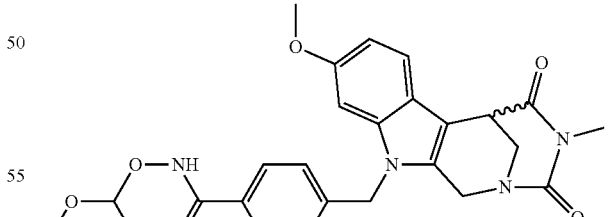

According to GP8 from 4-((9-methoxy-4-methyl-3,5-dioxo-3,4,5,6-tetrahydro-2,6-methano[1,3]diazocino[5,6-b]indol-11(1H)-yl)methyl)benzoic acid (34b) (0.55 g; 1.31 mmol). 0.56 g (1.11 mmol; 77%) colorless foam after silica gel chromatography (dichloromethane, ethyl acetate (1:2)); mp 105.8-108.1° C. IR (KBr): 2950, 1726, 1681 cm$^{-1}$. ESI-MS m/z (%): 519 [MH$^+$] (100).

4-((8-Acrylamido-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37c)

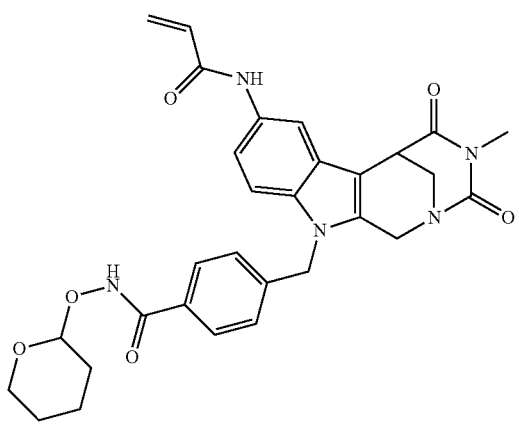 [SMILES: C=CC(=O)Nc1ccc2c(c1)c1c(n2Cc2ccc(C(=O)NOC3CCCCO3)cc2)CN2CC1C(=O)N(C)C2=O]

According to GP8 from 4-((8-Acrylamido-4-methyl-3,5-dioxo-3,4,5,6-tetrahydro-2,6-methano[1,3]diazocino[5,6-b]indol-11(1H)-yl)methyl)benzoic acid (34c) (0.30 g; 0.65 mmol). 0.36 g (0.64 mmol; 98%) colorless crystals after silica gel chromatography (methanol, ethyl acetate (1:10)) and crystallization from dichloromethane and petrolether; mp 205.7-209.5° C. $^1$H NMR (300 MHz, DMSO): δ 11.57 (s, 1H), 10.08 (s, 1H), 7.93 (s, 1H), 7.68 (d, J=8.2 Hz, 2H), 7.46-7.24 (m, 2H), 7.15 (d, J=8.3 Hz, 2H), 6.45 (dd, J=16.9, 10.0 Hz, 1H), 6.23 (dd, J=17.0, 2.2 Hz, 1H), 5.71 (dd, J=10.0, 2.2 Hz, 1H), 5.39 (s, 2H), 4.96 (s, 1H), 4.83 (d, J=16.6 Hz, 1H), 4.54 (d, J=16.5 Hz, 1H), 4.15-3.95 (m, 1H), 3.90 (d, J=12.7 Hz, 1H), 3.81 (s, 1H), 3.47 (t, J=12.2 Hz, 2H), 2.90 (s, 3H), 1.69 (s, 3H), 1.53 (s, 3H). ESI-MS m/z (%): 575 [MNH$_4^+$] (50), 558 [MH$^+$] (100).

4-((8-(Acrylamidomethyl)-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37d)

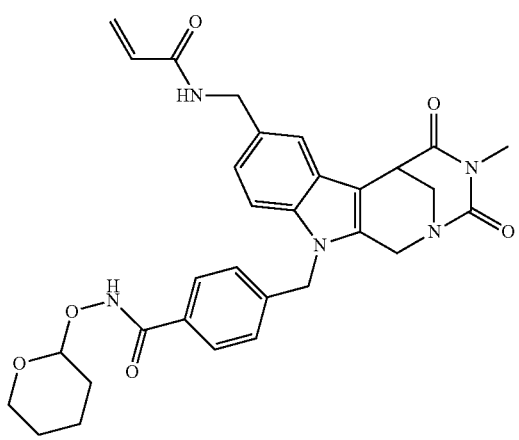 [SMILES: C=CC(=O)NCc1ccc2c(c1)c1c(n2Cc2ccc(C(=O)NOC3CCCCO3)cc2)CN2CC1C(=O)N(C)C2=O]

According to GP8 from 4-((8-(acrylamidomethyl)-4-methyl-3,5-dioxo-3,4,5,6-tetrahydro-2,6-methano[1,3]diazocino[5,6-b]indol-11(1H)-yl)methyl)benzoic acid (34d) (0.50 g; 1.06 mmol). 0.35 g (0.61 mmol; 58%) colorless crystals after silica gel chromatography (methanol, ethyl acetate (1:9)); IR (KBr): 3326, 3214, 1720, 1684 cm$^{-1}$. $^1$H NMR (300 MHz, DMSO): δ 11.59 (s, 1H), 8.57 (t, J=5.8 Hz, 1H), 7.67 (d, J=8.2 Hz, 2H), 7.43 (s, 1H), 7.36 (d, J=8.5 Hz, 1H), 7.11 (d, J=8.3 Hz, 2H), 7.04 (dd, J=8.5, 1.3 Hz, 1H), 6.26 (dd, J=17.1, 9.9 Hz, 1H), 6.11 (dd, J=17.1, 2.4 Hz, 1H), 5.60 (dd, J=9.9, 2.4 Hz, 1H), 5.41 (s, 2H), 4.95 (s, 1H), 4.84 (d, J=16.6 Hz, 1H), 4.55 (d, J=16.5 Hz, 1H), 4.47-4.30 (m, 2H), 4.03 (d, J=7.0 Hz, 1H), 3.90 (d, J=12.9 Hz, 1H), 3.84 (s, 1H), 3.46 (dd, J=14.7, 12.7 Hz, 2H), 2.90 (s, 3H), 1.69 (s, 3H), 1.53 (s, 3H). ESI-MS m/z (%): 572 [MH$^+$] (56), 488 [MH$^+$–C$_5$H$_8$O] (100).

4-((8-(2-Acrylamidoethoxy)-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37e)

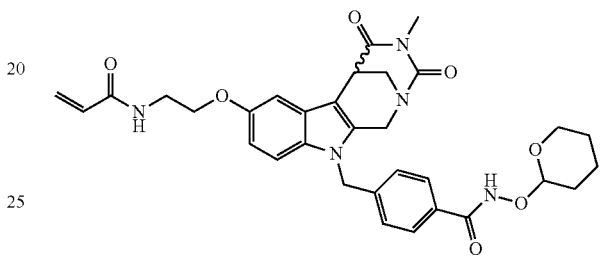

According to GP8 from 34e (0.17 g, 0.34 mmol). Purification by column chromatography (eluent: ethyl acetate/MeOH 10:1). Yield 0.17 g (0.28 mmol, 82%), colorless film. $^1$H NMR (300 MHz, DMSO-d$_6$) δ $^1$H NMR (300 MHz, DMSO-d$_6$) δ 11.60 (s, 1H), 8.39 (t, J=5.7 Hz, 1H), 7.67 (d, J=8.0 Hz, 2H), 7.30 (d, J=8.9 Hz, 1H), 7.12 (d, J=8.0 Hz, 2H), 7.00 (d, J=2.5 Hz, 1H), 6.76 (dd, J=8.9, 2.4 Hz, 1H), 6.28 (dd, J=17.0, 10.0 Hz, 1H), 6.10 (dd, J=17.1, 2.4 Hz, 1H), 5.59 (dd, J=10.1, 2.4 Hz, 1H), 5.37 (s, 2H), 4.96 (d, J=3.2 Hz, 1H), 4.82 (d, J=16.5 Hz, 1H), 4.56 (d, J=4.1 Hz, 2H), 3.99 (d, J=2.6 Hz, 1H), 3.94-3.81 (m, 2H), 3.80-3.71 (m, 1H), 3.52 (d, J=5.4 Hz, 2H), 3.47-3.41 (m, 2H), 2.89 (s, 3H), 1.67 (d, J=11.0 Hz, 4H), 1.53 (t, J=5.1 Hz, 3H).

4-((9-Acrylamido-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37f)

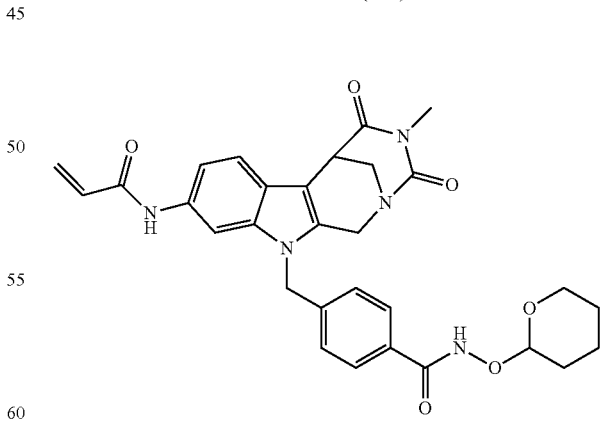

According to GP8 from 4-((9-acrylamido-4-methyl-3,5-dioxo-3,4,5,6-tetrahydro-2,6-methano[1,3]diazocino[5,6-b]indol-11(1H)-yl)methyl)benzoic acid (34f). Yield: Colorless crystals (0.32 g, 0.58 mmol, 56%) after silica gel chromatography dichloromethane/methanol (10:1), $^1$H NMR (300 MHz, DMSO): δ 11.61 (s, 1H), 10.12 (s, 1H), 7.95 (s, 1H), 7.69 (d, J=8.2 Hz, 2H), 7.46 (d, J=8.5 Hz, 1H), 7.24-7.18 (m, 1H), 7.13 (d, J=8.2 Hz, 2H), 6.42 (dd, J=16.9, 10.0 Hz, 1H), 6.20 (dd, J=16.9, 2.1 Hz, 1H), 5.70 (dd, J=10.0, 2.1 Hz, 1H), 5.35 (s, 2H), 4.96 (s, 1H), 4.84 (d, J=16.6 Hz, 1H), 4.56 (d, J=16.5 Hz, 1H), 4.09-3.96 (m, 1H), 3.94-3.81 (m, 2H), 3.55-3.41 (m, 2H), 2.90 (s, 3H), 1.85-1.55 (m, 3H), 1.53 (s, 3H). HR-MS m/z: Calcd. 558.2347 [MH$^+$]. found: 558.2341 [MH+].

4-((5-Methyl-3,6-dioxo-4,5,6,7-tetrahydro-1H-2,7-methano[1,4]diazonino[6,7-b]indol-12(3H)-yl)methyl)-N-((tetrahydro-2H-pyran-2-yl)oxy)benzamide (38)

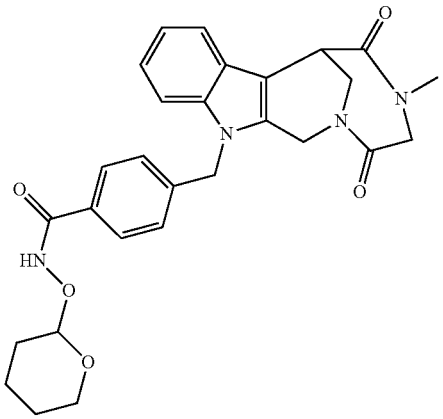 [SMILES: CN1CC(=O)N2Cc3c(c4ccccc4n3Cc3ccc(C(=O)NOC4CCCCO4)cc3)C(C2)C1=O]

According to GP8 from 4-((5-methyl-3,6-dioxo-4,5,6,7-tetrahydro-1H-2,7-methano[1,4]diazonino[6,7-b]indol-12(3H)-yl)methyl)benzoic acid (35) (0.40 g; 0.87 mmol). 0.27 g (0.54 mmol; 62%) colorless crystals after crystallization from ethyl acetate; mp 210.0-212.2° C. IR (KBr): 2938, 1670, 1609 cm$^{-1}$. $^1$H NMR (300 MHz, DMSO-d$_6$): δ 11.59 (s, 1H), 7.87 (dd, J=7.0, 1.7 Hz, 1H), 7.68 (d, J=8.3 Hz, 2H), 7.35 (d, J=7.3 Hz, 1H), 7.21 (d, J=8.0 Hz, 2H), 7.09-6.99 (m, 2H), 5.43 (s, 2H), 5.32 (d, J=16.0 Hz, 1H), 5.07-4.86 (m, 2H), 4.61 (d, J=15.0 Hz, 1H), 4.20 (d, J=15.6 Hz, 1H), 4.02 (s, 1H), 3.87 (d, J=13.7 Hz, 1H), 3.60 (d, J=13.7 Hz, 1H), 3.57-3.43 (m, 2H), 2.94 (s, 3H), 1.70 (s, 3H), 1.53 (s, 3H). ESI-MS m/z (%): 520 [MNH$_4^+$] (70), 503 [MH$^+$] (100). Anal. calcd for C$_{28}$H$_{30}$N$_4$O$_5$: C, 66.92; H, 6.02; N, 11.15; found: C, 66.29; H, 5.99; N, 11.16.

(E)-3-(4-((4-Methyl-3,5-dioxo-3,4,5,6-tetrahydro-2,6-methano[1,3]diazocino[5,6-b]indol-11(1H)-yl)methyl)phenyl)-N-((tetrahydro-2H-pyran-2-yl)oxy)acrylamide (48)

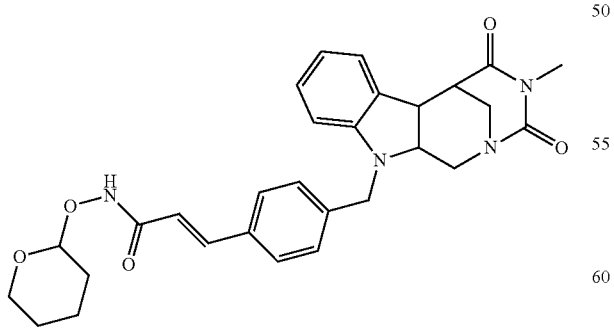

According to GP8 from (E)-3-(4-((4-methyl-3,5-dioxo-3,4,5,6-tetrahydro-2,6-methano[1,3]diazocino[5,6-b]indol-11(1H)-yl)methyl)phenyl)acrylic acid (46) (1.21 g; 2.91 mmol). 0.94 g (1.83 mmol; 63%) colorless crystals after crystallization from ethyl acetate; mp 226.0-230.1° C. IR (KBr): 3299, 2934, 1718, 1669 cm$^{-1}$. $^1$H NMR (300 MHz, DMSO-d$_6$): δ 11.22 (s, 1H), 7.58-7.39 (m, 5H), 7.15-7.02 (m, 4H), 6.45 (d, J=15.9 Hz, 1H), 5.38 (s, 2H), 4.86 (d, J=16.6 Hz, 2H), 4.57 (d, J=16.5 Hz, 1H), 3.90 (d, J=13.1 Hz, 3H), 3.49 (dd, J=18.7, 11.4 Hz, 2H), 2.89 (s, 3H), 1.68 (s, 3H), 1.52 (s, 3H). ESI-MS m/z (%): 515 [MH$^+$] (2), 431 [MH$^+$–C$_5$H$_8$O] (100). Anal. calcd for C$_{29}$H$_{30}$N$_4$O$_5$×¼ ethyl acetate: C, 66.90; H, 6.13; N, 10.89; found: C, 66.67; H, 5.84; N, 10.80.

(E)-3-(3-((4-Methyl-3,5-dioxo-3,4,5,6-tetrahydro-2,6-methano[1,3]diazocino[5,6-b]indol-11(1H)-yl)methyl)phenyl)-N-((tetrahydro-2H-pyran-2-yl)oxy)acrylamide (49)

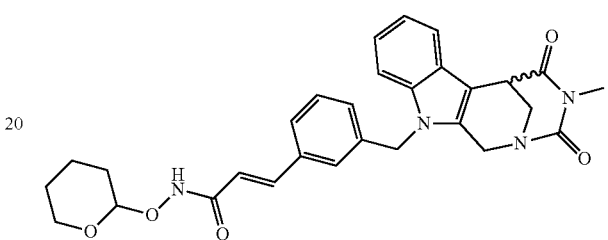

According to GP8 from (E)-3-(3-((4-methyl-3,5-dioxo-3,4,5,6-tetrahydro-2,6-methano[1,3]diazocino[5,6-b]indol-11(1H)-yl)methyl)phenyl)acrylic acid (47) (1.48 g; 3.56 mmol). 1.07 g (19.4 mmol; 55%) colorless solid; mp 146.0-151.8° C. IR (KBr): 3240, 2950, 1727, 1684 cm$^{-1}$. $^1$H NMR (300 MHz, DMSO-d$_6$): δ 11.24 (s, 1H), 7.55-7.29 (m, 6H), 7.16-7.02 (m, 3H), 6.45 (d, J=15.9 Hz, 1H), 5.38 (s, 2H), 4.99-4.80 (m, 2H), 4.61 (d, J=16.6 Hz, 1H), 3.91 (d, J=13.7 Hz, 3H), 3.58-3.28 (m, 3H), 2.90 (s, 3H), 1.68 (s, 3H), 1.53 (s, 3H). ESI-MS m/z (%): 515 [MH$^+$] (88), 431 [MH$^+$–C$_5$H$_8$O] (100). Anal. calcd for C$_{29}$H$_{30}$N$_4$O$_5$×¼ ethyl acetate: C, 66.90; H, 6.13; N, 10.89; found: C, 66.98; H, 5.86; N, 10.76.

1.9 General Procedure 9 (GP9)

The corresponding starting material (0.30 mmol) was dissolved in 10.0 mL of methanol, optionally with gentle heating. Carefully 0.6 M aqueous HCl was added dropwise until a slight turbidity by precipitating product is formed. Stirring at room temperature was continued until full implementation of the starting material. The crystallization of the hydroxamic acid was completed by further addition of 0.6 M HCl. The crystalline product was filtered off and dried in vacuo.

N-Hydroxy-4-((4-methyl-3,5-dioxo-3,4,5,6-tetrahydro-2,6-methano[1,3]diazocino[5,6-b]indol-11(1H)-yl)methyl)benzamide (MARB1; 39a)

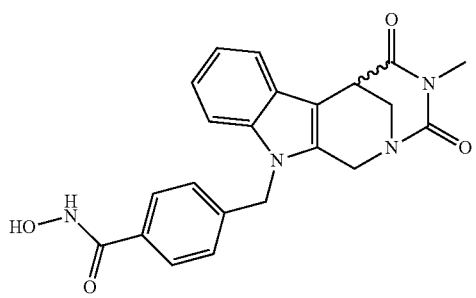 [SMILES: CN1C(=O)C2CN(Cc3c2c2ccccc2n3Cc2ccc(C(=O)NO)cc2)C1=O]

According to GP9 from 4-((4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36a) (0.16 g; 0.33 mmol). 0.06 g (0.148 mmol; 46%) colorless crystals after crystallization from $CH_2Cl_2$/n-heptane. mp 199.4-201.0° C. IR (KBr): 1727, 1684 cm$^{-1}$. $^1$H NMR (300 MHz, DMSO-d$_6$): δ 11.16 (s, 1H), 9.02 (s, 1H), 7.66 (d, J=8.3 Hz, 2H), 7.52 (dd, J=6.3, 2.3 Hz, 1H), 7.41 (dd, J=6.6, 1.9 Hz, 1H), 7.16-7.06 (m, 4H), 5.41 (s, 2H), 4.86 (d, J=16.6 Hz, 1H), 4.57 (d, J=16.5 Hz, 1H), 3.90 (d, J=12.9 Hz, 2H), 3.46 (d, J=11.2 Hz, 1H), 2.90 (s, 3H). ESI-MS m/z (%): 422 [MNH$_4^+$] (80), 405 [MH$^+$] (100). Anal. calcd for $C_{22}H_{20}N_4O_5 \times \frac{1}{2}H_2O$: C, 63.91; H, 5.12; N, 13.55; found: C, 64.00; H, 5.12; N, 13.40.

N-Hydroxy-4-((4-methyl-5-oxo-3-thioxo-3,4,5,6-tetrahydro-2,6-methano[1,3]diazocino[5,6-b]indol-11(1H)-yl)methyl)benzamide (39b)

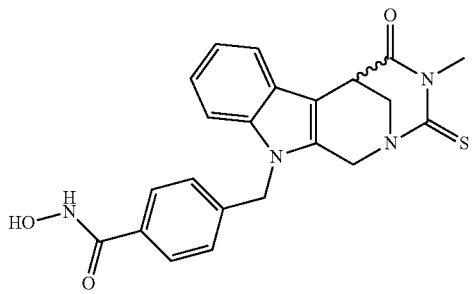 [SMILES: CN1C(=O)C2CN(Cc3c2c2ccccc2n3Cc2ccc(C(=O)NO)cc2)C1=S]

According to GP9 4-((4-methyl-5-oxo-3-thioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36b) (0.42 g; 0.83 mmol). 0.31 g (0.73 mmol; 88%) slightly yellow crystals after crystallization from 0.5N HCl$_{aq}$/methanol. mp 176.4-178.1° C. IR (KBr): 1718, 1653 cm$^{-1}$. $^1$H NMR (300 MHz, DMSO): δ 11.17 (s, 1H), 9.01 (s, 1H), 7.65 (d, J=8.2 Hz, 2H), 7.60-7.44 (m, 1H), 7.43-7.36 (m, 1H), 7.18 (d, J=8.2 Hz, 2H), 7.14-6.92 (m, 2H), 5.56 (d, J=16.1 Hz, 1H), 5.44 (d, J=14.6 Hz, 2H), 5.06 (d, J=16.0 Hz, 1H), 4.08 (d, J=12.6 Hz, 1H), 3.98 (s, 1H), 3.78 (dd, J=12.8, 1.9 Hz, 1H), 3.23 (s, 3H). ESI-MS m/z (%): 421 [MH$^+$] (100). Anal. calcd for $C_{22}H_{20}N_4O_5 \times \frac{1}{3}H_2O$: C, 61.96; H, 4.88, N, 13.14, S, 7.52; found: C, 61.92; H, 4.90; N, 13.00, S, 7.43.

N-Hydroxy-4-((4-methyl-3-oxo-5-thioxo-3,4,5,6-tetrahydro-2,6-methano[1,3]diazocino[5,6-b]indol-11(1H)-yl)methyl)benzamide (39c)

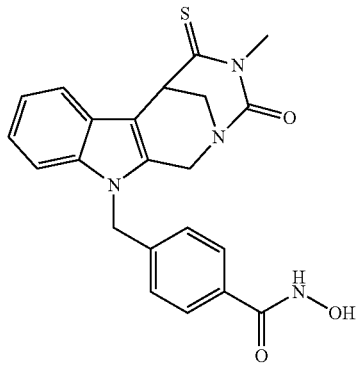 [SMILES: CN1C(=O)N2Cc3c(c4ccccc4n3Cc3ccc(C(=O)NO)cc3)C(C2)C1=S]

According to GP9 4-((4-methyl-3-oxo-5-thioxo-3,4,5,6-tetrahydro-2,6-methano[1,3]diazocino[5,6-b]indol-11(1H)-yl)methyl)-N-((tetrahydro-2H-pyran-2-yl)oxy) benzamide (36c) (0.19 g; 0.38 mmol) colorless crystals 0.10 g (0.23 mmol, 60%) after crystallization from 0.5N HCl$_{aq}$/methanol; $^1$H NMR (300 MHz, DMSO): δ 11.17 (s, 1H), 9.03 (s, 1H), 7.72-7.61 (m, 3H), 7.41 (dd, J=6.5, 2.2 Hz, 1H), 7.22-7.02 (m, 4H), 5.56-5.30 (m, 2H), 4.94 (dd, J=16.5, 5.3 Hz, 1H), 4.61 (d, J=16.4 Hz, 1H), 4.44 (s, 1H), 3.91 (d, J=12.8 Hz, 1H), 3.50 (dd, J=13.1, 2.1 Hz, 1H), 3.30 (s, 3H). ESI-MS m/z (%): 421 [MH$^+$] (100). Anal. calcd. for $C_{22}H_{20}N_4O_3S \times \frac{1}{3}$ EE$\times \frac{1}{3}$ PE): C, 63.58; H, 5.76; N, 11.71; S, 6.70; found: C, 63.63; H, 5.49; N, 12.10; 6.58.

N-hydroxy-4-((8-methoxy-4-methyl-5-oxo-3-thioxo-3,4,5,6-tetrahydro-2,6-methano[1,3]diazocino[5,6-b]indol-11(1H)-yl)methyl)benzamide (39d)

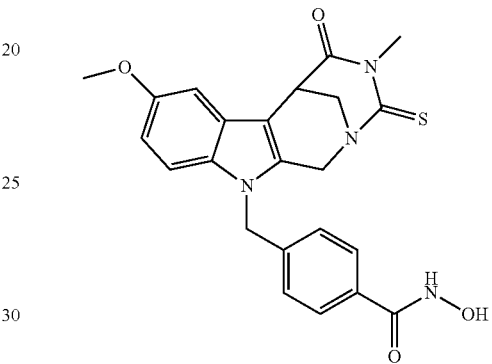

According to GP9 from 4-((8-methoxy-4-methyl-5-oxo-3-thioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36d). Yield: Colorless crystals (0.25 g, 0.56 mmol, 62%), mp: 222.6-223.6° C.; IR (KBr): 1696, 1620 cm$^{-1}$; $^1$H NMR (300 MHz, DMSO): δ 11.17 (d, J=1.6 Hz, 1H), 9.02 (d, J=1.8 Hz, 1H), 7.65 (d, J=8.3 Hz, 2H), 7.29 (d, J=8.9 Hz, 1H), 7.15 (d, J=8.3 Hz, 2H), 6.97 (d, J=2.4 Hz, 1H), 6.74 (dd, J=8.9, 2.5 Hz, 1H), 5.53 (d, J=16.1 Hz, 1H), 5.37 (s, 2H), 5.03 (d, J=16.0 Hz, 1H), 4.08 (d, J=12.3 Hz, 1H), 3.95 (s, 1H), 3.83-3.69 (m, 4H), 3.24 (s, 3H). ESI-MS m/z (%): 451 [MH$^+$] (100). Anal. ($C_{23}H_{22}N_4O_4S + \frac{1}{6}H_2O + \frac{1}{3}$ MeOH): Calcd. C, 60.37; H, 5.14; N, 12.07; found. C, 60.78; H, 5.26; N, 11.64.

4-((8-(Benzyloxy)-4-methyl-3,5-dioxo-3,4,5,6-tetrahydro-2,6-methano[0,3]diazocino[5,6-b]indol-11(1H)-yl)methyl)-N-hydroxybenzamide (39e)

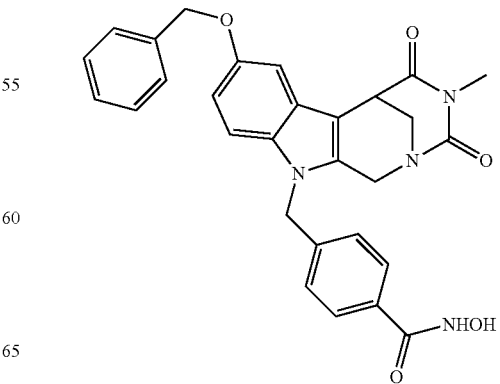

According to GP9 from 4-((8-(benzyloxy)-4-methyl-3,5-dioxo-3,4,5,6-tetrahydro-2,6-methano[1,3]diazocino[5,6-b]indol-11(1H)-yl)methyl)benzoic acid (36e). Yield 0.15 g (0.29 mmol; 44%) Colorless crystals; mp: 140.3-155.4° C. $^1$H NMR (300 MHz, DMSO): δ 11.16 (s, 1H), 9.02 (s, 1H), 7.65 (d, J=8.3 Hz, 2H), 7.48 (d, J=6.8 Hz, 2H), 7.42-7.29 (m, 5H), 7.14-7.07 (m, 4H), 6.83 (dd, J=8.9, 2.4 Hz, 1H), 5.36 (s, 2H), 5.08 (s, 2H), 4.83 (d, J=16.7 Hz, 1H), 4.54 (d, J=16.2 Hz, 1H), 3.89 (d, J=12.9 Hz, 3H), 3.45 (d, J=11.2 Hz, 1H), 2.90 (s, 3H). ESI-MS m/z (%): 523.23 [MH$^+$] (100), 1067.44 [2MNa$^+$] (3.37). Anal. calcd for $C_{29}H_{26}N_4O_5 \times 0.33 C_4H_8O_2$: C, 67.5; H, 5.31; N, 10.39; found: C, 67.37; H, 5.40; N, 10.47.

4-((7-(Benzyloxy)-4-methyl-3,5-dioxo-3,4,5,6-tetrahydro-2,6-methano[1,3]diazocino[5,6-b]indol-11(1H)-yl)methyl)-N-hydroxybenzamide (39f)

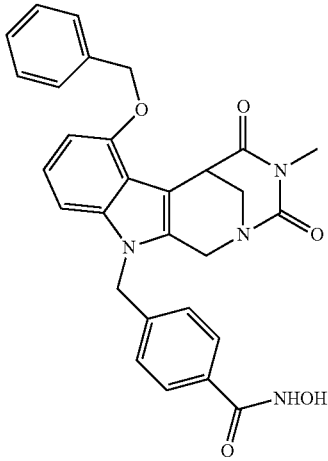

According to GP9 from 4-((7-(benzyloxy)-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (36f). Yield 0.15 g (0.20 mmol; 53%) Colorless crystals; mp: 138.3-142.4° C. $^1$H NMR (300 MHz, DMSO): δ 11.17 (s, 1H), 9.03 (s, 1H), 7.75 (d, J=7.2 Hz, 2H), 7.66 (d, J=8.2 Hz, 2H), 7.39 (d, J=7.6 Hz, 2H), 7.32 (d, J=7.2 Hz, 1H), 7.21 (d, J=6.4 Hz, 1H), 7.10 (d, J=8.1 Hz, 2H), 7.00-6.96 (m, 1H), 6.66-6.60 (m, 1H), 5.37 (s, 2H), 5.23 (d, J=6.3 Hz, 2H), 4.85 (d, J=16.5 Hz, 1H), 4.51 (d, J=16.5 Hz, 1H), 4.14 (s, 1H), 3.86 (d, J=12.9 Hz, 1H), 3.44 (d, J=13.3 Hz, 1H), 2.93 (s, 4H).

N-((tert-butylcarbamoyl)oxy)-4-((4-methyl-3,5-dioxo-3,4,5,6-tetrahydro-2,6-methano[1,3]diazocino[5,6-b]indol-11(1H)-yl)methyl)benzamide (39h)

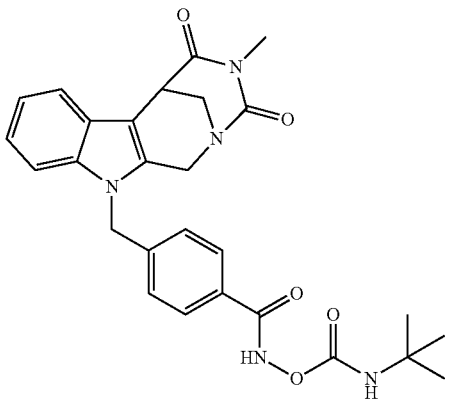 [SMILES: CN1C(=O)C2CN(Cc3c2c2ccccc2n3Cc2ccc(C(=O)NOC(=O)NC(C)(C)C)cc2)C1=O]

According to Schlimmer et al. (2011), from N-hydroxy-4-((4-methyl-3,5-dioxo-3,4,5,6-tetrahydro-2,6-methano[1,3]diazocino[5,6-b]indol-11(1H)-yl)methyl)benzamide (MARB1; 39a). Yield: Colorless crystals. (0.09 g, 0.18 mmol, 36%). $^1$H NMR (300 MHz, DMSO): δ 11.91 (s, 1H), 7.73 (d, J=8.2 Hz, 2H), 7.62 (s, 1H), 7.53 (dd, J=6.3, 2.2 Hz, 1H), 7.42 (dd, J=6.6, 1.9 Hz, 1H), 7.17 (d, J=8.3 Hz, 2H), 7.15-7.03 (m, 2H), 5.44 (s, 2H), 4.85 (d, J=16.6 Hz, 1H), 4.56 (d, J=16.5 Hz, 1H), 3.90 (d, J=12.2 Hz, 2H), 3.46 (d, J=11.1 Hz, 1H), 2.90 (s, 3H), 1.25 (s, 9H).

N-Hydroxy-4-((8-methoxy-4-methyl-3,5-dioxo-3,4,5,6-tetrahydro-2,6-methano[1,3]diazocino[5,6-b]indol-11(1H)-yl)methyl)benzamide (40a)

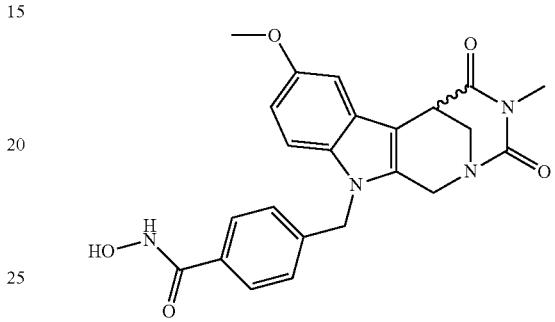

According to GP9 from 4-((8-methoxy-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37a) (0.10 g; 0.20 mmol) 0.02 g (0.05 mmol; 25%) colorless crystals after crystallization from water/methanol; mp 178.5-181.4° C. IR (KBr): 1716 cm$^{-1}$. $^1$H NMR (400 MHz, MeOD): δ 7.65 (d, J=8.3 Hz, 2H), 7.17 (d, J=8.9 Hz, 1H), 7.12 (d, J=2.4 Hz, 1H), 7.06 (d, J=8.3 Hz, 2H), 6.77 (dd, J=8.9, 2.4 Hz, 1H), 5.37-5.25 (m, 2H), 4.81 (d, J=16.5 Hz, 1H), 4.48 (d, J=16.3 Hz, 1H), 3.93 (d, J=13.2 Hz, 1H), 3.84 (s, 1H), 3.82 (s, 3H), 3.44 (dd, J=13.2, 2.2 Hz, 1H), 3.01 (s, 3H). ESI-MS m/z (%): 435 [MH$^+$] (100). RP-HPLC (220 nm): 98.4% (gradient: 0-30 min: MeCN/0.1% aq. TFA 20/80-95/5, 31-40 min: 95/5, tR=13.3 min).

N-hydroxy-4-((9-methoxy-4-methyl-3,5-dioxo-3,4,5,6-tetrahydro-2,6-methano[1,3]diazocino[5,6-b]indol-11(1H)-yl)methyl)benzamide (40b)

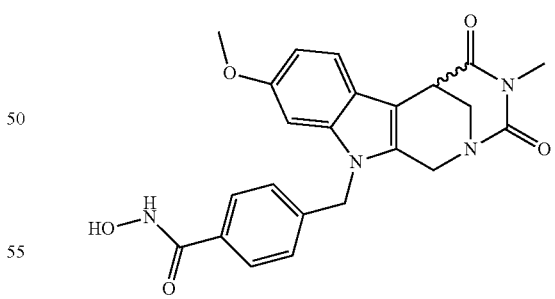

According to GP9 from 4-((9-methoxy-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37b) (0.50 g; 0.97 mmol) 0.18 g (0.41 mmol; 42%) colorless crystals after crystallization from 0.5 N HCl$_{aq}$/methanol; mp 169.4-173.1° C. IR (KBr): 1725 cm$^{-1}$. $^1$H NMR (300 MHz, DMSO): δ 11.07 (s, 1H), 7.85 (s, 1H), 7.68 (d, J=8.3 Hz, 2H), 7.39 (d, J=8.6 Hz, 1H), 7.14 (d, J=8.3 Hz, 2H), 7.00 (d, J=2.1 Hz, 1H), 6.73 (dt, J=6.6, 3.3 Hz, 1H), 5.40 (d, J=17.5 Hz, 1H), 5.34 (d, J=17.6 Hz, 1H), 4.79 (d, J=16.2 Hz, 1H), 4.49 (d, J=16.2 Hz, 1H), 3.86 (d, J=13.1 Hz, 1H), 3.79 (d, J=18.6 Hz, 1H), 3.71 (s, 3H), 3.41 (dd, J=13.0, 1.9 Hz, 1H), 2.89 (s, 3H). ESI-MS m/z (%): 435 [MH$^+$] (100).

4-((8-Acrylamido-4-methyl-3,5-dioxo-3,4,5,6-tetrahydro-2,6-methano[1,3]diazocino[5,6-b]indol-11(1H)-yl)methyl)-N-hydroxybenzamide (40c)

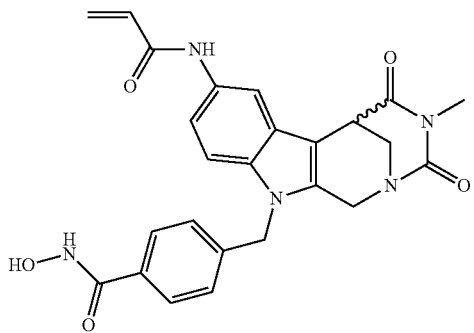 [SMILES: C=CC(=O)Nc1ccc2c(c1)c1c(n2Cc2ccc(C(=O)NO)cc2)CN2CC1C(=O)N(C)C2=O]

According to GP9 from 4-((8-acrylamido-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37c) (0.28 g; 0.50 mmol). 0.14 g (0.29 mmol; 58%) colorless crystals after crystallization from 0.5 N HCl$_{aq}$/methanol; mp 259.8-261.8° C. $^1$H NMR (300 MHz, DMSO): δ 11.17 (s, 1H), 10.09 (s, 1H), 9.03 (s, 1H), 7.93 (s, 1H), 7.66 (d, J=8.2 Hz, 2H), 7.46-7.27 (m, 2H), 7.13 (d, J=8.2 Hz, 2H), 6.45 (dd, J=16.9, 10.0 Hz, 1H), 6.23 (dd, J=17.0, 2.2 Hz, 1H), 5.71 (dd, J=10.0, 2.2 Hz, 1H), 5.38 (s, 2H), 4.84 (d, J=16.6 Hz, 1H), 4.56 (d, J=16.5 Hz, 1H), 3.90 (d, J=12.7 Hz, 1H), 3.81 (s, 1H), 3.46 (d, J=11.2 Hz, 1H), 2.90 (s, 3H). ESI-MS m/z (%): 491 [MNH$_4^+$] (75) 474 [MH$^+$] (100).

4-((8-(Acrylamidomethyl)-4-methyl-3,5-dioxo-3,4,5,6-tetrahydro-2,6-methano[1,3]diazocino[5,6-b]indol-11(1H)-yl)methyl)-N-hydroxybenzamide (40d)

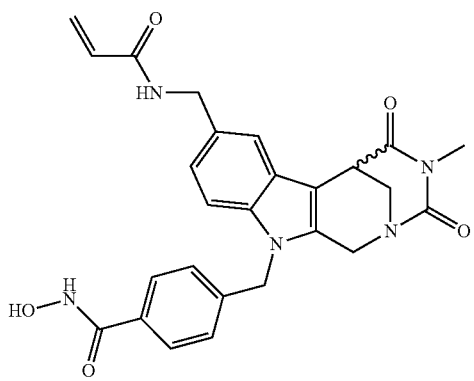 [SMILES: C=CC(=O)NCc1ccc2c(c1)c1c(n2Cc2ccc(C(=O)NO)cc2)CN2CC1C(=O)N(C)C2=O]

According to GP9 from 4-((8-(acrylamidomethyl)-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37d) (0.20 g; 0.35 mmol). 0.15 g (0.31 mmol; 90%) colorless crystals after crystallization from 0.5 N HCl$_{aq}$/methanol; mp 185.0-187.1° C. IR (KBr): 3458, 3246, 1720, 1672 cm$^{-1}$. $^1$H NMR (300 MHz, DMSO): δ 11.16 (s, 1H), 9.02 (s, 1H), 8.57 (t, J=5.8 Hz, 1H), 7.65 (d, J=8.2 Hz, 2H), 7.43 (s, 1H), 7.36 (d, J=8.5 Hz, 1H), 7.09 (d, J=8.2 Hz, 2H), 7.04 (dd, J=8.5, 1.3 Hz, 1H), 6.26 (dd, J=17.1, 9.9 Hz, 1H), 6.11 (dd, J=17.1, 2.4 Hz, 1H), 5.60 (dd, J=9.9, 2.4 Hz, 1H), 5.39 (s, 2H), 4.84 (d, J=16.6 Hz, 1H), 4.56 (d, J=16.5 Hz, 1H), 4.49-4.28 (m, 2H), 4.01-3.74 (m, 2H), 3.52-3.42 (m, 1H), 3.37 (s, 2H), 2.90 (s, 3H). ESI-MS m/z (%): 505 [MNH$_4^+$] (75) 488 [MH$^+$] (100).

4-((8-(2-Acrylamidoethoxy)-4-methyl-3,5-dioxo-3,4,5,6-tetrahydro-2,6-methano[1,3]diazocino[5,6-b]indol-1(1H)-yl)methyl)-N-hydroxybenzamide (40e)

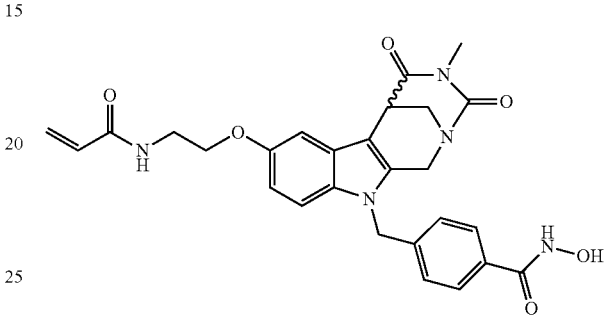

37e (0.17 g, 0.28 mmol) was dissolved in methanol (20 mL). 5-6 drops of 6N HCl in 2-propanol were added. The mixture was stirred at room temperature for 4 h (TLC monitoring). The solvent was evaporated and the residue dissolved in ethyl acetate (30 mL) and water (10 mL). The organic phase was separated, dried over Na$_2$SO$_4$ and the solvent removed under reduced pressure. The crystalline product was dried in vacuo.

0.10 g (0.19 mmol; 68%) beige crystals; mp 174-176° C. IR (KBr): 3329, 2948, 1726 cm$^{-1}$. $^1$H NMR (300 MHz, DMSO-d$_6$) 11.19 (s, 1H), 9.03 (s, 1H), 8.43 (d, J=5.9 Hz, 1H), 7.66 (d, J=7.9 Hz, 2H), 7.30 (d, J=8.9 Hz, 1H), 7.10 (d, J=8.0 Hz, 2H), 7.00 (d, J=2.5 Hz, 1H), 6.76 (dd, J=9.0, 2.5 Hz, 1H), 6.28 (dd, J=17.1, 10.0 Hz, 1H), 6.10 (dd, J=17.2, 2.4 Hz, 1H), 5.59 (dd, J=10.1, 2.5 Hz, 1H), 5.36 (s, 2H), 4.68 (dd, J=85.0, 16.6 Hz, 2H), 4.03-3.94 (m, 2H), 3.92-3.80 (m, 2H), 3.55-3.41 (m, 3H), 2.89 (s, 3H). ESI-MS m/z (%): 518 [MH]$^+$ (100).

4-((9-Acrylamido-4-methyl-3,5-dioxo-3,4,5,6-tetrahydro-2,6-methano[1,3]diazocin[5,6-b]indol-11(1H)-yl)methyl)-N-hydroxybenzamide (40f)

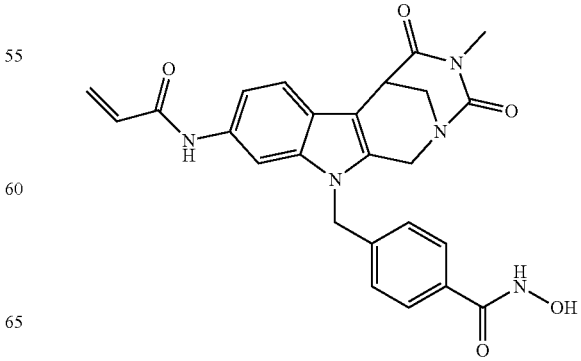

According to GP9 from 4-((9-Acrylamido-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (37f). Yield: Colorless crystals (0.16 g, 0.38 mmol, 65%), mp: decomposition at 200° C.; IR (KBr): 3374, 1725, 1682 cm$^{-1}$; $^1$H NMR (300 MHz, DMSO): δ 11.18 (s, 1H), 10.13 (s, 1H), 9.03 (s, 1H), 7.95 (d, J=1.1 Hz, 1H), 7.67 (d, J=8.3 Hz, 2H), 7.46 (d, J=8.5 Hz, 1H), 7.22 (dd, J=8.5, 1.5 Hz, 1H), 7.11 (d, J=8.3 Hz, 2H), 6.42 (dd, J=16.9, 10.0 Hz, 1H), 6.20 (dd, J=17.0, 2.1 Hz, 1H), 5.70 (dd, J=10.0, 2.1 Hz, 1H), 5.37 (d, J=17.3 Hz, 1H), 5.31 (d, J=17.7 Hz, 1H), 4.84 (d, J=16.6 Hz, 1H), 4.57 (d, J=16.5 Hz, 1H), 3.89 (d, J=13.2 Hz, 1H), 3.86 (s, J=11.0 Hz, 1H), 3.44 (dd, J=11.2, 1.8 Hz, 1H), 2.90 (s, 3H). ESI-MS m/z (%): 474 [MH$^+$] (100). Anal. ($C_{25}H_{23}N_5O_5$+2 $H_2O$): Calcd. C, 58.93; H, 5.34; N, 13.75; found: C, 58.95; H, 5.39; N, 13.49.

N-Hydroxy-4-((5-methyl-3,6-dioxo-4,5,6,7-tetrahydro-1H-2,7-methano[1,4]diazonino[6,7-b]indol-12(3H)-yl)methyl)benzamide (MARB2, 41)

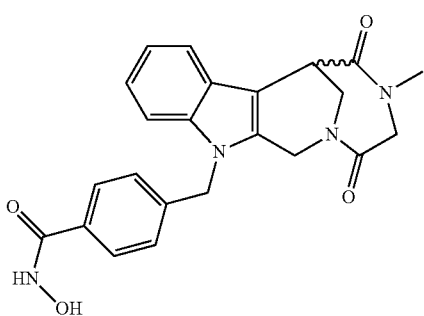 [SMILES: CN1CC(=O)N2Cc3c(c4ccccc4n3Cc3ccc(C(=O)NO)cc3)C(C2)C1=O]

According to GP9 from 4-((5-methyl-3,6-dioxo-4,5,6,7-tetrahydro-1H-2,7-methano[1,4]diazonino[6,7-b]indol-12(3H)-yl)methyl)-N-((tetrahydro-2H-pyran-2-yl)oxy)benzamide (38) (0.18 g; 0.36 mmol). 0.12 g (0.29 mmol; 80%) colorless crystals mp 252.9-253.8° C. IR (KBr): 3210, 2894, 1676, 1647 cm$^{-1}$. $^1$H NMR (300 MHz, DMSO-d$_6$): δ 11.59 (s, 1H), 7.87 (dd, J=7.0, 1.7 Hz, 1H), 7.68 (d, J=8.3 Hz, 2H), 7.35 (d, J=7.3 Hz, 1H), 7.21 (d, J=8.0 Hz, 2H), 7.04 (pd, J=7.1, 1.3 Hz, 2H), 5.43 (s, 2H), 5.32 (d, J=16.0 Hz, 1H), 5.01-4.91 (m, 2H), 4.61 (d, J=15.0 Hz, 1H), 4.20 (d, J=15.6 Hz, 1H), 4.02 (s, 1H), 3.87 (s, 1H), 3.66-3.43 (m, 3H), 2.94 (s, 3H), 1.70 (s, 3H), 1.53 (s, 3H). ESI-MS m/z (%): 436 [MNH$_4^+$] (90), 419 [MH$^+$] (100). Anal. calcd for $C_{23}H_{22}N_4O_4$×$H_2O$: C, 65.31; H, 5.36; N, 13.25; found: C, 65.21; H, 5.30; N, 13.23.

(E)-N-Hydroxy-3-(4-((4-methyl-3,5-dioxo-3,4,5,6-tetrahydro-2,6-methano[1,3]diazocino[5,6-b]indol-11(1H)-yl)methyl)phenyl)acrylamide (50)

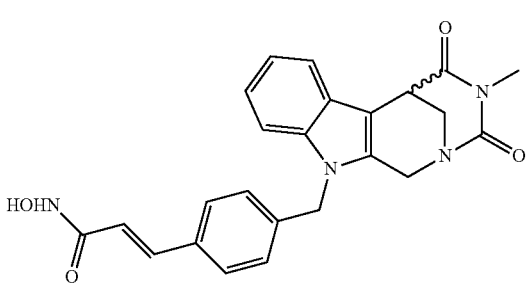

According to GP9 from (E)-3-(4-((4-methyl-3,5-dioxo-3,4,5,6-tetrahydro-2,6-methano[1,3]diazocino[5,6-b]indol-11(1H)-yl)methyl)phenyl)-N-((tetrahydro-2H-pyran-2-yl)oxy)acrylamide (48) (0.50 g; 0.97 mmol). 0.30 g (0.70 mmol; 72%) colorless crystals; mp 238.1-239.3° C. IR (KBr): 3245, 1727, 1653 cm$^{-1}$. $^1$H NMR (300 MHz, DMSO-d$_6$): $^1$H NMR (300 MHz, DMSO): δ 10.71 (s, 1H), 9.07 (s, 1H), 7.61-7.34 (m, 5H), 7.16-6.96 (m, 4H), 6.40 (d, J=15.8 Hz, 1H), 5.37 (s, 2H), 4.86 (d, J=16.6 Hz, 1H), 4.57 (d, J=16.5 Hz, 1H), 3.90 (d, J=13.1 Hz, 2H), 3.45 (d, J=11.3 Hz, 1H), 2.89 (s, 3H). ESI-MS m/z (%): 431 [MH$^+$] (100). Anal. calcd for $C_{24}H_{22}N_4O_4$×% $H_2O$: C, 65.15; H, 5.32; N, 12.66; found: C, 64.94; H, 5.24; N, 12.50.

(E)-N-Hydroxy-3-(3-((4-methyl-3,5-dioxo-3,4,5,6-tetrahydro-2,6-methano[1,3]diazocino[5,6-b]indol-11(1H)-yl)methyl)phenyl)acrylamide (51)

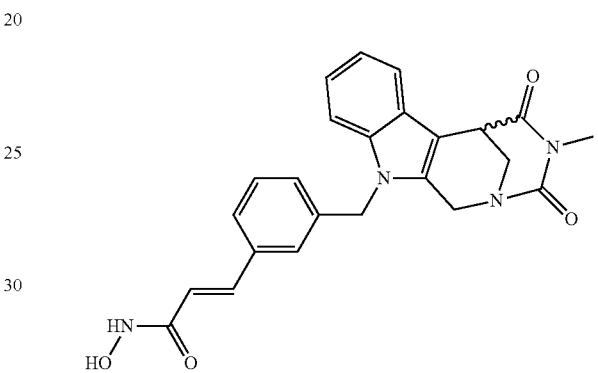

According to GP9 from (E)-3-(3-((4-methyl-3,5-dioxo-3,4,5,6-tetrahydro-2,6-methano[1,3]diazocino[5,6-b]indol-11(1H)-yl)methyl)phenyl)-N-((tetrahydro-2H-pyran-2-yl)oxy)acrylamide (49) (0.95 g; 1.84 mmol). 0.25 g (0.56 mmol; 52%) colorless crystals; mp 218.1-219.0° C. IR (KBr): 1727, 1684 cm$^{-1}$. $^1$H NMR (300 MHz, DMSO-d$_6$): $^1$H NMR (300 MHz, DMSO): δ 10.77 (s, 1H), 9.06 (s, 1H), 7.56-7.25 (m, 6H), 7.17-6.98 (m, 3H), 6.41 (d, J=15.8 Hz, 1H), 5.37 (s, 2H), 4.89 (d, J=16.6 Hz, 1H), 4.61 (d, J=16.5 Hz, 1H), 3.91 (d, J=13.5 Hz, 2H), 3.48 (d, J=11.2 Hz, 1H), 3.05 (dd, J=13.1, 6.0 Hz, 1H), 2.90 (s, 3H). ESI-MS m/z (%): 431 [MH$^+$] (100). Anal. calcd for $C_{24}H_{22}N_4O_4$×$H_2O$: C, 64.28; H, 5.39; N, 12.49; found: C, 64.60; H, 5.58; N, 12.37.

N-Methyl-2,3,4,9-tetrahydro-1H-pyrido[3,4-b]indole-4-carboxamide hydrochloride (52a)

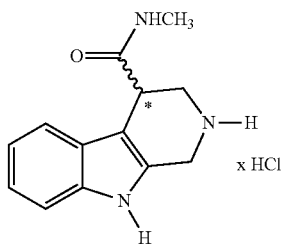 [SMILES: CNC(=O)C1CNCc2[nH]c3ccccc3c21]

Based on the procedure published by the Perez-Alvarez et al. (1997) 1.0 g (3.75 mmol) 13a were dissolved in 18 mL methylamine (40% in methanol). After three days of stirring at room temperature (TLC: SiO$_2$, ethyl acetate/methanol, 1:1) the solvent was removed in vacuo and the residue purified by CC. 0.77 g (2.90 mmol; 77%) colorless crystals after chromatography with methanol and ethyl acetate (1:1); mp 187° C. (decomp.). IR (KBr): 3293, 2931, 1726, 1643 cm$^{-1}$. $^1$H NMR (300 MHz, DMSO-d$_6$) δ 11.29 (s, 1H), 9.57 (s, 2H), 8.76 (q, J=4.5 Hz, 1H), 7.60 (d, J=7.8 Hz, 1H), 7.37 (d, J=8.0 Hz, 1H), 7.15-6.96 (m, 2H), 4.49-4.24 (m, 2H), 4.06-3.96 (m, 1H), 3.60-3.39 (m, 2H), 2.66 (d, J=4.4 Hz, 3H). ESI-MS m/z (%): 230 [MH]$^+$ (100). Anal. calcd for C$_{13}$H$_{16}$ClN$_3$O×0.33 CH$_3$OH: C, 57.94; H, 6.32; N, 15.21; found: C, 57.79; H, 6.56; N, 15.37.

6-Methoxy-N-methyl-2,3,4,9-tetrahydro-1H-pyrido [3,4-b]indole-4-carboxamide hydrochloride (52b)

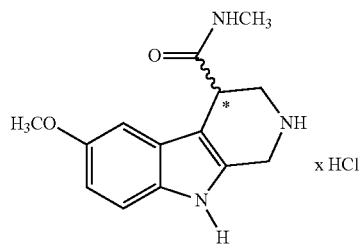 [SMILES: CNC(=O)C1CNCc2[nH]c3ccc(OC)cc3c21]

9.75 g (32.86 mmol) of 14a were dissolved in 140.0 mL of methylamine (40% in methanol). After three days of stirring at room temperature (TLC: SiO$_2$, ethyl acetate/methanol, 1:1). the solvent was removed in vacuo and the residue purified by CC. 7.65 g (25.87 mmol, 79%) colorless powder after CC (SiO$_2$, ethyl acetate/methanol, 1:1); mp 110-112° C. IR (KBr): 3254, 2937, 2812, 1648 cm$^{-1}$. $^1$H NMR (300 MHz, DMSO-d$_6$) δ 11.14 (s, 1H), 9.57 (s, 2H), 8.86 (q, J=4.5 Hz, 1H), 7.26 (d, J=8.8 Hz, 1H), 7.17 (d, J=2.4 Hz, 1H), 6.74 (dd, J=8.8, 2.4 Hz, 1H), 4.44-4.22 (m, 2H), 4.03-3.93 (m, 1H), 3.74 (s, 3H), 3.58-3.39 (m, 2H), 2.67 (d, J=4.4 Hz, 3H). ESI-MS m/z (%): 260 [MH]$^+$ (100).

4-Methyl-3,4,6,11-tetrahydro-2,6-methano[1,3]di-azocino[5,6-b]indole-5(1H)-one (53a)

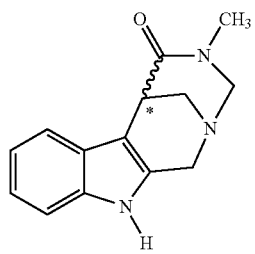 [SMILES: CN1CN2Cc3[nH]c4ccccc4c3C(C2)C1=O]

Based on the procedure published by Perez-Alvarez et al. (1997) 0.46 g (2.0 mmol) of 52b was dissolved in 20.0 mL of methanol. After addition of 0.6 mL formaldehyde (36% in water) the mixture was stirred at 70° C. for 2 h. The solvent was removed and the residue purified by CC. 0.43 g (1.78 mmol, 89%) yellow solid after CC (SiO$_2$, ethyl acetate/methanol 1:1); mp 165° C. (decomp.). IR (KBr): 3249, 2932, 1641 cm$^{-1}$. $^1$H NMR (300 MHz, DMSO-d$_6$) δ 10.92 (s, 1H), 7.45 (dd, J=7.1, 1.6 Hz, 1H), 7.30-7.23 (m, 1H), 7.04-6.91 (m, 2H), 4.58-4.40 (m, 2H), 4.24 (dd, J=12.0, 1.6 Hz, 1H), 4.06 (d, J=17.8 Hz, 1H), 3.55-3.37 (m, 2H), 3.11 (dt, J=12.9, 1.7 Hz, 1H), 2.57 (s, 3H). ESI-MS m/z (%): 242 [MH]$^+$ (98).

8-Methoxy-4-methyl-3,4,6,11-tetrahydro-2,6-methano[1,3]diazocino[5,6-b]indole-5(1H)-one (53b)

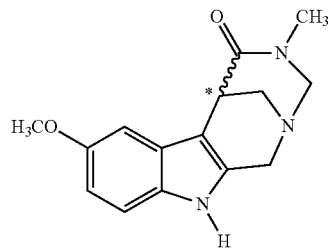 [SMILES: COc1ccc2[nH]c3c(c2c1)C1CN(C3)CN(C)C1=O]

2.07 g (8.0 mmol) of 52b were dissolved in 80 mL of methanol. After addition of 2.4 mL formaldehyde (36% in water) the mixture was stirred at 70° C. for 2 h. On evaporation of the solvent under vacuum a yellowish solid precipitates. It is filtered off, washed with methanol and dried. 1.60 g (5.90 mmol, 74%) yellow solid; mp 268.0-268.5° C. IR (KBr): 3188, 2935, 2871, 1622 cm$^{-1}$. $^1$H NMR (300 MHz, DMSO-d$_6$) δ 10.71 (s, 1H), 7.15 (d, J=8.7 Hz, 1H), 6.93 (d, J=2.4 Hz, 1H), 6.64 (dd, J=8.7, 2.5 Hz, 1H), 4.56-4.37 (m, 2H), 4.22 (dd, J=11.9, 1.6 Hz, 1H), 4.03 (d, J=17.8 Hz, 1H), 3.74 (s, 3H), 3.48 (dd, J=13.0, 2.1 Hz, 1H), 3.38 (d, J=1.9 Hz, 1H), 3.09 (dt, J=13.0, 1.6 Hz, 1H), 2.57 (s, 3H). ESI-MS m/z (%): 272 [MH]$^+$ (100). Anal. calcd for C$_{15}$H$_{17}$N$_3$O$_2$×0.25 CH$_3$OH: C, 65.57; H, 6.50; N, 15.04; found: C, 65.60; H, 6.31; N, 15.10.

Methyl 4-((4-methyl-5-oxo-3,4,5,6-tetrahydro-2,6-methano[1,3]diazocino[5,6-b]indol-11(1H)-yl) methyl)benzoate (55a)

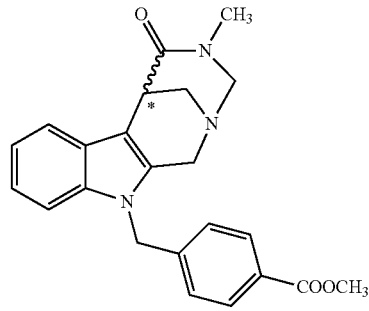 [SMILES: COC(=O)c1ccc(Cn2c3c(c4ccccc42)C2CN(C3)CN(C)C2=O)cc1]

3.34 g (13.83 mmol) of 53a were dissolved in DMF (100 mL) and cooled to 0° C. After addition of 0.66 g (16.31 mmol) of NaH (60% in paraffine) the mixture was stirred for 30 min at 0° C. 4.26 g (15.71 mmol) of methyl 4-(bromomethyl)benzoate (54) in 20.0 mL of DMF were added dropwise and the mixture stirred at room temperature for 3 h. The mixture was poured into 500 mL of water and extracted with ethyl acetate. The organic phase was dried, the solvent removed and the residue purified by CC. 2.96 g (7.60 mmol, 55%) colorless foam after CC (SiO$_2$, ethyl acetate/methanol 10:1); mp 66.8° C. (decomp.). IR (KBr): 3422, 2952, 1718, 1652 cm$^{-1}$. $^1$H NMR (300 MHz, DMSO-d$_6$) δ 7.94-7.83 (m, 2H), 7.58-7.47 (m, 1H), 7.40-7.29 (m, 1H), 7.22-7.12 (m, 2H), 7.09-6.97 (m, 2H), 5.52-5.26 (m, 2H), 4.53 (d, J=12.1 Hz, 1H), 4.35 (d, J=17.9 Hz, 1H), 4.23-4.07 (m, 2H), 3.82 (s, 3H), 3.57-3.44 (m, 2H), 3.11 (d, J=12.6 Hz, 1H), 2.58 (s, 3H). ESI-MS m/z (%): 390 [MH]$^+$ (100). Anal. calcd for C$_{23}$H$_{23}$N$_3$O$_3$×H$_2$O: C, 67.80; H, 6.18; N, 10.31; found: C, 67.43; H, 6.07; N, 9.92.

Methyl 4-((8-methoxy-4-methyl-5-oxo-3,4,5,6-tetra-hydro-2,6-methano[1,3]diazocino[5,6-b]indol-11(1H)-yl)methyl)benzoate (55b)

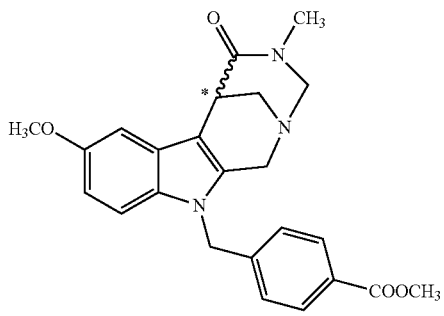 [SMILES: COC(=O)c1ccc(Cn2c3c(c4cc(OC)ccc42)C2CN(C3)CN(C)C2=O)cc1]

0.40 g (1.50 mmol) of 53b were dissolved under heating in 10 mL DMSO and then cooled to room temperature. After addition of 66.0 mg (1.65 mmol) of NaH (60% in paraffine) the mixture was stirred for 30 min at 0° C. 0.40 g (1.7 mmol) of methyl 4-(bromomethyl)benzoate (54) were added and the mixture stirred at room temperature for 3 h. The mixture was poured into 120 mL of water. A yellowish solid precipitates, which was filtered off, dried and purified by CC. 0.32 g (0.76 mmol, 51%) yellowish foam after CC (SiO$_2$, ethyl acetate/methanol 5:1); mp 82-858° C. IR (KBr): 3416, 2943, 1720, 1648 cm$^{-1}$. $^1$H NMR (300 MHz, DMSO-d$_6$) δ 7.93-7.83 (m, 2H), 7.23 (d, J=8.8 Hz, 1H), 7.18-7.08 (m, 2H), 7.00 (d, J=2.4 Hz, 1H), 6.68 (dd, J=8.9, 2.4 Hz, 1H), 5.48-5.21 (m, 2H), 4.52 (d, J=12.0 Hz, 1H), 4.32 (d, J=17.9 Hz, 1H), 4.21-4.05 (m, 2H), 3.81 (s, 3H), 3.75 (s, 3H), 3.55-3.42 (m, 2H), 3.10 (d, J=12.9 Hz, 1H), 2.58 (s, 3H). ESI-MS m/z (%): 420 [MH]$^+$ (100).

N-Hydroxy-4-((4-methyl-5-oxo-3,4,5,6-tetrahydro-2,6-methano-[5,6-b]indol-11(1H)-yl)methyl)benzamide (56a)

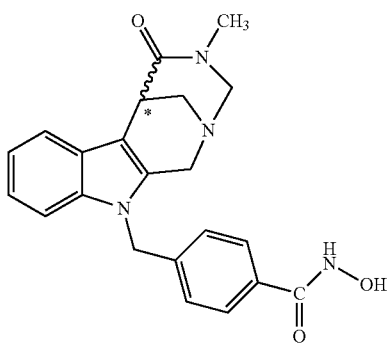 [SMILES: CN1CN2Cc3c(c4ccccc4n3Cc3ccc(C(=O)NO)cc3)C(C2)C1=O]

Based on Saiga et al. (1987) 2.15 g (31.00 mmol) of hydroxylamine hydrochloride were dissolved in 11.0 mL of methanol under heating. A solution of 2.58 g (46.00 mmol) KOH in 7 mL of methanol was added and the mixture was stirred for 30 min at room temperature. The precipitate was filtered off and 1.58 g (4:05 mmol) of 55a were dissolved in the filtrate. After two days of stirring at room temperature the solution was adjusted to pH 6-7 with acetic acid and the solvent removed in vacuo. The residue is purified by CC on a short column (SiO$_2$, ethyl acetate/methanol 2:1). When distilling off the solvent precipitation of a colorless solid occurred. It was filtered off, washed with methanol and dried. 1.18 g (3.02 mmol; 75%) colorless crystals; mp 190° C. (decomp.). IR (KBr): 3188, 2921, 1626 cm$^{-1}$. $^1$H NMR (300 MHz, DMSO-d$_6$) δ 11.15 (s, 1H), 9.02 (s, 1H), 7.71-7.61 (m, 2H), 7.57-7.48 (m, 1H), 7.38-7.30 (m, 1H), 7.14-6.97 (m, 4H), 5.49-5.18 (m, 2H), 4.53 (d, J=12.0 Hz, 1H), 4.38 (d, J=17.9 Hz, 1H), 4.23-4.12 (m, 2H), 3.59-3.43 (m, 2H), 3.12 (d, J=12.7 Hz, 1H), 2.58 (s, 3H). ESI-MS m/z (%): 391 [MH]$^+$ (100). Anal. calcd for C$_{22}$H$_{22}$N$_4$O$_3$×1.25 CH$_3$OH: C, 64.87; H, 6.32; N, 13.01; found: C, 64.67; H, 6.15; N, 13.15.

N-Hydroxy-4-((8-methoxy-4-methyl-5-oxo-3,4,5,6-tetrahydro-2,6-methano[1,3]diazocino[5,6-b]indol-11(1H)-yl)methyl)benzamide (56b)

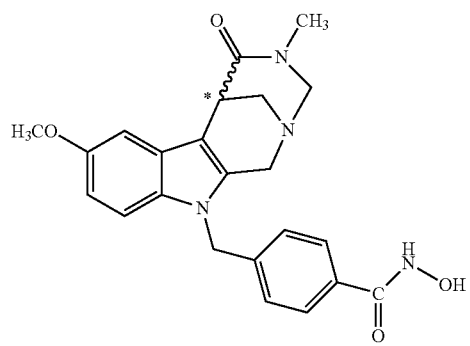 [SMILES: COc1ccc2c(c1)c1c(n2Cc2ccc(C(=O)NO)cc2)CN2CC1C(=O)N(C)C2]

1.82 g (26.4 mmol) of hydroxylamine hydrochloride were dissolved in 10 mL of methanol under heating. A solution of 2.19 (39.0 mmol) KOH in 6 mL of methanol was added and the mixture was stirred for 30 min. at room temperature. The precipitate was filtered off and 1.44 g (3:43 mmol) of 55b were dissolved in the filtrate. After 2 days of stirring at room temperature the solution was adjusted to pH 6-7 with acetic acid and the solvent removed in vacuo. When distilling off the solvent precipitation of a colorless solid occurred. It was filtered off, washed with methanol and dried. Purification by recrystallization from methanol. 0.85 g (2.17 mmol; 63%) colorless crystals; mp 162° C. (decomp.). IR (KBr): 3202, 2940, 1631 cm$^{-1}$. $^1$H NMR (300 MHz, DMSO-d$_6$) δ 11.16 (s, 1H), 9.03 (s, 1H), 7.65 (d, J=8.0 Hz, 2H), 7.23 (d, J=8.8 Hz, 1H), 7.06 (d, J=8.0 Hz, 2H), 7.00 (d, J=2.4 Hz, 1H), 6.67 (dd, J=8.7, 2.4 Hz, 1H), 5.42-5.14 (m, 2H), 4.52 (d, J=12.0 Hz, 1H), 4.35 (d, J=17.9 Hz, 1H), 4.18 (s, 1H), 4.13-4.05 (m, 1H), 3.75 (s, 3-1), 3.58-3.40 (m, 2H), 3.10 (d, J=12.9 Hz, 1H), 2.59 (s, 3H). ESI-MS m/z (%): 421 [MH]$^+$ (100). Anal. calcd for C$_{23}$H$_{24}$N$_4$O$_4$×1.5 CH$_3$OH: C, 62.81; H, 6.45; N, 11.96; found: C, 62.58; H, 6.20; N, 11.83.

N-Methyl-1-(2,3,4,9-tetrahydro-1H-pyrido[3,4-b]indol-4-yl)methanamine (57)

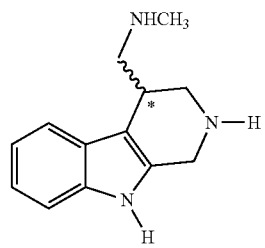 [SMILES: CNCC1CNCc2[nH]c3ccccc3c21]

Based on Van et al. (1981) 5.0 g (21.81 mmol) of 52 were dissolved in 200 mL of THF and cooled to 0° C. 2.5 g (65.88 mmol) of LiAlH$_4$ were added in portions at room temperature followed by 3 h stirring at room temperature and heating to reflux for 16 h. After cooling to 0° C. 50 mL of sat. Na₂SO₄ solution were added dropwise and stirring at room temperature continued for 2 h. The salts are filtered off and washed three times with 100 mL ethyl acetate. The aqueous phase is separated and extracted with ethyl acetate (3×50.0 mL). After drying and removal of the solvent the residue was purified by CC. (3.16 g; 14.70 mmol; 67%) beige foam after CC (SiO₂, 7N NH₃ in Methanol/Methanol; 1:10); mp 157-159° C. IR (KBr): 3390, 3315, 3045, 2931, 2857 cm⁻¹. ¹H NMR (300 MHz, DMSO-d₆) δ 10.67 (s, 1H), 7.48-7.41 (m, 1H), 7.25 (dd, J=7.4, 1.2 Hz, 1H), 7.02-6.86 (m, 2H), 3.80 (s, 2H), 3.13-3.02 (m, 1H), 2.91-2.78 (m, 3H), 2.69 (dd, J=11.4, 8.3 Hz, 1H), 2.33 (s, 3H). ESI-MS m/z (%): 216 [MH]⁺ (53), 156 (100). Anal. calcd for C₁₃H₁₇N₃×0.25H₂O: C, 71.04; H, 8.03; N, 19.12; found: C, 70.95; H, 8.01; N, 19.05.

4-Methyl-4,5,6,11-tetrahydro-2,6-methano[1,3]di-azocino[5,6-b]indole-3(1H)-one (58)

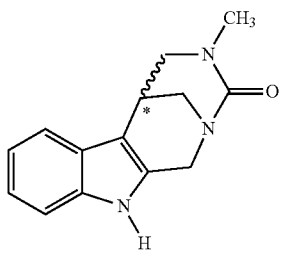 [SMILES: CN1CC2CN(Cc3[nH]c4ccccc4c32)C1=O]

Based on Lanning et al. (2013) 1.40 g (8.4 mmol) of CDI were added in portions to a solution 1.51 g (7.0 mmol) of 57 in 35 mL of THF. The mixture was stirred at room temperature for 3 h and at reflux for 18 h. The solvent was removed on a rotary evaporator and the residue purified by CC. 1.05 g (4.35 mmol; 62%) colorless crystals after CC (SiO₂, ethyl acetate); mp 223-225° C. IR (KBr): 2909, 1639 cm⁻¹. ¹H NMR (300 MHz, DMSO-d₆) δ 10.87 (s, 1H), 7.52-7.43 (m, 1H), 7.33-7.25 (m, 1H), 7.10-6.92 (m, 2H), 4.50 (d, J=16.3 Hz, 1H), 4.31-4.13 (m, 1H), 3.69 (dd, J=10.9, 5.6 Hz, 1H), 3.43-3.26 (m, 3H), 3.20-3.01 (m, 1H), 2.69 (s, 3H). ESI-MS m/z (%): 242 [MH]⁺ (100). Anal. calcd for C₁₄H₁₅N₃O: C, 69.69; H, 6.27; N, 17.41; found: C, 69.22; H, 6.19; N, 17.55.

tert-Butyl 4-((4-methyl-3-oxo-3,4,5,6-tetrahydro-2,6-methano[1,3]diazocino-[5,6-b]indol-11(1H)-yl)methyl)benzoate (59)

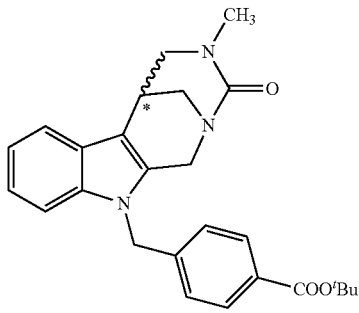

0.50 g (2:07 mmol) of 58 were dissolved in 40 mL of THF and the mixture cooled to 0° C. After adding 92.0 mg of sodium hydride (2.30 mmol, 60% in paraffine) the mixture was stirred for 30 min at 0° C. A solution of 0.62 g (2.30 mmol) tert-butyl 4-(bromomethyl) benzoate (23) in 5.0 mL of DMF was added dropwise and the mixture stirred at room temperature for 2 h. The mixture is poured into 100 mL of water and extracted with ethyl acetate. After drying over Na₂SO₄ the solvent is removed and the residue purified by CC.

0.58 g (1.34 mmol; 65%) beige powder after CC (SiO₂, ethyl acetate/Methanol 10:1); ¹H NMR (300 MHz, DMSO-d₆) δ 7.85-7.76 (m, 2H), 7.59-7.51 (m, 1H), 7.41-7.33 (m, 1H), 7.20-7.12 (m, 2H), 7.11-6.97 (m, 2H), 5.48-5.27 (m, 2H), 4.65 (d, J=16.5 Hz, 1H), 4.11 (d, J=16.4 Hz, 1H), 3.72 (dd, J=10.9, 5.8 Hz, 1H), 3.41 (d, J=12.4 Hz, 2H), 3.33-3.24 (m, 1H), 3.15 (d, J=10.9 Hz, 1H), 2.70 (s, 3H), 1.51 (s, 9H).

4-((4-Methyl-3-oxo-3,4,5,6-tetrahydro-2,6-methano[1,3]diazocino[5,6-b]indol-11(1H)-yl)methyl)benzoic acid (60)

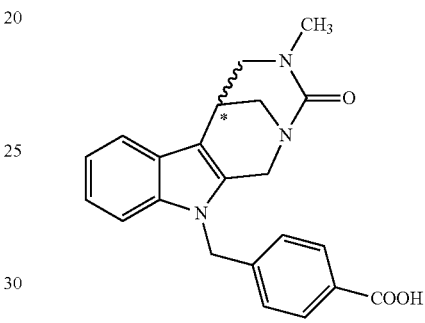

A solution of 59 (0.33 g; 0.76 mmol) in 5.0 mL of CH₂Cl₂ and 3.0 mL of CF₃COOH was stirred at room temperature for 3.5 h. The mixture was poured into 50 mL ice-water and extracted with 30 mL CH₂Cl₂. The organic phase was dried and the solvent removed. The residue was digested with a small amount of dichloromethane and diethyl ether, the solid filtered off and dried. 0.25 g (0.67 mmol, 88%) light beige powder; mp 160.5° C. (decomp.). IR (KBr): 3432, 2909, 1702 cm⁻¹. ¹H NMR (300 MHz, DMSO-d₆) δ 7.96-7.75 (m, 2H), 7.55 (dd, J=7.1, 1.8 Hz, 1H), 7.45-7.32 (m, 1H), 7.22-6.98 (m, 4H), 5.49-5.27 (m, 2H), 4.65 (d, J=16.5 Hz, 1H), 4.11 (d, J=16.4 Hz, 1H), 3.72 (dd, J=11.0, 5.8 Hz, 1H), 3.48-3.23 (m, 3H), 3.15 (d, J=10.9 Hz, 1H), 2.70 (s, 3H). ESI-MS m/z (%): 376 [MH]⁺ (100). Anal. calcd for C₂₂H₂₁N₃O₃×0.66 CH₂Cl₂: C, 63.08; H, 5.21; N, 9.74; found: C, 62.97; H, 5.45; N, 9.44.

4-((4-Methyl-3-oxo-3,4,5,6-tetrahydro-2,6-methano[1,3]diazocino[5,6-b]indol-11(1H)-yl)methyl)-N-((tetrahydro-2H-pyran-2-yl)oxy)benzamide (61)

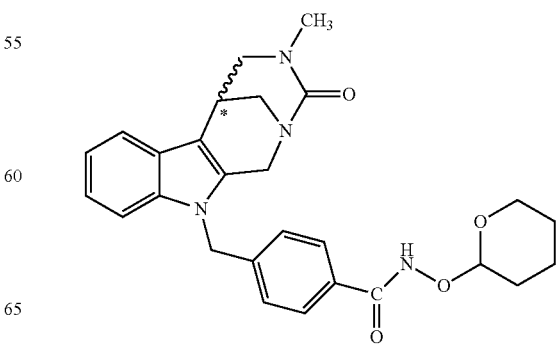

0.25 g (0.67 mmol) of 60 were dissolved in 10 mL of THF. After addition of benzotriazol-1-yloxy-tris (dimethylamino) phosphonium hexafluorophosphate (BOP) (0.33 g, 0.74 mmol), O-(tetrahydro-2H-pyran-2-yl) hydroxylamine (0.17 g, 1.40 mmol) and 0.25 mL of triethylamine the mixture was stirred at room temperature for 16 h. The mixture was poured into 50 mL water and extracted with ethyl acetate. After drying of the organic phase the solvent was removed and the residue purified by CC. 0.20 g (0.42 mmol, 63%) colorless foam after CC (SiO$_2$, ethyl acetate/methanol 10:1); mp 193-196° C. IR (KBr): 3435, 2943, 1619 cm$^{-1}$. $^1$H NMR (300 MHz, DMSO-d$_6$) δ 11.59 (s, 1H), 7.76-7.60 (m, 2H), 7.55 (dd, J=6.9, 1.9 Hz, 1H), 7.45-7.31 (m, 1H), 7.23-6.94 (m, 4H), 5.49-5.20 (m, 2H), 4.95 (d, J=2.8 Hz, 1H), 4.68 (d, J=16.6 Hz, 1H), 4.22-3.94 (m, 2H), 3.72 (dd, J=11.0, 5.8 Hz, 1H), 3.56-3.23 (m, 4H), 3.15 (d, J=10.8 Hz, 1H), 2.71 (s, 3H), 1.69 (d, J=3.7 Hz, 3H), 1.52 (d, J=7.0 Hz, 3H). ESI-MS m/z (%): 475 [MH]$^+$ (100), 391 (79). Anal. calcd for C$_{27}$H$_{30}$N$_4$O$_4$×0.66 CH$_3$OH: C, 67.02; H, 6.64; N, 11.30; found: C, 66.93; H, 6.75; N, 11.49.

N-Hydroxy-4-((4-methyl-3-oxo-3,4,5,6-tetrahydro-2, 6-methano[1,3]diazocino-[5,6-b]indol-11(1H)-yl) methyl)benzamide (62)

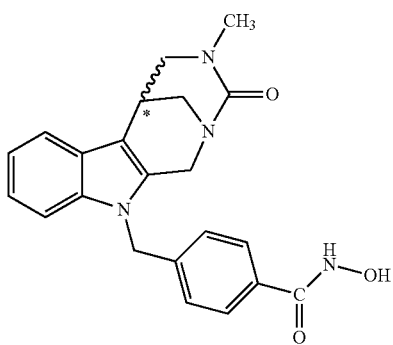 [SMILES: CN1CC2CN(Cc3c2c2ccccc2n3Cc2ccc(C(=O)NO)cc2)C1=O]

0.20 g (0.42 mmol) of 61 were dissolved in 20 mL of methanol, treated with 5 drops of 5N HCl in isopropanol and stirred at room temperature for 16 h. The solvent was removed completely on the rotary evaporator and the residue recrystallized from methanol. 0.12 g; 0.31 mmol, 74%) colorless powder; mp 245° C. IR (KBr): 3454, 2838, 1623 cm$^{-1}$. $^1$H NMR (300 MHz, DMSO-d$_6$) δ 11.14 (s, 1H), 9.02 (s, 1H), 7.70-7.60 (m, 2H), 7.55 (dd, J=7.1, 1.9 Hz, 1H), 7.42-7.34 (m, 1H), 7.17-6.98 (m, 4H), 5.47-5.21 (m, 2H), 4.68 (d, J=16.5 Hz, 1H), 4.20-4.06 (m, 1H), 3.72 (dd, J=10.9, 5.7 Hz, 1H), 3.45-3.13 (m, 4H), 2.71 (s, 3H). ESI-MS m/z (%): 391 [MH]$^+$ (100). Anal. calcd for C$_{22}$H$_{22}$N$_4$O$_3$×0.5 CH$_3$OH: C, 66.49; H, 5.95; N, 13.78; found: C, 66.51; H, 5.85; N, 13.74.

3-(1H-Indol-3-yl)pyrrolidine-2,5-dione (64)

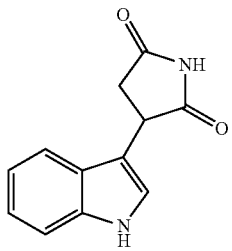 [SMILES: O=C1CC(c2c[nH]c3ccccc23)C(=O)N1]

Modified from references Andrianjara et al. (2002), Da Silva et al. (2009) and Hamilton et al. (1995), indole (6a) (10.0 mmol) and maleimide (63) (30.0 mmol) were dissolved in acetic acid (50.0 mL) under nitrogen atmosphere and refluxed for 48 h (TLC monitoring). The reaction mixture was concentrated on a rotary evaporator and dissolved again in ethyl acetate (50.0 mL) and sat. NaHCO$_3$ solution (50.0 mL). The mixture was extracted with ethyl acetate (2×50.0 mL). The organic phases were combined, dried over sodium sulfate and concentrated on a rotary evaporator. The oily residue was purified by column chromatography on silica gel (mobile phase: dichloromethane/ ethyl acetate 2:1). 1.92 g (8.97 mmol, 89%) yellow crystals; $^1$H NMR (300 MHz, DMSO-d$_6$): δ 11.28 (s, 1H), 11.03 (s, 1H), 7.42 (d, J=7.9 Hz, 1H), 7.37 (d, J=8.1 Hz, 1H), 7.33 (d, J=2.4 Hz, 1H), 7.10 (m, 1H), 7.00 (m, 1H), 4.33 (dd, J=9.5, 5.3 Hz, 1H), 3.18 (dd, J=18.0, 9.5 Hz, 1H), 2.75 (m, 1H).

3-(Pyrrolidin-3-yl)-1H-indole (65)

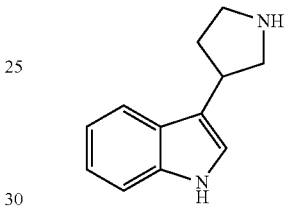

Following references Andrianjara et al. (2002), Da Silva et al. (2009), Li et al., 2008 and Makki et al. (2008), 64 (9.0 mmol) was dissolved with stirring in a solution of LiAlH$_4$ (45.0 mmol, 5 eq.) in anhydrous THF (50 mL, 0° C.). The solution was stirred at 65° C. for 16 h (TLC monitoring), cooled to room temperature and quenched with Na$_2$SO$_4$×10 H$_2$O (15 g). Water (1.0 mL) and ethyl acetate (150 mL) were added and stirring continued overnight. The suspension was filtered over Celite, the solvent evaporated and the residue chromatographed on silica gel (eluent DCM/MeOH/ammonia 3:1:0.1). 1.10 g (5.91 mmol, 65%) red-brown foam; $^1$H NMR (300 MHz, DMSO-d$_6$): δ 10.93 (s, 11H), 7.56 (d, J=7.8 Hz, 1H), 7.36 (d, J=8.0 Hz, 1H), 7.16 (s, 1H), 7.07 (m, 1H), 6.97 (m, 1H), 3.91 (bs, 1H), 3.45-3.23 (m, 2H), 3.13-2.89 (m, 2H), 2.87-2.73 (m, 1H), 2.33-2.07 (m, 1H), 1.95-1.73 (m, 1H). EI-MS (70 eV) m/z (%): 186 [M$^+$] (100), 144 (92).

3,4,5,10-Tetrahydro-1H-2,5-methanoazepino[3,4-b] indole (66)

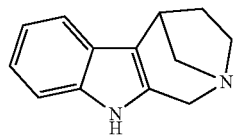

The Pictet-Spengler reaction was carried out in analogy to Göttlicher et al. (2001). Compound 65 (3.22 mmol) was dissolved in ethanol (50.0 mL). 1 eq. TFA and 3 eq. of formaldehyde (36% in water) were added and the mixture was heated to reflux for 3 h. 2 eq. methoxyamine hydrochloride and 6.0 mL H$_2$O were added and heating to reflux continued for 2 h. The reaction mixture was concentrated on a rotary evaporator and extracted with ethyl acetate (3×50.0 mL). The organic phase was washed with sat. NaHCO$_3$ solution and dried over sodium sulfate. Crystallization overnight in a refrigerator afforded colorless-red crystals 0.41 g (2.10 mmol, 65%) after crystallization from ethyl acetate; $^1$H NMR (300 MHz, DMSO-d$_6$): δ 10.61 (s, 1H), 7.47-7.38 (m, 1H), 7.28-7.19 (m, 1H), 7.01-6.87 (m, 2H), 4.31 (d, J=16.9 Hz, 1H), 3.64 (d, J=16.9 Hz, 1H), 3.30-3.22 (m, 1H), 3.20-3.05 (m, 1H), 2.90 (d, J=10.6 Hz, 1H), 2.83-2.65 (m, 2H), 1.98-1.80 (m, 2H). ESI-MS m/z (%): 239 [MH$^+$+MeCN] (100), 198 [MH$^+$] (40).

tert-Butyl-4-((4,5-dihydro-1H-2,5-methanoazepino[3,4-b]indol-10(3H)-yl)methyl)benzoate (67)

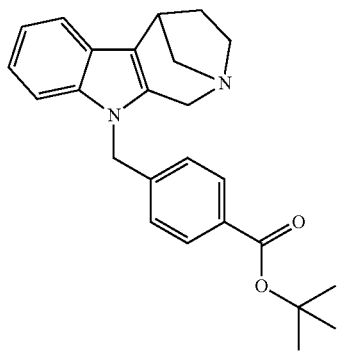 [SMILES: CC(C)(C)OC(=O)c1ccc(Cn2c3c(c4ccccc42)C2CCN(C3)C2)cc1]

According to GP6, modification a, from 66. 0.30 g (0.80 mmol, 38%) brown crystals after chromatography on SiO$_2$ with ethyl acetate and methanol (2:1); mp 149-154° C. IR (KBr): 1713, 1684, 1652 cm$^{-1}$. $^1$H NMR (300 MHz, DMSO-d$_6$): δ 7.82 (d, J=8.3 Hz, 2H), 7.54-7.47 (m, 1H), 7.33-7.26 (m, 1H), 7.09 (d, J=8.3 Hz, 2H), 7.04-6.94 (m, 2H), 5.37-5.22 (m, 2H), 4.20 (d, J=17.0 Hz, 1H), 3.67 (d, J=17.0 Hz, 1H), 2.89 (d, J=10.7 Hz, 1H), 2.75-2.66 (m, 2H), 1.98-1.90 (m, 2H), 1.51 (s, 9H). ESI-MS m/z (%): 389 [MH$^+$] (100). Anal. calcd for C$_{25}$H$_{28}$N$_2$O$_2$×¼ ethyl acetate): C, 76.07; H, 7.37; N, 6.82; found: C, 76.18; H, 7.10; N, 7.06.

4-((4,5-Dihydro-1H-2,5-methanoazepino[3,4-b]indol-10(3H)-yl)methyl)benzoic acid 2,2,2-trifluoroacetate (68)

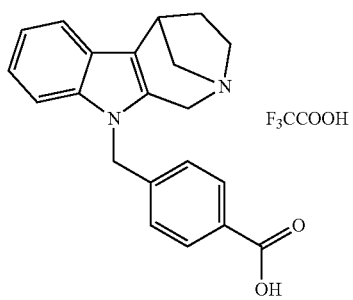

According to GP7 from 67. Yield 0.25 g (0.64 mmol; 97%) red crystals; mp 145.3-150.1° C. (decomp.). IR (KBr): 1699, 1612 cm$^{-1}$. $^1$H NMR (300 MHz, DMSO-d$_6$): δ 10.90 (s, 1H), 7.88 (d, J=8.2 Hz, 2H), 7.67-7.61 (m, 1H), 7.44-7.37 (m, 1H), 7.22-7.06 (m, 4H), 5.50 (d, J=17.2 Hz, 1H), 5.34 (d, J=17.2 Hz, 1H), 4.79 (d, J=15.1 Hz, 1H), 4.55 (d, J=15.5 Hz, 1H), 3.90-3.70 (m, 2H), 3.63 (d, J=10.1 Hz, 1H), 3.58-3.45 (m, 1H), 3.43-3.26 (m, 1H), 2.44-2.26 (m, 1H), 2.26-2.11 (m, 1H). ESI-MS m/z (%): 374 [MH$^+$+MeCN] (100), 332 [MH$^+$] (51). Anal. calcd for C$_{23}$H$_{21}$F$_3$N$_2$O$_4$×½H$_2$O: C, 60.66; H, 4.87; N, 6.15; found: C, 60.48; H, 4.92; N, 6.18.

4-((4,5-Dihydro-1H-2,5-methanoazepino[3,4-b]indol-10(3H)-yl)methyl)-N-((tetrahydro-2H-pyran-2-yl)oxy)benzamide (69)

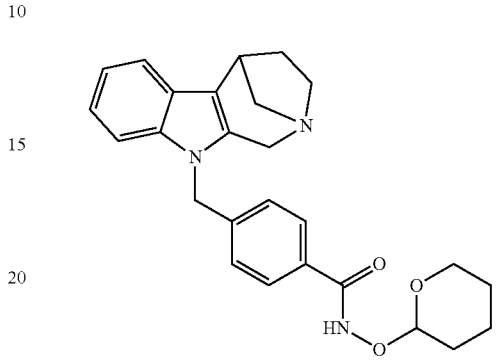

According to GP8 from 68. The product was purified by chromatography and reacted directly. 0.11 g (0.25 mmol, 20%) colorless solid after chromatography with dichloromethane, methanol and ammonia (10.0:1.0:0.05). ESI-MS m/z (%): 473 [MH$^+$+MeCN] (57), 432 [MH$^+$] (100).

4-((4,5-Dihydro-1H-2,5-methanoazepino[3,4-b]indol-10(3H)-yl)methyl)-N-hydroxybenzamide 2,2,2-trifluoroacetate (70)

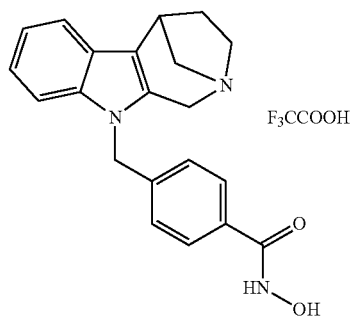

According to GP9 from 69. 0.02 g (0.05 mmol, 20%) colorless-orange crystals after preparative HPLC with 0.10% TFA/acetonitrile (80:20) gradient to ≤0.10% TFA/acetonitrile (20:80); $^1$H NMR (600 MHz, MeOD): δ 7.68 (d, J=8.3 Hz, 2H), 7.63 (d, J=7.8 Hz, 1H), 7.35 (d, J=8.2 Hz, 1H), 7.20-7.16 (m, 1H), 7.16-7.12 (m, 1H), 7.09 (d, J=8.3 Hz, 2H), 5.39 (m, 2H), 4.81 (d, J=15.5 Hz, 2H), 4.49 (d, J=15.3 Hz, 1H), 3.96-3.86 (m, 2H), 3.69-3.58 (m, 2H), 3.45-3.36 (m, 1H), 2.53-2.45 (m, 1H), 2.34 (dd, J=11.3, 9.0 Hz, 1H). 13C NMR (151 MHz, MeOD): δ 167.89 (s), 142.63 (s), 139.00 (s), 128.79 (s, 2C), 127.64 (s, 3C), 125.65 (s), 125.20 (s), 123.81 (s), 121.46 (s), 119.08 (s), 115.92 (s), 111.03 (s), 59.17 (s), 55.48 (s), 55.08 (s), 49.57 (s), 36.43 (s), 32.90 (s). ESI-MS m/z (%): 348 [MH$^+$] (100). RP-HPLC (220 nm): 97.9% (gradient: 0-30 min: MeCN/0.1% aq. TFA 20/80-95/5, 31-40 min: 95/5, tR=11.7 min).

Methyl 5-((2-(1H-indol-3-yl)ethyl)amino)-5-oxopentanoate (74)

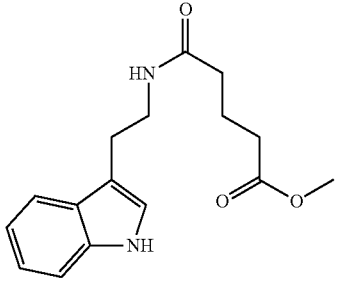 [SMILES: COC(=O)CCCC(=O)NCCc1c[nH]c2ccccc12]

According to Nguyen et al. (2011), and Yu et al. (2003), tryptamine (71) (31.3 mmol) was dissolved in THF (100.0 mL), glutaric anhydride (72) (31.3 mmol in 10.0 mL THF) was added and the mixture was stirred for 20 minutes at RT. The solvent was evaporated and the residue dissolved in methanol (40.0 mL). 1.2 equivalents of thionyl chloride (37.5 mmol) were added dropwise and stirring at RT was continued for 3 h. The solvent was removed and the product purified by CC (eluent ethyl acetate/methanol 20:1). 8.1 g (28 mmol, 89% over 2 steps) colorless crystals; mp 109-114° C.; lit. 101-102° C.; $^1$H NMR (300 MHz, MeOD): δ 7.58-7.52 (m, 1H), 7.34-7.28 (m, 1H), 7.11-7.03 (m, 2H), 7.03-6.95 (m, 1H), 3.64 (s, 3H), 3.47 (t, J=7.3 Hz, 2H), 2.93 (t, J=7.2 Hz, 2H), 2.28 (t, J=7.4 Hz, 2H), 2.17 (t, 2H), 1.92-1.77 (m, 2H). (Da Silva et al., 2009)

Methyl 4-(4,9-dihydro-3H-pyrido[3,4-b]indol-1-yl)butanoate (75)

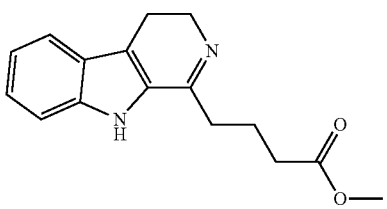 [SMILES: COC(=O)CCCC1=NCCc2c1[nH]c1ccccc21]

To a solution of 74 (22.5 mmol) in toluene (160.0 mL) and acetonitrile (70.0 mL) 3 eq. phosphorus oxychloride (66.0 mmol) were added and the mixture was heated to reflux for 5 h. The solvent was removed and the gummy residue dissolved in dichloromethane (400.0 mL), The Solution was washed with 1 M NaHCO$_3$ solution (300.0 mL) and dried over sodium sulfate (Nguyen et al., 2011). 4.80 g (17.0 mmol; 80%) red crystals; mp 235-242° C.; $^1$H NMR (300 MHz, CDCl$_3$): δ 9.79 (s, 1H), 7.59 (d, J=8.0 Hz, 1H), 7.46 (d, J=8.2 Hz, 1H), 7.31-7.26 (m, 1H), 7.17-7.13 (m, 1H), 3.88 (br t, J=8.5 Hz, 2H), 3.76 (s, 3H), 2.92-2.84 (m, 2H), 2.68 (m, 2H), 2.51 (m, 2H), 2.09-1.96 (m, 2H). (Da Silva et al., 2009)

1,2,3,6,7,12b-Hexahydroindolo[2,3-a]quinolizin-4(12H)-one (77)

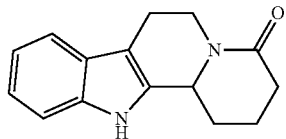 [SMILES: O=C1CCCC2c3[nH]c4ccccc4c3CCN12]

The reduction of the imine and the ring closure to the lactam is performed as a modification of a procedure from references Nguyen et al. (2011), and Nimmanapalli et al. (2003). 75 (20.0 mmol) was dissolved in methanol p. a. (100.0 mL) and 1 eq. sodium borohydride (20.0 mmol) was added. The mixture was stirred for 1 h at room temperature. The mixture was acidified with 10% HCl, stirred for 1 h and extracted with dichloromethane (3 200.0 mL). The combined organic phases were dried over sodium sulfate and chromatographed on silica gel (eluent ethyl acetate/methanol 2:1). 2.82 g (11.70 mmol, 58%) yellow crystals after chromatography on silica gel followed by crystallization from CH$_2$Cl$_2$; $^1$H NMR (300 MHz, DMSO-d$_6$): 10.93 (s, 1H), 7.40 (d, J=7.7 Hz, 1H), 7.32 (d, J=8.0 Hz, 1H), 7.11-7.02 (m, 1H), 7.01-6.93 (m, 1H), 5.01-4.85 (m, 1H), 4.85-4.61 (m, 1H), 2.86-2.52 (m, 4H), 2.44-2.17 (m, 2H), 1.86-1.53 (m, 3H). $^1$H NMR (300 MHz, CDCl$_3$): δ 7.85 (s, 1H), 7.51 (d, J=7.6 Hz, 1H), 7.38-7.31 (m, 1H), 7.23-7.16 (m, 1H), 7.16-7.08 (m, 1H), 5.24-5.11 (m, 1H), 4.83-4.74 (m, 1H), 2.94-2.73 (m, 3H), 2.65-2.33 (m, 3H), 2.05-1.70 (m, 3H). ESI-MS m/z (%): 241 [MH$^+$] (100), 481 [2MH$^+$] (18) (Da Silva et al., 2009)

tert-Butyl 4-((4-oxo-1,3,4,6,7,12b-hexahydroindolo[2,3-a]quinolizin-12(2H)-yl)methyl)benzoate (78)

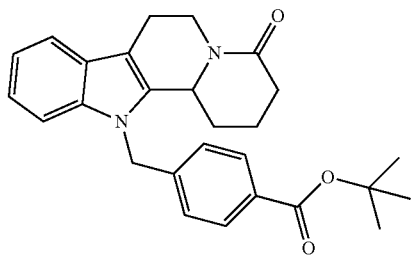 [SMILES: CC(C)(C)OC(=O)c1ccc(Cn2c3c(c4ccccc42)CCN2C(=O)CCCC32)cc1]

According to GP6, modification a, from 77 und 29. 1.2 g (2.79 mmol, 67%) colorless-yellow crystals after chromatography with ethyl acetate and dichloromethane (6:1) and subsequent crystallization by dropwise addition of diethyl ether solution to light petroleum; mp 145.5-148.4° C. IR (KBr): 1711, 1634 cm$^{-1}$. $^1$H NMR (300 MHz, DMSO-d$_6$): δ 7.83 (d, J=8.3 Hz, 2H), 7.54-7.47 (m, 1H), 7.19-7.13 (m, 1H), 7.12-7.01 (m, 4H), 5.63 (d, J=18.0 Hz, 1H), 5.46 (d, J=18.3 Hz, 1H), 5.01-4.81 (m, 2H), 2.81-2.56 (m, 3H), 2.37-2.17 (m, 3H), 1.78-1.59 (m, 2H), 1.49 (s, 9H). ESI-MS m/z (%): 472 [MH$_4^+$+MeCN] (100), 431 [MH$^+$] (31). Anal. calcd for C$_{27}$H$_{30}$N$_2$O$_3$×⅓H$_2$O: C, 74.29; H, 7.08; N, 6.42; found: C, 74.24; H, 6.83; N, 6.52.

147

(E)-tert-Butyl 3-(4-((4-oxo-1,3,4,6,7,12b-hexahydroindolo[2,3-a]quinolizin-12(2H)-yl)methyl)phenyl)acrylate (79)

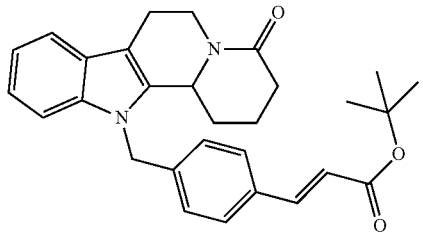 [SMILES: CC(C)(C)OC(=O)/C=C/c1ccc(Cn2c3c(c4ccccc42)CCN2C(=O)CCCC32)cc1]

According to GP6, modification a, from 77 und 42. 0.71 g (1.55 mmol; 75%) colorless green crystals after chromatography (eluent $CH_2Cl_2$/ethyl acetate 1:2); mp 157.7-158.8° C. IR (KBr): 1699, 1662 $cm^{-1}$, 1635 $cm^{-1}$. $^1$H NMR (300 MHz, DMSO-$d_6$): δ 7.62 (d, J=8.2 Hz, 2H), 7.53-7.45 (m, 2H), 7.22-7.15 (m, 1H), 7.11-7.01 (m, 2H), 6.99 (d, J=8.2 Hz, 2H), 6.46 (d, J=16.0 Hz, 1H), 5.49 (m, 2H), 5.01-4.80 (m, 2H), 2.81-2.55 (m, 3H), 2.40-2.18 (m, 3H), 1.81-1.61 (m, 2H), 1.46 (s, 9H), 1.39 (m, 1H). ESI-MS m/z (%): 457 [MH$^+$] (100), 401 [M–$C_4H_8$] (26). Anal. ($C_{29}H_{32}N_2O_3\times\frac{1}{6}$ ethyl acetate): C, 75.61; H, 7.13; N, 5.94; found: C, 75.75; H, 7.08; N, 5.90.

4-((4-Oxo-1,3,4,6,7,12b-hexahydroindolo[2,3-a]quinolizin-12(2H)-yl)methyl)benzoic acid (80)

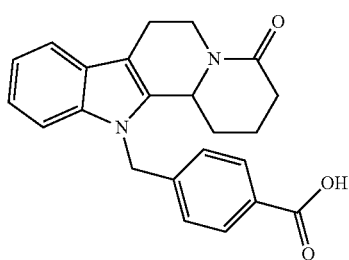 [SMILES: O=C(O)c1ccc(Cn2c3c(c4ccccc42)CCN2C(=O)CCCC32)cc1]

According to GP7 from 78. The compound was reacted directly without further purification. 0.73 g (1.95 mmol, 90%) red rubber.

(E)-3-(4-((4-Oxo-1,3,4,6,7,12b-hexahydroindolo[2,3-a]quinolizin-12(2H)-yl)methyl)phenyl)acrylic acid (81)

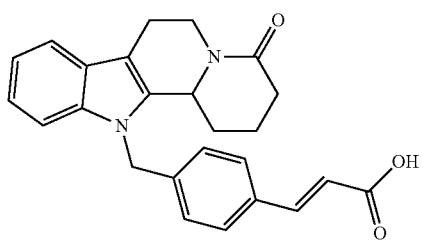 [SMILES: O=C(O)/C=C/c1ccc(Cn2c3c(c4ccccc42)CCN2C(=O)CCCC32)cc1]

According to GP7 from 79. The compound was reacted directly without further purification. 0.40 g (1.0 mmol, 95%) red rubber.

148

4-((4-Oxo-1,3,4,6,7,12b-hexahydroindolo[2,3-a]quinolizin-12(2H)-yl)methyl)-N-((tetrahydro-2H-pyran-2-yl)oxy)benzamide (82)

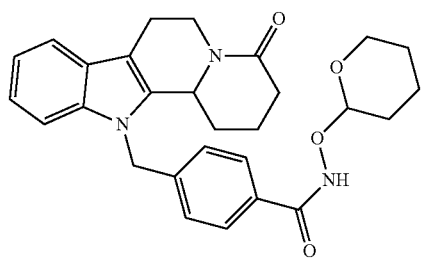 [SMILES: O=C(NOC1CCCCO1)c1ccc(Cn2c3c(c4ccccc42)CCN2C(=O)CCCC32)cc1]

According to GP8 from 80. Yield 0.75 g (1.60 mmol, 80%) colorless crystals after chromatography with dichloromethane and methanol (30:1); mp 219.0-219.3° C. IR (KBr): 1666, 1606 $cm^{-1}$. $^1$H NMR (300 MHz, CDCl$_3$): δ 7.70 (d, J=8.2 Hz, 2H), 7.60-7.51 (m, 1H), 7.19-7.10 (m, 2H), 7.09-6.98 (m, 3H), 5.44-5.26 (m, 2H), 5.22-5.09 (m, 1H), 5.06 (s, 1H), 4.69 (d, J=9.1 Hz, 1H), 4.06-3.91 (m, 1H), 3.72-3.56 (m, 1H), 2.94-2.64 (m, 3H), 2.55 (d, J=16.5 Hz, 1H), 2.47-2.21 (m, 2H), 1.93-1.48 (m, 9H). ESI-MS m/z (%): 474 [MH$^+$] (100), 947 [2MH$^+$] (19). Anal. calcd for $C_{26}H_{27}N_3O_4\times\frac{1}{4}$ ethyl acetate: C, 70.09; H, 6.11; N, 9.43; found: C, 70.02; H, 6.02; N, 9.35.

(E)-3-(4-((4-Oxo-1,3,4,6,7,12b-hexahydroindolo[2,3-a]quinolizin-12(2H)-yl)methyl)phenyl)-N-((tetrahydro-2H-pyran-2-yl)oxy)acrylamide (83)

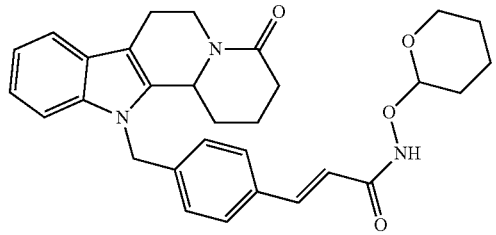 [SMILES: O=C(/C=C/c1ccc(Cn2c3c(c4ccccc42)CCN2C(=O)CCCC32)cc1)NOC1CCCCO1]

According to GP8 from 81. Yield 0.16 g (0.32 mmol, 30%) colorless film after chromatography (eluent DCM/MeOH 20:1); mp 150.0-153.1° C. IR (KBr): 2926, 1627 $cm^{-1}$. $^1$H NMR (300 MHz, CDCl$_3$): δ 7.70 (d, J=15.7 Hz, 1H), 7.61-7.52 (m, 1H), 7.45 (d, J=8.1 Hz, 2H), 7.20-7.07 (m, 3H), 7.00 (d, J=8.1 Hz, 2H), 5.44-5.23 (m, 2H), 5.22-5.10 (m, 1H), 4.99 (s, 1H), 4.69 (br d, J=9.2 Hz, 1H), 4.07-3.87 (m, 1H), 3.73-3.59 (m, 1H), 2.97-2.64 (m, 3H), 2.63-2.48 (m, 1H), 2.48-2.25 (m, 2H), 1.91-1.76 (m, 4H), 1.68-1.58 (m, 3H), 1.56-1.48 (m, 2H). ESI-MS m/z (%): 500 [MH$^+$] (20), 416 [M–$C_5H_8O$] (100). Anal. calcd for $C_{30}H_{33}N_3O_4\times\frac{1}{4}$Heptan$\times\frac{1}{4}CH_2Cl_2$: C, 70.41; H, 6.92; N, 7.70; found: C, 70.47; H, 7.31; N, 7.41.

N-Hydroxy-4-((4-oxo-1,3,4,6,7,12b-hexahydroindolo[2,3-a]quinolizin-12(2H)-yl)methyl)benzamide (84)

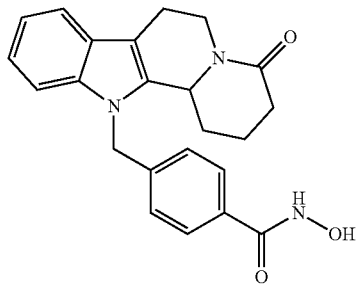 [SMILES: O=C(NO)c1ccc(Cn2c3c(c4ccccc42)CCN2C(=O)CCCC32)cc1]

According to GP9 from 82. Yield 0.03 g (0.06 mmol, 64%) colorless crystals after crystallization from methanol and 0.5 N HCl solution; mp 150.2-151.9° C. IR (KBr): 2921, 1611 cm$^{-1}$. $^1$H NMR (300 MHz, Acetone): δ 7.77 (d, J=8.3 Hz, 2H), 7.58-7.50 (m, 1H), 7.23-7.03 (m, 5H), 5.66 (d, J=18.0 Hz, 1H), 5.49 (d, J=18.0 Hz, 1H), 5.14-5.01 (m, 1H), 4.96-4.83 (m, 1H), 2.79-2.61 (m, 3H), 2.55-2.20 (m, 3H), 1.85-1.72 (m, 2H), 1.62-1.45 (m, 1H). ESI-MS m/z (%): 390 [MH$^+$] (100). Anal. calcd for C$_{23}$H$_{23}$N$_3$O$_4$×½MeOH×½H$_2$O: C, 68.10; H, 6.32; N, 10.14; found: C, 68.06; H, 6.17; N, 9.94.

(E)-N-Hydroxy-3-(4-((4-oxo-1,3,4,6,7,12b-hexahydroindolo[2,3-a]quinolizin-12(2H)-yl)methyl)phenyl)acrylamide (85)

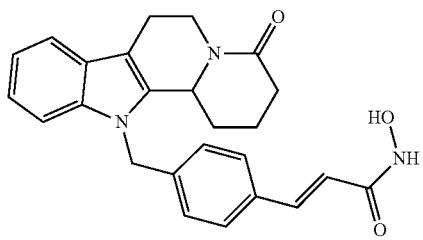 [SMILES: O=C(/C=C/c1ccc(Cn2c3c(c4ccccc42)CCN2C(=O)CCCC32)cc1)NO]

According to GP9 from 83. 0.05 g (0.11 mmol; 60%) orange crystals after crystallization from methanol and 0.5 N HCl solution; mp 185.0-188.0° C. IR (KBr): 1703, 1652 cm$^{-1}$. $^1$H NMR (300 MHz, MeOD) δ 7.58-7.43 (m, 4H), 7.19-6.96 (m, 5H), 6.41 (d, J=15.8 Hz, 1H), 5.53 (d, J=18.0 Hz, 1H), 5.38 (d, J=18.0 Hz, 1H), 5.12-4.98 (m, 1H), 4.85-4.79 (m, 1H), 2.87-2.62 (m, 3H), 2.56-2.28 (m, 3H), 1.86-1.63 (m, 2H), 1.60-1.41 (m, 1H). $^1$H NMR (400 MHz, Acetone): δ 7.61-7.48 (m, 4H), 7.22-7.17 (m, 1H), 7.13-7.03 (m, 4H), 6.54 (d, J=15.8 Hz, 1H), 5.54 (m, 2H), 5.13-5.04 (m, 1H), 4.84-4.94 (m, 1H), 2.85-2.64 (m, 3H), 2.58-2.48 (m, 1H), 2.47-2.37 (m, 1H), 2.37-2.25 (m, 1H), 1.85-1.73 (m, 2H), 1.62-1.48 (m, 1H). ESI-MS m/z (%): 416 [MH$^+$] (100). Anal. calcd for C$_{25}$H$_{25}$N$_3$O$_3$×MeOH×H$_2$O: C, 67.08; H, 6.71; N, 9.03; found: C, 67.48; H, 6.04; N, 9.40.

1.10 Synthesizing the fluorene derivative of 4-((9H-fluoren-9-yl) methyl)-N-hydroxybenz-amide (88) and (E)-3-(4-((9H-fluoren-9-yl) methyl) phenyl)-N-hydroxyacrylamide (93)

4-((9H-Fluoren-9-yl)methyl)benzoic acid (86)

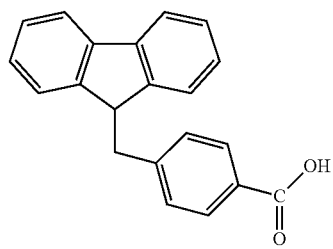 [SMILES: O=C(O)c1ccc(CC2c3ccccc3-c3ccccc32)cc1]

According to literature (Hamilton et al., 1995). $^1$H NMR (300 MHz, DMSO-d$_6$): δ 12.84 (s, 1H), 7.90-7.70 (m, 4H), 7.30 (m, 8H), 4.37 (t, J=7.0 Hz, 1H), 3.25 (d, J=7.0 Hz, 2H).

4-((9H-Fluoren-9-yl)methyl)-N-((tetrahydro-2H-pyran-2-yl)oxy)benzamide (87)

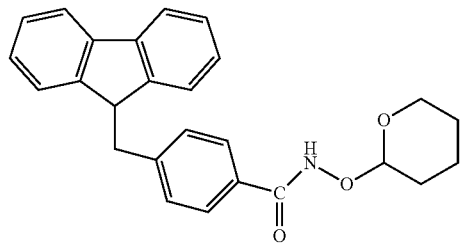 [SMILES: O=C(NOC1CCCCO1)c1ccc(CC2c3ccccc3-c3ccccc32)cc1]

0.50 g (1.66 mmol) 86 were dissolved in 15 mL of THF. 0.82 g (1.85 mmol) of BOP={(benzotriazol-1-yloxy) tris (dimethylamino)phosphonium hexafluorophosphate}, 0.41 g (3.50 mmol) of O-(tetrahydro-2H-pyran-2-yl)hydroxylamine and 0.25 mL triethylamine were added. The reaction mixture was stirred at room temp for 3 h. The solvent was removed and the residue dissolved in 20 mL ethyl acetate and 20 mL water. The organic phase was separated, dried and the solvent removed. 0.60 g (1.50 mmol, 90%) colorless foam after CC (SiO$_2$, ethyl acetate); mp 60° C. (decomp.). IR (KBr): 3229, 2942, 1653 cm$^{-1}$. $^1$H NMR (300 MHz, DMSO-d$_6$) δ 11.56 (s, 1H), 7.85-7.77 (m, 2H), 7.65-7.57 (m, 2H), 7.34 (t, J=6.4 Hz, 4H), 7.29-7.21 (m, 4H), 4.97 (t, J=2.6 Hz, 1H), 4.37 (t, J=6.9 Hz, 1H), 4.09-3.99 (m, 1H), 3.55-3.46 (m, 1H), 3.26 (d, J=6.9 Hz, 2H), 1.70 (d, J=3.1 Hz, 3H), 1.53 (d, J=4.9 Hz, 3H). ESI-MS m/z (%): 422 [MNa]$^+$ (30), 316 (100). Anal. calcd for C$_{26}$H$_{25}$NO$_3$×0.33 ethyl acetate: C, 76.57; H, 6.50; N, 3.27; found: C, 76.37; H, 6.57; N, 3.36.

4-((9H-Fluoren-9-yl)methyl)-N-hydroxybenzamide (88)

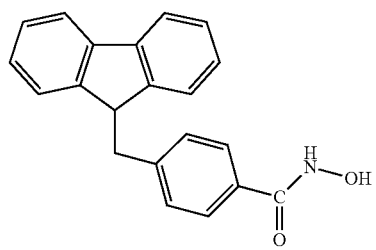 [SMILES: O=C(NO)c1ccc(CC2c3ccccc3-c3ccccc32)cc1]

0.66 g (1.66 mmol) of 87 were dissolved in a mixture of methanol and acetonitrile 1:1. After addition of 4 mL 1N HCl the mixture was stirred at room temperature for 4 h. The solvent was removed and the residue mixed with 40 mL of ethyl acetate and 30 mL of water. The organic phase was separated, dried and the solvent was distilled off. A colorless solid precipitates. 0.32 g (1.01 mmol, 61%) colorless cotton-like substance; mp 210.5° C. IR (KBr): 3366, 3056, 1619 cm$^{-1}$. $^1$H NMR (300 MHz, DMSO-d$_6$) δ 11.13 (s, 1H), 8.98 (s, 1H), 7.82 (dd, J=7.4, 1.3 Hz, 2H), 7.69-7.49 (m, 2H), 7.45-7.11 (m, 8H), 4.36 (t, J=6.9 Hz, 1H), 3.24 (d, J=7.0 Hz, 2H). ESI-MS m/z (%): 316 [MH]$^+$ (100). Anal. calcd for C$_{21}$H$_{17}$NO$_2$: C, 79.98; H, 5.43; N, 4.44; found: C, 79.90; H, 5.43; N, 4.38.

4-((9H-Fluoren-9-yl)methyl)benzaldehyde (89)

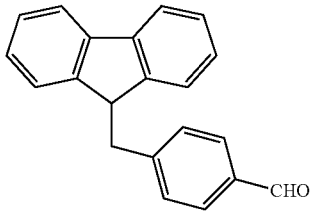 [SMILES: O=Cc1ccc(CC2c3ccccc3-c3ccccc32)cc1]

Based on Mahboobi et al., 2009. 0.17 g (4.43 mmol) of sodium borohydride were suspended in 10 mL of THF. A solution of 86, 1.33 g (4.43 mmol), in 10 mL of THF and 0.48 mL (4.87 mmol) of dimethyl sulfate were added dropwise. The mixture was stirred at room temperature for 12 h. This solution was added dropwise to 1.09 g (5:05 mmol) of PCC in 10 mL CH$_2$Cl$_2$ and stirring at room temperature was continued for 6 h. After addition of CH$_2$Cl$_2$ (20 mL) the suspension was filtered over celite and the filtrate concentrated to dryness. Purification by CC. 1.33 g (3.70 mmol; 83%) colorless powder; mp 160.4-161.1° C. IR (KBr): 3031, 2928, 1702 cm$^{-1}$. $^1$H NMR (300 MHz, DMSO-d$_6$) δ 9.93 (s, 1H), 7.82 (dd, J=8.1, 1.2 Hz, 2H), 7.78-7.70 (m, 2H), 7.42-7.30 (m, 6H), 7.30-7.19 (m, 2H), 4.40 (t, J=6.9 Hz, 1H), 3.31 (d, J=7.0 Hz, 2H). ESI-MS m/z (%): 285 [MH]$^+$ (100), 165 (23). Anal. calcd for C$_{21}$H$_{16}$O: C, 88.70; H, 5.67; found: C, 88.64; H, 5.61.

(E)-tert-Butyl 3-(4-((9H-fluoren-9-yl)methyl)phenyl)acrylate (90)

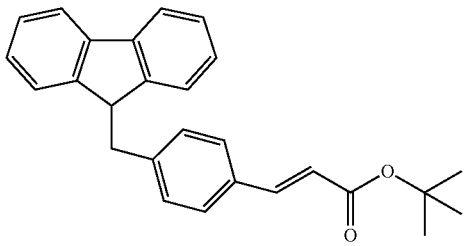 [SMILES: CC(C)(C)OC(=O)/C=C/c1ccc(CC2c3ccccc3-c3ccccc32)cc1]

Based on Wen et al., 2012. 0.31 g (1.10 mmol) of 89 and 0.45 g (1.10 mmol) (tert-butoxycarbonylmethyl)triphenyl phosphonium chloride were placed in 10 mL of CH$_2$Cl$_2$. To this mixture was added a solution of 0.09 g (2.20 mmol) of NaOH and 0.5 mL of triethylamine in 4.6 mL of water. The mixture was stirred at room temperature for 1 h. The organic phase was separated, washed with 5 mL of 1N HCl and dried. After removal of the solvent the residue was purified by CC. 0.30 g (0.78 mmol, 71%) beige solid after SC (SiO$_2$, CH$_2$Cl$_2$); mp 176-177° C. IR (KBr): 2971, 2928, 1696 cm$^{-1}$. $^1$H NMR (300 MHz, DMSO-d$_6$) δ 7.81 (dd, J=7.4, 1.4 Hz, 2H), 7.57-7.45 (m, 3H), 7.37-7.29 (m, 4H), 7.28-7.16 (m, 4H), 6.46 (d, J=15.9 Hz, 1H), 4.35 (t, J=7.0 Hz, 1H), 3.22 (d, J=6.9 Hz, 2H), 1.47 (s, 9H). EI-MS m/z (%): 382 [M]$^+$ (11), 165 (100). Anal. calcd for C$_{27}$H$_{26}$O$_2$: C, 84.78; H, 6.85; found: C, 84.58; H, 6.85.

(E)-3-(4-((9H-Fluoren-9-yl)methyl)phenyl)acrylic acid (91)

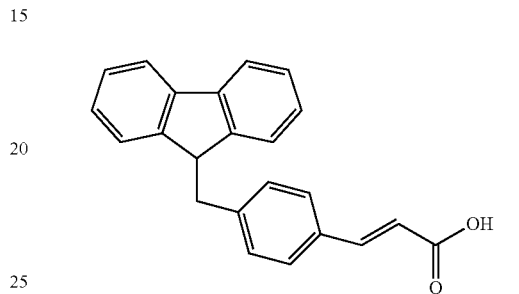

1.52 g (3.97 mmol) of 90 were dissolved in a mixture of 10 mL of CF$_3$COOH and 50 mL of CH$_2$Cl$_2$ and stirred at room temperature for 1 h. The mixture was treated with 50 mL CH$_2$Cl$_2$ and 50 mL of water, the organic phase was separated, dried, mixed with 30 mL of methanol and concentrated on a rotary evaporator. The precipitated crystals were filtered off, washed with a little cold diethyl ether and dried. 1.10 g (3.77 mmol, 85%) colorless crystals; mp 250-251° C. IR (KBr): 2910, 1679, 1624 cm$^{-1}$. $^1$H NMR (300 MHz, DMSO-d$_6$) δ 12.36 (s, 1H), 7.85-7.78 (m, 2H), 7.58-7.48 (m, 3H), 7.38-7.30 (m, 4H), 7.29-7.15 (m, 4H), 6.47 (d, J=16.0 Hz, 1H), 4.35 (t, J=6.9 Hz, 1H), 3.23 (d, J=6.9 Hz, 2H). ESI-MS m/z (%): 325 [M–H]$^-$ (100). Anal. calcd for C$_{23}$H$_{18}$O$_2$: C, 84.64; H, 5.56; found: C, 84.51; H, 5.60.

(E)-3-(4-((9H-Fluoren-9-yl)methyl)phenyl)-N-((tetrahydro-2H-pyran-2-yl)oxy)acrylamide (92)

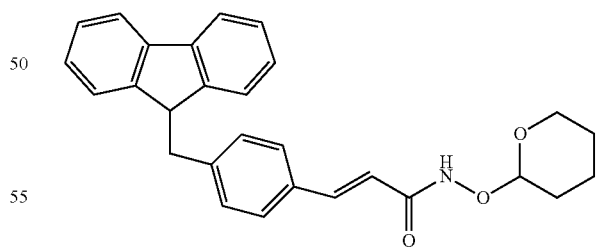

To a solution of 0.60 g (1.84 mmol) of 91 in 20 mL of THF 0.93 g (2.10 mmol) of BOP={(benzotriazol-1-yloxy) tris (dimethylamino)phosphonium hexafluorophosphate}, 0.43 g (3.67 mmol) of O-(tetrahydro-2H-pyran-2-yl)hydroxylamine and 0.30 mL of triethylamine were added. The mixture was stirred at room temperature for 16 h and poured into 100 mL of water. The precipitation is filtered off, dried and purified by CC. 0.62 g (1.46 mmol, 79%) colorless solid after CC (SiO$_2$/Ethylacetat); mp 205-206° C. IR (KBr):

3169, 2958, 1658, 1623 cm$^{-1}$. $^1$H NMR (300 MHz, DMSO-d$_6$) δ 11.20 (s, 1H), 7.82 (d, J=7.4 Hz, 2H), 7.51-7.15 (m, 11H), 6.45 (d, J=15.8 Hz, 1H), 4.90 (s, 1H), 4.35 (t, J=7.0 Hz, 1H), 4.03-3.86 (m, 1H), 3.53 (dt, J=11.3, 4.2 Hz, 1H), 3.20 (d, J=7.1 Hz, 2H), 1.83-1.39 (m, 6H). ESI-MS m/z (%): 426 [M+H]$^+$ (10), 342 (100). Anal. calcd for C$_{28}$H$_{27}$NO$_3$: C, 79.03; H, 6.40; N, 3.29; found: C, 78.93; H, 6.43; N, 3.25.

(E)-3-(4-((9H-Fluoren-9-yl)methyl)phenyl)-N-hydroxyacrylamide (93)

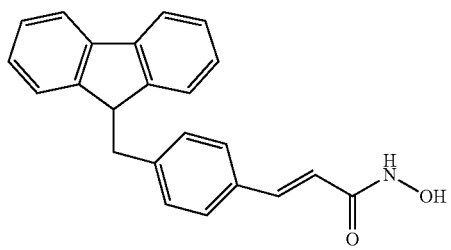 [SMILES: O=C(/C=C/c1ccc(CC2c3ccccc3-c3ccccc32)cc1)NO]

To a solution of 92, 0.30 g (0.71 mmol) in 50 mL methanol and 50 mL THF 3 mL of 3N HCl were added. After 6 h of stirring at room temperature the solvent was removed and the residue recrystallized from methanol. 0.16 g (0.48 mmol, 68%) colorless crystals; mp 171-172° C. IR (KBr): 3223, 3057, 1652 cm$^{-1}$. $^1$H NMR (300 MHz, DMSO-d$_6$): δ 10.72 (s, 1H), 9.04 (s, 1H), 7.82 (d, J=7.1 Hz, 2H), 7.47-7.13 (m, 11H), 6.41 (d, J=15.9 Hz, 1H), 4.34 (t, J=7.0 Hz, 1H), 3.20 (d, J=7.0 Hz, 2H). ESI-MS m/z (%): 342 [MH]$^+$ (100). Anal. calcd for C$_{23}$H$_{19}$NO$_2$×0.5 CH$_3$OH: C, 78.97; H, 5.92; N, 3.92; found: C, 78.76; H, 5.82; N, 3.61.

1.11 Synthesis of inhibitors by modifying the 4-methyl-6,11-dihydro-2,6-methano[1,3]diazocino[5,6-b]indole-3,5 (1H,4H)-dione head structure.
Example: 4-((4-(2-Acrylamidoethyl)-3,5-dioxo-3,4,5,6-tetrahydro-2,6-methano[1,3]diazocino[5,6-b]indol-11(1H)-yl)methyl)-N-hydroxybenzamide (101)

Methyl 2-((2-((tert-butoxycarbonyl)amino)ethyl) carbamoyl)-2,3,4,9-tetrahydro-1H-pyrido[3,4-b]indole-4-carboxylate (95a)

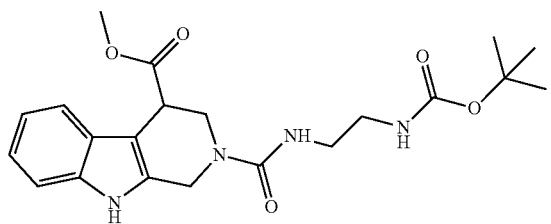 [SMILES: COC(=O)C1CN(C(=O)NCCNC(=O)OC(C)(C)C)Cc2[nH]c3ccccc3c21]

Methyl 2,3,4,9-tetrahydro-1H-pyrido[3,4-b]indole-4-carboxylate hydrochloride (13a) (4.04 g, 15.16 mmol) was suspended in CH$_3$CN (40.4 mL). With stirring at room temperature diisopropylethylamine (4.04 mL) and tert-butyl (2-isocyanatoethyl) carbamate (94a) (Gwanmesia et al., 2009) (18.20 mmol) in toluene (40.0 mL) were added. The mixture was stirred overnight at room temperature. Water (200 mL) was added and the mixture concentrated under reduced pressure until the product precipitates as a crystalline solid. It was filtered off, washed with water and dried in vacuum. 5.91 g (14.20 mmol; 94%) colorless crystals. mp 211-214° C. IR (KBr): 3414, 2976, 1729, 1706 cm$^{-1}$. $^1$H NMR (300 MHz, DMSO-d$_6$): δ 11.05 (s, 1H), 7.32 (d, J=8.7 Hz, 2H), 7.10-7.01 (m, 1H), 7.01-6.92 (m, 1H), 6.81 (t, J=5.3 Hz, 1H), 6.75 (t, J=5.1 Hz, 1H), 4.61 (d, J=16.5 Hz, 1H), 4.51 (d, J=16.5 Hz, 1H), 4.02-3.86 (m, 2H), 3.76 (dd, J=10.6, 8.0 Hz, 1H), 3.64 (s, 3H), 3.08 (dd, J=11.2, 5.6 Hz, 2H), 2.99 (dd, J=11.2, 5.5 Hz, 2H), 1.37 (s, 9H). ESI-MS m/z (%): 417 [MH$^-$] (100), 361 [MH$^+$–C$_4$H$_8$] (100), Methyl 2-((3-((tert-butoxycarbonyl)amino)propyl) carbamoyl)-2,3,4,9-tetrahydro-1H-pyrido[3,4-b]indol-4-carboxylate (95b)

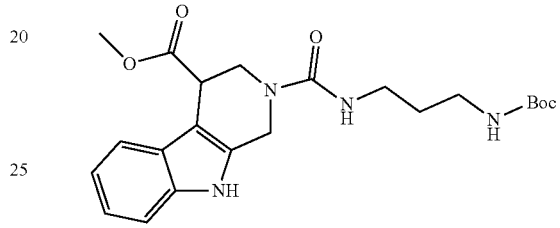

Methyl 2,3,4,9-tetrahydro-1H-pyrido[3,4-b]indole-4-carboxylate hydrochloride (13a) (2.90 g, 13.00 mmol) was suspended in acetonitrile (40.4 mL). With stirring at room temperature diisopropylethylamine (2.90 mL) and tert-butyl-(3-isocyanatopropyl)carbamate (94b) (Li et al., 2008) (13.00 mmol) in toluene (40.0 mL) were added. The mixture was stirred overnight at room temperature. Water (200 mL) was added and the mixture concentrated under reduced pressure until the product precipitates as a crystalline solid. It was filtered off, washed with water and dried in vacuum. Colorless crystals 5.03 g (11.70 mmol, 90%) after crystallization from toluene/water/acetonitrile, mp 189-192° C., IR (KBr): 3333, 1730 cm$^{-1}$, $^1$H NMR (300 MHz, CDCl3): δ 8.47 (s, 1H), 7.64 (d, J=7.2 Hz, 1H), 7.34 (dd, J=6.9, 1.3 Hz, 1H), 7.22-7.10 (m, 2H), 6.14 (t, J=5.4 Hz, 1H), 5.04 (d, J=16.4 Hz, 2H), 4.51-4.19 (m, 2H), 3.91 (s, J=10.5 Hz, 1H), 3.70 (s, 3H), 3.48-3.15 (m, 5H), 1.76-1.65 (m, 2H), 1.44 (s, 9H), ESI-MS m/z (%): 431 [MH$^+$] (100). Anal. calcd. for C$_{22}$H$_{30}$N$_4$O$_5$: C, 61.38; H, 7.02; N, 13.01; found: C, 61.33; H, 7.03; N, 13.03.

Methyl 2-((3-((tert-butoxycarbonyl)amino)propyl) carbamoyl)-6-methoxy-2,3,4,9-tetrahydro-1H-pyrido[3,4-b]indol-4-carboxylate (95c)

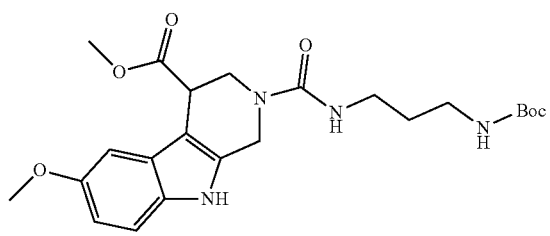 [SMILES: COC(=O)C1CN(C(=O)NCCCNC(=O)OC(C)(C)C)Cc2[nH]c3ccc(OC)cc3c21]

According to the procedure of 95a methyl 6-methoxy-2,3,4,9-tetrahydro-1H-pyrido[3,4-b]indole-4-carboxylate hydrochloride (14a) was suspended in acetonitrile. With stirring at room temperature diisopropylethylamine and tert-butyl-(3-isocyanatopropyl)carbamate (94b) (Li et al., 2008) in toluene were added. The mixture was stirred overnight at room temperature. Water was added and the mixture was concentrated under reduced pressure until the product precipitated as a crystalline solid. The solid was filtered off, washed with water and dried in vacuum. Colorless crystals (9.22 g, 20.00 mmol, 99%), $^1$H NMR (300 MHz, DMSO): δ 10.88 (s, 1H), 7.21 (d, J=8.7 Hz, 1H), 6.86-6.74 (m, 2H), 6.73-6.61 (m, 2H), 4.53 (q, J=16.5 Hz, 2H), 3.96 (dd, J=13.1, 5.7 Hz, 1H), 3.91-3.84 (m, 1H), 3.77-3.60 (m, 7H), 3.10-2.98 (m, 2H), 2.92 (q, J=6.5 Hz, 2H), 1.59-1.42 (m, 2H), 1.37 (s, 9H).

tert-Butyl (2-(3,5-dioxo-5,6-dihydro-2,6-methano[1,3]diazocino[5,6-b]indol-4(1H,3H,11H)-yl)ethyl)carbamate (96a)

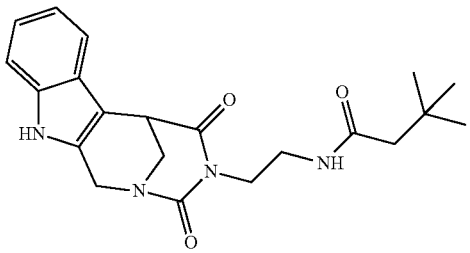 [SMILES: CC(C)(C)CC(=O)NCCN1C(=O)C2CN(Cc3[nH]c4ccccc4c32)C1=O]

According to GP4 from methyl 2-((2-((tert-butoxycarbonyl)amino)ethyl)carbamoyl)-2,3,4,9-tetrahydro-1H-pyrido[3,4-b]indole-4-carboxylate (95a). Yield 0.43 g (1.12 mmol; 45%) colorless crystals after CC (SiO$_2$, CH$_2$Cl$_2$/ethyl acetate; 1:1); mp 243-245° C. IR (KBr): 3344, 3275, 2969, 1729, 1679 cm$^{-1}$. $^1$H NMR (300 MHz, DMSO-d$_6$): δ 11.13 (s, 1H), 7.45 (d, J=7.2 Hz, 1H), 7.33 (d, J=7.5 Hz, 1H), 7.04 (dtd, J=17.7, 7.1, 1.2 Hz, 2H), 6.94 (t, J=6.1 Hz, 1H), 4.65 (s, 2H), 3.93 (d, J=12.6 Hz, 1H), 3.81 (s, 1H), 3.56 (t, J=5.7 Hz, 2H), 3.41 (dd, J=13.0, 2.0 Hz, 1H), 3.01 (ddd, J=19.7, 13.2, 6.3 Hz, 2H), 1.37 (s, 9H). ESI-MS m/z (%): 791 [2MNa$^+$] (48), 385 [MH$^+$] (2), 329 [MH$^+$–C$_4$H$_8$] (29), 285 [MH$^+$–BOC] (100).

tert-Butyl (3-(3,5-dioxo-5,6-dihydro-2,6-methano[1,3]diazocino[5,6-b]indol-4(1H,3H,11H)-yl)propyl)carbamate (96b)

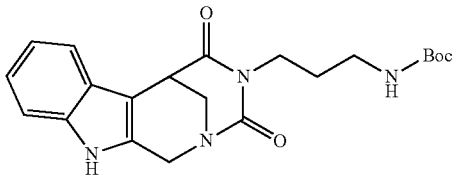 [SMILES: CC(C)(C)OC(=O)NCCCN1C(=O)C2CN(Cc3[nH]c4ccccc4c32)C1=O]

According to GP4 from methyl 2-((3-((tert-butoxycarbonyl)amino)propyl)carbamoyl)-2,3,4,9-tetrahydro-1H-pyrido[3,4-b]indole-4-carboxylate (95b). Colorless crystals 2.15 g (5.40 mmol, 57%) after chromatography over silica gel with dichloromethane and petrol ether (3:1). Crystallization from dichloromethane after addition of petrol ether; mp 166-168° C.; IR (KBr): 1724 cm$^{-1}$, $^1$H NMR (300 MHz, DMSO): δ 11.14 (s, 1H), 7.46 (d, J=7.5 Hz, 1H), 7.34 (d, J=7.6 Hz, 1H), 7.13-6.97 (m, 2H), 6.76 (t, J=5.6 Hz, 1H), 4.76-4.57 (m, 2H), 3.89 (d, J=13.0 Hz, 1H), 3.55-3.39 (m, 3H), 2.92-2.80 (m, 2H), 1.60-1.41 (m, 2H), 1.36 (s, J=6.8 Hz, 9H). ESI-MS m/z (%): 399 [MH$^+$] (5), 299 [MH$^+$–Boc] (100). Anal. calcd. for C$_{21}$H$_{26}$N$_4$O$_4$: C, 63.30; H, 6.58; N, 14.06; found: C, 63.04; H, 6.64; N, 13.77.

tert-butyl (3-(8-methoxy-3,5-dioxo-1,5,6,11-tetrahydro-2,6-methano[1,3]diazocino[5,6-b]indol-4(3H)-yl)propyl)carbamate (96c)

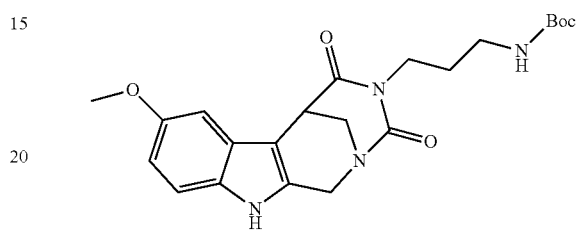

According to GP4 from Methyl 2-((3-((tert-butoxycarbonyl)amino)propyl)carbamoyl)-6-methoxy-2,3,4,9-tetrahydro-1H-pyrido[3,4-b]indole-4-carboxylate (95c). Yield: Colorless crystals (1.85 g, 4.3 mmol, 23%). $^1$H NMR (300 MHz, DMSO): δ 10.97 (s, 1H), 7.23 (d, J=8.8 Hz, 1H), 6.91 (d, J=2.4 Hz, 1H), 6.81-6.68 (m, 2H), 4.63 (s, J=17.1 Hz, 2H), 3.87 (d, J=12.9 Hz, 1H), 3.76 (s, J=4.3 Hz, 1H), 3.75 (s, 3H), 3.49 (t, J=7.2 Hz, 2H), 3.42 (dd, J=13.1, 2.0 Hz, 1H), 2.86 (dd, J=12.7, 6.6 Hz, 2H), 1.58-1.42 (m, 2H), 1.36 (s, 9H).

N-(2-(3,5-dioxo-5,6-dihydro-2,6-methano[1,3]diazocino[5,6-b]indol-4(1H,3H,11H)-yl)ethyl)acrylamide (97a)

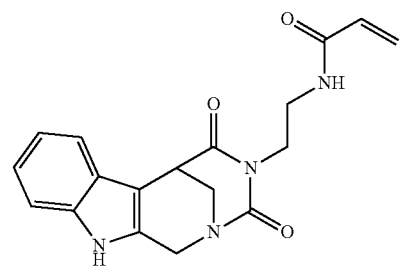 [SMILES: C=CC(=O)NCCN1C(=O)C2CN(Cc3[nH]c4ccccc4c32)C1=O]

tert-butyl (2-(3,5-dioxo-5,6-dihydro-2,6-methano[1,3]diazocino[5,6-b]indol-4(1H,3H,11H)-yl)ethyl)carbamate (96a) (1.00 g, 2.60 mmol) was dissolved in 5.0 mL of CF$_3$COOH and stirred at room temperature for 15 min. The excess trifluoroacetic acid was removed completely under reduced pressure. The residue was dissolved in dichloromethane (50.0 mL), NEt(iProp)$_2$ (5.20 mmol, 0.905 mL) was added, and the mixture was cooled to 0° C. Acryloyl chloride (2.60 mmol, 0.21 mL) was added and the mixture was allowed to warm to room temperature overnight. The organic phase was extracted with 1N HCl (2×50 mL), washed with water, and dried over Na$_2$SO$_4$. The solvent was removed. 0.38 g (1.00 mmol, 38%) colorless crystals were obtained after recrystallization from ethyl acetate; mp 205-205° C. IR (KBr): 3352, 3190, 1727, 1614 cm$^{-1}$. $^1$H NMR (300 MHz, DMSO-d$_6$): δ 11.14 (s, 1H), 8.24 (t, J=6.0 Hz, 1H), 7.46 (d, J=7.4 Hz, 1H), 7.33 (d, J=7.7 Hz, 1H), 7.04 (dtd, J=17.6, 7.1, 1.1 Hz, 2H), 6.17 (dd, J=17.1, 9.5 Hz, 1H), 6.06 (dd, J=17.1, 2.8 Hz, 1H), 5.59 (dd, J=9.5, 2.8 Hz, 1H), 4.67 (d, J=16.7 Hz, 2H), 4.62 (d, J=17.1 Hz, 1H), 3.91-3.78 (m, 2H), 3.63 (t, J=6.0 Hz, 2H), 3.40 (dd, J=13.0, 2.1 Hz, 1H), 3.34-3.15 (m, 2H). ESI-MS m/z (%): 677 [2MH$^+$] (30), 339 [MH$^+$] (100).

N-(3-(3,5-Dioxo-1,5,6,11-tetrahydro-2,6-methano[1,3]diazocino[5,6-b]indol-4(3H)-yl)propyl)acrylamide (97b)

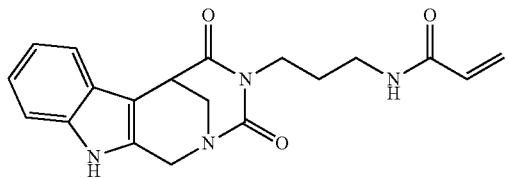 [SMILES: C=CC(=O)NCCCN1C(=O)C2CN(Cc3[nH]c4ccccc4c32)C1=O]

tert-Butyl (3-(3,5-dioxo-5,6-dihydro-2,6-methano[1,3]diazocino[5,6-b]indol-4(1H,31H,11H)-yl)propyl)carbamate (96b) (1.63 g, 4.10 mmol) was dissolved in 10.0 mL of CF$_3$COOH and stirred at room temperature for 15 min. The excess trifluoroacetic acid was removed completely under reduced pressure. The residue was dissolved in dichloromethane (50.0 mL), NEt(iProp)$_2$ (1.38 mL) was added, and the mixture was cooled to 0° C. Acryloyl chloride (4.00 mmol, 0.32 mL) was added and the mixture was allowed to warm to room temperature overnight. The organic phase was extracted with 1N HCl (2×50 mL), washed with water, and dried over Na$_2$SO$_4$. The solvent was removed. Colorless crystals (0.38 g, 1.07 mmol, 26% over 2 steps) after chromatography over silica gel with dichloromethane and methanol (10:1). Crystallization from ethyl acetate; mp 350.5-355.2° C., IR (KBr): 1725, 3380 cm$^{-1}$, $^1$H NMR (300 MHz, DMSO): δ 11.13 (s, 1H), 7.95 (s, 1H), 7.34 (d, J=8.0 Hz, 1H), 7.19 (d, J=7.7 Hz, 1H), 7.11-7.01 (m, 1H), 7.00-6.91 (m, 1H), 6.54 (dd, J=7.4, 3.4 Hz, 1H), 5.93 (dd, J=7.7, 3.4 Hz, 1H), 5.21 (d, J=16.1 Hz, 1H), 4.36 (d, J=14.6 Hz, 1H), 4.19-3.89 (m, 1H), 3.70-3.39 (m, 4H), 2.88-2.80 (m, 1H), 2.72-2.60 (m, 1H), 1.74-1.56 (m, 1H), 1.56-1.38 (m, 1H). ESI-MS m/z (%): 353 [MH$^+$] (100). Anal. calcd. for C$_{19}$H$_{20}$N$_4$O$_3$×⅓ DCM: C, 61.00; H, 5.47; N, 14.72; found: C, 61.06; H, 5.87; N, 14.58.

N-(3-(8-methoxy-3,5-dioxo-1,5,6,11-tetrahydro-2,6-methano[1,3]diazocino[5,6-b]indol-4(3H)-yl)propyl)acrylamide (97c)

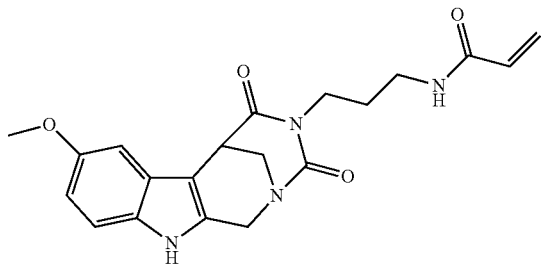 [SMILES: C=CC(=O)NCCCN1C(=O)C2CN(Cc3[nH]c4ccc(OC)cc4c32)C1=O]

tert-butyl (3-(8-methoxy-3,5-dioxo-1,5,6,11-tetrahydro-2,6-methano[1,3]diazocino[5,6-b]indol-4(3H)-yl)propyl)carbamate (96c) was dissolved in 10.0 mL of CF$_3$COOH and stirred at room temperature for 15 min. The excess trifluoroacetic acid was removed completely under reduced pressure. The residue was dissolved in dichloromethane (50.0 mL), NEt(iProp)$_2$ was added, and the mixture was cooled to 0° C. Acryloyl chloride was added and the mixture was allowed to warm to room temperature overnight. The organic phase was extracted with 1N HCl (2×50 mL), washed with water, and dried over sodium sulfate. The solvent was removed. Colorless crystals (0.48 g, 1.25 mmol, 39% over 2 steps) after chromatography over silica gel with dichloromethane and methanol (10:1). Crystallization from ethyl acetate. $^1$H NMR (300 MHz, DMSO): δ 10.97 (s, 1H), 8.07 (t, J=5.5 Hz, 1H), 7.23 (d, J=8.8 Hz, 1H), 6.91 (d, J=2.4 Hz, 1H), 6.72 (dd, J=8.8, 2.5 Hz, 1H), 6.17 (dd, J=17.1, 9.8 Hz, 1H), 6.04 (dd, J=17.1, 2.6 Hz, 1H), 5.55 (dd, J=9.8, 2.6 Hz, 1H), 4.63 (s, J=16.9 Hz, 2H), 3.88 (d, J=12.8 Hz, 1H), 3.77 (s, 1H), 3.75 (s, 3H), 3.52 (t, J=7.2 Hz, 2H), 3.42 (dd, J=13.1, 2.2 Hz, 1H), 3.07 (q, J=7.0 Hz, 2H), 1.68-1.42 (m, 2H).

tert-Butyl 4-((4-(2-acrylamidoethyl)-3,5-dioxo-3,4,5,6-tetrahydro-2,6-methano[1,3]diazo-cino[5,6-b]indol-11(1H)-yl)methyl)benzoate (98a)

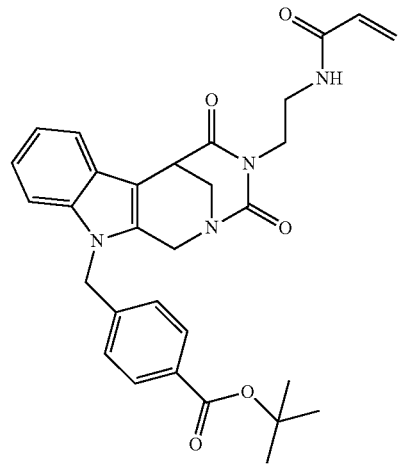 [SMILES: C=CC(=O)NCCN1C(=O)C2CN(Cc3c2c2ccccc2n3Cc2ccc(C(=O)OC(C)(C)C)cc2)C1=O]

A mixture of N-(2-(3,5-dioxo-5,6-dihydro-2,6-methano[1,3]diazocino[5,6-b]indol-4-(1H,3H, 11H)-yl)ethyl)acrylamide (97a) (0.58 g, 1.71 mmol), K$_2$CO$_3$ (17.1 mmol, 2.36 g) and tert-butyl 4-(bromomethyl)benzoate (23) (Sui et al., 2007) (0.51 g, 2.00 mmol) in 2-butanone (20.0 mL) was heated for 16 h to reflux. After the solids are filtered off, the solvent was removed and the product purified by CC on SiO$_2$ using ethyl acetate as eluent. 0.60 g (1.14 mmol, 66%) colorless solid; mp 119-122° C. IR (KBr): 3388, 2959, 2929, 1712, 1685 cm$^{-1}$. $^1$H NMR (300 MHz, DMSO-d$_6$): δ 8.23 (t, J=6.0 Hz, 1H), 7.81 (d, J=8.3 Hz, 1H), 7.51 (dd, J=6.1, 2.6 Hz, 1H), 7.39 (dd, J=6.4, 2.3 Hz, 1H), 7.14 (d, J=8.2 Hz, 1H), 7.11-7.03 (m, 1H), 6.16 (dd, J=17.1, 9.5 Hz, 1H), 6.06 (dd, J=17.1, 2.8 Hz, 1H), 5.58 (dd, J=9.5, 2.8 Hz, 1H), 5.44 (s, 1H), 4.81 (d, J=16.6 Hz, 1H), 4.53 (d, J=16.5 Hz, 1H), 3.86 (d, J=9.7 Hz, 1H), 3.64 (t, J=6.0 Hz, 1H), 3.41 (dd, J=13.2, 2.3 Hz, 1H), 3.25 (dt, J=12.9, 6.9 Hz, 1H), 1.50 (s, 1H). ESI-MS m/z (%): 529 [MH$^+$] (100), 473 [MH$^+$-C$_4$H$_8$] (21).

tert-Butyl 4-((4-(3-acrylamidopropyl)-3,5-dioxo-3,4,5,6-tetrahydro-2,6-methano[1,3]diazocino[5,6-b]indol-11(1H)-yl)methyl)benzoate (98b)

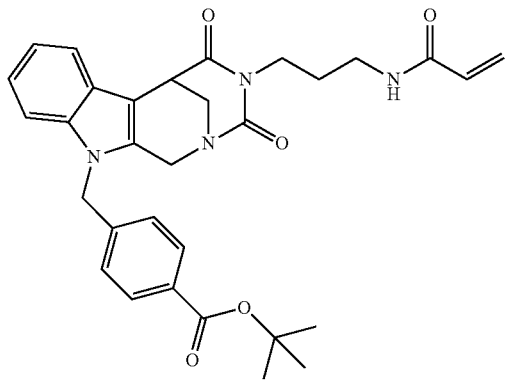 [SMILES: C=CC(=O)NCCCN1C(=O)C2CN(Cc3c2c2ccccc2n3Cc2ccc(C(=O)OC(C)(C)C)cc2)C1=O]

A mixture of N-(3-(3,5-Dioxo-1,5,6,11-tetrahydro-2,6-methano[1,3]diazocino[5,6-b]indol-4(3H)-yl)propyl)acrylamide (97b) (0.38 g, 1.08 mmol), $K_2CO_3$ (10.8 mmol, 1.48 g) and tert-butyl 4-(bromomethyl)benzoate (23)) (Sui et al., 2007) (0.35 g, 1.10 mmol) in 2-butanone (20.0 mL) was heated for 16 h to reflux. After the solids are filtered off, the solvent was removed and the product purified by CC on $SiO_2$ using ethyl acetate as eluent. Colorless crystals 0.32 g (0.59 mmol, 55%) after chromatography and crystallization from dichloromethane and heptane; mp 106.1-110.3° C., IR (KBr): 1711 cm$^{-1}$, $^1$H NMR (300 MHz, CDCl3): δ 7.90 (d, J=8.3 Hz, 2H), 7.73-7.66 (m, 1H), 7.24-7.12 (m, 3H), 7.01 (d, J=8.3 Hz, 2H), 6.34 (t, J=5.7 Hz, 1H), 6.25 (dd, J=17.0, 1.6 Hz, 1H), 6.08 (dd, J=17.0, 10.1 Hz, 1H), 5.60 (dd, J=10.1, 1.6 Hz, 1H), 5.33 (d, J=17.1 Hz, 1H), 5.15 (d, J=17.1 Hz, 1H), 4.84 (d, J=16.4 Hz, 1H), 4.29 (d, J=16.4 Hz, 1H), 3.90 (d, J=11.9 Hz, 2H), 3.85-3.62 (m, 2H), 3.33 (dt, J=6.3, 3.2 Hz, 1H), 3.29-3.18 (m, 1H), 3.17-3.02 (m, 1H), 1.73 (p, J=6.3 Hz, 2H), 1.55 (s, 9H). ESI-MS m/z (%): 543 [MH$^+$] (100). Anal. calcd. for $C_{19}H_{20}N_4O_3$×½ DCM×½Heptan: C, 66.18; H, 6.82; N, 8.82; found: C, 66.26; H, 6.92; N, 8.65.

tert-Butyl 4-((4-(3-acrylamidopropyl)-8-methoxy-3,5-dioxo-3,4,5,6-tetrahydro-2,6-methano[1,3]diazocino[5,6-b]indol-11(1H)-yl)methyl)benzoate (98c)

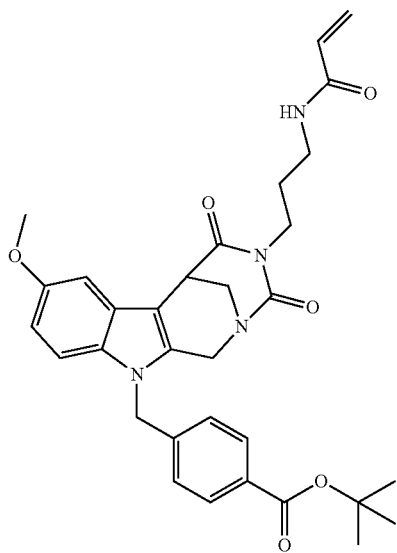 [SMILES: C=CC(=O)NCCCN1C(=O)C2CN(Cc3c2c2cc(OC)ccc2n3Cc2ccc(C(=O)OC(C)(C)C)cc2)C1=O]

According to GP6 modification b from N-(3-(8-methoxy-3,5-dioxo-1,5,6,11-tetrahydro-2,6-methano[1,3]diazocino[5,6-b]indol-4(3H)-yl)propyl)acrylamide (97c). Yield: Colorless crystals (0.42 g, 0.73 mmol, 58%) after crystallization from ethyl acetate/petroleum ether. $^1$H NMR (300 MHz, DMSO): δ 8.07 (t, J=5.5 Hz, 1H), 7.80 (d, J=8.3 Hz, 2H), 7.29 (d, J=8.9 Hz, 1H), 7.09 (d, J=8.3 Hz, 2H), 6.97 (d, J=2.4 Hz, 1H), 6.74 (dd, J=8.9, 2.4 Hz, 1H), 6.17 (dd, J=17.1, 9.8 Hz, 1H), 6.04 (dd, J=17.1, 2.6 Hz, 1H), 5.55 (dd, J=9.8, 2.6 Hz, 1H), 5.41 (s, 2H), 4.79 (d, J=16.6 Hz, 1H), 4.52 (d, J=16.5 Hz, 1H), 3.97-3.80 (m, 2H), 3.75 (s, 3H), 3.54 (t, J=7.2 Hz, 2H), 3.44 (dd, J=13.1, 1.9 Hz, 1H), 3.08 (q, J=6.9 Hz, 2H), 1.57 (ddd, J=17.1, 12.0, 5.3 Hz, 2H), 1.50 (s, 9H).

4-(4-(2-Acrylamidoethyl)-3,5-dioxo-3,4,5,6-tetrahydro-2,6-methano[1,3]diazocino[5,6-b]indol-11(1H)-yl)methyl)benzoic acid 99a

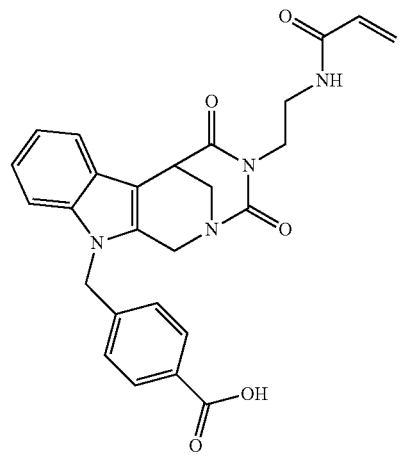 [SMILES: C=CC(=O)NCCN1C(=O)C2CN(Cc3c2c2ccccc2n3Cc2ccc(C(=O)O)cc2)C1=O]

tert-butyl 4-((4-(2-acrylamidoethyl)-3,5-dioxo-3,4,5,6-tetrahydro-2,6-methano[1,3]diazo-cino[5,6-b]indol-11(1H)-yl)methyl)benzoate (98a) (0.43 g, 0.81 mmol) was dissolved in $CF_3COOH$ (4.3 mL) and stirred for 15 min. at room temperature. The clear solution was poured into water, the crystalline product was filtered off with suction, washed with water and dried in vacuo. 0.34 g (0.72 mmol, 88%) colorless solid; mp 150° C. IR (KBr): 1724, 1679 cm$^{-1}$. $^1$H NMR (300 MHz, DMSO-d$_6$): δ 12.96 (s, 1H), 8.24 (t, J=6.1 Hz, 1H), 7.85 (d, J=8.3 Hz, 2H), 7.52 (dd, J=6.4, 2.4 Hz, 1H), 7.41 (dd, J=6.6, 2.0 Hz, 1H), 7.14 (d, J=8.2 Hz, 2H), 7.08 (ddd, J=12.3, 5.9, 3.7 Hz, 2H), 6.16 (dd, J=17.1, 9.5 Hz, 1H), 6.06 (dd, J=17.1, 2.8 Hz, 1H), 5.58 (dd, J=9.5, 2.8 Hz, 1H), 5.45 (s, 2H), 4.82 (d, J=16.6 Hz, 1H), 4.53 (d, J=16.5 Hz, 1H), 3.86 (d, J=11.6 Hz, 2H), 3.64 (t, J=6.0 Hz, 2H), 3.41 (dd, J=13.3, 2.3 Hz, 2H), 3.37-3.08 (m, 3H). ESI-MS m/z (%): 473 [MH$^+$] (100).

4-((4-(3-acrylamidopropyl)-3,5-dioxo-3,4,5,6-tetrahydro-2,6-methano[1,3]diazocino[5,6-b]indol-11(1H)-yl)methyl)benzoic acid (99b)

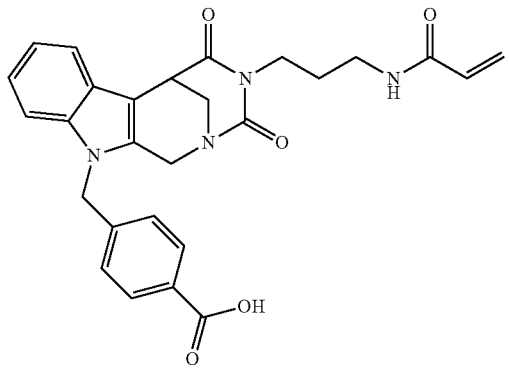 [SMILES: C=CC(=O)NCCCN1C(=O)C2CN(Cc3c2c2ccccc2n3Cc2ccc(C(=O)O)cc2)C1=O]

tert-Butyl 4-((4-(3-acrylamidopropyl)-3,5-dioxo-3,4,5,6-tetrahydro-2,6-methano[1,3]diazocino[5,6-b]indol-11(1H)-yl)methyl)benzoate (98b) (0.32 g, 0.59 mmol) was dissolved in $CF_3COOH$ (3.2 mL) and stirred for 15 min. at room temperature. The clear solution was poured into water, the crystalline product was filtered off with suction, washed with water and dried in vacuo. Colorless crystals 0.27 g (0.55 mmol, 93%) after crystallization from water; $^1H$ NMR (300 MHz, DMSO): δ 12.95 (s, 1H), 8.07 (t, J=5.5 Hz, 1H), 7.85 (d, J=8.2 Hz, 2H), 7.66-7.49 (m, 1H), 7.46-7.36 (m, 1H), 7.18-7.03 (m, 4H), 6.36-5.90 (m, 2H), 5.77-5.34 (m, 3H), 4.82 (d, J=16.6 Hz, 1H), 4.55 (d, J=16.5 Hz, 1H), 3.90 (d, J=14.2 Hz, 2H), 3.57-3.41 (m, 3H), 3.07 (dd, J=12.8, 6.8 Hz, 2H), 1.63-1.55 (m, 1H), 1.52-1.46 (m, 1H). ESI-MS m/z (%): 487 [MH$^+$] (100). Anal. calcd for $C_{19}H_{20}N_4O_3$×½ tert-Butyl 2,2,2-trifluoracetat×2H$_2$O: C, 61.11; H, 5.56; N, 9.50; found: C, 61.00; H, 5.38; N, 9.50.

4-((4-(3-Acrylamidopropyl)-8-methoxy-3,5-dioxo-3,4,5,6-tetrahydro-2,6-methano[1,3]diazocino[5,6-b]indol-1(1H)-yl)methyl)benzoic acid (99c)

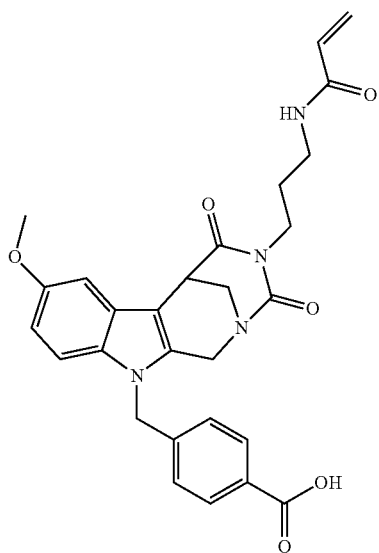 [SMILES: C=CC(=O)NCCCN1C(=O)C2CN(Cc3c2c2cc(OC)ccc2n3Cc2ccc(C(=O)O)cc2)C1=O]

According to GP7 from tert-butyl 4-((4-(3-acrylamidopropyl)-8-methoxy-3,5-dioxo-3,4,5,6-tetrahydro-2,6-methano[1,3]diazocino[5,6-b]indol-11(1H)-yl)methyl)benzoate (98c). Yield: Colorless crystals (0.27 g, 0.53 mmol, 90%) after crystallization from water/trifluoroacetic acid, RP-HPLC: 96% ($t_R$=14.58 min); $^1H$ NMR (300 MHz, DMSO): δ 12.99 (s, 1H), 8.08 (t, J=5.5 Hz, 1H), 7.84 (d, J=8.3 Hz, 2H), 7.30 (d, J=8.9 Hz, 1H), 7.10 (d, J=8.3 Hz, 2H), 6.97 (d, J=2.4 Hz, 1H), 6.74 (dd, J=8.9, 2.4 Hz, 1H), 6.17 (dd, J=17.1, 9.8 Hz, 1H), 6.04 (dd, J=17.1, 2.6 Hz, 1H), 5.55 (dd, J=9.8, 2.6 Hz, 1H), 5.41 (s, 2H), 4.79 (d, J=16.6 Hz, 1H), 4.52 (d, J=16.5 Hz, 1H), 3.95-3.80 (m, 2H), 3.75 (s, 3H), 3.53 (t, J=7.1 Hz, 2H), 3.44 (d, J=11.2 Hz, 1H), 3.08 (dd, J=12.9, 6.9 Hz, 2H), 1.66-1.53 (m, 2H). HR-MS m/z: Calcd. 517.2082 [MH$^+$]. found. 517.2087 [MH$^+$].

4-((4-(2-Acrylamidoethyl)-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (100a)

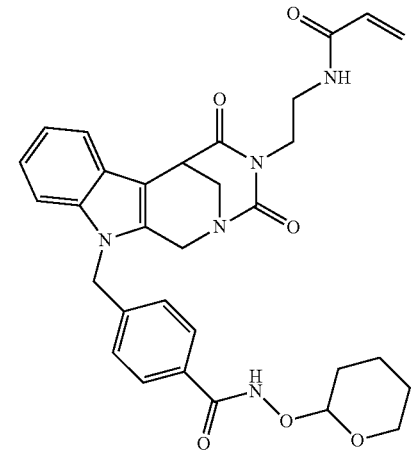 [SMILES: C=CC(=O)NCCN1C(=O)C2CN(Cc3c2c2ccccc2n3Cc2ccc(C(=O)NOC3CCCCO3)cc2)C1=O]

According to GP8 from 4-((4-(2-acrylamidoethyl)-3,5-dioxo-3,4,5,6-tetrahydro-2,6-methano[1,3]diazocino[5,6-b]indol-11(1H)-yl)methyl)benzoic acid (99a) (0.31 g; 0.66 mmol). 0.30 g (0.53 mmol; 80%) colorless foam after CC ($SiO_2$, ethyl acetate); mp 90-92° C. $^1H$ NMR (300 MHz, DMSO-d$_6$): δ 11.59 (s, 1H), 8.24 (t, J=6.2 Hz, 1H), 7.67 (d, J=8.3 Hz, 2H), 7.51 (dd, J=6.2, 2.5 Hz, 1H), 7.40 (dd, J=6.5, 2.1 Hz, 1H), 7.13 (d, J=8.3 Hz, 2H), 7.10-7.02 (m, 2H), 6.16 (dd, J=17.1, 9.5 Hz, 1H), 6.06 (dd, J=17.1, 2.8 Hz, 1H), 5.99 (s, 2H), 5.59 (dd, J=9.5, 2.8 Hz, 1H), 5.42 (s, 1H), 4.95 (s, 1H), 4.84 (d, J=16.6 Hz, 1H), 4.63-4.46 (m, 1H), 4.02 (s, 1H), 3.86 (d, J=8.9 Hz, 2H), 3.64 (t, J=6.0 Hz, 2H), 3.40 (s, 1H), 3.24 (ddd, J=19.5, 13.2, 6.5 Hz, 2H), 1.69 (s, 3H), 1.47-1.39 (m, 3H). ESI-MS m/z (%): 572 [MH$^+$] (100), 488 [MH$^+$−Dihydropyranyl] (74).

4-((4-(3-Acrylamidopropyl)-8-methoxy-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (100c)

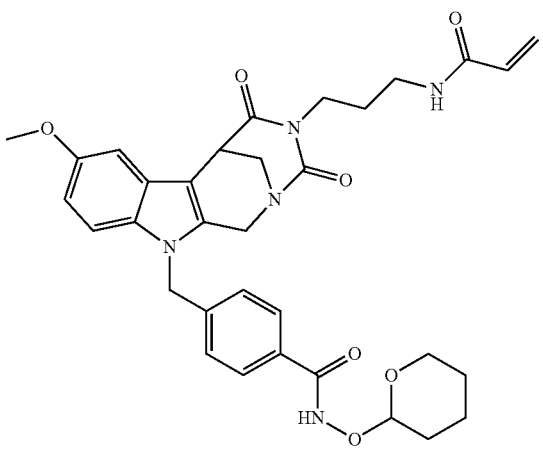 [SMILES: C=CC(=O)NCCCN1C(=O)C2CN(Cc3c2c2cc(OC)ccc2n3Cc2ccc(C(=O)NOC3CCCCO3)cc2)C1=O]

According to GP 8 from 4-((4-(3-acrylamidopropyl)-8-methoxy-3,5-dioxo-3,4,5,6-tetrahydro-2,6-methano[1,3]diazocino[5,6-b]indol-11(1H)-yl)methyl)benzoic acid (99c). Yield: Colorless (0.12 g, 0.20 mmol, 43%) after crystallization from ethyl acetate/petroleum ether, $^1$H NMR (400 MHz, DMSO): δ 11.58 (s, 1H), 8.07 (t, J=5.5 Hz, 1H), 7.66 (d, J=8.2 Hz, 2H), 7.29 (d, J=9.0 Hz, 1H), 7.08 (d, J=8.3 Hz, 2H), 6.97 (d, J=2.4 Hz, 1H), 6.74 (dd, J=8.9, 2.5 Hz, 1H), 6.17 (dd, J=17.1, 10.0 Hz, 1H), 6.06 (dd, J=17.1, 2.4 Hz, 1H), 5.56 (dd, J=10.0, 2.4 Hz, 1H), 5.38 (s, 2H), 4.96 (s, 1H), 4.81 (d, J=16.6 Hz, 1H), 4.54 (d, J=16.5 Hz, 1H), 4.11-3.97 (m, 1H), 3.90 (d, J=13.0 Hz, 1H), 3.84 (s, 1H), 3.75 (s, 3H), 3.57-3.47 (m, 3H), 3.45 (dd, J=13.3, 2.1 Hz, 1H), 3.14-3.05 (m, 2H), 1.74-1.63 (m, 3H), 1.60-1.48 (m, 5H). ESI-MS m/z (%): 616 [MH$^+$] (100); 638 [MH$^+$+Na$^+$] (79).

4-((4-(2-Acrylamidoethyl)-3,5-dioxo-3,4,5,6-tetrahydro-2,6-methano[1,3]diazocino[5,6-b]indol-11(1H)-yl)methyl)-N-hydroxybenzamide (101a)

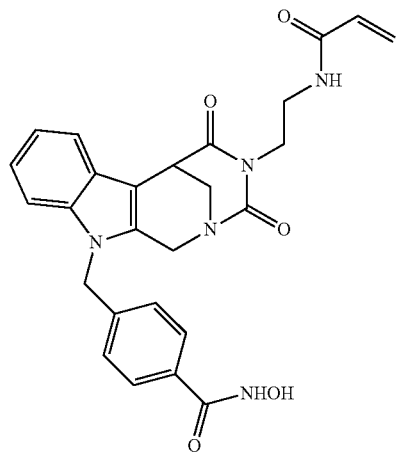

According to GP9 from 4-((4-(2-acrylamidoethyl)-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (100a) (0.22 g; 0.38 mmol). 0.09 g (0.18 mmol; 48%) colorless crystals. mp 212-214° C. IR (KBr): 1725, 1679 cm$^{-1}$. $^1$H NMR (300 MHz, DMSO-d$_6$): $^1$H NMR (300 MHz, DMSO): δ 11.16 (s, 1H), 9.02 (s, 1H), 8.25 (t, J=6.0 Hz, 1H), 7.65 (d, J=8.3 Hz, 2H), 7.51 (dd, J=6.3, 2.5 Hz, 1H), 7.40 (dd, J=6.6, 2.1 Hz, 1H), 7.15-6.93 (m, 4H), 6.16 (dd, J=17.1, 9.5 Hz, 1H), 6.06 (dd, J=17.1, 2.8 Hz, 1H), 5.59 (dd, J=9.5, 2.8 Hz, 1H), 5.41 (s, 2H), 4.84 (d, J=16.6 Hz, 1H), 4.55 (d, J=16.5 Hz, 1H), 3.86 (d, J=8.8 Hz, 2H), 3.64 (t, J=6.0 Hz, 2H), 3.42 (d, J=11.1 Hz, 1H), 3.23 (ddd, J=17.0, 11.4, 5.1 Hz, 2H). ESI-MS m/z (%): 488 [MH$^+$] (100).

4-((4-(3-acrylamidopropyl)-3,5-dioxo-3,4,5,6-tetrahydro-2,6-methano[1,3]diazocino[5,6-b]indol-11(1H)-yl)methyl)benzoic acid (101b)

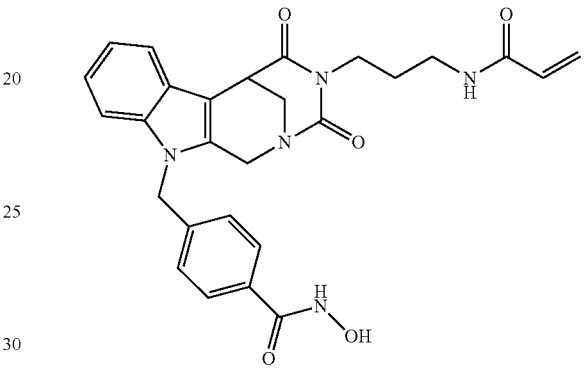

According to GP 8 from 4-((4-(3-acrylamidopropyl)-3,5-dioxo-3,4,5,6-tetrahydro-2,6-methano[1,3]diazocino[5,6-b]indol-11(1H)-yl)methyl)benzoic acid (100b) and directly converted after GP 9 gave colorless crystals (0.03 g, 0.06 mmol, 44%) after crystallization from 0.5 N HCl$_{aq}$/methanol; $^1$H NMR (600 MHz, MeOD): δ 7.63 (dd, J=17.4, 7.8 Hz, 3H), 7.29 (d, J=8.0 Hz, 1H), 7.10 (dt, J=21.7, 7.1 Hz, 2H), 7.02 (d, J=8.0 Hz, 2H), 6.18 (d, J=5.9 Hz, 2H), 5.67-5.56 (m, 1H), 5.35 (d, J=24.4 Hz, 2H), 4.81-4.75 (m, 1H), 4.52 (d, J=16.3 Hz, 1H), 3.98 (dd, J=24.2, 9.4 Hz, 1H), 3.88 (s, 1H), 3.72-3.64 (m, 2H), 3.47 (d, J=13.0 Hz, 1H), 3.22-3.16 (m, 2H), 1.76-1.61 (m, 2H). ESI-MS m/z (%): 502 [MH$^+$] (100), RP-HPLC (220 nm): 100.0% (gradient: 0-30 min: MeCN/0.1% aq. TFA 20/80-95/5, 31-40 min: 95/5, tR=13.6 min).

4-((4-(3-Acrylamidopropyl)-8-methoxy-3,5-dioxo-3,4,5,6-tetrahydro-2,6-methano[1,3]diazocino[5,6-b]indol-11(1H)-yl)methyl)-N-hydroxybenzamide (101c)

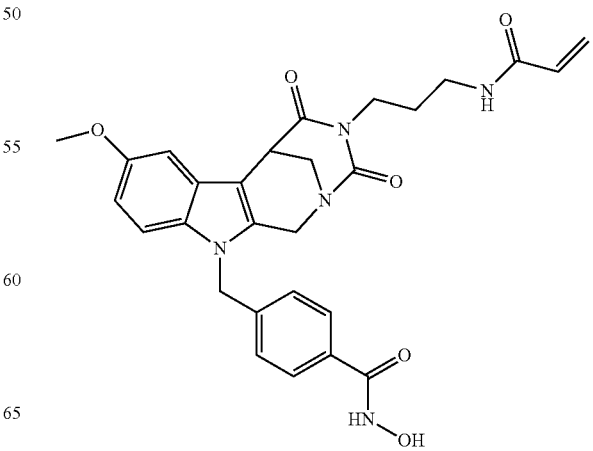

According to GP9 from 4-((4-(3-acrylamidopropyl)-8-methoxy-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (100c). Yield: Colorless crystals (0.05 g, 0.10 mmol, 63%) after crystallization from 0.6 N HCl$_{(aq)}$/methanol, mp: 134.2-134.3° C.; IR (KBr): 1724, 1674, 1624 cm$^{-1}$; $^1$H NMR (300 MHz, DMSO): δ 11.18 (s, 1H), 9.03 (s, 1H), 8.10 (t, J=5.6 Hz, 1H), 7.64 (d, J=8.2 Hz, 2H), 7.29 (d, J=8.9 Hz, 1H), 7.06 (d, J=8.3 Hz, 2H), 6.96 (d, J=2.4 Hz, 1H), 6.73 (dd, J=8.9, 2.4 Hz, 1H), 6.17 (dd, J=17.1, 9.8 Hz, 1H), 6.05 (dd, J=17.1, 2.6 Hz, 1H), 5.56 (dd, J=9.8, 2.6 Hz, 1H), 5.37 (s, 2H), 4.81 (d, J=16.6 Hz, 1H), 4.55 (d, J=16.6 Hz, 1H), 3.90 (d, J=12.8 Hz, 1H), 3.83 (s, 1H), 3.75 (s, 3H), 3.54 (t, J=7.4 Hz, 2H), 3.50-3.39 (m, 2H), 3.08 (dd, J=13.3, 6.6 Hz, 2H), 1.68-1.44 (m, 2H). ESI-MS m/z (%): 532 [MH$^+$] (100). Anal. (C$_{28}$H$_{29}$N$_5$O$_6$+2 H$_2$O): Calcd. C, 59.25; H, 5.86; N, 12.34; found. C, 59.55; H, 5.91; N, 11.98.

Methyl 2-amino-3-(1H-indol-3-yl)propanoate hydrochloride (103)

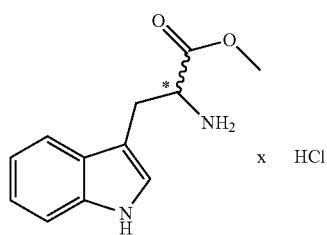 [SMILES: COC(=O)C(N)Cc1c[nH]c2ccccc12 ; Cl]

Tryptophane (102) (10.00 g, 49.0 mmol)) was dissolved in methanol, and thionyl chloride was added at 0° C. The solution was refluxed for 18 h and the solvent removed. The white residue was used without further purification (Packer et al., 2011). Yield 12.27 g (48.0 mmol, 98%) colorless crystals after crystallization from methanol. mp 213.1-216.4° C.; IR (KBr): 3263, 1749 cm$^{-1}$, $^1$H NMR (300 MHz, DMSO): δ 11.10 (s, 1H), 8.51 (s, 3H), 7.50 (d, J=7.7 Hz, 1H), 7.37 (d, J=8.0 Hz, 1H), 7.24 (d, J=2.4 Hz, 1H), 7.09 (dd, J=11.0, 4.0 Hz, 1H), 7.04-6.95 (m, 1H), 4.24 (t, J=6.2 Hz, 1H), 3.66 (s, 3H), 3.33-3.21 (m, 2H). ESI-MS m/z (%): 219 [MH$^+$] (100). Anal. calcd for C$_{12}$H$_{15}$N$_2$O$_2$Cl×½₀HCl: C, 56.58; H, 5.96; N, 11.08; found: C, 56.59; H, 5.99; N, 10.99.

Methyl 2,3,4,9-tetrahydro-1H-pyrido[3,4-b]indole-3-carboxylate hydrochloride (104a)

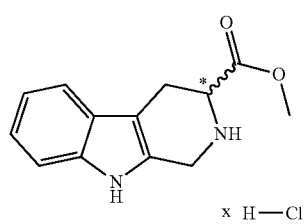

According to GP2 from methyl 2-amino-3-(1H-indol-3-yl)propanoate hydrochloride (103) (12.27 g; 48.00 mmol); Yield 11.90 g (93%) colorless crystals after crystallization from methanol/H$_2$O, mp.: 273.4-275.8° C.; IR (KBr): 1750, 3230 cm$^{-1}$, $^1$H NMR (300 MHz, DMSO): δ 11.24 (s, 1H), 10.30 (s, 2H), 7.48 (d, J=7.7 Hz, 1H), 7.37 (d, J=8.0 Hz, 1H), 7.16-7.07 (m, 1H), 7.06-6.98 (m, 1H), 4.72-4.57 (m, 1H), 4.48-4.32 (m, 2H), 3.83 (s, 3H), 3.30 (dd, J=15.9, 5.3 Hz, 1H), 3.07 (dd, J=15.9, 10.1 Hz, 1H), $^1$H NMR (300 MHz, MeOD) δ 7.51-7.45 (m, 1H), 7.38-7.32 (m, 1H), 7.19-7.11 (m, 1H), 7.11-7.02 (m, 1H), 4.56 (dd, J=9.5, 4.2 Hz, 3H), 3.92 (s, 3H), 3.46 (dd, J=16.2, 5.4 Hz, 1H), 3.25-3.10 (m, 1H). ESI-MS m/z (%): 231 [MH$^+$] (100). Anal. calcd for C$_{13}$H$_{15}$N$_2$O$_2$Cl: C, 58.54; H, 5.67; N, 10.50; found: C, 58.36; H, 5.68; N, 10.04.

Methyl (1S,3S)-1-methyl-2,3,4,9-tetrahydro-1H-pyrido[3,4-b]indole-3-carboxylate hydrochloride (104b)

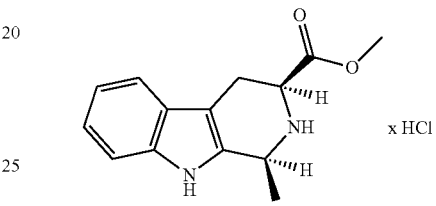

Synthesis modified after Zhao et al. (2006). Precipitation was performed by addition of ether to the methanolic solution. Colorless crystals (5.05 g, 18.00 mmol, 78%), mp: 250.0-251.0° C.; IR (KBr): 3223, 1724, 1608 cm$^{-1}$; $^1$H NMR (300 MHz, DMSO): δ 11.39 (s, 1H), 10.17 (s, 2H), 7.49 (d, J=7.7 Hz, 1H), 7.38 (d, J=8.0 Hz, 1H), 7.13 (t, J=7.3 Hz, 1H), 7.03 (t, J=7.3 Hz, 1H), 4.74 (d, J=6.3 Hz, 1H), 4.63 (dd, J=11.8, 4.8 Hz, 1H), 3.86 (s, 3H), 3.29 (dd, J=15.7, 4.6 Hz, 1H), 3.12-2.97 (m, 1H), 1.73 (d, J=6.7 Hz, 3H). ESI-MS m/z (%): 245 [MH$^+$] (100). Anal. (C$_{14}$H$_{17}$N$_4$O$_4$Cl+½H$_2$O+½ MeOH): Anal. Calcd. C, 56.96; H, 6.39; N, 8.74; found: C, 56.65; H, 6.53; N, 8.82.

2-Methyl-5,6,11,11a-tetrahydro-1H-imidazo[1',5':1,6]pyrido[3,4-b]indole-1,3(2H)-dione (108)

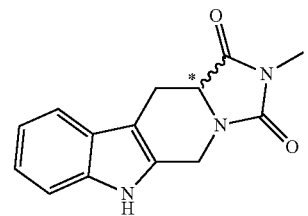 [SMILES: CN1C(=O)C2Cc3c([nH]c4ccccc34)CN2C1=O]

Methyl-2,3,4,9-tetrahydro-1H-pyrido[3,4-b]indole-3-carboxylate hydrochloride (104a) (2.43 g, 9.00 mmol) was suspended in acetonitrile (25.0 mL), and diisopropylethylamine (2.5 mL) was added with stirring. To the resulting solution N-succinimidyl-N-methyl-carbamate (1.88 g, 10.80 mol) was added and the mixture stirred at room temperature for 16 h. The solvent was evaporated completely and the residue reacted without further purification. In the second step dioxane and cesium carbonate (2 eq.) were added and the mixture heated to 90° C. for 1 h. Yield 1.65 g (6.46 mmol, 71% over 2 steps) colorless crystals after column chromatography with dichloromethane and ethyl acetate (10:1); mp: 243-245° C., IR (KBr): 1713, 1761, 3313 cm$^{-1}$ $^{1}$H NMR (400 MHz, DMSO): δ 11.02 (s, 1H), 7.47 (t, J=8.3 Hz, 1H), 7.35 (d, J=8.0 Hz, 1H), 7.17-6.90 (m, 2H), 4.97-4.81 (m, 1H), 4.48-4.35 (m, 2H), 3.23 (dd, J=14.9, 4.7 Hz, 1H), 2.93 (s, J=9.6 Hz, 3H), 2.83-2.61 (m, 1H). ESI-MS m/z (%): 256 [MH$^{+}$] (100). Anal. calcd for $C_{14}H_{13}N_{3}O_{2}$: C, 65.87; H, 5.13; N, 16.46; found: C, 65.63; H, 5.16; N, 16.03.

2-Butyl-5,6,11,11a-tetrahydro-1H-imidazo[1',5':1,6]pyrido[3,4-b]indole-1,3(2H)-dione (109a)

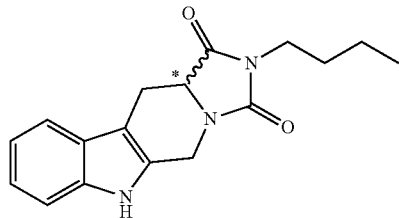 [SMILES: CCCCN1C(=O)C2Cc3c([nH]c4ccccc34)CN2C1=O]

Methyl-2,3,4,9-tetrahydro-1H-pyrido[3,4-b]indole-3-carboxylate hydrochloride (104a) (5 g; 18.80 mmol) was reacted analogously to 108 with butyl isocyanate (105a) (1 eq). 1.66 g (4.91 mmol, 29% over 2 steps) colorless crystals after crystallization from diethyl ether. mp 172-175° C., IR (KBr): 1767, 1713 cm$^{-1}$ $^{1}$H NMR (300 MHz, DMSO): δ 11.04 (s, 1H), 7.47 (d, J=7.6 Hz, 1H), 7.34 (d, J=8.0 Hz, 1H), 7.11-7.04 (m, 1H), 7.03-6.94 (m, 1H), 4.90 (d, J=16.3 Hz, 1H), 4.47-4.34 (m, 2H), 3.44 (t, J=7.0 Hz, 2H), 3.24 (dd, J=15.0, 5.2 Hz, 1H), 2.76-2.60 (m, 1H), 1.62-1.45 (m, 2H), 1.39-1.18 (m, 2H), 0.89 (t, J=7.3 Hz, 3H). ESI-MS m/z (%): 298 [MH$^{+}$] (100). Anal. calcd for $C_{14}H_{13}N_{3}O_{2}$: C, 68.67; H, 6.44; N, 14.13; found: C, 68.59; H, 6.35; N, 14.25.

2-Ethyl-5,6,11,11a-tetrahydro-1H-imidazo[1',5':1,6]pyrido[3,4-b]indol-1,3(2H)-dione (109b)

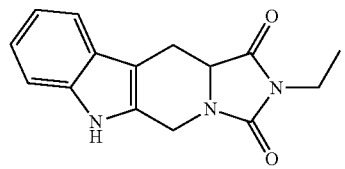 [SMILES: CCN1C(=O)C2Cc3c([nH]c4ccccc34)CN2C1=O]

Methyl-2,3,4,9-tetrahydro-1H-pyrido[3,4-b]indole-3-carboxylate hydrochloride (104a) was reacted analogously to 108 with ethyl isocyanate (105b) (1 eq). Colorless crystals (1.81 g, 6.69 mmol, 59% over 2 Steps). mp: 155.9-156.3° C.; IR (KBr): 1772, 1703, 1622 cm$^{-1}$; $^{1}$H NMR (300 MHz, DMSO): δ 11.03 (s, 1H), 7.47 (d, J=7.7 Hz, 1H), 7.34 (d, J=7.9 Hz, 1H), 7.12-7.04 (m, 1H), 7.03-6.95 (m, 1H), 4.90 (d, J=16.2 Hz, 1H), 4.40 (dd, J=10.9, 5.5 Hz, 2H), 3.48 (q, J=7.1 Hz, 2H), 3.23 (dd, J=14.7, 5.3 Hz, 1H), 2.77-2.62 (m, 1H), 1.13 (t, J=7.2 Hz, 3H). ESI-MS m/z (%): 270 [MH$^{+}$] (100). Anal. ($C_{15}H_{15}N_{3}O_{2}$+⅙ DCM): Calcd. C, 64.27; H, 5.54; N, 14.88; found: C, 64.51; H, 5.57; N, 14.80.

2-Propyl-5,6,11,11a-tetrahydro-1H-imidazo[1',5':1,6]pyrido[3,4-b]indol-1,3(2H)-dione (109c)

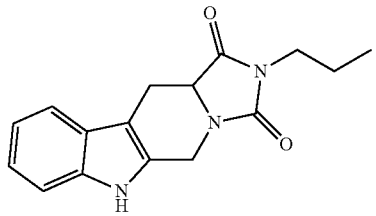 [SMILES: CCCN1C(=O)C2Cc3c([nH]c4ccccc34)CN2C1=O]

Methyl-2,3,4,9-tetrahydro-1H-pyrido[3,4-b]indole-3-carboxylate hydrochloride (104a) was reacted analogously with propyl isocyanate (105c) (1 eq). Colorless crystals (1.62 g, 5.72 mmol, 51% over 2 steps). mp: 178.0-178.5° C.; IR (KBr): 1761, 1700 cm$^{-1}$; $^{1}$H NMR (300 MHz, DMSO): δ 11.04 (s, 1H), 7.48 (d, J=7.7 Hz, 1H), 7.34 (d, J=8.0 Hz, 1H), 7.08 (t, J=7.0 Hz, 1H), 6.99 (t, J=7.1 Hz, 1H), 4.91 (d, J=16.2 Hz, 1H), 4.51-4.31 (m, 2H), 3.40 (t, J=7.1 Hz, 2H), 3.24 (dd, J=14.9, 5.4 Hz, 1H), 2.84-2.62 (m, 1H), 1.69-1.45 (m, 2H), 0.86 (t, J=7.4 Hz, 3H). ESI-MS m/z (%): 284 [MH$^{+}$] (100). Anal. ($C_{16}H_{17}N_{3}O_{2}$): Calcd. C, 67.83; H, 6.05; N, 14.83; found. C, 67.70; H, 6.00; N, 14.75.

tert-Butyl 4-((2-methyl-1,3-dioxo-2,3,11,11a-tetrahydro-1H-imidazo[1',5':1,6]pyrido[3,4-b]indol-6(5H)-yl)methyl)benzoate (110)

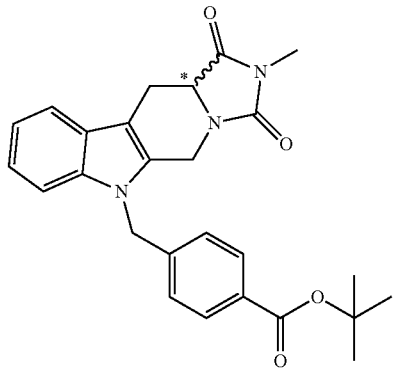 [SMILES: CN1C(=O)C2Cc3c(n(Cc4ccc(C(=O)OC(C)(C)C)cc4)c4ccccc34)CN2C1=O]

2-Methyl-5,6,11,11a-tetrahydro-1H-imidazo[1',5':1,6]pyrido[3,4-b]indole-1,3(2H)-dione (108) (1.96 mmol) was dissolved under a nitrogen atmosphere in butanone and potassium carbonate was added (10 eq.). After addition of 1.2 eq. of the alkylating reagent (23) the mixture was refluxed for 48 h. After completion of the reaction (TLC monitoring), the reaction mixture is carefully poured into water with stirring. If the product crystallizes, it was filtered off and dried under vacuum. Alternatively, the aqueous phase was extracted with dichloromethane (4×50.0 mL), the combined organic phases were washed with brine (50.0 mL), dried over sodium sulfate and the solvent was removed. Purification was carried out in both cases by chromatography on silica gel with a suitable eluent.

0.57 g (1.27 mmol, 65%) colorless crystals after crystallization (dropwise addition of a solution in ethyl acetate to diethyl ether). mp 232-235 cm$^{-1}$1, IR (KBr): 1768, 1710 cm$^{-1}$, $^{1}$H NMR (300 MHz, CDCl$_{3}$): δ 7.96-7.81 (m, 2H), 7.54 (dt, J=7.7, 4.0 Hz, 1H), 7.26-7.14 (m, 3H), 7.02 (d, J=8.3 Hz, 2H), 5.43-5.16 (m, 2H), 5.00 (dd, J=16.1, 1.5 Hz, 1H), 4.37-4.12 (m, 2H), 3.63-3.35 (m, 1H), 3.09 (s, 3H), 2.97-2.78 (m, 1H), 1.56 (s, 9H). ESI-MS m/z (%): 446 [MH⁺] 390 [M–C₄H₈] (100) (50) 372 [M-tert-butanol] (64). Anal. calcd for C₂₆H₂₇N₃O₄×⅕ ethyl acetate: C, 69.50; H, 6.22; N, 9.07. found: C, 69.20, H, 6.03, N, 9.43.

tert-Butyl 4-((2-butyl-1,3-dioxo-2,3,11,11a-tetrahydro-1H-imidazo[1',5':1,6]pyrido[3,4-b]indol-6(5H)-yl)methyl)benzoate (111a)

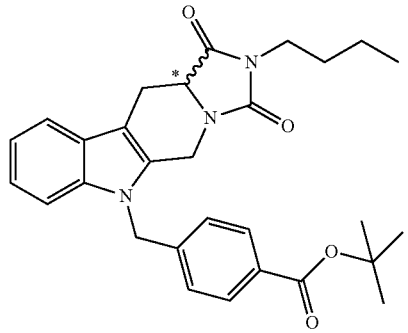 [SMILES: CCCCN1C(=O)C2Cc3c(n(Cc4ccc(C(=O)OC(C)(C)C)cc4)c4ccccc34)CN2C1=O]

2-Butyl-5,6,11,11a-tetrahydro-1H-imidazo[1',5':1,6]pyrido[3,4-b]indole-1,3(2H)-dione (109a) (0.85 g; 2.86 mmol) was reacted analogously to 108. Yield 0.87 g (1.79 mmol, 62%) yellowish-colorless crystals; mp: 163-165° C., ¹H NMR (300 MHz, CDCl₃): δ 7.90 (d, J=8.3 Hz, 2H), 7.55 (dd, J=6.7, 1.6 Hz, 1H), 7.25-7.13 (m, 3H), 7.04 (d, J=8.3 Hz, 2H), 5.40-5.22 (m, 2H), 5.00 (d, J=16.1 Hz, 1H), 4.30-4.14 (m, 2H), 3.56 (t, J=7.3 Hz, 2H), 3.46 (dd, J=14.9, 5.2 Hz, 1H), 2.96-2.73 (m, 1H), 1.69-1.60 (m, 2H), 1.56 (s, 9H), 1.43-1.30 (m, 2H), 0.94 (t, J=7.3 Hz, 3H). ESI-MS m/z (%): 488 [MH⁺] (14); 432 [MH⁺–C₄H₈] (100). Anal. calcd for C₂₉H₃₃N₃O₄: C, 71.44; H, 6.82; N, 8.62; found: C, 71.21; H, 6.53; N, 8.56.

tert-Butyl 4-((2-ethyl-1,3-dioxo-1,2,3,5,11,11a-hexahydro-6H-imidazo[1',5':1,6]pyrido[3,4-b]indol-6-yl)methyl)benzoate (111b)

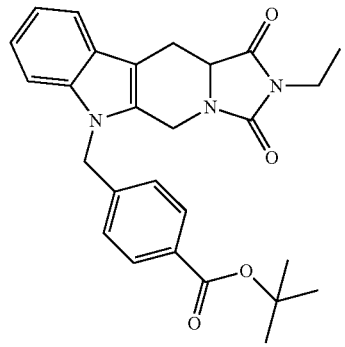 [SMILES: CCN1C(=O)C2Cc3c(n(Cc4ccc(C(=O)OC(C)(C)C)cc4)c4ccccc34)CN2C1=O]

109b was reacted analogously to 108 to obtain 111b. Colorless crystals (1.50 g, 3.30 mmol, 46%); mp: 186.4-186.7° C.; IR (KBr): 1771, 1713, 1610 cm⁻¹; ¹H NMR (300 MHz, DMSO): δ 7.83 (d, J=8.3 Hz, 2H), 7.56 (d, J=7.3 Hz, 1H), 7.45 (d, J=7.9 Hz, 1H), 7.20-7.09 (m, 3H), 7.07 (dd, J=11.0, 3.7 Hz, 1H), 5.63-5.43 (m, 2H), 4.89 (d, J=16.3 Hz, 1H), 4.39 (dd, J=10.9, 5.4 Hz, 1H), 4.30 (d, J=16.5 Hz, 1H), 3.46 (q, J=7.1 Hz, 2H), 3.29 (dd, J=15.0, 5.3 Hz, 1H), 2.85-2.63 (m, 1H), 1.51 (s, 9H), 1.12 (t, J=7.1 Hz, 3H). ESI-MS m/z (%): 404 [MH⁺–C₄H₈] (100); 460 [MH⁺] (60). Anal. (C₂₇H₂₉N₃O₄+¼ ETHYL ACETATE): Calcd. C, 69.84; H, 6.49; N, 8.73; found. C, 69.44; H, 6.24; N, 8.91.

tert-Butyl 4-((1,3-dioxo-2-propyl-1,2,3,5,11,11a-hexahydro-6H-imidazo[1',5':1,6]pyrido[3,4-b]indol-6-yl)methyl)benzoate (111c)

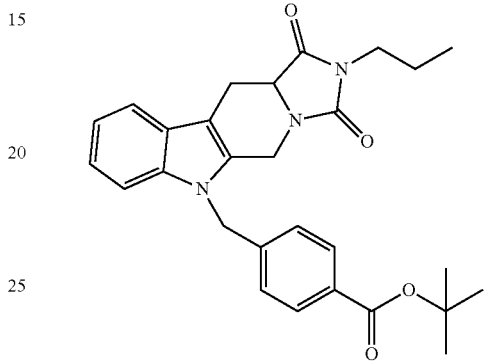

109c was reacted analogously to 108 to obtain 11c. Colorless crystals (1.90 g, 4.00 mmol, 53%) mp: Decomposition at 135° C.; IR (KBr): 1769, 1708, 1612 cm⁻¹; ¹H NMR (300 MHz, DMSO): δ 7.83 (d, J=8.3 Hz, 2H), 7.56 (d, J=7.8 Hz, 1H), 7.46 (d, J=7.9 Hz, 1H), 7.19-7.01 (m, 4H), 5.66-5.42 (m, 2H), 4.89 (d, J=16.3 Hz, 1H), 4.41 (dd, J=11.0, 5.4 Hz, 1H), 4.30 (d, J=16.5 Hz, 1H), 3.38-3.25 (m, 3H), 2.82-2.67 (m, 1H), 1.61-1.51 (m, 2H), 1.51 (s, 9H), 0.84 (t, J=7.4 Hz, 3H). ESI-MS m/z (%): 418 [MH⁺–C₄H₈] (100); 474 [MH⁺] (90). Anal. (C₂₅H₂₆N₄O₄): Calcd. C, 71.02; H, 6.60; N, 8.87; found. C, 70.97; H, 6.55; N, 8.69.

4-((-2-Methyl-1,3-dioxo-2,3,11,11a-tetrahydro-1H-imidazo[1',5':1,6]pyrido[3,4-b]indol-6(5H)-yl)methyl)-N-((tetrahydro-2H-pyran-2-yl)oxy)benzamide (114)

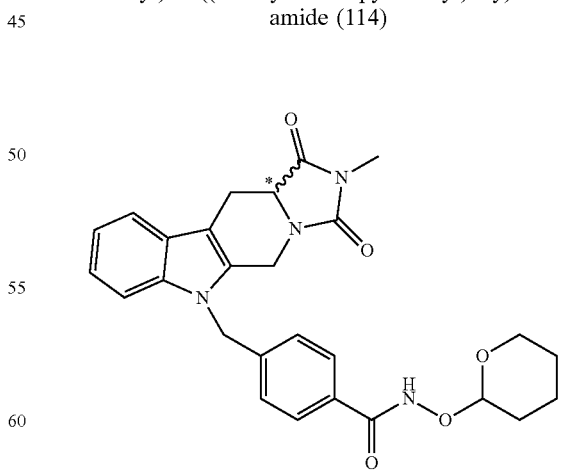

tert-butyl 4-((2-methyl-1,3-dioxo-2,3,11,11a-tetrahydro-1H-imidazo[1',5':1,6]pyrido[3,4-b]indol-6(5H)-yl)methyl)benzoate (110) (1.71 mmol) was dissolved in 5.00 mL of trifluoroacetic acid and stirred at room temperature for 15 minutes. After complete reaction (TLC monitoring), the solvent was removed and the residue was dissolved in 15.00 mL dimethylformamide. After addition of benzotriazol-1-yloxy-tris(dimethylamino)phosphonium hexafluorophosphate (BOP) (1 eq.), triethylamine (3 eq.), and O-(tetrahydro-2H-pyran-2-yl)hydroxylamine (4 eq) the mixture was stirred at 20° C. After completion of the reaction (TLC monitoring), the mixture was poured into water. If the crude product crystallized it was filtered off and dried in vacuo. Alternatively, it was extracted with dichloromethane (4×25.0 mL). The combined organic phases were washed with brine (25.0 mL) and dried over sodium sulfate. The solvent was removed and the residue dried in vacuo. Chromatography over silica gel in the specified eluent afforded the product. Yield 0.40 g (0.83 mmol, 48% over 2 steps) colorless-yellow crystals after crystallization by dropwise addition of a solution in dichloromethane to diethyl ether. mp 138-141° C. $^1$H NMR (300 MHz, CDCl$_3$): δ 8.84 (s, 1H), 7.67 (d, J=8.2 Hz, 2H), 7.58-7.52 (m, 1H), 7.26-7.14 (m, 3H), 7.04 (d, J=8.2 Hz, 2H), 5.38-5.21 (m, 2H), 5.09-4.93 (m, 2H), 4.29-4.17 (m, 2H), 4.04-3.89 (m, 1H), 3.69-3.55 (m, 1H), 3.46 (dd, J=15.1, 5.0 Hz, 1H), 3.09 (s, 3H), 2.90-2.78 (m, 1H), 1.91-1.79 (m, 3H), 1.63 (s, 3H). ESI-MS m/z (%): 498 [MH$^+$] (7); 405 [MH$^+$−C$_5$H$_8$O] (100). Anal. calcd for C$_{27}$H$_{48}$N$_4$O$_5$×⅕ CH$_2$Cl$_2$: C, 64.62; H, 5.66; N, 11.08; found: C, 64.68; H, 5.83; N, 11.57.

4-((-2-Butyl-1,3-dioxo-2,3,11,11a-tetrahydro-1H-imidazo[1',5':1,6]pyrido[3,4-b]indol-6(5H)-yl)methyl)-N-((tetrahydro-2H-pyran-2-yl)oxy)benzamide (115a)

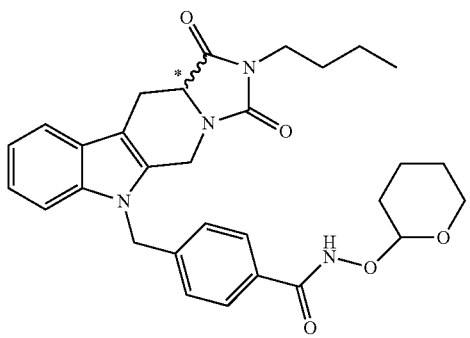 [SMILES: CCCCN1C(=O)C2Cc3c(n(Cc4ccc(C(=O)NOC5CCCCO5)cc4)c4ccccc34)CN2C1=O]

tert-Butyl 4-((2-butyl-1,3-dioxo-2,3,11,11a-tetrahydro-1H-imidazo[1',5':1,6]pyrido[3,4-b]indol-6(5H)-yl)methyl)benzoate (111a) (1.23 mmol) was reacted according to 110. Colorless-yellow crystals after crystallization by dropwise addition of a solution in dichloromethane/diethyl ether to light petroleum mp: 158-161° C. $^1$H NMR (300 MHz, CDCl$_3$): δ 8.83 (s, 1H), 7.67 (d, J=8.2 Hz, 2H), 7.58-7.52 (m, 1H), 7.25-7.13 (m, 3H), 7.05 (d, J=8.2 Hz, 2H), 5.40-5.19 (m, 2H), 5.08-4.91 (m, 2H), 4.28-4.13 (m, 2H), 4.04-3.88 (m, 1H), 3.68-3.53 (m, 3H), 3.45 (dd, J=15.2, 5.2 Hz, 1H), 2.89-2.75 (m, 1H), 1.94-1.76 (m, 3H), 1.73-1.63 (m, 2H), 1.59 (d, J=7.4 Hz, 3H), 1.37-1.23 (m, 2H), 0.93 (t, J=7.3 Hz, 3H). ESI-MS m/z (%): 531 [MH$^+$] (9); 447 [MH$^+$−C$_5$H$_8$O] (100). Anal. calcd. for C$_{30}$H$_{34}$N$_4$O$_5$×1/10CH$_2$Cl$_2$: C, 67.07; H, 6.39; N, 10.39; found: C, 67.14; H, 6.35; N, 10.47.

4-((2-Ethyl-1,3-dioxo-1,2,3,5,11,11a-hexahydro-6H-imidazo[1',5':1,6]pyrido[3,4-b]indol-6-yl)methyl)-N-((tetrahydro-2H-pyran-2-yl)oxy)benzamide (115b)

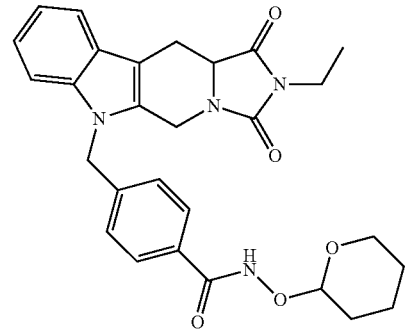 [SMILES: CCN1C(=O)C2Cc3c(n(Cc4ccc(C(=O)NOC5CCCCO5)cc4)c4ccccc34)CN2C1=O]

115b was obtained after reaction analogously to 110 from 114b. Colorless crystals (0.60 g, 1.19 mmol, 48%) mp: 147.5-147.8° C.; IR (KBr): 1759, 1707, 1674 cm$^{-1}$; $^1$H NMR (300 MHz, DMSO): δ 11.60 (s, 1H), 7.69 (d, J=8.2 Hz, 2H), 7.56 (d, J=7.6 Hz, 1H), 7.46 (d, J=8.0 Hz, 1H), 7.18-7.01 (m, 4H), 5.58-5.41 (m, 2H), 5.00-4.84 (m, 2H), 4.43-4.21 (m, 2H), 4.07-3.98 (m, 1H), 3.57-3.39 (m, 3H), 3.32-3.20 (m, 1H), 2.84-2.67 (m, 1H), 1.69 (s, J=27.2 Hz, 3H), 1.53 (s, 3H), 1.12 (t, J=7.1 Hz, 3H). HR-MS m/z: Calcd. 503.2289 [MH$^+$]. found. 503.2289 [MH$^+$].

4-((1,3-Dioxo-2-propyl-1,2,3,5,11,11a-hexahydro-6H-imidazo[1',5':1,6]pyrido[3,4-b]indol-6-yl)methyl)-N-((tetrahydro-2H-pyran-2-yl)oxy)benzamide (115c)

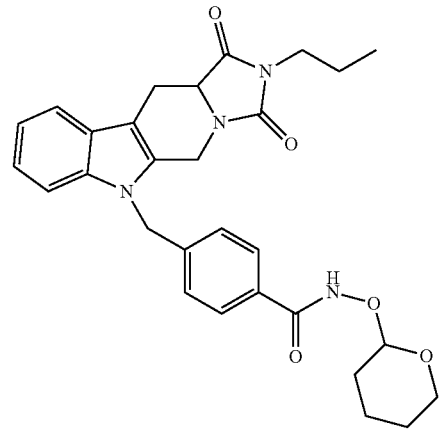 [SMILES: CCCN1C(=O)C2Cc3c(n(Cc4ccc(C(=O)NOC5CCCCO5)cc4)c4ccccc34)CN2C1=O]

114c was reacted analogously to 110 to obtain 116c. Colorless crystals (1.36 g, 2.63 mmol, 57%) after chromatography over silica gel with DCM/MeOH (10:1) and crystallization from ethyl acetate, mp: 110.3-110.6° C.; IR (KBr): 1769, 1710 cm$^{-1}$; $^1$H NMR (300 MHz, DMSO): δ 11.60 (s, 1H), 7.69 (d, J=8.2 Hz, 2H), 7.56 (d, J=7.4 Hz, 1H), 7.47 (d, J=8.0 Hz, 1H), 7.30-6.96 (m, 4H), 5.68-5.35 (m, 2H), 4.92 (d, J=21.7 Hz, 2H), 4.42 (dd, J=10.9, 5.4 Hz, 1H), 4.32 (d, J=16.4 Hz, 1H), 4.08-3.95 (m, 1H), 3.49 (d, J=11.9 Hz, 1H), 3.38 (t, J=7.0 Hz, 2H), 3.30 (dd, J=15.0, 5.3 Hz, 1H), 2.88-2.66 (m, 1H), 1.69 (s, 3H), 1.60-1.49 (m, 5H), 0.85 (t, J=7.4 Hz, 3H). HR-MS m/z: Calcd.: 517.2445 [MH⁺] Calcd.: 517.2449 [MH⁺]. Anal. ($C_{29}H_{32}N_4O_5$+½ ethyl acetate): Found. C, 66.41; H, 6.47; N, 9.99; found. C, 66.29; H, 6.40; N, 10.33.

N-hydroxy-4-((2-methyl-1,3-dioxo-2,3,11,11a-tetra-hydro-1H-imidazo[1',5':1,6]pyrido[3,4-b]indol-6 (5H)-yl)methyl)benzamide (116)

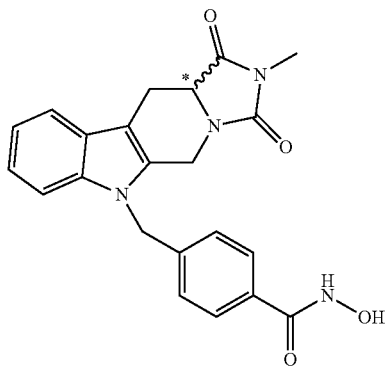 [SMILES: CN1C(=O)C2Cc3c(n(Cc4ccc(C(=O)NO)cc4)c4ccccc34)CN2C1=O]

4-((8-Methoxy-4-methyl-3,5-dioxo-3,4,5,6-tetrahydro-2, 6-methano[1,3]diazocino[5,6-b]indol-11(1H)-yl)methyl)-N-((tetrahydro-2H-pyran-2-yl)oxy)benzamide (114) (0.20 mmol) was dissolved in 8.0 mL of methanol, optionally with gentle heating. Carefully 0.6 M aqueous HCl was added dropwise until a slight turbidity by precipitating product was formed. Stirring at room temperature was continued until full implementation of the starting material. The crystallization of the hydroxamic acid was completed by further addition of 0.6 M HCl. The crystalline product was filtered off and dried in vacuo. 0.07 g (0.31 mmol, 55%) colorless-yellow crystals after crystallization from water/methanol with 1 M HCl aq; mp: 178-181° C., ¹H NMR (300 MHz, Acetone): δ 7.76 (d, J=8.3 Hz, 2H), 7.63-7.56 (m, 1H), 7.43 (d, J=7.7 Hz, 1H), 7.22-7.07 (m, 4H), 5.61-5.45 (m, 2H), 4.98 (dd, J=16.3, 1.6 Hz, 1H), 4.42-4.27 (m, 2H), 3.40-3.28 (m, 1H), 2.96 (s, 3H), 2.90-2.73 (m, 2H). ESI-MS m/z (%): 405 [MH⁺] (100). Anal. calcd. For $C_{22}H_{20}N_4O_4$+3/2H₂O: C, 61.24; H, 5.37; N, 12.99; found: C, 61.59; H, 5.37; N, 12.68.

4-((2-Butyl-1,3-dioxo-2,3,11,11a-tetrahydro-1H-imidazo[1',5':1,6]pyrido[3,4-b]indol-6(5H)-yl) methyl)-N-hydroxybenzamide (117a)

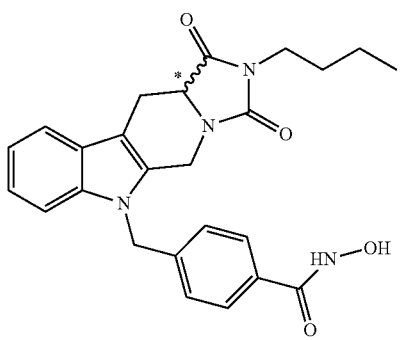 [SMILES: CCCCN1C(=O)C2Cc3c(n(Cc4ccc(C(=O)NO)cc4)c4ccccc34)CN2C1=O]

4-((-2-Butyl-1,3-dioxo-2,3,11,11a-tetrahydro-1H-imidazo[1',5':1,6]pyrido[3,4-b]indol-6(5H)-yl)methyl)-N-((tetrahydro-2H-pyran-2-yl)oxy)benzamide (0.28 mmol) (115a) was reacted according to 116.

Yield 0.08 g (0.18 mmol, 64%) colorless-yellow crystals after crystallization from water/methanol. mp: 200-202° C., 1H NMR (300 MHz, Acetone) δ 8.21 (s, 1H), 7.77 (d, J=8.3 Hz, 4H), 7.60 (d, J=8.1 Hz, 2H), 7.43 (d, J=7.7 Hz, 2H), 7.23-7.05 (m, 8H), 5.62-5.46 (m, 4H), 4.99 (dd, J=16.3, 1.5 Hz, 2H), 4.49-4.20 (m, 4H), 3.49 (t, J=7.1 Hz, 4H), 3.35 (dd, J=15.1, 5.4 Hz, 2H), 2.85-2.73 (m, 4H), 1.68-1.48 (m, 4H), 1.44-1.21 (m, 5H), 0.91 (t, J=7.3 Hz, 6H). ESI-MS m/z (%): 447 [MH⁺] (100). Anal. Calcd. For $C_{25}H_{26}N_4O_4$+½H₂O: C, 65.92; H, 5.97; N, 12.30; found: C, 66.05; H, 5.98; N, 12.10.

4-((2-Ethyl-1,3-dioxo-1,2,3,5,11,11a-hexahydro-6H-imidazo[1',5':1,6]pyrido[3,4-b]indol-6-yl)methyl)-N-hydroxybenzamide (117b)

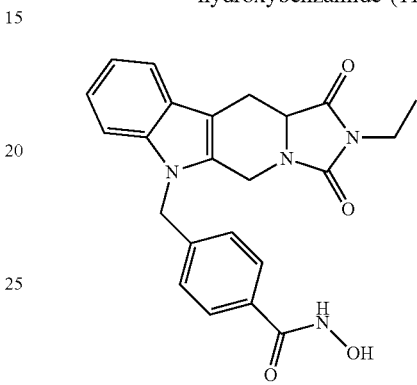

4-((2-Ethyl-1,3-dioxo-1,2,3,5,11,11a-hexahydro-6H-imidazo[1',5':1,6]pyrido[3,4-b]indol-6-yl)methyl)-N-((tetrahydro-2H-pyran-2-yl)oxy)benzamide (115b) was reacted according to 116 and yielded colorless crystals (0.21 g, 0.50 mmol, 50%) after crystallization from methanol/water; mp: 159.7-160.9° C.; IR (KBr): 1754, 1699, 1652 cm⁻¹; ¹H NMR (300 MHz, DMSO): δ 11.16 (s, 1H), 9.03 (s, 1H), 7.67 (d, J=8.3 Hz, 2H), 7.56 (d, J=7.5 Hz, 1H), 7.47 (d, J=8.1 Hz, 1H), 7.16-7.06 (m, 4H), 5.49 (q, J=17.1 Hz, 2H), 4.90 (d, J=16.4 Hz, 1H), 4.45-4.30 (m, 2H), 3.46 (q, J=7.1 Hz, 2H), 3.32-3.22 (m, 1H), 2.83-2.70 (m, 1H), 1.12 (t, J=7.1 Hz, 3H). ESI-MS m/z (%): 419 [MH⁺] (100). Anal. ($C_{23}H_{22}N_4O_4$+1 H₂O): Calcd. C, 63.29; H, 5.54; N, 12.84; found. C, 63.23; H, 5.47; N, 12.50.

4-((1,3-Dioxo-2-propyl-1,2,3,5,11,11a-hexahydro-6H-imidazo[1',5':1,6]pyrido[3,4-b]indol-6-yl) methyl)-N-hydroxybenzamide (117c)

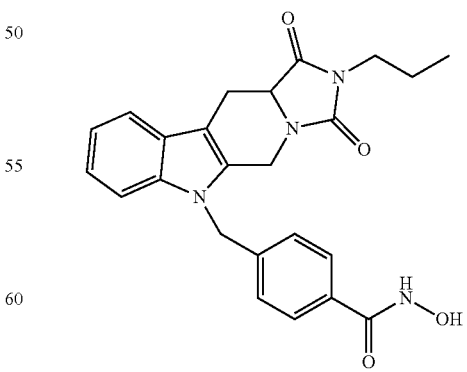

4-((1,3-Dioxo-2-propyl-1,2,3,5,11,11a-hexahydro-6H-imidazo[1',5':1,6]pyrido[3,4-b]indol-6-yl)methyl)-N-((tetrahydro-2H-pyran-2-yl)oxy)benzamide (115c) was reacted according to 116 and yielded 117c. Colorless crystals (0.15 g, 0.35 mmol, 55%) after crystallization from methanol/water. mp: 189.5-190.0° C.; IR (KBr): 1767, 1708, 1658 cm$^{-1}$; $^1$H NMR (300 MHz, DMSO): δ 11.16 (s, 1H), 7.67 (d, J=8.3 Hz, 2H), 7.56 (d, J=7.3 Hz, 1H), 7.47 (d, J=8.0 Hz, 1H), 7.25-6.95 (m, 4H), 5.65-5.32 (m, 2H), 4.91 (d, J=16.5 Hz, 1H), 4.53-4.29 (m, 2H), 3.38 (dd, J=9.7, 4.4 Hz, 2H), 3.30 (dd, J=14.9, 5.3 Hz, 1H), 2.87-2.67 (m, 1H), 1.63-1.47 (m, 2H), 0.85 (t, J=7.4 Hz, 3H). ESI-MS m/z (%): 433 [MH$^+$] (100). Anal. (C$_{24}$H$_{24}$N$_4$O$_4$+1 H$_2$O): Calcd. C, 63.99; H, 5.82; N, 12.44; found. C, 64.24; H, 5.65; N, 12.22.

Methyl 4-((8-methoxy-4-methyl-5-thioxo-3,4,5,6-tetrahydro-2,6-methano[1,3]diazocino [5,6-b]indol-11(1H)-yl)methyl)benzoate (118)

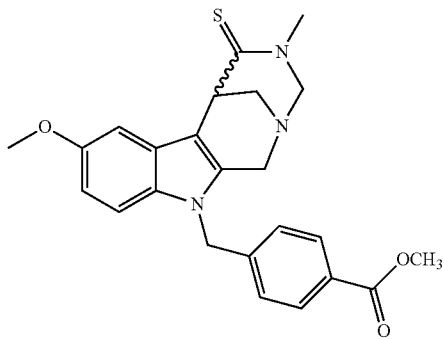 [SMILES: COC(=O)c1ccc(Cn2c3c(c4cc(OC)ccc42)C2CN(C3)CN(C)C2=S)cc1]

A solution of 55b (0.50 g, 1.20 mmol) and lawesson's reagent (0.25 g, 0.60 mmol) in THF (25 mL) was stirred at room temperature for 16 h. The mixture was poured into water (80 mL) and extracted with ethyl acetate (2×30 mL). The organic phase was separated, dried over Na$_2$SO$_4$ and the solvent removed under reduced pressure. The residue was purified by column chromatography (eluent: ethyl acetate/MeOH 10:1).

0.25 g (0.57 mmol, 48%) beige powder. mp 197-200° C. IR (KBr): 2936, 2837, 1719 cm$^{-1}$. $^1$H NMR (300 MHz, DMSO-d$_6$): δ 7.96-7.83 (m, 2H), 7.28-7.13 (m, 4H), 6.68 (dd, J=8.9, 2.5 Hz, 1H), 5.48-5.17 (m, 2H), 4.55 (dd, J=73.9, 13.5 Hz, 2H), 4.37-4.11 (m, 2H), 4.08 (d, J=1.8 Hz, 11H), 3.82 (s, 3H), 3.74 (s, 3H), 3.49 (dd, J=13.1, 2.0 Hz, 1H), 3.12-3.00 (m, 4H). ESI-MS m/z (%): 436 [MH]$^+$ (100). Anal. calcd for C$_{24}$H$_{25}$N$_3$O$_3$S×C$_4$H$_8$O$_2$: C, 65.36; H, 5.98; N, 9.38; found: C, 65.57; H, 5.80; N, 9.00.

4-((8-Methoxy-4-methyl-5-thioxo-3,4,5,6-tetrahydro-2,6-methano[1,3]diazocino[5,6-b]indol-11(1H)-yl)methyl)benzoic acid (119)

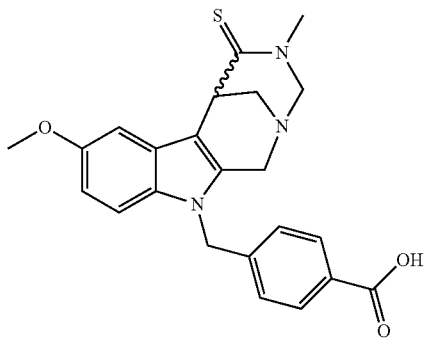 [SMILES: COc1ccc2c(c1)c1c(n2Cc2ccc(C(=O)O)cc2)CN2CC1C(=S)N(C)C2]

118 (0.60 g, 1.38 mmol) was dissolved in THF (10 mL) and MeOH (3 mL). After addition of a solution of LiOH (0.16 g, 6.66 mmol) in water (4 mL) the mixture was stirred at room temperature for 5 h (TLC monitoring). The solution was adjusted to pH 7 with acetic acid, poured into water (60 mL) and extracted with ethyl acetate (3×20 mL). The combined organic phases were dried over Na$_2$SO$_4$ and the solvent evaporated under reduced pressure.

0.56 g (1.32 mmol, 96%) beige solid. $^1$H NMR (300 MHz, DMSO-d$_6$) δ $^1$H NMR (300 MHz, DMSO-d$_6$) δ 12.84 (s, 1H), 7.92-7.80 (m, 2H), 7.29-7.08 (m, 4H), 6.68 (dd, J=8.9, 2.5 Hz, 1H), 5.46-5.17 (m, 2H), 4.56 (dd, J=73.0, 13.5 Hz, 2H), 4.38-4.11 (m, 2H), 4.08 (s, 1H), 3.74 (s, 3H), 3.49 (dd, J=13.0, 2.0 Hz, 1H), 3.14-2.98 (m, 4H).

4-((8-Methoxy-4-methyl-5-thioxo-3,4,5,6-tetrahydro-2,6-methano[1,3]diazocino[5,6-b]indol-11(1H)-yl)methyl)-N-((tetrahydro-2H-pyran-2-yl)oxy)benzamide (120)

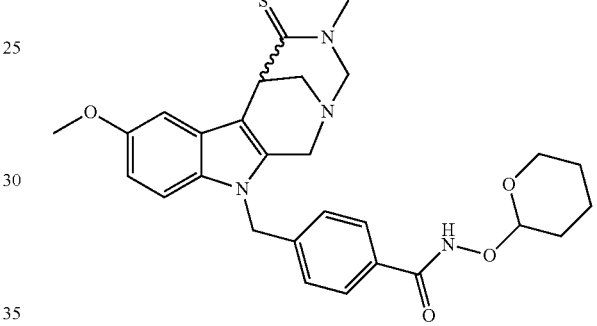

According to GP8 from 119 (0.56 g, 1.32 mmol). Purification by column chromatography (eluent: ethyl acetate/MeOH 10:1). Yield 0.60 g (1.15 mmol, 87%), colorless solid. $^1$H NMR (300 MHz, DMSO-d$_6$) δ 11.58 (s, 1H), 7.72-7.63 (m, 2H), 7.28-7.18 (m, 2H), 7.12 (d, J=8.1 Hz, 2H), 6.67 (dd, J=8.9, 2.5 Hz, 1H), 5.44-5.15 (m, 2H), 4.96 (d, J=3.0 Hz, 1H), 4.68 (d, J=13.5 Hz, 1H), 4.44 (d, J=13.6 Hz, 1H), 4.38-4.12 (m, 2H), 4.08 (s, 1H), 3.74 (s, 3H), 3.48-3.40 (m, 3H), 3.07 (s, 4H), 1.72-1.66 (m, 3H), 1.55-1.50 (m, 3H).

N-hydroxy-4-((6-methoxy-4-(methylcarbamothioyl)-3,4-dihydro-1H-pyrido[3,4-b]indol-9(2H)-yl)methyl)benzamide hydrochloride (121)

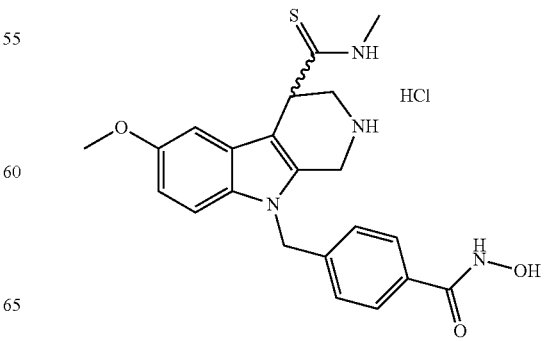

120 (0.60 g, 1.15 mmol) was dissolved in methanol (50 mL) and dichloromethane (50 mL). 5-6 drops of 6N HCl in 2-propanol were added. The mixture was stirred at room temperature for 3 h (TLC monitoring). The solvent was reduced under reduced pressure until a light yellow precipitation occurs. The crystalline product was filtered off and dried in vacuo.

0.20 g (0.46 mmol, 40%) light yellow powder; mp 222-225° C. IR (KBr): 3424, 3194, 2995, 1673 cm$^{-1}$. $^1$H NMR (300 MHz, DMSO-d$_6$) 11.21 (s, 1H), 11.04 (q, J=4.5 Hz, 1H), 10.04 (s, 1H), 9.61 (s, 1H), 9.04 (s, 1H), 7.75-7.61 (m, 2H), 7.32 (d, J=8.9 Hz, 1H), 7.12 (d, J=8.0 Hz, 2H), 6.93 (d, J=2.4 Hz, 1H), 6.76 (dd, J=9.0, 2.4 Hz, 1H), 5.44 (s, 2H), 4.59 (t, J=5.8 Hz, 1H), 4.40 (q, J=15.7 Hz, 2H), 3.71 (s, 3H), 3.63 (s, 2H), 3.08 (d, J=4.3 Hz, 3H). ESI-MS m/z (%): 425 [MH]$^+$ (100). Anal. calcd for C$_{22}$H$_{25}$ClN$_4$O$_4$S×1.33 H$_2$O: C, 54.53; H, 5.76; N, 11.57; found: C, 54.40; H, 5.62; N, 11.26.

Ethyl 3-bromo-2-(hydroxyimino)propanoate (123)

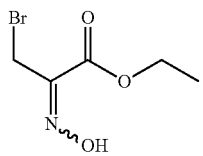

Synthesized analogue to Park et al. (2009) from ethyl bromopyruvate. $^1$H NMR (300 MHz, CDCl3): δ 4.38 (q, J=7.1 Hz, 3H), 4.26 (s, J=4.7 Hz, 3H), 1.38 (t, J=7.1 Hz, 5H).

Ethyl 3-(5-(benzyloxy)-1H-indol-3-yl)-2-(hydroxyimino)propanoate (124a)

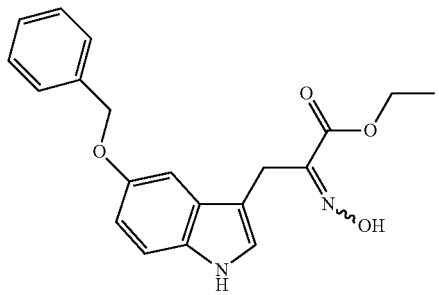 [SMILES: CCOC(=O)C(Cc1c[nH]c2ccc(OCc3ccccc3)cc12)=NO]

Was obtained from 5-benzyloxyindole 122a and 123 modified after Park et al. (Cha et al., 2012). Colorless crystals (3.40 g, 9.65 mmol, 43%) after silica gel chromatography with DCM/ethyl acetate (5:1), mp: 125.1-125.7° C.; IR (KBr): 3424, 1720 cm$^{-1}$; $^1$H NMR (300 MHz, DMSO): δ 12.40 (s, 1H), 10.72 (s, 1H), 7.48 (d, J=6.9 Hz, 2H), 7.44-7.36 (m, 2H), 7.36-7.30 (m, 1H), 7.25-7.18 (m, 2H), 7.03 (d, J=2.3 Hz, 1H), 6.78 (dd, J=8.8, 2.3 Hz, 1H), 5.05 (s, 2H), 4.13 (q, J=7.1 Hz, 2H), 3.85 (s, 2H), 3.31 (s, 1H), 1.18 (t, J=7.1 Hz, 3H). ESI-MS m/z (%): 353 [MH$^+$] (100). Anal. (C$_{20}$H$_{20}$N$_2$O$_4$): Calc. C, 68.17; H, 5.72; N, 7.95; found. C, 67.76; H, 5.63; N, 7.84.

Ethyl-2-(hydroxyimino)-3-(5-methoxy-1H-indol-3-yl)propanoate (124b)

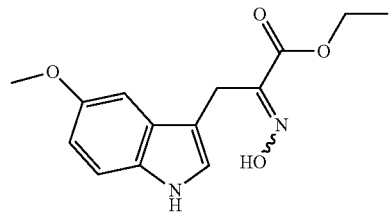 [SMILES: CCOC(=O)C(Cc1c[nH]c2ccc(OC)cc12)=NO]

Was obtained from 5-methoxyindole 122b and 123 modified after Park et al. (Cha et al., 2012). Colorless crystals (4.06 g, 14.00 mmol, 20%) after silica gel chromatography with ether/petroleum ether (1:1), $^1$H NMR (300 MHz, DMSO): δ 12.39 (s, 1H), 10.70 (s, 1H), 7.21 (d, J=8.7 Hz, 1H), 7.10 (d, J=2.4 Hz, 1H), 7.03 (d, J=2.3 Hz, 1H), 6.71 (dd, J=8.7, 2.4 Hz, 1H), 4.14 (q, J=7.1 Hz, 2H), 3.87 (s, 2H), 3.74 (s, 3H), 1.19 (t, J=7.1 Hz, 3H).

Ethyl 2-amino-3-(5-(benzyloxy)-1H-indol-3-yl)propanoate hydrochloride (125a)

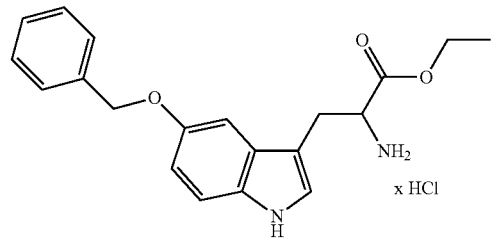 [SMILES: CCOC(=O)C(N)Cc1c[nH]c2ccc(OCc3ccccc3)cc12]

Ethyl 3-(5-(benzyloxy)-1H-indol-3-yl)-2-(hydroxyimino)propanoate (124a) was reacted analogously to Park et al. (Cha, Lee et al. 2012) and yielded 125a in colorless crystals (2.06 g, 6.08 mmol, 63%) after precipitation with HCl$_{(iProp)}$ from tetrahydrofuran, mp: 234.7-235.0° C.; IR (KBr): 3276, 1738 cm$^{-1}$; $^1$H NMR (300 MHz, DMSO): δ 10.97 (s, J=2.1 Hz, 1H), 8.63 (s, 3H), 7.52-7.43 (m, 2H), 7.43-7.29 (m, 3H), 7.27 (d, J=8.8 Hz, 1H), 7.21 (dd, J=10.7, 2.3 Hz, 2H), 6.82 (dd, J=8.8, 2.4 Hz, 1H), 5.10 (s, 2H), 4.17 (s, 1H), 4.09 (q, J=7.1 Hz, 2H), 3.26 (dq, J=14.8, 6.4 Hz, 2H), 1.10 (t, J=7.1 Hz, 3H). ESI-MS m/z (%): 339 [MH$^+$] (100). Anal. (C$_{20}$H$_{22}$N$_2$O$_3$): Calcd. C, 64.08; H, 6.00; N, 7.24; found. C, 63.72; H, 6.06; N, 7.33.

Ethyl 2-amino-3-(5-methoxy-1H-indol-3-yl)propanoate hydrochloride (125b)

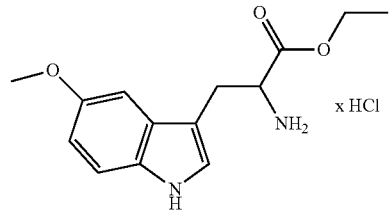 [SMILES: CCOC(=O)C(N)Cc1c[nH]c2ccc(OC)cc12]

Ethyl-2-(hydroxyimino)-3-(5-methoxy-1H-indol-3-yl) propanoate (124b) yielded 125b modified after Park et al. (Cha et al., 2012). Colorless crystals (7.26 g, 24.30 mmol, 91%) after precipitation with HCl$_{(iProp)}$ from tetrahydrofuran, $^1$H NMR (300 MHz, DMSO): δ 10.94 (s, 1H), 8.55 (s, 3H), 7.26 (d, J=8.8 Hz, 1H), 7.19 (d, J=2.4 Hz, 1H), 7.06 (d, J=2.3 Hz, 1H), 6.74 (dd, J=8.8, 2.4 Hz, 1H), 4.20 (t, J=6.2 Hz, 1H), 4.15-4.05 (m, 2H), 3.29 (dd, J=14.9, 5.9 Hz, 1H), 3.21 (dd, J=14.8, 7.0 Hz, 1H), 1.10 (t, J=7.1 Hz, 3H).

Ethyl 6-(benzyloxy)-2,3,4,9-tetrahydro-1H-pyrido[3,4-b]indole-3-carboxylate (126a)

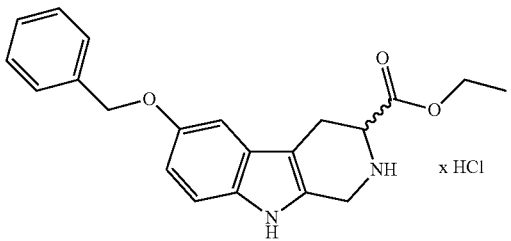 [SMILES: CCOC(=O)C1Cc2c([nH]c3ccc(OCc4ccccc4)cc23)CN1]

According to GP2 from ethyl 2-amino-3-(5-(benzyloxy)-1H-indol-3-yl)propanoate hydrochloride (125a) colorless crystals (6.07 g, 15.70 mmol, 95%) after crystallization from ether/methanol, mp: 230.5-231.0° C.; IR (KBr): 2604, 2483, 1741 cm$^{-1}$; $^1$H NMR (400 MHz, DMSO): δ 11.04 (s, 1H), 10.22 (s, 2H), 7.47 (d, J=7.1 Hz, 2H), 7.42-7.36 (m, 2H), 7.36-7.30 (m, 1H), 7.28 (d, J=8.8 Hz, 1H), 7.14 (d, J=2.4 Hz, 1H), 6.83 (dd, J=8.8, 2.4 Hz, 1H), 5.10 (s, 2H), 4.59 (dd, J=10.3, 5.3 Hz, 1H), 4.38 (s, 2H), 4.30 (q, J=7.1 Hz, 2H), 3.27 (dd, J=15.9, 5.2 Hz, 1H), 3.03 (dd, J=15.8, 10.3 Hz, 1H), 1.29 (t, J=7.1 Hz, 3H). ESI-MS m/z (%): 351 [MH$^+$] (100). Anal. (C$_{21}$H$_{23}$N$_2$O$_3$Cl): Calcd. C, 65.20; H, 5.99; N, 7.24; found. C, 64.88; H, 5.88; N, 7.02.

Ethyl 6-methoxy-2,3,4,9-tetrahydro-1H-pyrido[3,4-b]indole-3-carboxylate (126b)

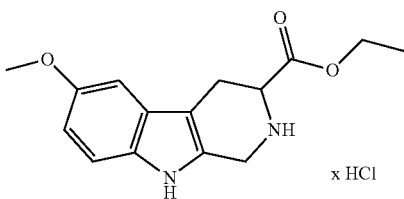 [SMILES: CCOC(=O)C1Cc2c([nH]c3ccc(OC)cc23)CN1]

According to GP2 from Ethyl 2-amino-3-(5-methoxy-1H-indol-3-yl)propanoate (125b) colorless crystals (6.94 g, 22.38 mmol, 92%) after crystallization from methanol by ether addition, $^1$H NMR (300 MHz, DMSO): δ 11.02 (s, 1H), 10.19 (s, 2H), 7.26 (d, J=8.8 Hz, 1H), 7.02 (d, J=2.4 Hz, 1H), 6.74 (dd, J=8.8, 2.5 Hz, 1H), 4.60 (dd, J=10.2, 5.2 Hz, 1H), 4.37 (s, 2H), 4.30 (q, J=7.1 Hz, 2H), 3.75 (s, 3H), 3.29 (dd, J=15.9, 5.2 Hz, 1H), 3.02 (dd, J=15.8, 10.5 Hz, 1H), 1.29 (t, J=7.1 Hz, 3H).

1.10 General Procedure 10 (GP10)

Modified after Fourtillan et al. (2008) 1.1 equivalent chloroacetyl chloride was dissolved in dry dichloromethane and added drop wise to the corresponding starting which was dissolved in dry dichloromethane and cooled to −20° C. After 1 h the solution was allowed to reach room temperature and was carefully quenched with water. The organic phase was separated and dried over anhydrous Na$_2$SO$_4$. The resulting solid compound was dissolved in methanol reacted overnight with the desired primary amines (with a minimum of 3 equivalents). After completion of the reaction was observed by TLC, the mixture was poured into water and extracted with ethyl acetate 3 times. The desired compounds were concentrated until crystallization started. Otherwise silica gel chromatography yielded the tetrahydro-fi-carboline derivatives.

10-(Benzyloxy)-2-propyl-2,3,6,7,12,12a-hexahydropyrazino[1',2':1,6]pyrido[3,4-b]indol-1,4-dione (130a)

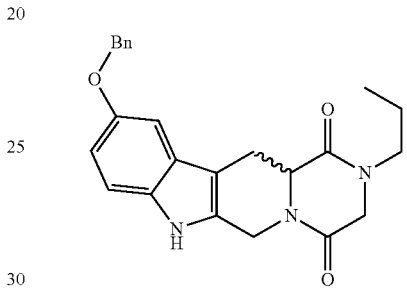

According to GP10 from ethyl 6-(benzyloxy)-2,3,4,9-tetrahydro-1H-pyrido[3,4-b]indole-3-carboxylate (126a) yielded colorless crystals (4.09 g, 10.15 mmol, 94%) crystallization from ethyl acetate, $^1$H NMR (300 MHz, DMSO): δ 10.81 (s, 1H), 7.54-7.43 (m, 2H), 7.42-7.35 (m, 2H), 7.34-7.27 (m, 1H), 7.23 (d, J=8.7 Hz, 1H), 7.08 (d, J=2.4 Hz, 1H), 6.78 (dd, J=8.7, 2.4 Hz, 1H), 5.35 (d, J=16.4 Hz, 1H), 5.08 (s, 2H), 4.31 (dd, J=11.7, 4.1 Hz, 1H), 4.19 (dd, J=17.1, 9.8 Hz, 2H), 3.99 (d, J=17.6 Hz, 1H), 3.41 (dd, J=13.3, 7.5 Hz, 1H), 3.32-3.20 (m, 11H), 3.16 (dd, J=15.2, 3.6 Hz, 1H), 2.89-2.70 (m, 1H), 1.56 (h, J=7.3 Hz, 2H), 0.86 (t, J=7.4 Hz, 3H).

10-Methoxy-2-propyl-2,3,6,7,12,12a-hexahydropyrazino[1',2':1,6]pyrido[3,4-b]indol-1,4-dione (130b)

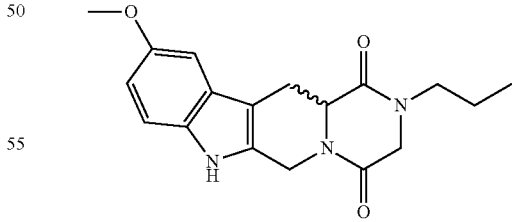

According to GP10 from ethyl 6-methoxy-2,3,4,9-tetrahydro-1H-pyrido[3,4-b]indole-3-carboxylate (126b) yielded colorless crystals (4.02 g, 12.27 mmol, 69% over 2 steps) after crystallization from ethyl acetate, $^1$H NMR (300 MHz, DMSO): δ 10.78 (s, 1H), 7.21 (d, J=8.7 Hz, 1H), 6.97 (d, J=2.4 Hz, 1H), 6.69 (dd, J=8.7, 2.4 Hz, 1H), 5.35 (d, J=16.4 Hz, 1H), 4.32 (dd, J=11.7, 4.1 Hz, 1H), 4.28-4.11 (m, 2H), 3.99 (d, J=17.6 Hz, 1H), 3.74 (s, 3H), 3.48-3.35 (m, 1H), 3.32-3.23 (m, 1H), 3.18 (dd, J=14.7, 3.8 Hz, 1H), 2.93-2.75 (m, 1H), 1.56 (h, J=7.3 Hz, 2H), 0.86 (t, J=7.5 Hz, 3H).

2-Methyl-2,3,6,7,12,12a-hexahydropyrazino[1',2':1,6]pyrido[3,4-b]indol-1,4-dione (132a)

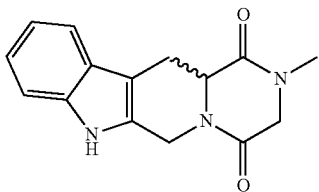 [SMILES: CN1CC(=O)N2Cc3[nH]c4ccccc4c3CC2C1=O]

According to GP10 from methyl 2,3,4,9-tetrahydro-1H-pyrido[3,4-b]indole-3-carboxylate hydrochloride (104a) yielded colorless crystals 0.14 g (0.48 mmol, 74%) after crystallization from ethyl acetate. $^1$H NMR (300 MHz, DMSO): δ 10.98 (s, 1H), 7.43 (d, J=7.6 Hz, 1H), 7.33 (d, J=7.9 Hz, 1H), 7.11-6.92 (m, 2H), 5.37 (d, J=16.5 Hz, 1H), 4.32 (dd, J=11.7, 4.1 Hz, 1H), 4.19 (d, J=17.8 Hz, 2H), 4.02 (d, J=17.6 Hz, 1H), 3.20 (dd, J=15.3, 3.3 Hz, 1H), 2.90 (s, 3H), 2.83 (d, J=15.2 Hz, 1H). (Fourtillan et al., 2008)

2-Ethyl-2,3,6,7,12,12a-hexahydropyrazino[1',2':1,6]pyrido[3,4-b]indol-1,4-dione (132b)

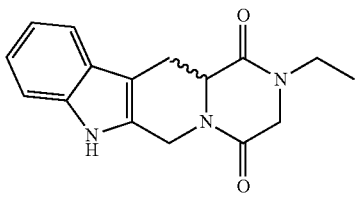 [SMILES: CCN1CC(=O)N2Cc3[nH]c4ccccc4c3CC2C1=O]

According to GP10 from methyl 2,3,4,9-tetrahydro-1H-pyrido[3,4-b]indole-3-carboxylate hydrochloride (104a) yielded colorless crystals (1.96 g, 6.92 mmol, 81%) after crystallization from ethyl acetate, mp: 230.0-230.5° C.; IR (KBr): 1670, 1627 cm$^{-1}$; $^1$H NMR (300 MHz, DMSO): δ 10.97 (s, 1H), 7.44 (d, J=7.7 Hz, 1H), 7.33 (d, J=7.9 Hz, 1H), 7.12-7.03 (m, 1H), 7.02-6.93 (m, 1H), 5.37 (d, J=16.5 Hz, 1H), 4.32 (dd, J=11.7, 4.2 Hz, 1H), 4.20 (dd, J=17.2, 4.4 Hz, 2H), 4.02 (d, J=17.6 Hz, 1H), 3.48-3.35 (m, 2H), 3.19 (dd, J=15.3, 3.1 Hz, 1H), 2.95-2.77 (m, 1H), 1.10 (t, J=7.2 Hz, 3H). ESI-MS m/z (%): 284 [MH$^+$] (100). Anal. (C$_{16}$H$_{17}$N$_3$O$_2$): Calcd. C, 67.83; H, 6.05; N, 14.83; found. C, 67.56; H, 5.99; N, 14.61.

2-Propyl-2,3,6,7,12,12a-hexahydropyrazino[1',2':1,6]pyrido[3,4-b]indole-1,4-dione (132c)

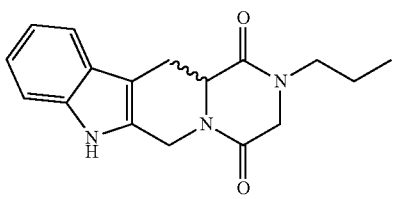 [SMILES: CCCN1CC(=O)N2Cc3[nH]c4ccccc4c3CC2C1=O]

According to GP10 from methyl 2,3,4,9-tetrahydro-1H-pyrido[3,4-b]indole-3-carboxylate hydrochloride (104a) yielded colorless crystals (2.6 g, 8.75 mmol, 86%) after crystallization from ethyl acetate, $^1$H NMR (300 MHz, CDCl$_3$): δ 8.18 (s, 1H), 7.47 (d, J=7.4 Hz, 1H), 7.33 (d, J=7.8 Hz, 1H), 7.22-7.16 (m, 1H), 7.13 (dd, J=10.8, 4.0 Hz, 1H), 5.61 (d, J=16.3 Hz, 1H), 4.31 (dd, J=11.7, 4.1 Hz, 1H), 4.24-3.99 (m, 3H), 3.59-3.44 (m, 2H), 3.44-3.33 (m, 1H), 3.00-2.77 (m, 1H), 1.65 (dt, J=14.7, 7.4 Hz, 2H), 0.97 (t, J=7.4 Hz, 3H). (Fourtillan et al., 2008) $^1$H NMR (300 MHz, DMSO): δ 10.97 (s, 1H), 7.44 (d, J=7.6 Hz, 1H), 7.33 (d, J=7.9 Hz, 1H), 7.13-7.02 (m, 1H), 7.02-6.94 (m, 1H), 5.37 (d, J=16.5 Hz, 1H), 4.33 (dd, J=11.7, 4.1 Hz, 1H), 4.21 (d, J=17.5 Hz, 2H), 4.00 (d, J=17.6 Hz, 1H), 3.44-3.35 (m, 1H), 3.34-3.13 (m, 2H), 2.93-2.78 (m, 1H), 1.56 (h, J=7.4 Hz, 2H), 0.87 (t, J=7.4 Hz, 3H).

2-Butyl-2,3,6,7,12,12a-hexahydropyrazino[1',2':1,6]pyrido[3,4-b]indol-1,4-dione (132d)

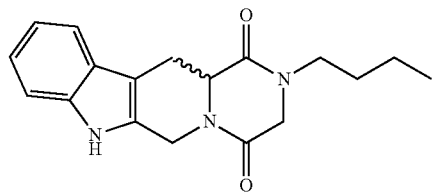 [SMILES: CCCCN1CC(=O)N2Cc3[nH]c4ccccc4c3CC2C1=O]

According to GP10 from methyl 2,3,4,9-tetrahydro-1H-pyrido[3,4-b]indole-3-carboxylate hydrochloride (104a) yielded colorless crystals (2.21 g, 7.11 mmol, 84%) after crystallization from ethyl acetate, mp: decomposition at 164.5° C.; IR (KBr): 1653, 1625 cm$^{-1}$; $^1$H NMR (300 MHz, CDCl3): δ 8.25 (s, 1H), 7.47 (d, J=7.7 Hz, 1H), 7.33 (d, J=7.7 Hz, 1H), 7.23-7.07 (m, 2H), 5.60 (d, J=16.5 Hz, 1H), 4.30 (dd, J=11.7, 4.1 Hz, 1H), 4.18 (d, J=15.1 Hz, 1H), 4.14-3.99 (m, 2H), 3.58-3.37 (m, 3H), 2.99-2.80 (m, 1H), 1.65-1.55 (m, 2H), 1.44-1.32 (m, 2H), 0.97 (t, J=7.3 Hz, 3H). $^1$H NMR (300 MHz, DMSO): δ 10.97 (s, 1H), 7.44 (d, J=7.7 Hz, 1H), 7.33 (d, J=7.9 Hz, 1H), 7.13-6.90 (m, 2H), 5.37 (d, J=16.5 Hz, 1H), 4.33 (dd, J=11.7, 4.1 Hz, 1H), 4.21 (d, J=17.5 Hz, 2H), 3.99 (d, J=17.6 Hz, 1H), 3.51-3.36 (m, 1H), 3.29 (dd, J=13.4, 7.1 Hz, 1H), 3.19 (dd, J=15.3, 3.3 Hz, 1H), 2.98-2.75 (m, 1H), 1.65-1.40 (m, 2H), 1.40-1.15 (m, 2H), 0.91 (t, J=7.3 Hz, 3H). ESI-MS m/z (%): 312 [MH$^+$] (100). Anal. (C$_{15}$H$_{21}$N$_3$O$_2$): Calcd. C, 69.43; H, 6.80; N, 13.49; found. C, 69.28; H, 6.67; N, 13.51. (Fourtillan et al., 2008; Lingnam et al., 2008).

2-iso-Butyl-2,3,6,7,12,12a-hexahydropyrazino[1',2':1,6]pyrido[3,4-b]indol-1,4-dione (132e)

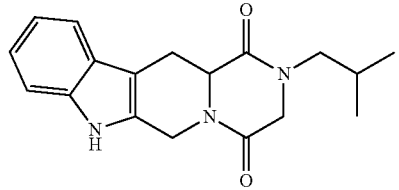 [SMILES: CC(C)CN1CC(=O)N2Cc3[nH]c4ccccc4c3CC2C1=O]

According to GP10 from methyl 2,3,4,9-tetrahydro-1H-pyrido[3,4-b]indole-3-carboxylate hydrochloride (104a) yielded colorless crystals (1.59 g, 5.11 mmol, 78%) after crystallization from ethyl acetate, $^1$H NMR (300 MHz, DMSO): δ 10.97 (s, 1H), 7.45 (d, J=7.7 Hz, 1H), 7.33 (d, J=7.9 Hz, 1H), 7.13-7.03 (m, 1H), 7.04-6.92 (m, 1H), 5.37 (d, J=16.4 Hz, 1H), 4.35 (dd, J=11.7, 4.1 Hz, 1H), 4.21 (d, J=17.3 Hz, 2H), 3.97 (d, J=17.6 Hz, 1H), 3.34-3.26 (m, 1H), 3.19 (dd, J=15.5, 3.7 Hz, 1H), 3.11 (dd, J=13.2, 7.0 Hz, 1H), 2.96-2.81 (m, 1H), 1.99 (dp, J=13.6, 6.7 Hz, 1H), 1.99 (hept, J=6.7 Hz, 1H), 0.87 (dd, J=6.6, 3.3 Hz, 6H). ESI-MS m/z (%): 326 [MH$^+$] (100). Anal. ($C_{18}H_{21}N_3O_2$): Calcd. C, 69.43; H, 6.80; N, 13.49; found. C, 69.35; H, 6.70; N, 13.43.

2-Isopentyl-2,3,6,7,12,12a-hexahydropyrazino[1',2': 1,6]pyrido[3,4-b]indole-1,4-dione (132f)

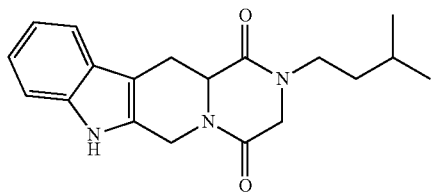 [SMILES: CC(C)CCN1CC(=O)N2Cc3[nH]c4ccccc4c3CC2C1=O]

According to GP10 from methyl 2,3,4,9-tetrahydro-1H-pyrido[3,4-b]indole-3-carboxylate hydrochloride (104a) yielded colorless crystals (1.61 g, 1.06 mmol, 76%) after crystallization from ethyl acetate, $^1$H NMR (300 MHz, DMSO): δ 10.97 (s, 1H), 7.44 (d, J=7.7 Hz, 1H), 7.33 (d, J=7.9 Hz, 1H), 7.12-7.02 (m, 1H), 7.02-6.91 (m, 1H), 5.36 (d, J=16.5 Hz, 1H), 4.32 (dd, J=11.7, 4.1 Hz, 1H), 4.20 (d, J=17.5 Hz, 2H), 3.99 (d, J=17.6 Hz, 1H), 3.51-3.38 (m, 1H), 3.34-3.26 (m, 1H), 3.18 (dd, J=15.3, 3.4 Hz, 1H), 2.94-2.75 (m, 1H), 1.62-1.47 (hept, J=6.5 Hz, 1H), 1.42 (q, J=7.2 Hz, 2H), 0.91 (d, J=6.5 Hz, 6H). ESI-MS m/z (%): 326 [MH$^+$] (100). Anal. ($C_{19}H_{23}N_3O_2$): Calcd. C, 70.13; H, 7.12; N, 12.91; found. C, 70.18; H, 6.87; N, 12.88.

2-(2-Morpholinoethyl)-2,3,6,7,12,12a-hexahydropyrazino[1',2':1,6]pyrido[3,4-b]indol-1,4-dione (132g)

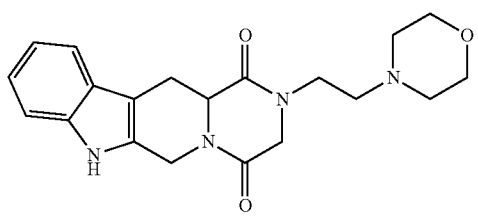 [SMILES: O=C1C2Cc3c([nH]c4ccccc34)CN2C(=O)CN1CCN1CCOCC1]

According to GP10 from methyl 2,3,4,9-tetrahydro-1H-pyrido[3,4-b]indole-3-carboxylate hydrochloride (104a) yielded colorless crystals (2.30 g, 6.25 mmol, 95%) after crystallization from ethyl acetate/ether, $^1$H NMR (300 MHz, DMSO): δ 10.98 (s, 1H), 7.43 (d, J=7.6 Hz, 1H), 7.33 (d, J=7.9 Hz, 1H), 7.12-7.02 (m, 1H), 7.02-6.93 (m, 1H), 5.37 (d, J=16.4 Hz, 1H), 4.35 (dd, J=11.7, 4.2 Hz, 1H), 4.29-4.16 (m, 2H), 4.11 (d, J=17.7 Hz, 1H), 3.64 (dd, J=13.7, 6.8 Hz, 1H), 3.56 (t, J=4.5 Hz, 4H), 3.40 (t, J=6.1 Hz, 1H), 3.19 (dd, J=15.2, 3.2 Hz, 1H), 2.92-2.79 (m, 1H), 2.59-2.51 (m, 1H), 2.49-2.31 (m, 5H). 2-(2-(Piperidin-1-yl)ethyl)-2,3,6,7,12, 12a-hexahydropyrazino[1',2':1,6]pyrido[3,4-b]indole-1,4-dione (132h)

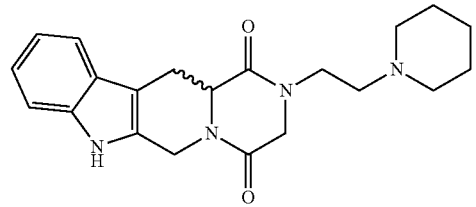 [SMILES: O=C1C2Cc3c([nH]c4ccccc34)CN2C(=O)CN1CCN1CCCCC1]

According to GP10 from methyl 2,3,4,9-tetrahydro-1H-pyrido[3,4-b]indole-3-carboxylate hydrochloride (104a) yielded colorless crystals (1.36 g, 3.71 mmol, 56%), $^1$H NMR (300 MHz, CDCl$_3$) δ 8.31 (s, 1H), 7.46 (d, J=7.5 Hz, 1H), 7.34 (d, J=7.8 Hz, 1H), 7.18 (t, J=7.3 Hz, 1H), 7.11 (t, J=7.4 Hz, 1H), 5.60 (d, J=16.4 Hz, 1H), 4.55-4.08 (m, 4H), 3.71 (dd, J=13.5, 6.5 Hz, 1H), 3.63-3.39 (m, 2H), 2.91 (t, J=13.4 Hz, 1H), 2.64 (s, 2H), 2.52 (s, 4H), 1.62 (s, 4H), 1.45 (s, 2H).

(6S,12aS)-6-Methyl-2-propyl-2,3,6,7,12,12a-hexahydropyrazino[1',2':1,6]pyrido[3,4-b]indol-1,4-dione (132i)

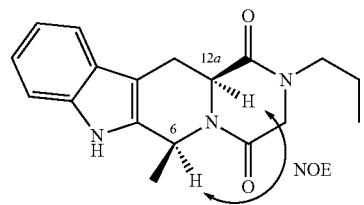

According to GP10 from methyl (1S,3S)-1-methyl-2,3,4, 9-tetrahydro-1H-pyrido[3,4-b]indole-3-carboxylate hydrochloride (104b) yielded colorless crystals (3.05 g, 9.81 mmol, 91%) after crystallization from propyl amine/methanol. $^1$H NMR (400 MHz, DMSO): δ 11.04 (s, 1H), 7.53 (d, J=7.7 Hz, 1H), 7.35 (d, J=8.0 Hz, 1H), 7.08 (t, J=7.1 Hz, 1H), 7.01 (t, J=7.3 Hz, 1H), 5.26 (q, J=6.2 Hz, 1H), 4.24 (dd, J=11.6, 4.2 Hz, 1H), 4.17 (d, J=16.9 Hz, 1H), 3.94 (d, J=16.9 Hz, 1H), 3.52-3.38 (m, 2H), 3.31-3.21 (m, 1-H), 2.80 (dd, J=15.4, 11.7 Hz, 1H), 1.63-1.47 (m, 2H), 1.41 (d, J=6.4 Hz, 3H), 0.85 (t, J=7.4 Hz, 3H). The stereochemistry was affirmed by NOESY and COSY.

tert-Butyl 4-((2-methyl-1,4-dioxo-1,3,4,6,12,12a-bexahydropyrazino[1',2':1,6]pyrido[3,4-b]indol-7 (2H)-yl)methyl)benzoate (133a)

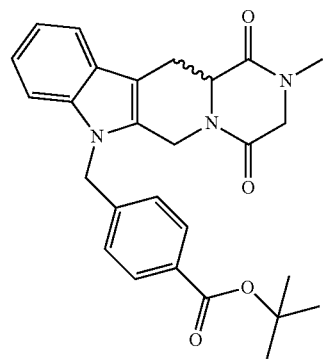 [SMILES: CN1CC(=O)N2Cc3c(c4ccccc4n3Cc3ccc(C(=O)OC(C)(C)C)cc3)CC2C1=O]

According to GP6 modification b from 2-methyl-2,3,6,7,12,12a-hexahydropyrazino[1',2':1,6]pyrido[3,4-b]indol-1,4-dione (132a) yielded colorless crystals (1.30 g, 2.83 mmol, 41%) after silica gel chromatography (DCM/MeOH 15:1), RP-HPLC: 94%; mp.: 202.5-204.0° C.; IR (KBR): 1699, 1664, 1622 cm$^{-1}$; $^1$H NMR (300 MHz, DMSO): δ 7.82 (d, J=8.3 Hz, 2H), 7.52 (d, J=7.1 Hz, 1H), 7.41 (d, J=7.8 Hz, 1H), 7.19-7.01 (m, 4H), 5.60-5.43 (m, 2H), 5.38 (d, J=16.7 Hz, 1H), 4.33 (dd, J=11.6, 4.0 Hz, 1H), 4.25-3.95 (m, 3H), 3.25 (dd, J=15.4, 3.6 Hz, 1H), 2.96-2.83 (m, 4H), 1.51 (s, 9H). ESI-MS m/z (%): 404 [MH$^+$–C$_4$H$_8$] (100), 460 [MH$^+$] (23). HR-MS m/z: Calcd. 460.2231, [MH$^+$]. found. 460.223 [MH$^+$].

tert-Butyl 4-((2-ethyl-1,4-dioxo-1,3,4,6,12,12a-hexahydropyrazino[1',2':1,6]pyrido[3,4-b]indol-7(2H)-yl)methyl)benzoate (133b)

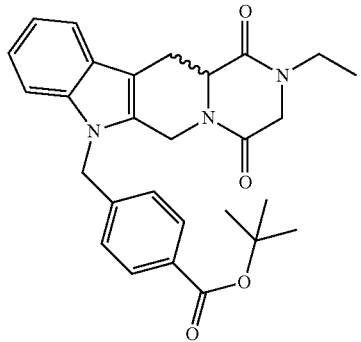 [SMILES: CCN1CC(=O)N2Cc3c(c4ccccc4n3Cc3ccc(C(=O)OC(C)(C)C)cc3)CC2C1=O]

According to GP6 modification b from 2-ethyl-2,3,6,7,12,12a-hexahydropyrazino[1',2':1,6]pyrido[3,4-b]indol-1,4-dione (132b) yielded colorless crystals (0.95 g, 2.01 mmol, 57%) after silica gel chromatography with dichloromethane and ethyl acetate, mp: 239.4-239.7° C.; IR (KBr): 1707, 1659, 1611 cm$^{-1}$; $^1$H NMR (300 MHz, DMSO): δ 7.82 (d, J=8.3 Hz, 2H), 7.52 (d, J=7.0 Hz, 1H), 7.41 (d, J=7.7 Hz, 1H), 7.16-7.01 (m, 4H), 5.65-5.45 (m, 2H), 5.39 (d, J=16.7 Hz, 1H), 4.32 (dd, J=11.7, 4.0 Hz, 1H), 4.21 (d, J=17.6 Hz, 1H), 4.12 (d, J=16.7 Hz, 1H), 4.01 (d, J=17.7 Hz, 1H), 3.46-3.35 (m, 2H), 3.25 (dd, J=15.3, 3.6 Hz, 1H), 2.98-2.83 (m, 1H), 1.51 (s, 9H), 1.09 (t, J=7.1 Hz, 3H). ESI-MS m/z (%): 418 [MH$^+$–C$_4$H$_8$] (100); 474 [MH$^+$] (21). Anal. (C$_{28}$H$_{31}$N$_3$O$_4$): Calcd. C, 71.02; H, 6.60; N, 8.87; found. C, 70.95; H, 6.50; N, 8.82.

tert-Butyl 4-((1,4-dioxo-2-propyl-1,3,4,6,12,12a-hexahydropyrazino[1',2':1,6]pyrido[3,4-b]indol-7(2H)-yl)methyl)benzoate (133c)

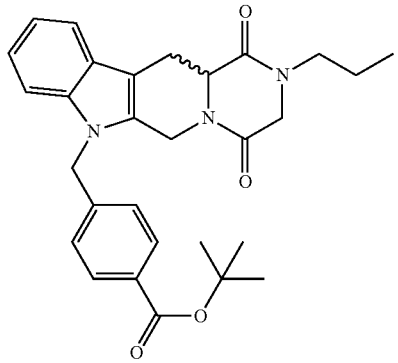 [SMILES: CCCN1CC(=O)N2Cc3c(c4ccccc4n3Cc3ccc(C(=O)OC(C)(C)C)cc3)CC2C1=O]

According to GP6 modification b from 2-propyl-2,3,6,7,12,12a-hexahydropyrazino[1',2':1,6]pyrido[3,4-b]indole-1,4-dione (132c) yielded colorless crystals (2.60 g, 5.34 mmol, 78%) after silica gel chromatography with dichloromethane and methanol (15:1) and crystallization from ethyl acetate and petroleum ether, mp: 161.5-162.4° C.; IR (KBr): 1708, 1655, 1612 cm$^{-1}$; $^1$H NMR (300 MHz, DMSO): δ 7.90-7.75 (m, 2H), 7.59-7.49 (m, 1H), 7.41 (d, J=7.7 Hz, 1H), 7.18-7.00 (m, 4H), 5.60-5.44 (m, 2H), 5.39 (d, J=16.6 Hz, 1H), 4.34 (dd, J=11.7, 4.1 Hz, 1H), 4.21 (d, J=17.7 Hz, 1H), 4.13 (d, J=16.8 Hz, 1H), 3.99 (d, J=17.7 Hz, 1H), 3.46-3.35 (m, 1H), 3.33-3.25 (m, 1H), 3.23 (t, J=6.7 Hz, 1H), 3.03-2.81 (m, 1H), 1.63-1.52 (m, 2H), 1.51 (s, 9H), 0.86 (t, J=7.4 Hz, 3H). ESI-MS m/z (%): 432 [MH$^+$–C$_4$H$_8$] (100), 488 [MH$^+$] (20). Anal. (C$_{29}$H$_{33}$N$_3$O$_4$): Calcd. C, 71.44; H, 6.82; N, 8.62; found. C, 71.40; H, 7.01; N, 8.50.

tert-Butyl 4-((2-butyl-1,4-dioxo-1,3,4,6,12,12a-hexahydropyrazino[1',2':1,6]pyrido[3,4-b]indol-7(2H)-yl)methyl)benzoate (133d)

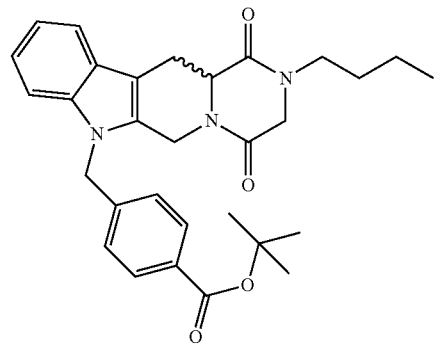 [SMILES: CCCCN1CC(=O)N2Cc3c(c4ccccc4n3Cc3ccc(C(=O)OC(C)(C)C)cc3)CC2C1=O]

According to GP6 modification b from 2-butyl-2,3,6,7,12,12a-hexahydropyrazino[1',2':1,6]pyrido[3,4-b]indol-1,4-dione (132d) yielded colorless crystals (1.30 g, 2.59 mmol, 80%) after silica gel chromatography with ethyl acetate, mp: 173.0-175.0° C.; IR (KBr): 1707, 1652 cm$^{-1}$; $^1$H NMR (300 MHz, DMSO): δ 7.82 (d, J=8.3 Hz, 2H), 7.53 (d, J=7.1 Hz, 1H), 7.41 (d, J=7.8 Hz, 1H), 7.17-6.98 (m, 4H), 5.60-5.43 (m, 2H), 5.39 (d, J=16.7 Hz, 1H), 4.33 (dd, J=11.7, 4.0 Hz, 1H), 4.19 (t, J=11.2 Hz, 1H), 4.12 (d, J=16.8 Hz, 1H), 3.98 (d, J=17.6 Hz, 1H), 3.49-3.36 (m, 1H), 3.33-3.20 (m, 2H), 2.99-2.81 (m, 1H), 1.52 (d, J=9.4 Hz, 11H), 1.38-1.20 (m, 2H), 0.90 (t, J=7.3 Hz, 3H). ESI-MS m/z (%): 446 [MH$^+$–C$_4$H$_6$] (100) 502 [MH$^+$] (27). Anal. (C$_{30}$H$_{35}$N$_3$O$_4$): Calcd. C, 71.83; H, 7.03; N, 8.38; found. C, 71.68; H, 6.85; N, 8.30.

tert-Butyl 4-((2-isobutyl-1,4-dioxo-1,3,4,6,12,12a-hexahydropyrazino[1',2':1,6]pyrido[3,4-b]indol-7(2H)-yl)methyl)benzoate (133e)

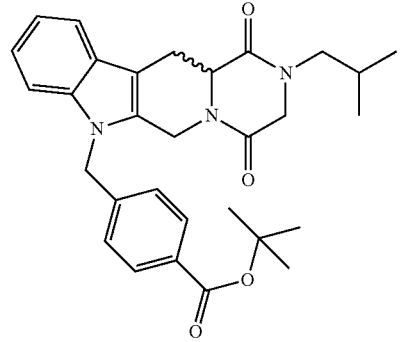 [SMILES: CC(C)CN1CC(=O)N2Cc3c(c4ccccc4n3Cc3ccc(C(=O)OC(C)(C)C)cc3)CC2C1=O]

According to GP6 modification b from 2-iso-Butyl-2,3,6,7,12,12a-hexahydropyrazino[1',2':1,6]pyrido[3,4-b]indol-1,4-dione (132e) yielded colorless crystals (1.25 g, 2.49 mmol, 78%) after silica gel chromatography with ethyl acetate and crystallization from ethyl acetate, mp: 174.7-174.9° C.; IR (KBr): 1709, 1656, 1620 cm$^{-1}$; $^1$H NMR (300 MHz, DMSO): δ 7.82 (d, J=8.3 Hz, 2H), 7.53 (d, J=7.2 Hz, 1H), 7.41 (d, J=7.8 Hz, 1H), 7.19-6.97 (m, 4H), 5.51 (s, 2H), 5.39 (d, J=16.6 Hz, 1H), 4.35 (dd, J=11.7, 4.0 Hz, 1H), 4.21 (d, J=17.7 Hz, 1H), 4.13 (d, J=16.8 Hz, 1H), 3.96 (d, J=17.7 Hz, 1H), 3.33-3.19 (m, 2H), 3.09 (dd, J=13.2, 6.9 Hz, 1H), 3.01-2.86 (m, 1H), 1.99 (hept, J=6.8 Hz, 1H), 1.51 (s, 9H), 0.87 (dd, J=6.6, 2.8 Hz, 6H). ESI-MS m/z (%): 446 [MH$^+$–C$_4$H$_4$] (100); 502 [MH$^+$] (28). Anal. (C$_{30}$H$_{35}$N$_3$O$_4$): Calcd. C, 71.83; H, 7.03; N, 8.38; found. C, 71.65; H, 6.83; N, 8.09.

tert-Butyl 4-((2-isopentyl-1,4-dioxo-1,3,4,6,12,12a-hexahydropyrazino[1',2':1,6]pyrido[3,4-b]indol-7(2H)-yl)methyl)benzoate (133f)

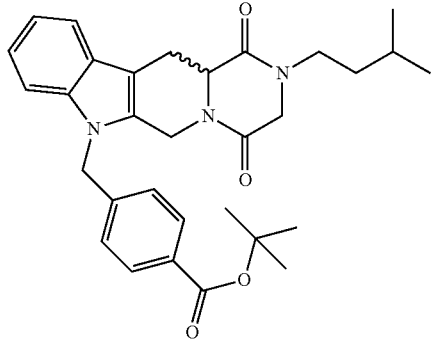 [SMILES: CC(C)CCN1CC(=O)N2Cc3c(c4ccccc4n3Cc3ccc(C(=O)OC(C)(C)C)cc3)CC2C1=O]

According to GP6 modification b from 2-isopentyl-2,3,6,7,12,12a-hexahydropyrazino[1',2':1,6]pyrido[3,4-b]indole-1,4-dione (132f) yielded colorless crystals (0.75 g, 1.45 mmol, 47%) after silica gel chromatography with ethyl acetate, mp: 157.7-157.9° C.; IR (KBr): 1710, 1656 cm$^{-1}$; $^1$H NMR (300 MHz, DMSO): δ 7.82 (d, J=8.3 Hz, 2H), 7.53 (d, J=7.1 Hz, 1H), 7.41 (d, J=7.7 Hz, 1H), 7.08 (ddd, J=15.2, 14.8, 7.4 Hz, 4H), 5.54 (d, J=17.8 Hz, 1H), 5.47 (d, J=17.9 Hz, 1H), 5.43-5.32 (m, 1H), 4.33 (dd, J=11.6, 3.9 Hz, 1H), 4.20 (d, J=17.7 Hz, 1H), 4.12 (d, J=16.6 Hz, 11), 3.98 (d, J=17.6 Hz, 1H), 3.52-3.34 (m, 2H), 3.33-3.20 (m, 2H), 2.99-2.81 (m, 1H), 1.52-1.35 (m, 12H), 0.91 (d, J=6.5 Hz, 6H). ESI-MS m/z (%): 460 [MH$^+$–C$_4$H$_8$] (100); 516 [MH$^+$] (23). Anal. (C$_{31}$H$_{37}$N$_3$O$_4$): Calcd. C, 72.21; H, 7.23; N, 8.15; found. C, 71.90; H, 7.04; N, 7.99.

tert-Butyl 4-((2-(2-morpholinoethyl)-1,4-dioxo-1,3,4,6,12,12a-hexahydropyrazino[1',2':1,6]pyrido[3,4-b]indol-7(2H)-yl)methyl)benzoate (133g)

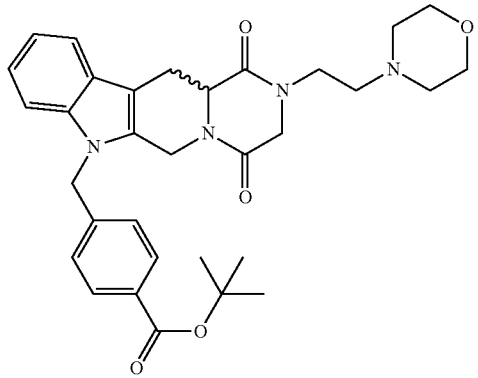 [SMILES: CC(C)(C)OC(=O)c1ccc(Cn2c3c(c4ccccc42)CC2C(=O)N(CCN4CCOCC4)CC(=O)N2C3)cc1]

According to GP6 modification b from 2-(2-morpholinoethyl)-2,3,6,7,12,12a-hexahydropyrazino[1',2':1,6]pyrido[3,4-b]indol-1,4-dione (132g) yielded colorless crystals (0.30 g, 0.54 mmol, 20%) after silica gel chromatography with dichloromethane/methanol/ammonia 25%$_{(aq)}$ (20:1:0.1), $^1$H NMR (300 MHz, DMSO): δ 7.82 (d, J=8.3 Hz, 2H), 7.52 (d, J=7.0 Hz, 1H), 7.41 (d, J=7.8 Hz, 1H), 7.13 (dd, J=6.8, 3.3 Hz, 2H), 7.12-6.98 (m, 2H), 5.54 (d, J=17.9 Hz, 1H), 5.48 (d, J=17.7 Hz, 1H), 5.39 (d, J=16.7 Hz, 1H), 4.35 (dd, J=11.6, 4.0 Hz, 1H), 4.25 (d, J=17.7 Hz, 1H), 4.11 (t, J=14.6 Hz, 2H), 3.64 (dd, J=13.7, 6.7 Hz, 1H), 3.56 (t, J=4.2 Hz, 4H), 3.42-3.36 (m, 1H), 3.25 (dd, J=15.5, 3.3 Hz, 1H), 2.99-2.81 (m, 1H), 2.52 (s, 1H), 2.42 (s, 5H), 1.51 (s, 9H).

tert-Butyl 4-(((6S,12aR)-6-methyl-1,4-dioxo-2-propyl-1,3,4,6,12,12a-hexahydropyrazin[1',2':1,6]pyrido[3,4-b]indol-7(2H)-yl)methyl)benzoate (133i)

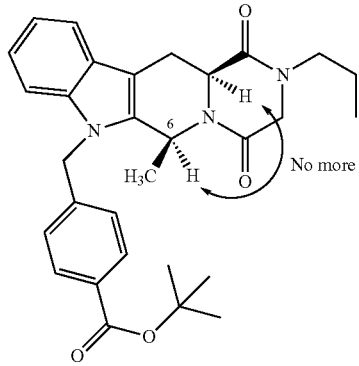

According to GP6 modification b from (6S,12aS)-6-methyl-2-propyl-2,3,6,7,12,12a-hexahydropyrazino[1',2':1,6]pyrido[3,4-b]indol-1,4-dione (132i) (0.37 g, 0.74 mmol, 46%) after silica gel chromatography with ethyl acetate and crystallization from ethyl acetate, $^1$H NMR (400 MHz, DMSO): δ 7.81 (d, J=8.3 Hz, 2H), 7.54 (d, J=7.1 Hz, 1H), 7.27 (d, J=7.6 Hz, 1H), 7.15-7.00 (m, 4H), 5.82 (q, J=6.6 Hz, 1H), 5.64 (d, J=17.8 Hz, 1H), 5.46 (d, J=17.9 Hz, 1H), 4.48 (dd, J=11.8, 4.3 Hz, 1H), 4.20 (d, J=17.6 Hz, 1H), 3.98 (d, J=17.6 Hz, 1H), 3.50-3.39 (m, 1H), 3.29 (dd, J=15.5, 4.4 Hz, 1H), 3.25-3.15 (m, 1H), 2.91 (dd, J=14.9, 12.1 Hz, 1H), 1.61-1.52 (m, 2H), 1.51 (s, 9H), 1.38 (t, J=8.0 Hz, 3H), 0.87 (t, J=7.4 Hz, 3H). Stereochemistry was determined by NOESY and COSY. The stereocenter at position 12a epimerizes from S to R which is in agreement to the literature (Xiao et al., 2010).

tert-Butyl 4-((10-(benzyloxy)-1,4-dioxo-2-propyl-1,3,4,6,12,12a-hexahydropyrazino[1',2':1,6]pyrido[3,4-b]indol-7(2H)-yl)methyl)benzoate (133j)

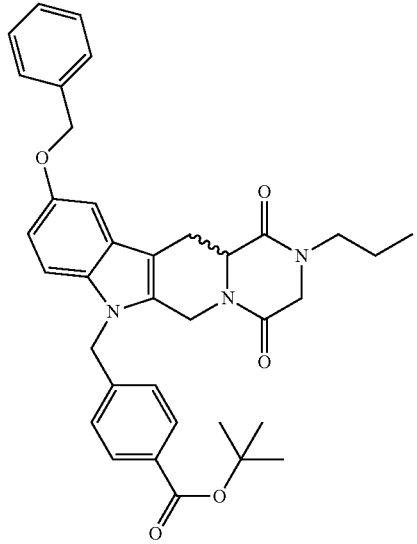 [SMILES: CCCN1CC(=O)N2Cc3c(c4cc(OCc5ccccc5)ccc4n3Cc3ccc(C(=O)OC(C)(C)C)cc3)CC2C1=O]

According to GP6 modification b from 10-(benzyloxy)-2-propyl-2,3,6,7,12,12a-hexahydropyrazino[1',2':1,6]pyrido[3,4-b]indol-1,4-dione (130a) yielded colorless crystals (3.90 g, 6.57 mmol, 74%) after chromatography over silica gel and crystallization from ethyl acetate/ether, $^1$H NMR (300 MHz, DMSO): δ 7.82 (d, J=8.3 Hz, 2H), 7.51-7.43 (m, 2H), 7.42-7.35 (m, 2H), 7.35-7.25 (m, 2H), 7.16 (d, J=2.3 Hz, 1H), 7.11 (d, J=8.3 Hz, 2H), 6.81 (dd, J=8.8, 2.4 Hz, 1H), 5.46 (s, 2H), 5.36 (d, J=16.9 Hz, 1H), 5.10 (s, 2H), 4.32 (dd, J=11.7, 3.9 Hz, 1H), 4.21 (d, J=17.7 Hz, 1H), 4.10 (d, J=16.7 Hz, 1H), 3.98 (d, J=17.7 Hz, 1H), 3.47-3.36 (m, 1H), 3.30-3.15 (m, 2H), 2.87 (t, J=13.5 Hz, 1H), 1.63-1.44 (m, 11H), 0.86 (t, J=7.4 Hz, 3H).

tert-Butyl 4-((10-methoxy-1,4-dioxo-2-propyl-1,3,4,6,12,12a-hexahydropyrazino[1',2':1,6]pyrido[3,4-b]indol-7(2H)-yl)methyl)benzoate (133k)

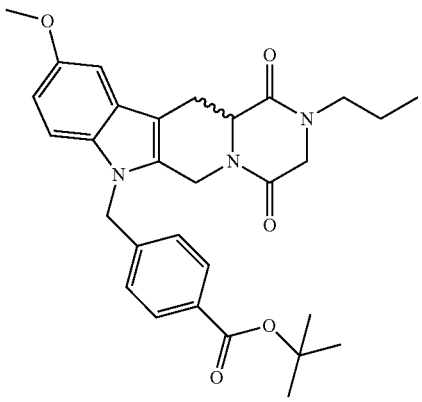 [SMILES: CCCN1CC(=O)N2Cc3c(c4cc(OC)ccc4n3Cc3ccc(C(=O)OC(C)(C)C)cc3)CC2C1=O]

According to GP6 modification b from 10-methoxy-2-propyl-2,3,6,7,12,12a-hexahydropyrazino[1',2':1,6]pyrido[3,4-b]indol-1,4-dione (130b) yielded colorless crystals (1.28 g, 2.47 mmol, 53%) after silica gel chromatography with ethyl acetate, $^1$H NMR (300 MHz, DMSO): δ 7.81 (d, J=8.3 Hz, 2H), 7.29 (d, J=8.9 Hz, 1H), 7.10 (d, J=8.3 Hz, 2H), 7.06 (d, J=2.4 Hz, 1H), 6.72 (dd, J=8.8, 2.4 Hz, 1H), 5.49 (d, J=17.7 Hz, 1H), 5.44 (d, J=17.7 Hz, 1H), 5.36 (d, J=16.7 Hz, 1H), 4.32 (dd, J=11.7, 4.0 Hz, 1H), 4.21 (d, J=17.7 Hz, 1H), 4.10 (d, J=16.7 Hz, 1H), 3.98 (d, J=17.6 Hz, 1H), 3.75 (s, 3H), 3.49-3.36 (m, 1H), 3.30-3.17 (m, 2H), 2.95-2.82 (m, 1H), 1.61-1.48 (m, 11H), 0.86 (t, J=7.4 Hz, 3H).

tert-Butyl 4-((10-hydroxy-1,4-dioxo-2-propyl-1,3,4,6,12,12a-hexahydropyrazino[1',2':1,6]pyrido[3,4-b]indol-7(2H)-yl)methyl)benzoate (133l)

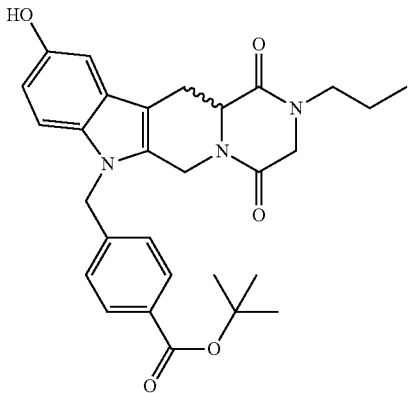 [SMILES: CCCN1CC(=O)N2Cc3c(c4cc(O)ccc4n3Cc3ccc(C(=O)OC(C)(C)C)cc3)CC2C1=O]

tert-Butyl 4-((10-(benzyloxy)-1,4-dioxo-2-propyl-1,3,4,6,12,12a-hexahydropyrazino[1',2':1,6]pyrido[3,4-b]indol-7(2H)-yl)methyl)benzoate (133j) was dissolved in methanol, transferred into an autoclave and reacted with 5 bar hydrogen overnight. Chromatography over silica gel (ethyl acetate) yielded colorless crystals (0.60 g, 1.19 mmol, 85%) $^1$H NMR (300 MHz, DMSO): δ 8.81 (s, 1H), 7.81 (d, J=8.3 Hz, 2H), 7.17 (d, J=8.7 Hz, 1H), 7.11 (d, J=8.2 Hz, 2H), 6.79 (d, J=2.2 Hz, 1H), 6.59 (dd, J=8.7, 2.3 Hz, 1H), 5.48-5.27 (m, 3H), 4.31 (dd, J=11.7, 4.1 Hz, 1H), 4.20 (d, J=17.7 Hz, 1H), 4.08 (d, J=16.5 Hz, 1H), 3.98 (d, J=17.7 Hz, 1H), 3.43-3.35 (m, 1H), 3.34-3.19 (m, 2H), 3.11 (dd, J=15.3, 3.8 Hz, 1H), 2.91-2.78 (m, 1H), 1.55 (dd, J=12.7, 5.3 Hz, 2H), 1.51 (s, 8H), 0.86 (t, J=7.4 Hz, 3H).

4-((2-Methyl-1,4-dioxo-1,3,4,6,12,12a-hexahydropyrazino[1'',2':1,6]pyrido[3,4-b]indol-7(2H)-yl)methyl)benzoic acid (134a)

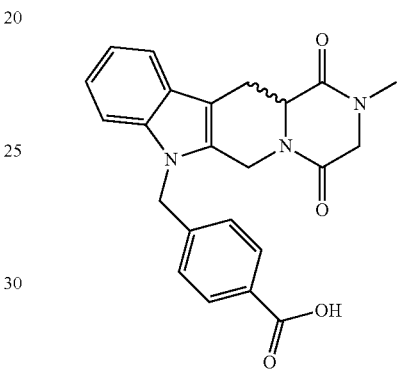

According to GP7 from tert-butyl 4-((2-methyl-1,4-dioxo-1,3,4,6,12,12a-hexahydropyrazino[1',2':1,6]pyrido[3,4-b]indol-7(2H)-yl)methyl)benzoate (133a) yielded colorless crystals (0.90 g, 2.23 mmol, 90%) after crystallization from trifluoroacetic acid/water, mp.: 288.8-288.9° C.; IR (KBr): 1711, 1662, 1626 cm$^{-1}$; $^1$H NMR (400 MHz, DMSO): δ 12.90 (s, 1H), 7.87 (d, J=8.2 Hz, 2H), 7.52 (d, J=7.6 Hz, 1H), 7.43 (d, J=8.1 Hz, 1H), 7.18-7.00 (m, 4H), 5.58-5.44 (m, 2H), 5.39 (d, J=16.5 Hz, 1H), 4.33 (dd, J=11.6, 3.9 Hz, 1H), 4.16 (t, J=18.7 Hz, 2H), 4.01 (d, J=17.6 Hz, 1H), 3.26 (dd, J=15.5, 3.3 Hz, 1H), 2.98-2.85 (m, 41H). ESI-MS m/z (%): 404 [MH$^+$] (100). Anal. ($C_{23}H_{21}N_3O_4$+⅓ $H_2O$): Calcd. C, 67.47; H, 5.40; N, 10.26; found. C, 67.71; H, 5.40; N, 10.08.

4-((2-Ethyl-1,4-dioxo-1,3,4,6,12,12a-hexahydropyrazino[1',2':1,6]pyrido[3,4-b]indol-7(2H)-yl)methyl)benzoic acid (134b)

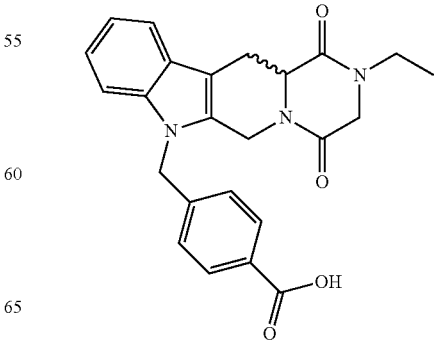

According to GP7 from tert-Butyl 4-((2-ethyl-1,4-dioxo-1,3,4,6,12,12a-hexahydropyrazino[1',2':1,6]pyrido[3,4-b]indol-7(2H)-yl)methyl)benzoate (133b) yielded colorless crystals (0.81 g, 1.84 mmol, 97%) after crystallization from trifluoroacetic acid, mp: 192.0-192.4° C.; IR (KBr): 1722, 1659, 1629 cm$^{-1}$; $^1$H NMR (300 MHz, DMSO): δ 12.92 (s, 1H), 7.87 (d, J=8.3 Hz, 2H), 7.53 (d, J=7.1 Hz, 1H), 7.42 (d, J=7.8 Hz, 1H), 7.26-6.96 (m, 4H), 5.64-5.43 (m, 2H), 5.39 (d, J=16.7 Hz, 1H), 4.33 (dd, J=11.6, 4.0 Hz, 1H), 4.21 (d, J=17.7 Hz, 1H), 4.13 (d, J=16.9 Hz, 1H), 4.01 (d, J=17.6 Hz, 1H), 3.39 (d, J=6.9 Hz, 2H), 3.25 (dd, J=15.4, 3.6 Hz, 1H), 3.00-2.81 (m, 1H), 1.09 (t, J=7.1 Hz, 3H). ESI-MS m/z (%): 418 [MH$^+$] (100). Anal. (C$_{24}$H$_{23}$N$_3$O$_4$): Calcd. C, 69.05; H, 5.55; N, 10.07; found. C, 68.68; H, 5.45; N, 10.02.

4-((1,4-Dioxo-2-propyl-1,3,4,6,12,12a-hexahydropyrazino[1',2':1,6]pyrido[3,4-b]indol-7(2H)-yl)methyl)benzoic acid (134c)

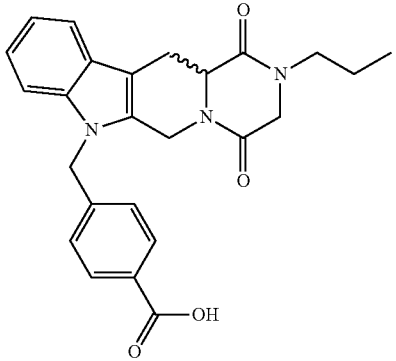 [SMILES: CCCN1CC(=O)N2Cc3c(c4ccccc4n3Cc3ccc(C(=O)O)cc3)CC2C1=O]

According to GP7 from tert-Butyl 4-((1,4-dioxo-2-propyl-1,3,4,6,12,12a-hexahydropyrazino[1',2':1,6]pyrido[3,4-b]indol-7(2H)-yl)methyl)benzoate (133c) yielded colorless crystals (1.95 g, 4.52 mmol, 85%) after crystallization from trifluoroacetic acid/water, mp: 159.4-160.7° C.; IR (KBr): 1714, 1663, 1614 cm$^{-1}$; $^1$H NMR (300 MHz, DMSO): δ 7.87 (d, J=8.3 Hz, 2H), 7.53 (d, J=7.3 Hz, 1H), 7.42 (d, J=7.9 Hz, 1H), 7.19-7.00 (m, 4H), 5.61-5.44 (m, 2H), 5.39 (d, J=16.6 Hz, 1H), 4.34 (dd, J=11.7, 4.0 Hz, 1H), 4.21 (d, J=17.8 Hz, 1H), 4.14 (d, J=17.5 Hz, 1H), 3.98 (d, J=17.6 Hz, 1H), 3.46-3.32 (m, 1H), 3.32-3.17 (m, 2H), 3.01-2.84 (m, 1H), 1.55 (h, J=7.3 Hz, 2H), 0.86 (t, J=7.4 Hz, 3H). ESI-MS m/z (%): 432 [MH$^+$] (100). Anal. (C$_{28}$H$_{29}$N$_5$O$_6$+⅕ TFA+⅔H$_2$O): Calcd. C, 66.11; H, 5.68; N, 9.11; found. C, 66.46; H, 5.99; N, 9.14.

4-((2-Butyl-1,4-dioxo-1,3,4,6,12,12a-hexahydropyrazino[1',2':1,6]pyrido[3,4-b]indol-7(2H)-yl)methyl)benzoic acid (134d)

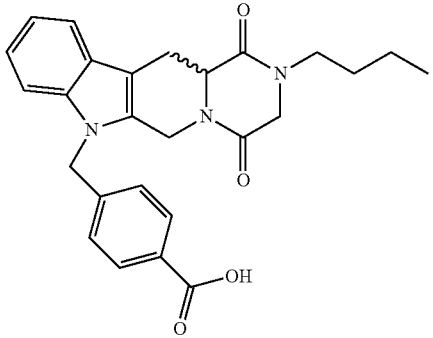 [SMILES: CCCCN1CC(=O)N2Cc3c(c4ccccc4n3Cc3ccc(C(=O)O)cc3)CC2C1=O]

According to GP7 from tert-Butyl 4-((2-butyl-1,4-dioxo-1,3,4,6,12,12a-hexahydropyrazino[1',2':1,6]pyrido[3,4-b]indol-7(2H)-yl)methyl)benzoate (133d) yielded colorless crystals (0.92 g, 2.07 mmol, 80%), mp: 250.0-250.2° C.; IR (KBr): 1687, 1657, 1611 cm$^{-1}$; $^1$H NMR (300 MHz, DMSO): δ 12.92 (s, 1H), 7.87 (d, J=8.2 Hz, 2H), 7.53 (d, J=7.3 Hz, 1H), 7.42 (d, J=7.9 Hz, 1H), 7.17-7.01 (m, 4H), 5.61-5.43 (m, 2H), 5.39 (d, J=16.7 Hz, 1H), 4.32 (dt, J=21.0, 10.5 Hz, 1H), 4.17 (t, J=19.4 Hz, 2H), 3.98 (d, J=17.6 Hz, 1H), 3.39-3.18 (m, 3H), 3.00-2.80 (m, 1H), 1.61-1.43 (m, 2H), 1.39-1.19 (m, 2H), 0.90 (t, J=7.3 Hz, 3H). ESI-MS m/z (%): 446 [MH$^+$] (100). Anal. (C$_{26}$H$_{27}$N$_3$O$_4$): Calcd. C, 70.09; H, 6.11; N, 9.43; found. C, 69.64; H, 6.10; N, 9.17.

4-((2-iso-Butyl-1,4-dioxo-1,3,4,6,12,12a-hexahydropyrazino[1',2':1,6]pyrido[3,4-b]indol-7(2H)-yl)methyl)benzoic acid (134e)

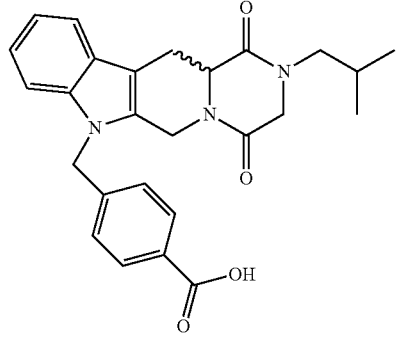 [SMILES: CC(C)CN1CC(=O)N2Cc3c(c4ccccc4n3Cc3ccc(C(=O)O)cc3)CC2C1=O]

According to GP7 from tert-Butyl 4-((2-isobutyl-1,4-dioxo-1,3,4,6,12,12a-hexahydropyrazino[1',2':1,6]pyrido[3,4-b]indol-7(2H)-yl)methyl)benzoate (133c) yielded colorless crystals (1.00 g, 2.25 mmol, 94%) after crystallization from trifluoroacetic acid/water and recrystallization from acetone, mp: 241.0-242.0° C.; IR (KBr): 1711, 1658, 1612 cm$^{-1}$; $^1$H NMR (300 MHz, DMSO): δ 12.92 (s, 1H), 7.87 (d, J=8.3 Hz, 2H), 7.54 (d, J=7.3 Hz, 1H), 7.42 (d, J=8.0 Hz, 1H), 7.18-7.00 (m, 4H), 5.62-5.44 (m, 2H), 5.39 (d, J=16.7 Hz, 1H), 4.35 (dd, J=11.7, 3.9 Hz, 1H), 4.18 (t, J=19.2 Hz, 2H), 3.96 (d, J=17.6 Hz, 1H), 3.32-3.21 (m, 2H), 3.09 (dd, J=13.1, 6.9 Hz, 1H), 3.02-2.87 (m, 1H), 1.98 (hept, J=6.6 Hz, 1H), 0.87 (dd, J=6.6, 2.8 Hz, 6H). ESI-MS m/z (%): 446 [MH$^+$] (100). Anal. (C$_{26}$H$_{27}$N$_3$O$_4$+½ Acetone): Calcd. C, 69.60; H, 6.37; N, 8.85; found. C, 69.23; H, 6.12; N, 9.03.

4-((2-iso-Pentyl-1,4-dioxo-1,3,4,6,12,12a-hexahydropyrazino[1',2':1,6]pyrido[3,4-b]indol-7(2H)-yl)methyl)benzoic acid (134f)

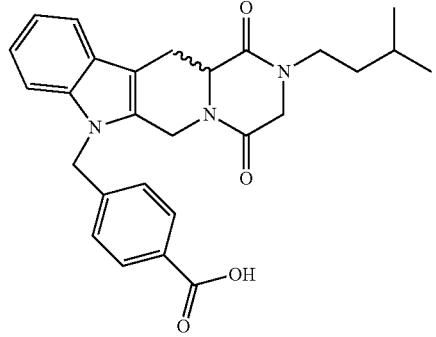 [SMILES: CC(C)CCN1CC(=O)N2Cc3c(c4ccccc4n3Cc3ccc(C(=O)O)cc3)CC2C1=O]

According to GP7 from tert-butyl 4-((2-isopentyl-1,4-dioxo-1,3,4,6,12,12a-hexahydropyrazino[1',2':1,6]pyrido[3,4-b]indol-7(2H)-yl)methyl)benzoate (133f) yielded colorless crystals (0.65 g, 1.42 mmol, 99%) after crystallization from trifluoroacetic acid/water and recrystallization from acetone, mp: 253.3-253.6° C.; IR (KBr): 1668, 1657 cm$^{-1}$; $^1$H NMR (300 MHz, DMSO): δ 12.93 (s, 1H), 7.87 (d, J=8.3 Hz, 2H), 7.53 (d, J=7.2 Hz, 1H), 7.42 (d, J=7.8 Hz, 1H), 7.25-6.97 (m, 4H), 5.55 (d, J=17.5 Hz, 1H), 5.48 (d, J=17.5 Hz, 1H), 5.39 (d, J=16.6 Hz, 1H), 4.33 (dd, J=11.7, 4.0 Hz, 1H), 4.17 (t, J=19.2 Hz, 2H), 3.98 (d, J=17.6 Hz, 1H), 3.52-3.39 (m, 1H), 3.34-3.20 (m, 2H), 2.98-2.83 (m, 1H), 1.54 (hept, J=6.5 Hz, 1H), 1.42 (q, J=7.2 Hz, 2H), 0.91 (d, J=6.5 Hz, 6H). ESI-MS m/z (%): 460 [MH$^+$] (100). Anal. (C$_{27}$H$_{29}$N$_3$O$_4$+½ Me$_2$CO): Calcd. C, 70.06; H, 6.60; N, 8.60; found. C, 69.80; H, 6.29; N, 8.93.

4-(((6S,12aR)-6-Methyl-1,4-dioxo-2-propyl-1,3,4,6,12,12a-hexahydropyrazino[1',2':1,6]pyrido[3,4-b]indol-7(2H)-yl)methyl)benzoic acid (134i)

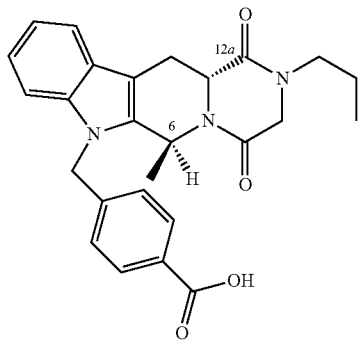 [SMILES: CCCN1CC(=O)N2[C@H](Cc3c(n(Cc4ccc(C(=O)O)cc4)c4ccccc34)[C@@H]2C)C1=O]

As a modification of GP7 tert-butyl 4-(((6S,12aR)-6-methyl-1,4-dioxo-2-propyl-1,3,4,6,12,12a-hexahydropyrazin[1',2':1,6]pyrido[3,4-b]indol-7(2H)-yl)methyl)benzoate (133i) was dissolved in dichloromethane with 10 percent trifluoroacetic acid. Solvent evaporation and recrystallization from acetone yielded colorless crystals (0.94 g, 2.10 mmol, 95%). $^1$H NMR (400 MHz, DMSO): δ 12.74 (s, 1H), 7.85 (d, J=8.3 Hz, 2H), 7.54 (d, J=7.3 Hz, 1H), 7.29 (d, J=7.9 Hz, 1H), 7.14-6.98 (m, 4H), 5.81 (q, J=6.6 Hz, 1H), 5.65 (d, J=17.8 Hz, 1H), 5.47 (d, J=17.9 Hz, 1H), 4.48 (dd, J=11.8, 4.3 Hz, 1H), 4.20 (d, J=17.5 Hz, 1H), 3.97 (d, J=17.6 Hz, 1H), 3.49-3.36 (m, 1H), 3.28 (dd, J=15.5, 4.4 Hz, 1H), 3.25-3.16 (m, 1H), 2.91 (dd, J=15.2, 12.0 Hz, 1H), 1.56 (h, J=7.4 Hz, 2H), 1.37 (d, J=6.7 Hz, 3H), 0.87 (t, J=7.4 Hz, 3H). Stereochemistry was determined by NOESY and COSY.

4-((10-(Benzyloxy)-1,4-dioxo-2-propyl-1,3,4,6,12,12a-hexahydropyrazino[1',2':1,6]pyrido[3,4-b]indol-7(2H)-yl)methyl)benzoic acid (134j)

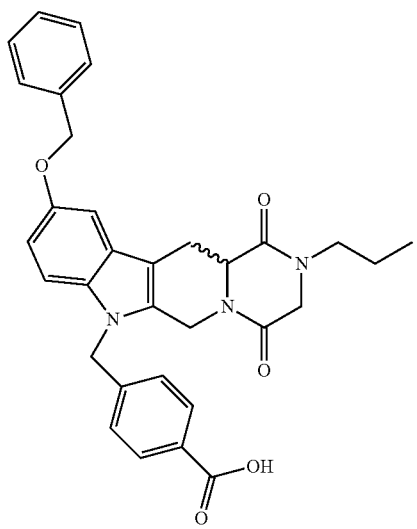 [SMILES: CCCN1CC(=O)N2Cc3c(c4cc(OCc5ccccc5)ccc4n3Cc3ccc(C(=O)O)cc3)CC2C1=O]

According to GP7 from tert-butyl 4-((10-(benzyloxy)-1,4-dioxo-2-propyl-1,3,4,6,12,12a-hexahydropyrazino[1',2':1,6]pyrido[3,4-b]indol-7(2H)-yl)methyl)benzoate (133j) yielded colorless crystals (0.89 g, 1.65 mmol, 98%) after crystallization from trifluoroacetic acid and water, $^1$H NMR (300 MHz, DMSO): δ 12.90 (s, 1H), 7.86 (d, J=8.3 Hz, 2H), 7.47 (d, J=6.9 Hz, 2H), 7.41-7.26 (m, 4H), 7.16 (d, J=2.3 Hz, 1H), 7.11 (d, J=8.3 Hz, 2H), 6.81 (dd, J=8.9, 2.4 Hz, 1H), 5.56-5.31 (m, 3H), 5.10 (s, 1H), 4.32 (dd, J=11.5, 3.9 Hz, 1H), 4.21 (d, J=17.7 Hz, 1H), 4.11 (d, J=16.8 Hz, 1H), 3.98 (d, J=17.6 Hz, 1H), 3.41 (dd, J=13.5, 7.3 Hz, 1H), 3.31-3.14 (m, 1H), 2.96-2.81 (m, 1H), 1.55 (sex, J=7.3 Hz, 1H), 0.86 (t, J=7.4 Hz, 3H).

4-((10-Methoxy-1,4-dioxo-2-propyl-1,3,4,6,12,12a-hexahydropyrazino[1',2':1,6]pyrido[3,4-b]indol-7(2H)-yl)methyl)benzoic acid (134k)

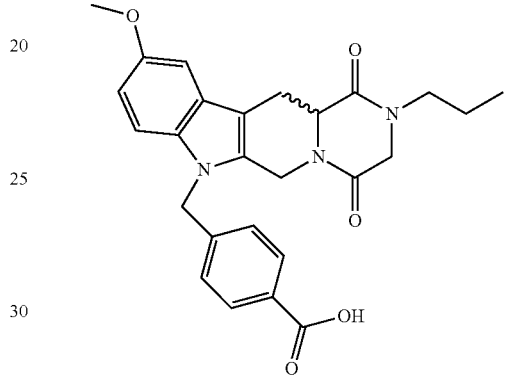

According to GP7 from tert-butyl 4-((10-methoxy-1,4-dioxo-2-propyl-1,3,4,6,12,12a-hexahydropyrazino[1',2':1,6]pyrido[3,4-b]indol-7(2H)-yl)methyl)benzoate (133k) yielded colorless crystals (1.05 g, 2.28 mmol, 97%) after crystallization from trifluoroacetic acid/water, $^1$H NMR (300 MHz, DMSO): δ 12.92 (s, 1H), 7.86 (d, J=8.2 Hz, 2H), 7.30 (d, J=8.9 Hz, 1H), 7.10 (d, J=8.3 Hz, 2H), 7.06 (d, J=2.4 Hz, 1H), 6.73 (dd, J=8.9, 2.4 Hz, 1H), 5.50 (d, J=17.5 Hz, 1H), 5.43 (d, J=17.5 Hz, 1H), 5.37 (d, J=17.0 Hz, 1H), 4.32 (dd, J=11.7, 4.0 Hz, 1H), 4.21 (d, J=17.7 Hz, 1H), 4.11 (d, J=16.8 Hz, 1H), 3.98 (d, J=17.6 Hz, 1H), 3.76 (s, 3H), 3.48-3.38 (m, 1H), 3.29-3.17 (m, 2H), 2.96-2.82 (m, 1H), 1.55 (h, J=7.3 Hz, 2H), 0.86 (t, J=7.4 Hz, 3H).

4-((10-hydroxy-1,4-dioxo-2-propyl-1,3,4,6,12,12a-hexahydropyrazino[1',2':1,6]pyrido[3,4-b]indol-7(2H)-yl)methyl)benzoic acid (134l)

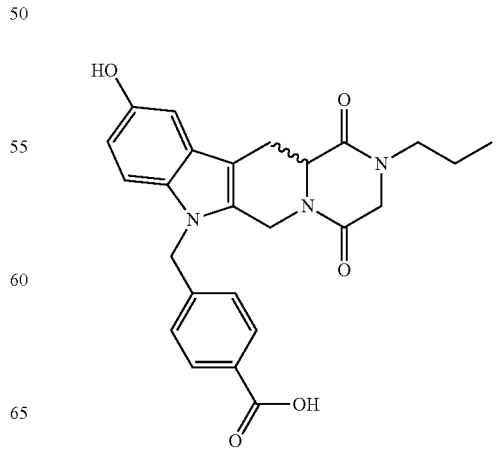

According to GP7 from tert-butyl 4-((10-hydroxy-1,4-dioxo-2-propyl-1,3,4,6,12,12a-hexahydropyrazino[1',2':1,6]pyrido[3,4-b]indol-7(2H)-yl)methyl)benzoate (133l) yielded colorless crystals (0.69 g, 1.41 mmol, 83%) after crystallization from trifluoroacetic acid, ¹H NMR (300 MHz, DMSO): δ 12.92 (s, 1H), 8.81 (s, 1H), 7.86 (d, J=8.3 Hz, 2H), 7.18 (d, J=8.8 Hz, 1H), 7.11 (d, J=8.3 Hz, 2H), 6.79 (d, J=2.2 Hz, 1H), 6.60 (dd, J=8.7, 2.2 Hz, 1H), 5.51-5.25 (m, 3H), 4.31 (dd, J=11.6, 4.0 Hz, 1H), 4.20 (d, J=17.6 Hz, 1H), 4.09 (d, J=16.7 Hz, 1H), 3.98 (d, J=17.6 Hz, 1H), 3.31 (d, J=7.6 Hz, 1H), 3.29-3.20 (m, 1H), 3.12 (dd, J=15.0, 3.6 Hz, 1H), 2.93-2.77 (m, 1H), 1.55 (h, J=7.3 Hz, 2H), 0.86 (t, J=7.4 Hz, 3H).

4-((2-Methyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135a)

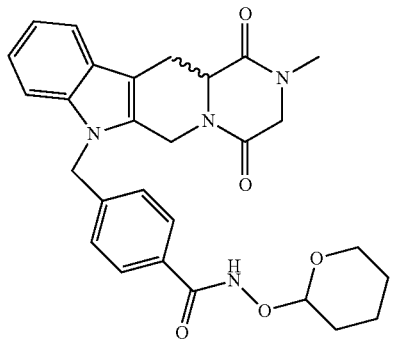 [SMILES: CN1CC(=O)N2Cc3c(c4ccccc4n3Cc3ccc(C(=O)NOC4CCCCO4)cc3)CC2C1=O]

According to GP8 from 4-((2-methyl-1,4-dioxo-1,3,4,6,12,12a-hexahydropyrazino[1',2':1,6]pyrido[3,4-b]indol-7(2H)-yl)methyl)benzoic acid (134a) yielded colorless crystals (0.50 g, 1.00 mmol, 44%) eluent (DCM/MeOH 15:1) crystallization from ethyl acetate/ether, mp.: 148.6-148.7° C.; IR (KBr): 1657 cm⁻¹, ¹H NMR (300 MHz, DMSO): δ 11.59 (s, 1H), 7.68 (d, J=8.2 Hz, 1H), 7.51 (d, J=7.2 Hz, 1H), 7.42 (d, J=7.8 Hz, 1H), 7.16-7.00 (m, 4H), 5.60-5.31 (m, 3H), 4.95 (s, 1H), 4.33 (dd, J=11.6, 3.9 Hz, 1H), 4.16 (t, J=16.3 Hz, 2H), 4.09-3.96 (m, 2H), 3.49 (d, J=11.0 Hz, 1H), 3.26 (dd, J=15.4, 3.4 Hz, 1H), 2.99-2.82 (m, 4H), 1.69 (s, 3H), 1.53 (s, 3H). ESI-MS m/z (%): 419 [MH⁺–C₅H₈O] (100), 503 [MH⁺] (13).

4-((2-Ethyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135b)

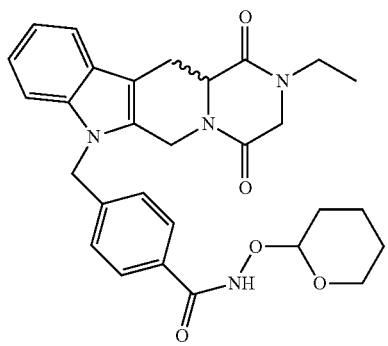 [SMILES: CCN1CC(=O)N2Cc3c(c4ccccc4n3Cc3ccc(C(=O)NOC4CCCCO4)cc3)CC2C1=O]

According to GP8 from 4-((2-ethyl-1,4-dioxo-1,3,4,6,12,12a-hexahydropyrazino[1',2':1,6]pyrido[3,4-b]indol-7(2H)-yl)methyl)benzoic acid (134b) yielded (1.26 g, 2.44 mmol, 85%) after silica gel chromatography (eluent ethyl acetate/methanol 10:1) and was immediately reacted to the final compound.

4-((1,4-Dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135c)

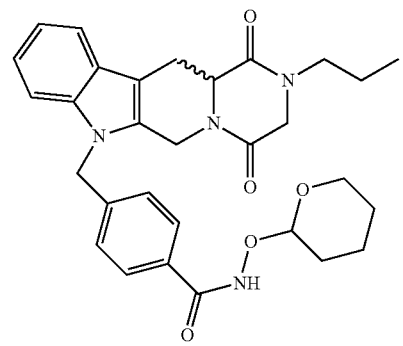 [SMILES: CCCN1CC(=O)N2Cc3c(c4ccccc4n3Cc3ccc(C(=O)NOC4CCCCO4)cc3)CC2C1=O]

According to GP8 from 4-((1,4-dioxo-2-propyl-1,3,4,6,12,12a-hexahydropyrazino[1',2':1,6]pyrido[3,4-b]indol-7(2H)-yl)methyl)benzoic acid (134c). ESI-MS m/z (%): 447 [MH⁺–C₅H₈O] (100), 531 [MH⁺] (14).

4-((2-Butyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135d)

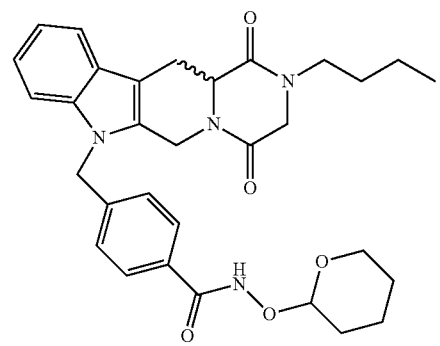 [SMILES: CCCCN1CC(=O)N2Cc3c(c4ccccc4n3Cc3ccc(C(=O)NOC4CCCCO4)cc3)CC2C1=O]

According to GP8 from 4-((2-Butyl-1,4-dioxo-1,3,4,6,12,12a-hexahydropyrazino[1',2':1,6]pyrido[3,4-b]indol-7(2H)-yl)methyl)benzoic acid (134d) yielded a pale gummi (0.47 g, 1.06 mmol, 62%) after silica gel chromatography with ethyl acetate/methanol (10:1) and was reacted immediately to the final compound.

4-((2-isobutyl-1,4-dioxo-1,3,4,6,12,12a-hexahydro-pyrazino[1',2':1,6]pyrido[3,4-b]indol-7(2H)-yl)methyl)-N-((tetrahydro-2H-pyran-2-yl)oxy)benzamide (135e)

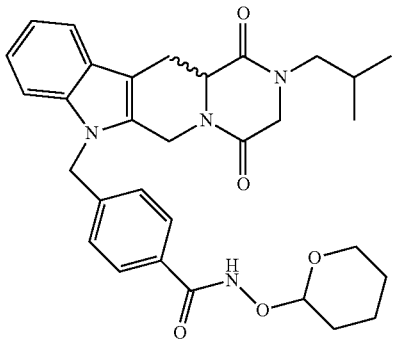 [SMILES: CC(C)CN1CC(=O)N2Cc3c(c4ccccc4n3Cc3ccc(C(=O)NOC4CCCCO4)cc3)CC2C1=O]

According to GP8 from 4-((2-iso-butyl-1,4-dioxo-1,3,4,6,12,12a-hexahydropyrazino[1',2':1,6]pyrido[3,4-b]indol-7(2H)-yl)methyl)benzoic acid (134e) yielded colorless crystals (0.85 g, 1.56 mmol, 73%) eluent ethyl acetate/methanol (10:1), ESI-MS m/z: Calcd.: 545.2758 [MH+]. found: 545.2762 [MH+].

4-((2-iso-Pentyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135f)

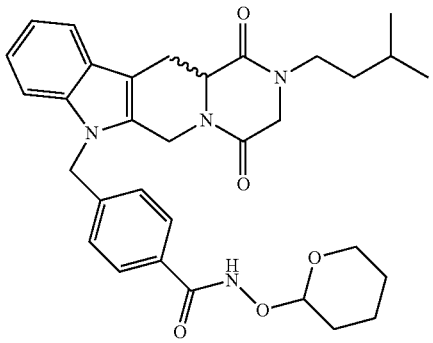 [SMILES: CC(C)CCN1CC(=O)N2Cc3c(c4ccccc4n3Cc3ccc(C(=O)NOC4CCCCO4)cc3)CC2C1=O]

According to GP8 from 4-((2-iso-Pentyl-1,4-dioxo-1,3,4,6,12,12a-hexahydropyrazino[1',2':1,6]pyrido[3,4-b]indol-7(2H)-yl)methyl)benzoic acid (134f) yielded colorless crystals (0.47 g, 1.06 mmol, 62%) eluent ethyl acetate/methanol (10:1), HR-MS m/z: Calcd.: 559.2915 [MH+]. found: 559.2918 [MH+].

4-(((6S,12aR)-6-Methyl-1,4-dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135i)

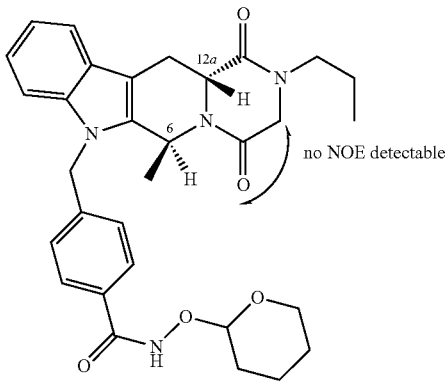

According to GP8 from 4-((((6S,12aR)-6-methyl-1,4-dioxo-2-propyl-1,3,4,6,12,12a-hexahydropyrazino[1',2':1,6]pyrido[3,4-b]indol-7(2H)-yl)methyl)benzoic acid (134i) yielded colorless crystals (0.98 g, 1.80 mmol, 76%) silica gel chromatography with dichloromethane/methanol (10:1), $^1$H NMR (400 MHz, DMSO): δ 11.57 (s, 1H), 7.66 (d, J=8.3 Hz, 2H), 7.54 (d, J=7.1 Hz, 1H), 7.27 (d, J=7.6 Hz, 1H), 7.14-6.99 (m, 4H), 5.84 (q, J=6.7 Hz, 1H), 5.61 (d, J=17.7 Hz, 1H), 5.45 (d, J=17.7 Hz, 1H), 4.96 (s, 1H), 4.48 (dd, J=11.7, 4.3 Hz, 1H), 4.21 (d, J=17.3 Hz, 1H), 4.07-3.95 (m, 2H), 3.54-3.47 (m, 1H), 3.47-3.40 (m, 1H), 3.28 (dd, J=15.5, 4.4 Hz, 1H), 3.25-3.16 (m, 1H), 2.91 (dd, J=14.9, 12.1 Hz, 1H), 1.70 (s, 3H), 1.59-1.50 (m, 5H), 1.38 (d, J=6.7 Hz, 3H), 0.87 (t, J=7.4 Hz, 3H). Stereochemistry was determined by NOESY and COSY.

4-((10-(Benzyloxy)-1,4-dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135j)

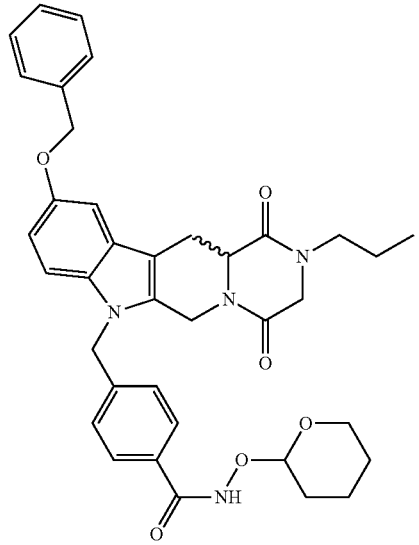 [SMILES: CCCN1CC(=O)N2Cc3c(c4cc(OCc5ccccc5)ccc4n3Cc3ccc(C(=O)NOC4CCCCO4)cc3)CC2C1=O]

According to GP8 from 4-((10-(Benzyloxy)-1,4-dioxo-2-propyl-1,3,4,6,12,12a-hexahydropyrazino[1',2':1,6]pyrido[3,4-b]indol-7(2H)-yl)methyl)benzoic acid (134j) yielded colorless crystals (0.77 g, 1.21 mmol, 77%) after chromatography over silica gel with methanol/ethyl acetate (1:10), $^1$H NMR (300 MHz, DMSO): δ 11.60 (s, 1H), 7.67 (d, J=8.2 Hz, 2H), 7.50-7.40 (m, 2H), 7.40-7.36 (m, 1H), 7.36-7.27 (m, 2H), 7.22-7.02 (m, 4H), 6.81 (dd, J=8.9, 2.4 Hz, 1H), 5.49-5.30 (m, 3H), 5.10 (s, 1H), 4.96 (s, 1H), 4.32 (dd, J=11.4, 3.7 Hz, 1H), 4.27-4.10 (m, 2H), 4.11-3.93 (m, 3H), 3.49 (d, J=11.4 Hz, 1H), 3.29-3.18 (m, 2H), 2.97-2.80 (m, 1H), 1.70 (s, 3H), 1.59-1.39 (m, 6H), 0.86 (t, J=7.4 Hz, 3H).

4-((10-methoxy-1,4-dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135k)

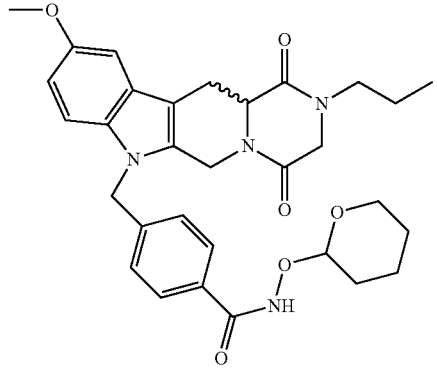 [SMILES: CCCN1CC(=O)N2Cc3c(c4cc(OC)ccc4n3Cc3ccc(C(=O)NOC4CCCCO4)cc3)CC2C1=O]

According to GP8 from 4-((10-methoxy-1,4-dioxo-2-propyl-1,3,4,6,12,12a-hexahydropyrazino[1',2':1,6]pyrido[3,4-b]indol-7(2H)-yl)methyl)benzoic acid (134k) yielded colorless crystals (0.91 g, 1.62 mmol, 92%) eluent dichloromethane/methanol (10:1), $^1$H NMR (300 MHz, DMSO): δ 11.60 (s, 1H), 7.67 (d, J=8.3 Hz, 2H), 7.29 (d, J=8.9 Hz, 1H), 7.09 (d, J=8.3 Hz, 2H), 7.05 (d, J=2.4 Hz, 1H), 6.73 (dd, J=8.9, 2.4 Hz, 1H), 5.52-5.32 (m, 3H), 4.96 (s, 1H), 4.32 (dd, J=11.7, 4.0 Hz, 1H), 4.21 (d, J=17.7 Hz, 1H), 4.12 (d, J=16.8 Hz, 1H), 3.98 (d, J=17.7 Hz, 1H), 3.75 (s, 3H), 3.54-3.45 (m, 1H), 3.45-3.39 (m, 1H), 3.31-3.17 (m, 2H), 2.84 (s, 1H), 1.70 (s, 3H), 1.62-1.47 (m, 1H), 0.86 (t, J=7.4 Hz, 3H).

N-hydroxy-4-((2-methyl-1,4-dioxo-1,3,4,6,12,12a-hexahydropyrazino[1',2':1,6]pyrido[3,4-b]indol-7(2H)-yl)methyl)benzamide (136a)

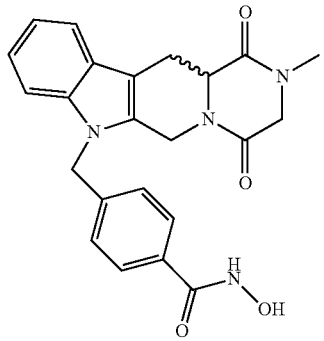 [SMILES: CN1CC(=O)N2Cc3c(c4ccccc4n3Cc3ccc(C(=O)NO)cc3)CC2C1=O]

According to GP9 from 4-((2-methyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135a) yielded colorless crystals (0.20 g, 0.48 mmol, 53%), mp.: 253.2° C.-253.7° C.; IR (KBr): 1669, 1643, 1614 cm$^{-1}$, $^1$H NMR (300 MHz, DMSO): δ 11.16 (s, 1H), 9.02 (s, 1H), 7.66 (d, J=8.3 Hz, 2H), 7.52 (d, J=7.1 Hz, 1H), 7.42 (d, J=7.8 Hz, 1H), 7.15-6.99 (m, 4H), 5.55-5.35 (m, 3H), 4.34 (dd, J=11.6, 4.0 Hz, 1H), 4.25-4.10 (m, 2H), 4.01 (d, J=17.6 Hz, 1H), 3.26 (dd, J=15.4, 3.4 Hz, 1H), 2.97-2.85 (m, 4H). ESI-MS m/z (%): 419 [MH$^+$] (100). Anal. (C$_{22}$H$_{20}$N$_4$O$_3$S+¼ ethyl acetate): Calcd. C, 65.44; H, 5.49; N, 12.42; found. C, 65.88; H, 5.65; N, 12.42.

4-((2-Ethyl-1,4-dioxo-1,3,4,6,12,12a-hexahydropyrazino[1',2':1,6]pyrido[3,4-b]indol-7(2H)-yl)methyl)-N-hydroxybenzamide (136b)

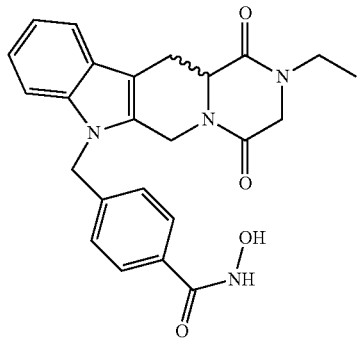 [SMILES: CCN1CC(=O)N2Cc3c(c4ccccc4n3Cc3ccc(C(=O)NO)cc3)CC2C1=O]

According to GP9 from 4-((2-Ethyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135b) yielded colorless crystals (0.25 g, 0.58 mmol, 27%), $^1$H NMR (300 MHz, DMSO): δ 11.25 (s, 1H), 9.04 (s, 1H=1.5 Hz, 1H), 7.68 (d, J=8.2 Hz, 2H), 7.52 (d, J=7.2 Hz, 1H), 7.41 (d, J=7.8 Hz, 1H), 7.14-6.99 (m, 4H), 5.45 (dt, J=16.6, 12.7 Hz, 3H), 4.33 (dd, J=11.6, 4.0 Hz, 1H), 4.19 (t, J=17.2 Hz, 2H), 4.01 (d, J=17.6 Hz, 1H), 3.41 (dd, J=12.9, 6.5 Hz, 1H), 3.36-3.29 (m, 1H), 3.24 (dd, J=15.3, 3.6 Hz, 1H), 2.99-2.83 (m, 1H), 1.09 (t, J=7.1 Hz, 3H).

4-((1,4-Dioxo-2-propyl-1,3,4,6,12,12a-hexahydropyrazino[1',2':1,6]pyrido[3,4-b]indol-7(2H)-yl)methyl)-N-hydroxybenzamide (136c)

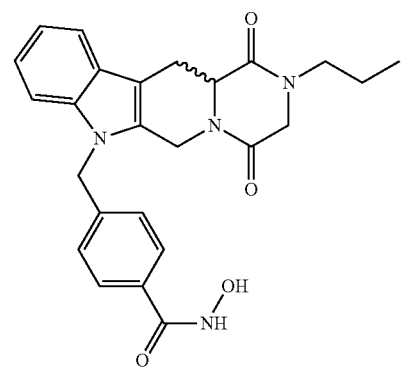 [SMILES: CCCN1CC(=O)N2Cc3c(c4ccccc4n3Cc3ccc(C(=O)NO)cc3)CC2C1=O]

According to GP9 from 4-((1,4-Dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135c) yielded colorless crystals (0.47 g, 1.06 mmol, 62%), mp: 231.3-231.6° C.; IR (KBr): 1658, 1640 cm$^{-1}$; $^1$H NMR (400 MHz, DMSO): δ 11.14 (s, 1H), 9.00 (s, 1H), 7.67 (d, J=8.2 Hz, 2H), 7.53 (d, J=7.6 Hz, 1H), 7.42 (d, J=8.1 Hz, 1H), 7.13-7.01 (m, 4H), 5.46 (dt, J=16.6, 12.9 Hz, 3H), 4.35 (dd, J=11.7, 4.0 Hz, 1H), 4.19 (t, J=17.9 Hz, 2H), 4.00 (d, J=17.6 Hz, 1H), 3.45-3.35 (m, 1H), 3.31-3.23 (m, 2H), 2.99-2.85 (m, 1H), 1.63-1.50 (m, 2H), 0.87 (t, J=7.4 Hz, 3H). ESI-MS m/z (%): 447 [MH$^+$] (100). Anal. (C$_{25}$H$_{26}$N$_4$O$_4$+1 H$_2$O): Calcd. C, 64.64; H, 6.08; N, 12.06; found. C, 64.95; H, 5.97; N, 11.73.

4-((2-Butyl-1,4-dioxo-1,3,4,6,12,12a-hexahydropyrazino[1,2':1,6]pyrido[3,4-b]indol-7(2H)-yl)methyl)-N-hydroxybenzamide (136d)

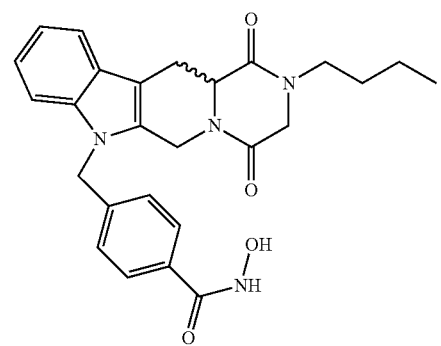 [SMILES: CCCCN1CC(=O)N2Cc3c(c4ccccc4n3Cc3ccc(C(=O)NO)cc3)CC2C1=O]

According to GP9 from 4-((2-Butyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135d) yielded colorless crystals (0.42 g, 0.91 mmol, 38%), $^1$H NMR (400 MHz, DMSO): δ 11.14 (s, 1H), 9.00 (s, 1H), 7.67 (d, J=8.3 Hz, 2H), 7.53 (d, J=7.6 Hz, 1H), 7.41 (d, J=8.1 Hz, 1H), 7.18-7.02 (m, 4H), 5.55-5.37 (m, 3H), 4.34 (dd, J=11.7, 4.0 Hz, 1H), 4.19 (t, J=18.1 Hz, 2H), 3.99 (d, J=17.6 Hz, 1H), 3.47-3.40 (m, 1H), 3.33-3.23 (m, 2H), 3.01-2.85 (m, 1H), 1.56-1.48 (m, 2H), 1.34-1.24 (m, 2H), 0.91 (t, J=7.3 Hz, 3H).

201

N-Hydroxy-4-((2-isobutyl-1,4-dioxo-1,3,4,6,12,12a-hexahydropyrazino[1',2':1,6]pyrido[3,4-b]indol-7(2H)-yl)methyl)benzamide (136e)

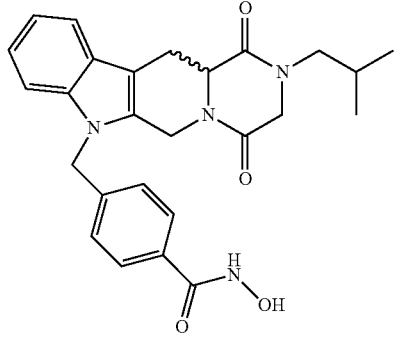 [SMILES: CC(C)CN1CC(=O)N2Cc3c(c4ccccc4n3Cc3ccc(C(=O)NO)cc3)CC2C1=O]

According to GP9 from 4-((2-isobutyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135e) yielded colorless crystals (0.32 g, 0.69 mmol, 44%), mp: 225.0-226.1° C.; IR (KBr): 3196, 1662, 1640 cm$^{-1}$; $^1$H NMR (300 MHz, DMSO): δ 11.18 (s, 1H), 9.02 (s, 1H), 7.67 (d, J=8.3 Hz, 2H), 7.53 (d, J=7.2 Hz, 1H), 7.41 (d, J=7.9 Hz, 1H), 7.18-6.98 (m, 4H), 5.62-5.30 (m, 3H), 4.36 (dd, J=11.7, 4.0 Hz, 1H), 4.19 (t, J=16.2 Hz, 2H), 3.96 (d, J=17.6 Hz, 1H), 3.35-3.23 (m, 2H), 3.09 (dd, J=13.2, 7.0 Hz, 1H), 2.94 (t, J=13.5 Hz, 1H), 1.99 (hept, J=6.7 Hz, 1H), 0.87 (dd, J=6.6, 3.0 Hz, 6H). ESI-MS m/z (%): 461 [MH$^+$] (100). Anal. (C$_{26}$H$_{28}$N$_4$O$_4$+2 H$_2$O): Calcd. C, 62.89; H, 6.50; N, 11.28; found. C, 62.76; H, 5.94; N, 11.10.

N-Hydroxy-4-((2-isopentyl-1,4-dioxo-1,3,4,6,12,12a-hexahydropyrazino[1',2':1,6]pyrido[3,4-b]indol-7(2H)-yl)methyl)benzamide (136f)

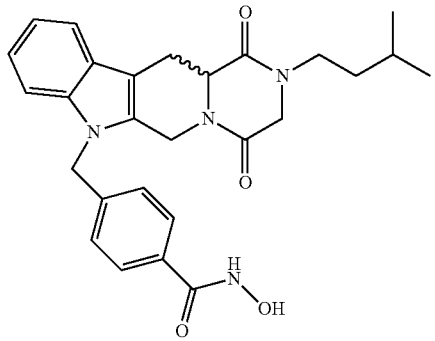 [SMILES: CC(C)CCN1CC(=O)N2Cc3c(c4ccccc4n3Cc3ccc(C(=O)NO)cc3)CC2C1=O]

According to GP9 from 4-((2-iso-Pentyl-1,4-dioxo-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135f) yielded colorless crystals (0.15 g, 0.31 mmol, 36%), mp: decomposition at 135.0° C.; IR (KBr): 1660 cm$^{-1}$; $^1$H NMR (300 MHz, DMSO): δ 11.16 (s, 1H), 9.12 (s, 1H), 7.66 (d, J=8.2 Hz, 2H), 7.52 (d, J=7.2 Hz, 1H), 7.41 (d, J=7.9 Hz, 1H), 7.17-7.00 (m, 4H), 5.45 (dt, J=16.6, 12.2 Hz, 3H), 4.34 (dd, J=11.7, 4.0 Hz, 1H), 4.18 (t, J=16.3 Hz, 2H), 4.00 (t, J=12.4 Hz, 1H), 3.51-3.39 (m, 1H), 3.35-3.17 (m, 2H), 2.99-2.81 (m, 1H), 1.54 (dq, J=12.6, 6.4 Hz, 1H), 1.42 (dd, J=14.4, 7.2 Hz, 1H), 0.89 (t, J=10.4 Hz, 6H). ESI-MS m/z (%): 475 [MH$^+$] (100). Anal. (C$_{27}$H$_{30}$N$_4$O$_4$+1¼H$_2$O): Calcd. C, 65.24; H, 6.59; N, 11.27; found. C, 65.25; H, 6.20; N, 10.98.

202

N-Hydroxy-4-(((6S,12aR)-6-methyl-1,4-dioxo-2-propyl-1,3,4,6,12,12a-hexahydropyrazino[1',2':1,6]pyrido[3,4-b]indol-7(2l)-yl)methyl)benzamide (136i)

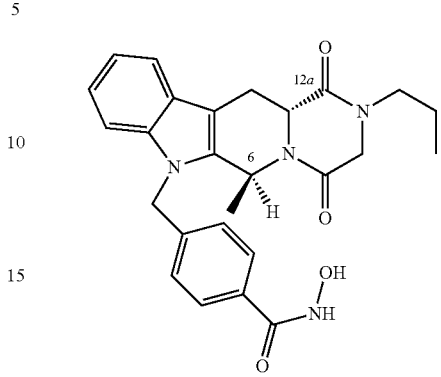

According to GP9 from 4-(((6S,12aR)-6-Methyl-1,4-dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135i) yielded (0.38 g, 0.82 mmol, 47%), $^1$H NMR (400 MHz, DMSO): δ 11.14 (s, J=53.9 Hz, 1H), 7.65 (d, J=8.3 Hz, 2H), 7.54 (d, J=7.2 Hz, 1H), 7.28 (d, J=7.8 Hz, 1H), 7.15-7.03 (m, 2H), 7.00 (d, J=8.2 Hz, 2H), 5.83 (q, J=6.6 Hz, 1H), 5.60 (d, J=17.7 Hz, 1H), 5.43 (d, J=17.7 Hz, 1H), 4.49 (dd, J=11.8, 4.3 Hz, 1H), 4.21 (d, J=17.6 Hz, 1H), 3.98 (d, J=17.6 Hz, 1H), 3.49-3.39 (m, 1H), 3.28 (dd, J=15.4, 4.4 Hz, 1H), 3.24-3.17 (m, 1H), 2.91 (dd, J=15.1, 12.1 Hz, 1H), 1.56 (h, J=7.4 Hz, 2H), 1.39 (d, J=6.7 Hz, 3H), 0.87 (t, J=7.4 Hz, 3H). Stereochemistry was affirmed by NOESY and COSY.

4-((10-(Benzyloxy)-1,4-dioxo-2-propyl-1,3,4,6,12,12a-hexahydropyrazino[1',2':1,6]pyrido[3,4-b]indol-7(2H)-yl)methyl)-N-hydroxybenzamide (136j)

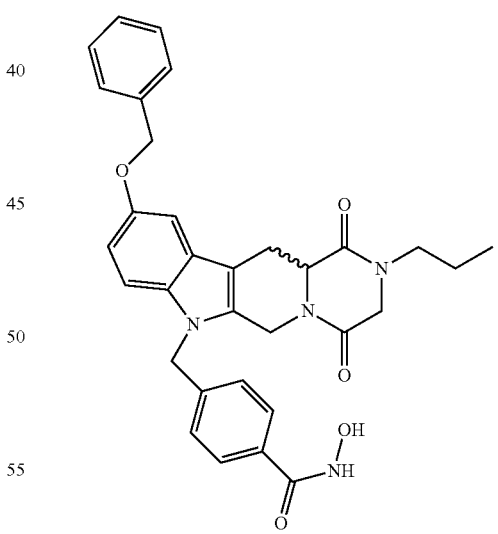

According to GP9 from 4-((10-(benzyloxy)-1,4-dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135j) yielded (0.12 g, 0.22 mmol, 18%), $^1$H NMR (300 MHz, DMSO): δ 11.16 (s, 1H), 9.02 (s, 1H), 7.66 (d, J=8.3 Hz, 2H), 7.46 (d, J=6.9 Hz, 2H), 7.43-7.35 (m, 2H), 7.36-7.28 (m, 2H), 7.16 (d, J=2.3 Hz, 1H), 7.07 (d, J=8.3 Hz, 2H), 6.81 (dd, J=8.9, 2.3 Hz, 1H), 5.42 (t, J=18.8 Hz, 3H), 5.10 (s, 2H), 4.33 (dd, J=11.7, 4.0 Hz, 1H), 4.21 (d, J=17.7 Hz, 1H), 4.13 (d, J=17.1 Hz, 1H), 3.98 (d, J=17.6 Hz, 1H), 3.49-3.37 (m, 1H), 3.30-3.17 (m, 2H), 2.94-2.81 (m, 1H), 1.54 (h, J=7.3 Hz, 2H), 0.86 (t, J=7.4 Hz, 3H).

N-Hydroxy-4-((10-methoxy-1,4-dioxo-2-propyl-1,3,4,6,12,12a-hexahydropyrazino[1',2':1,6]pyrido[3,4-b]indol-7(2H)-yl)methyl)benzamide (136k)

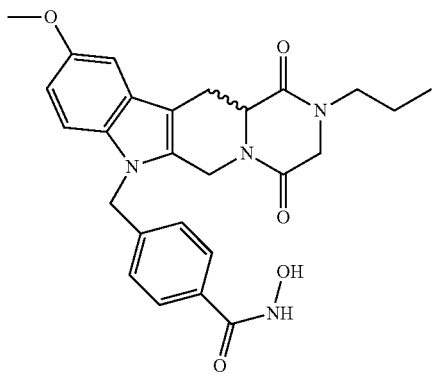 [SMILES: CCCN1CC(=O)N2Cc3c(c4cc(OC)ccc4n3Cc3ccc(C(=O)NO)cc3)CC2C1=O]

According to GP9 from 4-((10-methoxy-1,4-dioxo-2-propyl-1,3,4,6,12,12a-hexahydropyrazino[1',2':1,6]pyrido[3,4-b]indol-7(2H)-yl)methyl)-N-((tetrahydro-2H-pyran-2-yl)oxy)benzamide (135k) yielded (0.46 g, 0.96 mmol, 43%), ¹H NMR (300 MHz, DMSO): δ 11.16 (s, 1H), 7.66 (d, J=8.3 Hz, 2H), 7.30 (d, J=8.9 Hz, 1H), 7.12-7.01 (m, 3H), 6.72 (dd, J=8.9, 2.4 Hz, 1H), 5.56-5.27 (m, 3H), 4.33 (dd, J=11.7, 4.0 Hz, 1H), 4.21 (d, J=17.6 Hz, 1H), 4.14 (d, J=16.7 Hz, 1H), 3.99 (d, J=17.7 Hz, 1H), 3.75 (s, 3H), 3.48-3.36 (m, 1H), 3.31-3.18 (m, 2H), 2.89 (dd, J=14.2, 12.9 Hz, 1H), 1.55 (h, J=7.4 Hz, 2H), 0.86 (t, J=7.4 Hz, 3H).

N-Hydroxy-4-((10-hydroxy-1,4-dioxo-2-propyl-1,3,4,6,12,12a-hexahydropyrazino[1',2':1,6]pyrido[3,4-b]indol-7(2H)-yl)methyl)benzamide (136l)

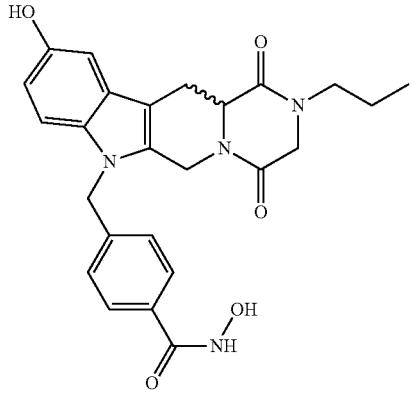 [SMILES: CCCN1CC(=O)N2Cc3c(c4cc(O)ccc4n3Cc3ccc(C(=O)NO)cc3)CC2C1=O]

Amidation according to GP8 from 4-((10-hydroxy-1,4-dioxo-2-propyl-1,3,4,6,12,12a-hexahydropyrazino[1',2':1,6]pyrido[3,4-b]indol-7(2H)-yl)methyl)benzoic acid (134l) and silica gel chromatography, was directly converted following GP9 to yield 136l (0.27 g, 0.58 mmol, 44%), ¹H NMR (300 MHz, DMSO): δ 11.16 (s, 1H), 8.82 (s, 1H), 7.65 (d, J=8.3 Hz, 2H), 7.18 (d, J=8.8 Hz, 1H), 7.07 (d, J=8.3 Hz, 2H), 6.78 (d, J=2.2 Hz, 1H), 6.59 (dd, J=8.7, 2.3 Hz, 1H), 5.54-5.24 (m, 3H), 4.32 (dd, J=11.6, 4.0 Hz, 1H), 4.20 (d, J=17.7 Hz, 1H), 4.11 (d, J=16.7 Hz, 1H), 3.98 (d, J=17.6 Hz, 1H), 3.40-3.22 (m, 3H), 3.11 (dd, J=15.2, 3.5 Hz, 1H), 2.82 (t, J=13.6 Hz, 1H), 1.56 (h, J=7.3 Hz, 2H), 0.86 (t, J=7.4 Hz, 3H).

N-((tert-butylcarbamoyl)oxy)-4-((1,4-dioxo-2-propyl-1,3,4,6,12,12a-hexahydropyrazino[3,4-b]indol-7(2H)-yl)methyl)benzamide (136m)

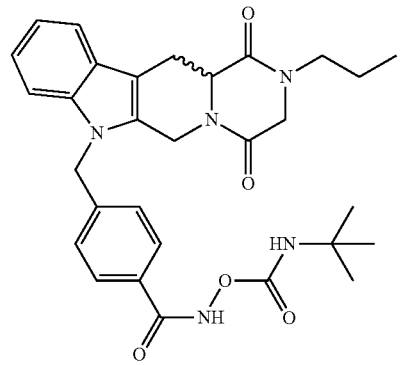 [SMILES: CCCN1CC(=O)N2Cc3c(c4ccccc4n3Cc3ccc(C(=O)NOC(=O)NC(C)(C)C)cc3)CC2C1=O]

According to Schlimme et al., 2011 from 4-((1,4-Dioxo-2-propyl-1,3,4,6,12,12a-hexahydropyrazino[1',2':1,6]pyrido[3,4-b]indol-7(2H)-yl)methyl)-N-hydroxybenzamide (136c). Yield: Colorless crystals. (0.03 g, 0.06 mmol, 12%), ¹H NMR (300 MHz, DMSO): δ 11.90 (s, 1H), 7.73 (d, J=8.2 Hz, 2H), 7.61 (s, 1H), 7.53 (d, J=7.7 Hz, 1H), 7.42 (d, J=7.8 Hz, 1H), 7.18-7.03 (m, 4H), 5.63-5.31 (m, 3H), 4.43-4.26 (m, 1H), 4.18 (t, J=17.0 Hz, 2H), 3.99 (d, J=17.3 Hz, 1H), 3.45-3.37 (m, 1H), 3.26 (dd, J=12.6, 5.4 Hz, 2H), 2.97-2.87 (m, 1H), 1.59-1.51 (m, 2H), 1.24 (s, 9H), 0.86 (t, J=6.9 Hz, 3H).

tert-Butyl 4-((8-hydroxy-4-methyl-3,5-dioxo-3.4.5.6-tetrahydro-2,6-methano[1.3]diazocino[5,6-b]indol-11(1H)-yl)methyl)benzoate (137a)

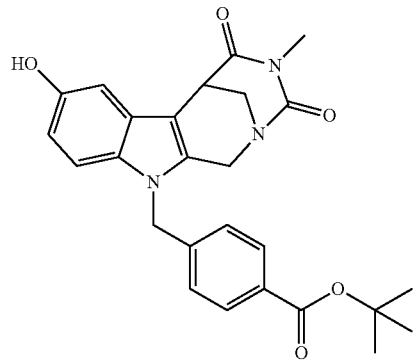 [SMILES: CN1C(=O)C2CN(Cc3c2c2cc(O)ccc2n3Cc2ccc(C(=O)OC(C)(C)C)cc2)C1=O]

tert-Butyl 4-((8-(benzyloxy)-4-methyl-3,5-dioxo-3.4.5.6-tetrahydro-2,6-methano[1.3]diazocino[5,6-b]indol-11(1H)-yl)methyl)benzoate (30e) 0.52 g (0.94 mmol) and 0.22 g Pd(10% Pd) were dissolved in Tetrahydrofuran (65 ml). The mixture was stirred under hydrogen atmosphere at room temperature and continued until completion of the reaction was observed by TLC (CH₂Cl₂:MeOH (10:1)). The product was collected by filtration over Na₂SO₄ and Tetrahydrofuran was removed under reduced pressure. The product was obtained as a colorless solid. Yield 0.42 g (0.91 mmol; 97%) Colorless crystals; mp: 201.2-205.1° C. ¹H NMR (300 MHz, DMSO): δ 8.89 (s, 1H), 7.81 (d, J=8.3 Hz, 2H), 7.16 (t, J=8.2 Hz, 3H), 6.86 (d, J=2.3 Hz, 1H), 6.58 (dd, J=8.8, 2.3 Hz, 1H), 5.34 (s, 2H), 4.78 (d, J=16.5 Hz, 1H), 4.49 (d, J=16.4 Hz, 1H), 3.86 (d, J=12.9 Hz, 1H), 3.75 (s, 1H), 3.42 (dd, 1H), 2.89 (s, 3H), 1.51 (s, 9H). ESI-MS m/z (%): 406.14 [MH⁺–C₄H₈] (100), 462.20 [MH⁺] (16.77), 479.23 [MNH₄⁺] (39.69), 945.38 [MNa⁺] (4.89). Anal. calcd for C₂₆H₂₇N₃O₅: C, 67.66; H, 5.90; N, 9.10; found: C, 67.41; H, 5.98; N, 8.84.

205 tert-butyl 4-((8-ethoxy-4-methyl-3.5-dioxo-3.4.5.6-tetrahydro-2.6-methano[1.3]diazocino[5.6-b]indol-11(1H)-yl)methyl)benzoate (138a)

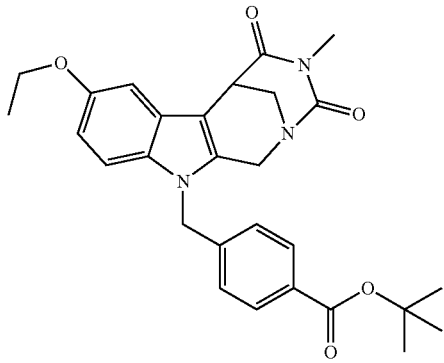 [SMILES: CCOc1ccc2c(c1)c1c(n2Cc2ccc(C(=O)OC(C)(C)C)cc2)CN2CC1C(=O)N(C)C2=O]

According to GP6, modification a, tert-butyl 4-((8-hydroxy-4-methyl-3.5-dioxo-3.4.5.6-tetrahydro-2.6-methano[1.3]diazocino[5.6-b]indol-11(1H)-yl)methyl)benzoate (137a). Yield 0.05 g (0.10 mmol; 46%) yellow oil after crystallization from Ethylacetate. $^1$H NMR (300 MHz, DMSO): δ 7.81 (d, J=8.3 Hz, 2H), 7.28 (d, J=8.9 Hz, 1H), 7.14 (d, J=8.3 Hz, 2H), 6.97 (d, J=2.3 Hz, 1H), 6.73 (dd, J=8.9, 2.4 Hz, 1H), 5.39 (s, 2H), 4.80 (d, J=16.6 Hz, 1H), 4.51 (d, J=16.5 Hz, 1H), 4.05-3.93 (m, 2H), 3.93-3.79 (m, 2H), 3.43 (dd, J=13.1, 2.0 Hz, 1H), 2.89 (s, 3H), 1.51 (s, 9H), 1.33 (t, J=6.9 Hz, 3H).

tert-butyl 4-((4-methyl-3.5-dioxo-8-propoxy-3.4.5.6-tetrahydro-2.6-methano[1.3]diazocino[5.6-b]indol-11(1H)-yl)methyl)benzoate (138b)

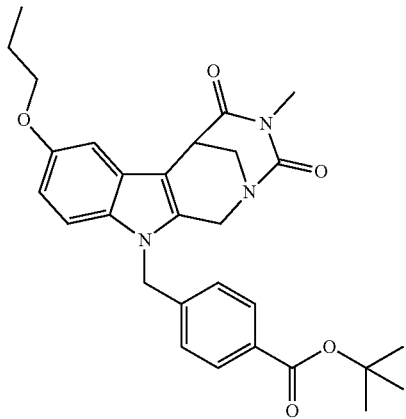 [SMILES: CCCOc1ccc2c(c1)c1c(n2Cc2ccc(C(=O)OC(C)(C)C)cc2)CN2CC1C(=O)N(C)C2=O]

According to GP6, modification a, tert-butyl 4-((8-hydroxy-4-methyl-3.5-dioxo-3.4.5.6-tetrahydro-2.6-methano[1.3]diazocino[5.6-b]indol-11(1H)-yl)methyl)benzoate (137a). Yield 0.06 g (0.12 mmol; 54%) colorless crystals; mp: 232.1-235.3° C. $^1$H NMR (300 MHz, DMSO): δ 7.81 (d, J=8.2 Hz, 21H), 7.28 (d, J=8.9 Hz, 1H), 7.14 (d, J=8.2 Hz, 2H), 6.97 (d, J=2.3 Hz, 1H), 6.74 (dd, J=8.9, 2.4 Hz, 1H), 5.39 (s, 2H), 4.80 (d, J=16.6 Hz, 1H), 4.51 (d, J=16.5 Hz, 1H), 3.92-3.88 (m, 2H), 3.87 (d, J=2.9 Hz, 1H), 3.83 (s, 1H), 3.43 (d, J=11.3 Hz, 1H), 2.89 (s, 3H), 1.81-1.66 (m, 2H), 1.51 (s, 9H), 0.99 (t, J=7.4 Hz, 3H). ESI-MS m/z (%): 448.19 [MH$^+$–C$_4$H$_8$] (100), 504.25 [MH$^+$] (30.49), 526.23 [MNa$^+$] (29.02), 1029.48 [2MNa$^+$] (6). Anal. calcd for C$_{29}$H$_{33}$N$_3$O$_5$×0.125 C$_4$H$_8$O$_2$: C, 68.57; H, 6.61; N, 8.17; found: C, 68.49; H, 6.55; N, 8.06.

206 tert-Butyl 4-((8-butoxy-4-methyl-3.5-dioxo-3.4.5.6-tetrahydro-2.6-methano[1.3]diazocino[5.6-b]indol-11(1H)-yl)methyl)benzoate (138c)

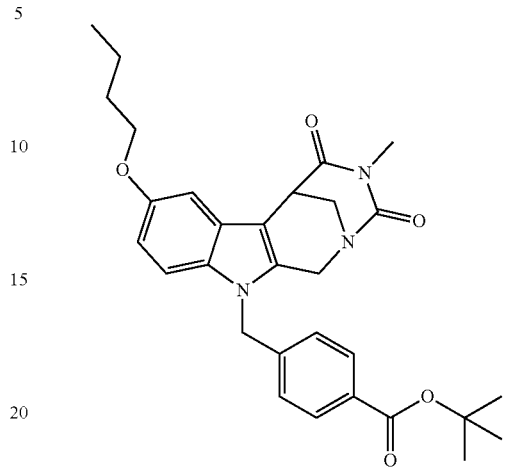

According to GP6, modification a, tert-butyl 4-((8-Hydroxy-4-methyl-3.5-dioxo-3.4.5.6-tetrahydro-2.6-methano[1.3]diazocino[5.6-b]indol-11(1H)-yl)methyl)benzoate (137a). Yield 0.065 g (0.13 mmol; 57%) colorless crystals after crystallization from ethylacetate; mp: 205.5-207.2° C. $^1$H NMR (300 MHz, DMSO): δ 7.81 (d, J=8.3 Hz, 2H), 7.27 (d, J=8.9 Hz, 1H), 7.13 (d, J=8.3 Hz, 2H), 6.97 (d, J=2.3 Hz, 1H), 6.73 (dd, J=8.9, 2.4 Hz, 1H), 5.39 (s, 2H), 4.79 (d, J=16.6 Hz, 1H), 4.51 (d, J=16.4 Hz, 1H), 3.94 (ddd, J=13.2, 8.1, 4.9 Hz, 2H), 3.86 (s, 1H), 3.83 (s, 1H), 3.42 (dd, J=9.1, 3.9 Hz, 1H), 2.89 (s, 3H), 1.75-1.64 (m, 2H), 1.51 (s, 9H), 1.47-1.39 (m, 2H), 0.94 (t, J=7.4 Hz, 3H). ESI-MS m/z (%): 462.20 [MH$^+$–C$_4$H$_8$] (100), 518.27 [MH$^+$] (32.91), 540.25 [MNa$^+$] (33.64), 1057.51 [2MNa$^+$] (4.48). Anal. calcd for C$_{30}$H$_{35}$N$_3$O$_5$: C, 69.61; H, 6.82; N, 8.12; found: C, 69.28; H, 6.82; N, 7.86.

4-((8-Ethoxy-4-methyl-3.5-dioxo-3.4.5.6-tetrahydro-2.6-methano[1.3]diazocino[5.6-b]indol-11(1H)-yl)methyl)benzoic acid (139a)

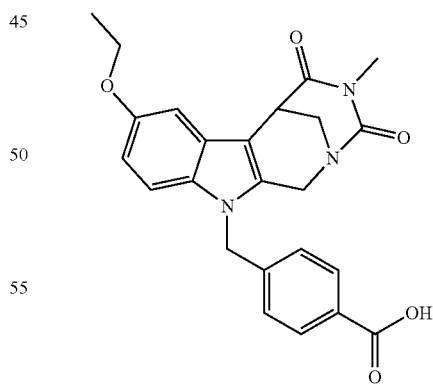

According to GP7, from tert-butyl 4-((8-butoxy-4-methyl-3.5-dioxo-3.4.5.6-tetrahydro-2.6-methano[1.3]diazocino[5.6-b]indol-11(1H)-yl)methyl)benzoate (138a). Yield 0.39 g (0.90 mmol; 88%) colorless crystals; mp: 236.3-239.9° C. $^1$H NMR (300 MHz, DMSO): δ 12.93 (s, 1H), 7.85 (d, J=8.3 Hz, 2H), 7.29 (d, J=8.9 Hz, 1H), 7.14 (d, J=8.3 Hz, 2H), 6.97 (d, J=2.4 Hz, 1H), 6.74 (dd, J=8.9, 2.4 Hz, 1H), 5.40 (s, 2H), 4.80 (d, J=16.5 Hz, 1H), 4.51 (d, J=16.4 Hz, 1H), 4.07-3.94 (m, 2H), 3.88 (d, J=13.1 Hz, 1H), 3.83 (s, 1H), 3.45 (s, 1H), 2.89 (s, 3H), 1.33 (t, J=6.9 Hz, 3H). ESI-MS m/z (%): 434.17 [MH$^+$] (100), 889.32 [2MNa$^+$](1.37). Anal. calcd for $C_{24}H_{23}N_3O_5 \times 0.33\ C_4H_8O_2$: C, 65.76; H, 5.55; N, 9.09; found: C, 65.87; H, 5.50; N, 9.15.

4-((4-Methyl-3,5-dioxo-8-propoxy-3,4,5,6-tetrahydro-2,6-methano[1,3]diazocino[5,6-b]indol-11(1H)-yl)methyl)benzoic acid (139b)

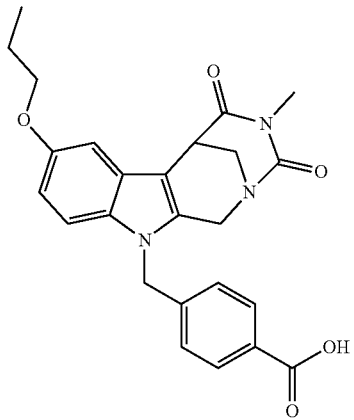 [SMILES: CCCOc1ccc2c(c1)c1c(n2Cc2ccc(C(=O)O)cc2)CN2CC1C(=O)N(C)C2=O]

According to GP7, from tert-butyl 4-((4-methyl-3,5-dioxo-8-propoxy-3,4,5,6-tetrahydro-2,6-methano[1,3]diazocino[5,6-b]indol-11(1H)-yl)methyl)benzoate (138b). Yield 0.43 g (0.90 mmol; 96%) colorless crystals; mp: 262.3-263.3° C. $^1$H NMR (300 MHz, DMSO): δ 12.92 (s, 1H), 7.85 (d, J=8.3 Hz, 2H), 7.29 (d, J=8.9 Hz, 1H), 7.13 (d, J=8.3 Hz, 2H), 6.97 (d, J=2.4 Hz, 1H), 6.74 (dd, J=8.9, 2.4 Hz, 1H), 5.40 (s, 2H), 4.80 (d, J=16.6 Hz, 1H), 4.52 (d, J=16.5 Hz, 1H), 3.90 (dd, J=9.7, 6.7 Hz, 2H), 3.86 (s, 1H), 3.84 (s, 1H), 3.44 (d, J=11.3 Hz, 1H), 2.89 (s, 3H), 1.74 (dd, J=14.0, 6.9 Hz, 2H), 0.99 (t, J=7.4 Hz, 3H). ESI-MS m/z (%): 448.19 [MH$^+$] (100), 917.35 [2MNa$^+$] (1.55). Anal. calcd for $C_{25}H_{25}N_3O_5 \times 0.125\ C_4H_8O_2 \times 0.75\ H_2O$: C, 64.9; H, 5.83; N, 8.91; found: C, 65.25; H, 5.72; N, 8.91.

4-((8-Butoxy-4-methyl-3,5-dioxo-3,4,5,6-tetrahydro-2,6-methano[1,3]diazocino[5,6-b]indol-11(1H)-yl)methyl)benzoic acid (139c)

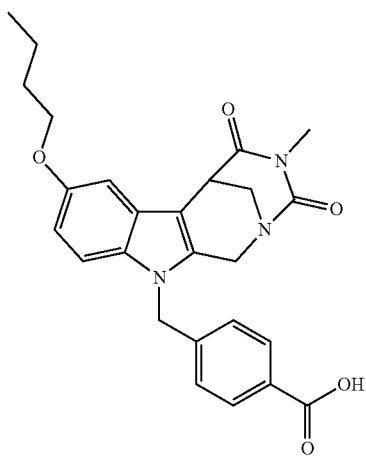 [SMILES: CCCCOc1ccc2c(c1)c1c(n2Cc2ccc(C(=O)O)cc2)CN2CC1C(=O)N(C)C2=O]

According to GP 7 from tert-butyl 4-((8-butoxy-4-methyl-3,5-dioxo-3,4,5,6-tetrahydro-2,6-methano[1,3]diazocino[5,6-b]indol-11(1H)-yl)methyl)benzoate (138c). Yield 0.47 g (1.02 mmol; 95%) colorless crystals; mp: 268.9-271.4° C. $^1$H NMR (300 MHz, DMSO): δ 12.93 (s, 1H), 7.85 (d, J=8.3 Hz, 1H), 7.29 (d, J=8.9 Hz, 2H), 7.13 (d, J=8.3 Hz, 1H), 6.97 (d, J=2.3 Hz, 2H), 6.74 (dd, J=8.9, 2.4 Hz, 1H), 5.40 (s, 2H), 4.80 (d, J=16.7 Hz, 1H), 4.51 (d, J=16.1 Hz, 1H), 3.94 (dd, J=11.8, 8.1 Hz, 2H), 3.86 (s, 1H), 3.84 (s, 1H), 3.43 (d, J=13.0 Hz, 2H), 2.89 (s, 3H), 1.69 (dd, J=14.7, 6.5 Hz, 2H), 1.45 (dd, J=15.1, 7.4 Hz, 2H), 0.94 (t, 0.1=7.4 Hz, 3H). ESI-MS m/z (%): 462.20 [MH$^+$] (100), 945.38 [2MNa$^+$] (1.71). Anal. calcd for $C_{26}H_{27}N_3O_5 \times 0.125\ C_4H_8O_2 \times 0.5\ H_2O$: C, 66.11; H, 6.03; N, 8.73; found: C, 66.48; H, 5.85; N, 8.65.

4-((8-Ethoxy-4-methyl-3,5-dioxo-3,4,5,6-tetrahydro-2,6-methano[1,3]diazocino[5,6-b]indol-11(1H)-yl)methyl)-N-((tetrahydro-2H-pyran-2-yl)oxy)benzamide (140a)

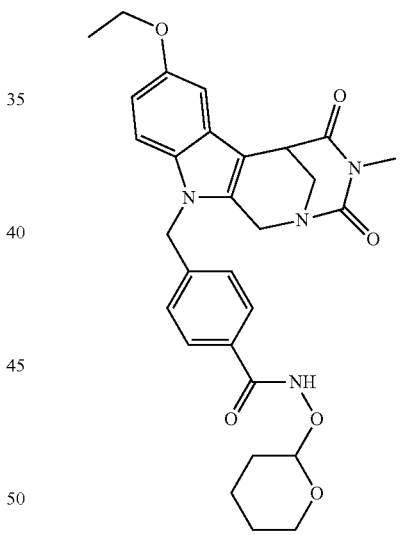

According to GP 8 from 4-((8-ethoxy-4-methyl-3,5-dioxo-3,4,5,6-tetrahydro-2,6-methano[1,3]diazocino[5,6-b]indol-11(1H)-yl)methyl)benzoic acid (139a). Yield 0.29 g (0.54 mmol; 61%) slightly yellow oil after chromatography over silica gel with CH$_2$Cl$_2$/CH$_4$O (10:1). $^1$H NMR (300 MHz, DMSO): δ 11.60 (s, 1H), 7.67 (d, J=8.3 Hz, 2H), 7.28 (d, J=8.9 Hz, 1H), 7.13 (d, J=8.3 Hz, 2H), 6.96 (d, J=2.4 Hz, 1H), 6.73 (dd, J=8.9, 2.4 Hz, 1H), 6.00 (s, 1H), 5.37 (s, 1H), 4.95 (s, 1H), 4.82 (d, J=16.5 Hz, 1H), 4.55 (s, 1H), 4.00 (dd, J=7.0, 2.6 Hz, 2H), 3.89 (d, J=13.1 Hz, 1H), 3.83 (s, 1H), 3.43 (dd, J=10.6, 4.2 Hz, 1H), 2.89 (d, J=1.4 Hz, 3H), 1.69 (s, 3H), 1.56-1.42 (m, 5H), 1.33 (t, J=6.9 Hz, 3H).

4-((4-Methyl-3.5-dioxo-8-propoxy-3.4.5.6-tetrahydro-2.6-methano[1.3]diazocino[5.6-b]indol-11(1H)-yl)methyl)-N-((tetrahydro-2H-pyran-2-yl)oxy)benzamide (140b)

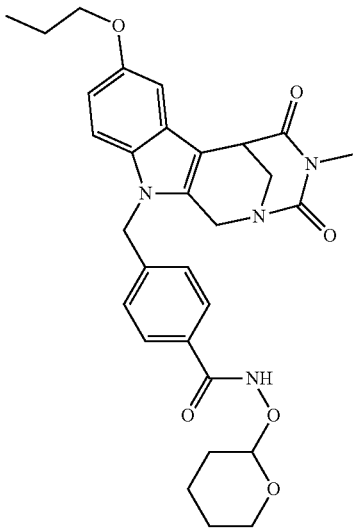 [SMILES: CCCOc1ccc2c(c1)c1c(n2Cc2ccc(C(=O)NOC3CCCCO3)cc2)CN2CC1C(=O)N(C)C2=O]

According to GP8 from 4-((4-methyl-3.5-dioxo-8-propoxy-3.4.5.6-tetrahydro-2.6-methano[1.3]diazocino[5.6-b]indol-11(1H)-yl)methyl)benzoic acid (139b). Yield 0.39 g (0.85 mmol; 85%) slightly yellow oil after chromatography over silica gel with $CH_2Cl_2/C_4H_8O_2$ (1:2). $^1$H NMR (300 MHz, DMSO): δ 11.60 (s, 1H), 7.67 (d, J=8.2 Hz, 2H), 7.28 (d, J=8.9 Hz, 1H), 7.13 (d, J=8.2 Hz, 2H), 6.97 (d, J=2.3 Hz, 1H), 6.74 (dd, J=8.9, 2.4 Hz, 1H), 5.37 (s, 2H), 4.96 (s, 1H), 4.82 (d, J=16.6 Hz, 1H), 4.53 (d, J=16.5 Hz, 1H), 4.03 (q, J=7.1 Hz, 2H), 3.95-3.88 (m, 2H), 3.86 (s, 1H), 3.83 (s, 1H), 3.43 (dd, 1H), 2.89 (s, 3H), 1.82 (d, J=6.9 Hz, 1H), 1.73 (d, J=7.2 Hz, 1H), 1.49 (d, J=24.8 Hz, 5H), 1.17 (t, J=7.1 Hz, 3H).

4-((8-Butoxy-4-methyl-3.5-dioxo-3.4.5.6-tetrahydro-2.6-methano[1.3]diazocino[5.6-b]indol-11(1H)-yl)methyl)-N-((tetrahydro-2H-pyran-2-yl)oxy)benzamide (140c)

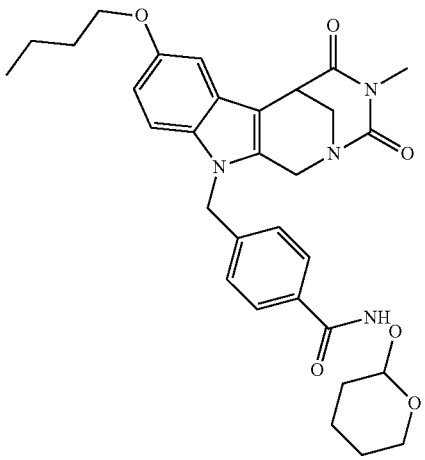

According to GP8 from 4-((8-butoxy-4-methyl-3.5-dioxo-3.4.5.6-tetrahydro-2.6-methano[1.3]diazocino[5.6-b]indol-11(1H)-yl)methyl)benzoic acid (139c). Yield 0.34 g (0.61 mmol; 60%) colorless solid after chromatography over silica gel with $CH_2Cl_2/CH_4O$ (10:1); mp: 123.7-126.5° C.

$^1$H NMR (300 MHz, DMSO): δ 11.60 (s, 1H), 7.67 (d, J=8.2 Hz, 2H), 7.28 (d, J=8.9 Hz, 1H), 7.13 (d, J=8.3 Hz, 2H), 6.97 (d, J=2.3 Hz, 1H), 6.73 (dd, J=8.9, 2.4 Hz, 1H), 5.37 (s, 2H), 4.95 (s, 1H), 4.82 (d, J=16.6 Hz, 1H), 4.53 (d, J=16.7 Hz, 1H), 3.94 (ddd, J=10.5, 6.8, 3.5 Hz, 2H), 3.86 (s, 1H), 3.83 (s, 1H), 3.44 (dd, J=11.2 Hz, 1H), 2.89 (s, 3H), 1.76-1.64 (m, 5H), 1.56-1.37 (m, 7H), 0.94 (t, J=7.4 Hz, 3H). ESI-MS m/z (%): 477.22 [MH$^+$–3,4-dihydro-2H-pyran] (100), 561.27 [MH$^+$] (9.6), 583.25 [MNa$^+$] (8.41), 1143.52 [2MNa$^+$] (8.92). Anal. calcd for $C_{31}H_{36}N_4O_6 \times 1.0\ H_2O$: C, 64.36; H, 6.57; N, 9.69; found: C, 64.40; H, 6.57; N, 9.68.

4-((8-Ethoxy-4-methyl-3.5-dioxo-3.4.5.6-tetrahydro-2.6-methano[1.3]diazocino[5.6-b]indol-11(1H)-yl)methyl)-N-hydroxybenzamide (141a)

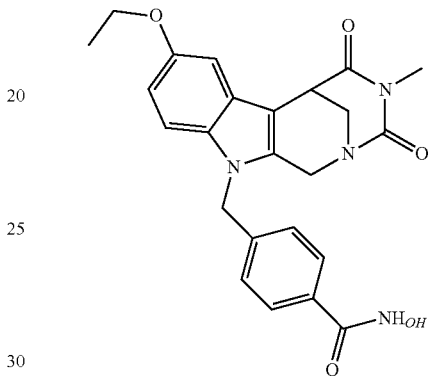

According to GP9 from 4-((8-ethoxy-4-methyl-3.5-dioxo-3.4.5.6-tetrahydro-2.6-methano[1.3]diazocino[5.6-b]indol-11(1H)-yl)methyl)-N-((tetrahydro-2H-pyran-2-yl)oxy)benzamide (140a). Yield 0.1 g (0.22 mmol; 41%) colorless crystals; mp: 207.3-210.1° C. $^1$H NMR (300 MHz, DMSO): δ 11.17 (s, 1H), 9.02 (s, 1H), 7.66 (d, J=8.3 Hz, 2H), 7.29 (d, J=8.9 Hz, 1H), 7.11 (d, J=8.3 Hz, 2H), 6.97 (d, J=2.3 Hz, 1H), 6.73 (dd, J=8.9, 2.4 Hz, 1H), 5.35 (s, 2H), 4.83 (d, J=16.6 Hz, 1H), 4.54 (d, J=16.5 Hz, 1H), 4.06-3.94 (m, 2H), 3.89 (d, J=13.0 Hz, 1H), 3.83 (s, 1H), 3.44 (dd, J=13.1, 2.0 Hz, 1H), 2.89 (s, 3H), 1.33 (t, J=6.9 Hz, 3H). ESI-MS m/z (%): 449.18 [MH$^+$] (100), 897.36 [2MH$^+$] (13.2).

N-Hydroxy-4-((4-methyl-3.5-dioxo-8-propoxy-3.4.5.6-tetrahydro-2.6-methano[1.3]diazocino[5.6-b]indol-11(1H)-yl)methyl)benzamide (141b)

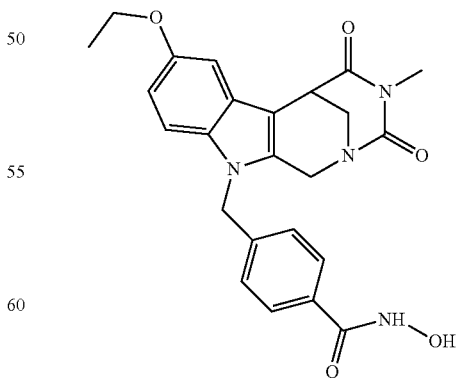

According to GP9 from 4-((4-methyl-3.5-dioxo-8-propoxy-3.4.5.6-tetrahydro-2.6-methano[1.3]diazocino[5.6-b]indol-11(1H)-yl)methyl)-N-((tetrahydro-2H-pyran-2-yl)oxy)benzamide (140b). Yield 0.10 g (0.22 mmol; 25%)

colorless crystals; mp: 166.8-169.1° C. ¹H NMR (300 MHz, DMSO): δ 11.16 (s, 1H), 9.02 (s, 1H), 7.65 (d, J=8.2 Hz, 2H), 7.28 (d, J=8.9 Hz, 1H), 7.10 (d, J=8.3 Hz, 2H), 6.97 (d, J=2.3 Hz, 1H), 6.74 (dd, J=8.9, 2.4 Hz, 1H), 5.35 (s, 2H), 4.83 (d, J=16.6 Hz, 1H), 4.54 (d, J=16.5 Hz, 1H), 3.90 (dd, J=6.3, 3.0 Hz, 2H), 3.87 (s, 1H), 3.83 (s, 1H), 3.44 (dd, J=13.1, 1.9 Hz, 1H), 2.89 (s, 3H), 1.80-1.66 (m, 2H), 0.99 (t, J=7.4 Hz, 3H). ESI-MS m/z (%): 463.20 [MH⁺] (100), 925.39 [2MH⁺] (19.69). Anal. calcd for C₂₅H₂₆N₄O₅×0.5 H₂O: C, 63.69; H, 5.73; N, 11.89; found: C, 63.62; H, 5.96; N, 11.50.

4-((8-Butoxy-4-methyl-3.5-dioxo-3.4.5.6-tetrahydro-2.6-methano[1.3]diazocino[5.6-b]indol-11(1H)-yl)methyl)-N-hydroxybenzamide (141c)

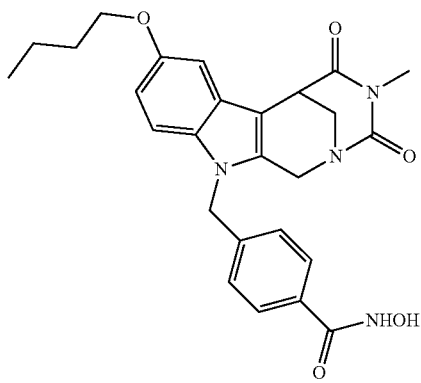

According to GP9 from 4-((8-butoxy-4-methyl-3.5-dioxo-3.4.5.6-tetrahydro-2.6-methano[1.3]diazocino[5.6-b]indol-11(1H)-yl)methyl)-N-((tetrahydro-2H-pyran-2-yl)oxy)benzamide (140c). Yield 0.08 g (0.17 mmol; 28%) colorless crystals; mp: 146.5-149.2° C. ¹H NMR (300 MHz, DMSO): δ 11.17 (s, 1H), 9.02 (s, 1H), 7.65 (d, J=8.3 Hz, 2H), 7.28 (d, J=8.9 Hz, 1H), 7.10 (d, J=8.3 Hz, 2H), 6.97 (d, J=2.3 Hz, 1H), 6.73 (dd, J 8.9, 2.4 Hz, 1H), 5.35 (s, 2H), 4.83 (d, J=16.6 Hz, 1H), 4.54 (d, J=16.5 Hz, 1H), 3.96-3.89 (m, 2H), 3.87 (s, 1H), 3.83 (s, 1H), 3.44 (dd, J=13.1, 2.0 Hz, 1H), 2.89 (s, 3H), 1.76-1.64 (m, 2H), 1.45 (dq, J=14.4, 7.3 Hz, 2H), 0.94 (t, J=7.4 Hz, 3H). ESI-MS m/z (%): 477.21 [MH⁺] (100), 953.42 [2MH⁺] (24.14). Anal. calcd for C₂₆H₂₈N₄O₅×0.125 C₄H₈O₂×1.25 H₂O: C, 62.41; H, 6.18; N, 10.99; found: C, 62.74; H, 6.16; N, 11.08.

4-((8-Hydroxy-4-methyl-3.5-dioxo-3.4.5.6-tetrahydro-2.6-methano[1.3]diazocino[5.6-b]indol-11(1H)-yl)methyl)benzoic acid (139d)

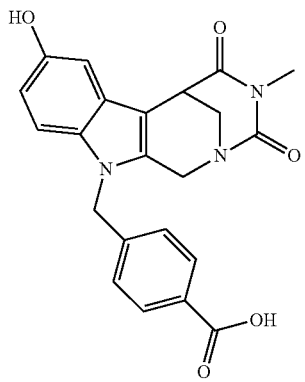 [SMILES: CN1C(=O)C2CN(Cc3c2c2cc(O)ccc2n3Cc2ccc(C(=O)O)cc2)C1=O]

According to GP7 from tert-butyl 4-((8-hydroxy-4-methyl-3.5-dioxo-3.4.5.6-tetrahydro-2.6-methano[1.3]diazocino[5.6-b]indol-11(1H)-yl)methyl)benzoate (137a). Yield 0.33 g (0.81 mmol; 75%) The crude product was isolated by extraction of the aqueous phase with CH₂Cl₂ (4×50.0 mL) and a slightly brown solid was obtained after recrystallization from Ethylacetate; mp: 270.5-273.4° C. ¹H NMR (300 MHz, DMSO): δ 12.91 (s, 1H), 8.90 (s, 1H), 7.85 (d, J=8.2 Hz, 2H), 7.16 (dd, J=14.5, 8.5 Hz, 3H), 6.86 (d, J=2.2 Hz, 1H), 6.59 (dd, J=8.8, 2.3 Hz, 1H), 5.35 (s, 2H), 4.78 (d, J=16.5 Hz, 1H), 4.50 (d, J=16.5 Hz, 1H), 3.86 (d, J=12.9 Hz, 1H), 3.75 (s, 1H), 3.42 (d, J=14.3 Hz, 1H), 2.89 (s, 3H). ESI-MS m/z (%): 406.14 [MH⁺] (100), 833.25 [2MNa⁺] (3.23).

4-((8-Hydroxy-4-methyl-3.5-dioxo-3.4.5.6-tetrahydro-2.6-methano[1.3]diazocino[5.6-b]indol-11(1H)-yl)methyl)-N-((tetrahydro-2H-pyran-2-yl)oxy)benzamide (140d)

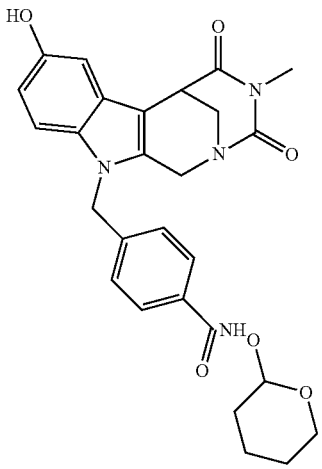

According to GP8 from 4-((8-hydroxy-4-methyl-3.5-dioxo-3.4.5.6-tetrahydro-2.6-methano[1.3]diazocino[5.6-b]indol-11(1H)-yl)methyl)benzoic acid (139d). Yield 0.28 g (0.55 mmol; 69%) colorless crystals after chromatography over silica gel with ethylacetate and recrystallization from methanol; mp: 213.6-214.9° C. ¹H NMR (300 MHz, DMSO): δ 11.60 (s, 1H), 8.89 (s, 1H), 7.67 (d, J=8.2 Hz, 2H), 7.15 (dd, J=12.7, 8.5 Hz, 3H), 6.86 (d, J=2.2 Hz, 1H), 6.58 (dd, J=8.8, 2.3 Hz, 1H), 5.32 (s, 2H), 4.96 (s, 1H), 4.80 (d, J=16.6 Hz, 1H), 4.51 (d, J=16.4 Hz, 1H), 4.02 (s, 1H), 3.87 (d, J=12.7 Hz, 1H), 3.75 (s, 1H), 3.42 (d, J=11.1 Hz, 1H), 2.89 (s, 3H), 1.61 (d, J=49.3 Hz, 7H). ESI-MS m/z (%): 421.15 [MH⁺−3,4-dihydro-2H-pyran] (100), 505.21 [MH⁺] (8.52), 527.19 [MNa⁺] (11.79), 1031.39 [2MNa⁺] (12.45). Anal. calcd for C₂₇H₂₈N₄O₆×0.33 H₂O: C, 63.54; H, 5.60; N, 10.98; found: C, 63.24; H, 5.83; N, 10.94.

N-Hydroxy-4-((8-hydroxy-4-methyl-3.5-dioxo-3.4.5.6-tetrahydro-2.6-methano[1.3]diazocino[5.6-b]indol-11(1H)-yl)methyl)benzamide (141d)

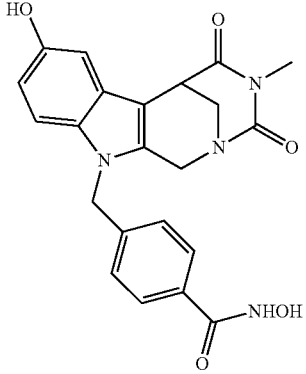

According to GP9 from 4-((8-hydroxy-4-methyl-3.5-dioxo-3.4.5.6-tetrahydro-2.6-methano[0.3]diazocino[5.6-b]indol-11(1H)-yl)methyl)-N-((tetrahydro-2H-pyran-2-yl)oxy)benzamide (140d). Yield 0.10 g (0.24 mmol; 38%) colorless crystals; mp: 259.8-261.0° C. $^1$H NMR (300 MHz, DMSO): δ 11.17 (s, 1H), 9.02 (s, 1H), 8.89 (s, 1H), 7.65 (d, J=8.2 Hz, 2H), 7.18 (d, J=8.8 Hz, 1H), 7.11 (d, J=8.2 Hz, 2H), 6.86 (d, J=2.2 Hz, 1H), 6.58 (dd, J=8.7, 2.3 Hz, 1H), 5.31 (s, 2H), 4.81 (d, J=16.5 Hz, 1H), 4.52 (d, J=16.5 Hz, 1H), 3.87 (d, J=12.9 Hz, 1H), 3.75 (s, 1H), 3.43 (d, J=13.2 Hz, 1H), 2.89 (s, 3H). ESI-MS m/z (%): 421.15 [MH$^+$] (100), 841.29 [2MH$^+$] (27.57). Anal. calcd for $C_{22}H_{20}N_4O_5 \times 0.33\ H_2O$: C, 61.98; H, 4.85; N, 13.15; found: 61.85; H, 5.27; N, 12.85.

4.5.6.7-Tetrahydro-3H-imidazo[4.5-c]pyridine-6-carboxylic acid (143)

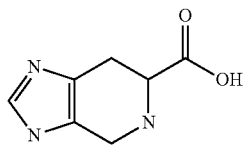 [SMILES: O=C(O)C1Cc2nc[nH]c2CN1]

2.0 g (9.54 mmol) of D,L-histidine monohydrochloride monohydrate (142) was dissolved in 20.0 mL of water. After addition of 1.2 equ. formaldehyde (36% in water) the mixture was stirred at 95° C. for 24 h. The solvent was removed and the obtained solid was dried. Yield 0.37 g (0.71 mmol; 97%) white solid; mp: 189.2-190.1° C. $^1$H NMR (300 MHz, D$_2$O) δ 8.57 (s, 1H), 4.44 (d, J=15.5 Hz, 1H), 4.29 (dt, J=15.6, 1.8 Hz, 1H), 4.08 (dd, J=10.4, 5.5 Hz, 1H), 3.29 (dd, J=17.0, 5.5 Hz, 1H), 2.98 (ddt, J=17.0, 10.4, 1.8 Hz, 1H). ESI-MS m/z (%): 168.08 [MH$^+$] (100). Anal. calcd for $C_7H_{10}ClN_3O_2 \times 0.25\ H_2O$: C, 40.48; H, 5.06; N, 20.24; found: C, 40.43; H, 5.09; N, 20.02.

Methyl 4.5.6.7-tetrahydro-3H-imidazo[4.5-c]pyridine-6-carboxylate (144)

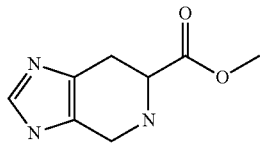

4,5,6,7-tetrahydro-3H-imidazo[4,5-c]pyridine-6-carboxylic acid (143) (1.57 g, 9.39 mmol)) was dissolved in methanol, and thionyl chloride was added at 0° C. The solution was refluxed for 24 h and the solvent removed. The white residue was used without further purification. Yield 1.50 g (6.89 mmol, 73%) colorless solid; mp: 140.8-142.3° C. $^1$H NMR (300 MHz, DMSO): δ 9.04 (s, 1H), 4.70 (dd, J=9.7, 5.5 Hz, 1H), 4.33 (d, J=7.6 Hz, 2H), 3.82 (s, 3H), 3.30 (dd, J=16.3, 5.3 Hz, 1H), 3.20-3.13 (m, 1H). ESI-MS m/z (%): 182.09 [MH$^+$] (100). Anal. calcd for $C_5H_{13}C_{12}N_3O_2 \times 1.5\ H_2O$: C, 34.29; H, 5.71; N, 15.0; found: C, 34.27; H, 5.50; N, 15.26.

7-Ethyl-3.4.8a.9-tetrahydro-6H-diimidazo[1.5-a:4'.5'-d]pyridine-6.8(7H)-dione (145)

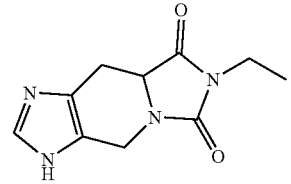 [SMILES: CCN1C(=O)C2Cc3nc[nH]c3CN2C1=O]

Based on Brana et al. (2005) ethylisocyanate (6.89 mmol), 1.5 g (6.89 mmol) methyl 4,5,6,7-tetrahydro-3H-imidazo[4,5-c]pyridine-6-carboxylate (144) and triethylamine (6.89 mmol) were dissolved in DMF (15 ml). The reaction mixture was heated to 60° C. for 24 hours. Yield 0.16 g (0.73 mmol; 11%) slightly yellow oil after chromatography over silica gel with CH$_2$Cl$_2$/MeOH (10:1). $^1$H NMR (300 MHz, DMSO): δ 12.01 (s, 1H), 7.59 (s, 1H), 4.63 (d, J=15.0 Hz, 1H), 4.38 (dd, J=10.8, 5.6 Hz, 1H), 4.14 (d, J=15.1 Hz, 1H), 3.44 (q, J=7.2 Hz, 2H), 2.99 (dd, J=14.5, 5.6 Hz, 1H), 2.78-2.64 (m, 1H), 1.11 (t, J=7.2 Hz, 3H). ESI-MS m/z (%): 221.10 [MH$^+$] (100).

(E)-N,N-dimethyl-2-(1-nitronaphthalen-2-yl)ethenamine (147a)

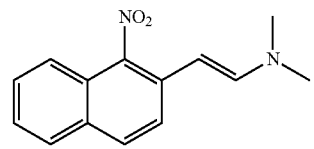 [SMILES: CN(C)/C=C/c1ccc2ccccc2c1[N+](=O)[O-]]

was prepared from 2-methyl-1-nitronaphthalene (146a) according to Riesgo et al. (1996).

1H-Benzo[g]indole (148a)

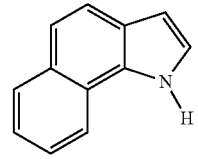 [SMILES: c1ccc2c(c1)ccc1cc[nH]c12]

was prepared from (E)-N,N-dimethyl-2-(1-nitronaphthalen-2-yl)ethenamine (147a) according to Siu et al. (2004).

$^1$H NMR (300 MHz, DMSO-d$_6$): δ 12.03 (s, 1H), 8.36 (d, J=8.2 Hz, 1H), 7.91 (d, J=8.1 Hz, 1H), 7.67 (d, J=8.6 Hz, 1H), 7.57-7.48 (m, 1H), 7.47-7.35 (m, 3H), 6.59 (dd, J=3.0, 1.9 Hz, 1H).

Methyl 2-(1H-benzo[g]indol-3-yl)-3-nitropropanoate (149a)

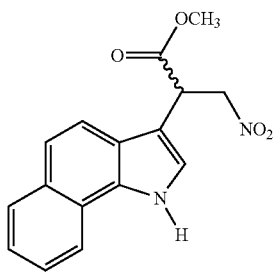 [SMILES: COC(=O)C(C[N+](=O)[O-])c1c[nH]c2c1ccc1ccccc12]

According to 8a (Ballini et al., 2008) from 1H-benzo[g]indole. Yield 1.19 g; 4.0 mmol (33%) beige foam. $^1$H NMR (300 MHz, DMSO-d$_6$): δ 12.18 (s, 1H), 8.34 (d, J=7.4 Hz, 1H), 7.93 (d, J=7.4 Hz, 1H), 7.77 (d, J=8.7 Hz, 1H), 7.59-7.38 (m, 4H), 5.36 (dd, J=15.0, 10.4 Hz, 1H), 5.01 (dd, J=15.0, 5.1 Hz, 1H), 4.84 (dd, J=10.4, 5.0 Hz, 1H), 3.63 (s, 3H).

Methyl 3-amino-2-(1H-benzo[g]indol-3-yl)propanoate hydrochloride (150a)

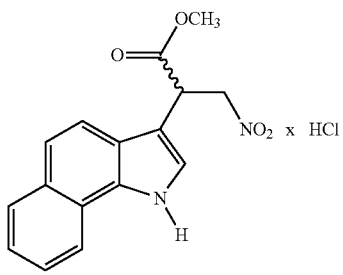 [SMILES: COC(=O)C(C[N+](=O)[O-])c1c[nH]c2c1ccc1ccccc12 ; Cl]

According to 10 (GP1) from methyl 2-(1H-benzo[g]indol-3-yl)-3-nitropropanoate (149a) Yield 1.05 g; 3.45 mmol (85%) grey foam. $^1$H NMR (300 MHz, DMSO-d$_6$): δ 12.25 (s, 1H), 8.39 (d, J=8.2 Hz, 1H), 8.13 (s, 3H), 7.93 (d, J=8.3 Hz, 1H), 7.70 (d, J=8.7 Hz, 1H), 7.59-7.48 (m, 2H), 7.47-7.35 (m, 2H), 4.42 (dd, J=8.1, 6.4 Hz, 1H), 3.64 (s, 3H), 3.57-3.48 (m, 1H), 3.30-3.14 (m, 1H).

Methyl 8,9,10,11-tetrahydro-7H-benzo[g]pyrido[3,4-b]indole-7-carboxylate hydrochloride (150b)

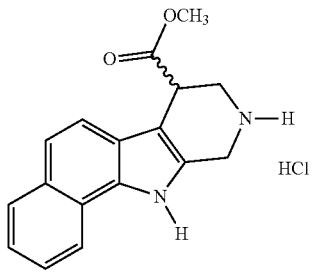 [SMILES: COC(=O)C1CNCc2[nH]c3c(ccc4ccccc43)c21 ; Cl]

According to 13a (GP2) from methyl 3-amino-2-(1H-benzo[g]indol-3-yl)propanoate hydrochloride (150a). Yield 0.88 g; 2.78 mmol (80%) beige crystals. $^1$H NMR (300 MHz, DMSO-d$_6$): δ 12.44 (s, 1H), 10.19 (s, 1H), 9.22 (s, 1H), 8.31 (d, J=8.2 Hz, 1H), 7.94 (d, J=8.1 Hz, 1H), 7.68 (d, J=8.7 Hz, 1H), 7.60-7.48 (m, 2H), 7.48-7.39 (m, 1H), 4.59-4.40 (m, 2H), 4.40-4.32 (m, 1H), 3.83-3.73 (m, 1H), 3.72 (s, 3H), 3.64-3.53 (m, 1H).

Methyl 9-(methylcarbamoyl)-8,9,10,11-tetrahydro-7H-benzo[g]pyrido[3,4-b]indole-7-carboxylate (150c)

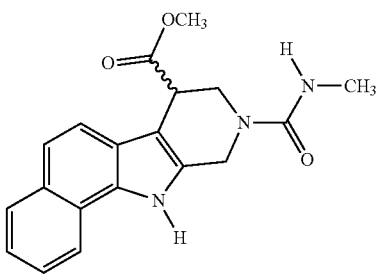 [SMILES: CNC(=O)N1Cc2[nH]c3c(ccc4ccccc43)c2C(C(=O)OC)C1]

According to 16a (GP3) from methyl 8,9,10,11-tetrahydro-7H-benzo[g]pyrido[3,4-b]indole-7-carboxylate hydrochloride (150b). Yield 0.90 g; 2.67 mmol (92%) beige crystals. $^1$H NMR (300 MHz, DMSO-d$_6$): δ 11.96 (s, 1H), 8.29 (d, J=8.3 Hz, 1H), 7.90 (d, J=8.1 Hz, 1H), 7.60-7.31 (m, 4H), 6.68 (q, J=4.3 Hz, 1H), 4.67 (q, J=16.2 Hz, 2H), 4.07-3.97 (m, 2H), 3.84-3.71 (m, 1H), 3.66 (s, 3H), 2.62 (d, J=4.2 Hz, 3H).

9-Methyl-12,13-dihydro-7,11-methanobenzo[g][1,3]diazocino[5,6-b]indole-8,10(7H,9H)-dione (150d)

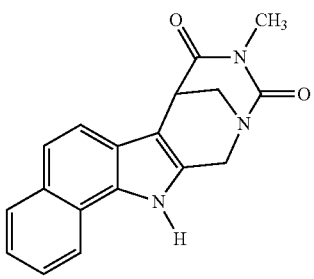 [SMILES: CN1C(=O)C2CN(Cc3[nH]c4c(ccc5ccccc54)c32)C1=O]

According to 18a (GP4) from methyl 9-(methylcarbamoyl)-8,9,10,11-tetrahydro-7H-benzo[g]pyrido[3,4-b]indole-7-carboxylate (150c). Yield 0.60 g; 1.97 mmol (73%) colorless crystals. $^1$H NMR (300 MHz, DMSO-d$_6$): δ 12.08 (s, 1H), 8.22 (d, J=8.3 Hz, 1H), 7.92 (d, J=7.5 Hz, 1H), 7.62 (d, J=8.6 Hz, 1H), 7.58-7.46 (m, 2H), 7.44-7.35 (m, 1H), 4.78 (s, 2H), 3.99-3.88 (m, 2H), 3.56-3.43 (m, 1H), 2.89 (s, 3H).

N,N-Dimethyl-1-(1H-pyrrolo[2,3-b]pyridin-3-yl)methanamine (152a)

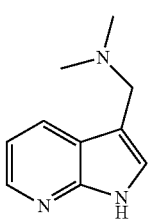

was prepared from 7 azaindole (151a) according to Pierce et al. (2011).

2-(1H-Pyrrolo[2,3-b]pyridin-3-yl)acetonitrile (153a)

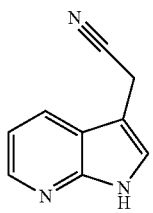 [SMILES: N#CCc1c[nH]c2ncccc12]

was prepared from N,N-Dimethyl-1-(1H-pyrrolo[2,3-b]pyridin-3-yl)methanamine (151a) according to Pierce et al. (2011).

2-(1-(tert-Butyldimethylsilyl)-1H-pyrrolo[2,3-b]pyridin-3-yl)acetonitrile (154a)

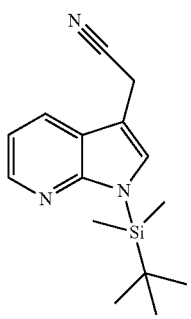 [SMILES: CC(C)(C)[Si](C)(C)n1cc(CC#N)c2cccnc21]

2-(1H-Pyrrolo[2,3-b]pyridin-3-yl)acetonitrile (153a) (3.92 g; 24.9 mmol) was dissolved in dry THF (39 ml) and NaH (60% in mineral oil, 1.10 g; 27.4 mmol) was added at room temperature. After 10 min. tert-butylchlorodimethylsilane was added and the mixture was stirred for 1 h. The reaction was quenched by pouring into a saturated aqueous solution of NH$_4$Cl (200 ml), the aqueous layer extracted with diethyl ether (3×50 ml), the combined organic layers dried (Na$_2$SO$_4$) and the solvent removed under reduced pressure. Purification by cc (SiO$_2$; CH$_2$Cl$_2$/light petrol 2:1) yielded the analytical pure product as white crystals. Yield 4.35 g; 16.0 mmol (64%) colorless crystals. $^1$H NMR (300 MHz, DMSO): δ 8.33 (dd, J=4.7, 1.6 Hz, 1H), 8.07 (dd, J=7.8, 1.6 Hz, 1H), 7.49 (s, 1H), 7.20 (dd, J=7.9, 4.7 Hz, 1H), 4.13 (d, J=0.7 Hz, 2H), 0.92 (s, 9H), 0.65 (s, J=3.2 Hz, 6H).

Methyl 2-(1-(tert-butyldimethylsilyl)-1H-pyrrolo[2,3-b]pyridin-3-yl)-2-cyanoacetate (155a)

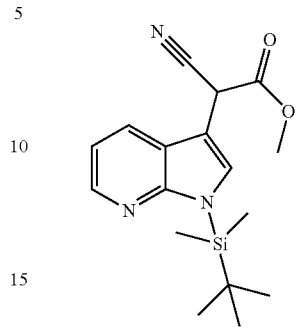

2-(1-(tert-Butyldimethylsilyl)-1H-pyrrolo[2,3-b]pyridin-3-yl)acetonitrile (154a) (0.50 g; 1.84 mmol) was dissolved in dry THF (10.0 ml) and NaH (60% in mineral oil, 0.147 g; 3.68 mmol) was added at room temperature. After 10 min. dimethyl carbonate was added and the mixture stirred for 16 h. The reaction was quenched by pouring into a saturated aqueous solution of NH$_4$Cl (100 ml), the aqueous layer extracted with diethyl ether (3×30 ml), the combined organic layers dried (Na$_2$SO$_4$) and the solvent removed under reduced pressure. Purification by cc (SiO$_2$; CH$_2$Cl$_2$/light petrol 2:1) yielded the analytical pure product as white crystals.

Yield 0.12 g; 0.36 mmol (20%) colorless crystals. $^1$H NMR (300 MHz, DMSO): δ 8.36 (dd, J=4.7, 1.6 Hz, 1H), 8.01 (dd, J=7.9, 1.6 Hz, 1H), 7.62 (s, 1H), 7.24 (dd, J=7.9, 4.7 Hz, 1H), 5.94 (s, 1H), 3.78 (s, 3H), 0.92 (s, 9H), 0.67 (s, 61H).

Example 2 Biological Evaluation

The novel HDAC6 inhibitors were tested in a panel of tumor cell lines for cytostatic/toxic activities (see Table 2).

Figure 1A:
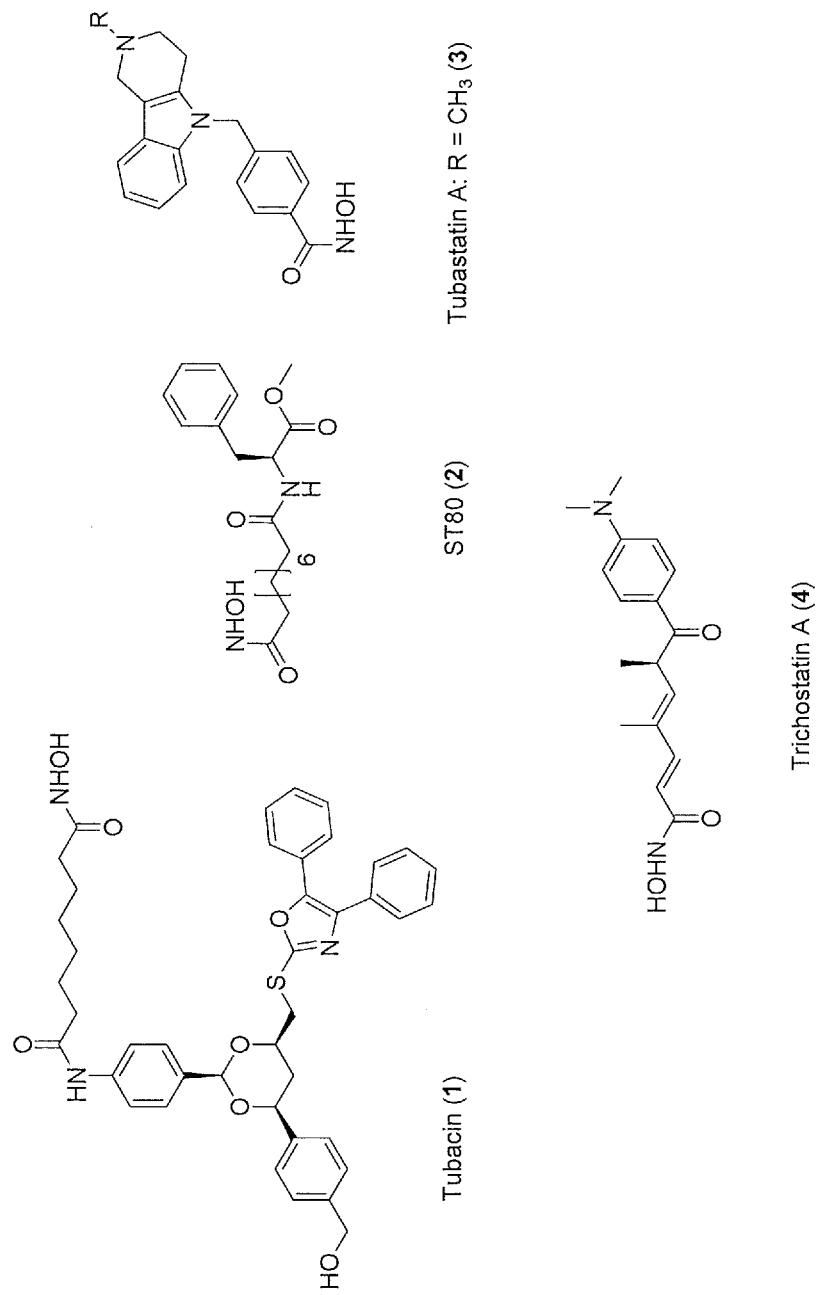
FIG. 1. Structure of HDAC inhibitors.
(A) Shown are the structures of the prior art HDAC inhibitors tubacin (1), ST80 (2), tubastatin A (3) and of the pan-HDACi trichostatin A (4).
(B) Overview: general structure of the novel HDAC6 inhibitors of the invention.
(C) Shown are the structures of two preferred novel HDAC6 inhibitors of the invention:
MARB1: (N-Hydroxy-4-((4-methyl-3,5-dioxo-3,4,5,6-tetrahydro-2,6-methano[1,3]diazo-cino[5,6-b]indol-11(1H)-yl)methyl)benzamide) (39a) and
MARB2: N-Hydroxy-4-((5-methyl-3,6-dioxo-4,5,6,7-tetrahydro-1H-2,7-methano[1,4]diazonino[6,7-b]indol-12 (3l)-yl)methyl)benzamide (41)
Figure 1:
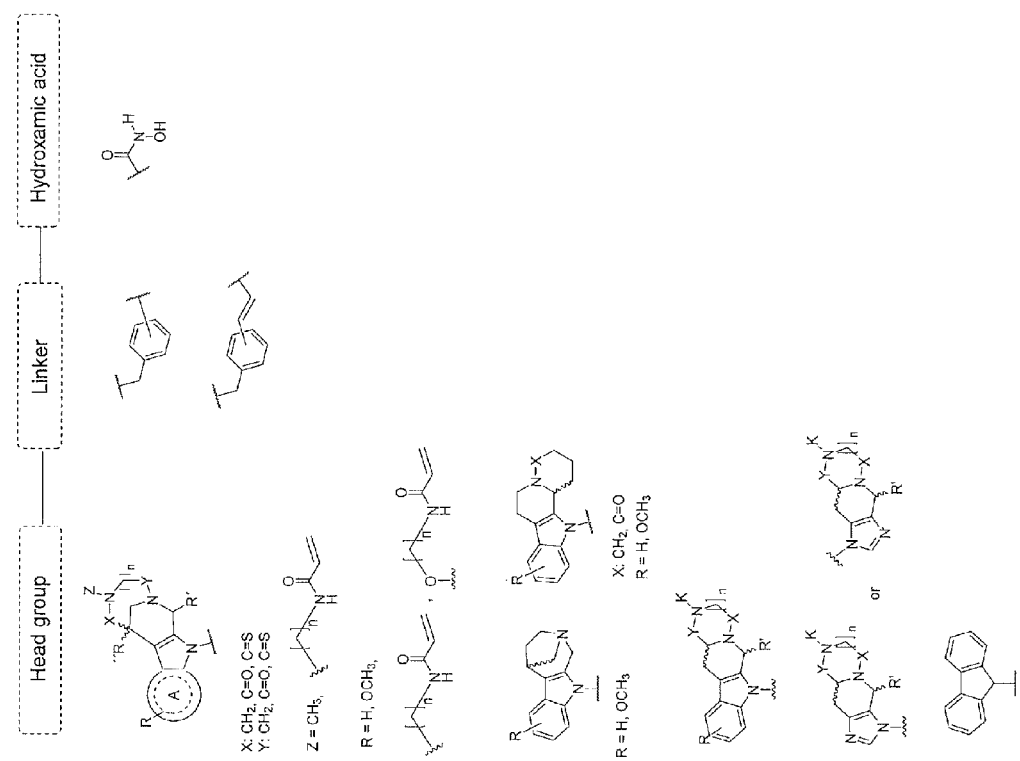

It was found that in particular the two inhibitors MARB1 and MARB2 (see also FIG. 1B)

MARB1: (N-Hydroxy-4-((4-methyl-3,5-dioxo-3,4,5,6-tetrahydro-2,6-methano[1,3]diazo-cino[5,6-b]indol-11(1H)-yl)methyl)benzamide) (39a) and MARB2: N-Hydroxy-4-((5-methyl-3,6-dioxo-4,5,6,7-tetrahydro-1H-2,7-methano[1,4]diazonino[6,7-b]indol-12(3H)-yl)methyl)benzamide (41)

have anti-proliferative effects on tumor cells/cell lines, wherein MARB1 is a more potent inhibitor to HDAC6 in vitro (Table 1) as well as in respect to cellular effects compared to MARB2 (Table 2). Derivatives with further modification of the indolyle-system, e.g. compound 40a, exhibit even improved activity on HDAC6.

TABLE 1

IC$_{50}$-Values for HDAC-Subtypes HDAC1, HDAC2, HDAC4, HDAC5, HDAC6, HDAC8 und HDAC11 compared to the Pan-HDACi TSA (4) and TMP 269 as standard compound.

| No. | HDAC1 IC$_{50}$ (mM) | HDAC2 IC$_{50}$ (mM) | HDAC4 IC$_{50}$ (mM) | HDAC5 IC$_{50}$ (mM) | HDAC6 IC$_{50}$ (mM) | HDAC8 IC$_{50}$ (mM) | HDAC11 IC$_{50}$ (mM) |
|---|---|---|---|---|---|---|---|
| MARB1 | (3.62 ± 0.2)E−06 | (7.45 ± 0.17)E−06 | 3.82E−06 | 1.57E−06 | 3.57 ± 1.27E−09 | 2.49 ± 0.07E−07 | 1.05E−05 |
| MARB2 | 8.40E−06 | 1.43E−05 | ND | ND | 7.72E−09 | 1.02E−06 | ND |
| 40a | ND | 4.98E−06 | ND | ND | 8.16E−10 | 7.59E−08 | ND |
| 51 | ND | 6.28E−06 | ND | ND | 3.06E−07 | 1.19E−08 | ND |
| 50 | ND | 7.26E−07 | ND | ND | 2.15E−08 | 2.99E−07 | ND |

TABLE 1-continued

IC$_{50}$-Values for HDAC-Subtypes HDAC1, HDAC2, HDAC4, HDAC5, HDAC6, HDAC8 und HDAC11 compared to the Pan-HDACi TSA (4) and TMP 269 as standard compound.

| No. | HDAC1 IC$_{50}$ (mM) | HDAC2 IC$_{50}$ (mM) | HDAC4 IC$_{50}$ (mM) | HDAC5 IC$_{50}$ (mM) | HDAC6 IC$_{50}$ (mM) | HDAC8 IC$_{50}$ (mM) | HDAC11 IC$_{50}$ (mM) |
|---|---|---|---|---|---|---|---|
| 56a | ND | 1.26E−05 | ND | ND | 1.07E−09 | 3.15E−07 | ND |
| 62 | ND | 7.18E−06 | ND | ND | 2.19E−09 | 5.57E−07 | ND |
| 70 | ND | 6.95E−05 | ND | ND | 2.70E−08 | 1.78E−06 | ND |
| 84 | ND | >1E−4 | ND | ND | 1.43E−07 | 1.47E−06 | ND |
| 85 | ND | 3.74E−06 | ND | ND | 6.84E−08 | 9.44E−07 | ND |
| 88 | ND | 1.12E−04 | ND | ND | 3.69E−07 | 9.95E−07 | ND |
| 93 | ND | 2.70E−05 | ND | ND | 3.55E−07 | 3.60E−06 | ND |
| TSA | 6.8E−09 | 10.1E−09 | ND | ND | 2.52E−09 | 11.0E−8 | 12.1E−9 |
| TMP 269 | ND | ND | 2.26E−07 | 1.87E−07 | ND | 3.90E−06 | ND |

ND: Not determined.
Testing was performed by Reaction Biology Corp., as described above.

TABLE 2

IC50 values [µM] (FACS analysis following method a):
In vitro activity of selective HDAC6 inhibitors MARB1 and MARB2 against a selection of 42 solid tumor cell lines; "Mean IC50 value" means the average IC50 value from all 42 measurements. High sensitivity in particular show the cell lines MAXF 401 MAXF MCF-7, PRXF DU-145, LNCaP PRXF, PXF 1752 and UXF 1138

| Tumor type | Cell line | MARB1 | MARB2 |
|---|---|---|---|
| Breast | MAXF 401 | 2.28 | 13.7 |
|  | MAXF MCF-7 | 2.33 | 7.69 |
| Prostate | PRXF DU-145 | 2.34 | 10.3 |
|  | PRXF LNCaP | 1.62 | 4.80 |
|  | PRXF PC-3M | 5.14 | 20.8 |
| Uterus | UXF 1138 | 1.58 | 5.49 |
|  | mean IC50 [µM] | 5.03 | 16.4 |

Furthermore we could show, that inhibition of HDAC 6 by MARB1 and MARB2 in BV-173 leukemia cells leads to hyperacetylation of tubulin-α and reduction of the expression of survivin (FIG. 2). BCR-ABL p210-positive BV-173-cells were isolated from leukemia cells, which were in an advanced state (myeloid blast crisis). The pronounced acetylation of tubulin-α proves the excellent cellular availability of the novel HDAC6 inhibitors of the invention.

HSP90 regulates the stability of the pan-leukemic marker protein WT1. HDAC6 deacetylates HSP90, and the deacetylated form acts as chaperon/stabilisator of (proto-) oncoproteins. Therefore, the degradation of WT1 is a positive control of the efficiency of the novel HDAC6 inhibitors of the invention against HSP90. Survivin is crucial for tumorigenesis and the development of chemoresistance. For the first time our results show that the expression of survivin is dependent on HDAC6.

See FIG. 2.

The cellular selectivity of the compounds MARB1 and MARB2 for HDAC6 was proofed by determination of the acetylation of histone H3 by Western blot. Acetylation of histone H3 cannot be induced by HDAC6-selective inhibitors, since HDAC6 does not recognize histones as substrates in vivo (Boyault et al., 2007). As shown in FIG. 2, class I selective HDACi VPA (Gottlicher et al., 2001) induces hyperacetylation of histone H3. Neither MARB1, nor MARB2 cause these alterations, showing that these substances selectively inhibit HDAC6 in cells.

As known from several studies, pan-HDACi when used in combination with tyrosine kinase inhibitors have synergistic effects to BCR-ABL positive leukemia cells in vitro as well as in vivo (see e.g. Nguyen et al., 2011; Yu et al., 2003; Nimmanapalli et al., 2003).

Our results also show synergistic cytotoxic effects of the novel HDAC6 inhibitors of the invention with a tyrosine kinase inhibitor: The combination of MARB1 and MARB2 with imatinib, a selective inhibitor of kinase activity of BCR-ABL (Mahboobi et al., 2009), significantly increases the apoptotic and necrotic sub-Gi-populations in BCR-ABL positive BV-173 cells (FIG. 3A). Flow cytometric analyzes also point to an arrest of the cell cycle (FIG. 3B). The caspase activity is detectable by the appearance of sliced PARP1 in Western blot analyzes. PARP1 is processed by caspases 3 and 7 which are activated in the apoptosis cascade (Wen et al., 2012).

However, MARB1 and MARB2 do not affect the BCR-ABL expression on the protein level as shown by Western-Blot-analyzes. Nevertheless, both HDACi are able to significantly inhibit the unwanted stabilization of BCR-ABL, which is caused by the treatment of BCR-ABL-positive cells with imatinib (as described by Gwamnesia et al., 2009 and Packer et al., 2011) (see FIG. 3C).

These data demonstrate the possibility to efficiently combine the novel HDAC inhibitors of the invention, in particular MARB1 and MARB2, with other clinically highly relevant active agent(s), such as imatinib, preferably for synergistic treatment effects.

The data presented in FIG. 4 proof that the novel HDAC inhibitors of the invention, in particular MARB1 and MARB2, are noticeably more potent in HEL leukemic cells than the standard agent tubastatin A (Butler et al., 2010). HEL leukemic cells express a mutated form of Janus Kinase-2 as an oncogene. Western blot analysis demonstrate that 1 µM MARB1 or 2 µM MARB2, respectively, have about the same potency as 5 µM tubastatin A in hyperacetylation of the HDAC6 substrate tubulin-α.

Our data further demonstrate that neither tubastatin A nor the pan-HDACi LBH589 specifically inhibit HDAC6. Compared to other inhibitors LBH589 causes decreased acetylation of tubulin-α due to a high degradation of the scaffold protein (as shown below). Tubastatin A (see FIG. 1A, 3) is currently regarded as one of the most selective inhibitors of HDAC6.

Our data shown above demonstrate impressively that the novel HDAC inhibitors of the invention, in particular MARB1 and MARB2, highly and selectively inhibit the enzyme activity of HDAC6, without destroying the protein. Thus, MARB1 and MARB2 are valid highly selective and potent inhibitors of HDAC6. These compounds exceed both of the established HDACi tubastatin A and LBH589, with respect to specificity as well as potency concerning HDAC6.

The degradation of HDAC6 and tubulin by LBH589 can be seen in various colon cancer cells (FIG. 5). Again, MARB1 and MARB2 work as highly selective inhibitors of HDAC6, whereby both destroy neither HDAC6 nor tubulin.

Both LBH589 and butyrate, a HDACi frequently occurring in the colon, lead to a degradation of tubulin which results in a poor detectability of the acetylation in HCT-116 cells (see FIG. 5A). Furthermore, acetylated tubulin is better detectable while adding the pan-caspases inhibitor ZVAD-FMK, which is due to the fact that caspases induce the degradation process. The treatment with MARB1 and MARB2 starts the hyperacetylation of tubulin in colon carcinoma cells (RKO and HCT-116 cells) without destroying it (FIGS. 5B-C).

The plant alkaloid staurosporin (ST) is an unspecific inhibitor of kinases and a strong pro-aptoptotic substance. Interestingly, the treatment with MARB1 and MARB2 protects ST-treated RKO cells (FIG. 5D) against HDAC6 loss.

However, this is not due to a non-specific interference of the substances, since both the activation of apoptotic caspase-3 as well as the acetylation of tubulin do not vary compared to the individual treatments (FIG. 5D). It is most likely that HDAC6 inhibition by MARB1 and MARB2 in RKO cells effects an (small) induction of the inhibited HDAC6. Correspondingly, this could indicate that the enzyme activity of HDAC6 affects its stability.

MARB1 and MARB2 further give the opportunity to investigate the catalytic domain of HDAC6 separately from its ubiquitin binding behavior. The amount of HDAC6 remains constant and is still highly potent inhibited by MARB1 and MARB2.

Efficiency and Time Dependency of MARB1

The presented data shows that MARB1 is a specific and potent inhibitor. After incubation for 30 min an increase of acetylated tubulin is detectable at a concentration of 50 nM. In FIG. 4 it is shown that there are no detectable effects of MARB1 on nuclear proteins. Furthermore, the absence of acetylated Histone 3 underlined these findings.

The effectiveness of MARB1 was shown in a HDAC overexpression model. After transfecting the cells with HDAC6 flag there is a decrease in the expression of acetylated Tubulin. The transfected cells which are incubated with MARB1 exhibit a high induction of tubulin acetylation. In comparison to the cells transfected with the empty vector pcDNA3.1 the HDAC6 transfected cells show a lower level of acTub.

A comparison of MARB1 with the pan-HDACi LBH589 and the established HDAC6 inhibitor Tubastatin A shows how effective MARB1 works. The inhibition with MARB1 was faster and at later time points much more effective than Tubastatin A.

MARB1 has No Influence of the Cell Cycle

After staining BV173 cells with PI and measuring by flow cytometry it became clear, that there are no changes in the cell cycle. The subG1 population shows no increase. Therefore MARB1 does not lead to an increase on cell death in the investigated cell line.

Therefore, the novel HDAC6 inhibitors of the invention represent unique and precise tools for molecular and biochemical analyzes.

Evaluation in a Mouse Model

1 Experimental Animal 8-10-week old male DBA 1/J mice were used in the experiment. They were obtained from Elevage Janvier, Le Genest St. Isle, France and were maintained in a controlled environment (constant temperature and humidity and a 12 h light-dark cycle).

2 Animal Groups

Animals were divided into 3 groups each consisting of 5 animals.

Group 1 received the vehicle, Group 2 received Marb1 0,6 mg/mouse/day i.p. for 15 days and Group 3 received Tubastatin 0,498 mg/mouse/day (identical molar concentrations) i.p. for 15 days.

3 Administration of Drugs

Marb1 and Tubastatin were dissolved in Dimethylsulfoxide.

For administration the solution above was solved in a mixture of 95% Pharmasolve and 5% Dimethyl sulfoxide.

The vehicle solution consisted of 95% Pharmasolve and 5% Dimethylsulfoxide.

4 Experimental Method

The immunization of the animals was carried out on day 0 using an emulsion of Bovine Collagen Type 2 (MD Bioproducts) and complete Freund's adjuvant (Becton Dickinson and Company) mixed in ratio 1:1 using a homogenizer. 100 µl of the obtained emulsion were injected intradermally at the base of the tail of each animal. After the immunization the animals were divided into four groups. (see above).

The treatment was given from day 22 to 36.

The parameters body weight, clinical score and paw volume were measured once a week after immunization and from day 22 (starting point for the treatment) on a daily basis.

5 Experimental Results

Tubastatin, as a representative of a selective histone deacetylase 6 inhibitor, was studied previously for its ability to have positive effects in the rheumatic treatment and inflammatory disorders.

In the present study, an arthritis mouse model was taken to test the effect of Marb1, a novel selective HDAC 6 inhibitor, in comparison to Tubastatin.

Previous enzyme tests of Marb1 showed potent and selective inhibitory activity against HDAC 6 with an IC50 value of $3.57 \pm 1.27\ e^{-09}$ [mM].

The features disclosed in the foregoing description, in the claims and/or in the accompanying drawings may, both separately and in any combination thereof, be material for realizing the invention in diverse forms thereof.

REFERENCES

Andrianjara C, Ortwine D F, Pavlovsky A G, Roark W H. Preparation of substituted isophthalic acid derivatives, multicyclic pyrimidinediones and analogs thereof as matrix metalloproteinase inhibitors: Warner-Lambert Company, USA. 2002:173 pp.

Ballini R, Gabrielli S, Palmieri A, Petrini M. Improved preparation of alkyl 2-(3-indolyl)-3-nitroalkanoates under fully heterogenous conditions: stereoselective synthesis of alkyl (E)-2-(3-indolyl)-alkenoates. Tetrahedron 2008; 64: 5435-41.

Bartoli G, Bosco M, Giuli S, et al. Efficient Preparation of 2-Indolyl-1-nitroalkane Derivatives Employing Nitroalkenes as Versatile Michael Acceptors: New Practical Linear Approach to Alkyl 9H-β-Carboline-4-carboxylate. J. Org. Chem. 2005; 70: 1941-44.

Bazzaro, M., et al., (2008) Ubiquitin Proteasome System Stress Underlies Synergistic Killing of Ovarian Cancer Cells by Bortezomib and a Novel HDAC6 Inhibitor. Clin. Cancer Res. 14, 7340.

Boyault C, Sadoul K, Pabion M, Khochbin S. HDAC6, at the crossroads between cytoskeleton and cell signaling by acetylation and ubiquitination. Oncogene 2007; 26(37): 5468-76.

Brana, M. F., C. Guisado, et al. (2002). "Synthesis of 4, 7, 8a, 9-tetrahydro-3H-diimidazo-[1, 5-a: 4',5'-d]pyridine derivatives." *Journal of heterocyclic chemistry* 39(2): 417-420.

Brandl A, Heinzel T, Krämer O H. Histone deacetylases: salesmen and customers in the post-translational modification market. Biology of the Cell 2009; 101(4): 193-205

Brandl A, Wagner T, Uhlig K M, Knauer S K, Stauber R H, Melchior F, Schneider G, Heinzel T, Krämer O H. Dynamically regulated sumoylation of HDAC2 controls p53 deacetylation and restricts apoptosis following genotoxic stress. J Mol Cell Biol. 2012 (5):284-93.

Buchwald M, Krämer O H, Heinzel T. HDACi—Targets beyond chromatin. Cancer Letters 2009; 280(2): 160-67.

Buchwald M, Pietschmann K, Müller J P, Böhmer F D, Heinzel T, Krämer O H. Ubiquitin conjugase UBCH8 targets active FMS-like tyrosine kinase 3 for proteasomal degradation. Leukemia. 2010 24(8):1412-21.

Buchwald M, Pietschmann K, Brand P, Günther A, Mahajan N P, Heinzel T, Krämer O H. SIAH ubiquitin ligases target the nonreceptor tyrosine kinase ACK1 for ubiquitinylation and proteasomal degradation. Oncogene. 2013; 32(41):4913-20.

Cha, M. Y., K.-O. Lee, et al. (2012). "Synthesis and Biological Evaluation of Pyrimidine-Based Dual Inhibitors of Human Epidermal Growth Factor Receptor 1 (HER-1) and HER-2 Tyrosine Kinases." *J. Med. Chem.* 55(6): 2846-2857.

Chou C J, Inks E S, Josey B J, Jesinkey S R. Unique HDAC6 inhibitors targeting Hsp90 complexes. 243rd ACS National Meeting & Exposition. San Diego, Calif., United States, 2012.

Choudhary C, Kumar C, Gnad F, et al. Lysine Acetylation Targets Protein Complexes and Co-Regulates Major Cellular Functions. Science 2009; 325(5942): 834-40.

Da Silva W A, Rodrigues M T, Shankaraiah N, et al. Novel Supramolecular Palladium Catalyst for the Asymmetric Reduction of Imines in Aqueous Media. Org. Lett. 2009; 11: 3238-41.

Fourtillan, J. B. and M. Fourtillan (2008). Preparation of new derivatives of 1,2,3,4,6,7,12,12a-octahydropyrazino[1',2':1,6]pyrido[3,4-b]indoles for therapeutic use as sedatives, Fourtillan, Fr. 97 pp.

Goder, A., G. Nagel, et al. (2015). "Lipoic acid inhibits the DNA repair protein O 6-methylguanine-DNA methyltransferase (MGMT) and triggers its depletion in colorectal cancer cells with concomitant autophagy induction." Carcinogenesis.

Göttlicher M, Minucci S, Zhu P, et al. Valproic acid defines a novel class of HDAC inhibitors inducing differentiation of transformed cells. EMBO J. 2001; 20(24): 6969-78.

Gwanmesia P, Romanski A, Schwarz K, Bacic B, Ruthardt M, Ottmann O. The effect of the dual Src/Abl kinase inhibitor AZD0530 on Philadelphia positive leukaemia cell lines. BMC Cancer 2009; 9(1): 53.

Hamilton G S, Mewshaw R E, Bryant C M, et al. Fluorenylalkanoic and Benzoic Acids as Novel Inhibitors of Cell Adhesion Processes in Leukocytes. J. Med. Chem. 1995; 38: 1650-6.

Kalin J H, Butler K V, Akimova T, Hancock W W, Kozikowski A P. Second-Generation Histone Deacetylase 6 Inhibitors Enhance the Immunosuppressive Effects of Foxp3+T-Regulatory Cells. J. Med. Chem. 2012; 55(2): 639-51.

Kumar V, Khatik G L, Pal A, Praneeth M R, Bhattarai S, Nair V A. A facile synthesis and chemoselective reactions of dihydrothiouracils. Synlett 2012; 23: 2357-62.

Lanning M E, Fletcher S. Azodicarbonyl dimorpholide (ADDM): an effective, versatile, and water-soluble Mitsunobu reagent. Tetrahedron Lett. 2013; 54: 4624-28.

Lee Y-S, Lim K-H, Guo X, et al. The Cytoplasmic Deacetylase HDAC6 Is Required for Efficient Oncogenic Tumorigenesis. Cancer Res. 2008; 68: 7561-69.

Li H-Y, Brooks H B, Crich J Z, Henry J R, Sawyer J S, Wang Y. Preparation of (imidazolidinonylethylamino)pyrimidine derivatives for treatment of cancer: Eli Lilly and Company, USA. 2008:60 pp.

Lingam, Y., D. M. Rao, et al. (2008). "A facile synthesis 3-carbolines and studies on their antimicrobial activities." *Org. Chem.: Indian J.* 4: 28-31.

Mahboobi S, Sellmer A, Winkler M, et al. Novel designed chimeric HDAC- and tyrosine kinase inhibitors: A series of Imatinib hybrides as potent inhibitors of wild-type and mutant BCR-ABL, PDGF-R B and histone deacetylases. J. Med. Chem. 2009; 52(8): 2265-79.

Makki M S, Heinzel T, Englert C. TSA downregulates Wilms tumor gene 1 (Wt1) expression at multiple levels. Nucleic Acids Res. 2008; 36(12): 4067-78.

Motoshima K, Ishikawa M, Hashimoto Y, Sugita K. Peroxisome proliferator-activated receptor agonists with phenethylphenylphthalimide skeleton derived from thalidomide-related liver X receptor antagonists: Relationship between absolute configuration and subtype selectivity. Bioorg. Med. Chem. 2011; 19: 3156-72.

Müller S, Krämer O H. Inhibitors of HDACs—Effective Drugs Against Cancer? Current Cancer Drug Targets 2010; 10(2): 210-28.

Nguyen T, Dai Y, Attkisson E, et al. HDAC Inhibitors potentiate the activity of the Bcr/Abl kinase inhibitor KW-2449 in Imatinib-sensitive or resistant Bcr/Abl+ leukemia cells in vitro and in vivo. Clin. Cancer Res. 2011; 17(11): 3219-32.

Nimmanapalli R, Fuino L, Stobaugh C, Richon V, Bhalla K. Cotreatment with the histone deacetylase inhibitor suberoylanilide hydroxamic acid (SAHA) enhances imatinib-induced apoptosis of Bcr-Abl-positive human acute leukemia cells. Blood 2003; 101(8): 3236-39.

Oleinick N L, Balasubramaniam U, Xue L, Chiu S. Nuclear structure and the microdistribution of radiation damage in DNA. Int J Radiat Biol. 1994; 66(5):523-9.

Packer Leisl M, Rana S, Hayward R, et al. Nilotinib and MEK Inhibitors Induce Synthetic Lethality through Paradoxical Activation of RAF in Drug-Resistant Chronic Myeloid Leukemia. Cancer Cell 2011; 20(6): 715-27.

Pandey U B, Nie Z, Batlevi Y, et al. HDAC6 rescues neurodegeneration and provides an essential link between autophagy and the UPS. Nature 2007; 447(7146): 860-64.

Park, K., A. Gopalsamy, et al. (2009). "Synthesis and activity of tryptophan sulfonamide derivatives as novel non-hydroxamate TNF-α converting enzyme (TACE) inhibitors." *Bioorganic & Medicinal Chemistry* 17(11): 3857-3865.

Perez-Alvarez V, Morales-Rios M S, Hong E, Joseph-Nathan P. Synthesis of 3-amino-2-(3-indolyl)propanol and propanoate derivatives and preliminary cardiovascular evaluation in rats. J. Pharm. Pharmacol. 1997; 49: 246-52.

Pierce, L. T., M. M. Cahill, et al. (2011). "Synthesis of novel 3,4-diaryl-5-aminopyrazoles as potential kinase inhibitors." *Tetrahedron* 67: 4601-4611.

Pietschmann K, Buchwald M, Müller S, et al. Differential regulation of PML-RARα stability by the ubiquitin ligases SIAH1/SIAH2 and TRIAD1. The International Journal of Biochemistry & Cell Biology 2012; 44(1): 132-38.

Pietsclnann K, Bolck H A, Buchwald M, Spielberg S, Polzer H, Spiekermann K, Bug G, Heinzel T, Böhmer F D, Krämer O H. Breakdown of the FLT3-ITD/STAT5 axis and synergistic apoptosis induction by the histone deacetylase inhibitor panobinostat and FLT3-specific inhibitors. Mol Cancer Ther. 2012 (11):2373-83.

Quintas-Cardama A, Santos F P S, Garcia-Manero G. Histone deacetylase inhibitors for the treatment of myelodysplastic syndrome and acute myeloid leukemia. Leukemia 2011; 25: 226-35.

Riesgo, E. C., X. Jin, et al. (1996). "Introduction of benzo [h] quinoline and 1, 10-phenanthroline subunits by friedländer methodology." *The Journal of Organic Chemistry* 61(9): 3017-3022.

Saiga Y, Iijima I, Ishida A, et al. Synthesis of 1,2,3,4-tetrahydro-β-carboline derivatives as hepatoprotective agents. IV. Positional isomers of 1,2,3,4-tetrahydro-2-methylthiothiocarbonyl-β-carboline-3-carboxylic acid and its 1-alkylated derivatives. Chem. Pharm. Bull. 1987; 35: 3705-12.

Schlimme, S., A.-T. Hauser, et al. (2011). "Carbamate Prodrug Concept for Hydroxamate HDAC Inhibitors." *ChemMedChem* 6(7): 1193-1198

Schneider G, Krämer O H, Fritsche P, Schüler S, Schmid R M, Saur D. Targeting histone deacetylases in pancreatic ductal adenocarcinoma. Journal of Cellular and Molecular Medicine 2010; 14(6a): 1255-63.

Scott G K, Marx C, Berger C E, et al. Destabilization of ERBB2 Transcripts by Targeting 3 Untranslated Region Messenger RNA Associated HuR and Histone Deacetylase-6. Mol Cancer Res 2008; 6: 1250-58.

Shi X-X, Liu S-L, Xu W, Xu Y-L. Highly stereoselective Pictet-spengler reaction of D-tryptophan methyl ester with piperonal: convenient syntheses of Cialis (Tadalafil), 12a-epi-Cialis, and their deuterated analogues. Tetrahedron: Asymmetry 2008; 19: 435-42.

Siu, J., I. R. Baxendale, et al. (2004). "Microwave assisted Leimgruber-Batcho reaction for the preparation of indoles, azaindoles and pyrroylquinolines." *Organic & Biomolecular Chemistry* 2(2): 160-167.

Spange S, Wagner T, Heinzel T, Krämer O H. Acetylation of non-histone proteins modulates cellular signalling at multiple levels. The International Journal of Biochemistry & Cell Biology 2009; 41(1): 185-98.

Sui Y, Liu L, Wang D, Chen Y-J. An efficient synthetic method to non-natural α- and β-tryptophan analogs via Friedel-Crafts alkylation of indoles with nitroacrylates. Chin. J. Chem. 2007; 25: 977-85.

Tao L-M, Li Q-G, Liu W-Q, Zhou Y, Zhou J-F. An efficient and reusable PdCl2/TBAF system for the Heck reaction under ligand- and solvent-free conditions. J. Chem. Res. 2010; 34: 211-13.

Tercel M, Stevenson R J, Lu G-L, et al. Weight loss effects of quaternary salts of 5-amino-1-(chloromethyl)-1,2-dihydro-3H-benz[e]indoles; structure-activity relationships. Bioorg. Med. Chem. 2012; 20: 734-49.

Van D J W, Jr., Kurchacova E. Tetrahydropβ-carbolines having antihypertensive activity: Miles Laboratories, Inc., USA. 1981:5 pp.

Walton J G A, Patterson S, Liu G, et al. Synthesis and biological evaluation of functionalised tetrahydro-β-carboline analogues as inhibitors of *Toxoplasma gondii* invasion. Org. Biomol. Chem. 2009; 7: 3049-60.

Wen X, Lin Z, Liu B, Wei Y. Caspase-mediated programmed cell death pathways as potential therapeutic targets in cancer. Cell Prolif. 2012; 45(3): 217-24.

Xiao, S., X.-X. Shi, et al. (2010). "An Efficient and General Method for the Stereodivergent Syntheses of Tadalafil-Like Tetracyclic Compounds." *European Journal of Organic Chemistry* 2010(9): 1711-1716.

Yu C, Rahmani M, Almenara J, et al. Histone Deacetylase Inhibitors Promote STI571-mediated Apoptosis in STI571-sensitive and -resistant Bcr/Abl+Human Myeloid Leukemia Cells. Cancer Research 2003; 63(9): 2118-26.

Zhao, M., L. Bi, et al. (2006). "Synthesis and cytotoxic activities of β-carboline amino acid ester conjugates." *Bioorganic & Medicinal Chemistry* 14(20): 6998-7010.

The invention claimed is:

1. A compound having the general formula I

wherein
H is a head group

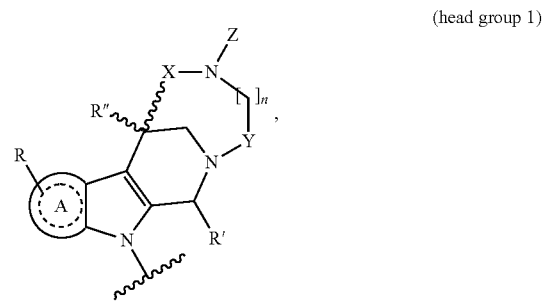

(head group 1)

wherein
A is chosen from phenyl or pyridyl ring;
n is 0 or 1;
X and Y are each independently selected from $CH_2$, C=O and C=S;
Z is selected from the group consisting of H, alkyl and

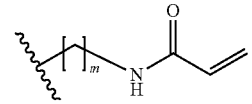

with m being 0 to 6;
R is selected from the group consisting of H, alkoxy, hydroxy, alkyl, alkoxyaryl, aryl, halogenyl, nitro, amino, amidyl, cyano, sulfanyl, sulfinyl, sulfonyl, formyl, acetyl,

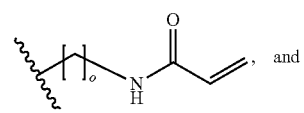, and

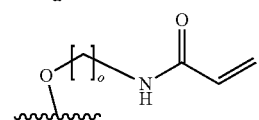

with o being 0 to 6;

R' and R" are each independently selected from the group consisting of H, alkyl, aryl and substituted aryl;

L is a linker comprising a hydroxamic acid (HA) and having the formula

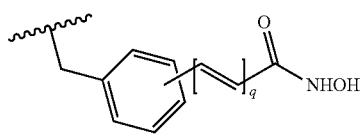

with q being 0 or 1;

or a pharmaceutically acceptable salt thereof.

2. The compound of claim 1, wherein the hydroxamic acid(s) HA is/are protected by carbamate.

3. The compound of claim 1, wherein H is

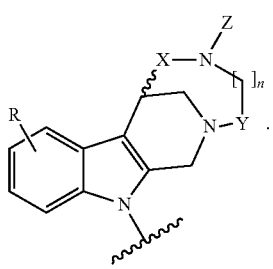

4. The compound of claim 1 having general formula II

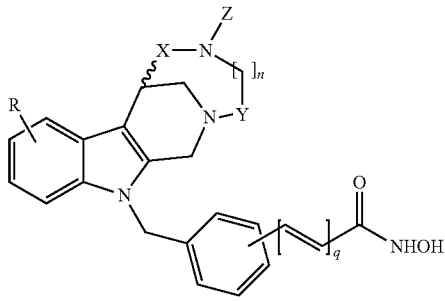

wherein
X and Y are each independently selected from CH$_2$, C=O and C=S;
Z is selected from the group consisting of alkyl and

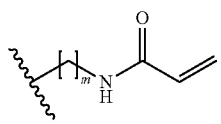

with m being 2 to 6; and

R is selected from the group consisting of H, alkoxy,

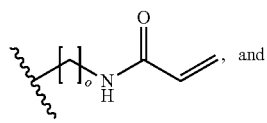, and

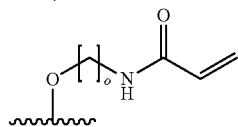

with o being 1 to 6.

5. The compound of claim 1, having the general formula IIa

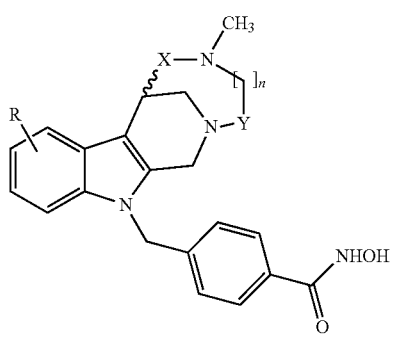

wherein
n is 0 or 1;
X and Y are each independently selected from C=O and C=S; and
R is selected from the group consisting of H, alkoxy,

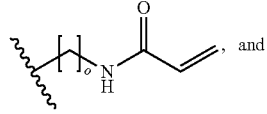, and

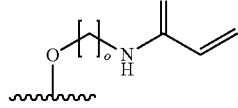

with o being 1 or 2.

6. The compound of claim 1 selected from

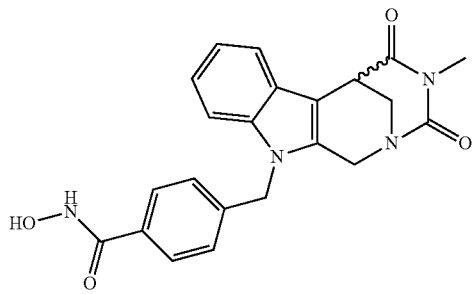

39a

-continued
39b
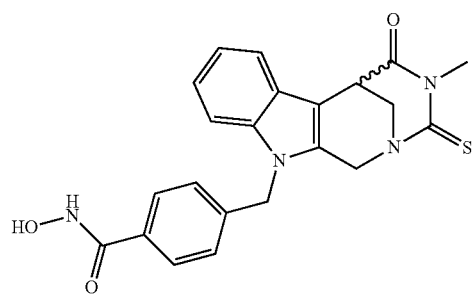
39c
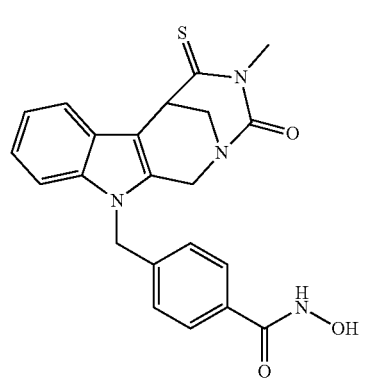
39e
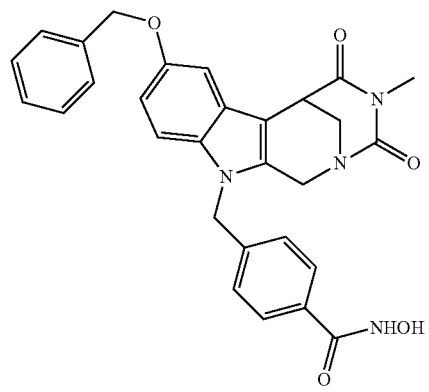
39f
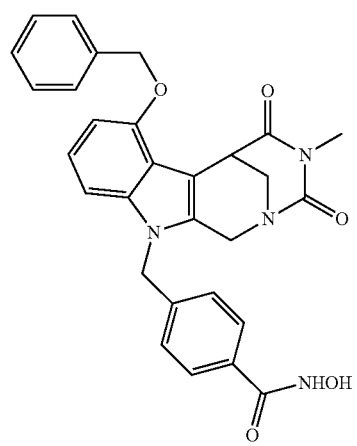
-continued
39h
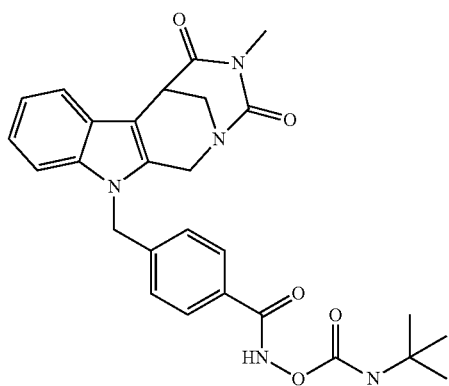
40a
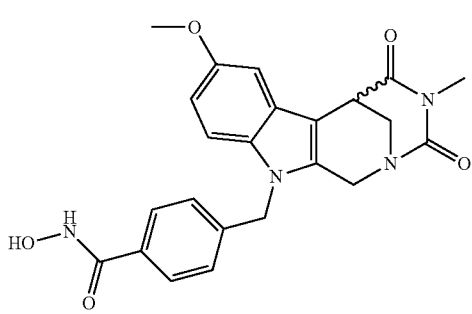
40b
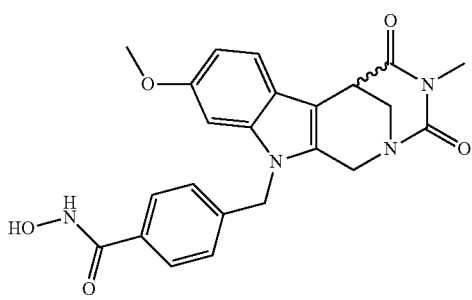
40c
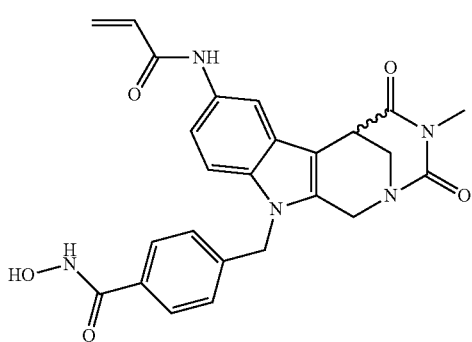

231
-continued
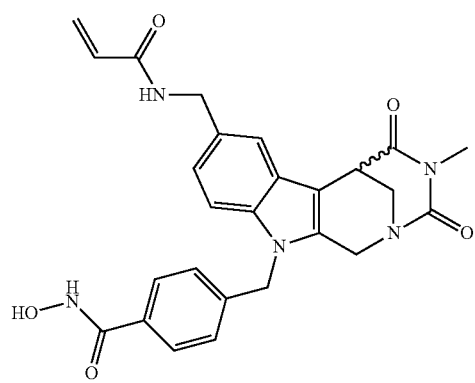
40d
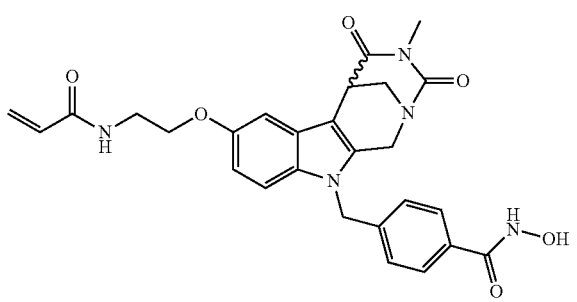
40e
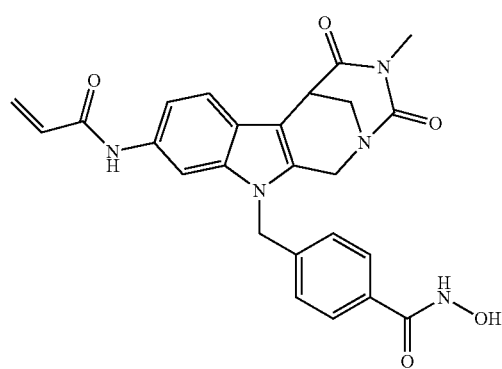
40f
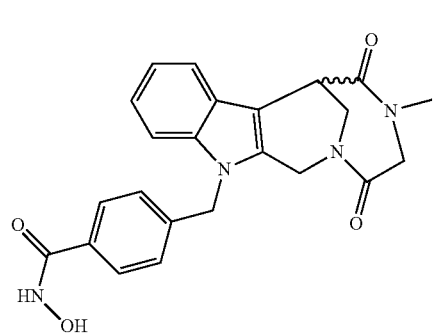
41
232
-continued
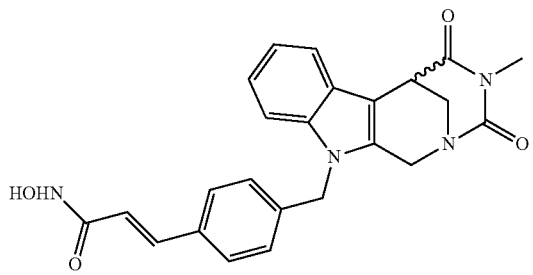
50
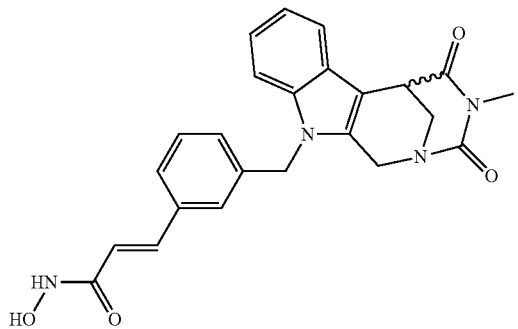
51
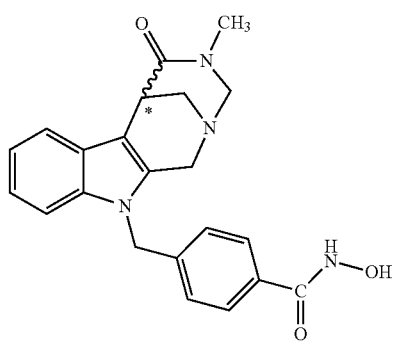
56a
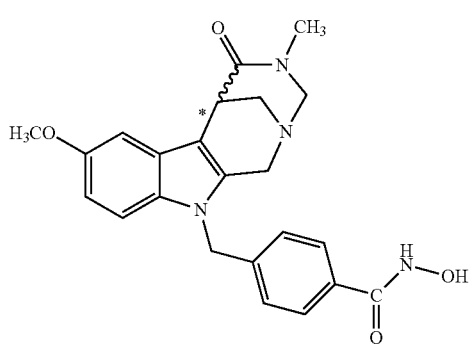
56b

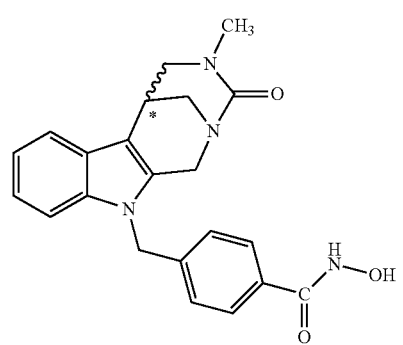

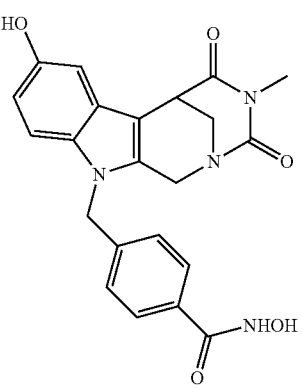

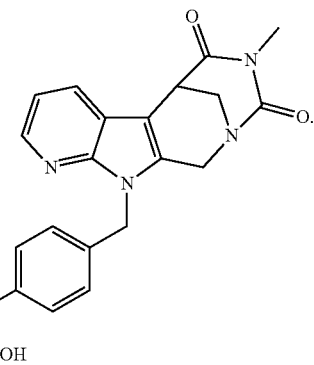

7. A pharmaceutical composition comprising
   at least one compound according to claim 1, and a pharmaceutically acceptable excipient and/or carrier.

8. A method for inhibiting a histone deacetylase (HDAC) wherein said method comprises administering to a subject a therapeutically effective amount of a compound according to claim 1.

9. A method of generating a compound of claim 1, comprising the steps of
   (1) reduction of a methyl 2-(1H-indol-3-yl)-3-nitropropanoate derivative,
   (2) ring closure employing a pictet-spengler reaction,
   (3) transformation to the respective urea or thiourea derivative by use of 2,5-dioxopyrrolidin-1-yl carbamate derivatives, isocyanates or isothiocyanates, and
   (4) ring closure mediated by a base.

10. A method of treatment of a disease, comprising the steps of
    administering to a subject a therapeutically effective amount of a compound according to claim 1,
    wherein the disease is selected from breast cancer, prostate cancer, uterus cancer, leukemia, and arthritis.

11. The method of claim 10, comprising
    administering the therapeutically effective amount of said compound
    in combination with further agent(s) or drug(s)
    and/or comprising sensitization of cancer cells, during radiation therapy.

12. The compound, according to claim 5, wherein R is H.

13. The compound, according to claim 6, wherein the compound is

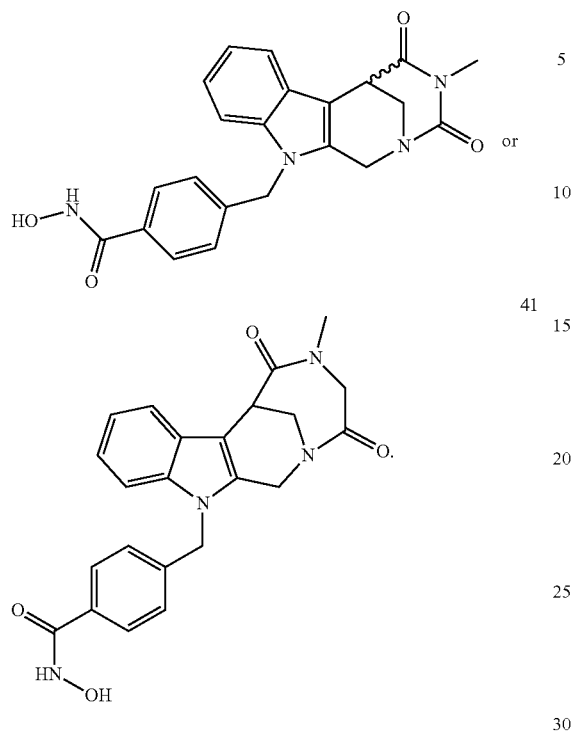
14. The method, according to claim 8, wherein the HDAC is HDAC6.
* * * * *

UNITED STATES PATENT AND TRADEMARK OFFICE
CERTIFICATE OF CORRECTION

PATENT NO. : 10,106,540 B2
APPLICATION NO. : 15/329175
DATED : October 23, 2018
INVENTOR(S) : Siavosh Mahboobi et al.

Page 1 of 11

It is certified that error appears in the above-identified patent and that said Letters Patent is hereby corrected as shown below:

In the Specification

Column 4,

Lines 8-12, " 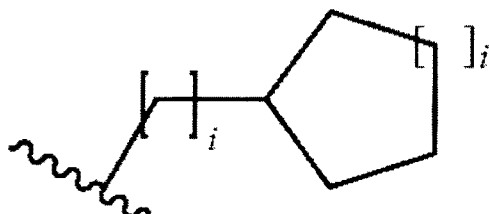 " should read

-- 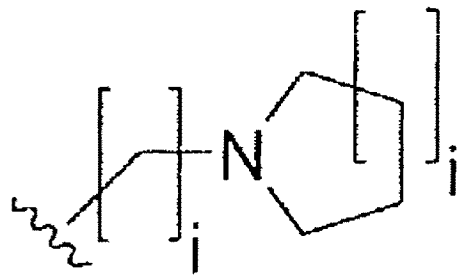 --.

Column 7,

Lines 10-15, " 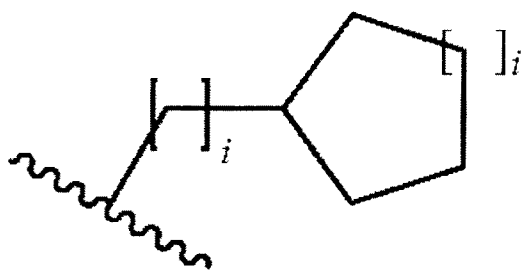 " should read

Signed and Sealed this
Fifth Day of November, 2019

Andrei Iancu
*Director of the United States Patent and Trademark Office*

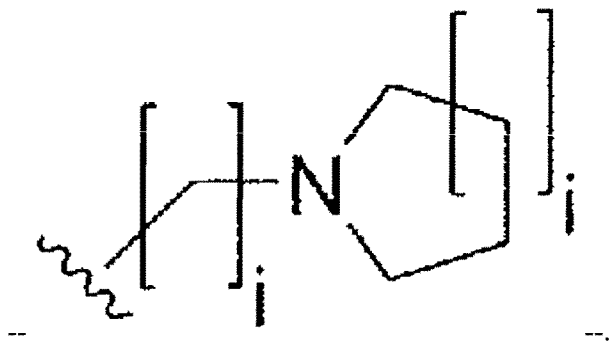

Column 21,
Lines 18-20, "N-hydroxy-4-((10-methoxy-1,4-dioxo-2-propyl-1,3,4,6,12,12a-hexahydropyrazino[1',2':,1,6]pyrido[3,4-b]indol-7(2H)-yl)methyl)benzamide (136k)" should read --4-((10-(Benzyloxy)-1,4-dioxo-2-propyl-1,3,4,6,12,12a-hexahydropyrazino[1',2':1,6]pyrido[3,4-b]indol-7(2H)-yl)methyl)-N-hydroxybenzamide (136j)--.
Lines 45-46, "indol-7(2R)-yl)" should read --indol-7(2H)-yl--.
Lines 66-67, "indol-7(2R)-yl)" should read --indol-7(2H)-yl--.

Column 25,
Lines 31-33, "7c: R = NHBoc
    7d: R = CH$_2$NHBOC
    7e: R = OBz" should read --7c: R = 5-NHBOC
                    7d: R = 5-CH$_2$NHBOC
                    7e: R = 5-OBz--.
Lines 35-37, "11c: R = NHBoc
    11d: R = CH$_2$NHBOC
    11e: R = OBz" should read --11c: R = 5-NHBOC
                    11d: R = 5-CH$_2$NHBOC
                    11e: R = 5-OBz--.

Column 26,
Lines 31-33, "9c: R = NHBoc
    9d: R = CH$_2$NHBOC
    9e: R = OBz" should read --9c: R = 5-NHBOC
                    9d: R = 5-CH$_2$NHBOC
                    9e: R = 5-OBz--.

CERTIFICATE OF CORRECTION (continued)
U.S. Pat. No. 10,106,540 B2

Column 26,

Lines 45-49, " 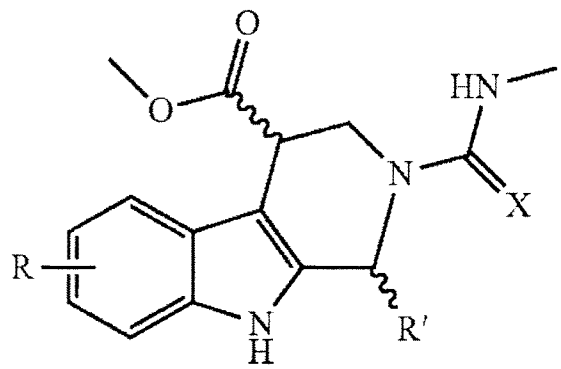 " should read

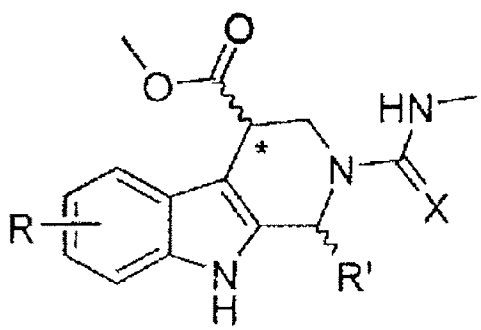

--       --.

Column 26,

Lines 45-49, " 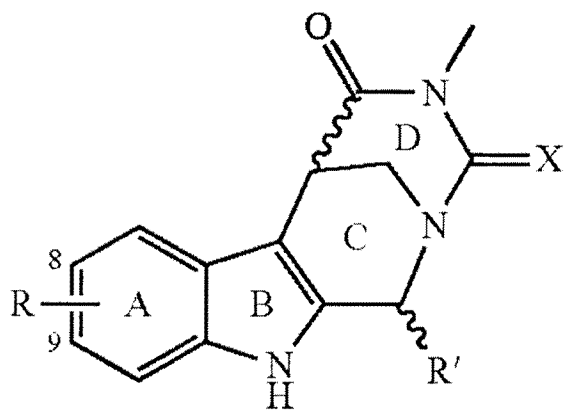 " should read

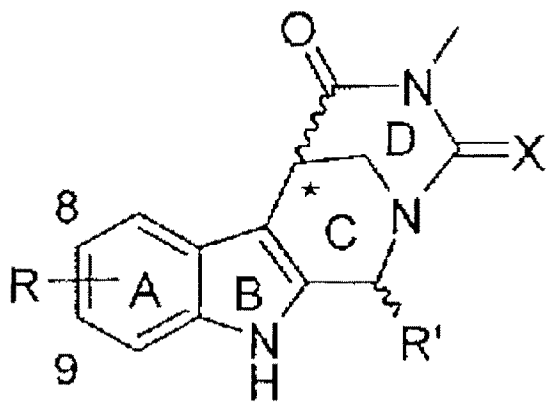

--       --.

Column 28,
Line 25, " 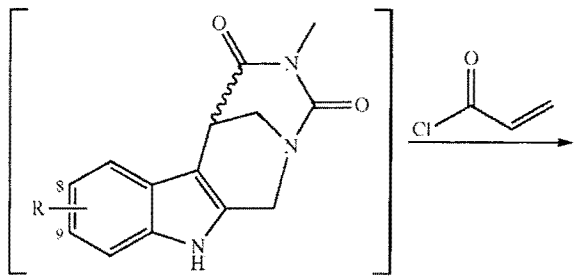 " should read
-- 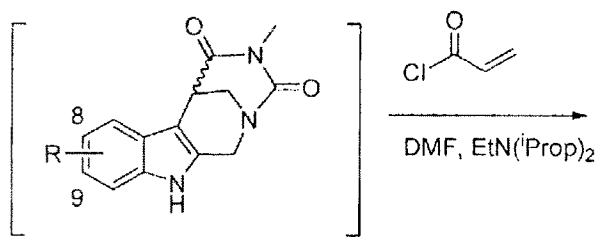 --.
Column 31/32,
Third column, "33b: R = H;" should read --33b: $R^1$ = H;--.
Column 33,
First column, "36b: R = H;" should read --36b: $R^1$ = H;--.
Second column, "41: $R^1$ = H" should read --41: R = H--.
Column 37,
Line 65, "37%" should read --67%--.
Column 52,
Lines 43-47, " 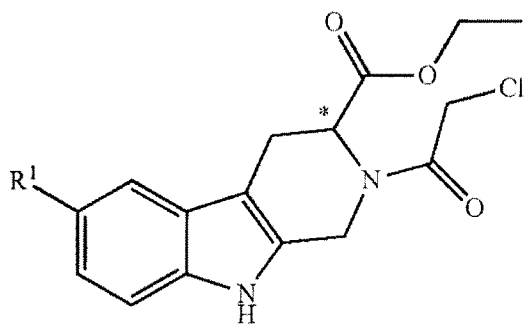 " should read

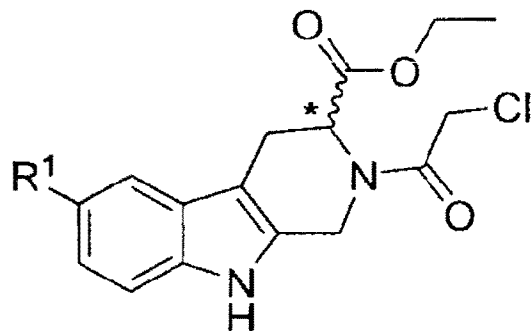
--                                          --.
Column 53,
Lines 3-10,
" 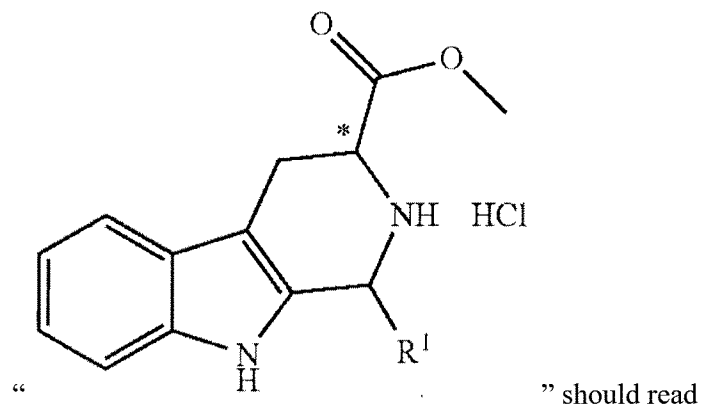 " should read
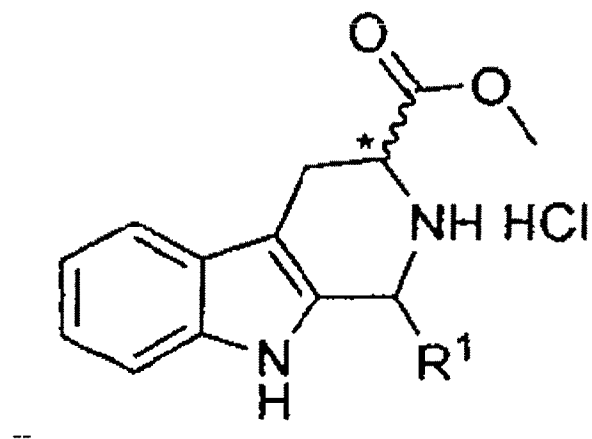
--                                          --.

Column 53,

Lines 21-27, " 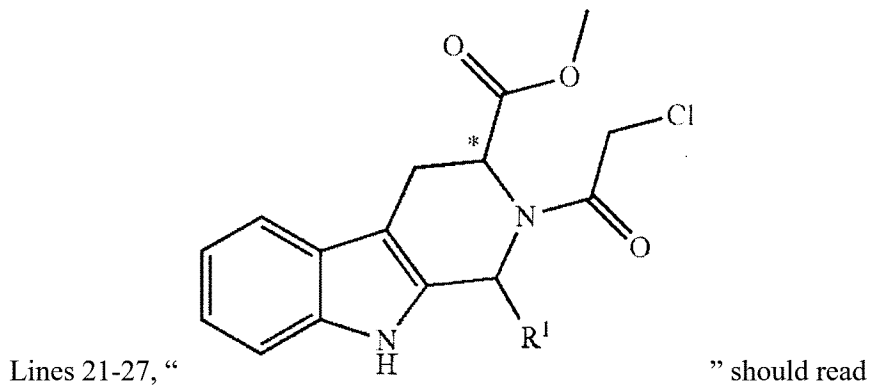 " should read

-- 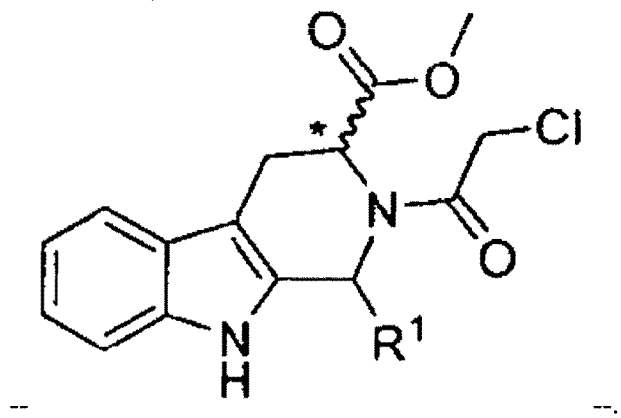 --.

Column 58,
Line 46, "134g: $R^1$ = H," should read --134h: $R^1$ = H,--.

Column 72,
Line 9, "40 mM 3-Glycerophosphat" should read --40 mM β-Glycerophosphat--.

Column 86,
Line 15, "hydrochloride (1e)" should read --hydrochloride (11e)--.

Column 97,
Line 30, "thioxo-3,4,6,1-tetrahydro" should read --thioxo-3,4,6,11-tetrahydro--.

Column 99,
Line 51, "$C_{21}H_{26}N_4O_8$" should read --$C_{21}H_{26}N_4O_5$--.

Column 105,
Line 65, "411)-dione" should read --4*H*)-dione--.

Column 107,
Line 8, "(s, 1711). ESI-MS" should read --(s, 17H). ESI-MS--.

Column 108,
Line 16, "[5,6-b]indol-1(1H)" should read --[5,6-b]indol-11(1$H$)--.
Line 36, "dioxo-1,3,4,5,6,1-hexahydro" should read --dioxo-1,3,4,5,6,11-hexahydro--.

Column 112,
Line 11, "$C_{22}H_9N_3O_4$" should read --$C_{22}H_{19}N_3O_4$--.
Line 45, "$C_{22}H_9N_3O_4$" should read --$C_{22}H_{19}N_3O_4$--.

Column 113,
Line 50, "2.6-methan[1.3]" should read --2.6-methano[1.3]--.

Column 114,
Lines 11-12, "496.19 [MH](100)." should read --496.19 [MH$^+$](100).--.

Column 117,
Line 29, "tetrahydro-H-2,7" should read --tetrahydro-1$H$-2,7--.
Line 38, "3.4 Hz, 11)" should read --3.4 Hz, 1H)--.

Column 128,
Line 49, "methano[0.3]diazocino" should read --methano[1.3]diazocino--.

Column 132,
Line 12, "indol-1 (1H)" should read --indol-11(1$H$)--.

Column 133,
Line 48, "$C_{23}H_{22}N_4O_4 \times H_2O$" should read --$C_{23}H_{22}N_4O_4 \times$ ¼ $H_2O$--.

Column 134,
Line 12, "$C_{24}H_{22}N_4O_4 \times$% $H_2O$:" should read --$C_{24}H_{22}N_4O_4 \times$ 2/3 $H_2O$:--.

Column 144,
Line 60, "13C NMR" should read --$^{13}$C NMR--.

Column 154,
Line 11, "417 [MH$^-$]" should read --417 [MH$^+$]--.

Column 155,
Lines 21-32, " 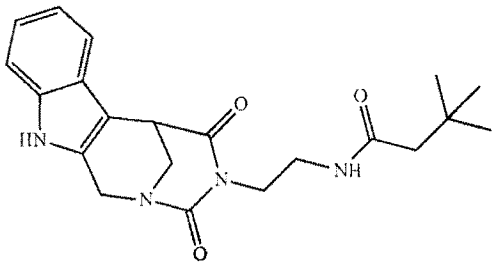 " should read

CERTIFICATE OF CORRECTION (continued)
U.S. Pat. No. 10,106,540 B2

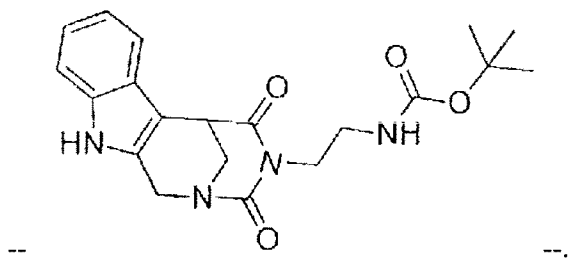
-- --.

Column 160,
Line 20, "4-(4-(2-Acrylamidoethyl)" should read --4-((4-(2-Acrylamidoethyl)--.

Column 170,
Line 30, "108 to obtain 11c." should read --108 to obtain 111c.--.

Column 175,
Line 43, "(d, J = 1.8 Hz, 11H)" should read --(d, *J* = 1.8 Hz, 1H)--.

Column 180,
Lines 12-13, "tetrahydro-fi-carboline" should read --tetrahydro-*β*-carboline--.

Column 183,
Line 65, "(m, 5H). 2-(2-(Piperidin" should read --(m, 5H).
2-(2-(Piperidin--.

Column 187,
Lines 13-14, "[MH$^+$ - CH$_4$]" should read --[MH$^+$ - C$_8$H$_4$]--.

Column 188,
Lines 13-18, " 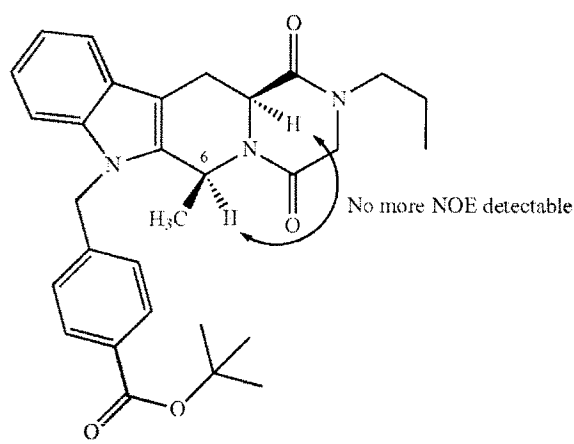 " should read

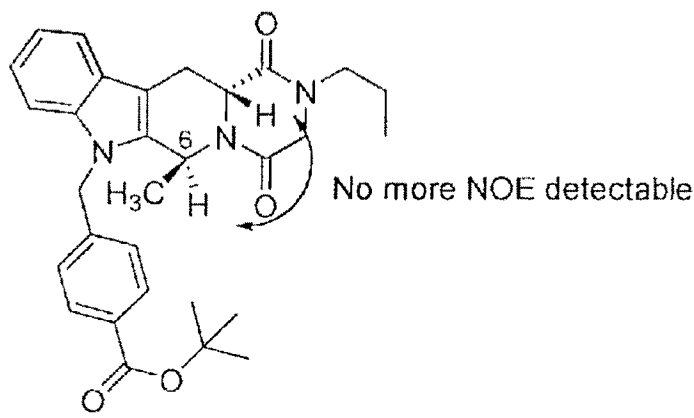
-- --.
Column 192,
Line 29, "(133c) yielded" should read --(133e) yielded--.
Column 202,
Line 3, "indol-7(21)" should read --indol-7(2*H*)--.
Column 204,
Line 2, "hexahydropyrazino[3,4-b]" should read --hexahydropyrazino[1',2':1,6]pyrido[3,4-*b*]--.
Line 66, "$C_{26}H_{27}N_3O_8$:" should read --$C_{26}H_{27}N_3O_5$:--.
Column 210,
Lines 48-51, " 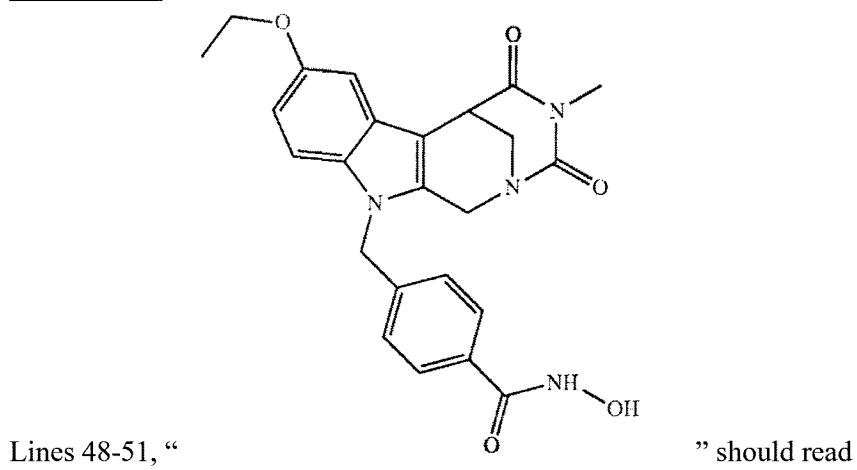 " should read

CERTIFICATE OF CORRECTION (continued)
U.S. Pat. No. 10,106,540 B2

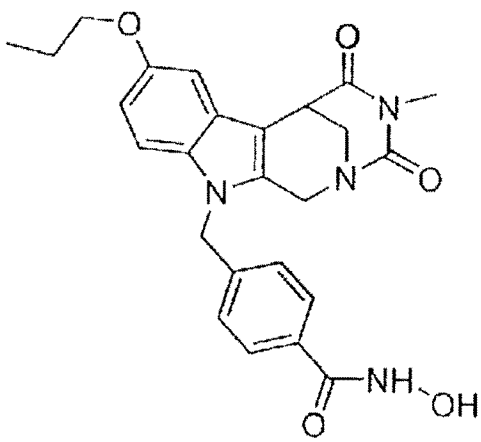

-- --.

Column 213,
Line 65, "C$_5$H$_{13}$C$_{12}$N$_3$O$_2$" should read --C$_8$H$_{13}$Cl$_2$N$_3$O$_2$--.

Column 215,

Lines 33-34, " 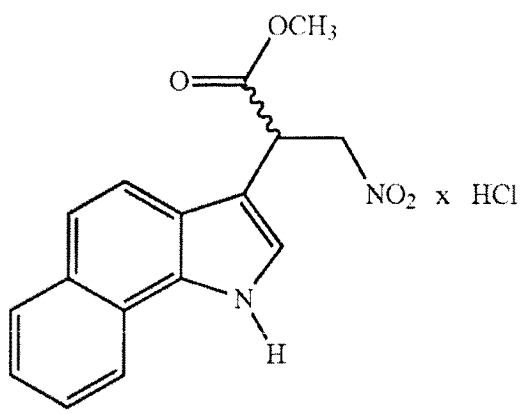 " should read

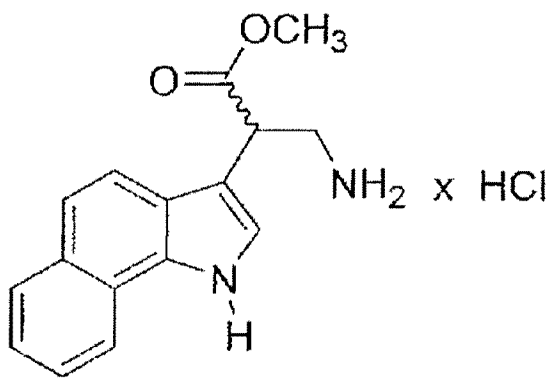

-- --.

Column 220,
Line 25, "sub-Gi-populations" should read --sub-G1-populations--.

Column 224,
Line 19, "3-carbolines and studies" should read --β-carbolines and studies--.
Line 24, "PDGF-R B and histone" should read --PDGF-Rβ and histone--.